(12) United States Patent
Flynn et al.

(10) Patent No.: US 12,319,655 B2
(45) Date of Patent: Jun. 3, 2025

(54) RAF KINASE INHIBITORS AND METHODS OF USE THEREOF

(71) Applicant: Deciphera Pharmaceuticals, LLC, Waltham, MA (US)

(72) Inventors: Daniel L. Flynn, Waltham, MA (US); Yu Mi Ahn, Waltham, MA (US); Lakshminarayana Vogeti, Waltham, MA (US); Bertrand Le Bourdonnec, Waltham, MA (US)

(73) Assignee: Deciphera Pharmaceuticals, LLC, Waltham, MA (US)

(*) Notice: Subject to any disclaimer, the term of this patent is extended or adjusted under 35 U.S.C. 154(b) by 0 days.

(21) Appl. No.: 18/078,271

(22) Filed: Dec. 9, 2022

(65) Prior Publication Data

US 2023/0257352 A1    Aug. 17, 2023

Related U.S. Application Data

(60) Provisional application No. 63/393,445, filed on Jul. 29, 2022, provisional application No. 63/287,873, filed on Dec. 9, 2021.

(51) Int. Cl.

| | |
|---|---|
| *C07D 213/81* | (2006.01) |
| *A61P 35/00* | (2006.01) |
| *C07D 213/74* | (2006.01) |
| *C07D 239/42* | (2006.01) |
| *C07D 401/04* | (2006.01) |
| *C07D 401/10* | (2006.01) |
| *C07D 401/12* | (2006.01) |
| *C07D 401/14* | (2006.01) |
| *C07D 403/12* | (2006.01) |
| *C07D 405/12* | (2006.01) |
| *C07D 405/14* | (2006.01) |
| *C07D 413/12* | (2006.01) |
| *C07D 413/14* | (2006.01) |
| *C07D 471/04* | (2006.01) |
| *C07D 487/04* | (2006.01) |

(52) U.S. Cl.
CPC ............ *C07D 213/81* (2013.01); *A61P 35/00* (2018.01); *C07D 213/74* (2013.01); *C07D 239/42* (2013.01); *C07D 401/04* (2013.01); *C07D 401/10* (2013.01); *C07D 401/12* (2013.01); *C07D 401/14* (2013.01); *C07D 403/12* (2013.01); *C07D 405/12* (2013.01); *C07D 405/14* (2013.01); *C07D 413/12* (2013.01); *C07D 413/14* (2013.01); *C07D 471/04* (2013.01); *C07D 487/04* (2013.01)

(58) Field of Classification Search
CPC ..... A61P 35/00; C07D 213/74; C07D 213/81; C07D 239/42; C07D 401/04; C07D 401/10; C07D 401/12; C07D 401/14; C07D 403/12; C07D 405/12; C07D 405/14; C07D 413/12; C07D 413/14; C07D 417/14; C07D 471/04; C07D 487/04

See application file for complete search history.

(56) References Cited

U.S. PATENT DOCUMENTS

| | | |
|---|---|---|
| 6,200,995 B1 | 3/2001 | De la Brouse-Elwood et al. |
| 7,144,888 B2 | 12/2006 | Doherty et al. |
| 7,144,911 B2 | 12/2006 | Flynn et al. |
| 7,202,257 B2 | 4/2007 | Flynn et al. |
| 7,279,576 B2 | 10/2007 | Flynn et al. |
| 7,300,931 B2 | 11/2007 | Hangauer, Jr. |
| 7,335,672 B2 | 2/2008 | Norman et al. |
| 7,342,037 B2 | 3/2008 | Flynn et al. |
| 7,504,401 B2 | 3/2009 | Kelly et al. |
| 7,521,470 B2 | 4/2009 | Zhu et al. |
| 7,531,566 B2 | 5/2009 | Flynn et al. |
| 7,666,895 B2 | 2/2010 | Flynn et al. |
| 7,737,283 B2 | 6/2010 | Flynn et al. |
| 7,767,669 B2 | 8/2010 | Nuss et al. |
| 7,790,756 B2 | 9/2010 | Flynn et al. |
| 7,893,063 B2 | 2/2011 | Pass |
| 7,897,762 B2 | 3/2011 | Flynn et al. |
| 7,923,556 B2 | 4/2011 | Wrobleski et al. |
| 8,143,293 B2 | 3/2012 | Flynn et al. |
| 8,163,756 B2 | 4/2012 | Flynn et al. |
| 8,188,113 B2 | 5/2012 | Flynn et al. |
| 8,278,331 B2 | 10/2012 | Flynn et al. |
| 8,343,966 B2 | 1/2013 | Adcock et al. |
| 8,461,179 B1 | 6/2013 | Flynn et al. |
| 8,486,951 B2 | 7/2013 | Flynn et al. |
| 8,569,319 B2 | 10/2013 | Flynn et al. |
| 8,586,565 B2 | 11/2013 | Flynn et al. |
| 8,618,141 B2 | 12/2013 | Dumas et al. |
| 8,637,672 B2 | 1/2014 | Flynn et al. |

(Continued)

FOREIGN PATENT DOCUMENTS

| | | |
|---|---|---|
| WO | WO-2014/151616 A1 | 9/2014 |
| WO | WO-2015/059618 A1 | 4/2015 |

(Continued)

OTHER PUBLICATIONS

U.S. Appl. No. 11/963,740, filed Dec. 21, 2007, Patented, U.S. Pat. No. 8,163,756.
U.S. Appl. No. 11/870,388, filed Oct. 10, 2007, Patented, U.S. Pat. No. 7,790,756.
U.S. Appl. No. 12/829,561, filed Jul. 2, 2010, Patented, U.S. Pat. No. 8,586,565.
U.S. Appl. No. 11/854,354, filed Sep. 12, 2007, Patented U.S. Pat. No. 8,188,113.
U.S. Appl. No. 10/746,460, filed Dec. 24, 2003, Patented, U.S. Pat. No. 7,144,911.

(Continued)

*Primary Examiner* — Sarah Pihonak
*Assistant Examiner* — Padmaja S Rao
(74) *Attorney, Agent, or Firm* — Goodwin Procter LLP

(57) ABSTRACT

Described herein are compounds that are RAF inhibitors and their use in the treatment of disorders such as cancers.

31 Claims, No Drawings

Specification includes a Sequence Listing.

(56) References Cited

U.S. PATENT DOCUMENTS

| | | |
|---|---|---|
| 8,741,911 B2 | 6/2014 | Allgeier et al. |
| 8,921,565 B2 | 12/2014 | Flynn et al. |
| 8,940,756 B2 | 1/2015 | Flynn et al. |
| 9,012,635 B2 | 4/2015 | Flynn et al. |
| 9,133,183 B2 | 9/2015 | Flynn et al. |
| 9,181,223 B2 | 11/2015 | Kaufman et al. |
| 9,187,474 B2 | 11/2015 | Flynn et al. |
| 9,193,719 B2 | 11/2015 | Flynn et al. |
| 9,242,969 B2 | 1/2016 | Barsanti et al. |
| 9,249,129 B2 | 2/2016 | Taylor et al. |
| 9,309,224 B2 | 4/2016 | Flynn et al. |
| 9,334,267 B2 | 5/2016 | Flynn et al. |
| 9,382,228 B2 | 7/2016 | Flynn et al. |
| 9,387,202 B2 | 7/2016 | Flynn et al. |
| 9,457,019 B2 | 10/2016 | Flynn et al. |
| 9,694,016 B2 | 7/2017 | Aversa et al. |
| 9,758,492 B2 | 9/2017 | Markwalder et al. |
| 9,802,960 B2 | 10/2017 | Bharathan et al. |
| 10,167,279 B2 | 1/2019 | Aversa et al. |
| 10,266,515 B2 | 4/2019 | McDonald et al. |
| 10,329,270 B2 | 6/2019 | Qiu et al. |
| 10,966,966 B2 | 4/2021 | Soto et al. |
| 11,098,031 B1 | 8/2021 | Kaldor et al. |
| 11,103,507 B2 | 8/2021 | Flynn et al. |
| RE48,731 E | 9/2021 | Flynn et al. |
| 11,185,535 B2 | 11/2021 | Kaufman et al. |
| 11,266,635 B2 | 3/2022 | Soto et al. |
| 11,266,643 B2 | 3/2022 | Fan et al. |
| 11,344,536 B1 | 5/2022 | Soto et al. |
| 11,377,431 B2 | 7/2022 | Kaldor et al. |
| 11,395,818 B2 | 7/2022 | Kaufman et al. |
| 11,407,737 B2 | 8/2022 | Kaldor et al. |
| 11,426,390 B2 | 8/2022 | Soto et al. |
| 11,433,056 B1 | 9/2022 | Soto et al. |
| 11,492,348 B2 | 11/2022 | Stocking et al. |
| 11,518,758 B2 | 12/2022 | Flynn et al. |
| 11,529,336 B2 | 12/2022 | Soto et al. |
| 11,530,206 B2 | 12/2022 | Flynn et al. |
| 11,534,432 B2 | 12/2022 | Soto et al. |
| 11,576,903 B2 | 2/2023 | Kaufman et al. |
| 11,576,904 B2 | 2/2023 | Soto et al. |
| 11,590,134 B2 | 2/2023 | Flynn et al. |
| 11,612,591 B2 | 3/2023 | Kaufman et al. |
| 11,679,110 B2 | 6/2023 | Flynn et al. |
| 2005/0014753 A1 | 1/2005 | Ding et al. |
| 2007/0078135 A1 | 4/2007 | Yuan et al. |
| 2008/0269265 A1 | 10/2008 | Miller et al. |
| 2009/0018145 A1 | 1/2009 | Kanne et al. |
| 2009/0239841 A1 | 9/2009 | Hutchison et al. |
| 2011/0092505 A1 | 4/2011 | Burgis et al. |
| 2011/0098325 A1 | 4/2011 | Raynham et al. |
| 2016/0038504 A1* | 2/2016 | Aversa .................. A61K 45/06 544/70 |
| 2020/0352920 A1 | 11/2020 | Flynn et al. |
| 2021/0047340 A1 | 2/2021 | Green et al. |
| 2021/0145805 A1 | 5/2021 | Flynn et al. |
| 2021/0261532 A1 | 8/2021 | Lennek et al. |
| 2021/0300904 A1 | 9/2021 | Kaldor et al. |
| 2022/0031678 A1 | 2/2022 | Flynn et al. |
| 2022/0047573 A1 | 2/2022 | Flynn et al. |
| 2022/0089569 A1 | 3/2022 | Kaldor et al. |
| 2022/0143018 A1 | 5/2022 | Flynn et al. |
| 2022/0184050 A1 | 6/2022 | Flynn |
| 2022/0184054 A1 | 6/2022 | Flynn |
| 2022/0184077 A1 | 6/2022 | Flynn |
| 2022/0184092 A1 | 6/2022 | Flynn |
| 2022/0184093 A1 | 6/2022 | Flynn |
| 2022/0193083 A1 | 6/2022 | Flynn |
| 2022/0265622 A1 | 8/2022 | Kaufman et al. |
| 2022/0265623 A1 | 8/2022 | Kaufman et al. |
| 2022/0370423 A1 | 11/2022 | Flynn et al. |
| 2022/0370424 A1 | 11/2022 | Flynn et al. |
| 2022/0370426 A1 | 11/2022 | Soto et al. |
| 2023/0039712 A1 | 2/2023 | Flynn et al. |
| 2023/0046018 A1 | 2/2023 | Ding et al. |
| 2023/0047915 A1 | 2/2023 | Flynn et al. |
| 2023/0145926 A1 | 5/2023 | Soto et al. |
| 2023/0201175 A1 | 6/2023 | Kaufman et al. |
| 2023/0201176 A1 | 6/2023 | Kaufman et al. |

FOREIGN PATENT DOCUMENTS

| | | |
|---|---|---|
| WO | WO-2016/038582 A1 | 3/2016 |
| WO | WO-2018/104307 A1 | 6/2018 |
| WO | WO-2020/198058 A1 | 10/2020 |
| WO | WO-2020/230028 A1 | 11/2020 |
| WO | WO-2021/081375 A1 | 4/2021 |
| WO | WO-2021/155316 A1 | 8/2021 |
| WO | WO-2021/180238 A1 | 9/2021 |
| WO | WO-2022/060996 A1 | 3/2022 |
| WO | WO-2022/066917 A1 | 3/2022 |

OTHER PUBLICATIONS

U.S. Appl. No. 10/886,329, filed Jul. 6, 2004, Patented, U.S. Pat. No. 7,202,257.
U.S. Appl. No. 11/450,840, filed Jun. 9, 2006, Patented, U.S. Pat. No. 7,342,037.
U.S. Appl. No. 11/336,708, filed Jan. 20, 2006, Patented, U.S. Pat. No. 7,531,566.
U.S. Appl. No. 11/450,850, filed Jun. 9, 2006, Patented, U.S. Pat. No. 7,666,895.
U.S. Appl. No. 10/746,607, filed Dec. 24, 2003, Patented, U.S. Pat. No. 7,279,576.
U.S. Appl. No. 11/854,293, filed Sep. 12, 2007, Patented, U.S. Pat. No. 7,897,762.
U.S. Appl. No. 12/105,408, filed Apr. 18, 2008, Patented, U.S. Pat. No. 8,143,293.
U.S. Appl. No. 13/590,955, filed Aug. 21, 2012, Patented, U.S. Pat. No. 8,486,951.
U.S. Appl. No. 11/450,849, filed Jun. 9, 2006, Patented, U.S. Pat. No. 7,737,283.
U.S. Appl. No. 13/785,575, filed Mar. 5, 2013, Patented, U.S. Pat. No. 8,741,911.
U.S. Appl. No. 12/608,578, filed Oct. 29, 2009, Patented, U.S. Pat. No. 8,278,331.
U.S. Appl. No. 13/098,247, filed Apr. 29, 2011, Patented, U.S. Pat. No. 8,569,319.
U.S. Appl. No. 13/559,170, filed Jul. 26, 2012, Patented, U.S. Pat. No. 8,637,672.
U.S. Appl. No. 14/214,134, filed Mar. 14, 2014, Patented, U.S. Pat. No. 9,133,183.
U.S. Appl. No. 14/383,803, filed Mar. 5, 2013, Patented, U.S. Pat. No. 9,187,474.
U.S. Appl. No. 13/491,394, filed Jun. 7, 2012, Patented, U.S. Pat. No. 8,461,179.
U.S. Appl. No. 13/801,753, filed Mar. 13, 2013, Patented, U.S. Pat. No. 8,940,756.
U.S. Appl. No. 16/387,315, filed Apr. 17, 2019, Patented, U.S. Pat. No. RE48,731.
U.S. Appl. No. 14/214,127, filed Mar. 14, 2014, Patented, U.S. Pat. No. 9,012,635.
U.S. Appl. No. 13/683,277, filed Nov. 21, 2012, Patented, U.S. Pat. No. 8,921,565.
U.S. Appl. No. 14/549,125, filed Nov. 20, 2014, Patented, U.S. Pat. No. 9,387,202.
U.S. Appl. No. 14/214,160, filed Mar. 14, 2014, Patented, U.S. Pat. No. 9,193,719.
U.S. Appl. No. 14/214,171, filed Mar. 14, 2014, Patented, U.S. Pat. No. 9,181,223.
U.S. Appl. No. 14/214,185, filed Mar. 14, 2014, Patented, U.S. Pat. No. 9,382,228.
U.S. Appl. No. 14/214,179, filed Mar. 14, 2014, Patented, U.S. Pat. No. 9,309,224.
U.S. Appl. No. 14/383,799, filed Mar. 5, 2013, Patented, U.S. Pat. No. 9,334,267.
U.S. Appl. No. 14/535,900, filed Nov. 7, 2014, Patented, U.S. Pat. No. 9,457,019.

(56) References Cited

OTHER PUBLICATIONS

U.S. Appl. No. 17/506,772, filed Oct. 21, 2021, Pending, US 2022-0031678 A1.
U.S. Appl. No. 17/845,275, filed Jun. 21, 2022, Pending, US 2022-0370423 A1.
U.S. Appl. No. 17/845,278, filed Jun. 21, 2022, Pending, US 2022-0370424 A1.
U.S. Appl. No. 16/943,821, filed Jul. 30, 2020, Pending, US 2021-0145805 A1.
U.S. Appl. No. 16/943,871, filed Jul. 30, 2020, Pending, US 2020-0352920 A1.
U.S. Appl. No. 16/725,282, filed Dec. 23, 2019, Patented, U.S. Pat. No. 11,103,507.
U.S. Appl. No. 17/358,137, filed Jun. 25, 2021, Pending, US 2022-0143018 A1.
U.S. Appl. No. 16/870,384, filed May 8, 2020, Patented, U.S. Pat. No. 11,530,206.
U.S. Appl. No. 17/833,272, filed Jun. 6, 2022, Pending, US 2023-0039712 A1.
U.S. Appl. No. 16/870,418, filed May 8, 2020, Patented, U.S. Pat. No. 11,518,758.
U.S. Appl. No. 17/832,224, filed Jun. 3, 2022, Pending, US 2023-0047915 A1.
U.S. Appl. No. 16/902,989, filed Jun. 16, 2020, Patented, U.S. Pat. No. 11,590,134.
U.S. Appl. No. 18/152,993, filed Jan. 11, 2023, Pending.
U.S. Appl. No. 16/991,644, filed Aug. 12, 2020, Pending, US 2022-0047573 A1.
U.S. Appl. No. 17/028,640, filed Sep. 22, 2020, Patented, U.S. Pat. No. 10,966,966.
U.S. Appl. No. 17/180,218, filed Feb. 19, 2021, Patented, U.S. Pat. No. 11,266,635.
U.S. Appl. No. 17/583,977, filed Jan. 25, 2022, Patented, U.S. Pat. No. 11,426,390.
U.S. Appl. No. 17/583,985, filed Jan. 25, 2022, Patented, U.S. Pat. No. 11,344,536.
U.S. Appl. No. 17/727,307, filed Apr. 22, 2022, Patented, U.S. Pat. No. 11,534,432.
U.S. Appl. No. 17/735,678, filed May 3, 2022, Patented, U.S. Pat. No. 11,529,336.
U.S. Appl. No. 17/735,682, filed May 3, 2022, Patented, U.S. Pat. No. 11,576,904.
U.S. Appl. No. 17/735,862, filed May 3, 2022, Patented, U.S. Pat. No. 11,433,056.
U.S. Appl. No. 18/091,743, filed Dec. 30, 2022, Pending.
U.S. Appl. No. 17/869,108, filed Jul. 20, 2022, Pending, US 2022-0370426 A1.
U.S. Appl. No. 17/180,234, filed Feb. 19, 2021, Patented, U.S. Pat. No. 11,185,535.
U.S. Appl. No. 17/504,133, filed Oct. 18, 2021, Pending, U.S. Pat. No. 11,576,903.
U.S. Appl. No. 17/735,741, filed May 3, 2022, Pending, US 2022-0265622 A1.
U.S. Appl. No. 17/735,784, filed May 3, 2022, Pending, US 2022-0265623 A1.
U.S. Appl. No. 17/180,241, filed Feb. 19, 2021, Patented, U.S. Pat. No. 11,395,818.
U.S. Appl. No. 17/735,820, filed May 3, 2022, Pending, U.S. Pat. No. 11,612,591.
U.S. Appl. No. 18/148,766, filed Dec. 30, 2022, Pending.
U.S. Appl. No. 18/178,789, filed Mar. 6, 2023, Pending.
U.S. Appl. No. 17/528,478, filed Nov. 17, 2021, Pending.
U.S. Appl. No. 17/534,795, filed Nov. 24, 2021, Pending, US 2022-0193083 A1.
U.S. Appl. No. 17/534,762, filed Nov. 24, 2021, Pending, US 2022-0184092 A1.
U.S. Appl. No. 17/534,764, filed Nov. 24, 2021, Pending, US 2022-0184054 A1.
U.S. Appl. No. 17/534,768, filed Nov. 24, 2021, Pending, US 2022-0184050 A1.
U.S. Appl. No. 17/534,769, filed Nov. 24, 2021, Pending, US 2022-0184077 A1.
U.S. Appl. No. 17/534,771, filed Nov. 24, 2021, US 2022-0184093 A1.
U.S. Appl. No. 18/073,886, filed Dec. 2, 2022, Pending.
U.S. Appl. No. 18/078,269, filed Dec. 9, 2022, Pending.
U.S. Appl. No. 18/078,271, filed Dec. 9, 2022, Pending.
U.S. Appl. No. 18/073,721, filed Dec. 2, 2022, Pending.
U.S. Appl. No. 17/938,353, filed Oct. 6, 2022, Pending.
Ramurthy, S. et al., "Design and Discovery of N(3-(2-(2-Hydroxyethoxy)-6-morpholinopyridin-4-yl)-4-methylphenyl)-2-(trifluoromethyl)isonicotinamide, a Selective, Efficacious, and Well-Tolerated RAF Inhibitor Targeting RAS Mutant Cancers: The Path to the Clinic," Journal of Medicinal Chemistry (2020), 63(5), pp. 2013-2027.
International Search Report and Written Opinion of PCT/US2022/081236 mailed Feb. 17, 2023, 13 pages.
International Search Report and Written Opinion of PCT/US2022/081242 mailed Feb. 17, 2023, 14 pages.
Man, R. et al., "A patent review of RAF kinase inhibitors (2010-2018)," Expert Opinion on Therapeutic Patents, vol. 29, No. 9, (Aug. 6, 2019), pp. 675-688.
Wang, P. et al., "A Patent review of BRAF inhibitors: 2013-2018," Expert Opinion on Therapeutic Patents, vol. 29, No. 8, (Jul. 13, 2019), pp. 595-603.

* cited by examiner

RAF KINASE INHIBITORS AND METHODS OF USE THEREOF

CROSS REFERENCE

This application claims priority to U.S. Provisional Application No. 63/287,873 filed Dec. 9, 2021 and U.S. Provisional Application No. 63/393,445, filed Jul. 29, 2022, each of which is incorporated herein by reference in its entirety.

This application contains a Sequence Listing which has been submitted electronically in XML format. The Sequence Listing XML is incorporated herein by reference. Said XML file, created on May 22, 2023, is named DCP-111_SL.xml and is 8,096 bytes in size.

BACKGROUND

The BRAF V600X (i.e., V600E) mutant form of BRAF is known to be oncogenic, and there are multiple BRAF inhibitors now marketed to inhibit the signaling of oncogenic BRAF V600E in melanoma and other cancers. BRAF V600E signals as a monomer and is constitutively active independent of upstream control by RAS. The marketed BRAF V600E inhibitors include vemurafenib, dabrafenib, and encorafenib.

Other than BRAF V600X mutants, almost all other oncogenic forms of BRAF signal through the formation of homodimers (BRAF-BRAF dimer) or heterodimers (e.g., BRAF-CRAF dimer) that are refractory to BRAF inhibitors such as vemurafenib, dabrafenib, and encorafenib. Such dimers are formed in cancers driven by BRAF fusions, atypical BRAF mutations, or RAS mutant cancers.

Oncogenic BRAF fusions originate from genomic rearrangements placing the 3-prime portion of the BRAF gene encoding the kinase domain behind another gene at the 5-prime position. The rearrangements result in the expression of oncoproteins that express constitutive kinase activity due to loss of the N-terminal auto-inhibitory domain of BRAF resulting from the genomic rearrangements. These BRAF fusions exhibit constitutive kinase activity due to spontaneous dimerization and as such are capable of aberrant signaling in cancer cells independent of upstream effectors or regulatory mechanisms. Additionally, some 5-prime translocated rearrangement genes contribute the N-terminal domains to be capable of further inducing dimerization, thereby enhancing activating dimerization of the BRAF fusion protein kinase domain. Since the expression of these genomic rearrangements are controlled by the promoter of the 5-prime partner, often there is overexpression of the BRAF fusion transcript due to efficient or excessive promoter activity. BRAF fusions are among the most common kinase translocations in solid tumors. Since their first description in 2005 as oncogenes in papillary thyroid carcinoma, hundreds of tumors in which the BRAF kinase domain is fused to one of more than 110 different 5-prime partner genes have been identified across at least 15 different tumor types. BRAF fusions are found in papillary thyroid carcinoma, astrocytomas, melanomas, and have also been identified in drug resistant EGFR mutant lung cancers. BRAF fusion proteins signal by dimerization in a RAS-independent manner and are resistant to many BRAF inhibitors such as vemurafenib and dabrafenib, that are not capable of inhibiting both protomers of the signaling homodimer BRAF fusions. Rare CRAF fusion proteins have also been demonstrated to be tumor drivers. Such CRAF fusion proteins signal as CRAF-CRAF homodimers.

Other so-called atypical BRAF mutations also lead to spontaneous dimerization and signaling independent of RAS control. Like BRAF fusions, these atypical BRAF mutants signal as aberrant homodimers.

RAS mutant cancers comprise approximately 26-30% of all human cancers. RAS mutant cancers signal through the RAS→RAF→MEK→ERK MAPK signaling pathway. In this signaling cascade, kinase-inactive RAF monomers (comprising ARAF, BRAF, CRAF isoforms) are recruited to oncogenic RAS where RAS induces the formation of kinase-active signaling RAF dimers. A predominant RAF heterodimer that is recruited to mutant RAS is the BRAF/CRAF heterodimer.

A combinatorial siRNA screening approach identified RAF as a dominant node in RAS mutant cancers, and that codepletion of both BRAF and CRAF, together with depletion of the autophagy gene ATG7, gave the best synthetic lethal inhibition of RAS mutant signaling, and additionally afforded the best therapeutic window for inhibiting signaling in RAS mutant cells versus normal, RAS wildtype cells. Additionally, it has been reported that inhibition of the RAF→MEK→ERK pathway in combination with autophagy-inhibiting agents effectively blocked RAS mutant cancer growth in vitro and in vivo.

Vertical inhibition of the RAF→MEK→ERK pathway through pan inhibition of RAF (specifically BRAF+CRAF) and ERK kinase activities were shown to illicit high synergy in blocking MAPK pathway signaling in KRAS-mutant pancreatic cancer cells, organoid studies, as well as in murine models of KRAS mutant pancreatic cancer. Vertical inhibition of RAF (BRAF+CRAF) and MEK kinase activities was also shown to be synergistic in KRAS mutant tumors.

The importance of inhibiting both BRAF and CRAF isoforms, as well as the requirement of inhibitor successfully binding to and inhibiting both protomers of signaling RAF dimers, has been well demonstrated. Failure of a RAF inhibitor, especially BRAF inhibitors, to successfully bind to and inhibit both protomers of signaling RAF dimers in RAS mutant cancers leads to paradoxical pathway stimulation rather than the desired pathway inhibition. Such BRAF inhibitors are contraindicated for the treatment of RAS mutant cancers.

There is a need to identify RAF inhibitors that can inhibit multiple RAF isoforms. Particularly, there is a need to identify RAF inhibitors that can inhibit both BRAF and CRAF isoforms. Especially, there is a need to identify RAF inhibitors that can inhibit both RAF protomers present in signaling BRAF/BRAF homodimers and both protomers in BRAF/CRAF heterodimers. Such pan RAF inhibitors find utility in the treatment of BRAF V600X driven cancers, atypical BRAF mutated cancers, BRAF fusion cancers, CRAF fusion cancers, and RAS mutant cancers.

SUMMARY

Described herein, are compounds that are RAF inhibitors. and methods of use thereof. In some embodiments, the compounds are BRAF or CRAF inhibitors. In some embodiments, the compounds are useful for the treatment of cancers driven by oncogenic forms of RAS or BRAF. In some embodiments, the compounds inhibit both BRAF and CRAF isoforms. In some other embodiments, the compounds inhibit both RAF protomers present in signaling BRAF/BRAF homodimers and both protomers present in signaling BRAF/CRAF heterodimers. In some other embodiments, the compounds inhibit ARAF, BRAF, and CRAF present in signaling homodimers or heterodimers.

In an embodiment, the present disclosure provides a compound represented by Formula I:

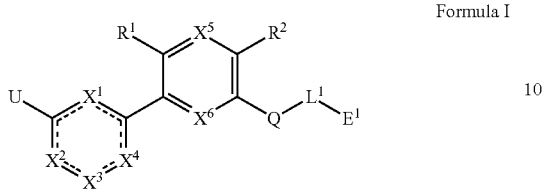

Formula I or a pharmaceutically acceptable salt, enantiomer, stereoisomer, or tautomer thereof, wherein:
  each of $X^1$ and $X^4$ is independently selected from $CR^3$ and N;
  $X^2$ is selected from the group consisting of N, CH, C=O, C—O-$L^2$-$E^2$, C-$L^2$-$E^2$, C—N($R^4$)-$L^2$-$E^2$, and N-$L^2$-$E^2$;
  $X^3$ is selected from the group consisting of CH, C-$L^3$-$E^3$, C—O-$L^3$-$E^3$, C—N($R^4$)-$L^3$-$E^3$, C=O, N, and N-$L^3$-$E^3$;
  provided that not more than two of $X^1$, $X^2$, $X^3$, and $X^4$ are N;
  when $X^2$ is N, $X^3$ is selected from the group consisting of CH, C-$L^3$-$E^3$, C—O-$L^3$-$E^3$, C—N($R^4$)-$L^3$-$E^3$, and N;
  when $X^3$ is N, $X^2$ is selected from the group consisting of N, CH, C—O-$L^2$-$E^2$, C-$L^2$-$E^2$, and C—N($R^4$)-$L^2$-$E^2$;
  when $X^2$ is C=O, $X^3$ is N-$L^3$-$E^3$;
  when $X^3$ is C=O, $X^2$ is N-$L^2$-$E^2$;
  $X^5$ is independently selected from the group consisting of CH, and N;
  $X^6$ is independently selected from the group consisting of CH, and CF;
  $L^1$ is selected from the group consisting of a direct bond and optionally substituted $C_1$-$C_6$alkyl, wherein the optionally substituted substituent, at each occurrence, is $(E^{11})_m$;
  $L^2$ is selected from the group consisting of a direct bond and optionally substituted $C_1$-$C_6$alkyl, wherein the optionally substituted substituent, at each occurrence, is $(E^{21})_p$;
  $L^3$ is selected from the group consisting of a direct bond and optionally substituted $C_1$-$C_6$alkyl, wherein the optionally substituted substituent, at each occurrence, is $(E^{31})_p$;
  Q is selected from the group consisting of —NH—C(O)— and —C(O)—NH—;
  $E^1$ is selected from the group consisting of H, alkoxy, cyano, haloalkoxy, halogen,
    optionally substituted alkyl wherein the optionally substituted substituent, at each occurrence, is independently selected from the group consisting of alkyl, alkoxy, amine, haloalkyl, haloalkoxy, halogen, hydroxy, and cyano,
    optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
    optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl, and heterocyclyl, wherein
      the alkyl substituent is independently optionally substituted, at each occurrence, with a substituent selected from the group consisting of cycloalkyl, cyano, alkoxy, and aminoalkyl,
      the cycloalkyl substituent is independently optionally substituted, at each occurrence, with a substituent selected from the group consisting of cycloalkyl, cyano, alkoxy, and aminoalkyl, and
      the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
    optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
      the alkyl substituent is independently optionally substituted, at each occurrence, with a substituent selected from the group consisting of cycloalkyl, cyano, alkoxy, and aminoalkyl,
      the cycloalkyl substituent is independently optionally substituted, at each occurrence, with a substituent selected from the group consisting of cycloalkyl, cyano, alkoxy, and aminoalkyl, and
      the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
    optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;
  $E^{11}$, at each occurrence, is independently selected from the group consisting of H, alkyl, cycloalkyl, alkoxy, cyano, haloalkoxy, haloalkyl, hydroxy, hydroxyalkyl, and halogen;
  or wherein two occurrences of $E^{11}$ taken together with the carbon atom to which they are attached form a cycloalkyl or a heterocyclyl ring having from 3 to 6 atoms in the ring structure;
  $E^2$ is selected from the group consisting of hydroxy, alkoxy, alkoxyalkyl, cyano, sulfonyl, H, alkyl, amine, amide, acyl, haloalkoxy, haloalkyl, and
  optionally substituted heterocyclyl wherein the optionally substituted substituent, at each occurrence, is independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

U is an optionally substituted heteroaryl, wherein the optionally substituted substituent, at each occurrence, is independently selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl$(CH_2)_m$NH—; wherein the optionally substituted heterocyclyl or heterocyclyl$(CH_2)_m$NH—, at each occurrence, is independently optionally substituted with one or more occurrences of $R^9$;

$R^1$ is selected from the group consisting of H, alkyl, alkoxy, haloalkyl, haloalkoxy, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each occurrence of p is independently 0, 1, or 2; and each occurrence of m is independently 0, 1, 2, 3, or 4; with the proviso that when $X^1$ and $X^2$ are N, each of $X^5$ and $X^6$ is independently selected from CH and CF, $X^4$ is $CR^3$, $R^3$ is selected from H and alkyl, $X^3$ is $C-L^3-E^3$, and $L^3$ is a direct bond, $E^3$ is not morpholinyl; or when $X^1$ and $X^4$ are N, each of $X^5$ and $X^6$ is independently selected from CH, and CF, $X^2$ is $C-L^2-E^2$, $L^2$ is a direct bond, $E^2$ is selected from H and alkyl, $X^3$ is $C-L^3-E^3$, and $L^3$ is a direct bond, $E^3$ is not morpholinyl; or when $X^2$ is selected from $C—O-L^2-E^2$ and $C—N(R^4)-L^2-E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $X^3$ is selected from $C—O-L^3-E^3$ and $C—N(R^4)-L^3-E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl;

when $X^6$ is CH, $X^5$ is CH or CF, $X^4$ is $CR^3$, $X^3$ is N, Q is —C(O)NH—, $L^1$ is direct bond, and $E^1$ is selected from the group consisting of $C_3$-$C_8$ cycloalkyl, $C_2$-$C_8$ heterocyclyl, $C_6$-$C_{14}$ aryl, and $C_1$-$C_9$ heteroaryl, $X^2$ is not $C—N(R^4)-L^2-E^2$; or when Q is —C(O)—NH— and $L^1$ is direct bond, $E^1$ is not H; or when Q is —NH—C(O)—, $L^1$-$E^1$ is not unsubstituted methyl; or when $X^3$ is N, $X^1$ is CH or N, $X^4$ is CH, $X^5$ and $X^6$ are CH, $X^2$ is CH or $C—NH_2$, and Q is —C(O)—NH—, then $L^1$-$E^1$ is not alkyl substituted with amine.

In another embodiment, described herein is a pharmaceutical composition comprising a compound described herein (e.g., a compound of the disclosure as described herein) and a pharmaceutically acceptable carrier or excipient.

In another embodiment, described herein is a method of treating a cancer in a patient in need thereof, comprising administering to the patient a therapeutically effective amount of a compound described herein (e.g., a compound of the disclosure as described herein).

In another embodiment, described herein is a method of treating a disorder selected from the group consisting of histiocytosis, melanoma, multiple myeloma, thyroid cancer, ovarian cancer, colorectal cancer, colon cancer, pancreatic cancer, lung cancer, bladder cancer, gastrointestinal stromal tumors, solid tumors, brain cancers, gliomas, glioblastomas, astrocytomas, blood-borne cancers, hairy cell leukemia, acute myelogenous leukemia (AML), and other cancers caused by activation of the RAS→RAF→MEK→ERK signaling pathway in a patient in need thereof, comprising administering to the patient a therapeutically effective amount of a compound described herein (e.g., a compound of the disclosure as described herein).

DETAILED DESCRIPTION

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The definitions set forth in this application are intended to clarify terms used throughout this application.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present disclosure.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used herein, the singular forms "a", "an", and "the" encompass plural references unless the context clearly indicates otherwise.

As used herein, the term "herein" means the entire application.

As used herein, "deuterated" mean that at least one hydrogen atom is replaced by deuterium. In any sample of a deuterated compound, some discrete molecules of the compound will likely have hydrogen, rather than deuterium, at the specified position. However, the percent of molecules of the deuterated compound which have deuterium at the specified position will be much greater than would naturally occur. The deuterium at the deuterated position is enriched.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the disclosed compounds can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure result.

As used herein, the term "optionally substituted" refers to the replacement of one to six hydrogen atoms in a given structure with the radical of a specified substituent including, but not limited to: hydroxyl, hydroxyalkyl, alkoxy, halogen, alkyl, aryl, cycloalkyl, heterocyclyl, amino, aminoalkyl, cyano, haloalkyl, haloalkoxy, —OC(=O)—CH$_2$—Oalkyl. Preferably, "optionally substituted" refers to the replacement of one to four hydrogen atoms in a given structure with the substituents mentioned above. More preferably, one to three hydrogen atoms are replaced by the substituents as mentioned above. It is understood that the substituent can be further substituted.

As used herein, the term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched, and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms.

Substituents can include any substituents described herein, for example, such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a heteroaralkyl, or an aromatic or heteroaromatic moiety. It will be understood by those skilled in the art that substituents can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN, and the like. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to a straight chained or branched non-aromatic hydrocarbon which is completely saturated. Typically, a straight chained or branched alkyl group has from 1 to about 20 carbon atoms, preferably from 1 to about 10, e.g., may be C$_1$-C$_{10}$alkyl or e.g., C$_1$-C$_6$alkyl unless otherwise defined. Examples of straight chained and branched alkyl groups include, but are not limited to, methyl, ethyl, 1-propyl (n-propyl), 2-propyl, n-butyl, sec-butyl, tertbutyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. Moreover, the term "alkyl" used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. The "alkyl" group may be optionally substituted.

The term "C$_x$-C$_y$" when used in conjunction with a chemical moiety, such as, acyl, acyloxy, alkyl, alkenyl, alkynyl, or alkoxy is meant to include groups that contain from x to y carbons in the chain. For example, the term "C$_x$-C$_y$" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal.

As used herein, the term "hydrocarbyl" refers to a group that is bonded through a carbon atom that does not have a =O or =S substituent, and typically has at least one carbon-hydrogen bond and a primarily carbon backbone but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof. The "hydrocarbyl" group may be optionally substituted.

As described herein, Q may be either an amide linkage —NH—C(O)— or an inverse amide linkage —C(O)—NH—. The amide linkage —NH—C(O)— occurs when —NH of the amide linkage is directly attached to a $R^1$- and $R^2$-containing ring as described herein (e.g., in a compound of Formula I, I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T). The inverse amide linkage —C(O)—NH— is defined wherein the —NH of the inverse amide linkage is directly attached to $E^1$ as described herein (e.g., in a compound of Formula I, I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T).

As used herein, the term "alkoxy" refers to a straight or branched, saturated aliphatic (alkyl) hydrocarbon radical bonded to an oxygen atom that is attached to a core structure. Preferably, alkoxy groups have one to six carbon atoms, i.e., may be $C_1$-$C_6$ alkoxy. Examples of alkoxy groups include but are not limited to methoxy, ethoxy, propoxy, isopropoxy, butoxy, isobutoxy, tert-butoxy, pentoxy, 3-methyl butoxy and the like. The "alkoxy" group may be optionally substituted.

As used herein, the term "alkoxyalkyl" refers to an alkyl group (as defined above) substituted with an alkoxy group and may be represented by the general formula alkyl-O-alkyl. Examples of alkoxyalkyl groups include but are not limited to methyl-O-ethylene-, ethyl-O-ethylene-. The "alkoxyalkyl" group may be optionally substituted.

As used herein, the term "haloalkyl" refers to alkyl group (as defined above) is substituted with one or more halogens. A monohaloalkyl radical, for example, may have a chlorine, bromine, iodine, or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl, and the like. The "haloalkyl" group may be optionally substituted.

As used herein, the term "haloalkoxy" refers to radicals wherein one or more of the hydrogen atoms of the alkoxy group are substituted with one or more halogens. Representative examples of "haloalkoxy" groups include, but not limited to, difluoromethoxy (—OCHF$_2$), trifluoromethoxy (—OCF$_3$), or trifluoroethoxy (—OCH$_2$CF$_3$). The "haloalkoxy" group may be optionally substituted.

As used herein, the term "aryl" includes substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings (fused rings) wherein at least one of the rings is aromatic. e.g., the other cyclic rings can be cycloalkyls, cycloalkenyls, cycloalkynyls, aryls, heteroaryls, and/or heterocyclyls. The term "fused" means that the second ring is attached or formed by having two adjacent atoms in common with the first ring. The term "fused" is equivalent to the term "condensed". Examples of aryl groups include but are not limited to phenyl, naphthyl, phenanthryl, phenol, aniline, or indanyl and the like. Unless otherwise specified, all aryl groups described herein may be optionally substituted.

As used herein, the terms "polycyclyl", "polycycle", and "polycyclic" refer to two or more rings (e.g., cycloalkyls, cycloalkenyls, cycloalkynyls, aryls, heteroaryls, and/or heterocyclyls) in which one or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

As used herein, the term "acyl" refers to a group —C(=O)—$R^w$ wherein $R^w$ is optionally substituted alkyl. Examples of "acyl" include, but are not limited to, instances where $R^w$ is $C_1$-$C_{10}$alkyl ($C_1$-$C_{10}$acyl) or $C_1$-$C_6$alkyl ($C_1$-$C_6$acyl). In some embodiments, each occurrence of the optionally substituted substituent is independently selected from the group consisting of H, OH, alkoxy, cyano, F, and amino. Additional examples of "acyl" include —C(=O)—CH$_3$, —C(=O)—CH$_2$—CH$_3$, —C(=O)—CH$_2$—CH$_2$—CH$_3$, or —C(=O)—CH(CH$_3$)$_2$.

As used herein, the term "carbamoyl" refers to a group represented by

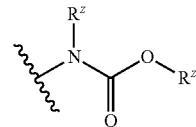

wherein $R^z$ independently represents a hydrogen or optionally substituted hydrocarbyl group, or $R^z$ groups taken together with the —N—C(=O)—O— moiety to which they are attached complete a heterocycle having from 5 to 8 atoms in the ring structure which may be optionally substituted.

As used herein, the term "formyl" refers to a group —C(=O)H.

As used herein, the terms "amine" and "amino" refer to both unsubstituted and substituted amines and salts thereof, e.g., a moiety that can be represented by:

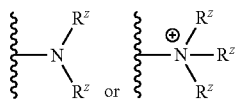

wherein $R^z$ independently represent a hydrogen or optionally substituted hydrocarbyl group, or $R^z$ groups are taken together with the N atom to which they are attached complete a heterocycle having from 4 to 8 atoms in the ring structure which may be optionally substituted.

As used herein, the terms "amide" and "amido" each refer to a group represented by

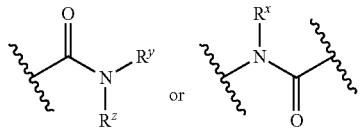

wherein $R^x$, $R^y$, and $R^z$ each independently represents a hydrogen or optionally substituted hydrocarbyl group, or $R^y$ and $R^z$ are taken together with the N atom to which they are attached complete a heterocycle having from 4 to 8 atoms in the ring structure which may be optionally substituted.

As used herein, the term "amidine" refers to a group represented by

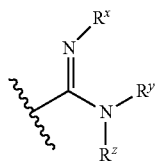

wherein $R^x$, $R^y$, and $R^z$ each independently represents a hydrogen or optionally substituted hydrocarbyl group, or $R^y$, and $R^z$ groups are taken together with the N atom to which they are attached complete a heterocycle having from 4 to 8 atoms in the ring structure which may be optionally substituted.

As used herein, the term "urea" refers to a group represented by

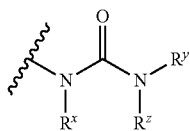

wherein $R^x$, $R^y$, and $R^z$ each independently represents a hydrogen or optionally substituted hydrocarbyl group, or $R^y$ and $R^z$ are taken together with the N atom to which they are attached complete a heterocycle having from 4 to 8 atoms in the ring structure which may be optionally substituted.

As used herein, "alkylamino" and "alkylamine" refer to an amino group, as defined above, substituted with at least one alkyl group.

As used herein, the term "aminoalkyl" refers to an alkyl group substituted with an amino group.

As used herein, the term "amidoalkyl" refers to an alkyl group substituted with an amido group.

As used herein, the term "cyanoalkyl" refers to an alkyl group substituted with a cyano group.

As used herein, the term "alkylthio" refers to a thiol group substituted with an alkyl group and may be represented by the general formula alkyl-S—.

As used herein, the term "thioalkyl" refers to an alkyl group substituted with a thiol group.

As used herein, the term "hydroxyalkyl" refers to an alkyl group substituted with a hydroxy group.

As used herein, the term "cycloalkyl" alone or in combination with other term(s) refers to a cyclic hydrocarbon which is completely saturated. "Cycloalkyl" includes monocyclic, bicyclic, and tricyclic rings. Typically, a monocyclic cycloalkyl group has from 3 to about 10 carbon atoms, more typically 3 to 8 carbon atoms (e.g., $C_3$-$C_{10}$cycloalkyl or e.g., $C_3$-$C_6$cycloalkyl unless otherwise defined. Examples of monocyclic cycloalkyls include cyclopropyl, cyclobutyl, cyclopentyl, cyclohexyl, cycloheptyl and the like. The second ring of a bicyclic cycloalkyl or, the second or third rings of a tricyclic cycloalkyl, may be selected from saturated, unsaturated and aromatic rings. Cycloalkyl includes bicyclic and tricyclic molecules in which one, two or three or more atoms are shared between the two rings. The term "fused cycloalkyl" refers to a bicyclic or tricyclic cycloalkyl in which each of the rings shares two adjacent atoms with the other ring. The second ring of a fused bicyclic cycloalkyl or, the second or third rings of a fused tricyclic cycloalkyl, may be selected from saturated, unsaturated, and aromatic rings. A "cycloalkenyl" group is a cyclic hydrocarbon containing one or more double bonds. Cycloalkyls can be further substituted with alkyls, alkenyls, alkoxys, alkylthios, aminoalkyls, carbonyl-substituted alkyls, —$CF_3$, —CN, and the like. A cycloalkyl may alternatively be polycyclic with more than two rings. Examples of polycyclic cycloalkyls include bridged, fused, and spirocyclic carbocyclyls.

As used herein, the term "cycloalkylalkyl" refers to an alkyl group substituted with a cycloalkyl group.

As used herein, the terms "carbocycle," or "carbocyclic" include bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, 4,5-naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

As used herein, the term "cyano" refers to —CN group.

As used herein, the term "hydroxy" or "hydroxyl" refers to —OH group.

As used herein, the term "halo" or "halogen" alone or in combination with other term(s) means chloro, fluoro, bromo, and iodo.

As used herein, the term "heteroatom" refers an atom of any element other than carbon or hydrogen. Exemplary heteroatoms are nitrogen (N), oxygen (O), sulfur (S), and silicon (Si).

As used herein, the terms "heterocyclyl", "heterocycloalkyl", "heterocycle", and "heterocyclic" refer to a non-aromatic, saturated or partially saturated, including monocyclic, polycyclic (e.g., bicyclic, tricyclic) bridged, or fused, ring system of 3 to 15 member having at least one heteroatom or heterogroup selected from O, N, S, S(O), S(O)$_2$, NH or C(O) with the remaining ring atoms being independently selected from the group consisting of carbon, oxygen, nitrogen, and sulfur. Examples of "heterocyclyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, 2-azabicyclo[2.2.2]octanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocyclyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl and N-oxides thereof. More preferably, "heterocyclyl" includes azetidinyl, pyrrolidinyl, morpholinyl and piperidinyl. All heterocyclyl are optionally substituted by one or more aforesaid groups.

As used herein, the term "heteroaryl" refers to substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also refers to substituted or unsubstituted aromatic or partly aromatic ring systems containing at least one heteroatom and having two or more cyclic rings (bicyclic, tricyclic, or polycyclic), containing 8 to 20 ring atoms, suitably 5 to 10 ring atoms, which may be linked covalently, or fused in which two or more atoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. The rings may contain an N or S atom, wherein the N or S atom is optionally oxidized, or the N atom is optionally quaternized. All heteroaryls are optionally substituted. Any suitable ring position of the heteroaryl moiety may be covalently linked to a defined chemical structure. Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, thiadiazolyl, triazolyl, pyridyl, pyrimidinyl, pyrazinyl, pyridazinyl, triazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, alpha-carboline, indolizinyl, benzoisothiazolyl, benzoxazolyl, pyrrolopyridyl, furopyridinyl, purinyl, benzothiadiazolyl, benzoxadiazolyl, benzotriazolyl, benzotriadiazolyl, 7-azaindolyl, 7-azaindazolyl, pyrrolopyridinyl, pyrrolopyrimidinyl, oxazolonepyridinyl, oxazolonepyrimidinyl, imidazolonepyridinyl, imidazolonepyrimidinyl, pyrazolopyridinyl, pyrazolopyrimidinyl, tetrahydronaphthyridinyl, tetrahydropyridolpyriminyl, dihydronaphthyridinonyl, naphthyridinonyl, oxazinanonepyridinyl, oxazinanonepyrimidinyl, carbazolyl, dibenzothienyl, acridinyl and the like.

With respect to $E^1$ as described herein, $E^1$ is not a ring selected from the group consisting of

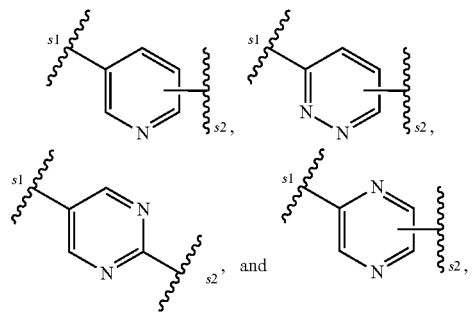

wherein s1 is the site covalently linked to $L^1$; and s2 is the site covalently linked to H or the optionally substituted substituent.

As used herein, the term "sulfonamide" is represented by:

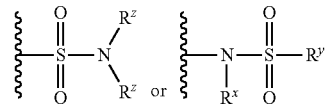

wherein $R^x$, $R^y$ and $R^z$, at each occurrence, independently represents a hydrogen, optionally substituted hydrocarbyl group, or $R^z$ groups taken together with the N atom to which they are attached complete a heterocycle having from 4 to 8 atoms in the ring structure which may be optionally substituted.

As used herein, the terms "sulfone" or "sulfonyl" refer to the group —$S(O)_2$—$R^{6d}$ wherein $R^{6d}$ represents an optionally substituted hydrocarbyl.

A "combination therapy" is a treatment that includes the administration of two or more therapeutic agents, e.g., a compound of the disclosure and a MAPK pathway inhibitor, to a patient in need thereof.

"Disease," "disorder," and "condition" are used interchangeably herein.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

The MAPK pathway as used herein is the signal transduction pathway comprising RAS→RAF→MEK→ERK.

A "MAPK pathway inhibitor" is an inhibitor of the MAP kinase signaling pathway. Inhibitors of this pathway include RAS inhibitors (e.g., AMG-510, MRTX 849), RAF inhibitors (e.g., dabrafenib, vemurafenib, LY3009120, encorafenib), MEK inhibitors (e.g., trametinib, binimetinib, selumetinib, cobimetinib), and ERK inhibitors (e.g., ulixertinib, SCH772984, LY3214996, ERAS-007). The terms "MAPK pathway inhibitor" and "MAPK kinase inhibitor are used interchangeably herein.

"Pharmaceutically or pharmacologically acceptable" include molecular entities and compositions that do not produce an adverse, allergic, or other untoward reaction when administered to an animal, or a human, as appropriate.

For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbol "R" or "S," depending on the configuration of substituents around the stereogenic carbon atom, but the skilled artisan will recognize that a structure may denote a chiral center implicitly. These compounds may also be designated by "(+)" and "(−)" based on their optical rotation properties. The presently described compounds encompasses various stereoisomers of these compounds and mixtures thereof. Mixtures of enantiomers or diastereomers may be designated by the symbol "(±)" in nomenclature, but the skilled artisan will recognize that a structure may denote a chiral center implicitly.

In the present specification, the term "therapeutically effective amount" means the amount of the subject compound that will elicit the biological or medical response of a tissue, system or animal, (e.g., mammal or human) that is being sought by the researcher, veterinarian, medical doctor or other clinician. The compounds described herein are administered in therapeutically effective amounts to treat a disorder.

"Treating" includes any effect, e.g., lessening, reducing, modulating, or eliminating, that results in the improvement of the condition, disease, disorder, and the like.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into the disclosed compounds include isotopes of hydrogen, carbon, nitrogen, oxygen, phosphorus, sulfur, fluorine, and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Individual enantiomers and diastereomers of the disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations and may involve the use of chiral auxiliaries. For examples, see Carreira and Kvaerno, *Classics in Stereoselective Synthesis*, Wiley-VCH: Weinheim, 2009.

As used herein, "compounds of the disclosure", comprise compounds of Formula I, Formula I-A, Formula I-AA, Formula I-AB, Formula I-AC, Formula I-B, Formula I-BA, Formula I-C, Formula I-CA, Formula I-D, Formula I-DA, Formula I-DB, Formula I-E, Formula I-EA, Formula I-EB, Formula I-F, Formula I-FA, Formula I-G, Formula I-GA, Formula I-H, Formula I-HA, Formula I-J, Formula I-JA, Formula I-K, Formula I-KA, Formula I-L, Formula I-LA, Formula I-M, Formula I-N, Formula I-NA, Formula I-O, Formula I-OA, Formula I-P, Formula I-PA, Formula I-Q, Formula I-QA, Formula I-R, Formula I-RA, Formula I-S, Formula I-SA-i, Formula I-SA-ii, and Formula I-T, or a pharmaceutically acceptable salt, enantiomer, stereoisomer, or tautomer thereof.

Compounds

In an embodiment, provided herein is a compound represented by Formula I:

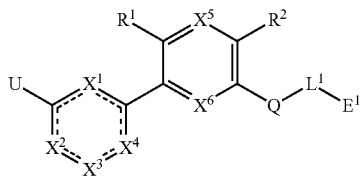

Formula I or a pharmaceutically acceptable salt, enantiomer, stereoisomer, or tautomer thereof,
wherein:
- each of $X^1$ and $X^4$ is independently selected from $CR^3$ and N;
- $X^2$ is selected from the group consisting of N, CH, C=O, C—O-$L^2$-$E^2$, C-$L^2$-$E^2$, C—N($R^4$)-$L^2$-$E^2$, and N-$L^2$-$E^2$;
- $X^3$ is selected from the group consisting of CH, C-$L^3$-$E^3$, C—O-$L^3$-$E^3$, C—N($R^4$)-$L^3$-$E^3$, C=O, N, and N-$L^3$-$E^3$;
    - provided that not more than two of $X^1$, $X^2$, $X^3$, and $X^4$ are N;
    - when $X^2$ is N, $X^3$ is selected from the group consisting of CH, C-$L^3$-$E^3$, C—O-$L^3$-$E^3$, C—N($R^4$)-$L^3$-$E^3$, and N;
    - when $X^3$ is N, $X^2$ is selected from the group consisting of N, CH, C—O-$L^2$-$E^2$, C-$L^2$-$E^2$, and C—N($R^4$)-$L^2$-$E^2$;
    - when $X^2$ is C=O, $X^3$ is N-$L^3$-$E^3$;
    - when $X^3$ is C=O, $X^2$ is N-$L^2$-$E^2$;
- $X^5$ is independently selected from the group consisting of CH, CF, and N;
- $X^6$ is independently selected from the group consisting of CH, and CF;
- $L^1$ is selected from the group consisting of a direct bond and optionally substituted $C_1$-$C_6$alkyl, wherein the optionally substituted substituent, at each occurrence, is $(E^{11})_m$;
- $L^2$ is selected from the group consisting of a direct bond and optionally substituted $C_1$-$C_6$alkyl, wherein the optionally substituted substituent, at each occurrence, is $(E^{21})_p$;
- $L^3$ is selected from the group consisting of a direct bond and optionally substituted $C_1$-$C_6$alkyl, wherein the optionally substituted substituent, at each occurrence, is $(E^{31})_p$;
- Q is selected from the group consisting of —NH—C(O)— and —C(O)—NH—;
- $E^1$ is selected from the group consisting of H, alkoxy, cyano, haloalkoxy, halogen,
    - optionally substituted alkyl wherein the optionally substituted substituent, at each occurrence, is independently selected from the group consisting of alkyl, alkoxy, amine, haloalkyl, haloalkoxy, halogen, hydroxy, and cyano,
    - optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
    - optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl, and heterocyclyl, wherein
        - the alkyl substituent is independently optionally substituted, at each occurrence, with a substituent selected from the group consisting of cycloalkyl, cyano, alkoxy, and aminoalkyl,
        - the cycloalkyl substituent is independently optionally substituted, at each occurrence, with a substituent selected from the group consisting of cycloalkyl, cyano, alkoxy, and aminoalkyl, and
        - the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
    - optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
        - the alkyl substituent is independently optionally substituted, at each occurrence, with a substituent selected from the group consisting of cycloalkyl, cyano, alkoxy, and aminoalkyl,
        - the cycloalkyl substituent is independently optionally substituted, at each occurrence, with a substituent selected from the group consisting of cycloalkyl, cyano, alkoxy, and aminoalkyl, and
        - the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
    - optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;
- $E^{11}$, at each occurrence, is independently selected from the group consisting of H, alkyl, cycloalkyl, alkoxy, cyano, haloalkoxy, haloalkyl, hydroxy, hydroxyalkyl, and halogen;
- or wherein two occurrences of $E^{11}$ taken together with the carbon atom to which they are attached form a cycloalkyl or a heterocyclyl ring having from 3 to 6 atoms in the ring structure;
- $E^2$ is selected from the group consisting of hydroxy, alkoxy, alkoxyalkyl, cyano, sulfonyl, H, alkyl, amine, amide, acyl, haloalkoxy, haloalkyl, and
- optionally substituted heterocyclyl wherein the optionally substituted substituent, at each occurrence, is independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;
or wherein two occurrences of $E^{21}$ taken together with the carbon atom to which they are attached form a cycloalkyl or a heterocyclyl ring having from 3 to 6 atoms in the ring structure;
$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone,
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone,
optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and
optionally substituted cycloalkyl, wherein the optionally substituted substituent, at each occurrence, is independently selected from the group consisting of alkyl, alkoxy, haloalkyl, haloalkoxy, halogen, hydroxy, and cyano;
$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;
or wherein two occurrences of $E^3$ taken together with the carbon atom to which they are attached form a cycloalkyl or a heterocyclyl ring having from 3 to 6 atoms in the ring structure;
U is an optionally substituted heteroaryl, wherein the optionally substituted substituent, at each occurrence, is independently selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl$(CH_2)_m$NH—; wherein the optionally substituted heterocyclyl or heterocyclyl$(CH_2)_m$NH—, at each occurrence, is independently optionally substituted with one or more occurrences of $R^9$;
$R^1$ is selected from the group consisting of H, alkyl, alkoxy, haloalkyl, haloalkoxy, cyano, and halogen;
$R^2$ is selected from the group consisting of H and F;
$R^3$, at each occurrence, is independently selected from the group consisting of H, alkyl, and halogen;
$R^4$, at each occurrence, is independently selected from H and alkyl;
$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;
each occurrence of p is independently 0, 1, or 2; and
each occurrence of m is independently 0, 1, 2, 3, or 4; with the proviso that
when $X^1$ and $X^2$ are N, each of $X^5$ and $X^6$ is independently selected from CH and CF, $X^4$ is $CR^3$, $R^3$ is selected from H and alkyl, $X^3$ is C-$L^3$-$E^3$, and $L^3$ is a direct bond, $E^3$ is not morpholinyl; or
when $X^1$ and $X^4$ are N, each of $X^5$ and $X^6$ is independently selected from CH, and CF, $X^2$ is C-$L^2$-$E^2$, $L^2$ is a direct bond, $E^2$ is selected from H and alkyl, $X^3$ is C-$L^3$-$E^3$, and $L^3$ is a direct bond, $E^3$ is not morpholinyl; or
when $X^2$ is selected from C—O-$L^2$-$E^2$ and C—N($R^4$)-$L^2$-$E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or
when $X^3$ is selected from C—O-$L^3$-$E^3$ and C—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or
when $L^1$ is direct bond, then $E^1$ is not N-bound heterocyclyl;
when $X^6$ is CH, $X^5$ is CH or CF, $X^4$ is $CR^3$, $X^3$ is N, Q is —C(O)NH—, $L^1$ is direct bond, and $E^1$ is selected from the group consisting of $C_3$-$C_8$ cycloalkyl, $C_2$-$C_8$ heterocyclyl, $C_6$-$C_{14}$ aryl, and $C_1$-$C_9$ heteroaryl, $X^2$ is not C—N($R^4$)-$L^2$-$E^2$; or
when Q is —C(O)—NH— and $L^1$ is direct bond, E is not H; or
when Q is —NH—C(O)—, $L^1$-$E^1$ is not unsubstituted methyl; or
when $X^3$ is N, $X^1$ is CH or N, $X^4$ is CH, $X^5$ and $X^6$ are CH, $X^2$ is CH or C—$NH_2$, and Q is —C(O)—NH—, then $L^1$-$E^1$ is not alkyl substituted with amine.

In some embodiments, U is an optionally substituted heteroaryl, wherein the optionally substituted substituent, at each occurrence, is independently selected from the group consisting of acyl, carbamoyl, formyl, amide, alkoxy, alkoxyalkyl, urea, amine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl$(CH_2)_m$NH—; wherein the optionally substituted heterocyclyl or heterocyclyl$(CH_2)_m$NH—, at each occurrence, is independently optionally substituted with one or more occurrences of $R^9$.

In some embodiments, U is

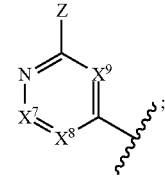

wherein $X^7$, $X^8$, and $X^9$ are independently selected from $CR^3$ and N, provided that not more than one of $X^7$, $X^8$ and $X^9$ is N; Z is —NHC(O)$R^6$, —NHC(O)O$R^6$, or —C(O)NH$R^7$, wherein
$R^6$, at each occurrence, is independently selected from the group consisting of H, alkyl, cycloalkyl, and heterocyclyl, wherein
each of alkyl and cycloalkyl is optionally substituted with one or more independent occurrences of $R^8$; and
the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and $R^7$ is selected from the group consisting of H, alkyl, cycloalkyl, and heterocyclyl, wherein each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and $R^8$ is selected from the group consisting of alkyl, cycloalkyl, and heterocyclyl, wherein each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, U is

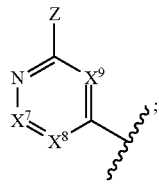

wherein $X^7$, $X^8$, and $X^9$ are independently selected from $CR^3$ and N, provided that not more than one of $X^7$, $X^8$ and $X^9$ is N; Z is —NHC(O)$R^6$, wherein $R^6$, at each occurrence, is independently selected from the group consisting of H, alkyl, cycloalkyl, and heterocyclyl, wherein each of alkyl and cycloalkyl is optionally substituted with one or more independent occurrences of $R^8$; and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and $R^8$ is selected from the group consisting of alkyl, cycloalkyl, and heterocyclyl, wherein each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, U is

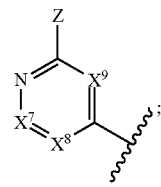

wherein $X^7$, $X^8$, and $X^9$ are independently selected from $CR^3$ and N, provided that not more than one of $X^7$, $X^8$ and $X^9$ is N; Z is —NHC(O)$R^6$, wherein $R^6$ is methyl, ethyl, or iso-propyl. In some embodiments, Z is —NHC(O)$R^6$, wherein $R^6$ is methyl. In some embodiments, Z is —NHC(O)$R^6$, wherein $R^6$ is cyclopropyl or cyclobutyl. In some embodiments, Z is —NHC(O)$R^6$, wherein $R^6$ is cyclopropyl. In some embodiments, Z is —NHC(O)$R^6$, wherein $R^6$ is H. In some embodiments, Z is —NHC(O)$R^6$, wherein $R^6$ is $CH_2N(R^4)_2$. In some embodiments, Z is —NHC(O)$R^6$, wherein $R^6$ is $CH_2$—CN. In some embodiments, Z is —NHC(O)$R^6$, wherein $R^6$ is $CH_2$—OH. In some embodiments, Z is —NHC(O)$R^6$, wherein $R^6$ is $CH_2$—OMe.

In some embodiments, U is

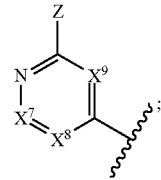

wherein $X^7$, $X^8$, and $X^9$ are independently selected from $CR^3$ and N, provided that not more than one of $X^7$, $X^8$ and $X^9$ is N; Z is —C(O)NH$R^7$, wherein $R^7$ is selected from the group consisting of H, alkyl, cycloalkyl, and heterocyclyl, wherein each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, Z is selected from the group consisting of acyl, carbamoyl, formyl, amide, alkoxy, alkoxyalkyl, urea, amine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)$_m$NH—, wherein the optionally substituted substituent on the heterocyclyl ring, at each occurrence, is independently $R^9$.

In some embodiments, Z is —C(O)NH$R^7$. In some embodiments, Z is —C(O)NH$R^7$ wherein $R^7$ is H. In some embodiments, Z is —C(O)NH$R^7$ wherein $R^7$ is alkyl. In some embodiments, Z is —C(O)NH$R^7$ wherein $R^7$ is methyl. In some embodiments, Z is —C(O)NH$R^7$ wherein $R^7$ is ethyl. In some embodiments, Z is —C(O)NH$R^7$ wherein $R^7$ is iso-propyl. In some embodiments, Z is —NH$_2$. In some embodiments, Z is carbamoyl. In some embodiments, Z is formyl. In some embodiments, Z is methylamino. In some embodiments, Z is ethylamino. In some embodiments, Z is beta-hydroxyethylamino. In some embodiments, Z is beta-methoxyethylamino. In some embodiments, Z is heterocyclyl. In some embodiments, Z is oxetanyl, tetrahydrofuranyl, or tetrahydropyranyl. In some embodiments, Z is morpholinyl. In some embodiments, Z is heterocyclylalkylamino. In some embodiments, Z is oxetanylalkylamino. In some embodiments, Z is azetidinylalkylamino. In some embodiments, Z is tetrahydropyranylalkylamino. In some embodiments, Z is heteroaryl. In some embodiments, Z is pyrazolyl. In some embodiments, Z is oxazolyl. In some embodiments, Z is oxadiazolyl. In some embodiments, Z is thiazolyl. In some embodiments, Z is selected from the group consisting of H, alkyl, and cycloalkyl. In some embodiments, Z is H. In some embodiments, Z is methyl. In some embodiments, Z is ethyl. In some embodiments, Z is iso-propyl. In some embodiments, Z is cyclopropyl.

In some embodiments, U is

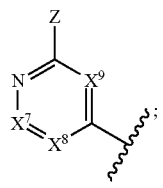

wherein $X^7$, $X^8$, and $X^9$ are independently selected from $CR^3$ and N, provided that not more than one of $X^7$, $X^8$ and $X^9$ is N; Z is —NHC(O)OR$^6$, wherein
  $R^6$, at each occurrence, is independently selected from the group consisting of H, alkyl, cycloalkyl, and heterocyclyl, wherein
    each of alkyl and cycloalkyl is optionally substituted with one or more independent occurrences of $R^8$; and
    the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and
  $R^8$ is selected from the group consisting of alkyl, cycloalkyl, and heterocyclyl, wherein
    each of alkyl and cycloalkyl is optionally substituted with one or more occurrences of a substituent independently selected from the group consisting of alkyl, cyano, amino, hydroxy, alkoxy, and heterocyclyl, and
    the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, U is

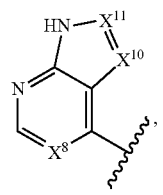

wherein each of $X^8$, $X^{10}$, and $X^{11}$ is independently selected from CH and N.

In some embodiments, U is

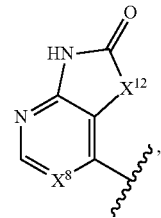

wherein $X^8$ is independently selected from CH and N; $X^{12}$ is $CH_2$, CHF, $CF_2$, $CH(CH_3)$, $C(CH_3)_2$, $NR^6$, or O.

In some embodiments, the compound is represented by Formula I-A:

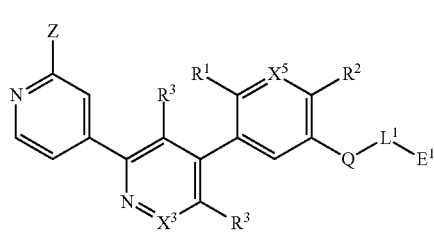

Formula I-A or a pharmaceutically acceptable salt, enantiomer, stereoisomer, or tautomer thereof,
wherein:
  $X^3$ is selected from the group consisting of CH, C-L$^3$-E$^3$, C—O-L$^3$-E$^3$, C—N(R$^4$)-L$^3$-E$^3$, and N;
  $X^5$ is selected from the group consisting of N, CH, and CF;
  $L^3$ is selected from the group consisting of a direct bond and optionally substituted $C_1$-$C_6$alkyl, wherein the optionally substituted substituent, at each occurrence, is $(E^{31})_p$;
  Q is selected from the group consisting of —NH—C(O)— and —C(O)—NH—;
  $L^1$ is selected from the group consisting of a direct bond and optionally substituted $C_1$-$C_6$alkyl, wherein the optionally substituted substituent, at each occurrence, is $(E^{11})_m$;
  $E^1$ is selected from the group consisting of H, alkoxy, cyano, haloalkoxy, halogen,
    optionally substituted alkyl wherein the optionally substituted substituent, at each occurrence, is independently selected from the group consisting of alkyl, alkoxy, amine, haloalkyl, haloalkoxy, halogen, hydroxy, and cyano,
    optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
    optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1, or 2; and each m is independently 0, 1, 2, 3, or 4; with the proviso that when $X^3$ is selected from C—O-L$^3$-E$^3$ and C—N(R$^4$)-L$^3$-E$^3$, $R^4$ is H, and each L$^3$ is a direct bond, each E$^3$ is not a 6-, 7-, 8-, 9-, 10- or 11-membered bicyclic ring containing 0, 1, 2, 3 or 4 atoms selected from N, O, and S; or when L$^1$ is direct bond, then E$^1$ is not N-bound heterocyclyl; or when Q is —C(O)—NH— and L$^1$ is direct bond, E$^1$ is not H; or when Q is —NH—C(O)—, L$^1$-E$^1$ is not unsubstituted methyl.

In some embodiments, the compound is represented by Formula I-AA:

Formula I-AA

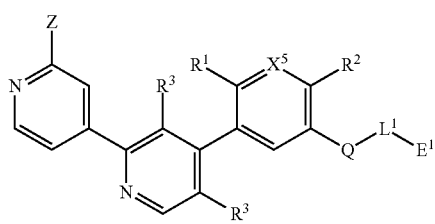

or a pharmaceutically acceptable salt, enantiomer, stereoisomer, or tautomer thereof, wherein:
X⁵ is selected from the group consisting of N, CH, and CF;
Q is selected from the group consisting of —NH—C(O)— and —C(O)—NH—;
L¹ is selected from the group consisting of a direct bond and optionally substituted $C_1$-$C_6$alkyl, wherein the optionally substituted substituent, at each occurrence, is $(E^{11})_m$;
E¹ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when L¹ is a direct bond and E¹ is an optionally substituted heterocyclyl or optionally substituted heteroaryl, the heterocyclyl or heteroaryl is C-bound;
E¹¹, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of E¹¹ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2)_m$NH—, wherein the optionally substituted substituent on the heterocyclyl ring, at each occurrence, is independently R⁹;
R¹ is selected from the group consisting of H, alkyl, alkoxy, haloalkyl, cyano, and halogen;
R² is selected from the group consisting of H and F;
R³, at each occurrence, is independently selected from the group consisting of H, alkyl, and halogen;
R⁹, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and
each m is independently 0, 1, 2, 3, or 4.

In some embodiments, the compound is represented by Formula I-AB:

Formula I-AB

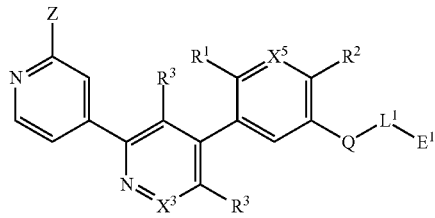

or a pharmaceutically acceptable salt, enantiomer, stereoisomer, or tautomer thereof,
wherein:
X³ is selected from the group consisting of C-L³-E³, C—O-L³-E³, and C—N(R⁴)-L³-E³;
X⁵ is selected from the group consisting of N, CH, and CF;
L³ is selected from the group consisting of a direct bond and optionally substituted $C_1$-$C_6$alkyl, wherein the optionally substituted substituent, at each occurrence, is $(E^{31})_p$;
Q is selected from the group consisting of —NH—C(O)— and —C(O)—NH—;
L¹ is selected from the group consisting of a direct bond and optionally substituted $C_1$-$C_6$alkyl, wherein the optionally substituted substituent, at each occurrence, is $(E^{11})_m$;
E¹ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted monocyclic heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl$(CH_2)_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1, or 2; and each m is independently 0, 1, 2, 3, or 4.

In some embodiments, the compound is represented by Formula I-AC:

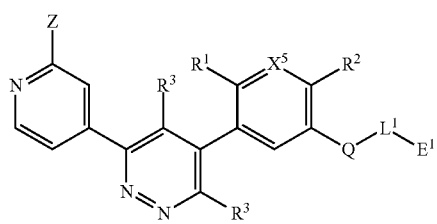

Formula I-AC or a pharmaceutically acceptable salt, enantiomer, stereoisomer, or tautomer thereof, wherein:

$X^5$ is selected from the group consisting of N, CH, and CF;

Q is selected from the group consisting of —NH—C(O)— and —C(O)—NH—;

L$^1$ is selected from the group consisting of a direct bond and optionally substituted C$_1$-C$_6$alkyl, wherein the optionally substituted substituent, at each occurrence, is (E$^{11}$)$_m$;

E$^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
  the alkyl substituent is independently optionally substituted, at each occurrence, with a substituent selected from the group consisting of cycloalkyl, cyano, alkoxy, and aminoalkyl,
  the cycloalkyl substituent is independently optionally substituted, at each occurrence, with a substituent selected from the group consisting of cycloalkyl, cyano, alkoxy, and aminoalkyl, and
  the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, sulfone, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
  the alkyl substituent is independently optionally substituted, at each occurrence, with a substituent selected from the group consisting of cycloalkyl, cyano, alkoxy, and aminoalkyl,
  the cycloalkyl substituent is independently optionally substituted, at each occurrence, with a substituent selected from the group consisting of cycloalkyl, cyano, alkoxy, and aminoalkyl, and
  the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when L$^1$ is a direct bond and E$^1$ is an optionally substituted heterocyclyl or optionally substituted heteroaryl, the heterocyclyl or heteroaryl is C-bound;

E$^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of E$^{11}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl(CH$_2$)$_m$NH—, wherein the optionally substituted substituent on the heterocyclyl ring, at each occurrence, is independently R$^9$;

R$^1$ is selected from the group consisting of H, alkyl, alkoxy, haloalkyl, cyano, and halogen;

R$^2$ is selected from the group consisting of H and F;

R$^3$, at each occurrence, is independently selected from the group consisting of H, alkyl, and halogen;

R$^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-B:

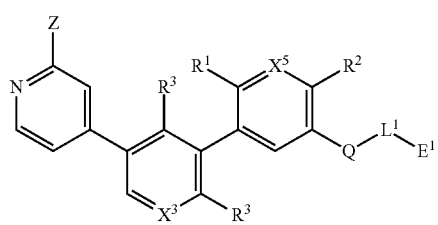

Formula I-B or a pharmaceutically acceptable salt, enantiomer, stereoisomer, or tautomer thereof, wherein:

X$^3$ is selected from the group consisting of CH, C-L$^3$-E$^3$, C—O-L$^3$-E$^3$, C—N(R$^4$)-L$^3$-E$^3$, and N;

X$^5$ is selected from the group consisting of N, CH, and CF;

L$^3$ is selected from the group consisting of a direct bond and optionally substituted C$_1$-C$_6$alkyl, wherein the optionally substituted substituent, at each occurrence, is (E$^{31}$);

Q is selected from the group consisting of —NH—C(O)— and —C(O)—NH—;

L$^1$ is selected from the group consisting of a direct bond and optionally substituted C$_1$-C$_6$alkyl, wherein the optionally substituted substituent, at each occurrence, is (E$^{11}$)$_m$;

E$^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl$(CH_2)_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1 or 2; and each m is independently 0, 1, 2, 3, or 4; with the proviso that when $X^3$ is selected from C—O-$L^3$-$E^3$ and C—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl; or when Q is —C(O)—NH— and $L^1$ is direct bond, $E^1$ is not H; or when Q is —NH—C(O)—, $L^1$-$E^1$ is not unsubstituted methyl; or when $X^3$ is N, $R^3$ is H, $X^5$ and $X^6$ are CH, and Q is —C(O)—NH—, then $L^1$-$E^1$ is not alkyl substituted with amine.

In some embodiments, the compound is represented by Formula I-BA:

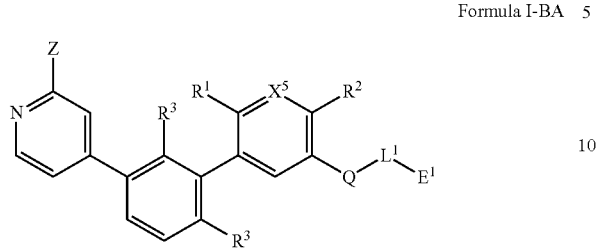

Formula I-BA or a pharmaceutically acceptable salt, enantiomer, stereoisomer, or tautomer thereof,
wherein:
$X^5$ is selected from the group consisting of N, CH, and CF;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;
$E^1$ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
  the alkyl substituent is independently optionally substituted, at each occurrence, with a substituent selected from the group consisting of cycloalkyl, cyano, alkoxy, and aminoalkyl,
  the cycloalkyl substituent is independently optionally substituted, at each occurrence, with a substituent selected from the group consisting of cycloalkyl, cyano, alkoxy, and aminoalkyl, and
  the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
  the alkyl substituent is independently optionally substituted, at each occurrence, with a substituent selected from the group consisting of cycloalkyl, cyano, alkoxy, and aminoalkyl,
  the cycloalkyl substituent is independently optionally substituted, at each occurrence, with a substituent selected from the group consisting of cycloalkyl, cyano, alkoxy, and aminoalkyl, and
  the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
  wherein when $L^1$ is a direct bond and $E^1$ is an optionally substituted heterocyclyl or optionally substituted heteroaryl, the heterocyclyl or heteroaryl is C-bound;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^1$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl$(CH_2)_m$NH—, wherein the optionally substituted substituent on the heterocyclyl ring, at each occurrence, is independently $R^9$;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and
each m is independently 0, 1, 2, 3, or 4.
In some embodiments, the compound is represented by Formula I-C:

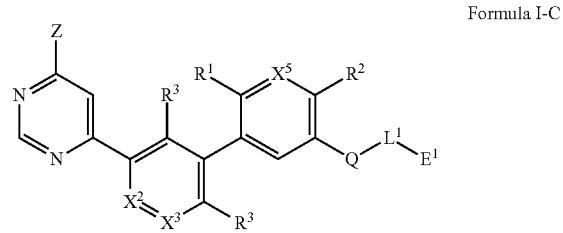

Formula I-C or a pharmaceutically acceptable salt, enantiomer, stereoisomer, or tautomer thereof,
wherein:
$X^2$ is selected from the group consisting of N, CH, C=O, C—O-$L^2$-$E^2$, C-$L^2$-$E^2$, C—N($R^4$)-$L^2$-$E^2$, and N-$L^2$-$E^2$;
$X^3$ is selected from the group consisting of CH, C-$L^3$-$E^3$, C—O-$L^3$-$E^3$, C—N($R^4$)-$L^3$-$E^3$, and N;

$X^5$ is selected from the group consisting of N, CH, and CF;

$L^2$ is selected from the group consisting of a direct bond and optionally substituted $C_1$-$C_6$alkyl, wherein the optionally substituted substituent, at each occurrence, is $(E^{21})_p$;

$L^3$ is selected from the group consisting of a direct bond and optionally substituted $C_1$-$C_6$alkyl, wherein the optionally substituted substituent, at each occurrence, is $(E^{31})_p$;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and optionally substituted heterocyclyl wherein the optionally substituted substituent, at each occurrence, is independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl($CH_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of is selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1, or 2; and
each m is independently 0, 1, 2, 3, or 4;

with the proviso that
when $X^2$ is selected from C—O-$L^2$-$E^2$ and C—N($R^4$)-$L^2$-$E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $X^3$ is selected from C—O-$L^3$-$E^3$ and C—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl; or when $X^6$ is CH, $X^5$ is CH or CF, $X^3$ is N, Q is —C(O)NH—, $L^1$ is direct bond, and $E^1$ is selected from the group consisting of $C_3$-$C_5$ cycloalkyl, $C_2$-$C_8$ heterocyclyl, $C_6$-$C_{14}$ aryl, and $C_1$-$C_9$ heteroaryl, $X^2$ is not C—N($R^4$)-$L^2$-$E^2$; or when Q is —C(O)—NH— and $L^1$ is direct bond, $E^1$ is not H; or when Q is —NH—C(O)—, $L^1$-$E^1$ is not unsubstituted methyl; or when $X^3$ is N, $R^3$ is H, $X^5$ and $X^6$ are CH, $X^2$ is CH or C—$NH_2$, and Q is —C(O)—NH, then $L^1$-$E^1$ is not alkyl substituted with amine.

In some embodiments, the compound is represented by Formula I-CA:

Formula I-CA

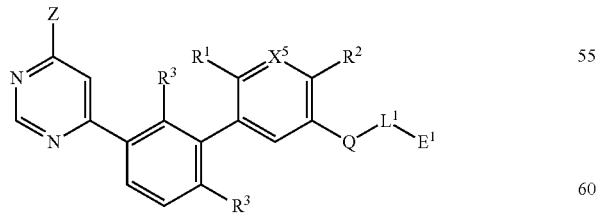

or a pharmaceutically acceptable salt, enantiomer, stereoisomer, or tautomer thereof,
wherein:
$X^5$ is selected from the group consisting of N, CH, and CF;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is ($E^{11}$)$_m$;

$E^1$ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
wherein when L is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently $R^9$;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^9$, at each occurrence, is independently selected from the group consisting of is selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and
each m is independently 0, 1, 2, 3, or 4.

In some embodiments, the compound is represented by Formula I-D:

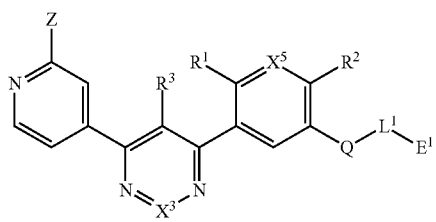

Formula I-D or a pharmaceutically acceptable salt, enantiomer, stereoisomer, or tautomer thereof,
wherein:
$X^3$ is selected from the group consisting of CH, C-$L^3$-$E^3$, C—O-$L^3$-$E^3$, and C—N($R^4$)-$L^3$-$E^3$;
$X^5$ is selected from the group consisting of N, CH, and CF;
$L^3$ is selected from the group consisting of a direct bond and optionally substituted $C_1$-$C_6$alkyl, wherein the optionally substituted substituent, at each occurrence, is ($E^{31}$)$_p$;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is ($E^{11}$)$_m$;
$E^1$ is selected from the group consisting of H, alkoxy, cyano, haloalkoxy, halogen,
optionally substituted alkyl wherein the optionally substituted substituent, at each occurrence, is independently selected from the group consisting of alkyl, alkoxy, amine, haloalkyl, haloalkoxy, halogen, hydroxy, and cyano,
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1 or 2; and each m is independently 0, 1, 2, 3, or 4; with the proviso that when $X^3$ is selected from C—O-$L^3$-$E^3$ and C—N(R$^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl; or when Q is —C(O)—NH— and $L^1$ is direct bond, $E^1$ is not H; or when Q is —NH—C(O)—, $L^1$-$E^1$ is not unsubstituted methyl.

In some embodiments, the compound is represented by Formula I-DA:

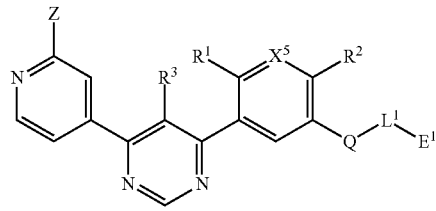

Formula I-DA or a pharmaceutically acceptable salt, enantiomer, stereoisomer, or tautomer thereof,
wherein:
$X^5$ is selected from the group consisting of N, CH, and CF;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;
$E^1$ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-DB:

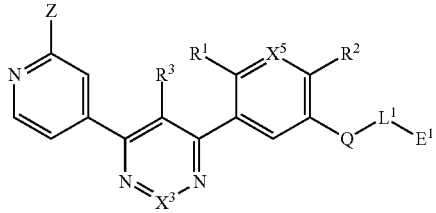

Formula I-DB or a pharmaceutically acceptable salt, enantiomer, stereoisomer, or tautomer thereof,
wherein:
$X^3$ is selected from the group consisting of C-$L^3$-$E^3$, C—O-$L^3$-$E^3$, and C—N($R^4$)-$L^3$-$E^3$;
$X^5$ is selected from the group consisting of N, CH, and CF;

$L^3$ is selected from the group consisting of a direct bond and optionally substituted $C_1$-$C_6$alkyl, wherein the optionally substituted substituent, at each occurrence, is ($E^{31}$)$_p$;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is ($E^{11}$)$_m$;

$E^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when L¹ is a direct bond and E¹ is an optionally substituted heterocyclyl or optionally substituted heteroaryl, the heterocyclyl or heteroaryl is C-bound;

E¹¹, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of E¹¹ taken together with the carbon atom to which they are attached form a cycloalkyl or a heterocyclyl ring having from 3 to 6 atoms in the ring structure;

E³ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted monocyclic heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

E³¹, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of E³¹ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently R⁹;

R¹ is selected from the group consisting of H, alkyl, alkoxy, haloalkyl, cyano, and halogen;

R² is selected from the group consisting of H and F;

R³, at each occurrence, is independently selected from the group consisting of H, alkyl, and halogen;

R⁴, at each occurrence, is independently selected from H and alkyl;

R⁹, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1 or 2; and each m is independently 0, 1, 2, 3, or 4.

In some embodiments, the compound is represented by Formula I-E:

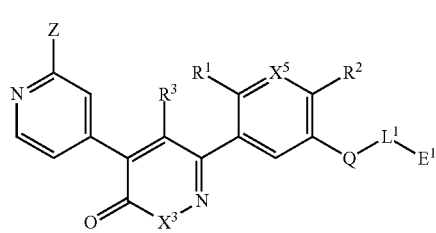

Formula I-E or a pharmaceutically acceptable salt, enantiomer, stereoisomer, or tautomer thereof, wherein:

X³ is N-L³-E³;

X⁴ is selected from CR³ and N;

X⁵ is selected from the group consisting of N, CH, and CF;

L³ is selected from the group consisting of a direct bond and optionally substituted $C_1$-$C_6$alkyl, wherein the optionally substituted substituent, at each occurrence, is (E³¹)$_p$;

Q is selected from the group consisting of —NH—C(O)— and —C(O)—NH—;

L¹ is selected from the group consisting of a direct bond and optionally substituted $C_1$-$C_6$alkyl, wherein the optionally substituted substituent, at each occurrence, is (E¹¹)$_m$;

E¹ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
  the alkyl substituent is independently optionally substituted, at each occurrence, with a substituent selected from the group consisting of cycloalkyl, cyano, alkoxy, and aminoalkyl,
  the cycloalkyl substituent is independently optionally substituted, at each occurrence, with a substituent selected from the group consisting of cycloalkyl, cyano, alkoxy, and aminoalkyl, and
  the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone,
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone,
optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and
optionally substituted cycloalkyl, wherein the optionally substituted substituent, at each occurrence, is independently selected from the group consisting of alkyl, alkoxy, haloalkyl, haloalkoxy, halogen, hydroxy, and cyano;
$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;
or wherein two occurrences of $E^{31}$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl($CH_2$)$_m$NH—,
wherein the optionally substituted substituent on the heterocyclyl ring, at each occurrence, is independently $R^9$;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;
each p is independently 0, 1, or 2; and
each m is independently 0, 1, 2, 3, or 4;
with the proviso that when $L^1$ is direct bond, then $E^1$ is not N-bound heterocyclyl.
In some embodiments, the compound is represented by Formula I-EA:

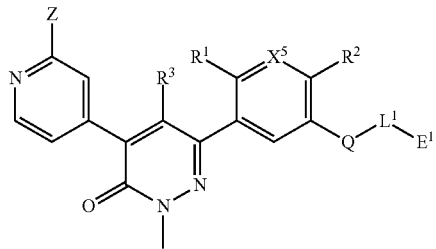

Formula I-EA or a pharmaceutically acceptable salt, enantiomer, stereoisomer, or tautomer thereof,
wherein:
  $X^5$ is selected from the group consisting of N, CH, and CF;
  Q is selected from the group consisting of —NH—C(O)— and —C(O)—NH—;
  $L^1$ is selected from the group consisting of a direct bond and optionally substituted $C_1$-$C_6$alkyl, wherein the optionally substituted substituent, at each occurrence, is $(E^{11})_m$;
  $E^1$ is selected from the group consisting of
  optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
  optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
    the alkyl substituent is independently optionally substituted, at each occurrence, with a substituent selected from the group consisting of cycloalkyl, cyano, alkoxy, and aminoalkyl,
    the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
- the alkyl substituent is independently optionally substituted, at each occurrence, with a substituent selected from the group consisting of cycloalkyl, cyano, alkoxy, and aminoalkyl,
- the cycloalkyl substituent is independently optionally substituted, at each occurrence, with a substituent selected from the group consisting of cycloalkyl, cyano, alkoxy, and aminoalkyl, and
- the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^1$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl(CH$_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-EB:

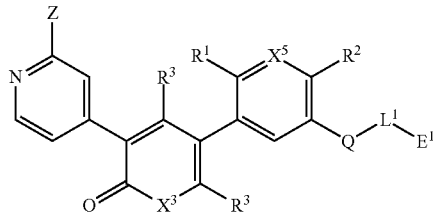

Formula I-EB or a pharmaceutically acceptable salt, enantiomer, stereoisomer, or tautomer thereof, wherein:

$X^3$ is N-L$^3$-E$^3$;

$X^5$ is selected from the group consisting of N, CH, and CF;

$L^3$ is selected from the group consisting of a direct bond and optionally substituted C$_1$-C$_6$alkyl, wherein the optionally substituted substituent, at each occurrence, is (E$^{31}$)$_p$;

Q is selected from the group consisting of —NH—C(O)— and —C(O)—NH—;

$L^1$ is selected from the group consisting of a direct bond and optionally substituted C$_1$-C$_6$alkyl, wherein the optionally substituted substituent, at each occurrence, is (E$^{11}$)$_m$;

$E^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
- the alkyl substituent is independently optionally substituted, at each occurrence, with a substituent selected from the group consisting of cycloalkyl, cyano, alkoxy, and aminoalkyl,
- the cycloalkyl substituent is independently optionally substituted, at each occurrence, with a substituent selected from the group consisting of cycloalkyl, cyano, alkoxy, and aminoalkyl, and
- the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1, or 2; and each m is independently 0, 1, 2, 3, or 4.

In some embodiments, the compound is represented by Formula I-F:

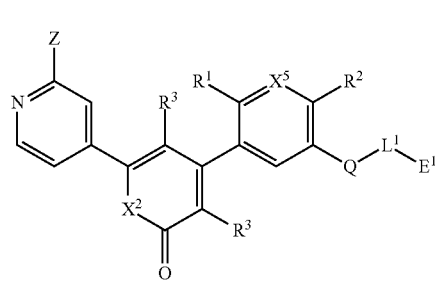

Formula I-F or a pharmaceutically acceptable salt, enantiomer, stereoisomer, or tautomer thereof, wherein:

$X^2$ is N-$L^2$-$E^2$;

$X^5$ is selected from the group consisting of N, CH, and CF;

$L^2$ is selected from the group consisting of a direct bond and optionally substituted $C_1$-$C_6$alkyl, wherein the optionally substituted substituent, at each occurrence, is $(E^{21})_p$, Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein
the heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)mNH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^9$ is selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;
each p is independently 0, 1 or 2; and
each m is independently 0, 1, 2, 3, or 4;
with the proviso that when $L^1$ is direct bond, then $E^1$ is not N-bound heterocyclyl.

In some embodiments, the compound is represented by Formula I-FA:

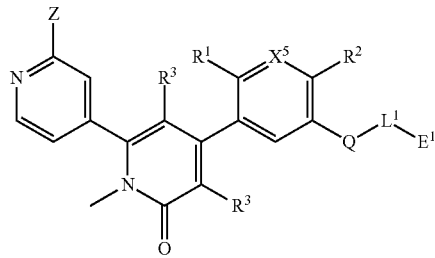

Formula I-FA or a pharmaceutically acceptable salt, enantiomer, stereoisomer, or tautomer thereof,
wherein:
$X^5$ is selected from the group consisting of N, CH, and CF;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;
$E^1$ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
- the alkyl substituent is independently optionally substituted, at each occurrence, with a substituent selected from the group consisting of cycloalkyl, cyano, alkoxy, and aminoalkyl,
- the cycloalkyl substituent is independently optionally substituted, at each occurrence, with a substituent selected from the group consisting of cycloalkyl, cyano, alkoxy, and aminoalkyl, and
- the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^1$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$ is selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-G:

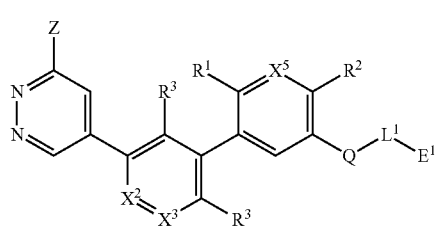

Formula I-G or a pharmaceutically acceptable salt, enantiomer, stereoisomer, or tautomer thereof,
wherein:
$X^2$ is selected from the group consisting of CH, C-$L^3$-$E^3$, C—O-$L^3$-$E^3$, C—N($R^4$)-$L^3$-$E^3$, and N;
$X^3$ is selected from the group consisting of CH, C-$L^2$-$E^2$, C—O-$L^2$-$E^2$, C—N($R^4$)-$L^2$-$E^2$, and N;
$X^5$ is selected from the group consisting of N, CH, and CF;
$L^3$ is selected from the group consisting of a direct bond and optionally substituted $C_1$-$C_6$alkyl, wherein the optionally substituted substituent, at each occurrence, is $(E^{31})_p$;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;
$E^1$ is selected from the group consisting of H, alkoxy, cyano, haloalkoxy, halogen,
optionally substituted alkyl wherein the optionally substituted substituent, at each occurrence, is independently selected from the group consisting of alkyl, alkoxy, amine, haloalkyl, haloalkoxy, halogen, hydroxy, and cyano,
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
- the alkyl substituent is independently optionally substituted, at each occurrence, with a substituent selected from the group consisting of cycloalkyl, cyano, alkoxy, and aminoalkyl,
- the cycloalkyl substituent is independently optionally substituted, at each occurrence, with a substituent selected from the group consisting of cycloalkyl, cyano, alkoxy, and aminoalkyl, and
- the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
  the alkyl substituent is independently optionally substituted, at each occurrence, with a substituent selected from the group consisting of cycloalkyl, cyano, alkoxy, and aminoalkyl,
  the cycloalkyl substituent is independently optionally substituted, at each occurrence, with a substituent selected from the group consisting of cycloalkyl, cyano, alkoxy, and aminoalkyl, and
  the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
$E^2$ is selected from the group consisting of hydroxy, alkoxy, alkoxyalkyl, cyano, sulfonyl, H, alkyl, amine, amide, acyl, haloalkoxy, haloalkyl, and
optionally substituted heterocyclyl wherein the optionally substituted substituent, at each occurrence, is independently selected from the group consisting of alkyl, alkoxy, amide, amine, acyl, haloalkyl, haloalkoxy, halogen, hydroxy, hydroxyalkyl, oxo, cyano, and cyanoalkyl;
$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;
or wherein two occurrences of $E^{21}$ taken together with the carbon atom to which they are attached form a cycloalkyl or a heterocyclyl ring having from 3 to 6 atoms in the ring structure;
$E^3$ is selected from the group consisting of hydroxy, alkoxy, alkoxyalkyl, cyano, sulfonyl, haloalkoxy, H, alkyl, acyl, amine, aminoalkyl, amide, haloalkyl, cyano, sulfone,
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone,
optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;
$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;
or wherein two occurrences of $E^{31}$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and
optionally substituted heterocyclyl(CH$_2$)mNH—, wherein the optionally substituted substituent on the heterocyclyl ring, at each occurrence, is independently R$^9$;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^4$, at each occurrence, is independently selected from H and alkyl;
$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;
each p is independently 0, 1 or 2; and
each m is independently 0, 1, 2, 3, or 4;
with the proviso that
$X^2$ and $X^3$ are both not N;
when $X^3$ is selected from C—O-L$^3$-E$^3$ and C—N(R$^4$)-L$^3$-E$^3$, R$^4$ is H, and each L$^3$ is a direct bond, each E$^3$ is not a 6-, 7-, 8-, 9-, 10- or 11-membered bicyclic ring containing 0, 1, 2, 3 or 4 atoms selected from N, O, and S; or
when $X^2$ is selected from C—O-L$^2$-E$^2$ and C—N(R$^4$)-L$^2$-E$^2$, R$^4$ is H, and each L$^2$ is a direct bond, each E$^2$ is not a 6-, 7-, 8-, 9-, 10- or 11-membered bicyclic ring containing 0, 1, 2, 3 or 4 atoms selected from N, O, and S; or
when $X^6$ is CH, $X^5$ is CH or CF, $X^3$ is N, Q is —C(O)NH—, L$^1$ is direct bond, and E$^1$ is selected from the group consisting of C$_3$-C$_8$ cycloalkyl, C$_2$-C$_8$ heterocyclyl, C$_6$-C$_{14}$ aryl, and C$_1$-C$_9$ heteroaryl, X$^2$ is not C—N(R$^4$)-L$^2$-E$^2$; or
when L$^1$ is direct bond, then E$^1$ is not N-bound heterocyclyl; or
when Q is —C(O)—NH— and L$^1$ is direct bond, E is not H; or
when Q is —NH—C(O)—, L$^1$-E$^1$ is not unsubstituted methyl; or
when $X^3$ is N, $R^3$ is H, $X^5$ and $X^6$ are CH, $X^2$ is CH or C—NH$_2$, and Q is —C(O)—NH, then L$^1$-E$^1$ is not alkyl substituted with amine.

In some embodiments, the compound is represented by Formula I-GA:

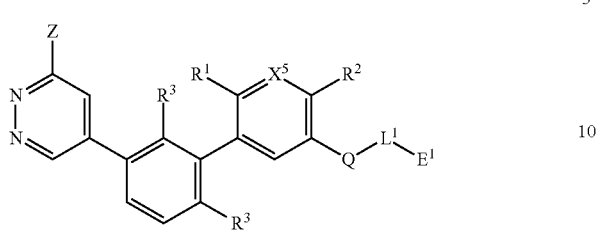

Formula I-GA or a pharmaceutically acceptable salt, enantiomer, stereoisomer, or tautomer thereof,
wherein:
$X^5$ is selected from the group consisting of N, CH, and CF;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;
$E^1$ is selected from the group consisting of
  optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
  optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
    the alkyl substituent is independently optionally substituted, at each occurrence, with a substituent selected from the group consisting of cycloalkyl, cyano, alkoxy, and aminoalkyl,
    the cycloalkyl substituent is independently optionally substituted, at each occurrence, with a substituent selected from the group consisting of cycloalkyl, cyano, alkoxy, and aminoalkyl, and
    the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
  optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
    the alkyl substituent is independently optionally substituted, at each occurrence, with a substituent selected from the group consisting of cycloalkyl, cyano, alkoxy, and aminoalkyl,
    the cycloalkyl substituent is independently optionally substituted, at each occurrence, with a substituent selected from the group consisting of cycloalkyl, cyano, alkoxy, and aminoalkyl, and
    the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
  optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
    wherein when $L^1$ is a direct bond and $E^1$ is an optionally substituted heterocyclyl or optionally substituted heteroaryl, the heterocyclyl or heteroaryl is C-bound;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently $R^9$;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and
each m is independently 0, 1, 2, 3, or 4.

In some embodiments, the compound is represented by Formula I-H:

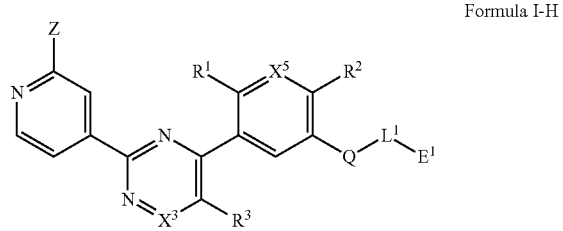

Formula I-H or a pharmaceutically acceptable salt, enantiomer, stereoisomer, or tautomer thereof,
wherein:
$X^3$ is selected from the group consisting of CH, C-$L^3$-$E^3$, C—O-$L^3$-$E^3$, and C—N($R^4$)-$L^3$-$E^3$.
$X^5$ is selected from the group consisting of N, CH, and CF;

$L^3$ is selected from the group consisting of a direct bond and optionally substituted $C_1$-$C_6$alkyl, wherein the optionally substituted substituent, at each occurrence, is $(E^{31})_p$;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
- the alkyl substituent is independently optionally substituted, at each occurrence, with a substituent selected from the group consisting of cycloalkyl, cyano, alkoxy, and aminoalkyl,
- the cycloalkyl substituent is independently optionally substituted, at each occurrence, with a substituent selected from the group consisting of cycloalkyl, cyano, alkoxy, and aminoalkyl, and
- the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
- the alkyl substituent is independently optionally substituted, at each occurrence, with a substituent selected from the group consisting of cycloalkyl, cyano, alkoxy, and aminoalkyl,
- the cycloalkyl substituent is independently optionally substituted, at each occurrence, with a substituent selected from the group consisting of cycloalkyl, cyano, alkoxy, and aminoalkyl, and
- the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxyalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)mNH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1 or 2; and each m is independently 0, 1, 2, 3, or 4;

with the proviso that
when R³ is selected from H and alkyl, X³ is C-L³-E³, and L³ is a direct bond, E³ is not morpholinyl; or
when X³ is selected from C—O-L³-E³ and C—N(R⁴)-L³-E³, R⁴ is H, and each L³ is a direct bond, each E³ is not a 6-, 7-, 8-, 9-, 10- or 11-membered bicyclic ring containing 0, 1, 2, 3 or 4 atoms selected from N, O, and S; or
when L¹ is direct bond, then E¹ is not N-bound heterocyclyl; or
when Q is —C(O)—NH— and L¹ is direct bond, E¹ is not H; or
when Q is —NH—C(O)—, L¹-E¹ is not unsubstituted methyl.

In some embodiments, the compound is represented by Formula I-HA:

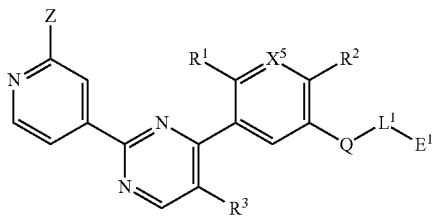

Formula I-HA or a pharmaceutically acceptable salt, enantiomer, stereoisomer, or tautomer thereof,
wherein:
X⁵ is selected from the group consisting of N, CH, and CF;
Q is selected from the group consisting of —NH—C(O)— and —C(O)—NH—;
L¹ is selected from the group consisting of a direct bond and optionally substituted $C_1$-$C_6$alkyl, wherein the optionally substituted substituent, at each occurrence, is $(E^{11})_m$;
E¹ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, amino-
alkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
wherein when L¹ is a direct bond and E¹ is an optionally substituted heterocyclyl or optionally substituted heteroaryl, the heterocyclyl or heteroaryl is C-bound;
E¹¹, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of E¹¹ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl(CH₂)$_m$NH—, wherein the optionally substituted substituent on the heterocyclyl ring, at each occurrence, is independently R⁹;
R¹ is selected from the group consisting of H, alkyl, alkoxy, haloalkyl, cyano, and halogen;
R² is selected from the group consisting of H and F;
R³, at each occurrence, is independently selected from the group consisting of H, alkyl, and halogen;
R⁹, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and
each m is independently 0, 1, 2, 3, or 4.

In some embodiments, the compound is represented by Formula I-J:

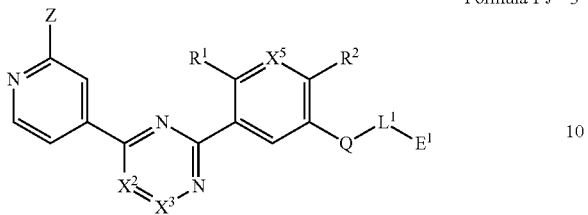

Formula I-J or a pharmaceutically acceptable salt, enantiomer, stereoisomer, or tautomer thereof,
wherein:
$X^2$ is selected from the group consisting of CH, C—O—$L^2$-$E^2$, C-$L^2$-$E^2$, and C—N($R^4$)-$L^2$-$E^2$;
$X^3$ is selected from the group consisting of CH, C-$L^3$-$E^3$, C—O-$L^3$-$E^3$, and C—N($R^4$)-$L^3$-$E^3$;
$X^5$ is selected from the group consisting of N, CH, and CF;
$L^2$ is selected from the group consisting of a direct bond and optionally substituted $C_1$-$C_6$alkyl, wherein the optionally substituted substituent, at each occurrence, is $(E^{21})_p$;
$L^3$ is selected from the group consisting of a direct bond and optionally substituted $C_1$-$C_6$alkyl, wherein the optionally substituted substituent, at each occurrence, is $(E^{31})_l$;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;
$E^1$ is selected from the group consisting of H, alkoxy, cyano, haloalkoxy, halogen,
  optionally substituted alkyl wherein the optionally substituted substituent, at each occurrence, is independently selected from the group consisting of alkyl, alkoxy, amine, haloalkyl, haloalkoxy, halogen, hydroxy, and cyano,
  optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
  optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
    the alkyl substituent is independently optionally substituted, at each occurrence, with a substituent selected from the group consisting of cycloalkyl, cyano, alkoxy, and aminoalkyl,
    the cycloalkyl substituent is independently optionally substituted, at each occurrence, with a substituent selected from the group consisting of cycloalkyl, cyano, alkoxy, and aminoalkyl, and
    the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
  optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
    the alkyl substituent is independently optionally substituted, at each occurrence, with a substituent selected from the group consisting of cycloalkyl, cyano, alkoxy, and aminoalkyl,
    the cycloalkyl substituent is independently optionally substituted, at each occurrence, with a substituent selected from the group consisting of cycloalkyl, cyano, alkoxy, and aminoalkyl, and
    the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
  optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;
$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;
or wherein two occurrences of $E^{21}$ taken together with the carbon atom to which they are attached form a cycloalkyl or a heterocyclyl ring having from 3 to 6 atoms in the ring structure;
$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone,
  optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)mNH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1 or 2; and each m is independently 0, 1, 2, 3, or 4;

with the proviso that when $X^2$ is C-$L^2$-$E^2$, $L^2$ is a direct bond, $E^2$ is selected from H and alkyl, $X^3$ is C-$L^3$-$E^3$, and $L^3$ is a direct bond, $E^3$ is not morpholinyl; or when $X^2$ is selected from C—O-$L^2$-$E^2$ and C—N($R^4$)-$L^2$-$E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $X^3$ is selected from C—O-$L^3$-$E^3$ and C—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl; or when Q is —C(O)—NH— and $L^1$ is direct bond, $E^1$ is not H; or when Q is —NH—C(O)—, $L^1$-$E^1$ is not unsubstituted methyl.

In some embodiments, the compound is represented by Formula I-JA:

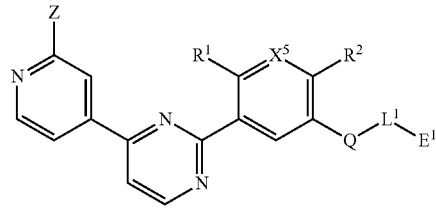

Formula I-JA or a pharmaceutically acceptable salt, enantiomer, stereoisomer, or tautomer thereof,
wherein:
$X^5$ is selected from the group consisting of N, CH, and CF;

Q is selected from the group consisting of —NH—C(O)— and —C(O)—NH—;

$L^1$ is selected from the group consisting of a direct bond and optionally substituted C$_1$-C$_6$alkyl, wherein the optionally substituted substituent, at each occurrence, is $(E^{11})_m$;

$E^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-K:

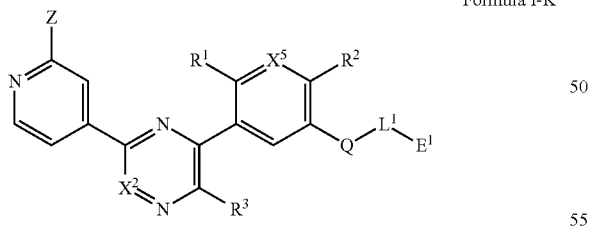

Formula I-K or a pharmaceutically acceptable salt, enantiomer, stereoisomer, or tautomer thereof,
wherein:
$X^2$ is selected from the group consisting of CH, C—O-$L^2$-$E^2$, C-$L^2$-$E^2$, and C—N($R^4$)-$L^2$-$E^2$;
$X^5$ is selected from the group consisting of N, CH, and CF;
$L^2$ is selected from the group consisting of a direct bond and optionally substituted $C_1$-$C_6$alkyl, wherein the optionally substituted substituent, at each occurrence, is $(E^{21})_p$;

Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;
$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl($CH_2$)mNH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1, or 2; and each m is independently 0, 1, 2, 3, or 4;

with the proviso that when $X^2$ is selected from C—O-$L^2$-$E^2$ and C—N($R^4$)-$L^2$-$E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl; or when $X^6$ is CH, $X^5$ is CH or CF, Q is —C(O)NH—, $L^1$ is direct bond, and $E^1$ is selected from the group consisting of $C_3$-$C_8$ cycloalkyl, $C_2$-$C_8$ heterocyclyl, $C_6$-$C_{14}$ aryl, and $C_1$-$C_9$ heteroaryl, $X^2$ is not C—N($R^4$)-$L^2$-$E^2$; or when Q is —C(O)—NH— and $L^1$ is direct bond, $E^1$ is not H; or when Q is —NH—C(O)—, $L^1$-$E^1$ is not unsubstituted methyl; or when $R^3$ is H, $X^5$ and $X^6$ are CH, $X^2$ is CH or C—$NH_2$, and Q is —C(O)—NH—, then $L^1$-$E^1$ is not alkyl substituted with amine.

In some embodiments, the compound is represented by Formula I-KA:

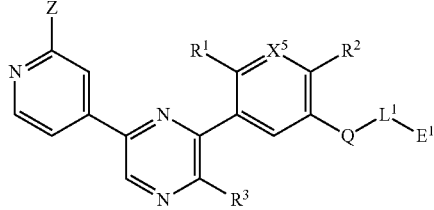

Formula I-KA or a pharmaceutically acceptable salt, enantiomer, stereoisomer, or tautomer thereof, wherein:

$X^5$ is selected from the group consisting of N, CH, and CF;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl, and
the cycloalkyl substituent is independently optionally substituted, at each occurrence, with a substituent selected from the group consisting of cycloalkyl, cyano, alkoxy, and aminoalkyl, the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^1$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl$(CH_2)_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-L:

Formula I-L

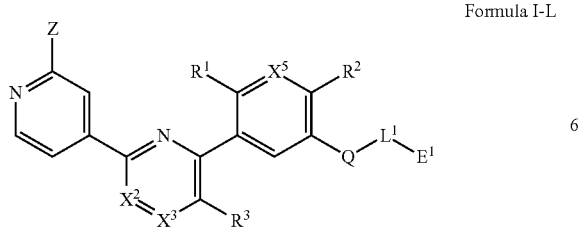

or a pharmaceutically acceptable salt, enantiomer, stereoisomer, or tautomer thereof, wherein:

$X^2$ is selected from the group consisting of CH, C—O-$L^2$-$E^2$, C-$L^2$-$E^2$, C—N($R^4$)-$L^2$-$E^2$, and N;

$X^3$ is selected from the group consisting of CH, C-$L^3$-$E^3$, C—O-$L^3$-$E^3$, and C—N($R^4$)-$L^3$-$E^3$;

$X^5$ is selected from the group consisting of N, CH, and CF;

$L^2$ is selected from the group consisting of a direct bond and optionally substituted $C_1$-$C_6$alkyl, wherein the optionally substituted substituent, at each occurrence, is $(E^{21})_p$;

$L^3$ is selected from the group consisting of a direct bond and optionally substituted $C_1$-$C_6$alkyl, wherein the optionally substituted substituent, at each occurrence, is $(E^{31})_p$;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^1$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)mNH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1 or 2; and each m is independently 0, 1, 2, 3, or 4;

with the proviso that when $X^2$ is N, $R^3$ is selected from H and alkyl, $X^3$ is C-$L^3$-$E^3$, and $L^3$ is a direct bond, $E^3$ is not morpholinyl; or when $X^2$ is selected from C—O-$L^2$-$E^2$ and C—N($R^4$)-$L^2$-$E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $X^3$ is selected from C—O-$L^3$-$E^3$ and C—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl; or when Q is —C(O)—NH— and $L^1$ is direct bond, $E^1$ is not H; or when Q is —NH—C(O)—, $L^1$-$E^1$ is not unsubstituted methyl.

In some embodiments, the compound is represented by Formula I-LA:

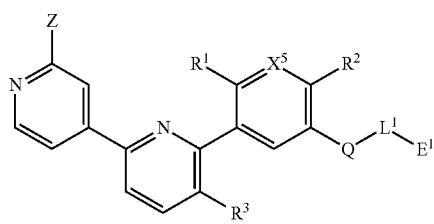

Formula I-LA or a pharmaceutically acceptable salt, enantiomer, stereoisomer, or tautomer thereof, wherein:

$X^5$ is selected from the group consisting of N, CH, and CF;

Q is selected from the group consisting of —NH—C(O)— and —C(O)—NH—;

L$^1$ is selected from the group consisting of a direct bond and optionally substituted C$_1$-C$_6$alkyl, wherein the optionally substituted substituent, at each occurrence, is (E$^{11}$)$_m$;

E$^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
   the alkyl substituent is independently optionally substituted, at each occurrence, with a substituent selected from the group consisting of cycloalkyl, cyano, alkoxy, and aminoalkyl,
   the cycloalkyl substituent is independently optionally substituted, at each occurrence, with a substituent selected from the group consisting of cycloalkyl, cyano, alkoxy, and aminoalkyl,
   the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
   the alkyl substituent is independently optionally substituted, at each occurrence, with a substituent selected from the group consisting of cycloalkyl, cyano, alkoxy, and aminoalkyl,
   the cycloalkyl substituent is independently optionally substituted, at each occurrence, with a substituent selected from the group consisting of cycloalkyl, cyano, alkoxy, and aminoalkyl, and
   the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when L$^1$ is a direct bond and E$^1$ is an optionally substituted heterocyclyl or optionally substituted heteroaryl, the heterocyclyl or heteroaryl is C-bound;

E$^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of E$^1$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl(CH$_2$)$_m$NH—, wherein the optionally substituted substituent on the heterocyclyl ring, at each occurrence, is independently R$^9$;

R$^1$ is selected from the group consisting of H, alkyl, alkoxy, haloalkyl, cyano, and halogen;

R$^2$ is selected from the group consisting of H and F;

R$^3$, at each occurrence, is independently selected from the group consisting of H, alkyl, and halogen;

R$^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-M:

Formula I-M

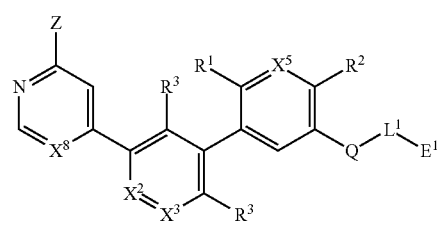

or a pharmaceutically acceptable salt, enantiomer, stereoisomer, or tautomer thereof, wherein:
  X$^2$ is selected from the group consisting of CH, C—O-L$^2$-E$^2$, C-L$^2$-E$^2$, C—N(R$^4$)-L$^2$-E$^2$, and N;
  X$^3$ is selected from the group consisting of CH, C-L$^3$-E$^3$, C—O-L$^3$-E$^3$, and C—N(R$^4$)-L$^3$-E$^3$;
  X$^5$ is selected from the group consisting of N, CH, and CF;
  X$^8$ is selected from the group consisting of N and CH;
  L$^2$ is selected from the group consisting of a direct bond and optionally substituted C$_1$-C$_6$alkyl, wherein the optionally substituted substituent, at each occurrence, is (E$^{21}$)$_p$;
  L$^3$ is selected from the group consisting of a direct bond and optionally substituted C$_1$-C$_6$alkyl, wherein the optionally substituted substituent, at each occurrence, is (E$^{31}$)$_p$;
  Q is selected from the group consisting of —NH—C(O)— and —C(O)—NH—;
  L$^1$ is selected from the group consisting of a direct bond and optionally substituted C$_1$-C$_6$alkyl, wherein the optionally substituted substituent, at each occurrence, is (E$^{11}$)$_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxyalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1 or 2; and each m is independently 0, 1, 2, 3, or 4;

with the proviso that when $X^2$ is N, $R^3$ is selected from H and alkyl, $X^3$ is C-$L^3$-$E^3$, and $L^3$ is a direct bond, $E^3$ is not morpholinyl; or when $X^2$ is selected from C—O-$L^2$-$E^2$ and C—N($R^4$)-$L^2$-$E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $X^3$ is selected from C—O-$L^3$-$E^3$ and C—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl;

when Q is —C(O)—NH— and $L^1$ is direct bond, $E^1$ is not H; or when Q is —NH—C(O)—, $L^1$-$E^1$ is not unsubstituted methyl.

In some embodiments, the compound is represented by Formula I-N:

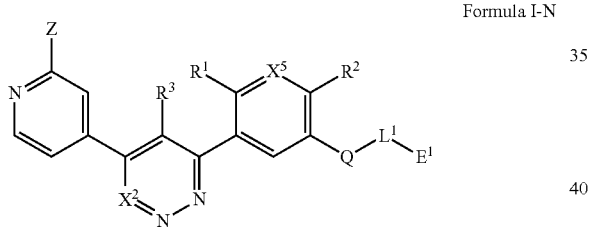

Formula I-N or a pharmaceutically acceptable salt, enantiomer, stereoisomer, or tautomer thereof, wherein:

$X^2$ is selected from the group consisting of CH, C—O-$L^2$-$E^2$, C-$L^2$-$E^2$, and C—N($R^4$)-$L^2$-$E^2$;

$X^5$ is selected from the group consisting of N, CH, and CF;

$L^2$ is selected from the group consisting of a direct bond and optionally substituted $C_1$-$C_6$alkyl, wherein the optionally substituted substituent, at each occurrence, is $(E^{21})_p$;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl(CH$_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1, or 2; and each m is independently 0, 1, 2, 3, or 4;

with the proviso that when $X^2$ is selected from C—O-L$^2$-E$^2$ and C—N(R$^4$)-L$^2$-E$^2$, R$^4$ is H, and each L$^2$ is a direct bond, each E$^2$ is not a 6-, 7-, 8-, 9-, 10- or 11-membered bicyclic ring containing 0, 1, 2, 3 or 4 atoms selected from N, O, and S; or when L$^1$ is direct bond, then E$^1$ is not N-bound heterocyclyl; or when Q is —C(O)—NH— and L$^1$ is direct bond, E$^1$ is not H; or when Q is —NH—C(O)—, L$^1$-E$^1$ is not unsubstituted methyl.

In some embodiments, the compound is represented by Formula I-NA:

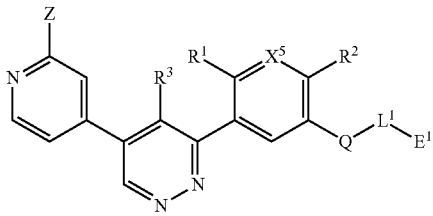

Formula I-NA or a pharmaceutically acceptable salt, enantiomer, stereoisomer, or tautomer thereof, wherein:

$X^5$ is selected from the group consisting of N, CH, and CF;

Q is selected from the group consisting of —NH—C(O)— and —C(O)—NH—;

L$^1$ is selected from the group consisting of a direct bond and optionally substituted C$_1$-C$_6$alkyl, wherein the optionally substituted substituent, at each occurrence, is (E$^{11}$)$_m$;

E$^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when L¹ is a direct bond and E is an optionally substituted heterocyclyl or optionally substituted heteroaryl, the heterocyclyl or heteroaryl is C-bound;

E¹¹, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of E¹¹ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl(CH₂)ₘNH—, wherein the optionally substituted substituent on the heterocyclyl ring, at each occurrence, is independently R⁹;

R¹ is selected from the group consisting of H, alkyl, alkoxy, haloalkyl, cyano, and halogen;

R² is selected from the group consisting of H and F;

R³, at each occurrence, is independently selected from the group consisting of H, alkyl, and halogen;

R⁹, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-O:

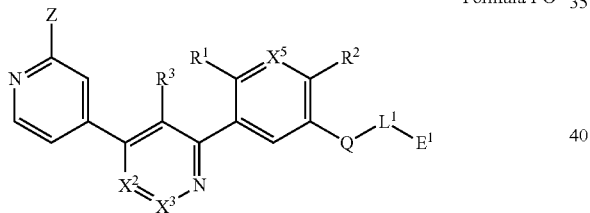

Formula I-O or a pharmaceutically acceptable salt, enantiomer, stereoisomer, or tautomer thereof,
wherein:
X² is selected from the group consisting of CH, C—O-L²-E², C-L²-E², C—N(R⁴)-L²-E², and N;
X³ is selected from the group consisting of CH, C-L³-E³, C—O-L³-E³, and C—N(R⁴)-L³-E³;
X⁵ is selected from the group consisting of N, CH, and CF;
Q is selected from the group consisting of —NH—C(O)— and —C(O)—NH—;
L² is selected from the group consisting of a direct bond and optionally substituted C₁-C₆alkyl, wherein the optionally substituted substituent, at each occurrence, is (E²¹)ₚ;
L³ is selected from the group consisting of a direct bond and optionally substituted C₁-C₆alkyl, wherein the optionally substituted substituent, at each occurrence, is (E³¹)ₚ;
L¹ is selected from the group consisting of a direct bond and optionally substituted C₁-C₆alkyl, wherein the optionally substituted substituent, at each occurrence, is (E¹¹)ₘ;

E¹ is selected from the group consisting of H, alkoxy, cyano, haloalkoxy, halogen,
optionally substituted alkyl wherein the optionally substituted substituent, at each occurrence, is independently selected from the group consisting of alkyl, alkoxy, amine, haloalkyl, haloalkoxy, halogen, hydroxy, and cyano,
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

E¹¹, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl($CH_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1 or 2; and each m is independently 0, 1, 2, 3, or 4;

with the proviso that when $X^2$ is N, $R^3$ is selected from H and alkyl, $X^3$ is C-$L^3$-$E^3$, and $L^3$ is a direct bond, $E^3$ is not morpholinyl; or when $X^2$ is selected from C—O-$L^2$-$E^2$ and C—N($R^4$)-$L^2$-$E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $X^3$ is selected from C—O-$L^3$-$E^3$ and C—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl; or when Q is —C(O)—NH— and $L^1$ is direct bond, $E^1$ is not H; or when Q is —NH—C(O)—, $L^1$-$E^1$ is not unsubstituted methyl.

In some embodiments, the compound is represented by Formula I-OA:

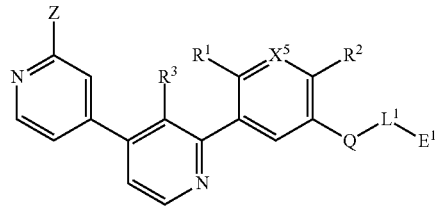

Formula I-OA or a pharmaceutically acceptable salt, enantiomer, stereoisomer, or tautomer thereof, wherein:

$X^5$ is selected from the group consisting of N, CH, and CF;

Q is selected from the group consisting of —NH—C(O)— and —C(O)—NH—;

$E^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and E is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl(CH$_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-P:

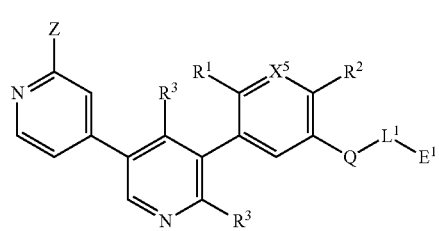

Formula I-P or a pharmaceutically acceptable salt, enantiomer, stereoisomer, or tautomer thereof, wherein:

$X^5$ is selected from the group consisting of N, CH, and CF;

Q is selected from the group consisting of —NH—C(O)— and —C(O)—NH—;

$L^1$ is selected from the group consisting of a direct bond and optionally substituted C$_1$-C$_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl$(CH_2)_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each m is independently 0, 1, 2, 3, or 4, with the proviso that when $L^1$ is direct bond, then $E^1$ is not N-bound heterocyclyl; or when Q is —C(O)—NH— and $L^1$ is direct bond, $E^1$ is not H; or when Q is —NH—C(O)—, $L^1$-E is not unsubstituted methyl; or when $R^3$ is H, $X^5$ and $X^6$ are CH, and Q is —C(O)—NH—, then $L^1$-$E^1$ is not alkyl substituted with amine.

In some embodiments, the compound is represented by Formula I-PA:

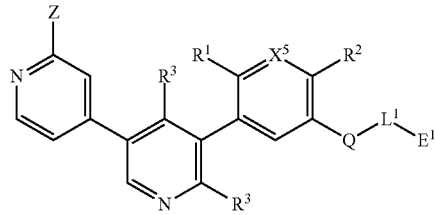

Formula I-PA or a pharmaceutically acceptable salt, enantiomer, stereoisomer, or tautomer thereof, wherein:

$X^5$ is selected from the group consisting of N, CH, and CF;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl$(CH_2)_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-Q:

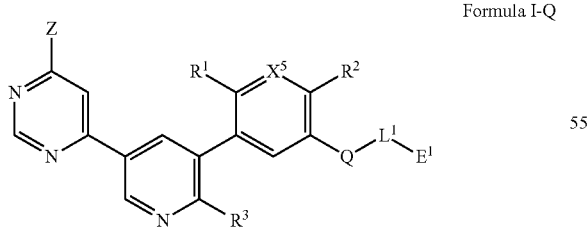

Formula I-Q or a pharmaceutically acceptable salt, enantiomer, stereoisomer, or tautomer thereof,
wherein:
$X^5$ is selected from the group consisting of N, CH, and CF;
Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^1$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl($CH_2$)$_m$NH—, wherein the optionally substituted substituent on the heterocyclyl ring, at each occurrence, is independently $R^9$;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;
each m is independently 0, 1, 2, 3, or 4,
with the proviso that
when $L^1$ is direct bond, then $E^1$ is not N-bound heterocyclyl; or
when Q is —C(O)—NH— and $L^1$ is direct bond, E is not H; or
when Q is —NH—C(O)—, $L^1$-$E^1$ is not unsubstituted methyl; or
when $R^3$ is H, $X^5$ and $X^6$ are CH, and Q is —C(O)—NH—, then $L^1$-$E^1$ is not alkyl substituted with amine.

In some embodiments, the compound is represented by Formula I-QA

Formula I-Q

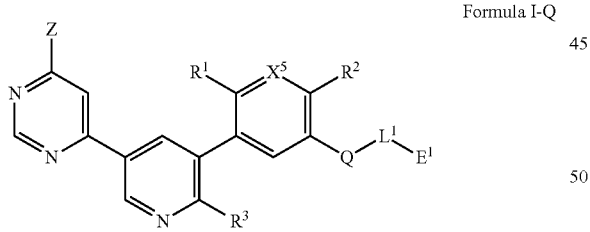

or a pharmaceutically acceptable salt, enantiomer, stereoisomer, or tautomer thereof,
wherein:
$X^5$ is selected from the group consisting of N, CH, and CF;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is ($E^{11}$)$_m$;
$E^1$ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
wherein when $L^1$ is a direct bond and $E^1$ is an optionally substituted heterocyclyl or optionally substituted heteroaryl, the heterocyclyl or heteroaryl is C-bound;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; and each m is independently 0, 1, 2, 3, or 4.

In some embodiments, the compound is represented by Formula I-R:

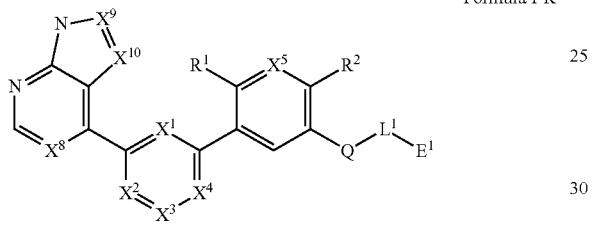

Formula I-R or a pharmaceutically acceptable salt, enantiomer, stereoisomer, or tautomer thereof, wherein:
each of $X^1$ and $X^4$ is independently selected from $CR^3$ and N;

$X^2$ is selected from the group consisting of N, CH, C=O, C—O-$L^2$-$E^2$, C-$L^2$-$E^2$, C—N($R^4$)-$L^2$-$E^2$, and N-$L^2$-$E^2$;

$X^3$ is selected from the group consisting of CH, C-$L^3$-$E^3$, C—O-$L^3$-$E^3$, C—N($R^4$)-$L^3$-$E^3$, C=O, N, and N-$L^3$-$E^3$;

provided that not more than two of $X^1$, $X^2$, $X^3$, and $X^4$ are N;

when $X^2$ is N, $X^3$ is selected from the group consisting of CH, C-$L^3$-$E^3$, C—O-$L^3$-$E^3$, C—N($R^4$)-$L^3$-$E^3$, and N;

when $X^3$ is N, $X^2$ is selected from the group consisting of N, CH, C—O-$L^2$-$E^2$, C-$L^2$-$E^2$, and C—N($R^4$)-$L^2$-$E^2$;

when $X^2$ is C=O, $X^3$ is N-$L^3$-$E^3$;

when $X^3$ is C=O, $X^2$ is N-$L^2$-$E^2$;

$X^5$ is selected from the group consisting of N, CH, and CF; each of $X^8$, $X^9$, and $X^{10}$ is independently selected from $CR^3$ and N;

$L^2$ is selected from the group consisting of a direct bond and optionally substituted $C_1$-$C_6$alkyl, wherein the optionally substituted substituent, at each occurrence, is $(E^{21})_p$;

$L^3$ is selected from the group consisting of a direct bond and optionally substituted $C_1$-$C_6$alkyl, wherein the optionally substituted substituent, at each occurrence, is $(E^{31})_p$;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

each p is independently 0, 1 or 2; and each m is independently 0, 1, 2, 3, or 4;

with the proviso that when $X^1$ and $X^2$ are N, each of $X^5$ and $X^6$ is independently selected from CH and CF, $X^4$ is $CR^3$, $R^3$ is selected from H and alkyl, $X^3$ is $C-L^3-E^3$, and $L^3$ is a direct bond, $E^3$ is not morpholinyl; or when $X^1$ and $X^4$ are N, each of $X^5$ and $X^6$ is independently selected from CH and CF, $X^2$ is $C-L^2-E^2$, $L^2$ is a direct bond, $E^2$ is selected from H and alkyl, $X^3$ is $C-L^3-E^3$, and $L^3$ is a direct bond, $E^3$ is not morpholinyl; or when $X^2$ is selected from $C-O-L^2-E^2$ and $C-N(R^4)-L^2-E^2$, $R^4$ is H, each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $X^3$ is selected from $C-O-L^3-E^3$ and $C-N(R^4)-L^3-E^3$, $R^4$ is H, each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then $E^1$ is not N-bound heterocyclyl; or when $X^6$ is CH, $X^5$ is CH or CF, $X^4$ is $CR^3$, $X^3$ is N, Q is —C(O)NH—, $L^1$ is direct bond, and E is selected from the group consisting of $C_3$-$C_8$ cycloalkyl, $C_2$-$C_8$ heterocyclyl, $C_6$-$C_{14}$ aryl, and $C_1$-$C_9$ heteroaryl, $X^2$ is not $C-N(R^4)-L^2-E^2$; or when Q is —C(O)—NH— and $L^1$ is direct bond, E is not H; or when Q is —NH—C(O)—, $L^1$-$E^1$ is not unsubstituted methyl; or when $X^3$ is N, $X^1$ is CH or N, $X^4$ is CH, $X^5$ and $X^6$ are CH, $X^2$ is CH or $C-NH_2$, and Q is —C(O)—NH—, then $L^1$-$E^1$ is not alkyl substituted with amine.

In some embodiments, the compound is represented by Formula I-RA:

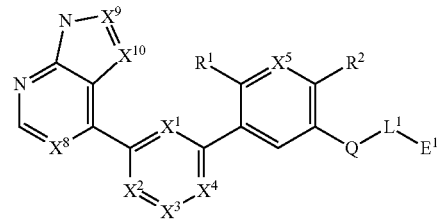

Formula I-RA or a pharmaceutically acceptable salt, enantiomer, stereoisomer, or tautomer thereof, wherein:

each of $X^1$ and $X^4$ is independently selected from $CR^3$ and N;

each of $X^2$ and $X^3$ is independently selected from the group consisting of N and CH;

provided that not more than two of $X^1$, $X^2$, $X^3$, and $X^4$ are N; each of $X^8$, $X^9$, and $X^{10}$ is independently selected from $CR^3$ and N;

$X^5$ is selected from the group consisting of N, CH, and CF;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen; and each m is independently 0, 1, 2, 3, or 4.

In some embodiments, the compound is represented by Formula I-S:

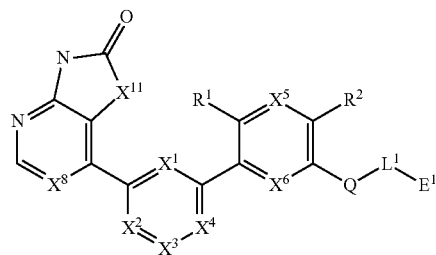

Formula I-S or a pharmaceutically acceptable salt, enantiomer, stereoisomer, or tautomer thereof, wherein:

each of $X^1$ and $X^4$ is independently selected from $CR^3$ and N;

$X^2$ is selected from the group consisting of N, CH, C=O, C—O-$L^2$-$E^2$, C-$L^2$-$E^2$, C—N($R^4$)-$L^2$-$E^2$, and N-$L^2$-$E^2$;

$X^3$ is selected from the group consisting of CH, C-$L^3$-$E^3$, C—O-$L^3$-$E^3$, C—N($R^4$)-$L^3$-$E^3$, C=O, N, and N-$L^3$-$E^3$;

provided that not more than two of $X^1$, $X^2$, $X^3$, and $X^4$ are N;

when $X^2$ is N, $X^3$ is selected from the group consisting of CH, C-$L^3$-$E^3$, C—O-$L^3$-$E^3$, C—N($R^4$)-$L^3$-$E^3$, and N;

when $X^3$ is N, $X^2$ is selected from the group consisting of N, CH, C—O-$L^2$-$E^2$, C-$L^2$-$E^2$, and C—N($R^4$)-$L^2$-$E^2$;

when $X^2$ is C=O, $X^3$ is N-$L^3$-$E^3$;

when $X^3$ is C=O, $X^2$ is N-$L^2$-$E^2$;

$X^5$ is selected from the group consisting of N, CH, and CF;

$X^8$ is selected from $CR^3$ and N;

$X^{11}$ is selected from the group consisting of O, $C(R^{10})_2$, and $NR^{11}$;

$L^2$ is selected from the group consisting of a direct bond and optionally substituted $C_1$-$C_6$alkyl, wherein the optionally substituted substituent, at each occurrence, is $(E^{21})_p$;

$L^3$ is selected from the group consisting of a direct bond and optionally substituted $C_1$-$C_6$alkyl, wherein the optionally substituted substituent, at each occurrence, is $(E^{31})_r$)

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
- the alkyl substituent is independently optionally substituted, at each occurrence, with a substituent selected from the group consisting of cycloalkyl, cyano, alkoxy, and aminoalkyl,
- the cycloalkyl substituent is independently optionally substituted, at each occurrence, with a substituent selected from the group consisting of cycloalkyl, cyano, alkoxy, and aminoalkyl, and
- the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
- the alkyl substituent is independently optionally substituted, at each occurrence, with a substituent selected from the group consisting of cycloalkyl, cyano, alkoxy, and aminoalkyl,
- the cycloalkyl substituent is independently optionally substituted, at each occurrence, with a substituent selected from the group consisting of cycloalkyl, cyano, alkoxy, and aminoalkyl, and
- the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^3$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^{10}$, at each occurrence, is independently selected from the group consisting of H, alkyl, cycloalkyl, and F;

$R^{11}$, at each occurrence, is independently selected from the group consisting of H, alkyl, and cycloalkyl;

each p is independently 0, 1 or 2; and each m is independently 0, 1, 2, 3, or 4;

with the proviso that
- when $X^1$ and $X^2$ are N, each of $X^5$ and $X^6$ is independently selected from CH and CF, $X^4$ is $CR^3$, $R^3$ is selected from H and alkyl, $X^3$ is $C-L^3-E^3$, and $L^3$ is a direct bond, $E^3$ is not morpholinyl; or
- when $X^1$ and $X^4$ are N, each of $X^5$ and $X^6$ is independently selected from CH, and CF, $X^2$ is $C-L^2-E^2$, $L^2$ is a direct bond, $E^2$ is selected from H and alkyl, $X^3$ is $C-L^3-E^3$, and $L^3$ is a direct bond, $E^3$ is not morpholinyl; or
- when $X^2$ is selected from $C$—$O-L^2-E^2$ and $C$—$N(R^4)$-$L^2-E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or when $X^3$ is selected from C—O-$L^3$-$E^3$ and C—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or when $L^1$ is direct bond, then E is not N-bound heterocyclyl; or when $X^6$ is CH, $X^5$ is CH or CF, $X^4$ is $CR^3$, $X^3$ is N, Q is —C(O)NH—, $L^1$ is direct bond, and $E^1$ is selected from the group consisting of $C_3$-$C_8$ cycloalkyl, $C_2$-$C_8$ heterocyclyl, $C_6$-$C_{14}$ aryl, and $C_1$-$C_9$ heteroaryl, $X^2$ is not C—N($R^4$)-$L^2$-$E^2$; or when Q is —C(O)—NH— and $L^1$ is direct bond, $E^1$ is not H; or when Q is —NH—C(O)—, $L^1$-$E^1$ is not unsubstituted methyl; or when $X^3$ is N, $X^1$ is CH or N, $X^4$ is CH, $X^5$ and $X^6$ are CH, $X^2$ is CH or C—$NH_2$, and Q is —C(O)—NH—, then $L^1$-$E^1$ is not alkyl substituted with amine.

In some embodiments, the compound is represented by Formula I-SA-i or Formula I-SA-ii:

Formula I-SA-i

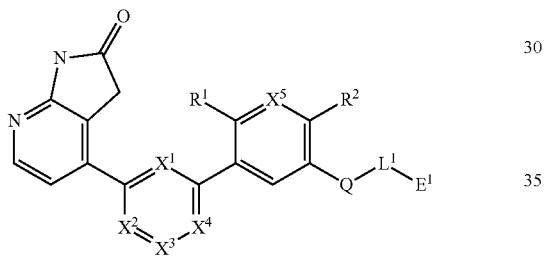

Formula I-SA-ii

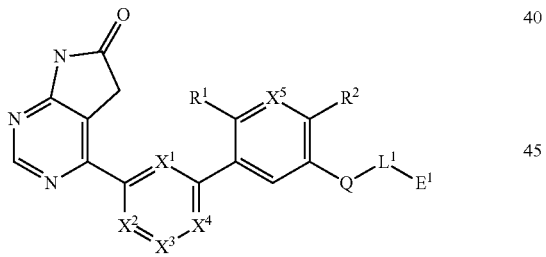

or a pharmaceutically acceptable salt, enantiomer, stereoisomer, or tautomer thereof,
wherein:
each of $X^1$ and $X^4$ is independently selected from $CR^3$ and N;
$X^2$ and $X^3$ are each independently selected from the group consisting of N and CH;
provided that not more than two of $X^1$, $X^2$, $X^3$, and $X^4$ are N;
$X^5$ is selected from the group consisting of N, CH, and CF;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen; and
each m is independently 0, 1, 2, 3, or 4.

In some embodiments, the compound is represented by Formula I-T:

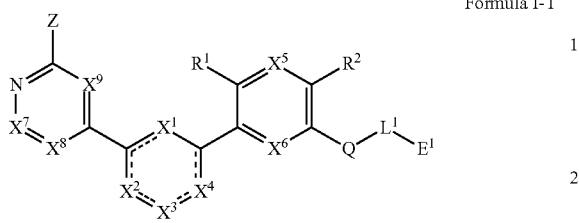

Formula I-T or a pharmaceutically acceptable salt, enantiomer, stereoisomer, or tautomer thereof,
wherein:
each of $X^1$ and $X^4$ is independently selected from $CR^3$ and N;
$X^2$ is selected from the group consisting of N, CH, C=O, C—O-$L^2$-$E^2$, C-$L^2$-$E^2$, C—N($R^4$)-$L^2$-$E^2$, and N-$L^2$-$E^2$;
$X^3$ is selected from the group consisting of CH, C-$L^3$-$E^3$, C—O-$L^3$-$E^3$, C—N($R^4$)-$L^3$-$E^3$, C=O, N, and N-$L^3$-$E^3$;
provided that not more than two of $X^1$, $X^2$, $X^3$, and $X^4$ are N;
when $X^2$ is N, $X^3$ is selected from the group consisting of CH, C-$L^3$-$E^3$, C—O-$L^3$-$E^3$, C—N($R^4$)-$L^3$-$E^3$, and N;
when $X^3$ is N, $X^2$ is selected from the group consisting of N, CH, C—O-$L^2$-$E^2$, C-$L^2$-$E^2$, and C—N($R^4$)-$L^2$-$E^2$;
when $X^2$ is C=O, $X^3$ is N-$L^3$-$E^3$;
when $X^3$ is C=O, $X^2$ is N-$L^2$-$E^2$;
$X^5$ is independently selected from the group consisting of CH, CF, and N;
$X^6$ is independently selected from the group consisting of CH, and CF;
$X^7$, $X^8$, and $X^9$ are independently selected from $CR^3$ and N;
provided that not more than one of $X^7$, $X^8$ and $X^9$ is N;
$L^2$ is selected from the group consisting of a direct bond and optionally substituted $C_1$-$C_6$alkyl, wherein the optionally substituted substituent, at each occurrence, is $(E^{21})_p$;
$L^3$ is selected from the group consisting of a direct bond and optionally substituted $C_1$-$C_6$alkyl, wherein the optionally substituted substituent, at each occurrence, is $(E^{31})_p$
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of H, alkoxy, cyano, haloalkoxy, halogen,
optionally substituted alkyl wherein the optionally substituted substituent, at each occurrence, is independently selected from the group consisting of alkyl, alkoxy, amine, haloalkyl, haloalkoxy, halogen, hydroxy, and cyano,
optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl, and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of H, hydroxy, alkoxy, alkoxyalkyl, cyano, sulfonyl, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from —C(O)NHR$^6$, —NHC(O)R$^7$, and —NHC(O)OR$^6$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^6$, at each occurrence, is independently selected from the group consisting of H, alkyl, cycloalkyl, and heterocyclyl, wherein
each of alkyl and cycloalkyl is optionally substituted with one or more independent occurrences of $R^8$; and
the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$R^7$ is selected from the group consisting of H, alkyl, cycloalkyl, and heterocyclyl, wherein
each of alkyl and cycloalkyl is optionally substituted with one or more occurrences of a substituent independently selected from the group consisting of alkyl, cyano, amino, hydroxy, alkoxy, and heterocyclyl, wherein
the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$R^8$ is selected from the group consisting of alkyl, cycloalkyl, and heterocyclyl, wherein
each of alkyl and cycloalkyl is optionally substituted with one or more occurrences of a substituent independently selected from the group consisting of alkyl, cyano, amino, hydroxy, alkoxy, and heterocyclyl, and
the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and each p is independently 0, 1 or 2;
each m is independently 0, 1, 2, 3, or 4;
with the proviso that
when $X^1$ and $X^2$ are N, each of $X^5$ and $X^6$ is independently selected from CH and CF, $X^4$ is CR$^3$, $R^3$ is selected from H and alkyl, $X^3$ is C-L$^3$-E$^3$, and L$^3$ is a direct bond, E$^3$ is not morpholinyl; or when $X^1$ and $X^4$ are N, each of $X^5$ and $X^6$ is independently selected from CH and CF, $X^2$ is C-L$^2$-E$^2$, L$^2$ is a direct bond, E$^2$ is selected from H and alkyl, $X^3$ is C-L$^3$-E$^3$, and L$^3$ is a direct bond, E$^3$ is not morpholinyl; or when $X^2$ is selected from C—O-L$^2$-E$^2$ and C—N(R$^4$)-L$^2$-E$^2$, R$^4$ is H, each L$^2$ is a direct bond, each E$^2$ is not a 6-, 7-, 8-, 9-, 10- or 11-membered bicyclic ring containing 0, 1, 2, 3 or 4 atoms selected from N, O, and S; or when $X^3$ is selected from C—O-L$^3$-E$^3$ and C—N(R$^4$)-L$^3$-E$^3$, R$^4$ is H, each L$^3$ is a direct bond, each E$^3$ is not a 6-, 7-, 8-, 9-, 10- or 11-membered bicyclic ring containing 0, 1, 2, 3 or 4 atoms selected from N, O, and S; or when L$^1$ is direct bond, then E$^1$ is not N-bound heterocyclyl;

when $X^6$ is CH, $X^5$ is CH or CF, $X^4$ is CR$^3$, $X^3$ is N, Q is —C(O)NH—, L$^1$ is direct bond, and E$^1$ is selected from the group consisting of C$_3$-C$_8$ cycloalkyl, C$_2$-C$_8$ heterocyclyl, C$_6$-C$_{14}$ aryl, and C$_1$-C$_9$ heteroaryl, $X^2$ is not C—N(R$^4$)-L$^2$-E$^2$; or when Q is —C(O)—NH— and L$^1$ is direct bond, E$^1$ is not H; or when Q is —NH—C(O)—, L$^1$-E$^1$ is not unsubstituted methyl; or when $X^3$ is N, $X^1$ is CH or N, $X^4$ is CH, $X^5$ and $X^6$ are CH, $X^2$ is CH or C—$NH_2$, and Q is —C(O)—NH—, then $L^1$-$E^1$ is not alkyl substituted with amine.

In some embodiments, Z is —NHC(O)$R^6$, —NHC(O)O$R^6$, or —C(O)NH$R^7$, wherein
- $R^6$, at each occurrence, is independently selected from the group consisting of H, alkyl, cycloalkyl, and heterocyclyl, wherein
  - each of alkyl and cycloalkyl is optionally substituted with one or more independent occurrences of $R^8$; and
  - the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and
- $R^7$ is selected from the group consisting of H, alkyl, cycloalkyl, and heterocyclyl, wherein
  - each of alkyl and cycloalkyl is optionally substituted with one or more occurrences of a substituent independently selected from the group consisting of alkyl, cyano, amino, hydroxy, alkoxy, and heterocyclyl, and
  - the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and
- $R^8$ is selected from the group consisting of alkyl, cycloalkyl, and heterocyclyl, wherein
  - each of alkyl and cycloalkyl is optionally substituted with one or more occurrences of a substituent independently selected from the group consisting of alkyl, cyano, amino, hydroxy, alkoxy, and heterocyclyl, and
  - the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, Z is —NHC(O)$R^6$, wherein
- $R^6$, at each occurrence, is independently selected from the group consisting of H, alkyl, cycloalkyl, and heterocyclyl, wherein
  - each of alkyl and cycloalkyl is optionally substituted with one or more independent occurrences of $R^8$; and
  - the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and
- $R^8$ is selected from the group consisting of alkyl, cycloalkyl, and heterocyclyl, wherein
  - each of alkyl and cycloalkyl is optionally substituted with one or more occurrences of a substituent independently selected from the group consisting of alkyl, cyano, amino, hydroxy, alkoxy, and heterocyclyl, and
  - the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, Z is —NHC(O)$R^6$, wherein $R^6$ is methyl, ethyl, or iso-propyl. In some embodiments, Z is —NHC(O)$R^6$, wherein $R^6$ is methyl. In some embodiments, Z is —NHC(O)$R^6$, wherein $R^6$ is cyclopropyl or cyclobutyl. In some embodiments, Z is —NHC(O)$R^6$, wherein $R^6$ is cyclopropyl. In some embodiments, Z is —NHC(O)$R^6$, wherein $R^6$ is H. In some embodiments, Z is —NHC(O)$R^6$, wherein $R^6$ is $CH_2N(R^4)_2$. In some embodiments, Z is —NHC(O)$R^6$, wherein $R^6$ is $CH_2$—CN. In some embodiments, Z is —NHC(O)$R^6$, wherein $R^6$ is $CH_2$—OH. In some embodiments, Z is —NHC(O)$R^6$, wherein $R^6$ is $CH_2$—OMe.

In some embodiments, Z is —C(O)NH$R^7$, wherein
- $R^7$ is selected from the group consisting of H, alkyl, cycloalkyl, and heterocyclyl, wherein
  - each of alkyl and cycloalkyl is optionally substituted with one or more occurrences of a substituent independently selected from the group consisting of alkyl, cyano, amino, hydroxy, alkoxy, and heterocyclyl, and
  - the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, Z is selected from the group consisting of acyl, amide, alkoxy, alkoxyalkyl, urea, amine, alkyl, cycloalkyl, H, cyano, cyanoalkyl, sulfonamide, hydroxy, hydroxyalkyl, halogen, sulfone, optionally substituted heterocyclyl, and optionally substituted heterocyclyl $(CH_2)_m$NH—, wherein the optionally substituted substituent on the heterocyclyl ring, at each occurrence, is independently $R^9$.

In some embodiments, Z is —C(O)NH$R^7$. In some embodiments, Z is —C(O)NH$R^7$ wherein $R^7$ is H. In some embodiments, Z is —C(O)NH$R^7$ wherein $R^7$ is alkyl. In some embodiments, Z is —C(O)NH$R^7$ wherein $R^7$ is methyl. In some embodiments, Z is —C(O)NH$R^7$ wherein $R^7$ is ethyl. In some embodiments, Z is —C(O)NH$R^7$ wherein $R^7$ is iso-propyl. In some embodiments, Z is —$NH_2$. In some embodiments, Z is carbamoyl. In some embodiments, Z is formyl. In some embodiments, Z is methylamino. In some embodiments, Z is ethylamino. In some embodiments, Z is beta-hydroxyethylamino. In some embodiments, Z is beta-methoxyethylamino. In some embodiments, Z is heterocyclyl. In some embodiments, Z is oxetanyl, tetrahydrofuranyl, or tetrahydropyranyl. In some embodiments, Z is morpholinyl. In some embodiments, Z is heterocyclylalkylamino. In some embodiments, Z is oxetanylalkylamino. In some embodiments, Z is azetidinylalkylamino. In some embodiments, Z is tetrahydropyranylalkylamino. In some embodiments, Z is heteroaryl. In some embodiments, Z is pyrazolyl. In some embodiments, Z is oxazolyl. In some embodiments, Z is oxadiazolyl. In some embodiments, Z is thiazolyl. In some embodiments, Z is selected from the group consisting of H, alkyl, and cycloalkyl. In some embodiments, Z is H. In some embodiments, Z is methyl. In some embodiments, Z is ethyl. In some embodiments, Z is iso-propyl. In some embodiments, Z is cyclopropyl.

In some embodiments, Z is —NHC(O)O$R^6$, wherein
- $R^6$, at each occurrence, is independently selected from the group consisting of H, alkyl, cycloalkyl, and heterocyclyl, wherein
  - each of alkyl and cycloalkyl is optionally substituted with one or more independent occurrences of $R^8$; and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and $R^8$ is selected from the group consisting of alkyl, cycloalkyl, and heterocyclyl, wherein each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, Q is —NH—C(O)—.

In some embodiments, Q is —C(O)—NH—.

In some embodiments, $X^1$, $X^4$, $X^5$, $X^6$, $X^7$, $X^8$, and $X^9$ are each CH; $X^2$ is N; and $X^3$ is selected from the group consisting of CH, C-$L^3$-$E^3$, C—O-$L^3$-$E^3$, and C—N($R^4$)-$L^3$-$E^3$.

In some embodiments, $X^1$, $X^4$, $X^5$, $X^6$, $X^7$, and $X^9$ are each CH; $X^2$ and $X^8$ are N; and $X^3$ is selected from the group consisting of CH, C-$L^3$-$E^3$, C—O-$L^3$-$E^3$, and C—N($R^4$)-$L^3$-$E^3$.

In some embodiments, $X^1$ and $X^4$ are each $CR^3$; $X^3$ is selected from the group consisting of CH, C-$L^3$-$E^3$, C—O-$L^3$-$E^3$, C—N($R^4$)-$L^3$-$E^3$, and N; and $X^2$, $X^5$, $X^6$, $X^7$, $X^8$, and $X^9$ are CH.

In some embodiments, $X^1$ and $X^4$ are each $CR^3$; $X^3$ is selected from the group consisting of CH, C-$L^3$-$E^3$, C—O-$L^3$-$E^3$, C—N($R^4$)-$L^3$-$E^3$, and N; $X^8$ is N; and $X^2$, $X^5$, $X^6$, $X^7$, and $X^9$ are CH.

In some embodiments, $X^1$ and $X^4$ are each $CR^3$; $X^3$ is selected from the group consisting of CH, C-$L^3$-$E^3$, C—O-$L^3$-$E^3$, C—N($R^4$)-$L^3$-$E^3$, and N; $X^5$ is N; and $X^2$, $X^6$, $X^7$, $X^8$, and $X^9$ are CH.

In some embodiments, $X^1$ and $X^4$ are each $CR^3$; $X^3$ is selected from the group consisting of CH, C-$L^3$-$E^3$, C—O-$L^3$-$E^3$, C—N($R^4$)-$L^3$-$E^3$, and N; $X^5$ and $X^8$ are N; and $X^2$, $X^6$, $X^7$, and $X^9$ are CH.

In some embodiments, $X^1$ is $CR^3$ and $X^3$ is selected from the group consisting of CH, C-$L^3$-$E^3$, C—O-$L^3$-$E^3$, and C—N($R^4$)-$L^3$-$E^3$, $X^2$ and $X^4$ are N; $X^5$, $X^6$, $X^7$, $X^8$, and $X^9$ are CH; and $X^1$ is $CR^3$.

In some embodiments, $X^1$ is $CR^3$; $X^4$ is selected from the group consisting of $CR^3$ and N; $X^3$ is N-$L^3$-$E^3$; $X^2$ is C=O; and $X^5$, $X^6$, $X^7$, $X^8$, and $X^9$ are CH.

In some embodiments, $X^1$ and $X^4$ are $CR^3$; $X^3$ is C=O; $X^2$ is N-$L^2$-$E^2$; and $X^5$, $X^6$, $X^7$, $X^8$, and $X^9$ are CH.

In some embodiments, $X^1$ and $X^4$ are $CR^3$; $X^2$ is N; $X^3$ is selected from the group consisting of CH, C-$L^3$-$E^3$, C—O-$L^3$-$E^3$, C—N($R^4$)-$L^3$-$E^3$, and N; $X^7$ is N; and $X^5$, $X^6$, $X^8$, and $X^9$ are CH.

In some embodiments, $X^1$ and $X^2$ are N; $X^4$ is $CR^3$; $X^3$ is selected from the group consisting of CH, C-$L^3$-$E^3$, C—O-$L^3$-$E^3$, and C—N($R^4$)-$L^3$-$E^3$; and $X^5$, $X^6$, $X^7$, $X^8$, and $X^9$ are CH.

In some embodiments, $X^1$ and $X^4$ are N; $X^5$, $X^6$, $X^7$, $X^8$, and $X^9$ are each CH; $X^2$ is selected from the group consisting of CH, C-$L^2$-$E^2$, C—O-$L^2$-$E^2$, C—N($R^4$)-$L^2$-$E^2$ and N; and $X^3$ is selected from the group consisting of CH, C-$L^3$-$E^3$, C—O-$L^3$-$E^3$, and C—N($R^4$)-$L^3$-$E^3$.

In some embodiments, $X^1$ and $X^3$ are N; $X^4$ is $CR^3$, $X^5$, $X^6$, $X^7$, $X^8$, and $X^9$ are each CH; and $X^2$ is selected from the group consisting of CH, C-$L^2$-$E^2$, C—O-$L^2$-$E^2$, and C—N($R^4$)-$L^2$-$E^2$.

In some embodiments, $X^1$ is N; $X^4$ is $CR^3$, $X^5$, $X^6$, $X^7$, $X^8$, and $X^9$ are each CH; $X^2$ is selected from the group consisting of CH, C-$L^2$-$E^2$, C—O-$L^2$-$E^2$, and C—N($R^4$)-$L^2$-$E^2$; and $X^3$ is selected from the group consisting of CH, C-$L^3$-$E^3$, C—O-$L^3$-$E^3$, and C—N($R^4$)-$L^3$-$E^3$.

In some embodiments, $X^1$ is $CR^3$; $X^2$, and $X^6$ are CH; and $X^3$, $X^4$, and $X^5$ are N.

In some embodiments, $X^1$ is $CR^3$; $X^2$, $X^5$, and $X^6$ are CH; and $X^3$ and $X^4$ are N.

In some embodiments, $X^1$ is $CR^3$; $X^2$, $X^5$, and $X^6$ are CH; and $X^3$, $X^4$, and $X^8$ are N.

In some embodiments, $E^3$ is selected from the group consisting of H, alkyl, and cycloalkyl, wherein cycloalkyl is optionally substituted with one or more occurrences of a substituent independently selected from the group consisting of alkyl, alkoxy, haloalkyl, haloalkoxy, halogen, hydroxy, and cyano.

In some embodiments, $E^3$ is selected from the group consisting of hydroxy, alkoxy, and cyano.

In some embodiments, $E^3$ is heterocyclyl, wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, $E^3$ is cycloalkyl, wherein cycloalkyl is optionally substituted with one or more occurrences of a substituent independently selected from the group consisting of alkyl, alkoxy, haloalkyl, haloalkoxy, halogen, hydroxy, and cyano. In some embodiments, $E^3$ is H. In some embodiments, $E^3$ is alkyl. In some embodiments, $E^3$ is methyl. In some embodiments, $E^3$ is ethyl. In some embodiments, $E^3$ is iso-propyl. In some embodiments, $E^3$ is cyclopropyl.

In some embodiments, $E^3$ is selected from the group consisting of hydroxyalkyl, cyanoalkyl, hydroxy, alkoxy, alkoxyalkyl, cyano, and sulfonyl. In some embodiments, $E^3$ is hydroxy. In some embodiments, $E^3$ is alkoxy. In some embodiments, $E^3$ is methoxy.

In some embodiments, $E^3$ is heterocyclyl, wherein the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone. In some embodiments, $E^3$ is oxatanyl. In some embodiments, $E^3$ is tetrahydrofuranyl. In some embodiments, $E^3$ is tetrahydropyranyl. In some embodiments, $E^3$ is azetidinyl. In some embodiments, $E^3$ is pyrrolidinyl. In some embodiments, $E^3$ is morpholino. In some embodiments, $E^3$ is piperazinyl. In some embodiments, $E^3$ is piperidinyl.

In some embodiments, $E^2$ is selected from the group consisting of H, hydroxy, alkoxy, alkoxyalkyl, cyano, sulfonyl, and heterocyclyl wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl, alkyl, amine, haloalkoxy, haloalkyl, and sulfone. In some embodiments, $E^2$ is heterocyclyl wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl. In some embodiments, $E^2$ is H. In some embodiments, $E^2$ is hydroxy or alkoxy. In some embodiments, $E^2$ is alkoxyalkyl. In some embodiments, $E^2$ is cyano. In some embodiments, $E^2$ is alkyl. In some embodiments, $E^2$ is oxetanyl. In some embodiments, $E^2$ is azetinyl. In some embodiments, $E^2$ is pyrrolidinyl. In some embodiments, $E^2$ is tetrahydropyranyl. In some embodiments, $E^2$ is morpholino. In some embodiments, $E^2$ is piperazinyl. In some embodiments, $E^2$ is piperidinyl. In some embodiments, $E^2$ is selected from the group consisting of hydroxy, alkoxy, alkoxyalkyl, cyano, sulfonyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl, H, alkyl, amine, haloalkoxy, haloalkyl, and sulfone.

In some embodiments, $R^1$ is selected from the group consisting of H, alkyl, haloalkyl, cyano, and halogen. In some embodiments, $R^1$ is methyl or fluorine. In some embodiments, $R^1$ is H. In some embodiments, $R^1$ is alkyl. In some embodiments, $R^1$ is methyl. In some embodiments, $R^1$ is ethyl. In some embodiments, $R^1$ is cyano. In some embodiments, $R^1$ is F. In some embodiments, $R^1$ is $C_1$. In some embodiments, $R^1$ is $CF_3$.

In some embodiments, $R^2$ is selected from H and F. In some embodiments, $R^2$ is H. In some embodiments, $R^2$ is F.

In some embodiments, $R^1$ is methyl and $R^2$ is H. In some embodiments, $R^1$ is methyl and $R^2$ is F.

In some embodiments, the Z-substituted ring is selected from the group consisting of

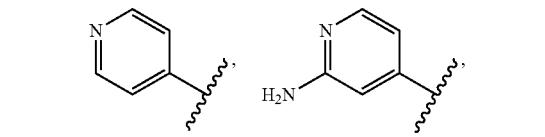

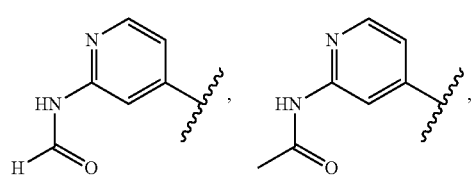

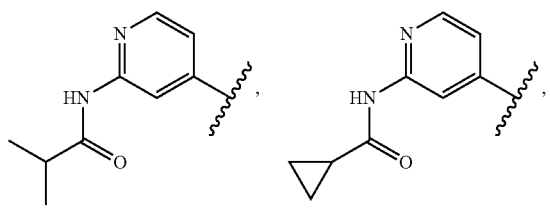

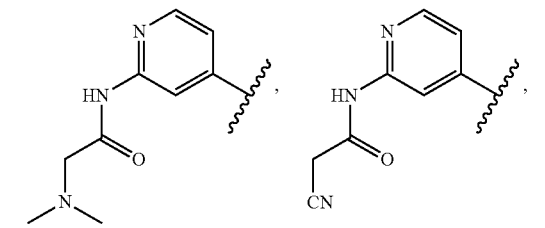

-continued

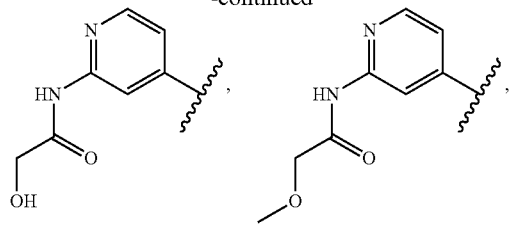

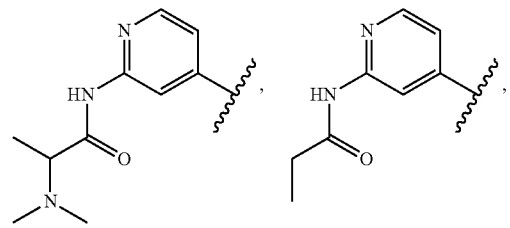

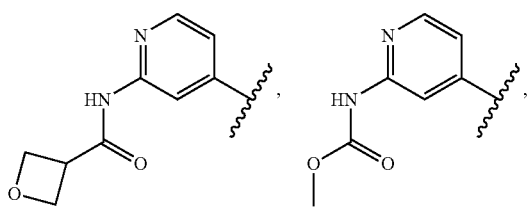

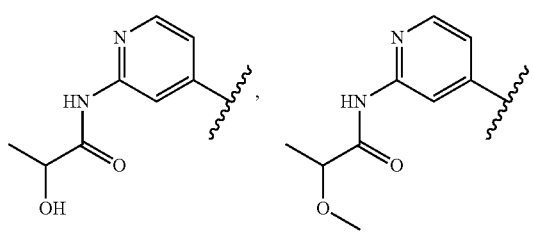

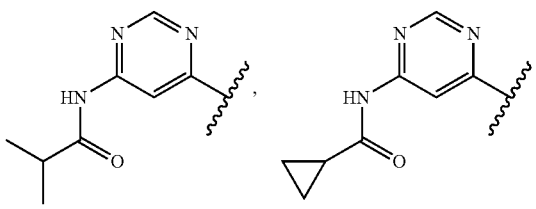

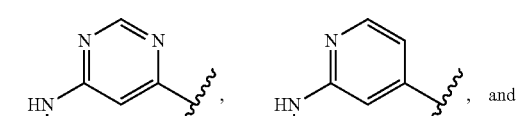

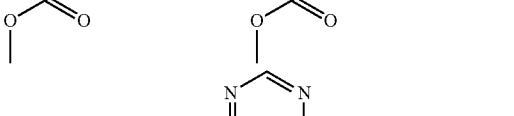, and

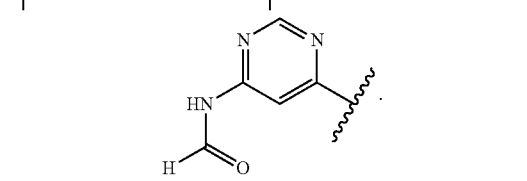.

In some embodiments, the Z-substituted ring is selected from the group consisting of
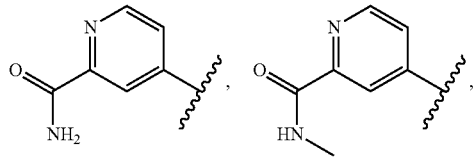
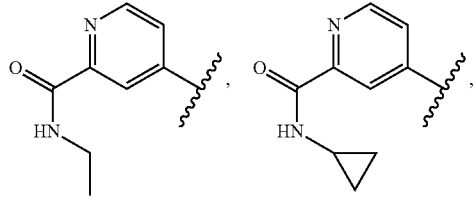
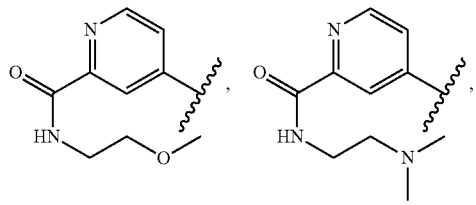
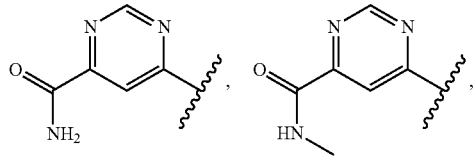
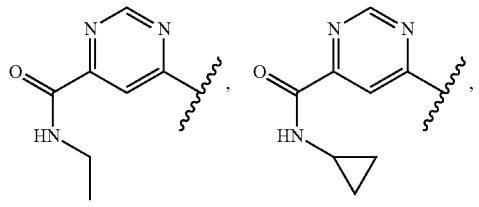
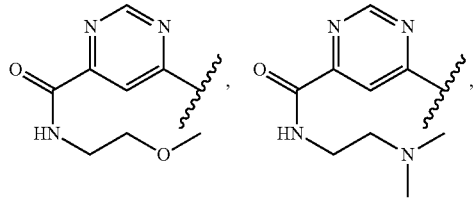
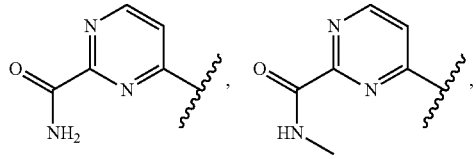
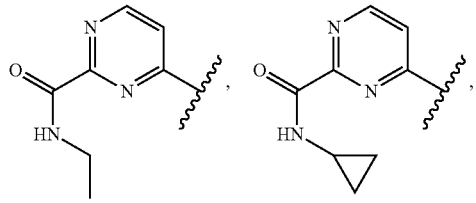
-continued
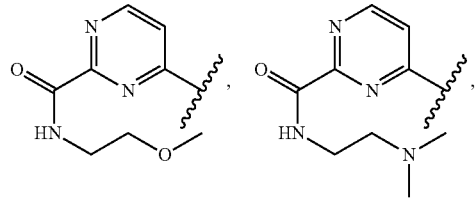
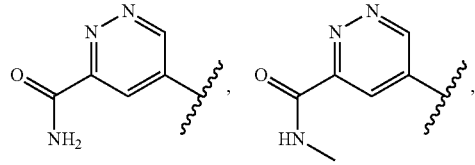
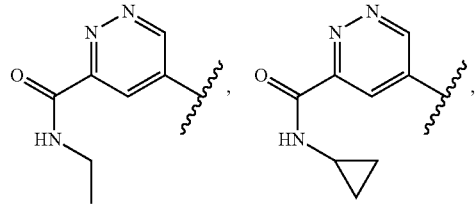
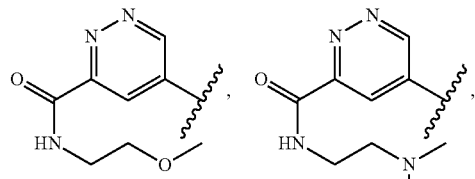
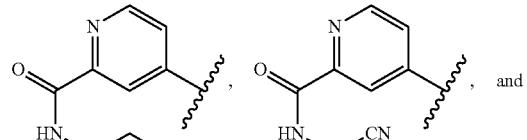, and
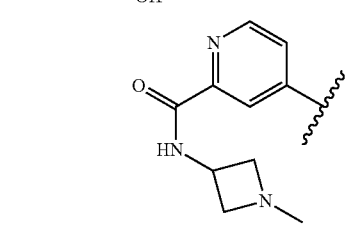.
In some embodiments, the Z-substituted ring is selected from the group consisting of
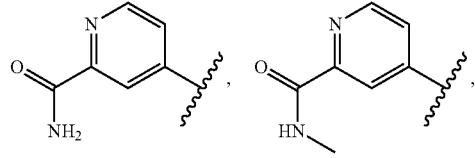
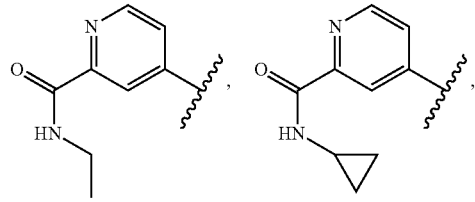

121
-continued
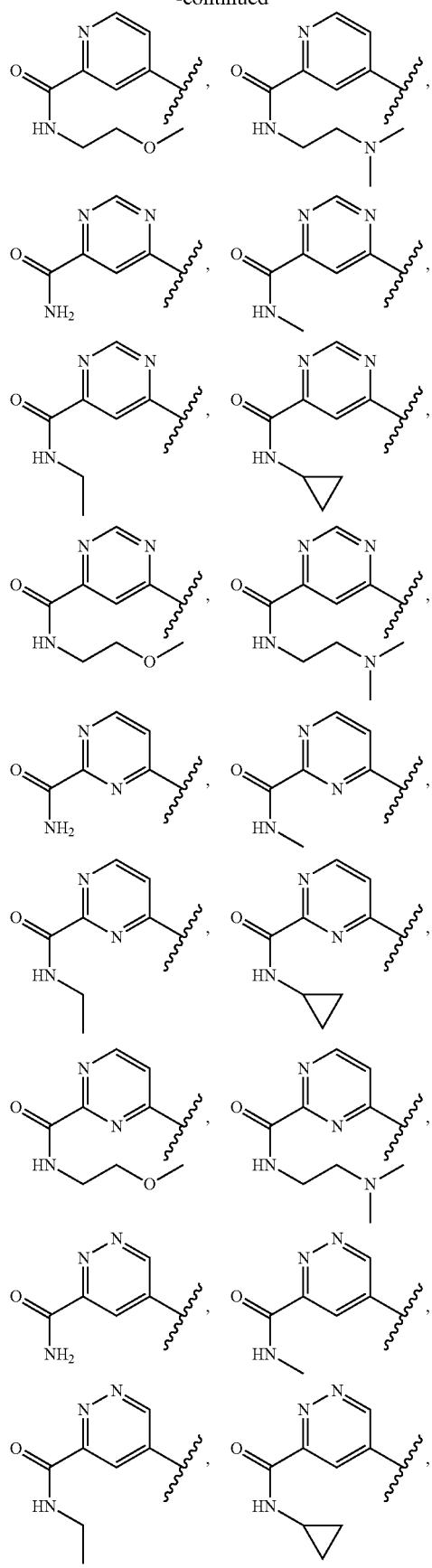
122
-continued
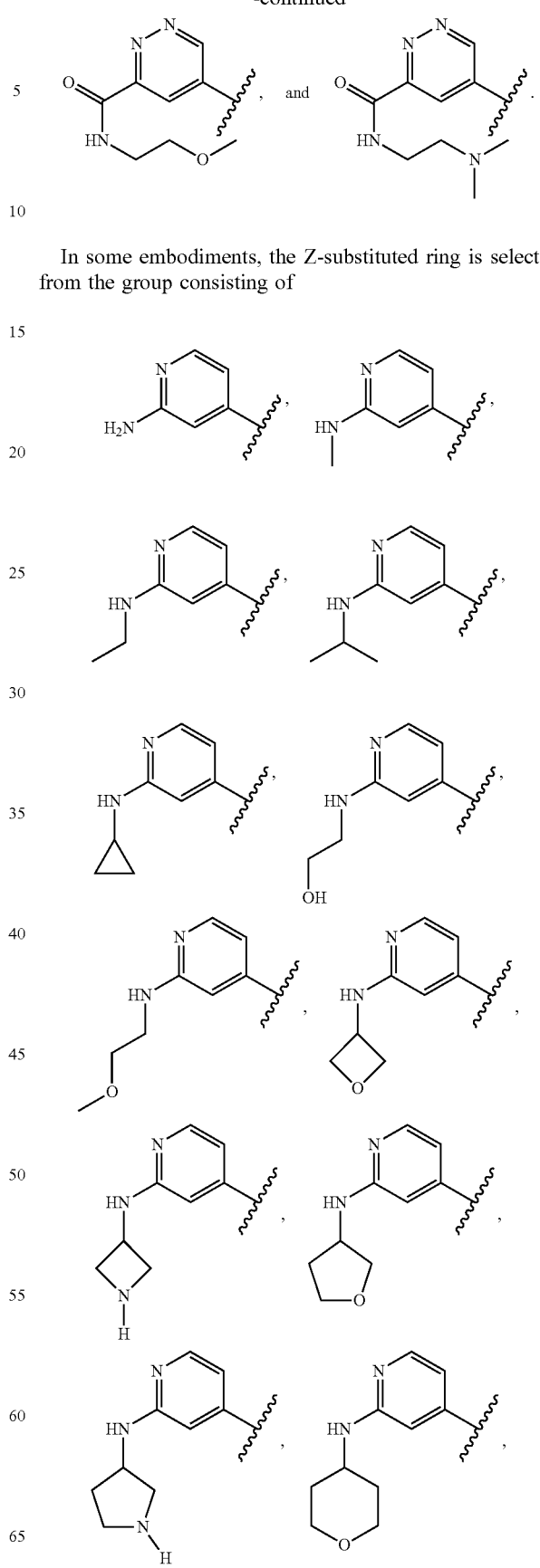
In some embodiments, the Z-substituted ring is selected from the group consisting of -continued
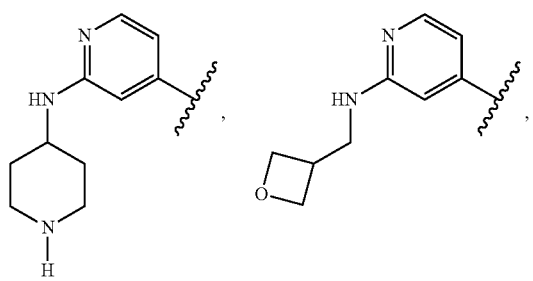
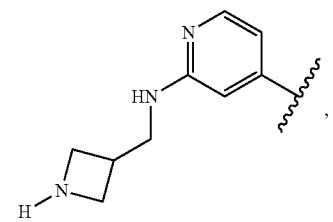
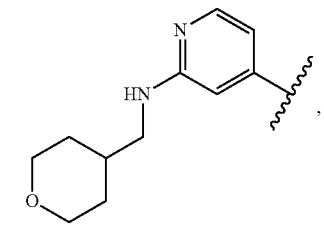
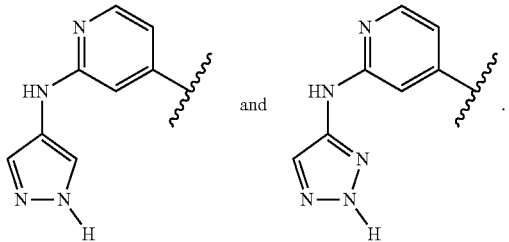
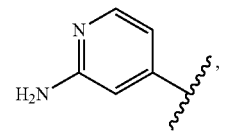, 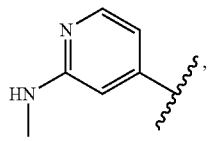 and 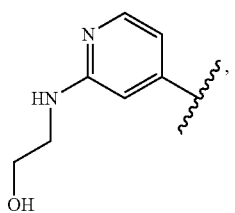.
In some embodiments, the Z-substituted ring is selected from the group consisting of
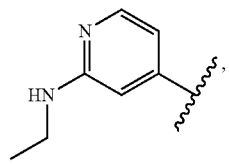
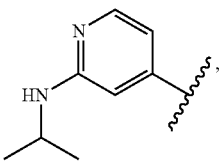
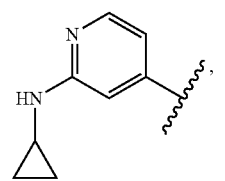
-continued
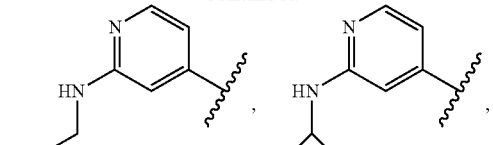
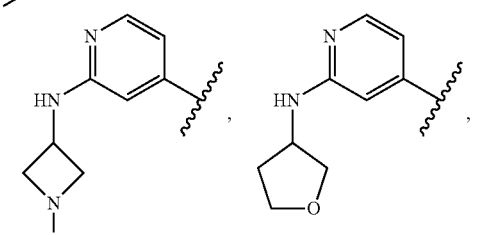
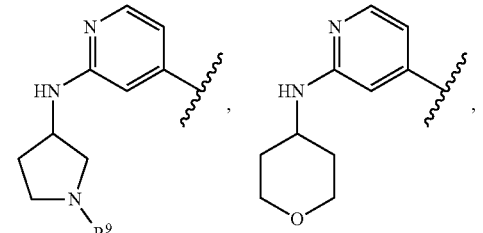
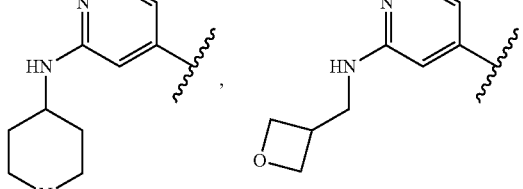
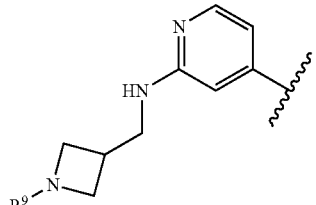
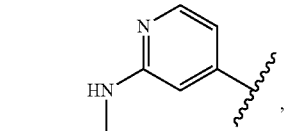
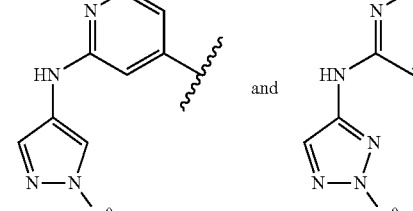
wherein each occurrence of $R^9$ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, the Z-substituted ring is selected from the group consisting of

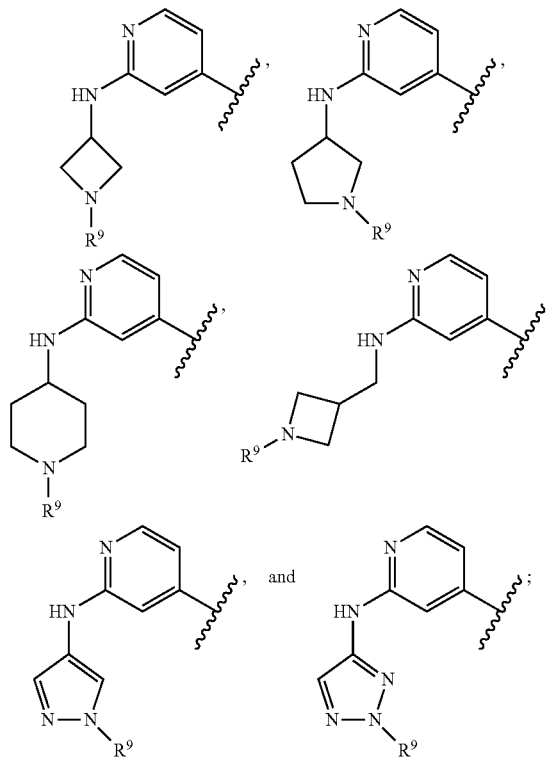

wherein each occurrence of $R^9$ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, the Z-substituted ring is selected from the group consisting of

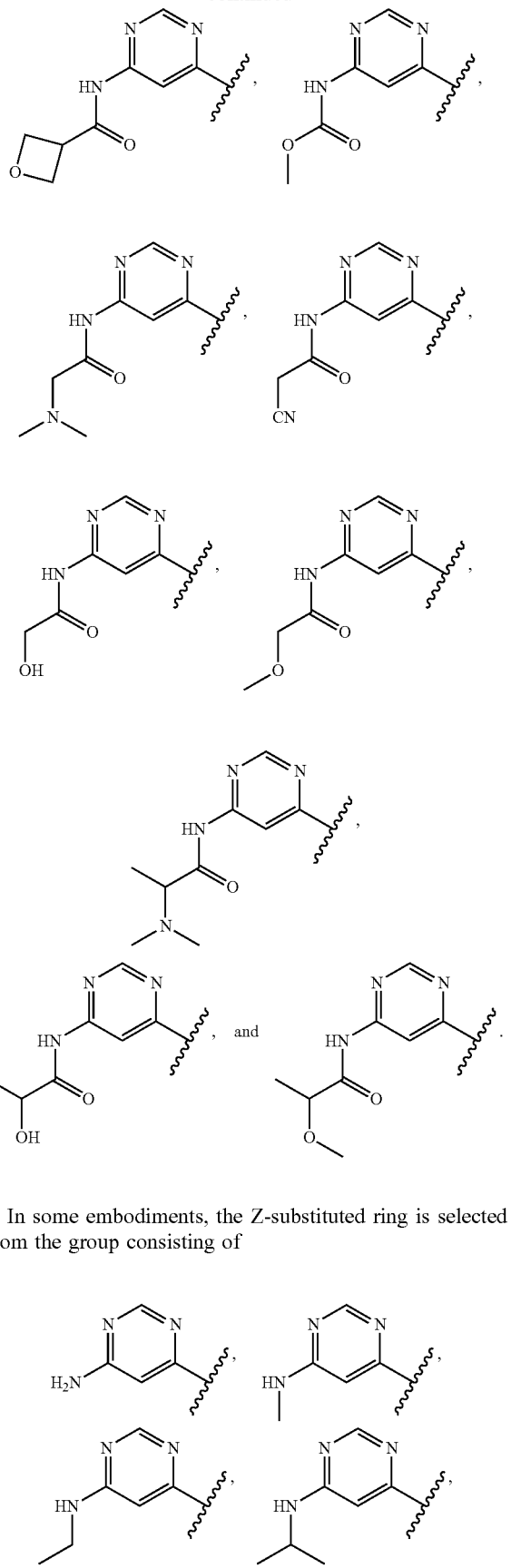

In some embodiments, the Z-substituted ring is selected from the group consisting of

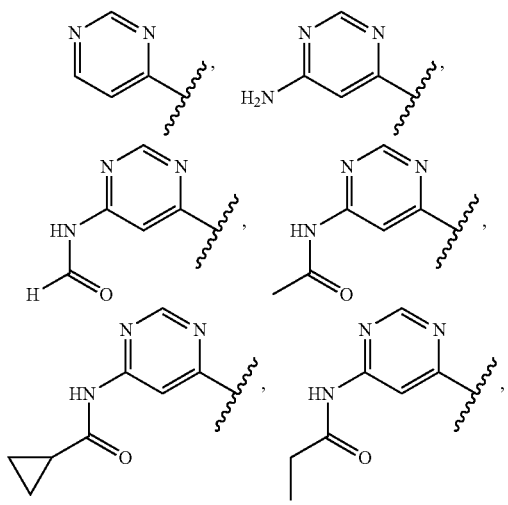

-continued
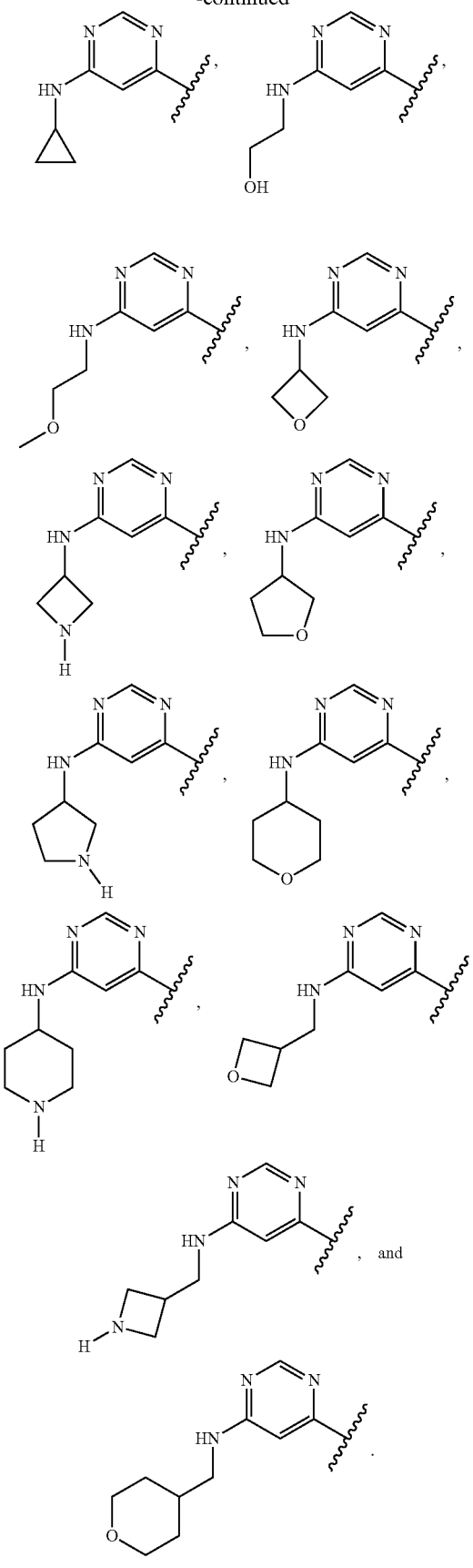
, and
In some embodiments, the Z-substituted ring is selected from the group consisting of
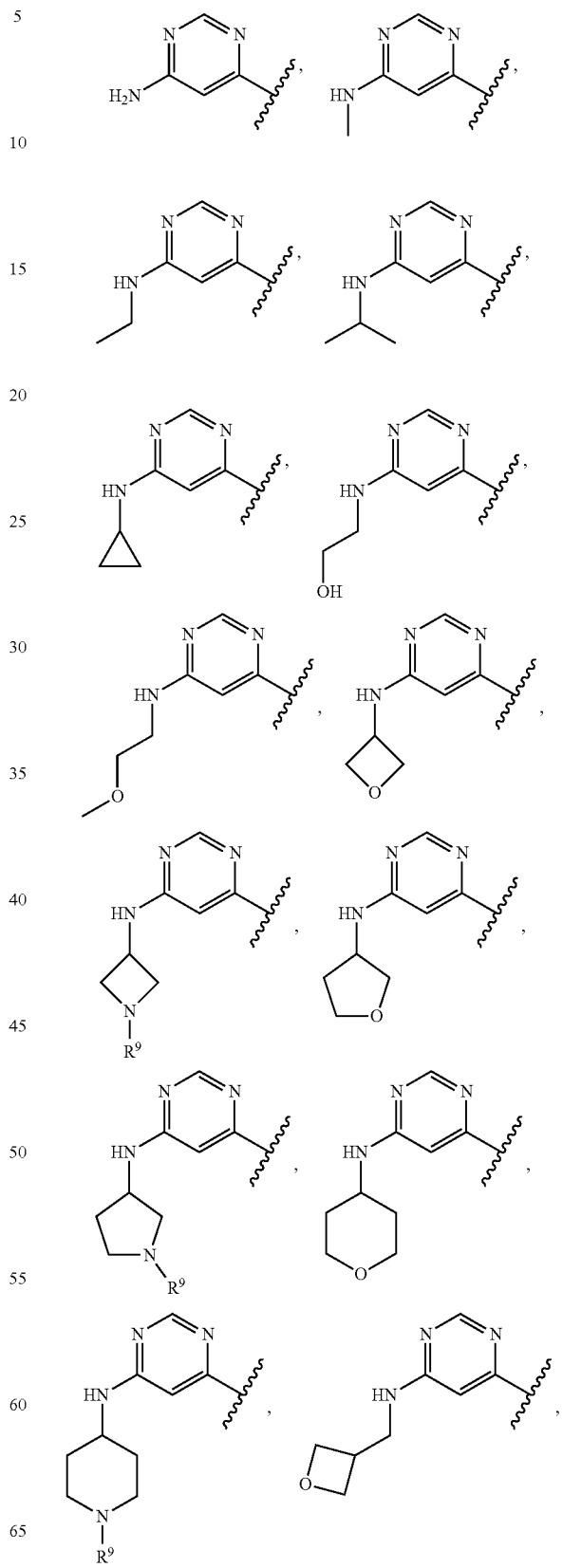

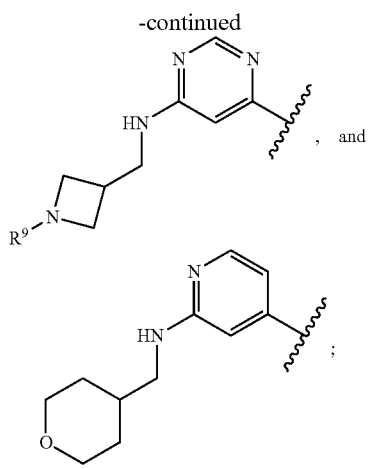

wherein each occurrence of R⁹ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, the Z-substituted ring is selected from the group consisting of

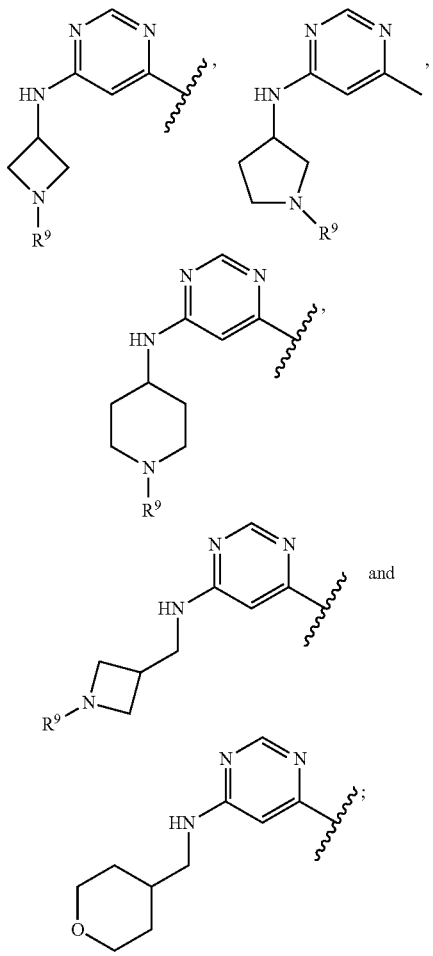

wherein each occurrence of R⁹ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, the Z-substituted ring is selected from the group consisting of

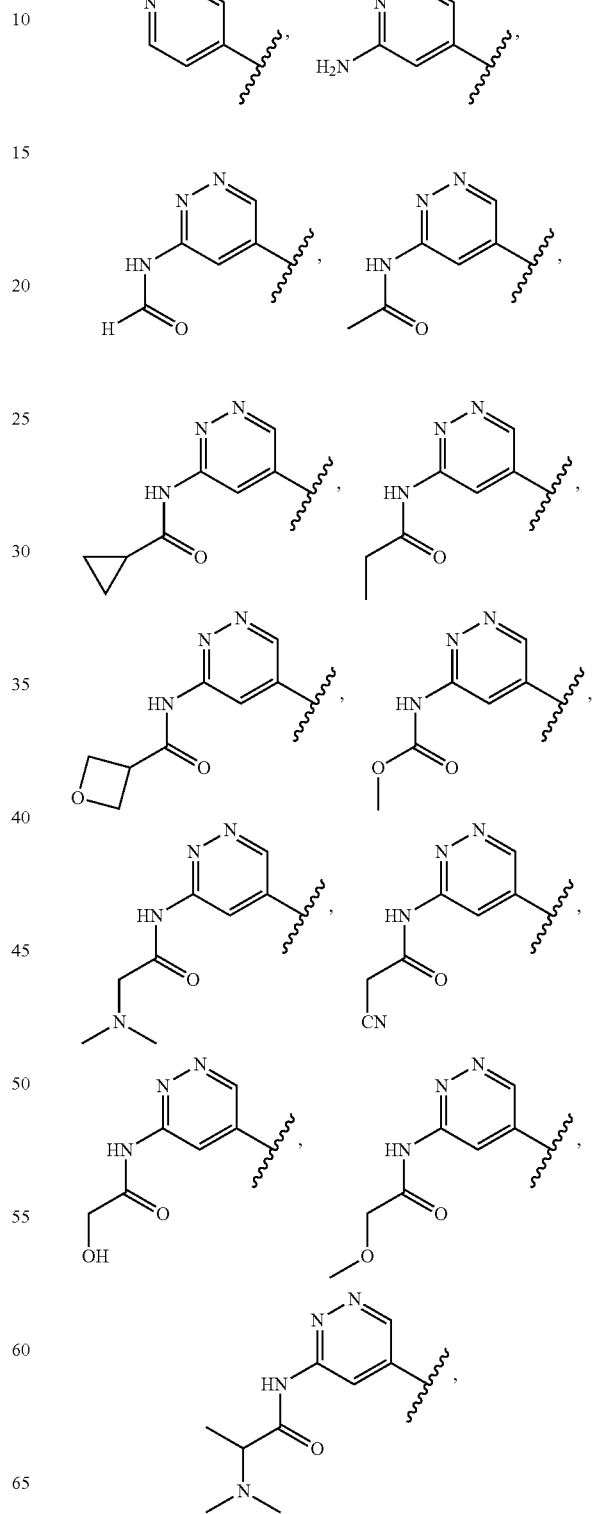

-continued
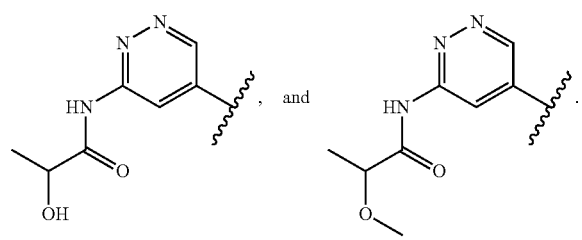 [SMILES: *c1cnnc(NC(=O)C(C)O)c1 ; *c1cnnc(NC(=O)C(C)OC)c1], and
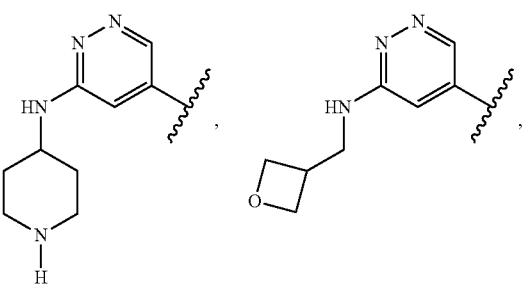
-continued
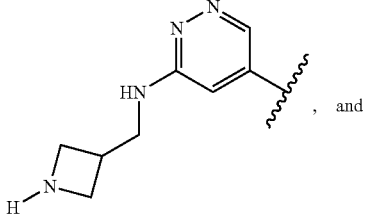,
In some embodiments, the Z-substituted ring is selected from the group consisting of
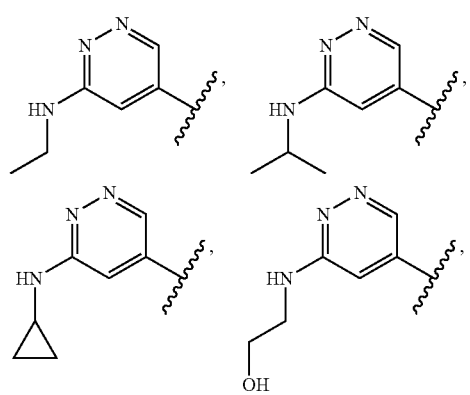
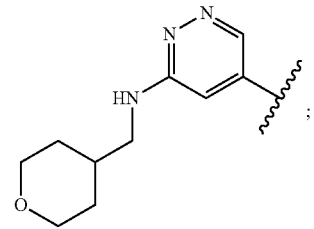, and
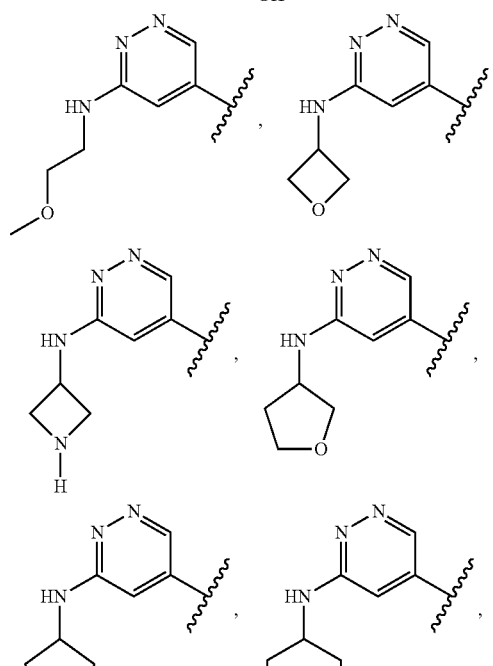
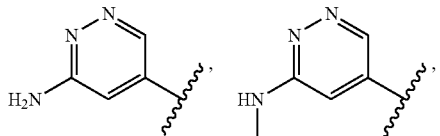;
In some embodiments, the Z-substituted ring is selected from the group consisting of
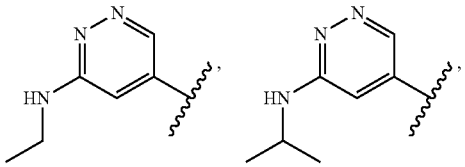
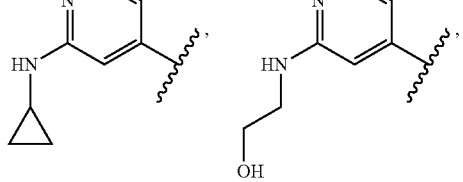
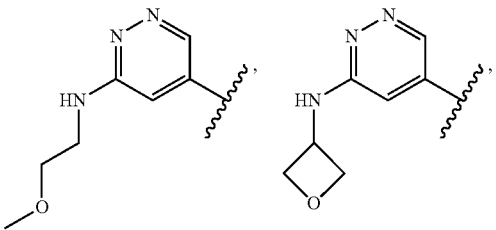

-continued

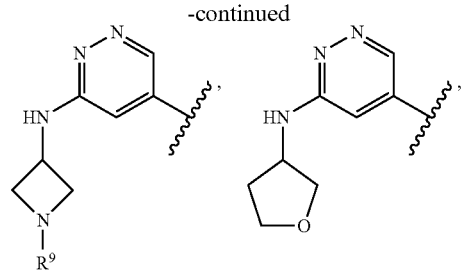

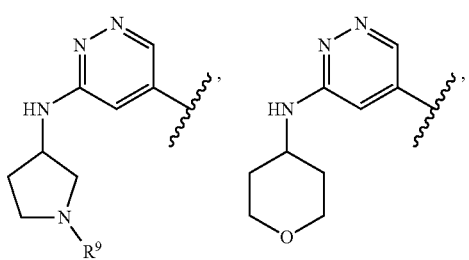

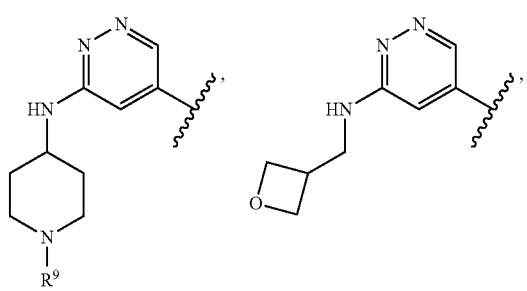

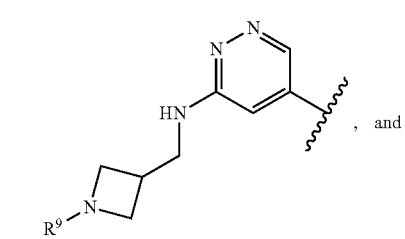

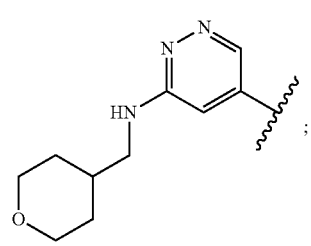

wherein each occurrence of R⁹ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, the Z-substituted ring is selected from the group consisting of

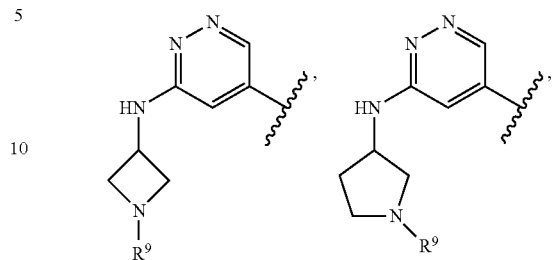

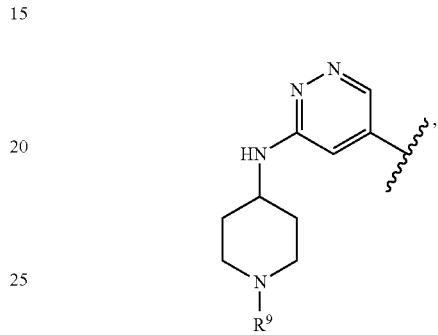

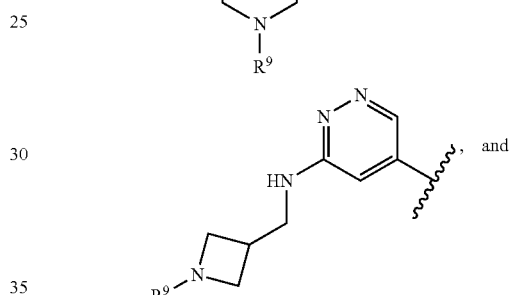

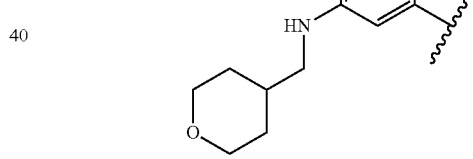

wherein each occurrence of R⁹ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, the Z-substituted ring is selected from the group consisting of

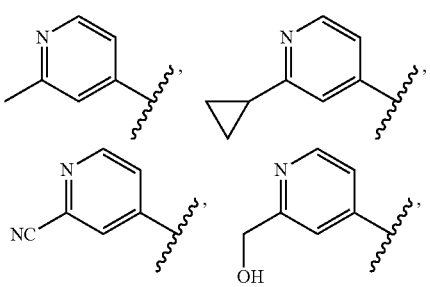

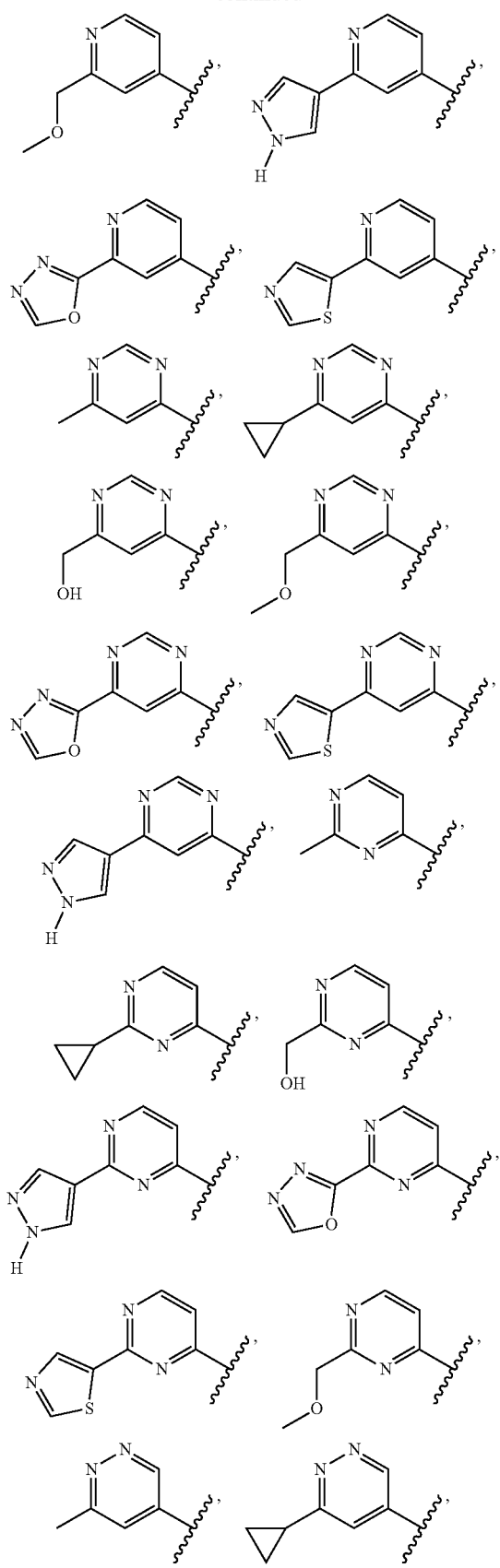
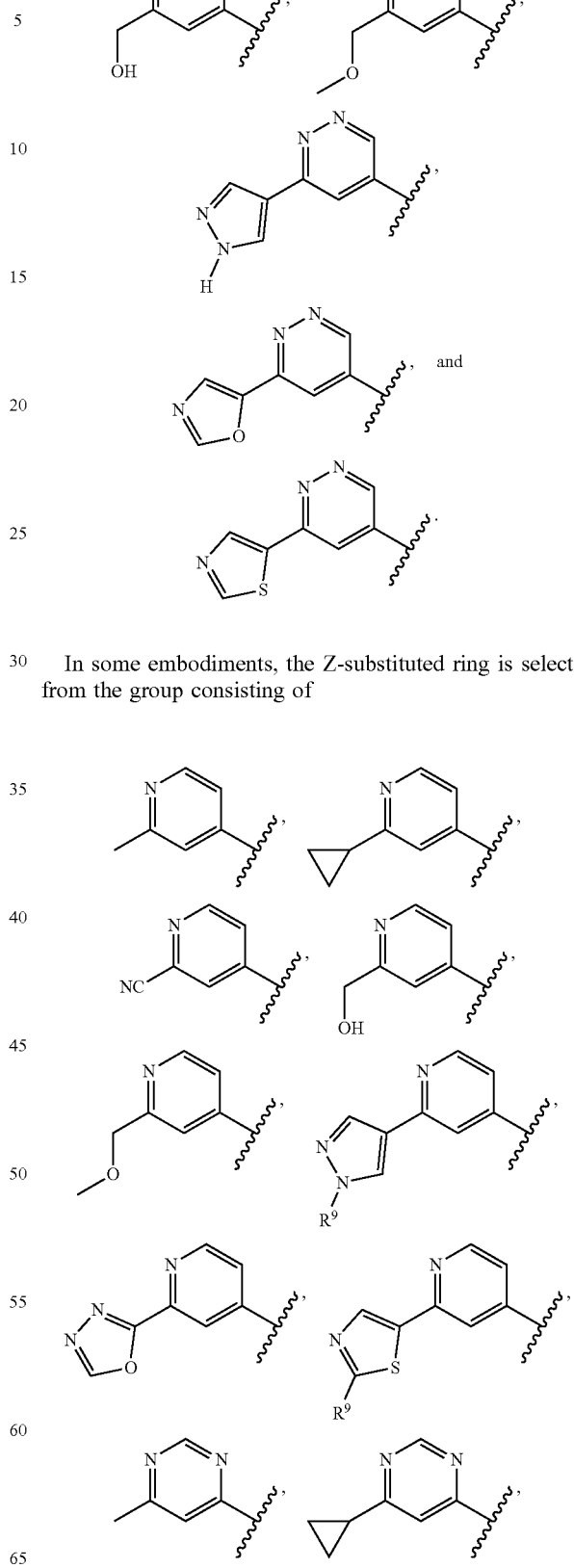
In some embodiments, the Z-substituted ring is selected from the group consisting of

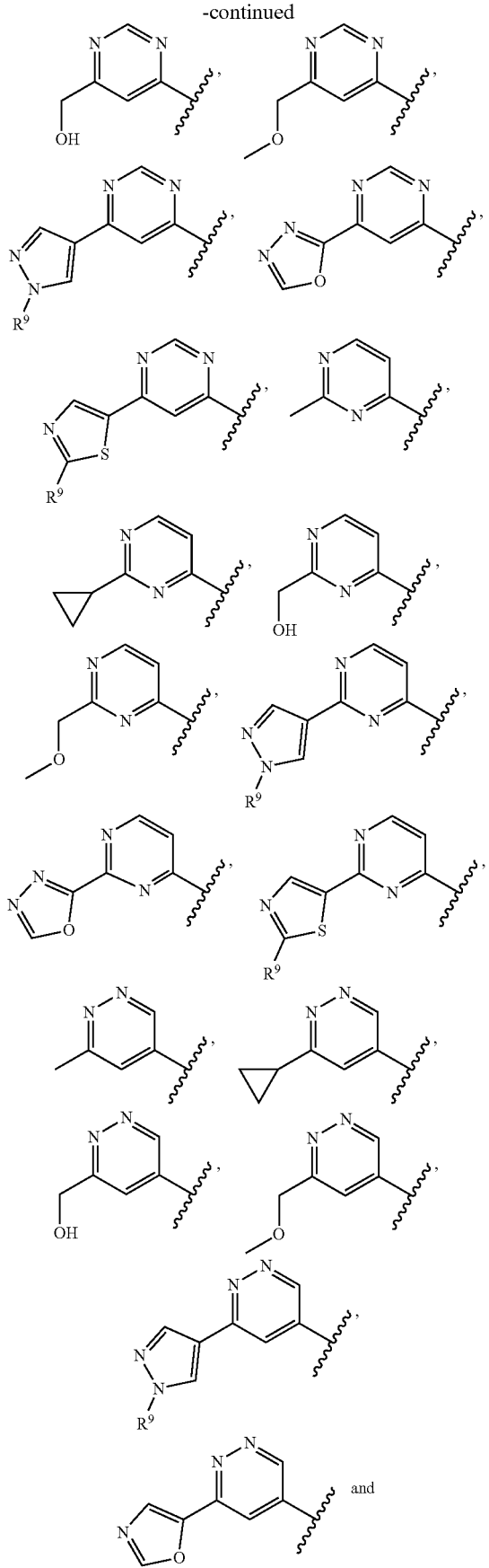
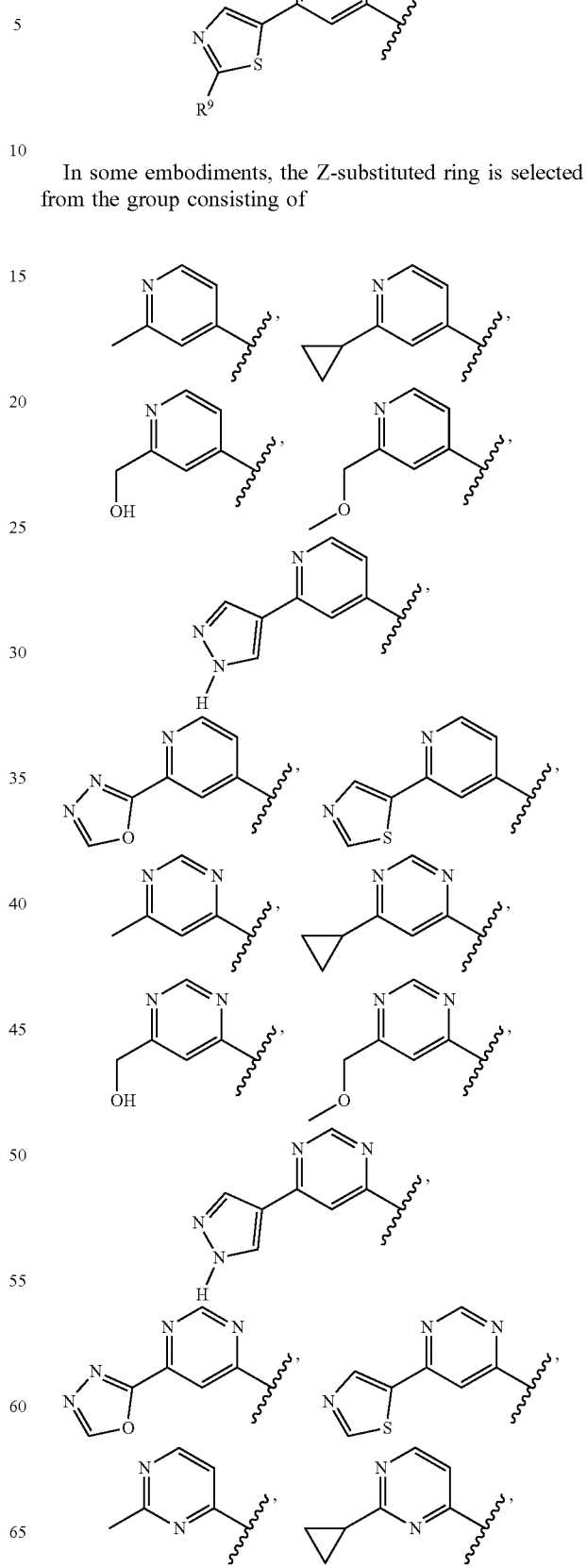
In some embodiments, the Z-substituted ring is selected from the group consisting of -continued

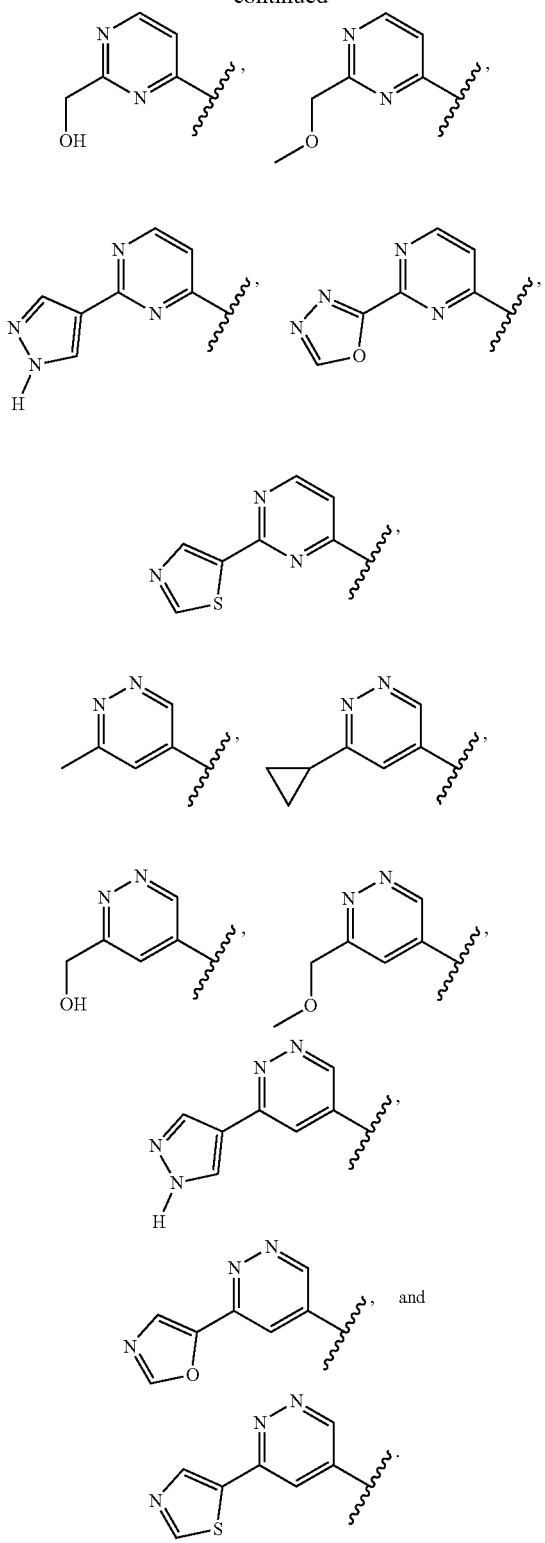

In some embodiments, the Z-substituted ring is selected from the group consisting of; wherein each occurrence of $R^9$ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, the Z-substituted ring is selected from the group consisting of

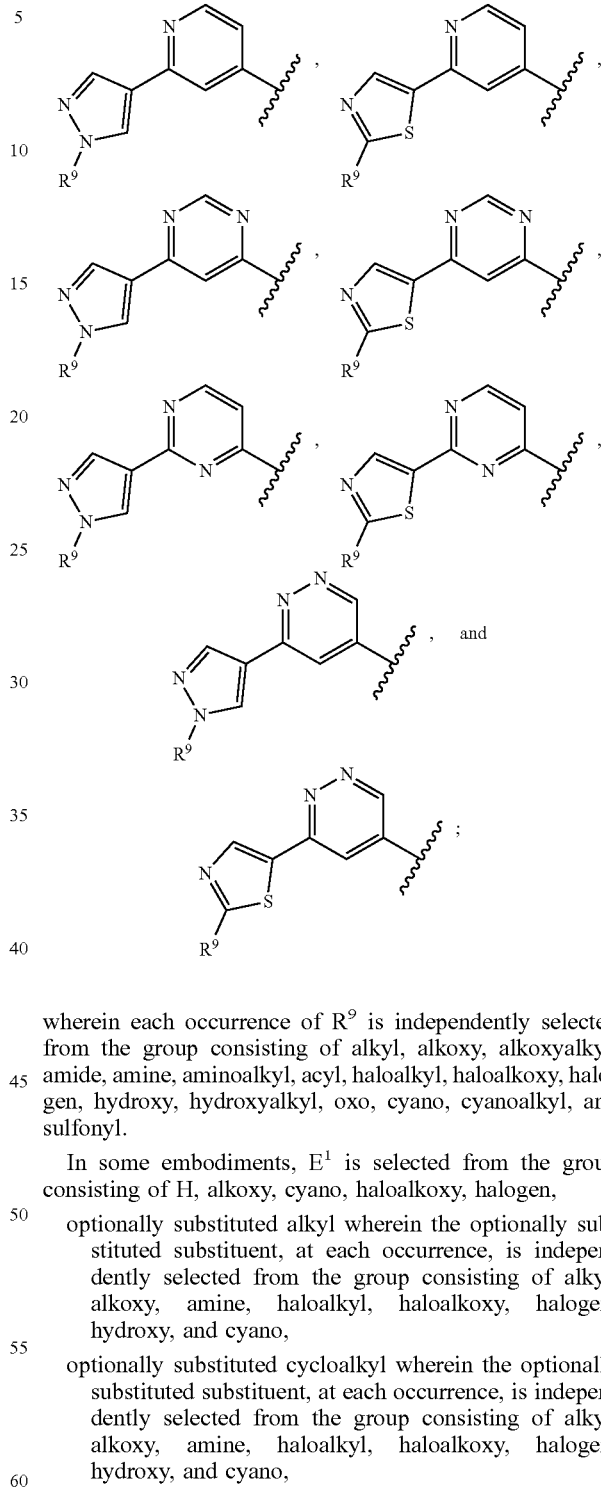

wherein each occurrence of $R^9$ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, $E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and the optionally substituted heteroaryl is not

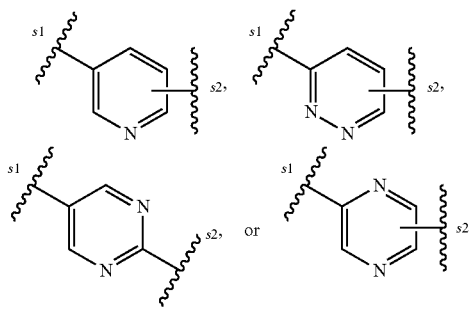

wherein s1 is the site covalently linked to $L^1$; and s2 is the site covalently linked to H or the optionally substituted substituent, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, $E^1$ is selected from the group consisting of H, alkoxy, cyano, haloalkoxy, halogen, optionally substituted alkyl wherein the optionally substituted substituent, at each occurrence, is independently selected from the group consisting of alkyl, alkoxy, amine, haloalkyl, haloalkoxy, halogen, hydroxy, and cyano, optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and the optionally substituted heteroaryl is not

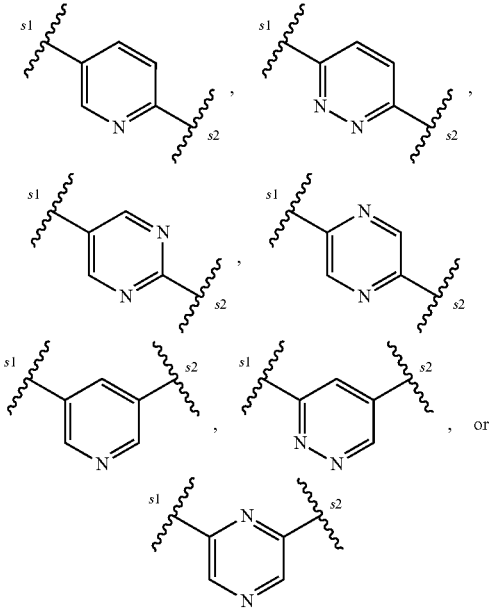

wherein s1 is the site covalently linked to $L^1$; and s2 is the site covalently linked to H or the optionally substituted substituent, optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, $E^1$ is optionally substituted 5-6 membered heteroaryl or optionally substituted phenyl, wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, $E^1$ is optionally substituted 5-6 membered heteroaryl or optionally substituted phenyl, wherein the optionally substituted substituent, at each occurrence, is independently selected from the group consisting of alkyl, alkoxy, alkoxyalkyl, haloalkyl, haloalkoxy halogen, cyano, cyanoalkyl, and cyclopropyl, wherein the alkyl substituent is independently optionally substituted, at each occurrence, with a substituent selected from the group consisting of cycloalkyl, cyano, alkoxy, and aminoalkyl, and the cycloalkyl substituent is independently optionally substituted, at each occurrence, with a substituent selected from the group consisting of cycloalkyl, cyano, alkoxy, and aminoalkyl.

In some embodiments, $E^1$ is selected from the group consisting of H, alkoxy, cyano, haloalkoxy, halogen, and optionally substituted alkyl wherein the optionally substituted substituent, at each occurrence, is independently selected from the group consisting of alkyl, alkoxy, amine, haloalkyl, haloalkoxy, halogen, hydroxy, and cyano.

In some embodiments, $E^1$ is selected from the group consisting of alkoxy, cyano, haloalkoxy, and optionally substituted alkyl wherein the optionally substituted substituent, at each occurrence, is independently selected from the group consisting of alkyl, alkoxy, amine, haloalkyl, haloalkoxy, halogen, hydroxy, and cyano.

In some embodiments, $E^1$ is optionally substituted cycloalkyl wherein the optionally substituted substituent, at each occurrence, is independently selected from the group consisting of alkyl, alkoxy, amine, haloalkyl, haloalkoxy, halogen, hydroxy, and cyano.

In some embodiments, $E^1$ is optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

In some embodiments, $E^1$ is selected from the group consisting of

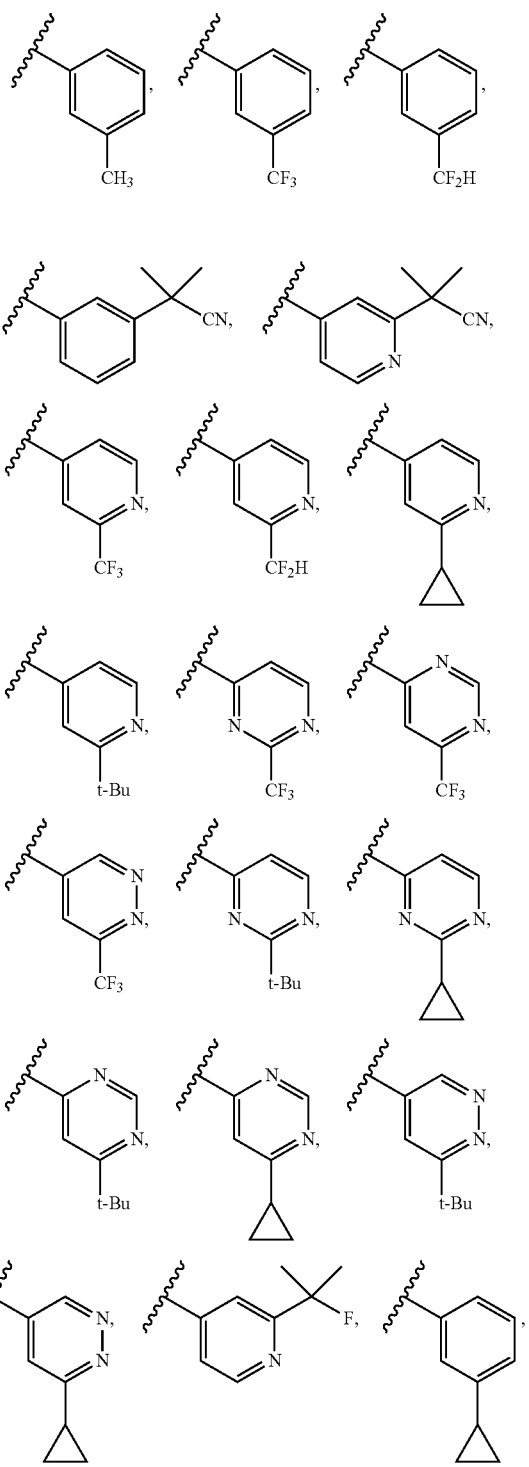

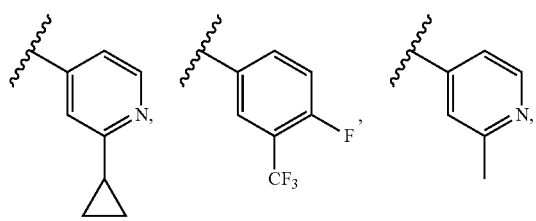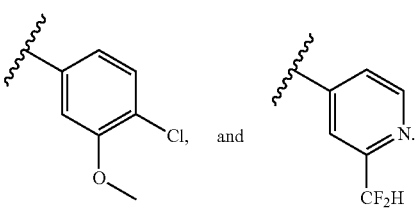
In some embodiments, E is selected from the group consisting of
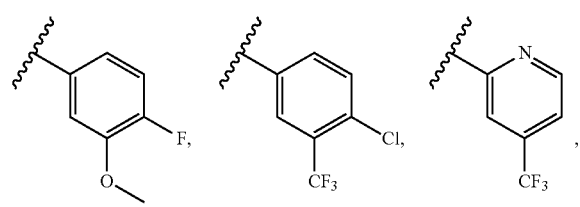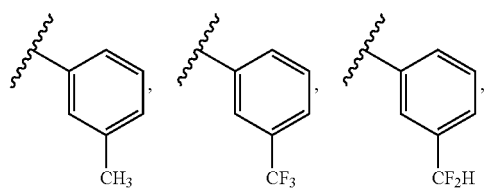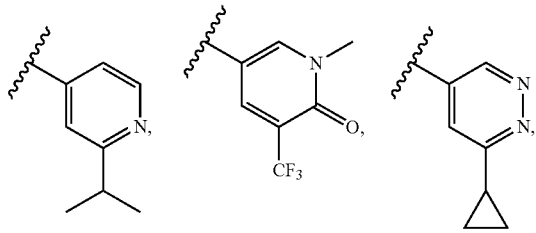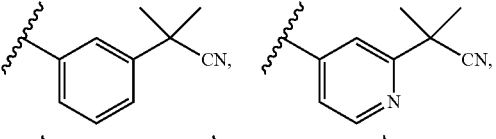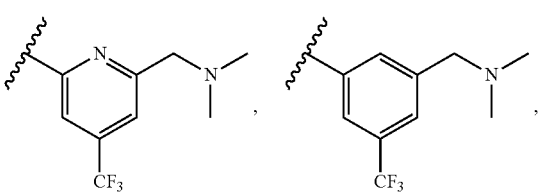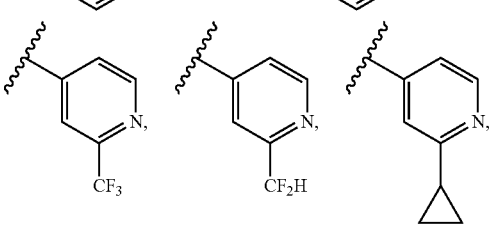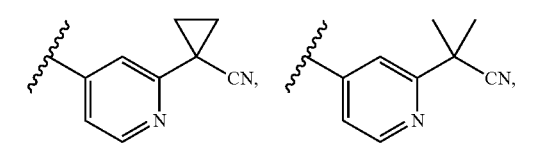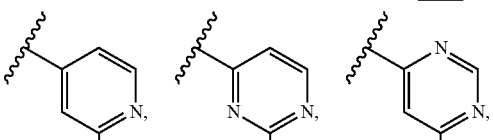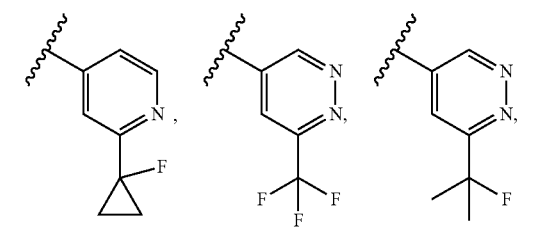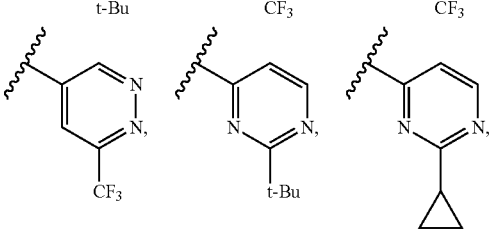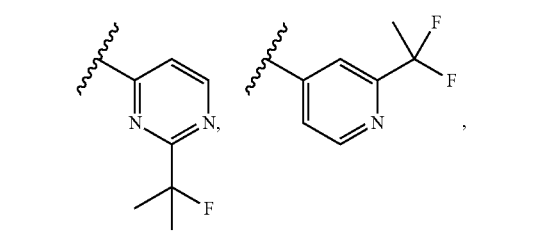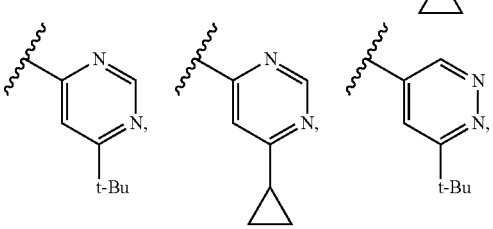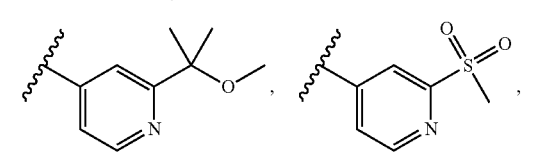

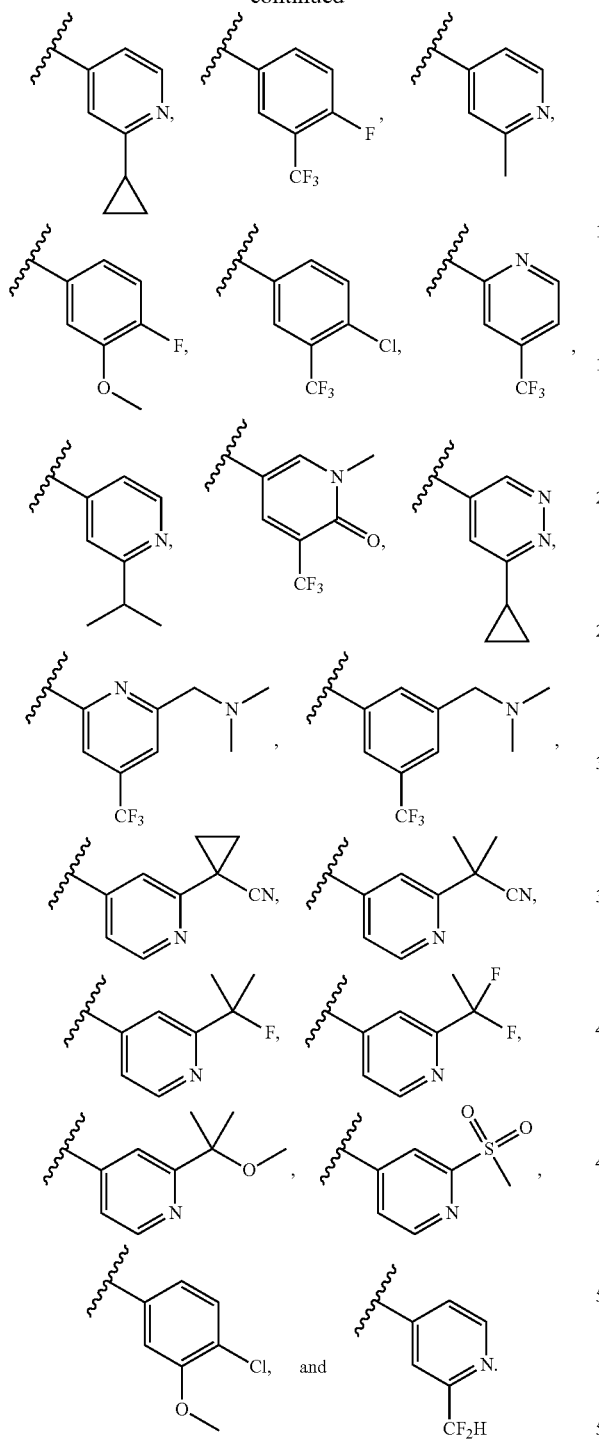
In some embodiments, E¹ is selected from the group consisting of
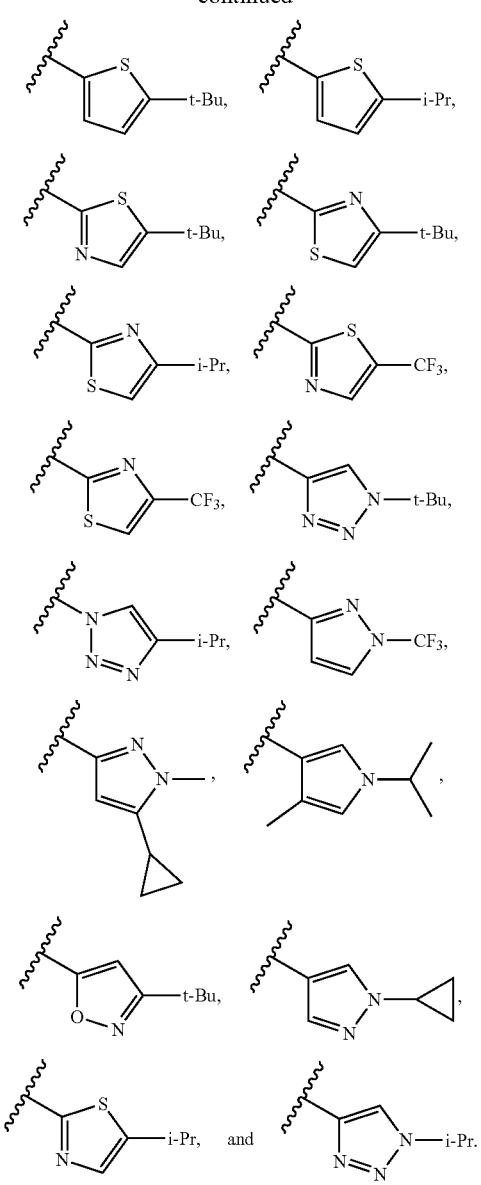
In some embodiments, E¹ is selected from the group consisting of
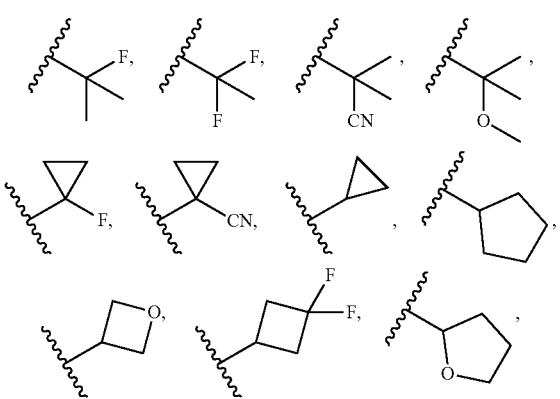

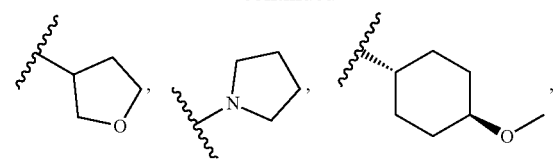

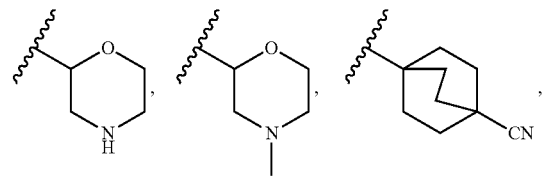

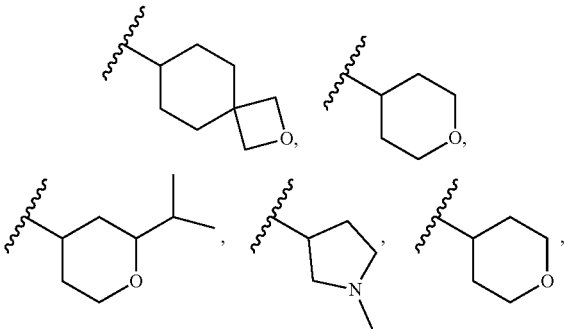

In some embodiments, E is selected from the group consisting of

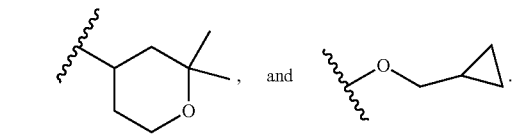

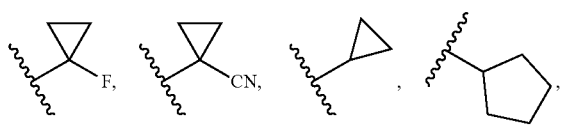

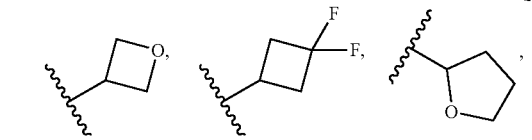

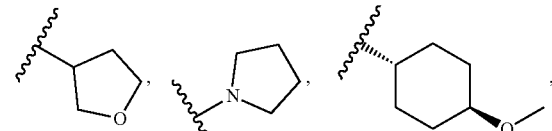

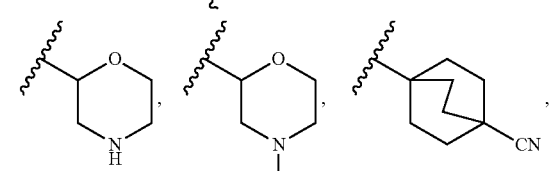

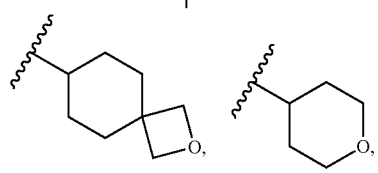

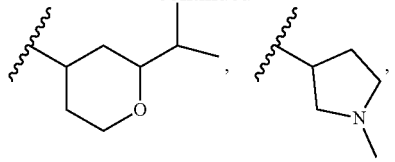

In some embodiments, $E^1$ is selected from the group consisting of

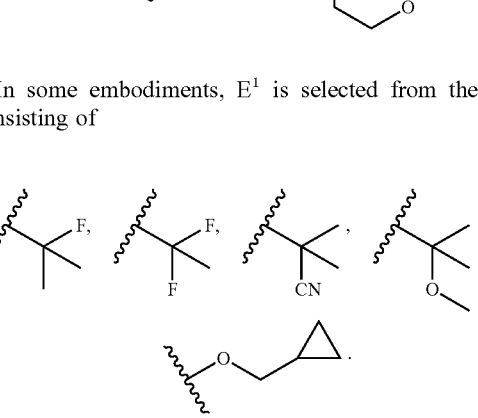

In some embodiments, $L^3$ is a direct bond. In some embodiments, $L^3$ is $C_1$-$C_6$alkyl optionally substituted with $(E^{31})_p$. In some embodiments, $L^3$ is ethylene. In some embodiments, $L^3$ is propylene.

In some embodiments, $X^3$ is selected from the group consisting of CH, C-$L^3$-$E^3$, C—O-$L^3$-$E^3$, C—N($R^4$)-$L^3$-$E^3$, C═O, N, and N-$L^3$-$E^3$. In some embodiments, $X^3$ is CH. In some embodiments, $X^3$ is C-$L^3$-$E^3$. In some embodiments, $X^3$ is C—O-$L^3$-$E^3$. In some embodiments, $X^3$ is C—N($R^4$)-$L^3$-$E^3$. In some embodiments, $X^3$ is C═O. In some embodiments, $X^3$ is N. In some embodiments, $X^3$ is N-$L^3$-$E^3$.

In some embodiments, $X^2$ is selected from the group consisting of N, CH, C═O, C—O-$L^2$-$E^2$, C-$L^2$-$E^2$, C—N($R^4$)-$L^2$-$E^2$, and N-$L^2$-$E^2$. In some embodiments, $X^2$ is N. In some embodiments, $X^2$ is CH. In some embodiments, $X^2$ is C(O). In some embodiments, $X^2$ is C—O-$L^2$-$E^2$. In some embodiments, $X^2$ is C-$L^2$-$E^2$. In some embodiments, $X^2$ is C—N($R^4$)-$L^2$-$E^2$. In some embodiments, $X^2$ is N-$L^2$-$E^2$.

In some embodiments, $L^1$ is selected from the group consisting of direct bond,

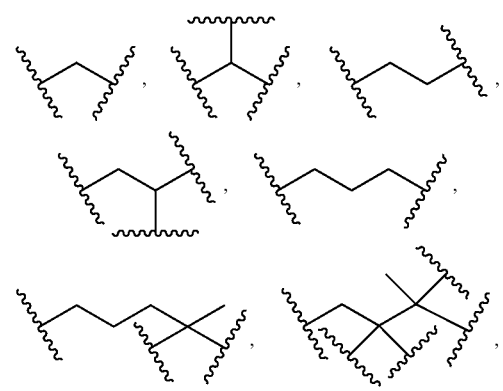

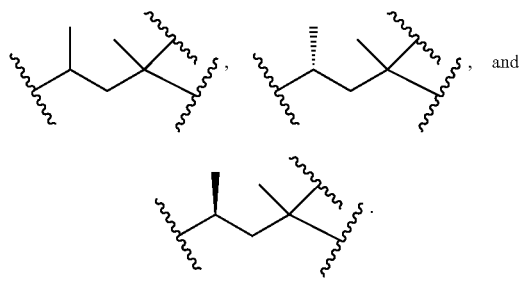

In some embodiments, $L^1$ is a direct bond. In some embodiments, $L^1$ is a $C_1$-$C_6$ alkyl optionally substituted with $(E^{11})_m$. In some embodiments, $L^1$ is taken together with $R^3$ and the N atom to which $L^1$ and $R^3$ are attached to form a heterocycle having from 4 to 6 atoms in the ring structure.

In some embodiments,

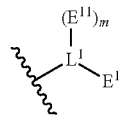

is selected from the group consisting of

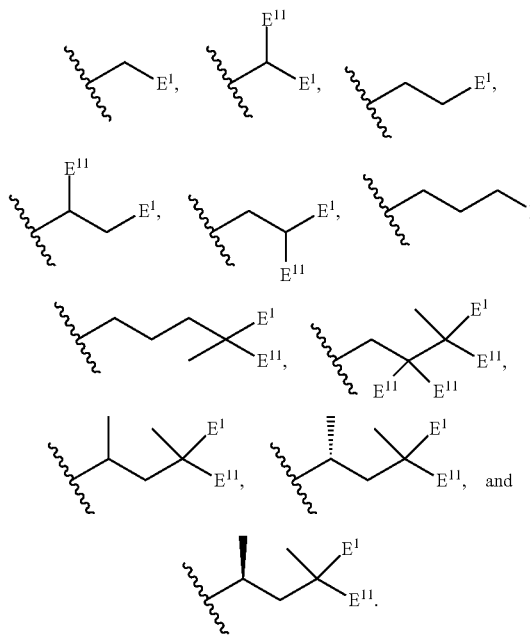

In some embodiments,

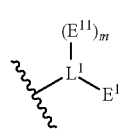

is selected from the group consisting of

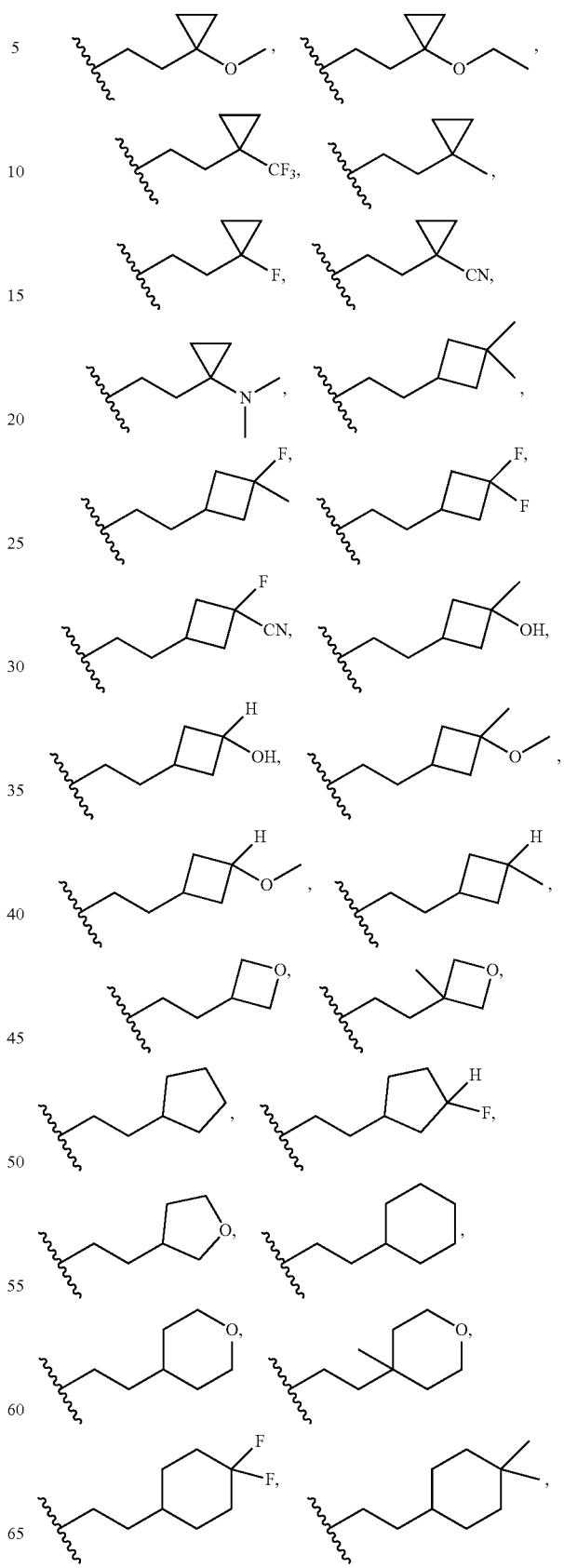

-continued
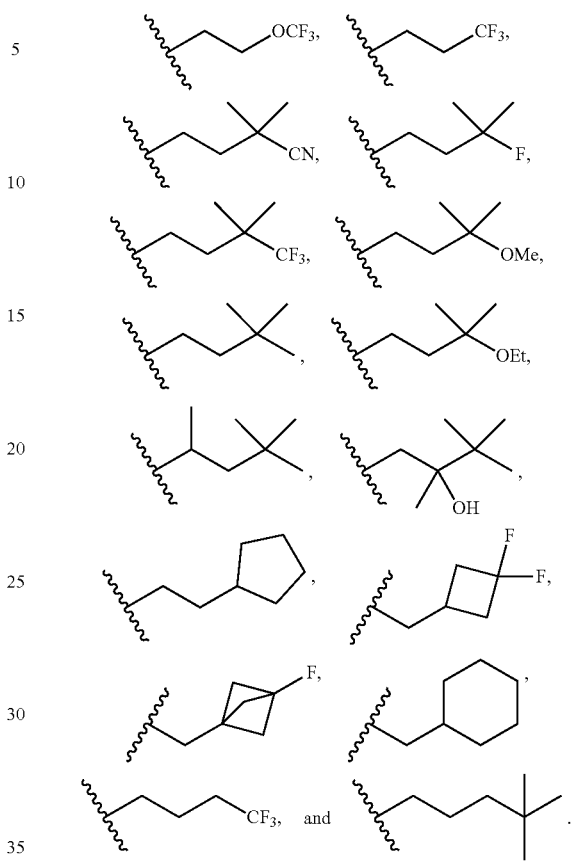
is selected from the group consisting of
In some embodiments, when L¹ is a direct bond,
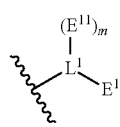
is selected from the group consisting of
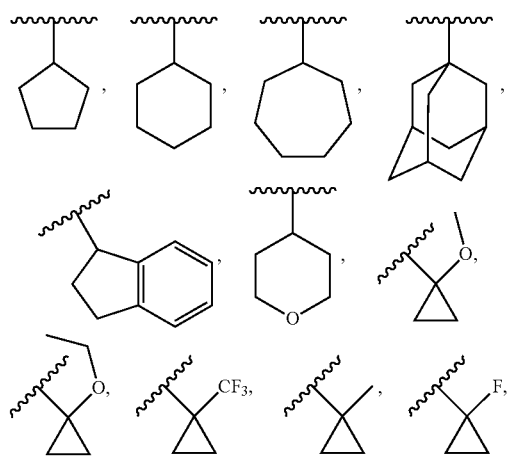
In some embodiments,
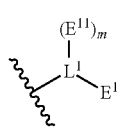

-continued
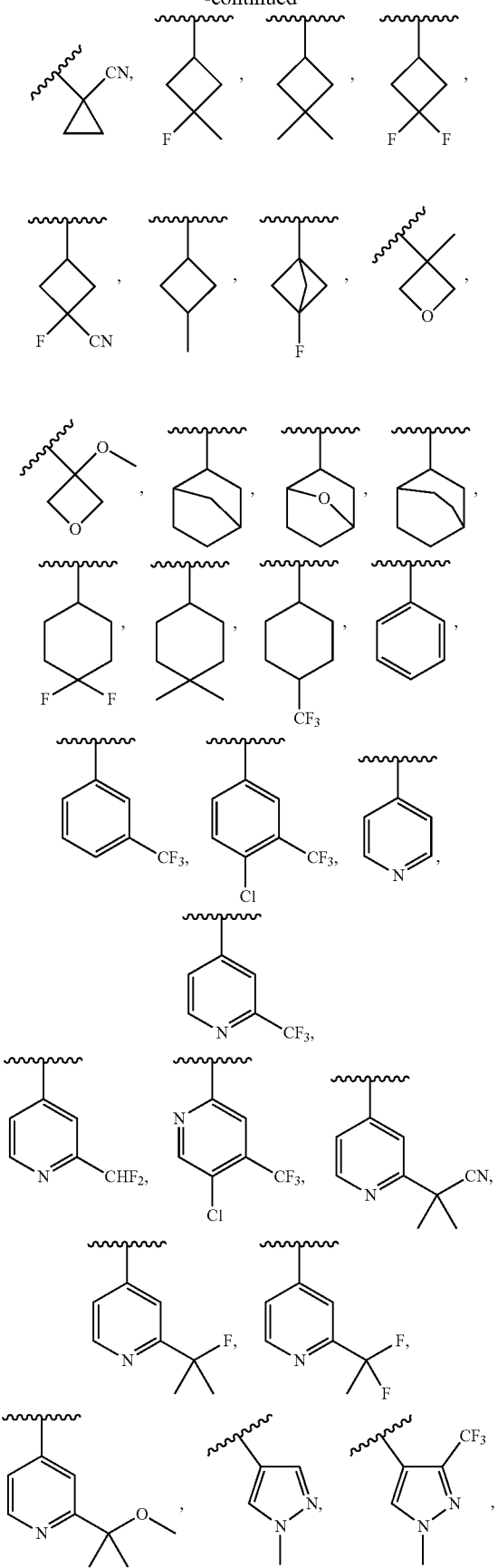
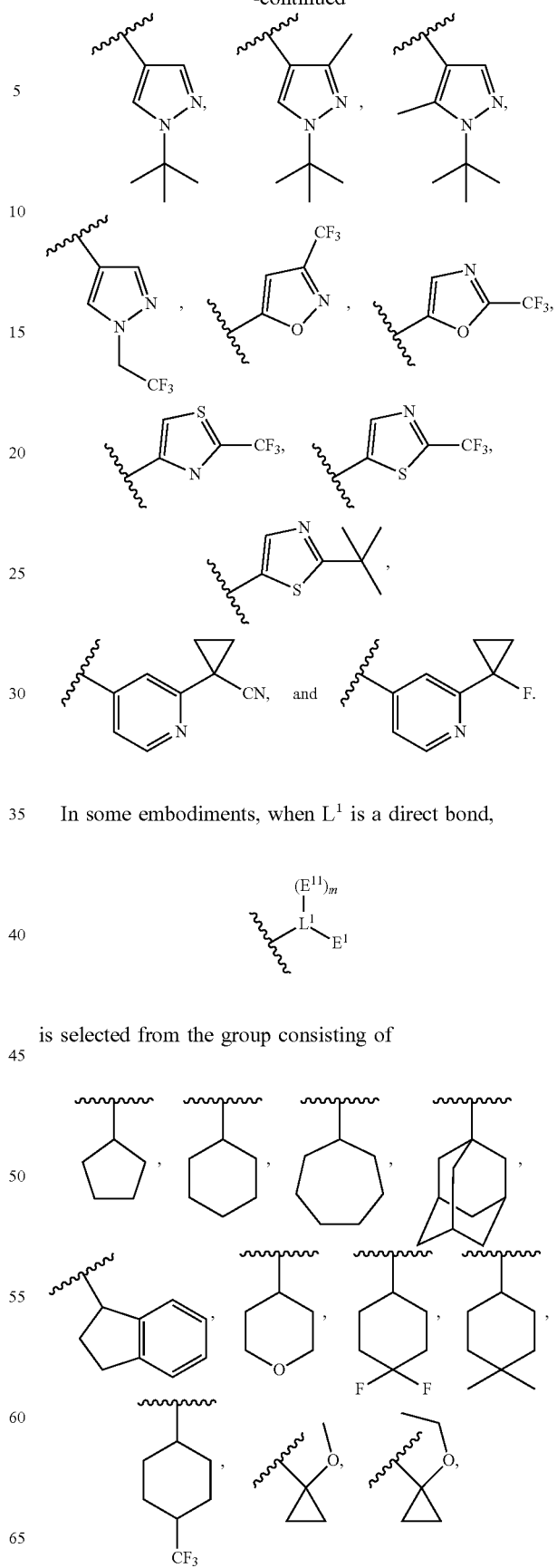
In some embodiments, when $L^1$ is a direct bond,
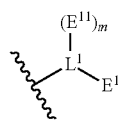
is selected from the group consisting of
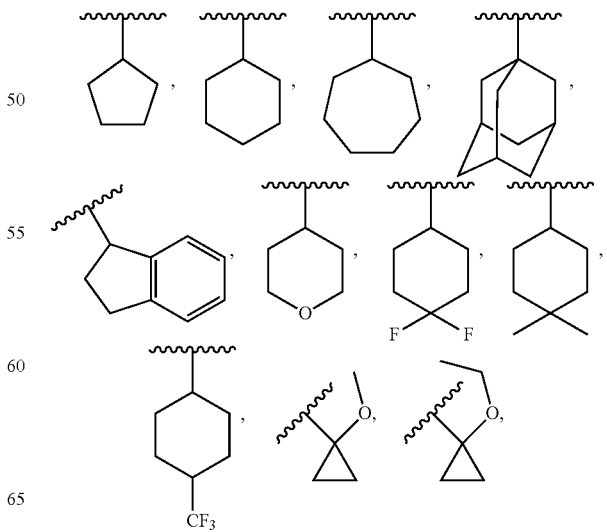

-continued
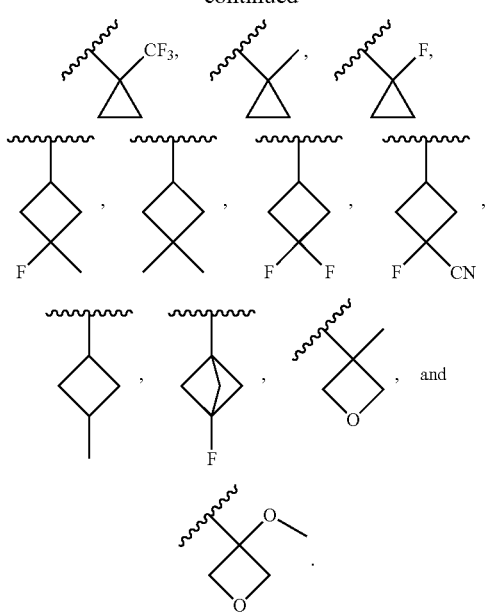
In some embodiments, $L^1$ is a direct bond,
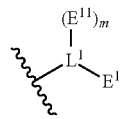
is selected from the group consisting of
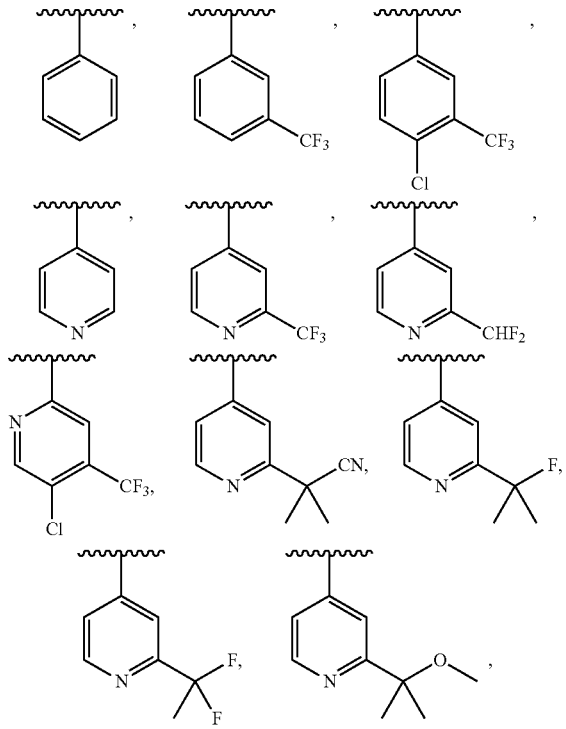
-continued
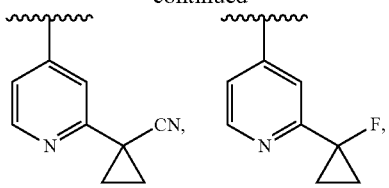
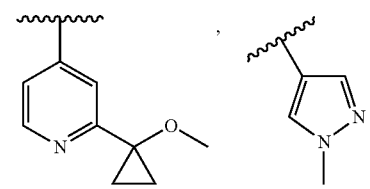
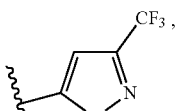
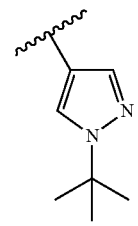 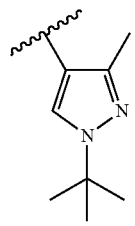
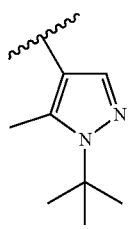 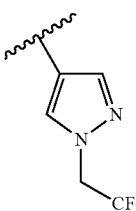 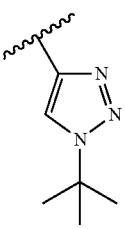
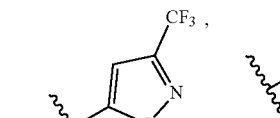 , 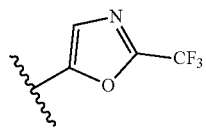 ,
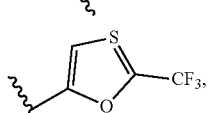 , 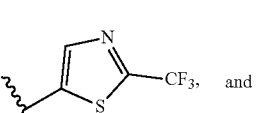 and
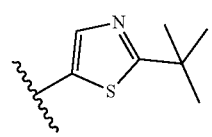 .
In some embodiments,
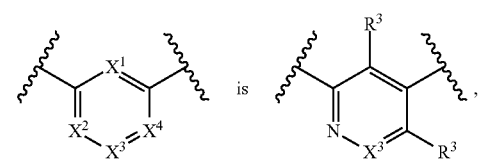
wherein $X^3$ is selected from the group consisting of CH, C-$L^3$-$E^3$, C—O-$L^3$-$E^3$, and C—N($R^4$)-$L^3$-$E^3$.

In some embodiments,

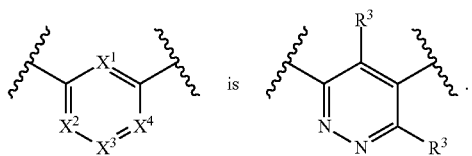

In some embodiments,

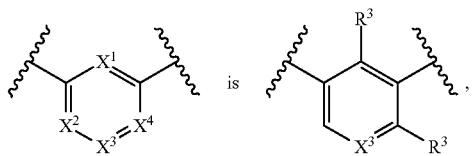

wherein $X^3$ is selected from the group consisting of CH, C-$L^3$-$E^3$, C—O-$L^3$-$E^3$, and C—N($R^4$)-$L^3$-$E^3$.

In some embodiments,

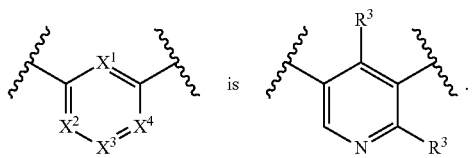

In some embodiments,

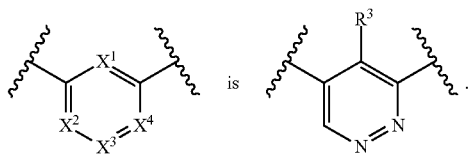

In some embodiments,

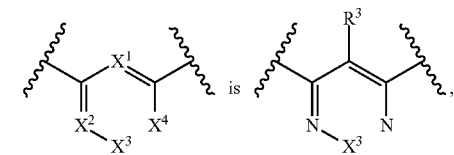

wherein $X^3$ is selected from the group consisting of CH, C-$L^3$-$E^3$, C—O-$L^3$-$E^3$, and C—N($R^4$)-$L^3$-$E^3$.

In some embodiments,

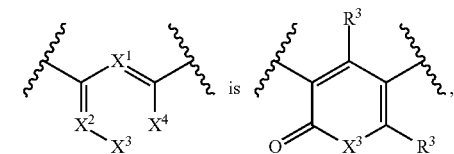

wherein $X^3$ is N-$L^3$-$E^3$.

In some embodiments,

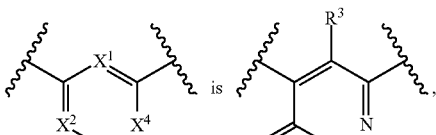

wherein $X^3$ is N-$L^3$-$E^3$.

In some embodiments,

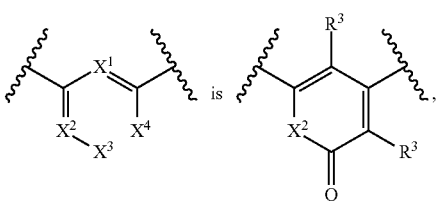

wherein $X^2$ is N-$L^2$-$E^2$.

In some embodiments,

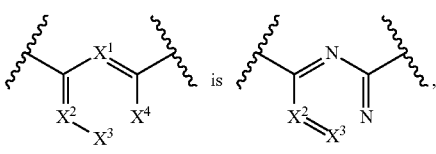

wherein $X^2$ is selected from the group consisting of CH, C—O-$L^2$-$E^2$, C-$L^2$-$E^2$, and C—N($R^4$)-$L^2$-$E^2$; and wherein $X^3$ is selected from the group consisting of CH, C-$L^3$-$E^3$, C—O-$L^3$-$E^3$, and C—N($R^4$)-$L^3$-$E^3$.

In some embodiments,

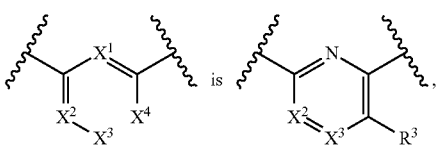

wherein $X^3$ is selected from the group consisting of CH, C-$L^3$-$E^3$, C—O-$L^3$-$E^3$, and C—N($R^4$)-$L^3$-$E^3$.

In some embodiments,

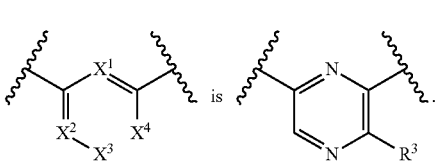

In some embodiments,

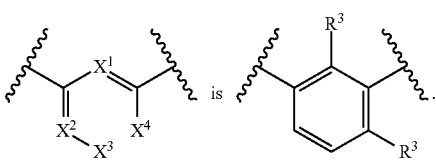

In some embodiments,
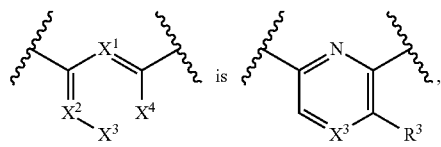 is
wherein X³ is selected from the group consisting of CH, C-L³-E³, C—O-L³-E³, and C—N(R⁴)-L³-E³.
In some embodiments, the compound is selected from the group consisting of:
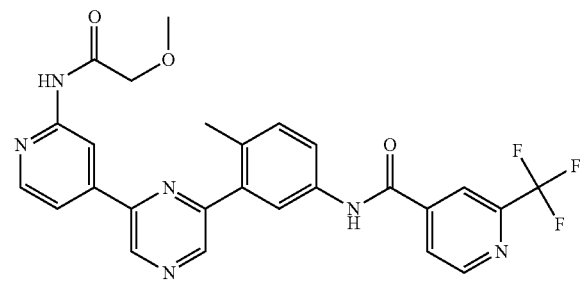
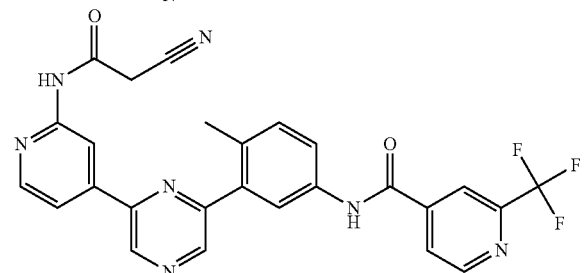
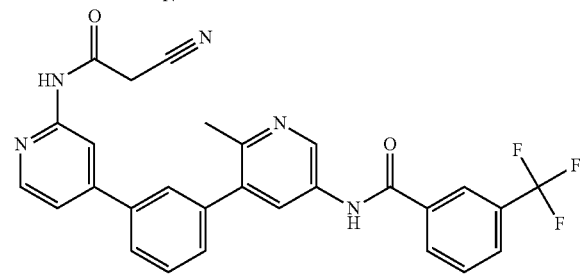
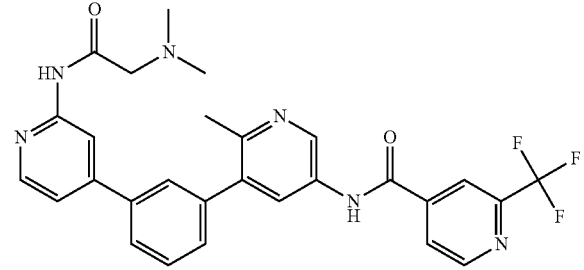
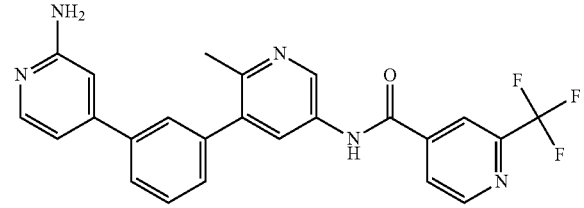
-continued
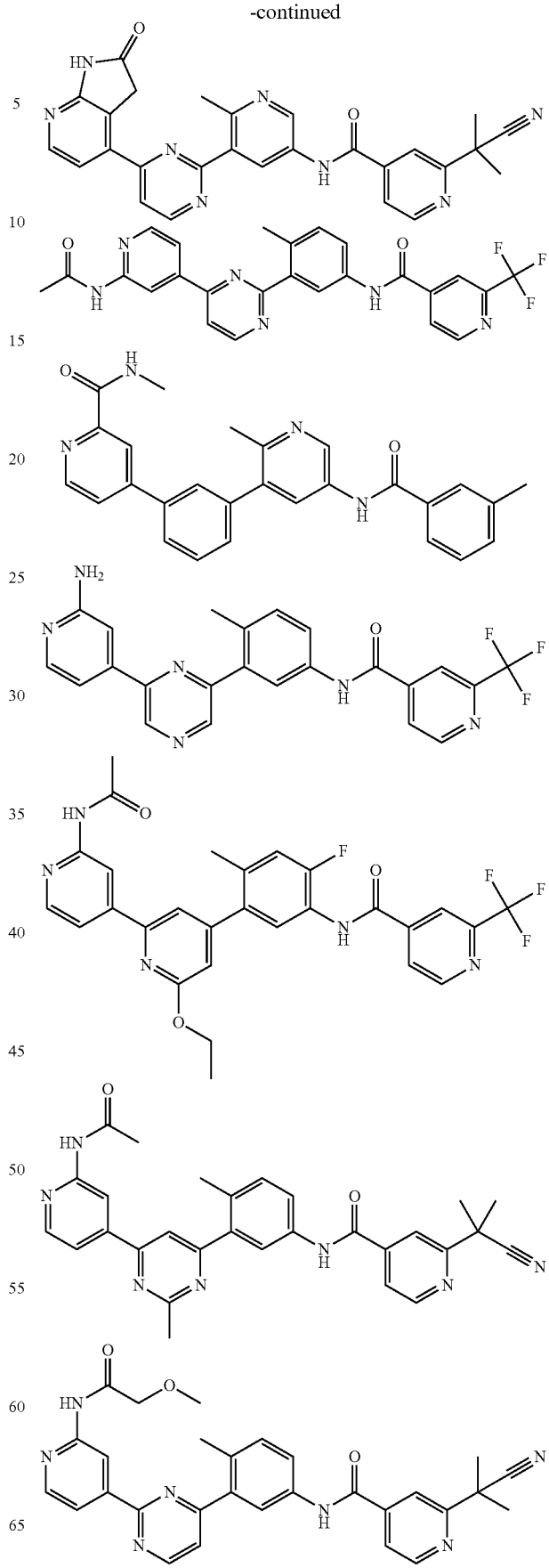

163
-continued
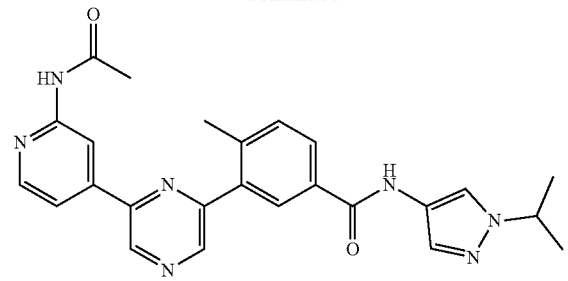
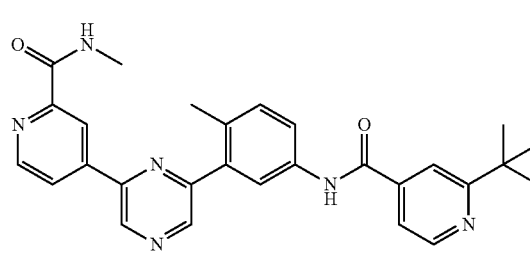
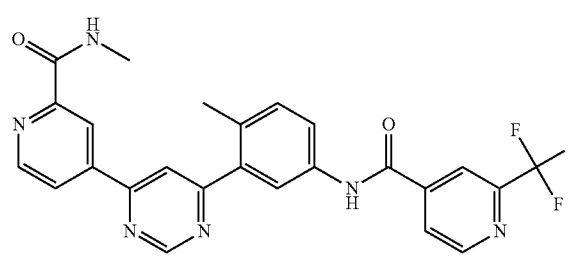
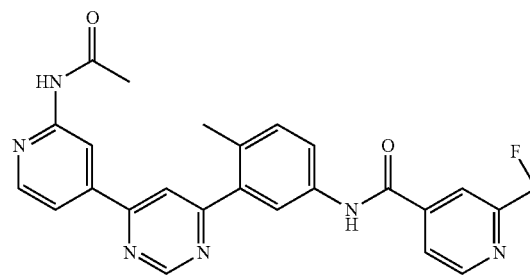
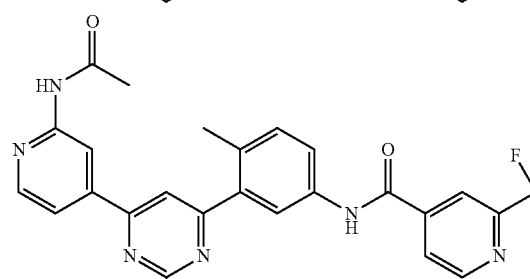
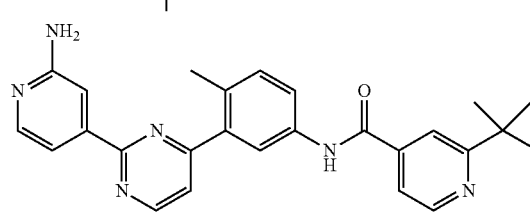
164
-continued
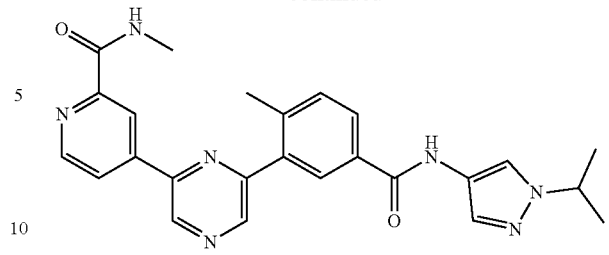
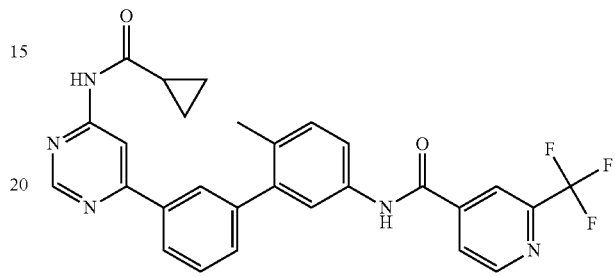
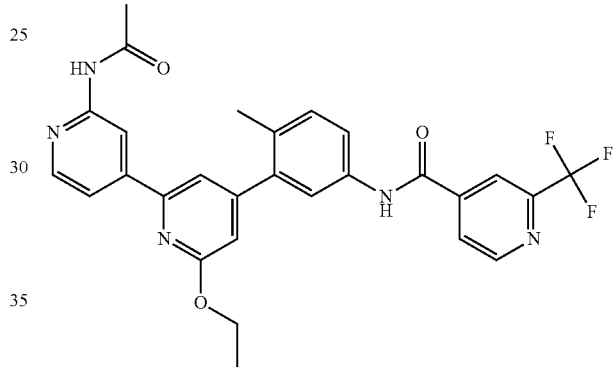
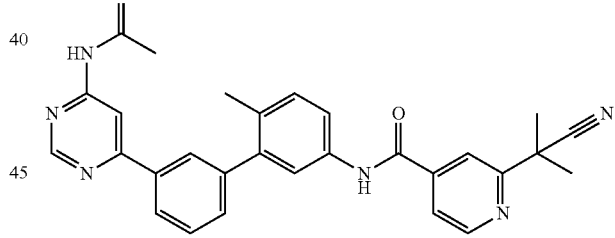
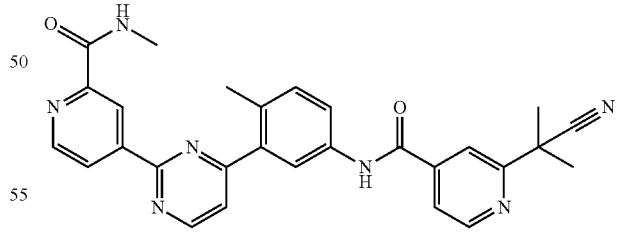
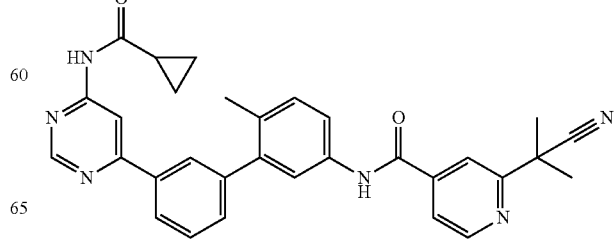

-continued
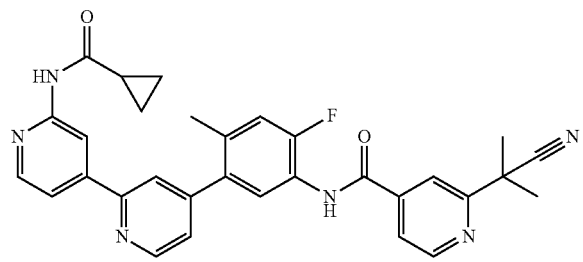
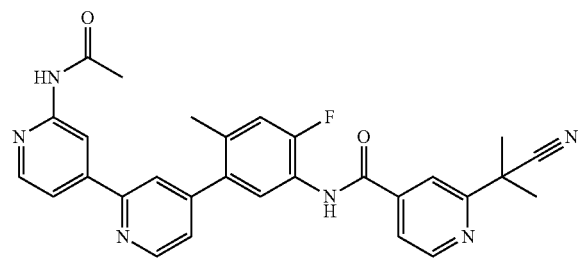
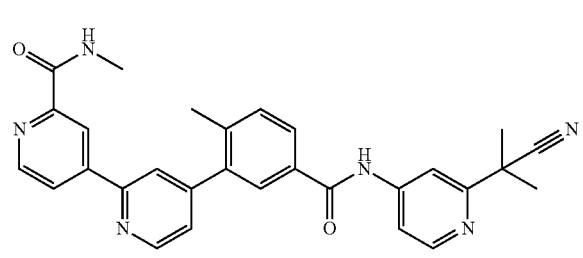
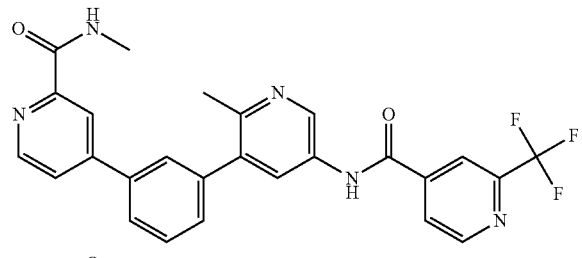
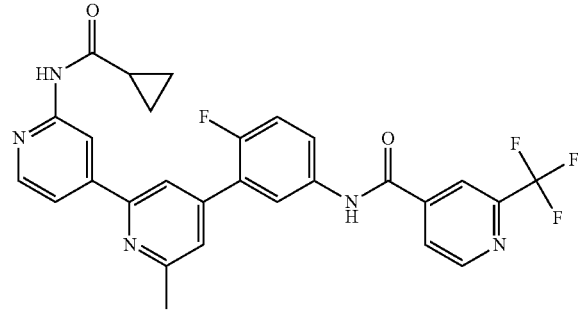
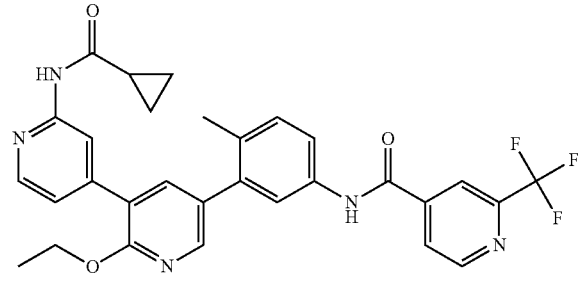
-continued
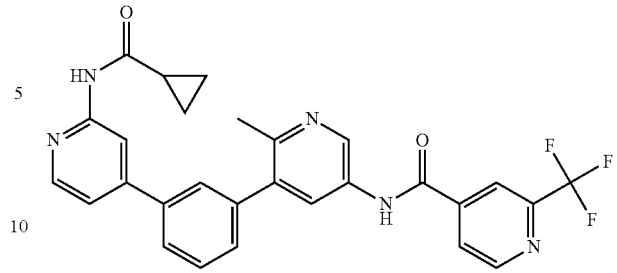
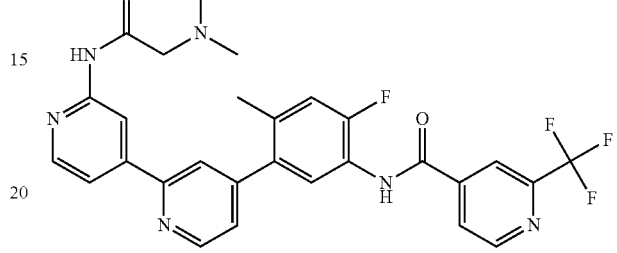
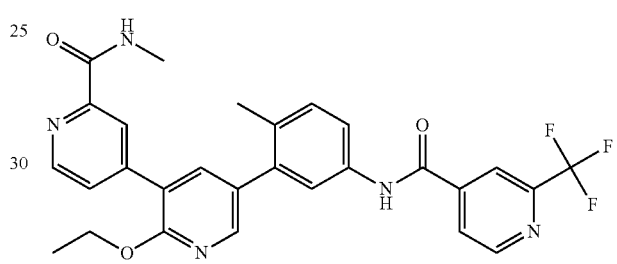
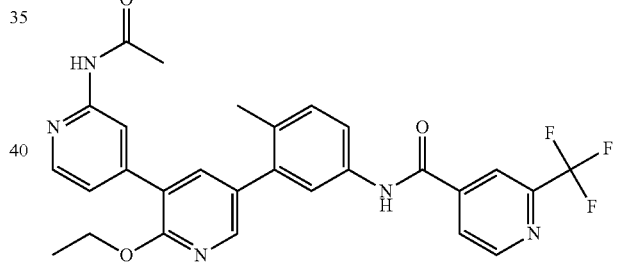
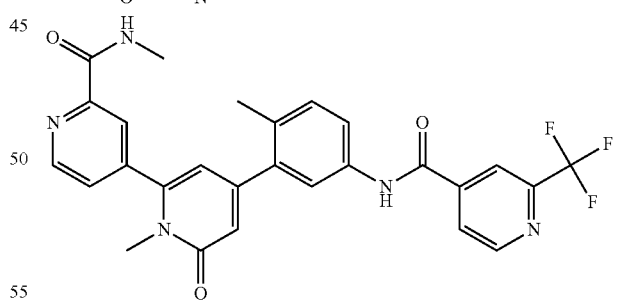
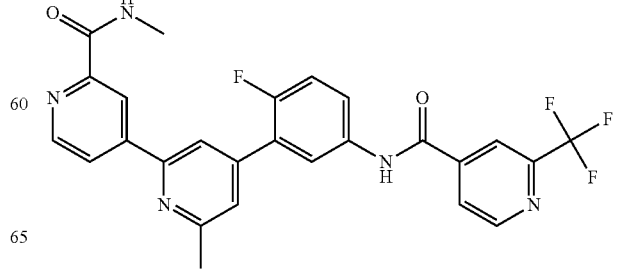

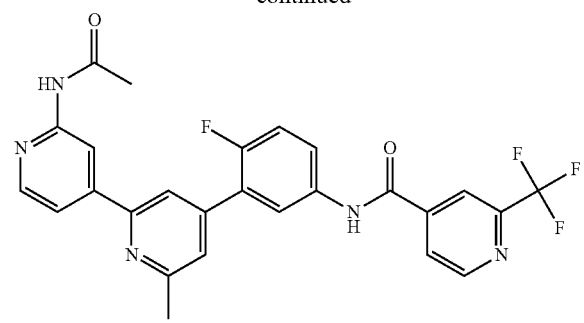
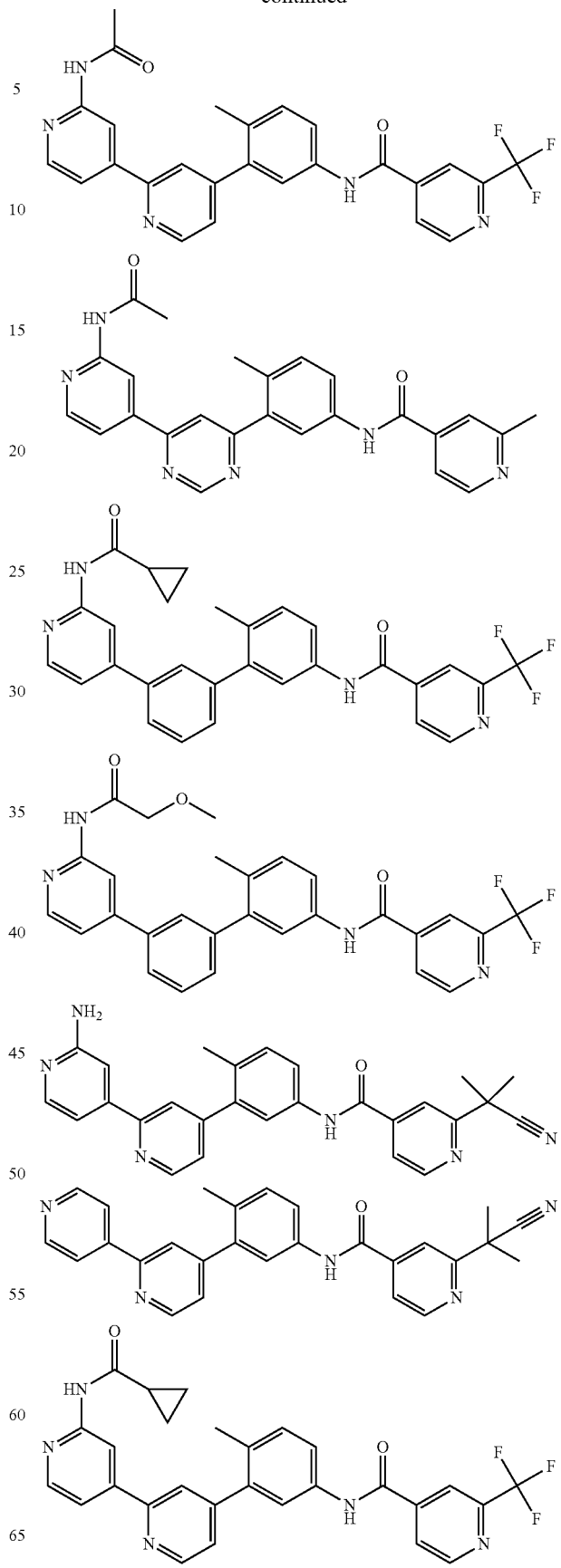

169
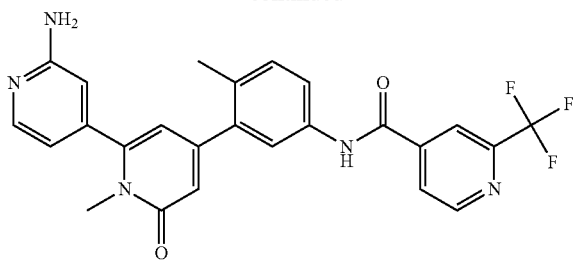
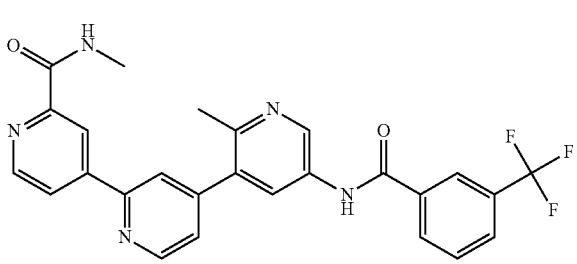
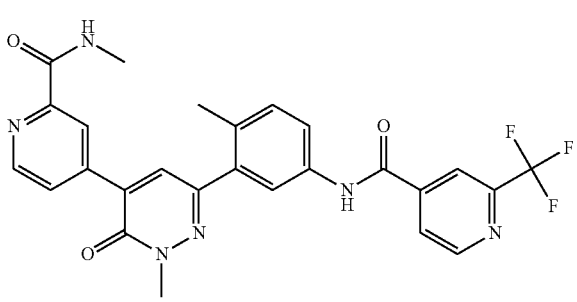
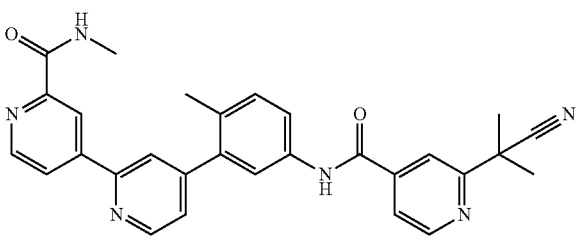
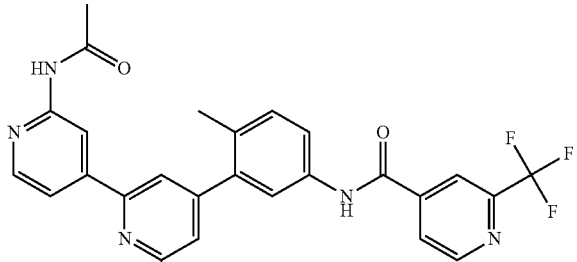
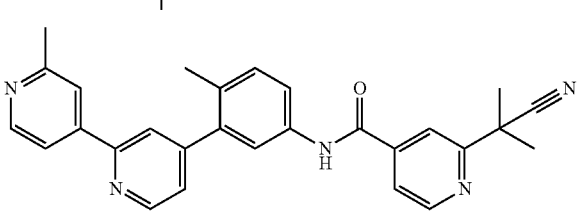
170
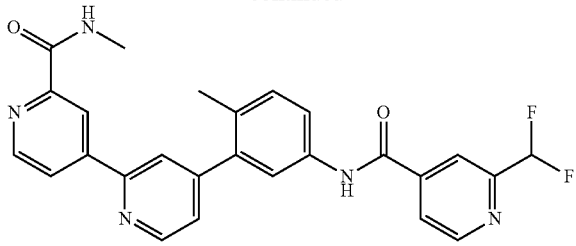
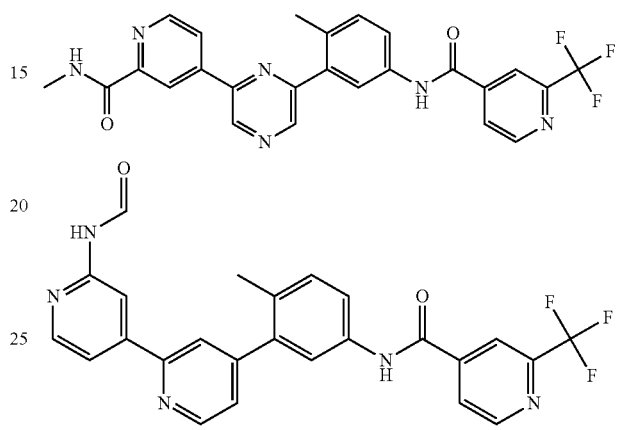
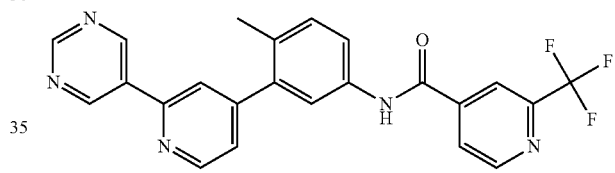
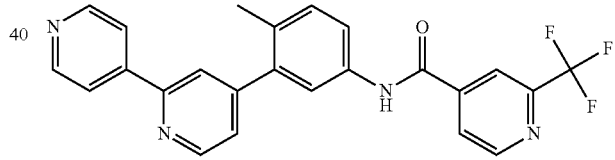
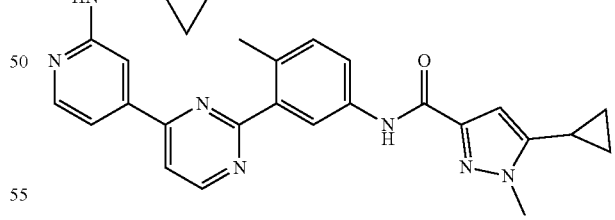
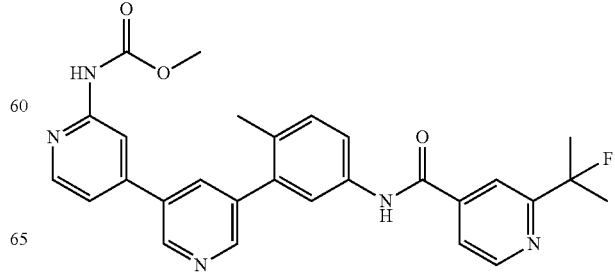

-continued
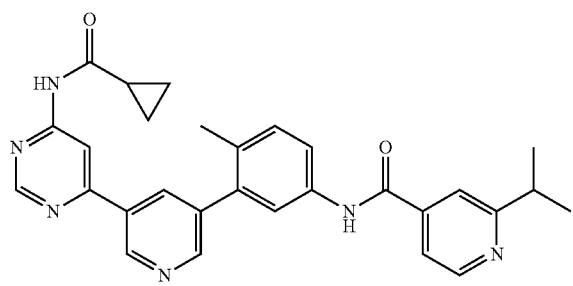
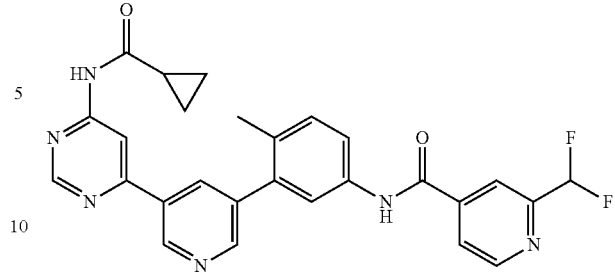
-continued
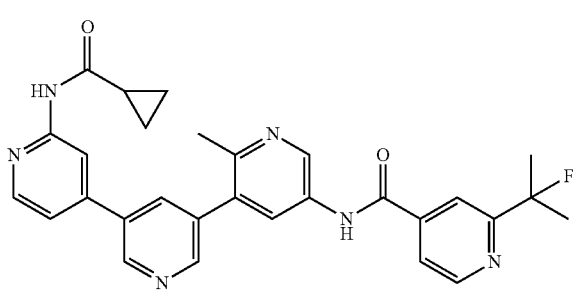
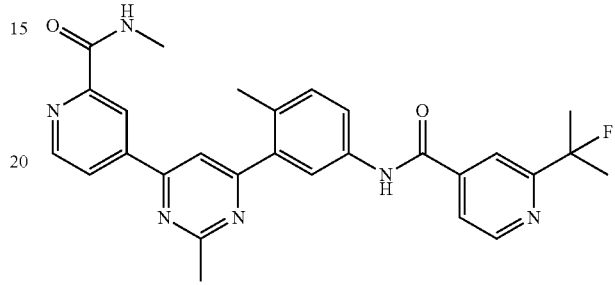
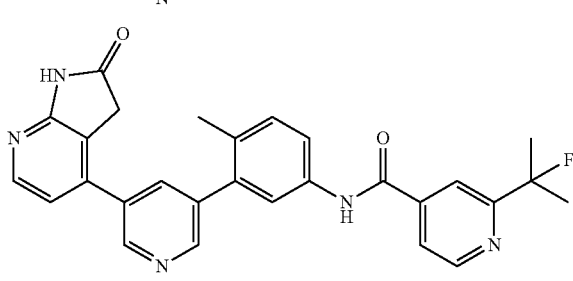
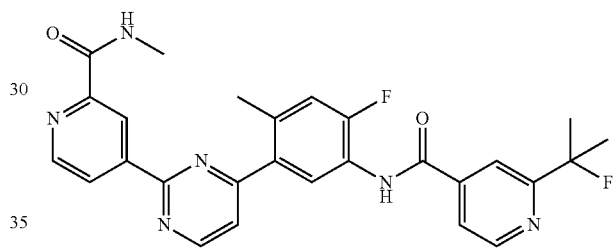
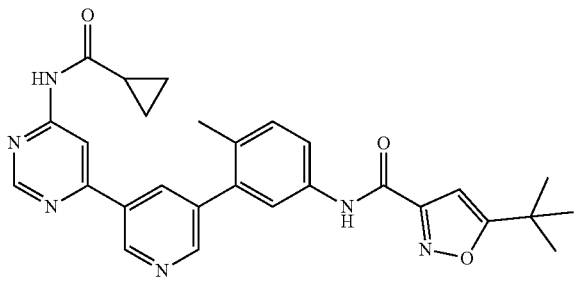
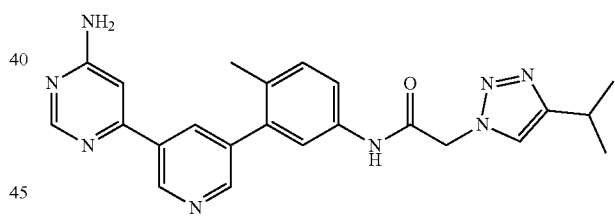
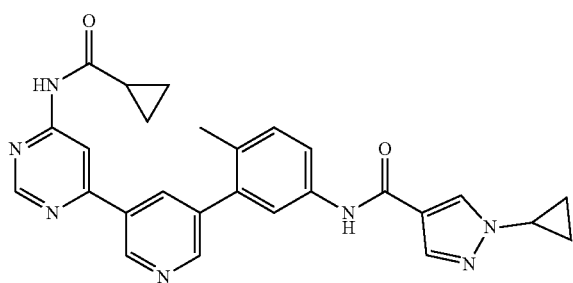
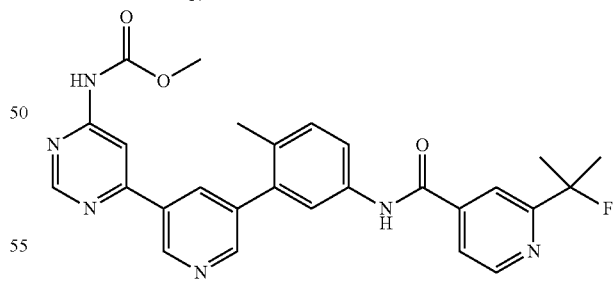
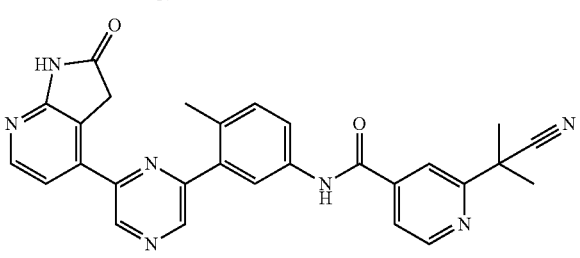
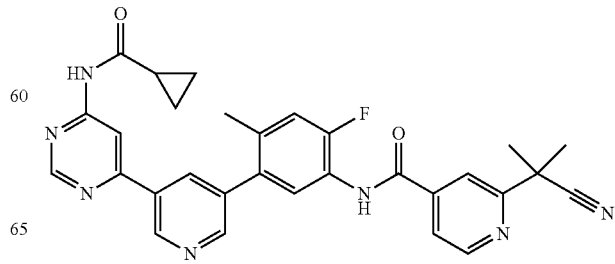

173
-continued
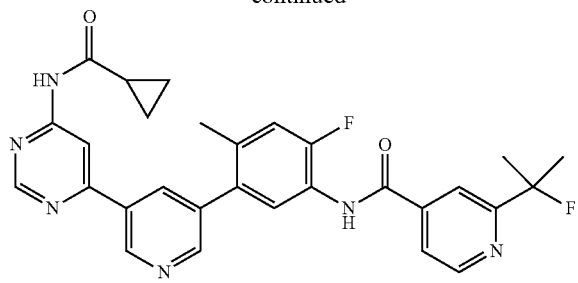
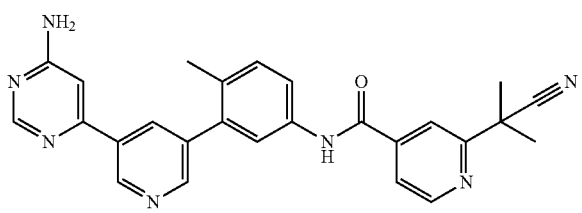
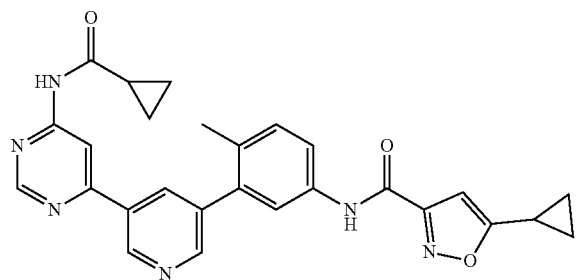
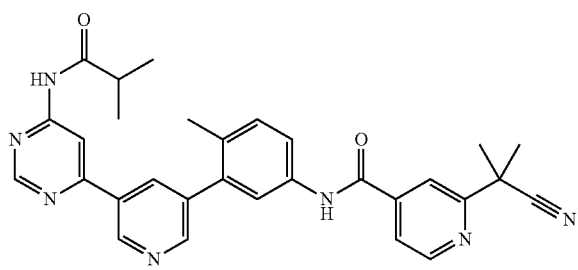
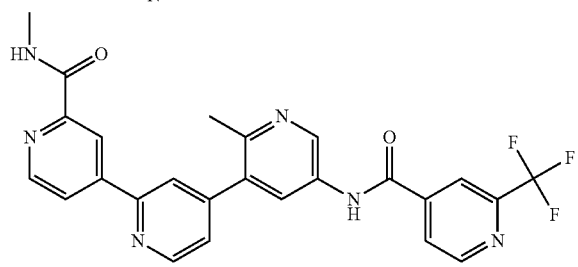
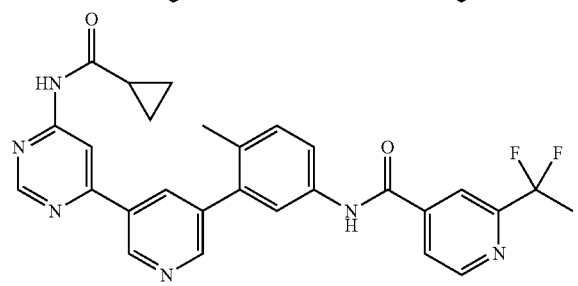
174
-continued
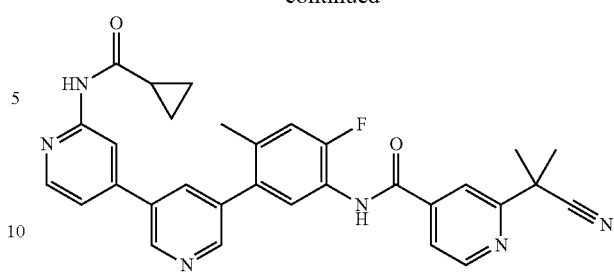
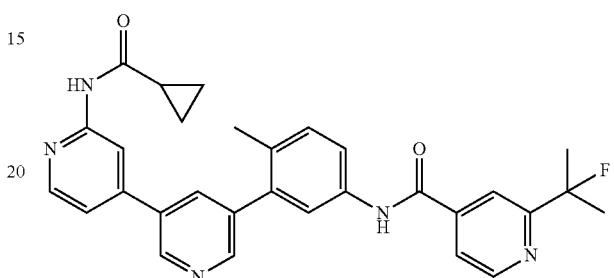
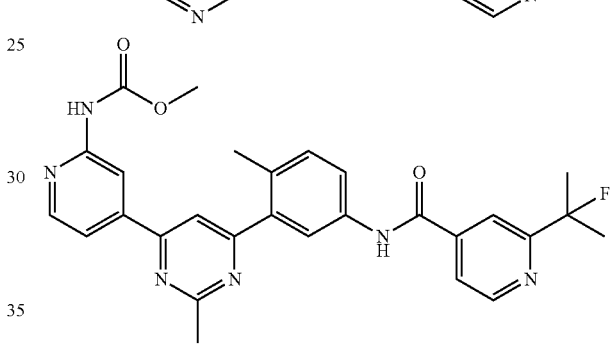
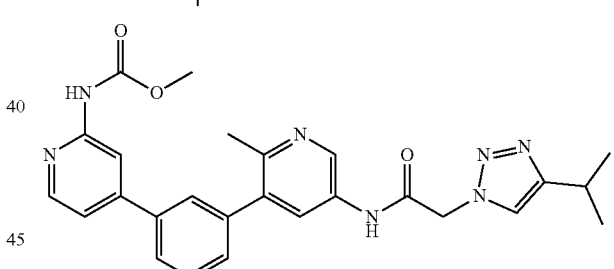
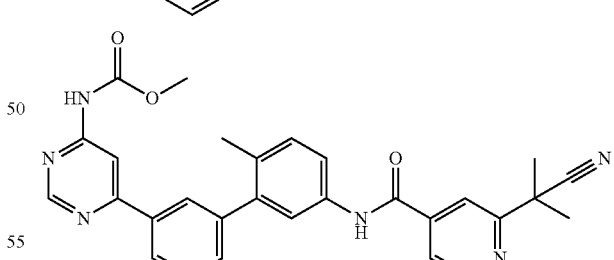
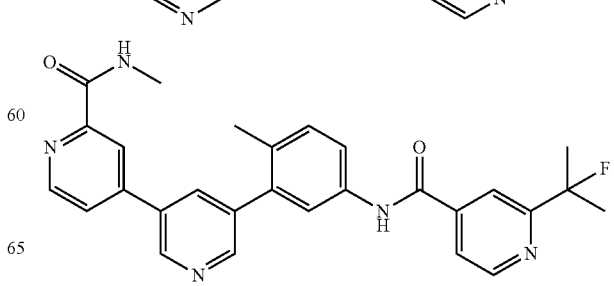

-continued
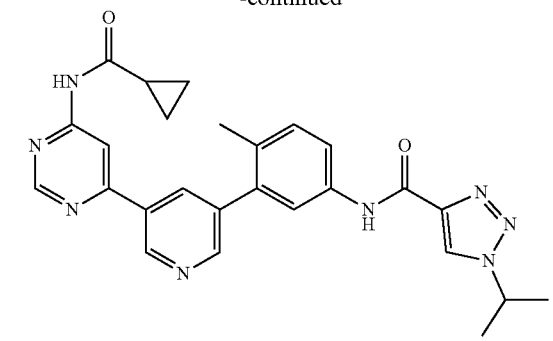
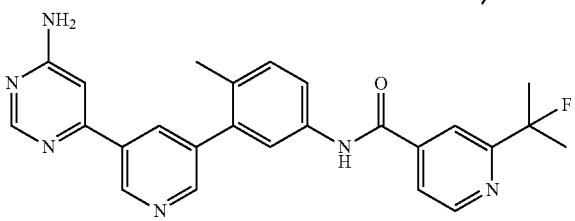
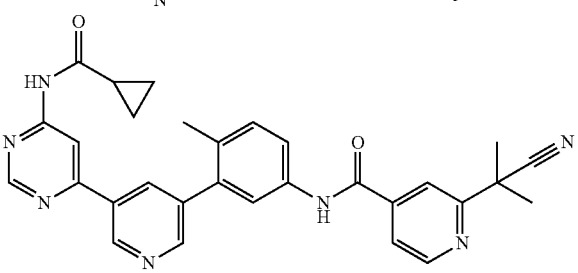
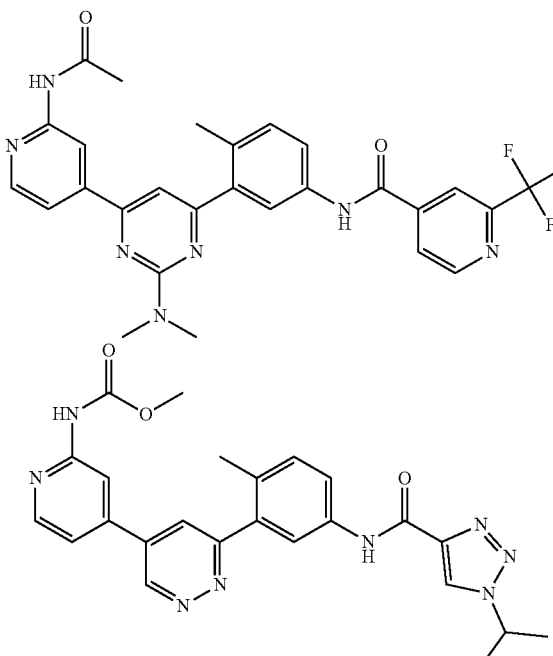
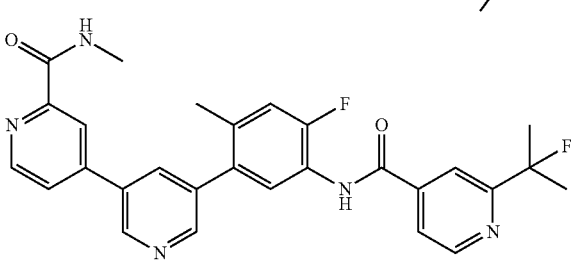
-continued
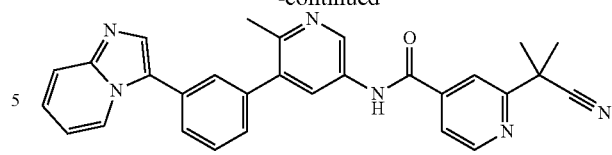
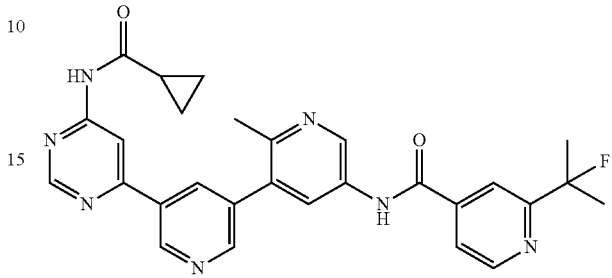
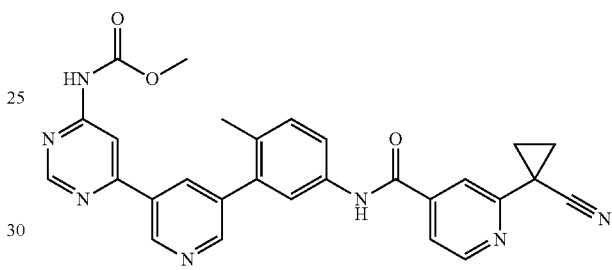
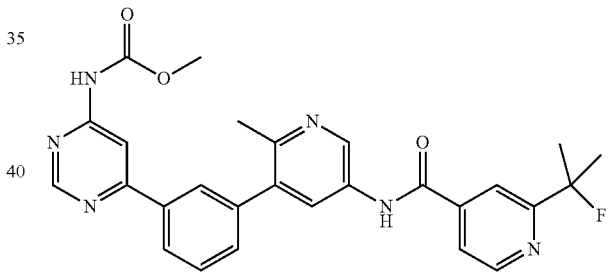
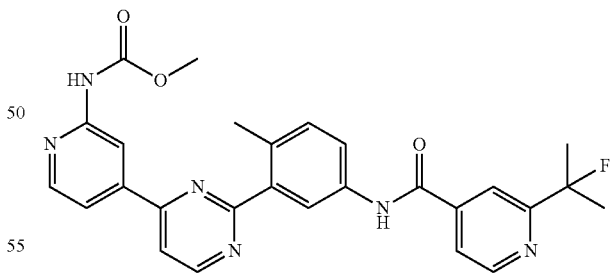
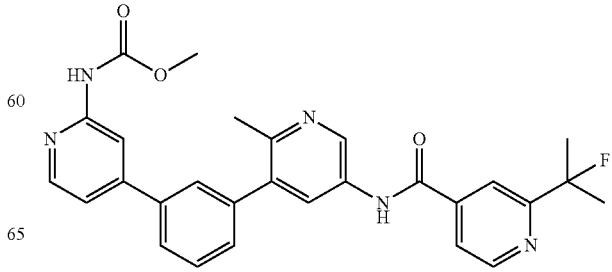

-continued
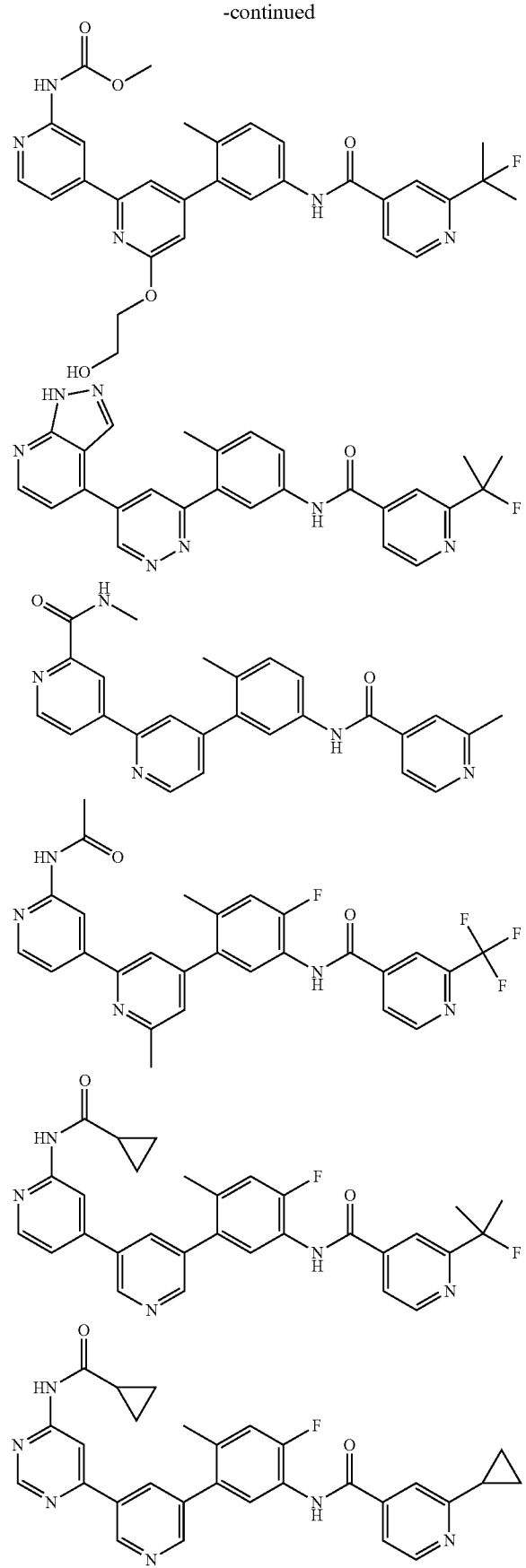
-continued
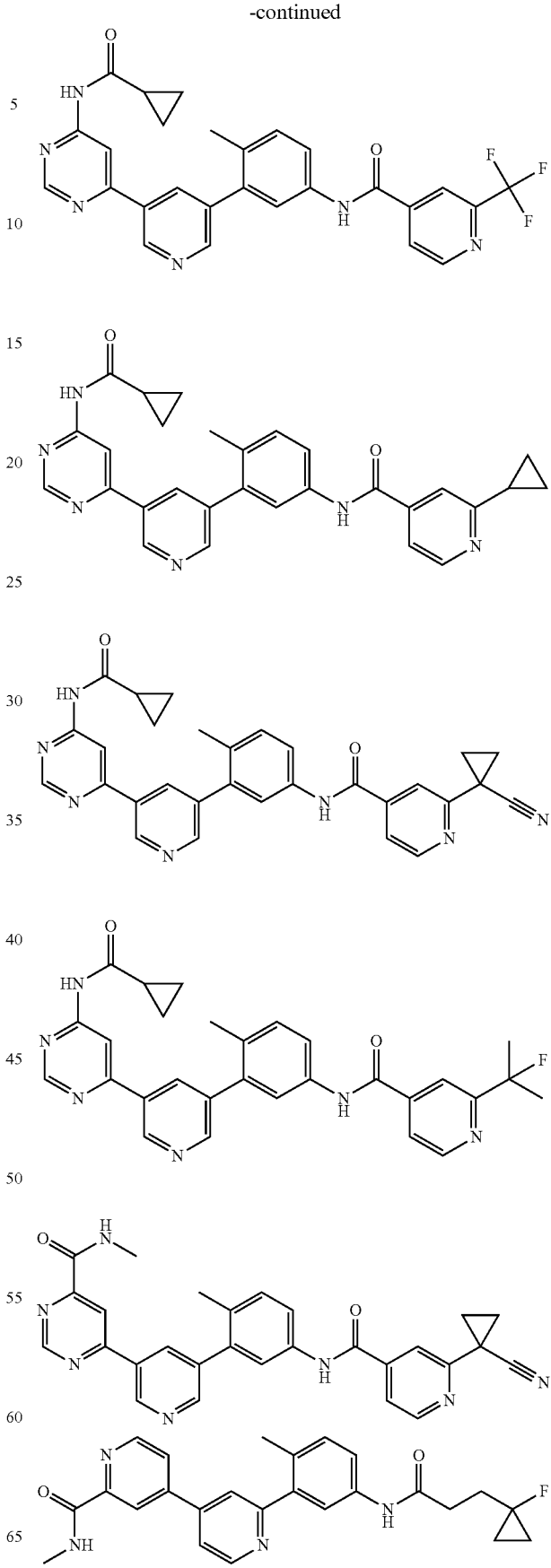

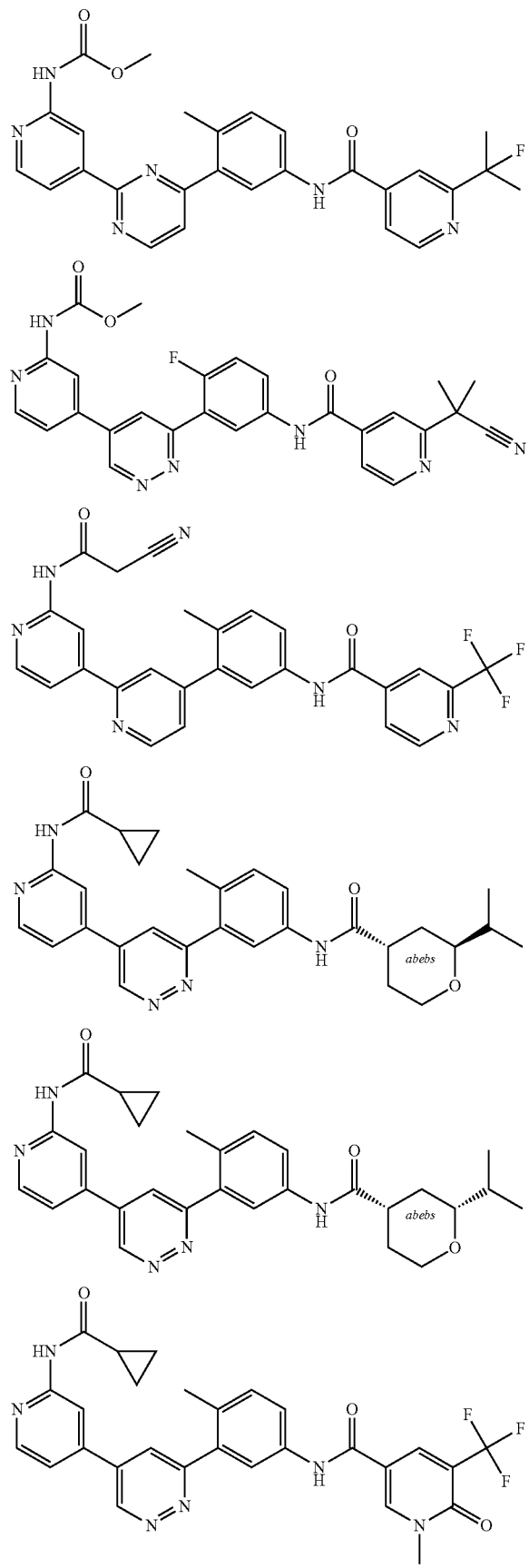
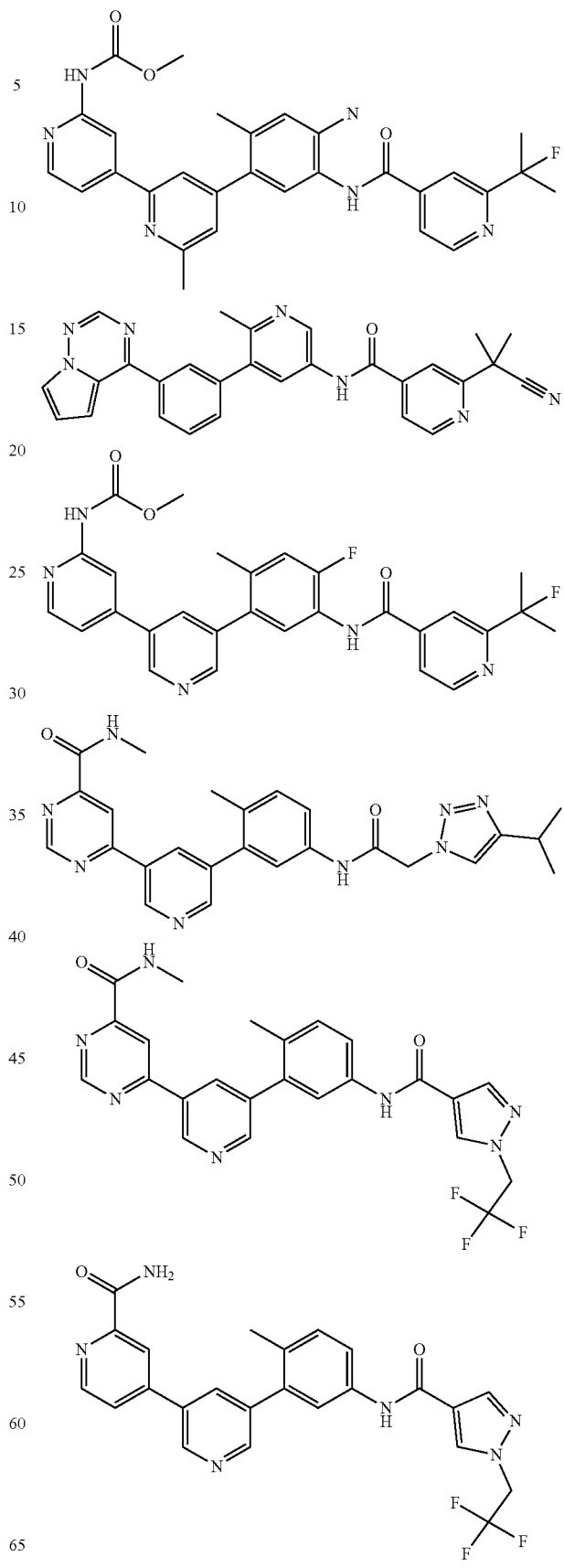

181
-continued
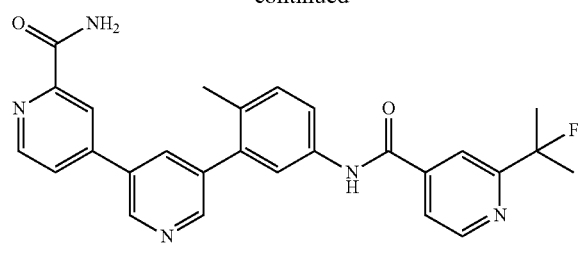
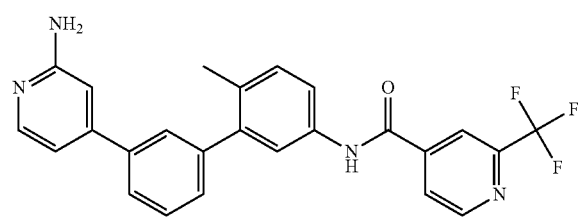
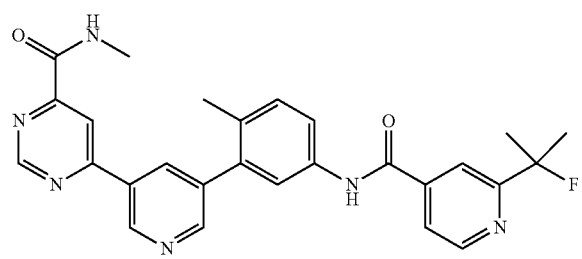
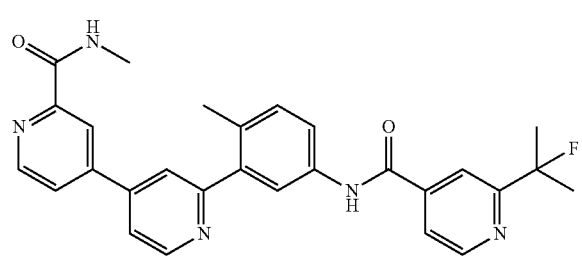
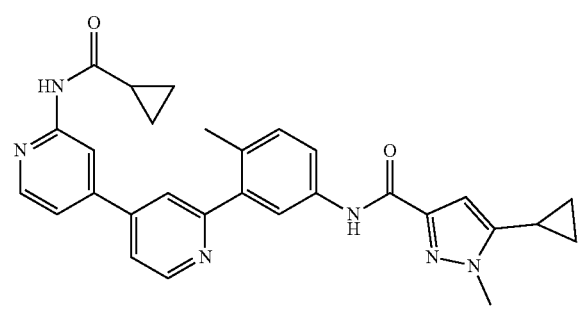
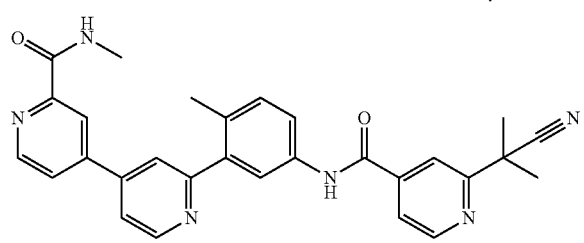
182
-continued
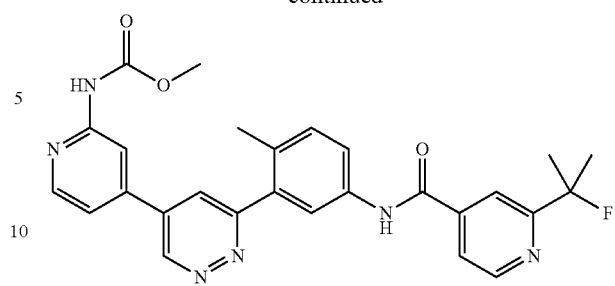
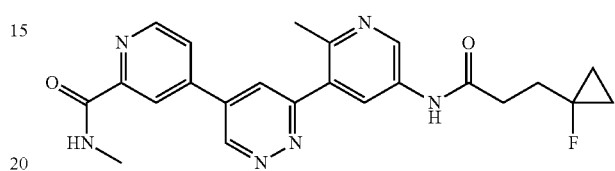
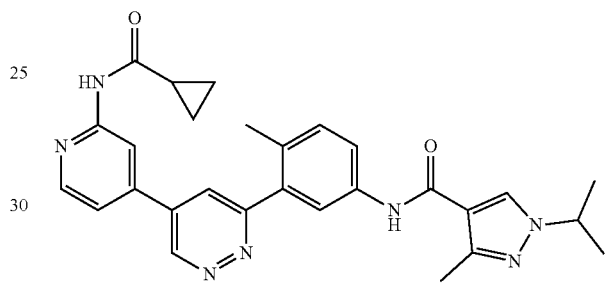
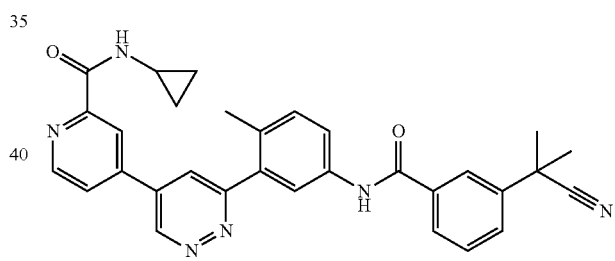
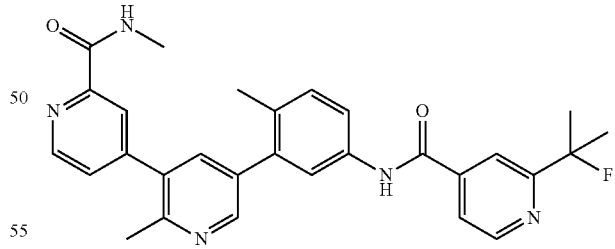
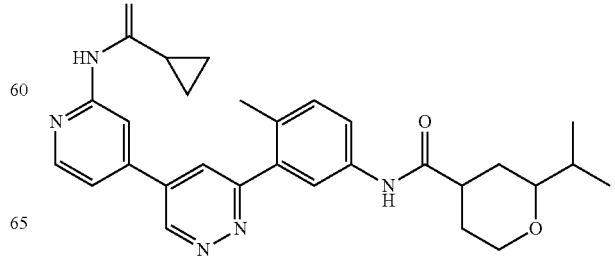

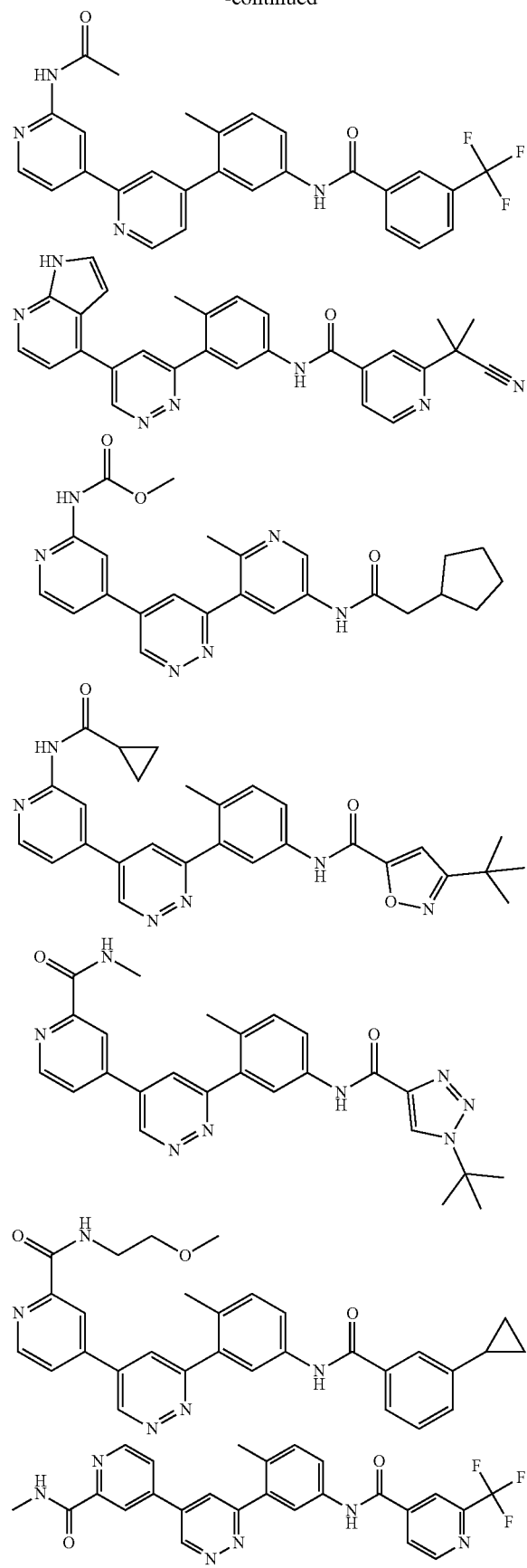
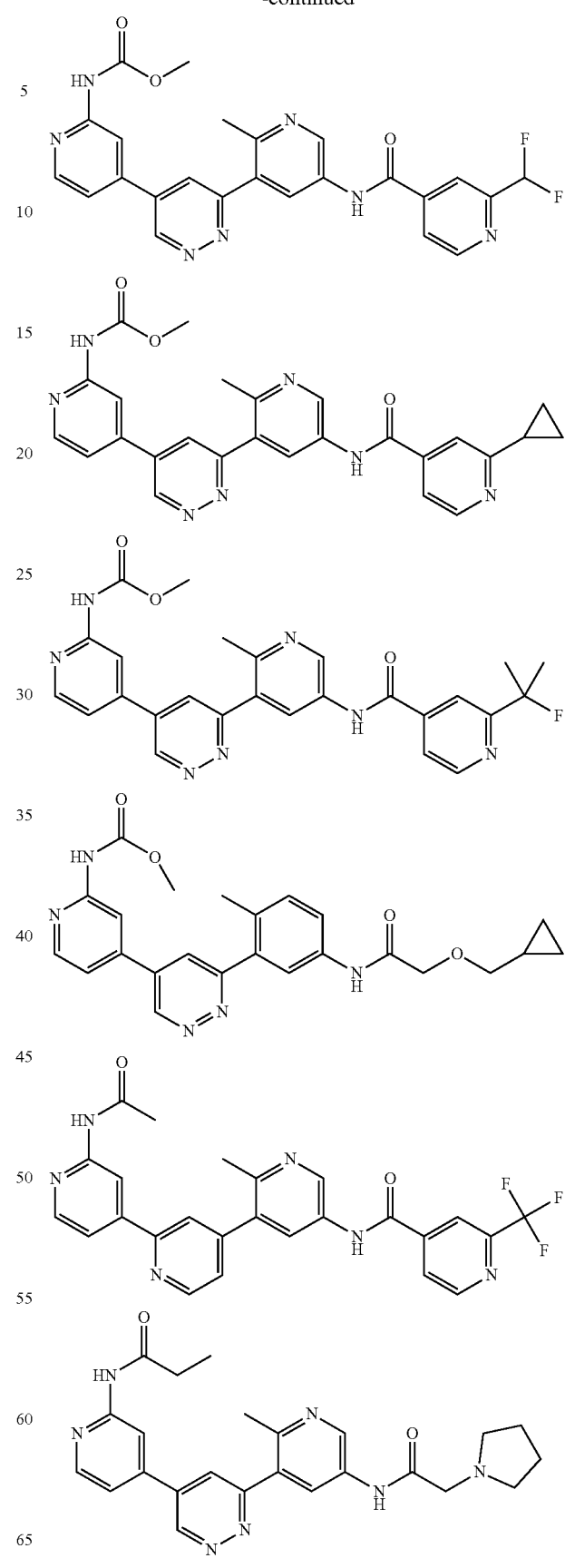

185
-continued
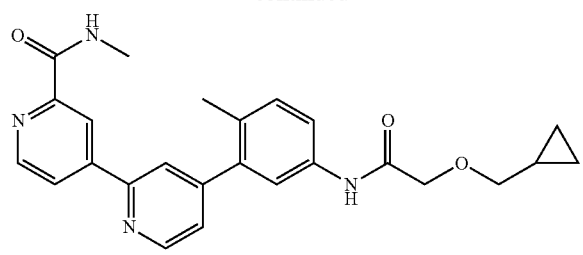
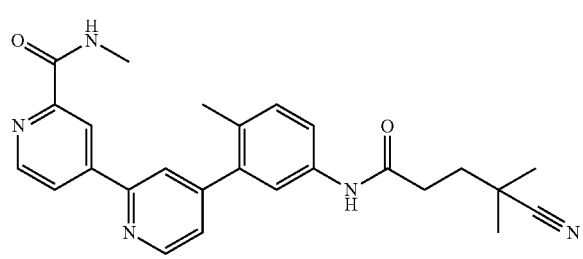
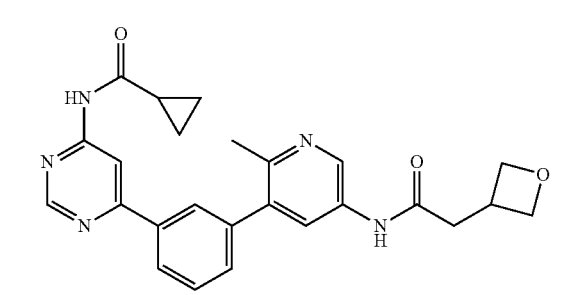
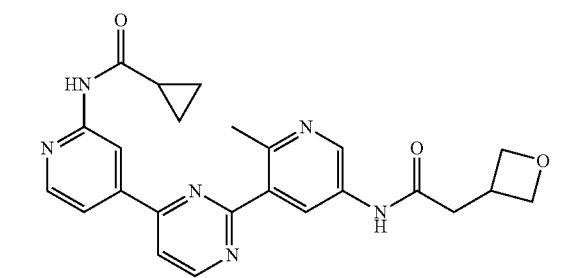
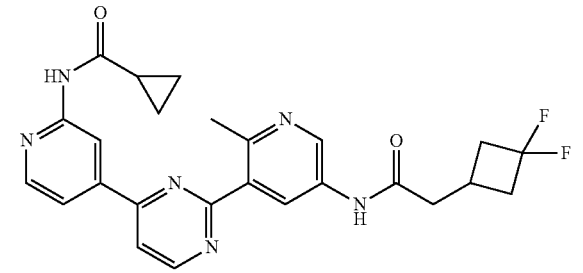
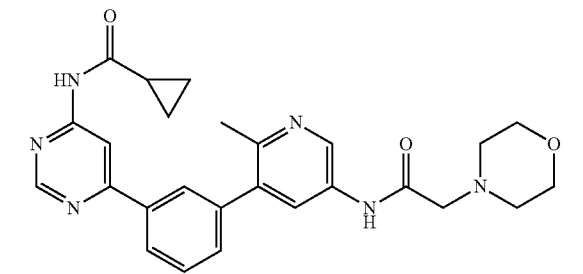
186
-continued
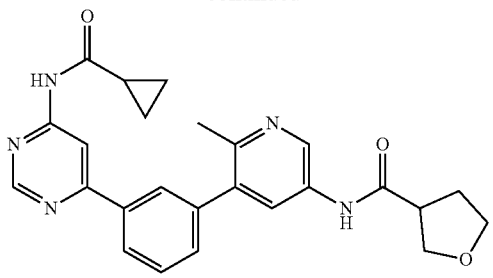
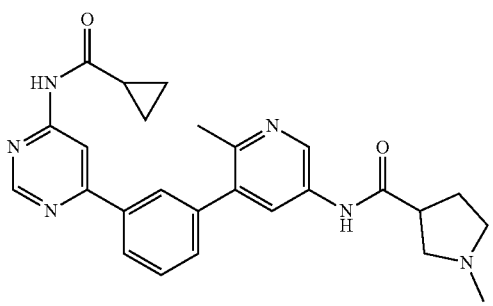
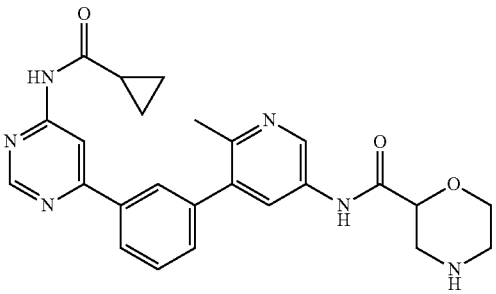
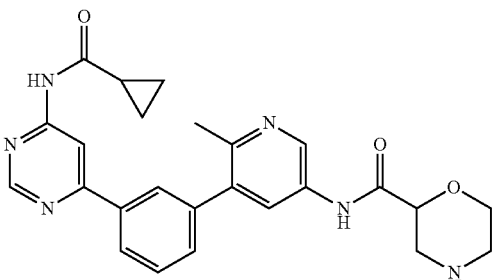
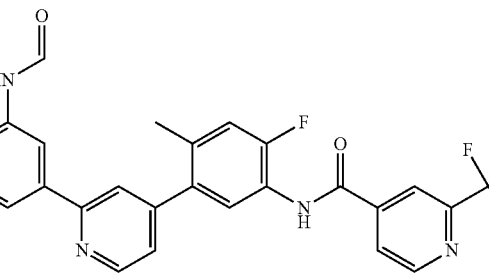
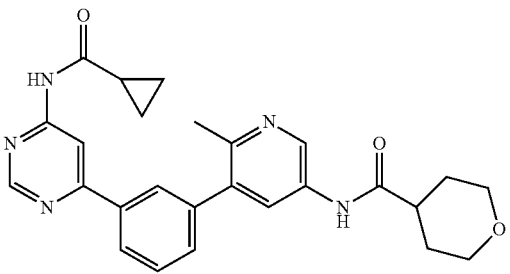

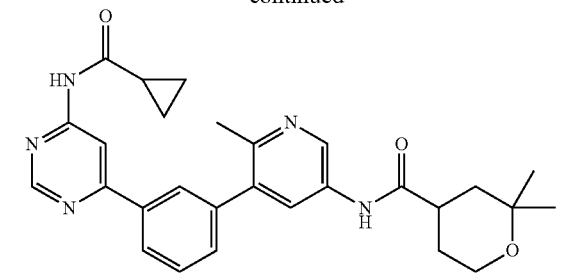
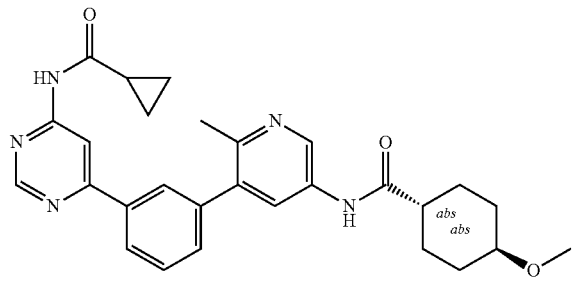
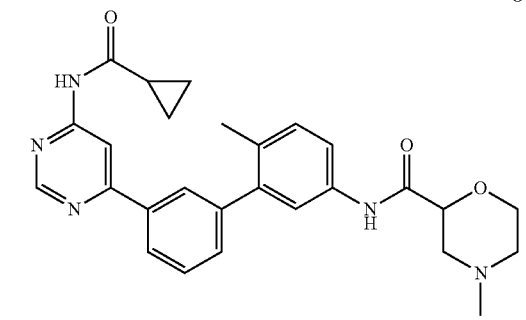
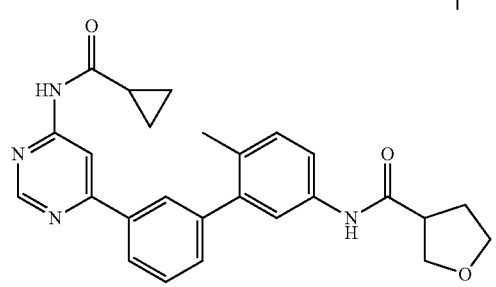
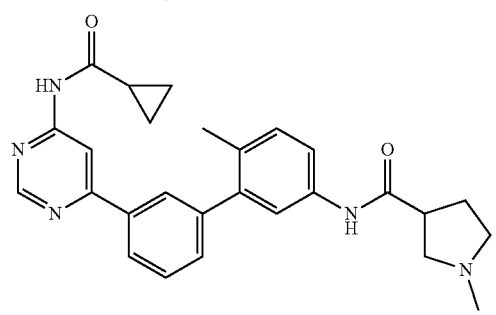
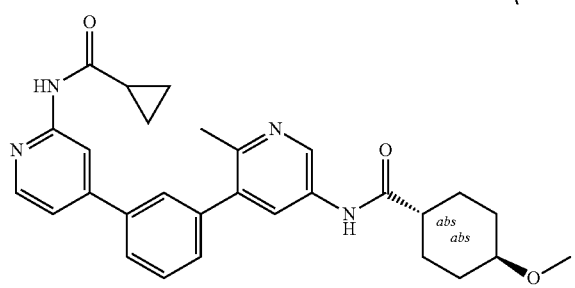
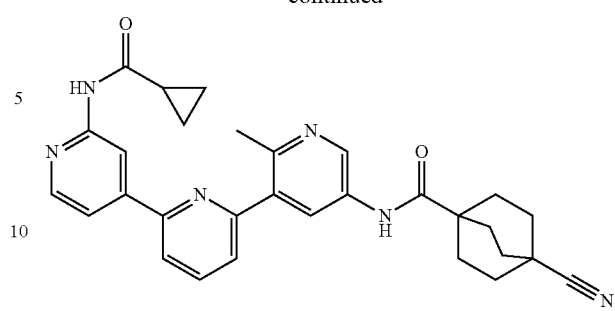
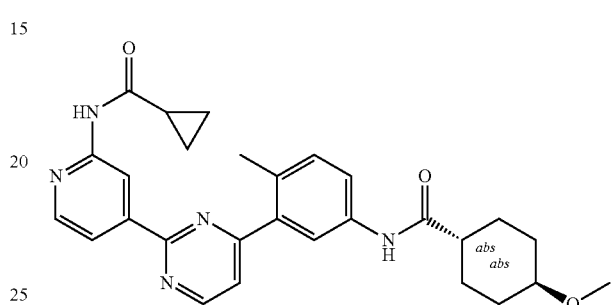
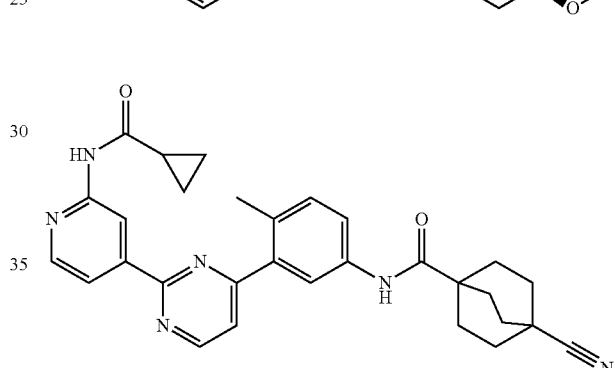
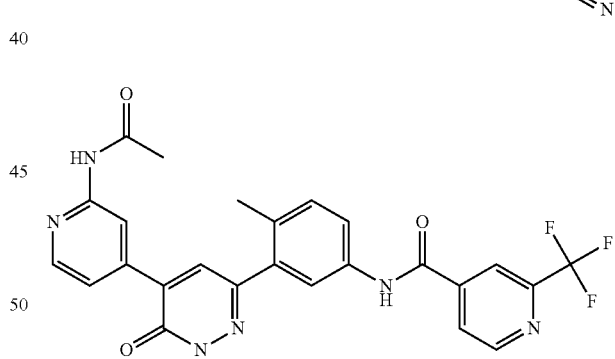
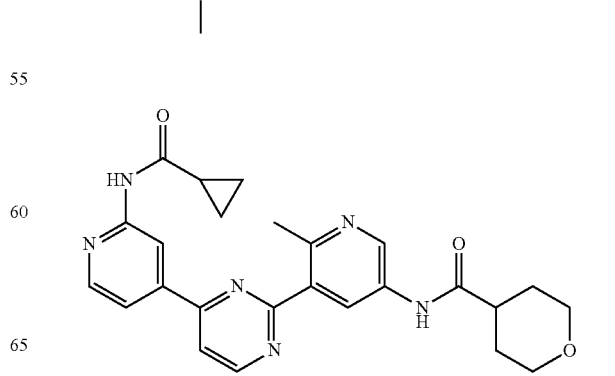

189
-continued
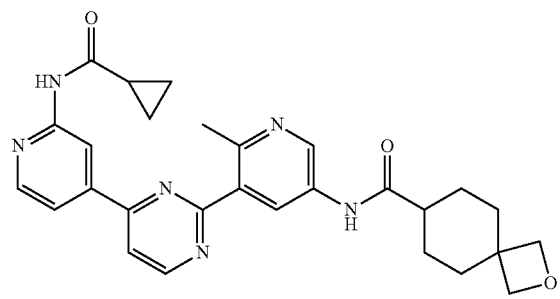
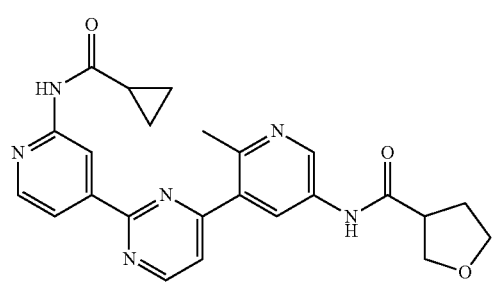
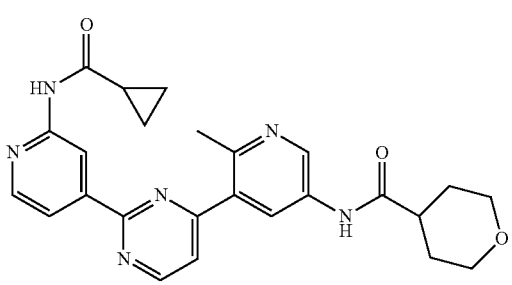
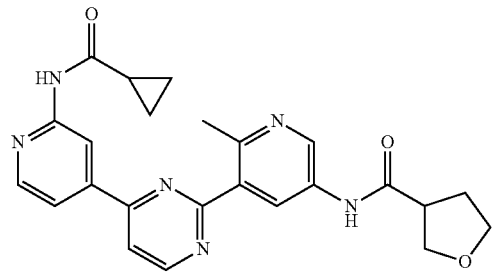
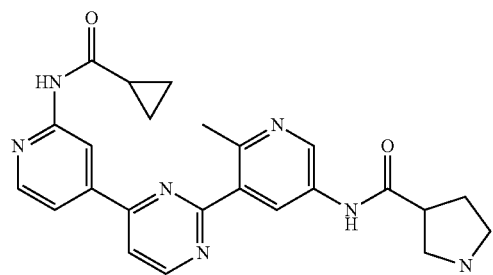
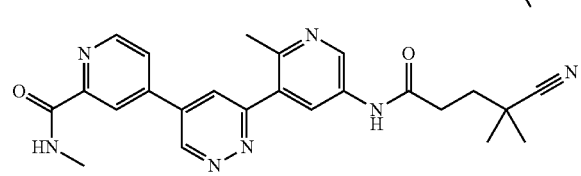
190
-continued
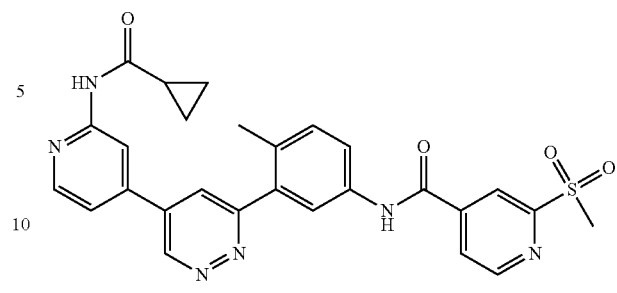
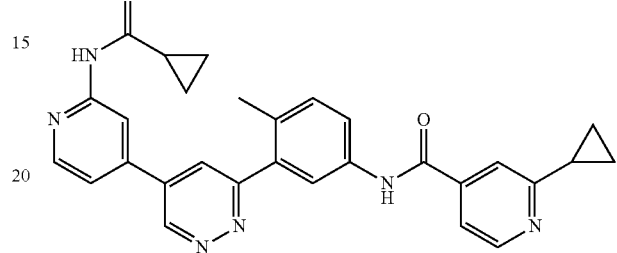
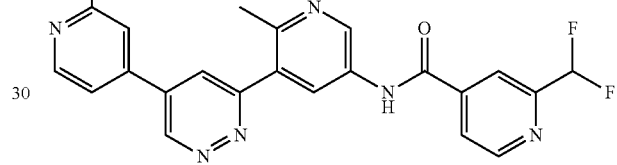
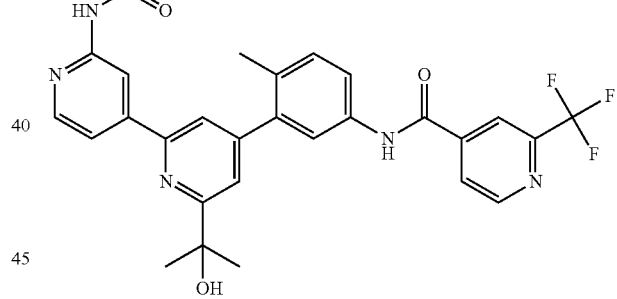
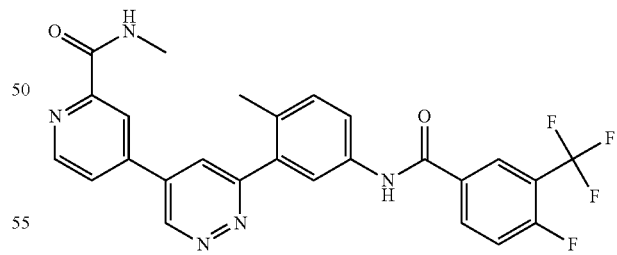
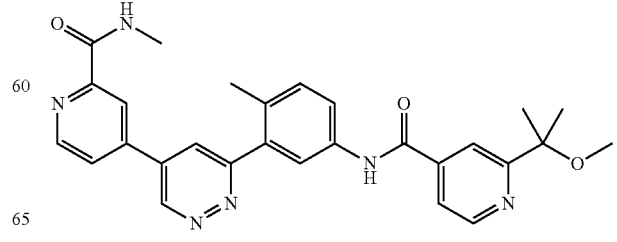

-continued
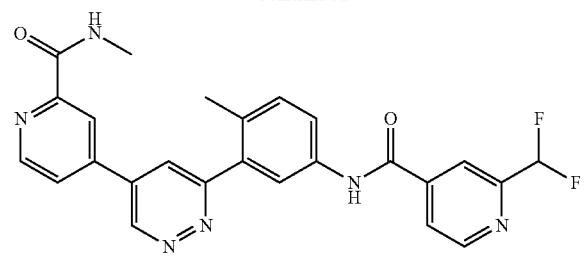
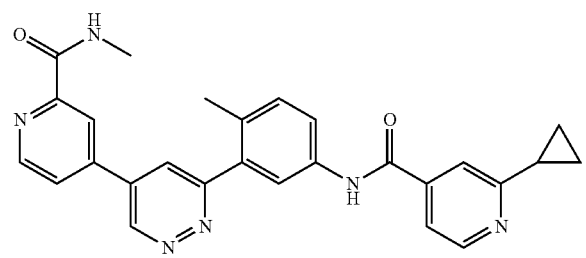
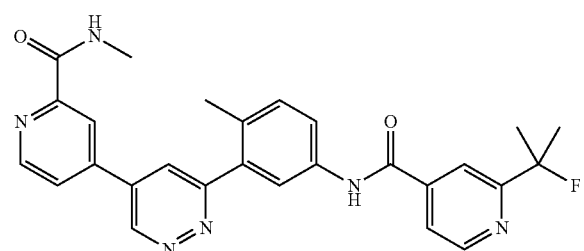
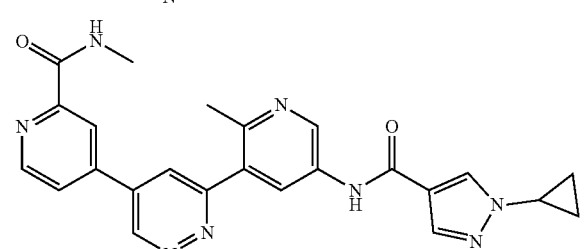
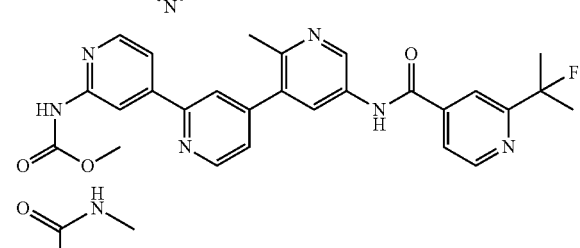
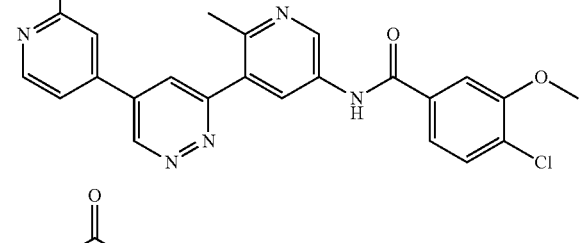
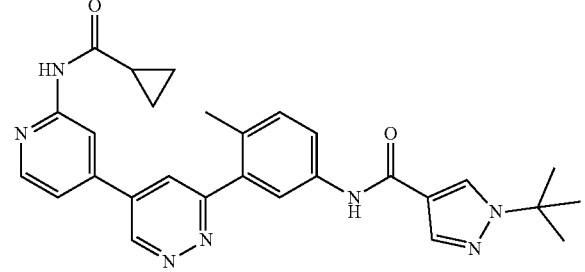
-continued
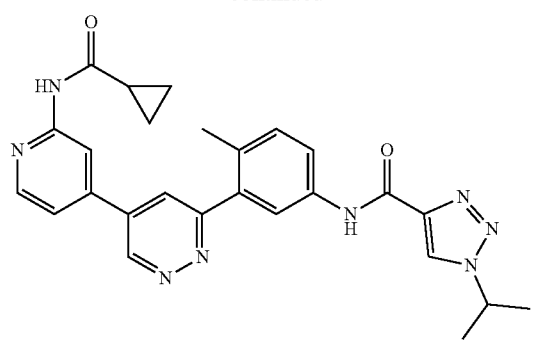
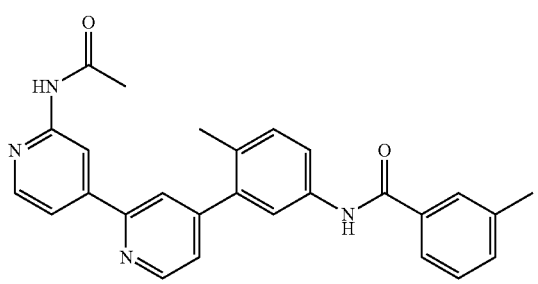
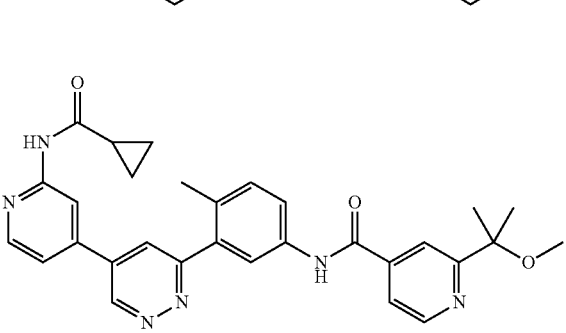
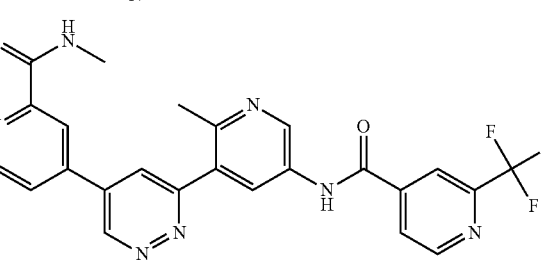
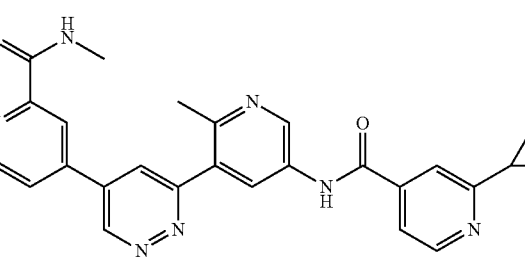
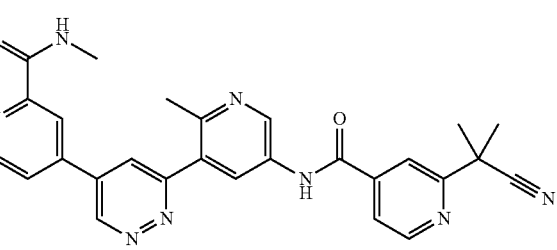

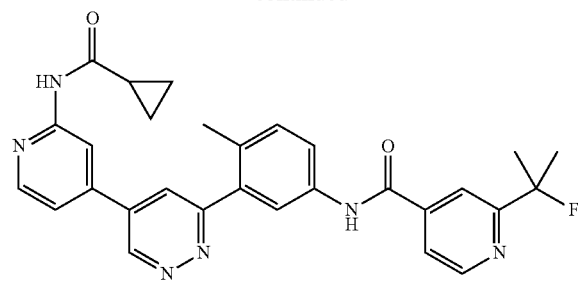
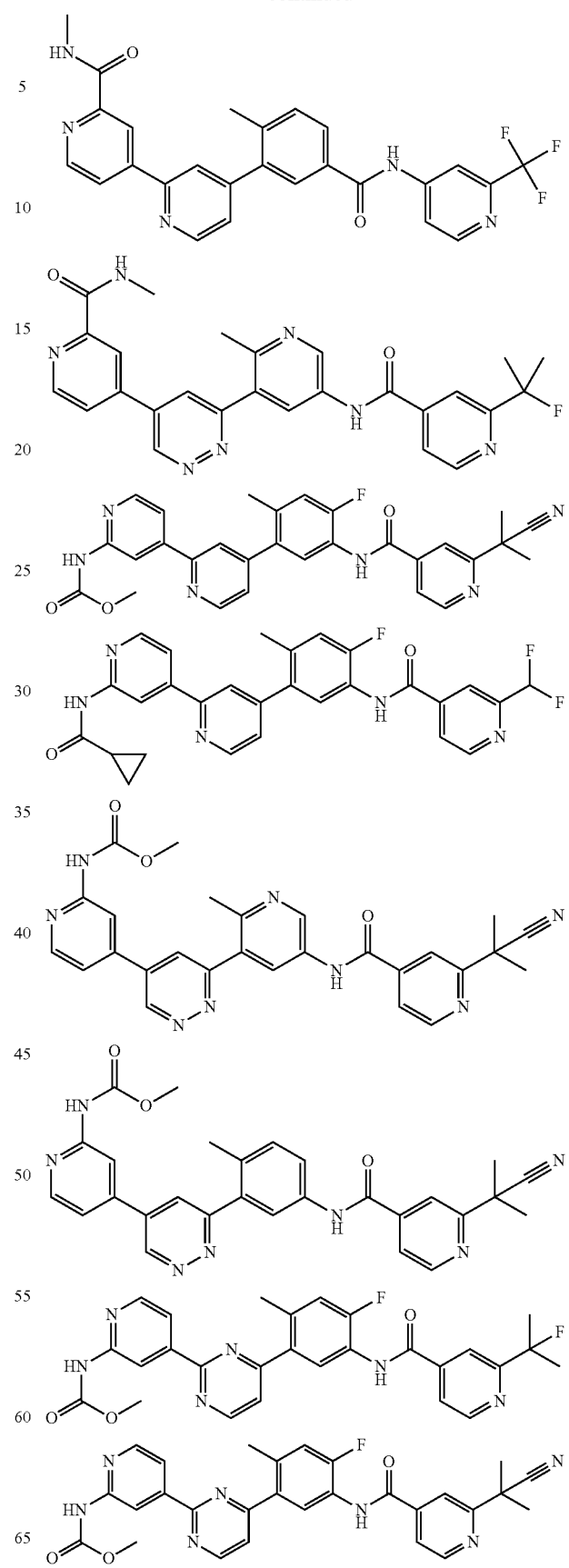

195
-continued
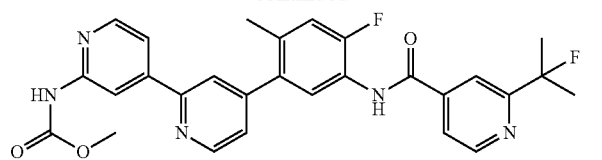
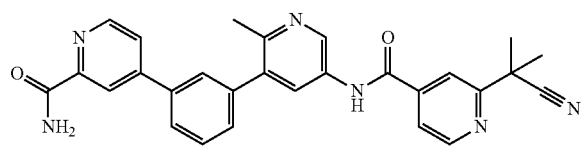
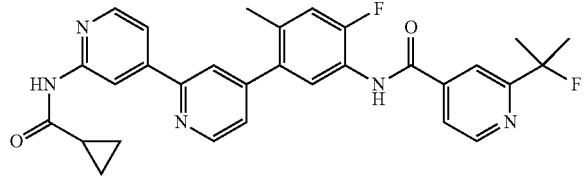
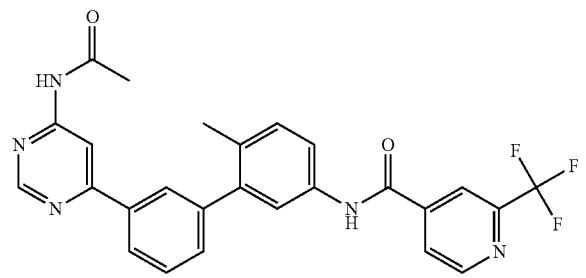
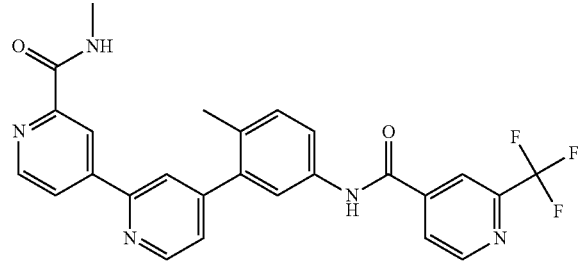
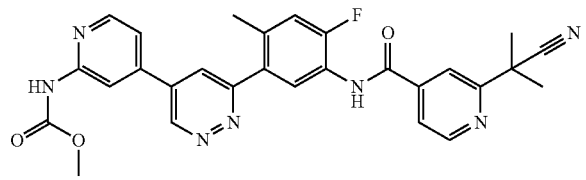
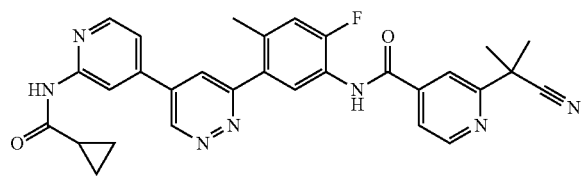
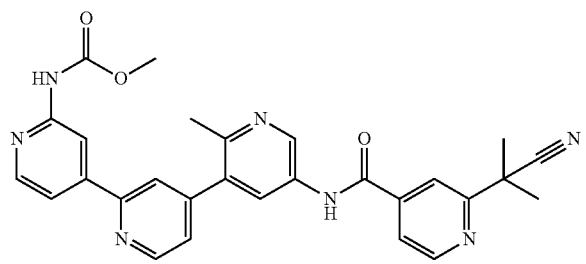
196
-continued
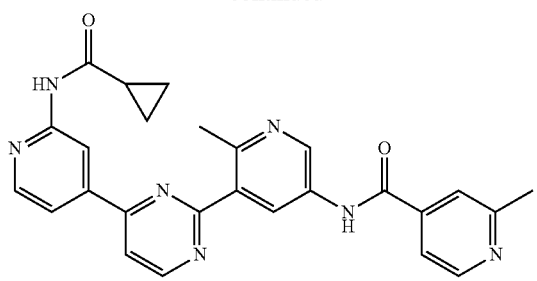
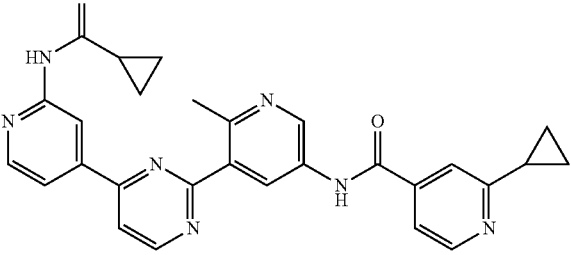
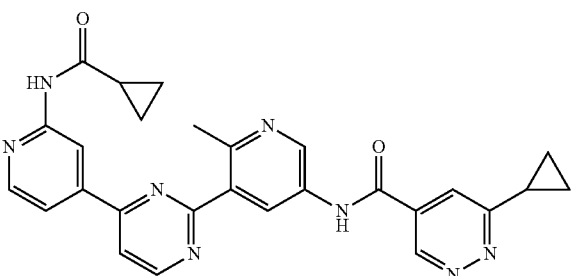
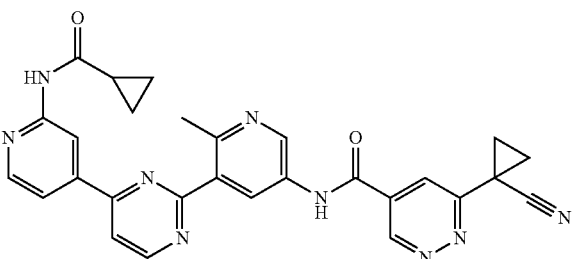
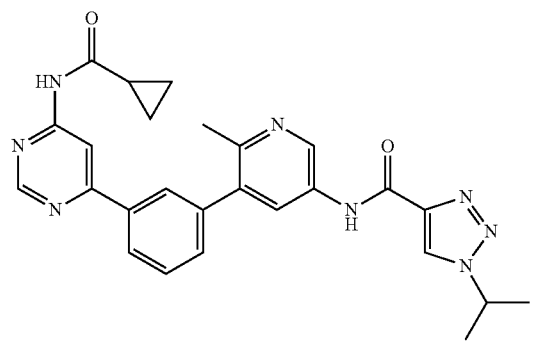
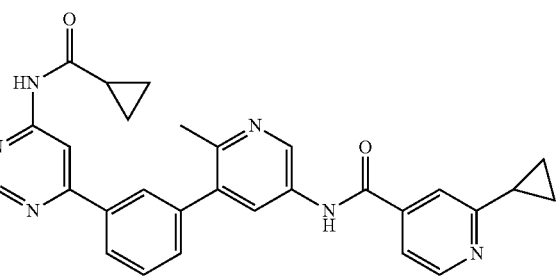

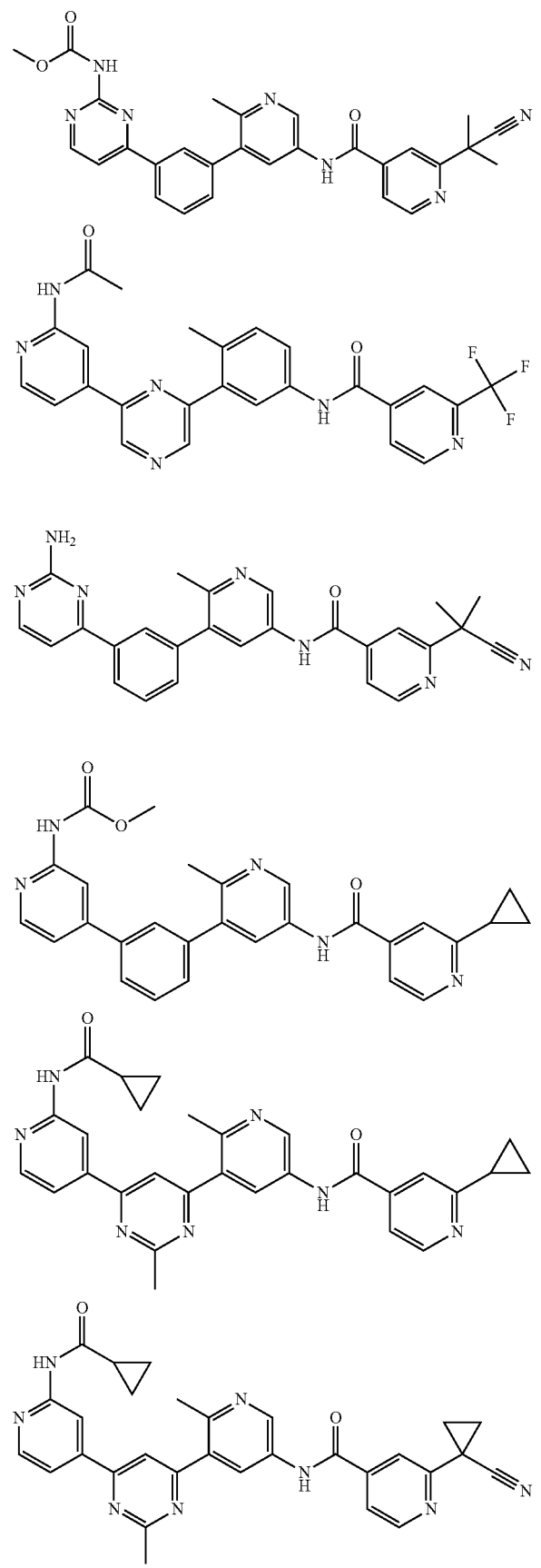
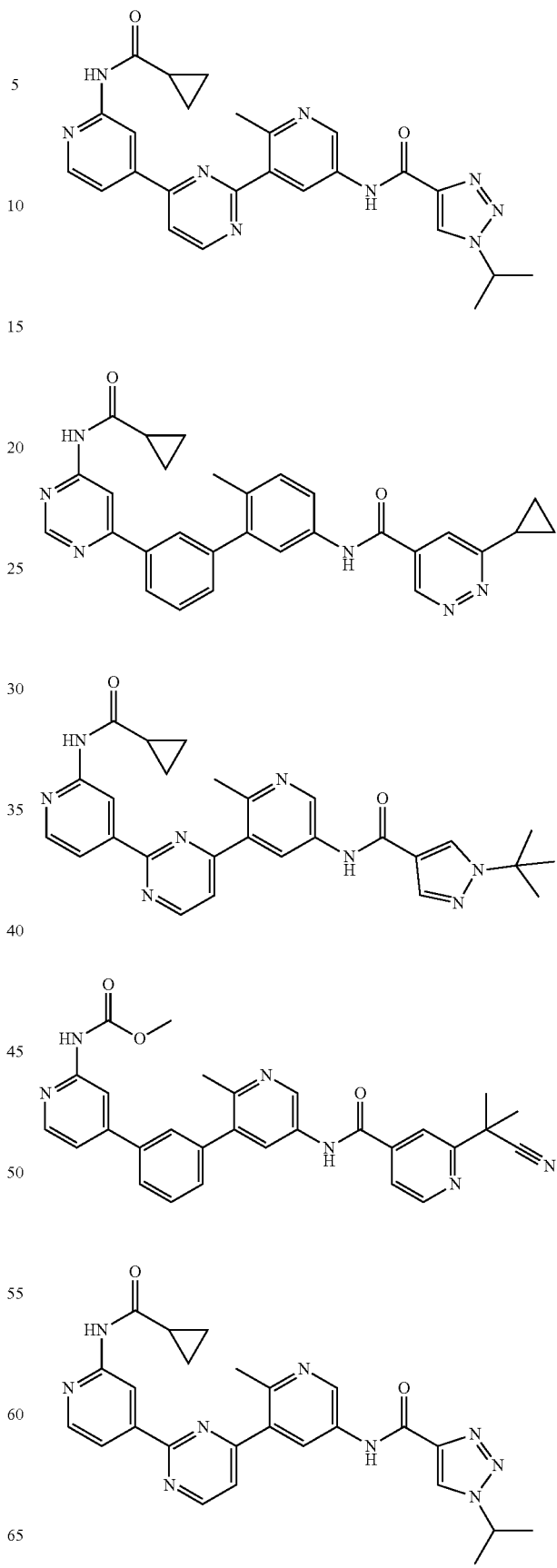

199
-continued
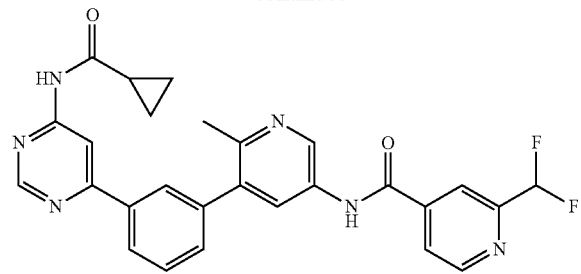
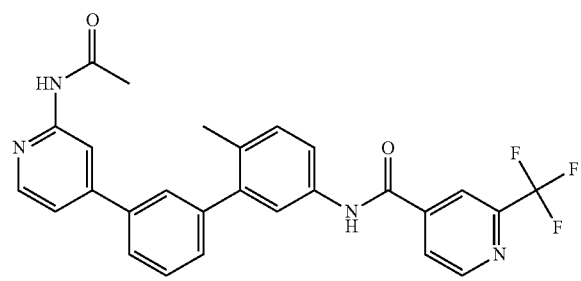
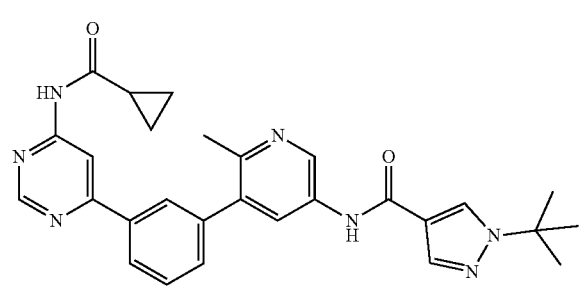
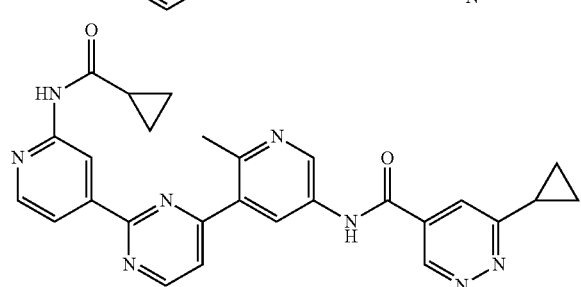
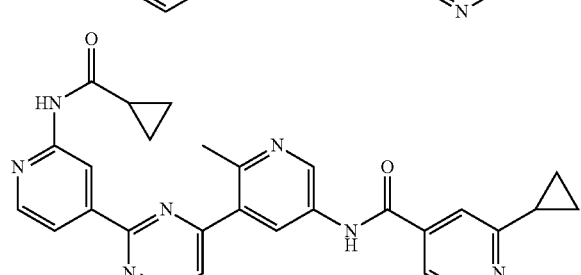
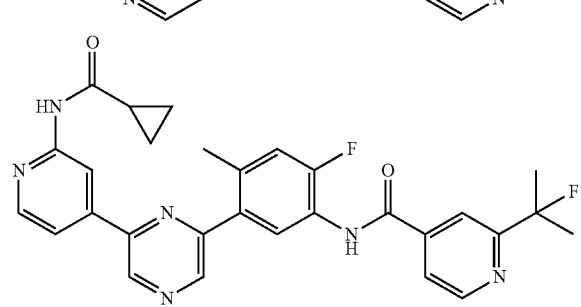
200
-continued
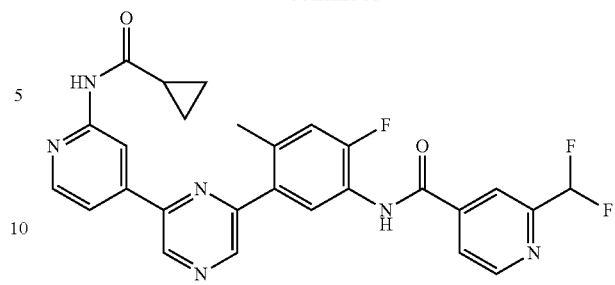
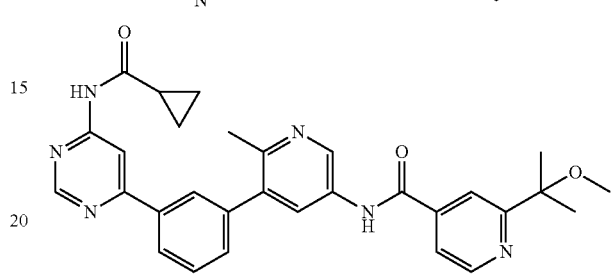
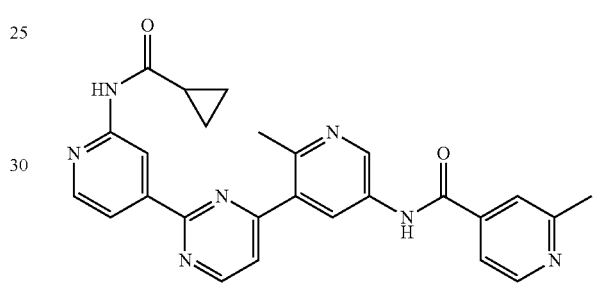
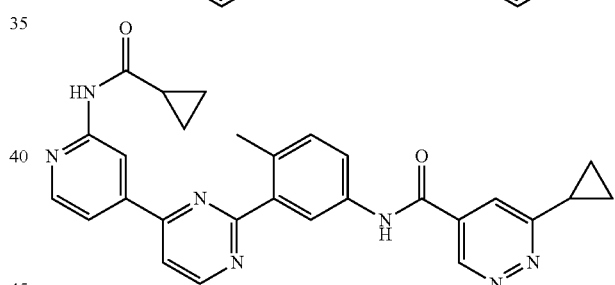
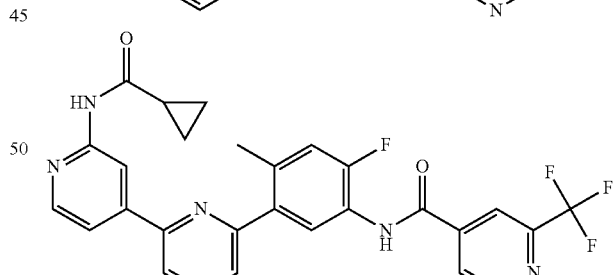
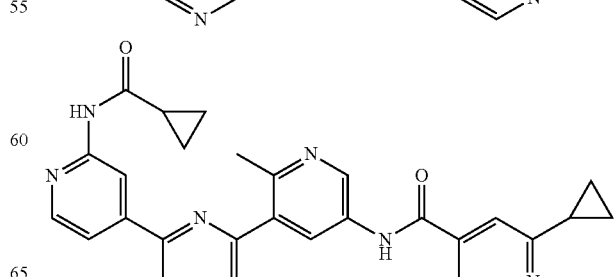

201
-continued
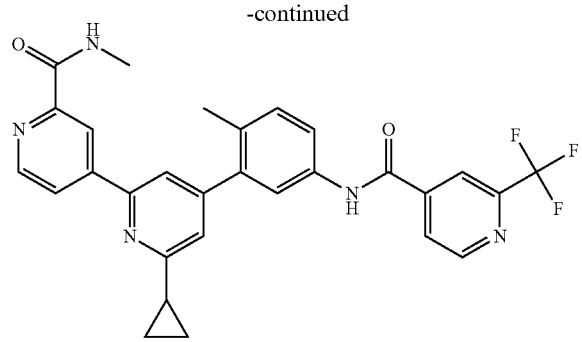
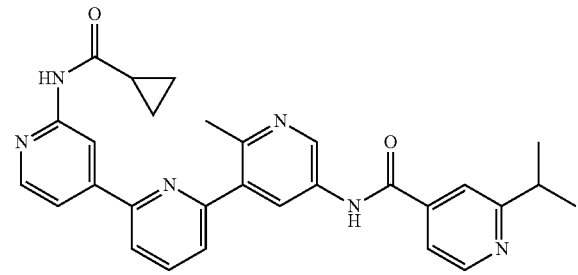
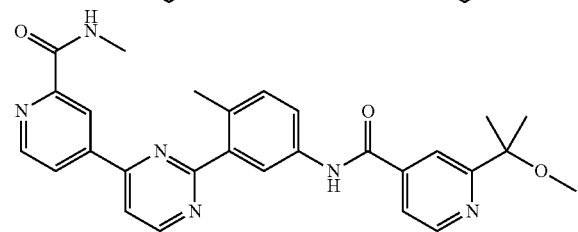
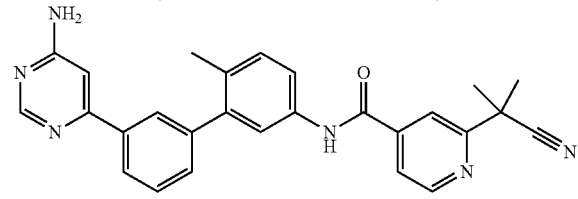
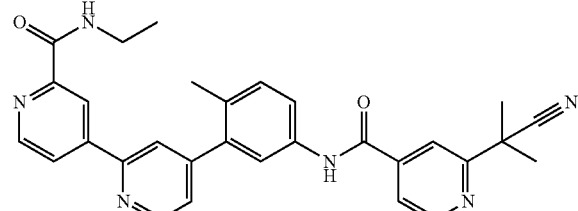
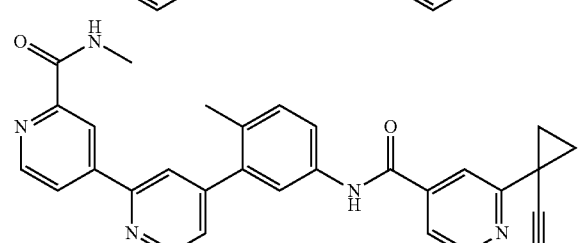
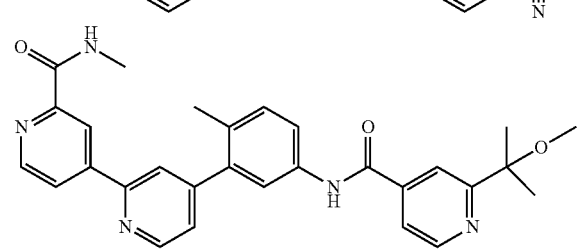
202
-continued
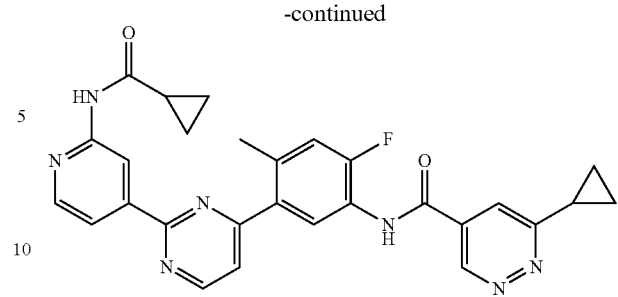
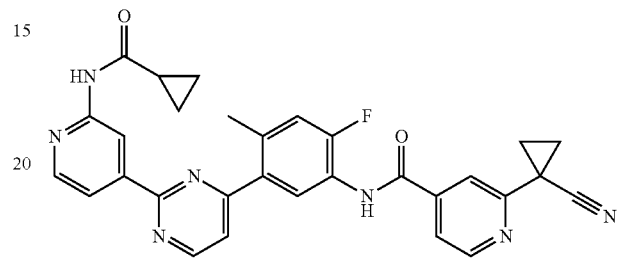
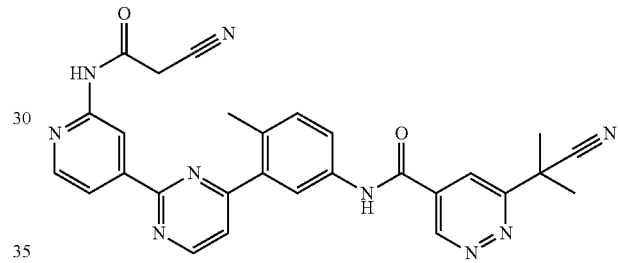
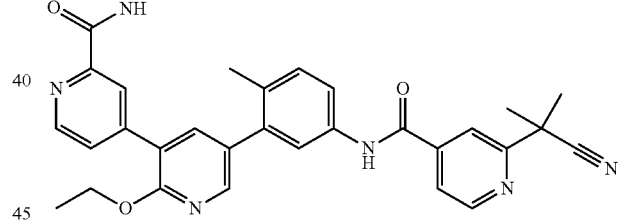
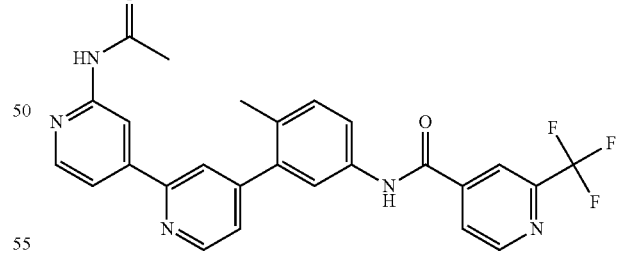
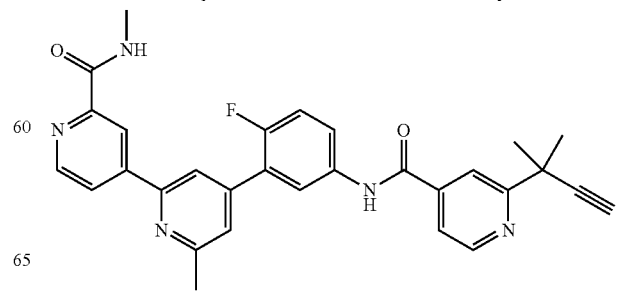

-continued
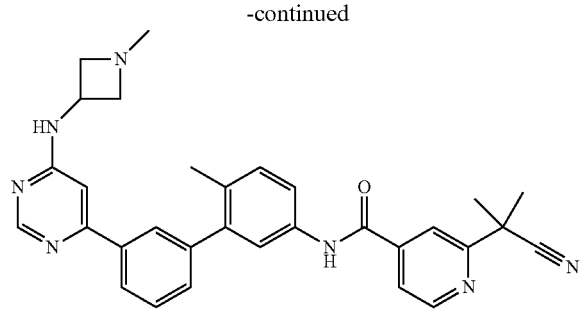
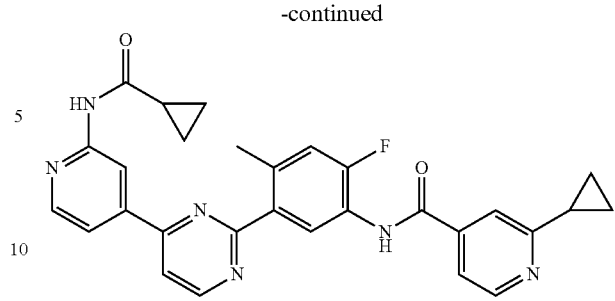
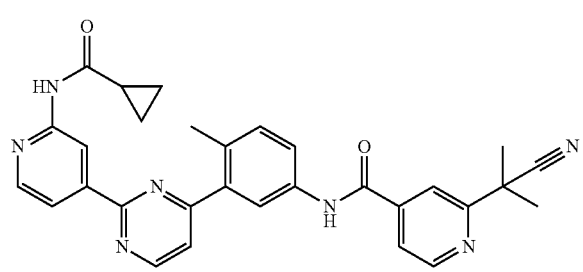
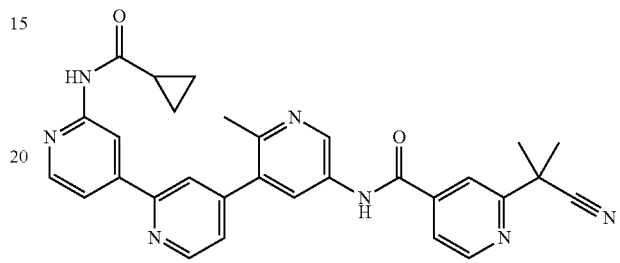
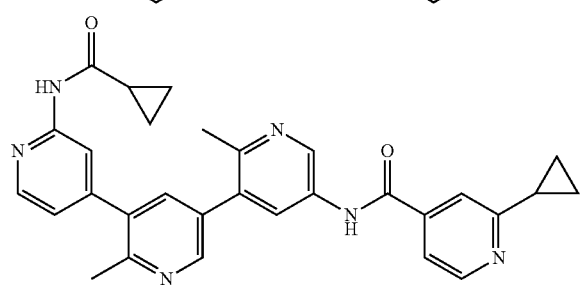
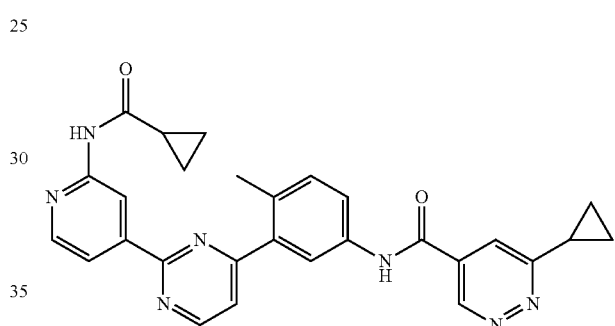
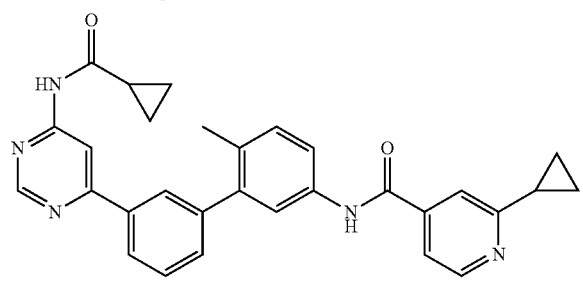
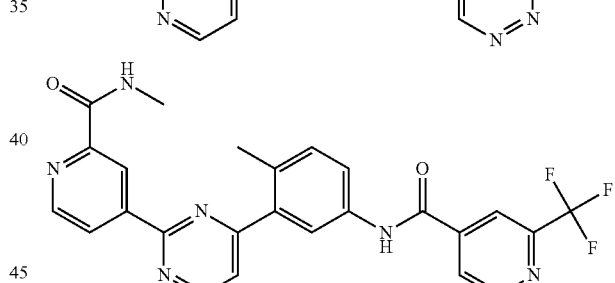
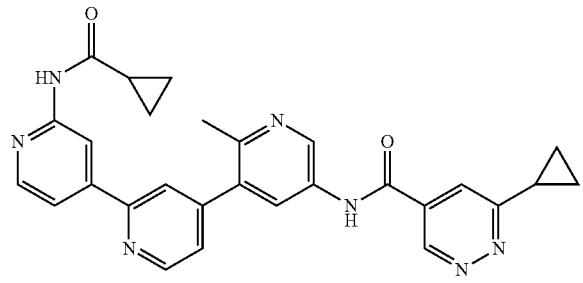
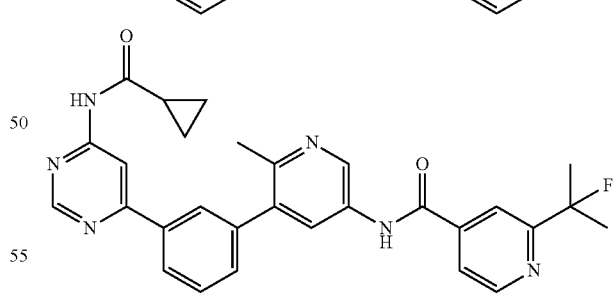
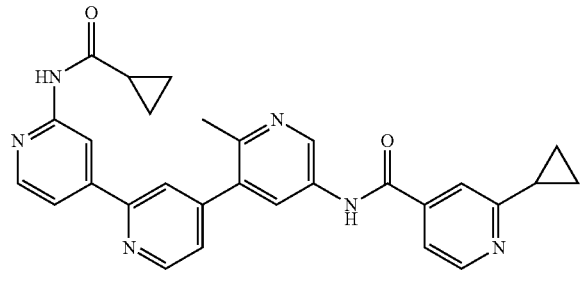
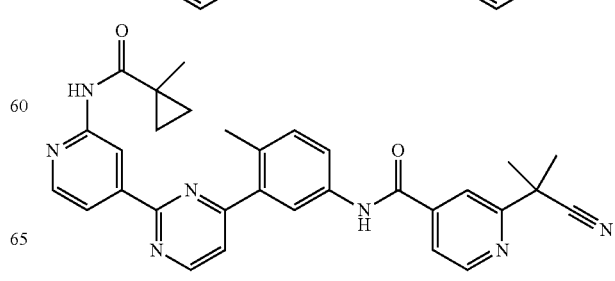

205
-continued
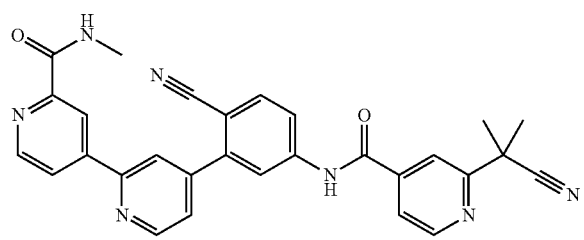
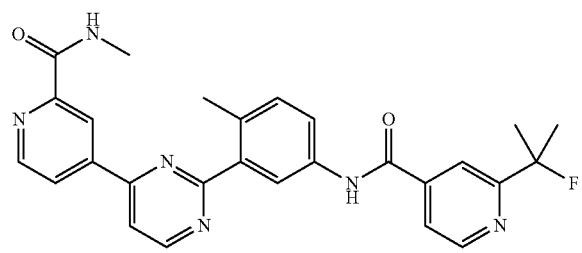
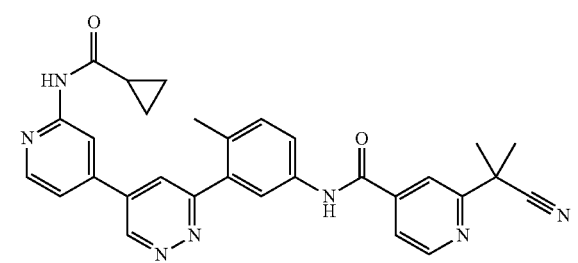
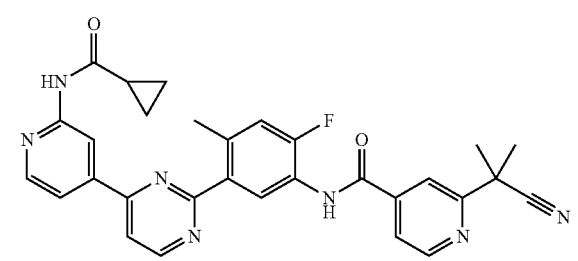
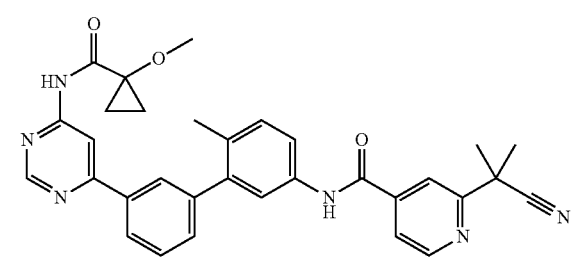
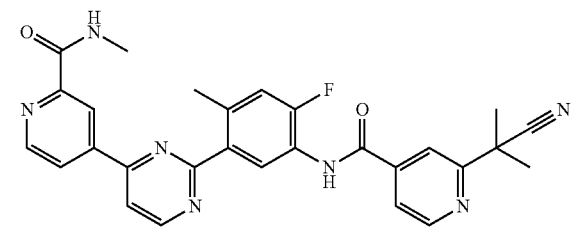
206
-continued
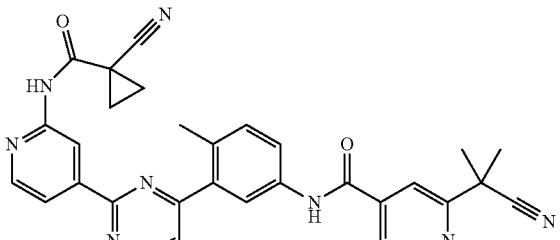
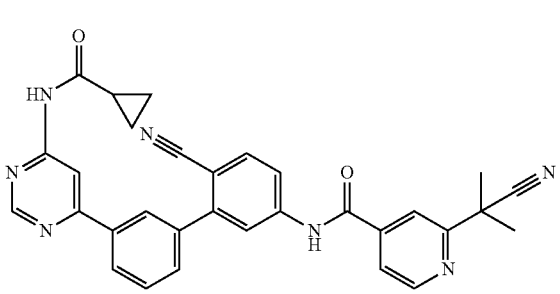
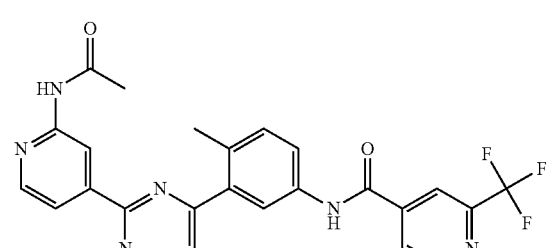
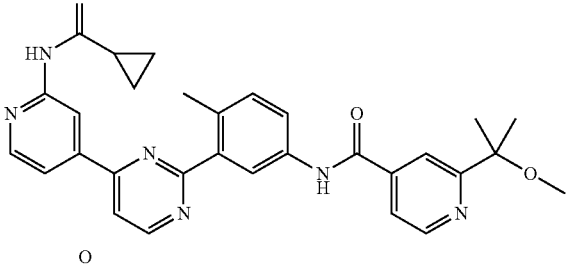
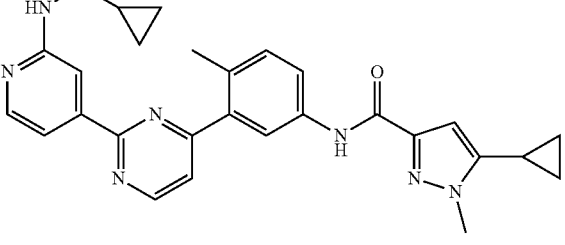
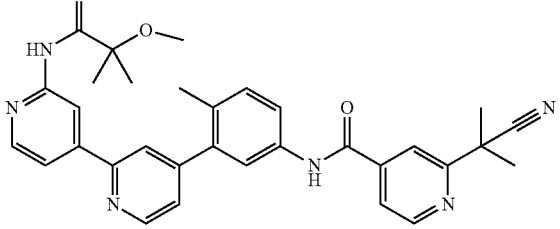

207
-continued
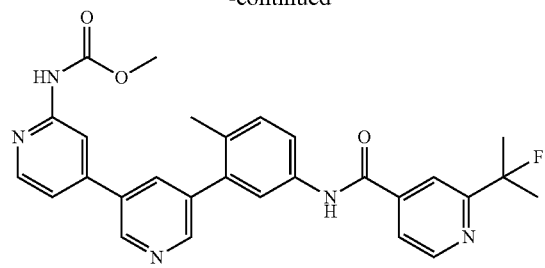
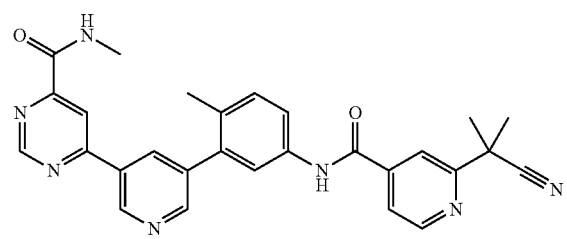
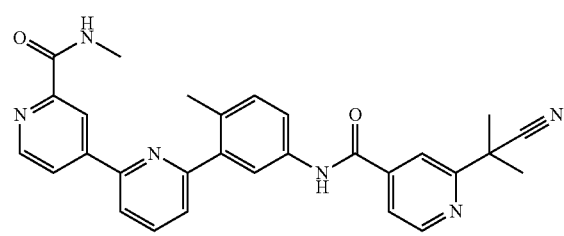
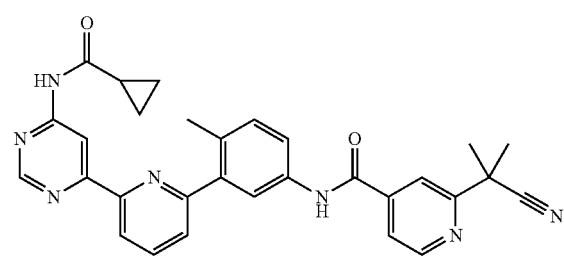
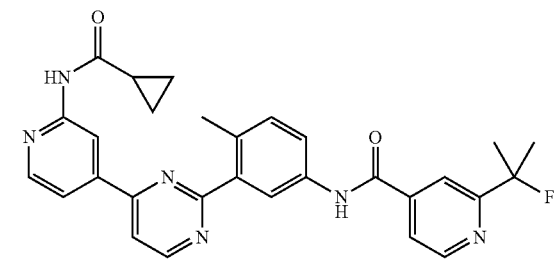
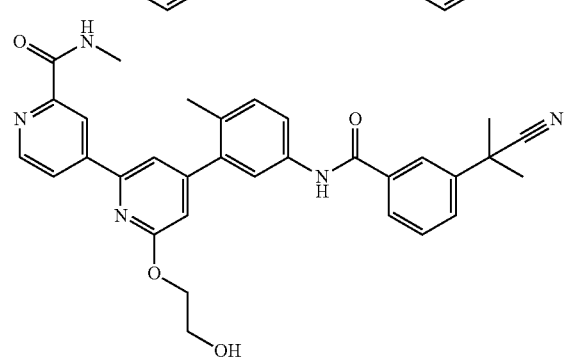
208
-continued
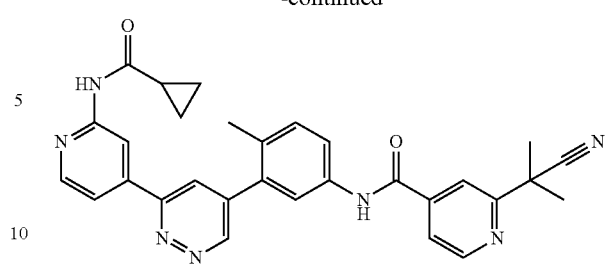
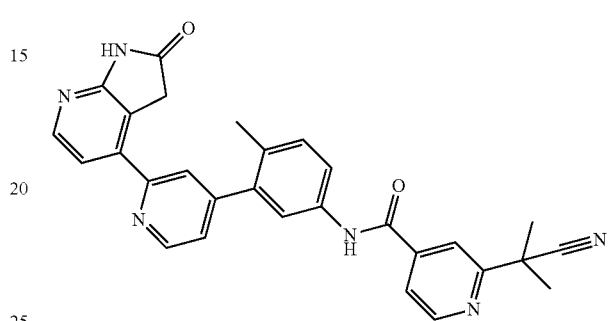
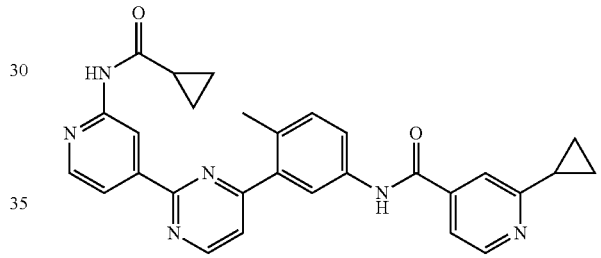
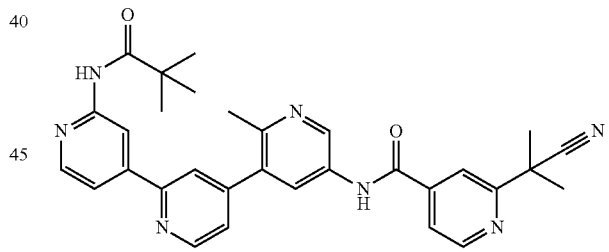
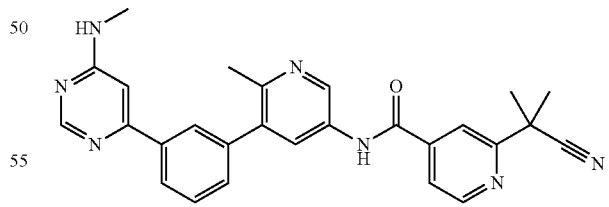
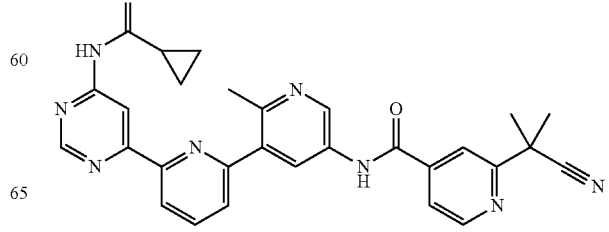

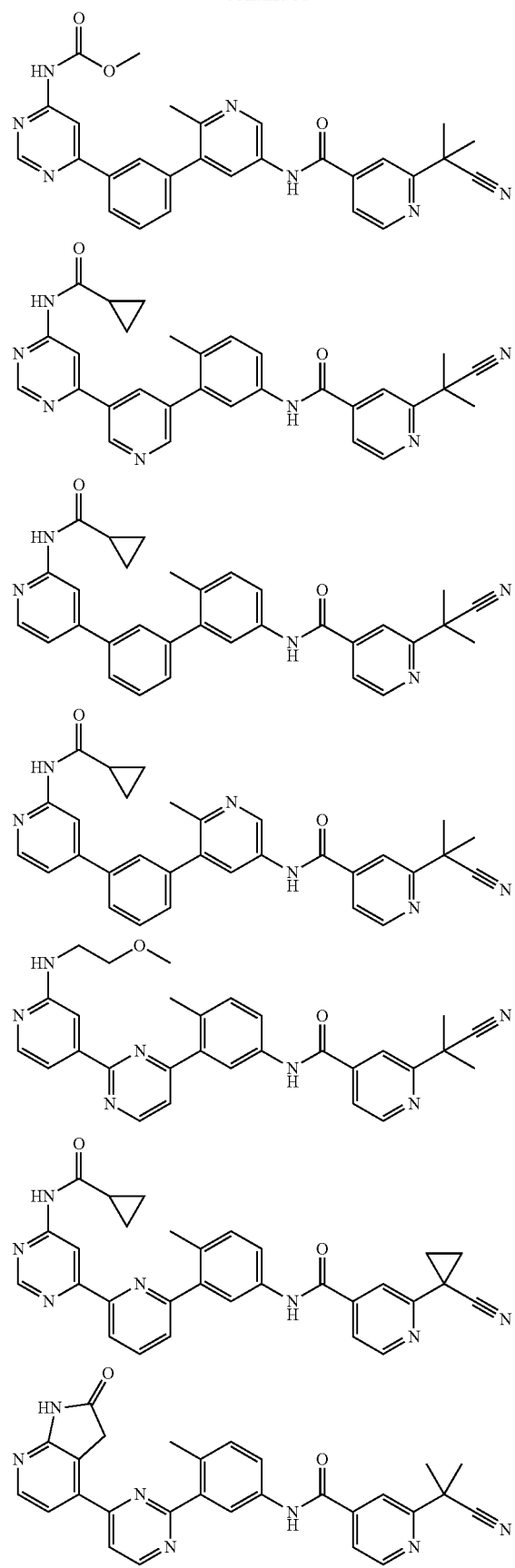
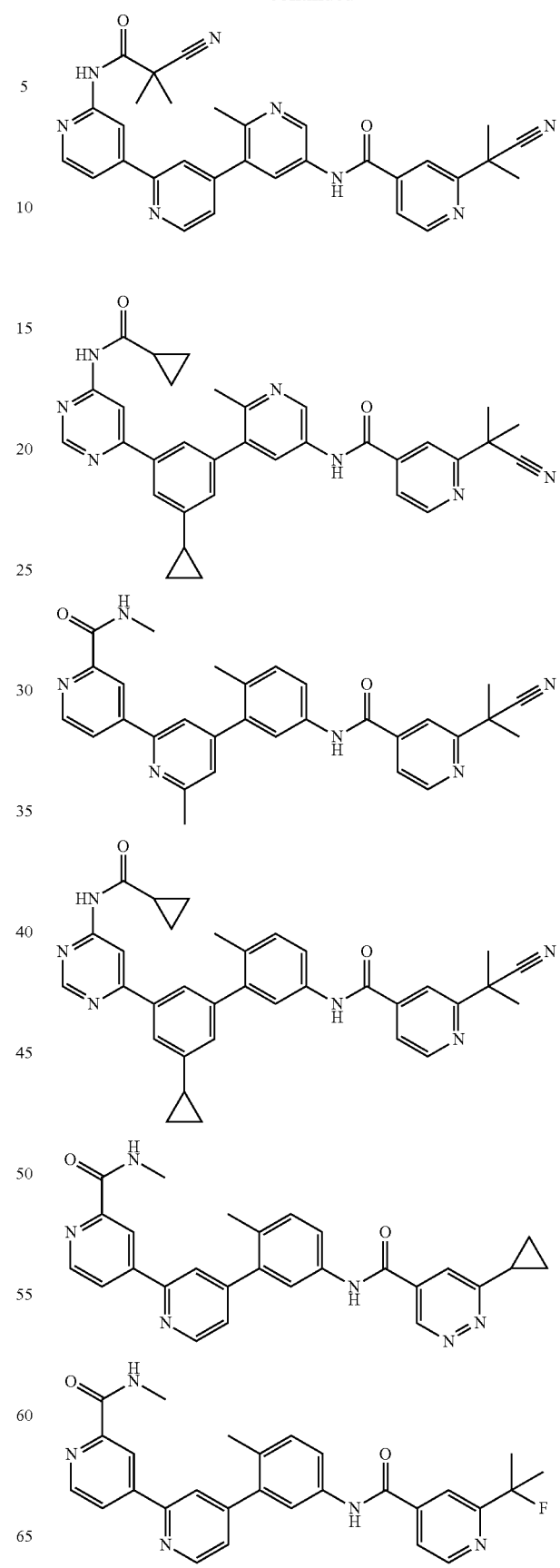

211
-continued
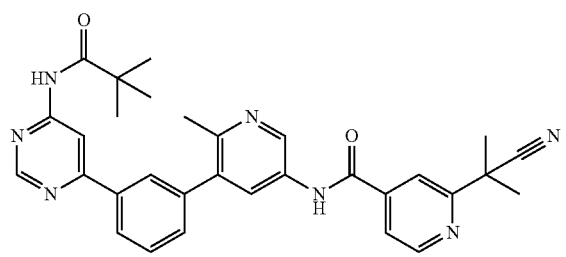
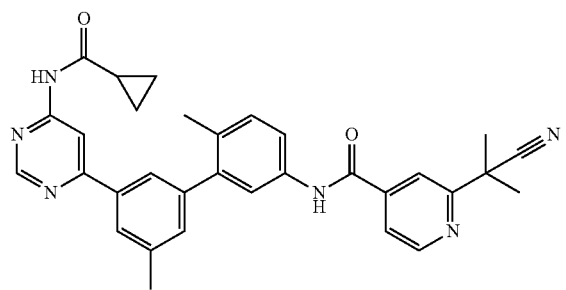
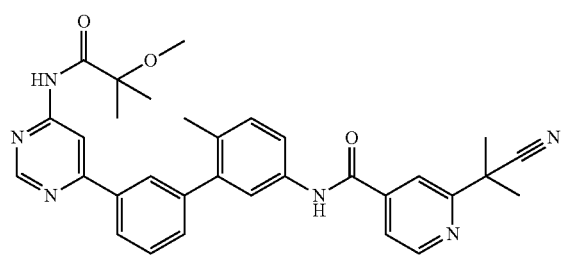
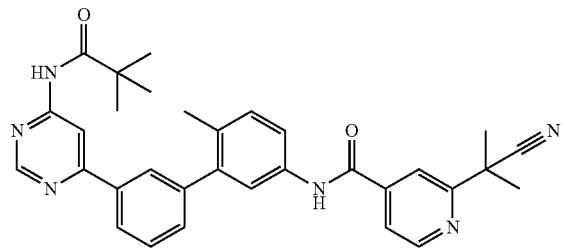
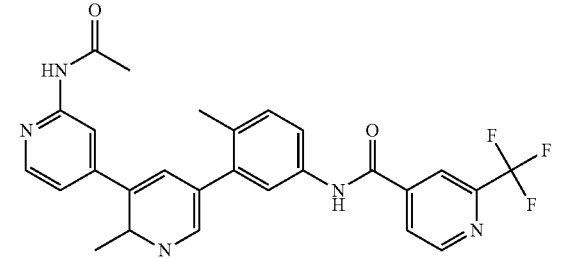
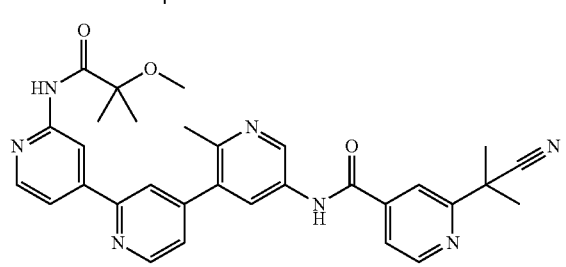
212
-continued
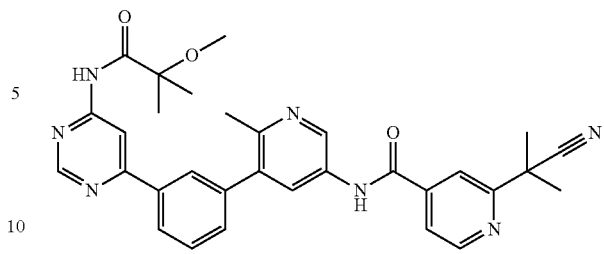
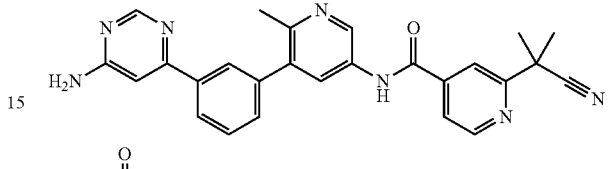
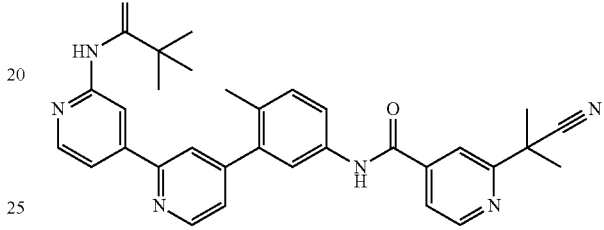
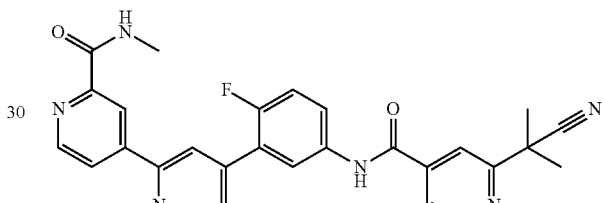
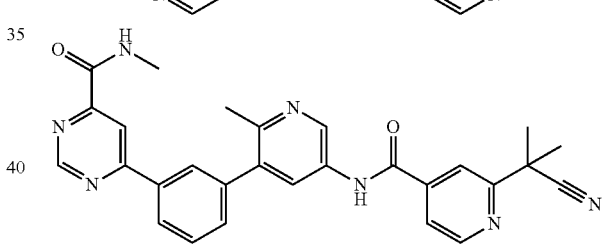
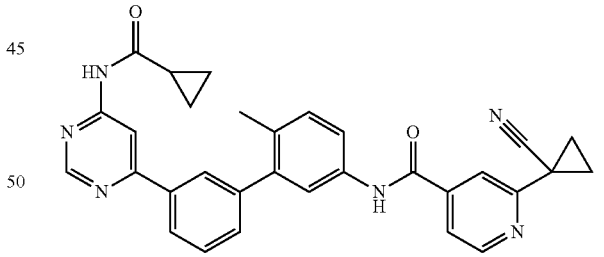
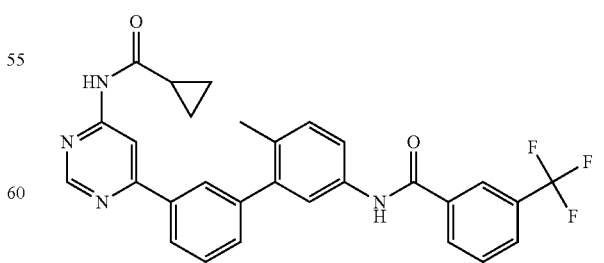

213
-continued
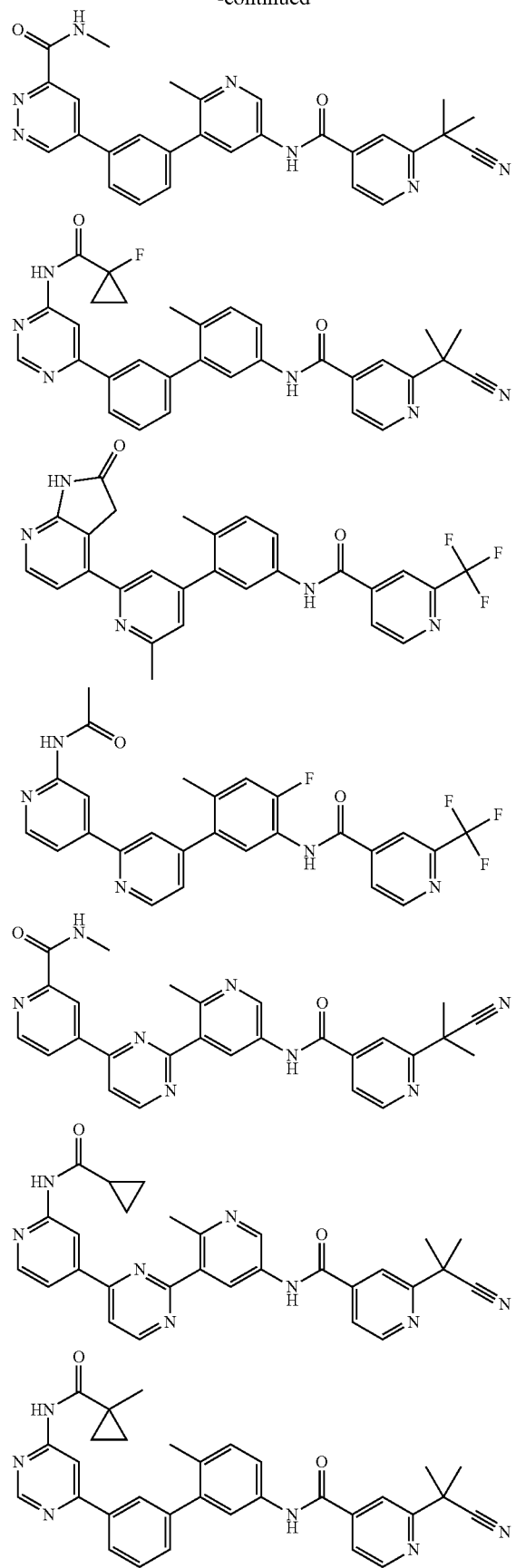
214
-continued
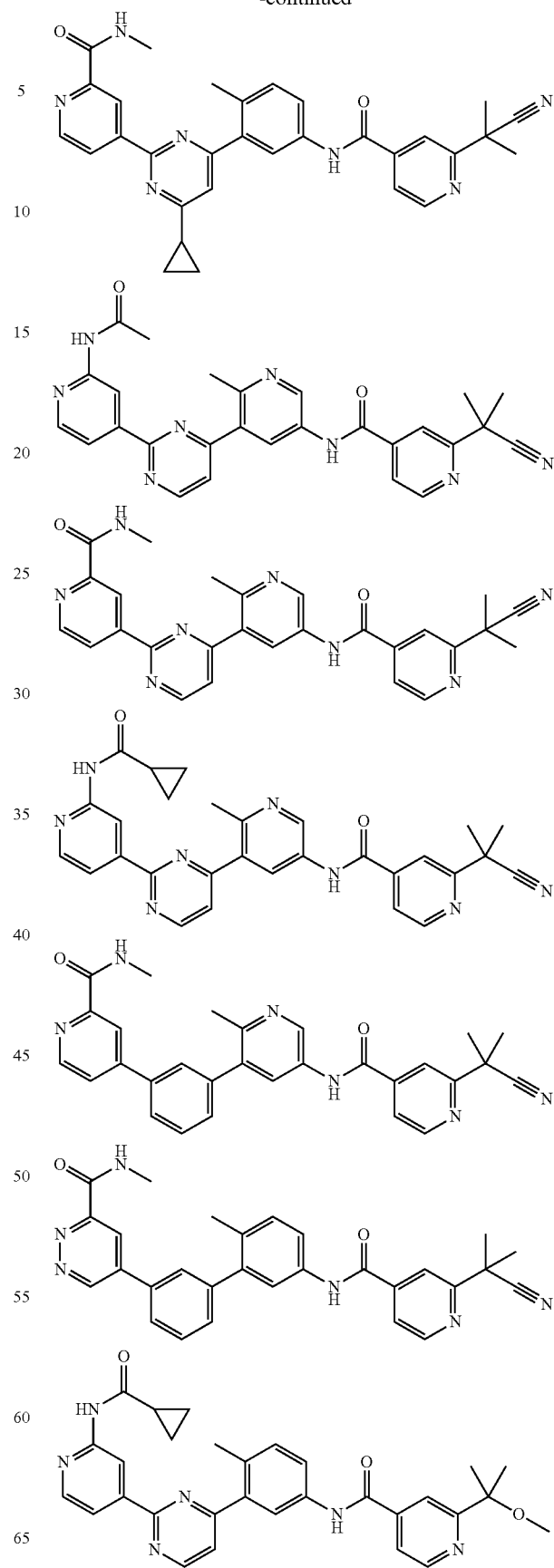

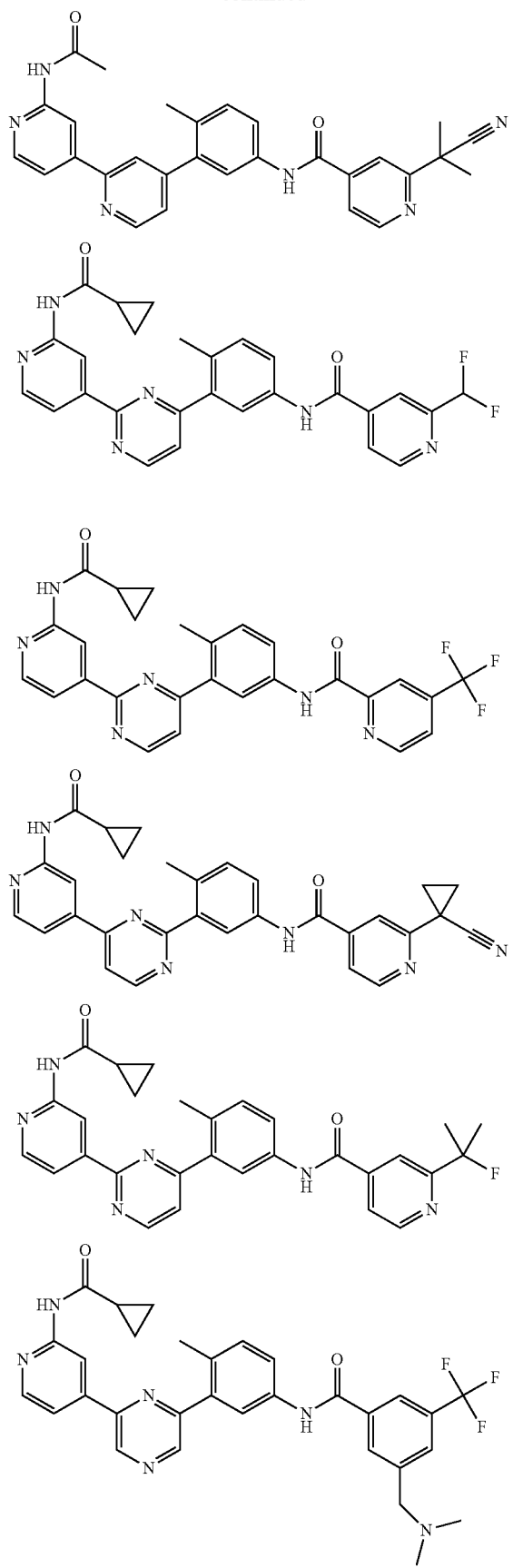
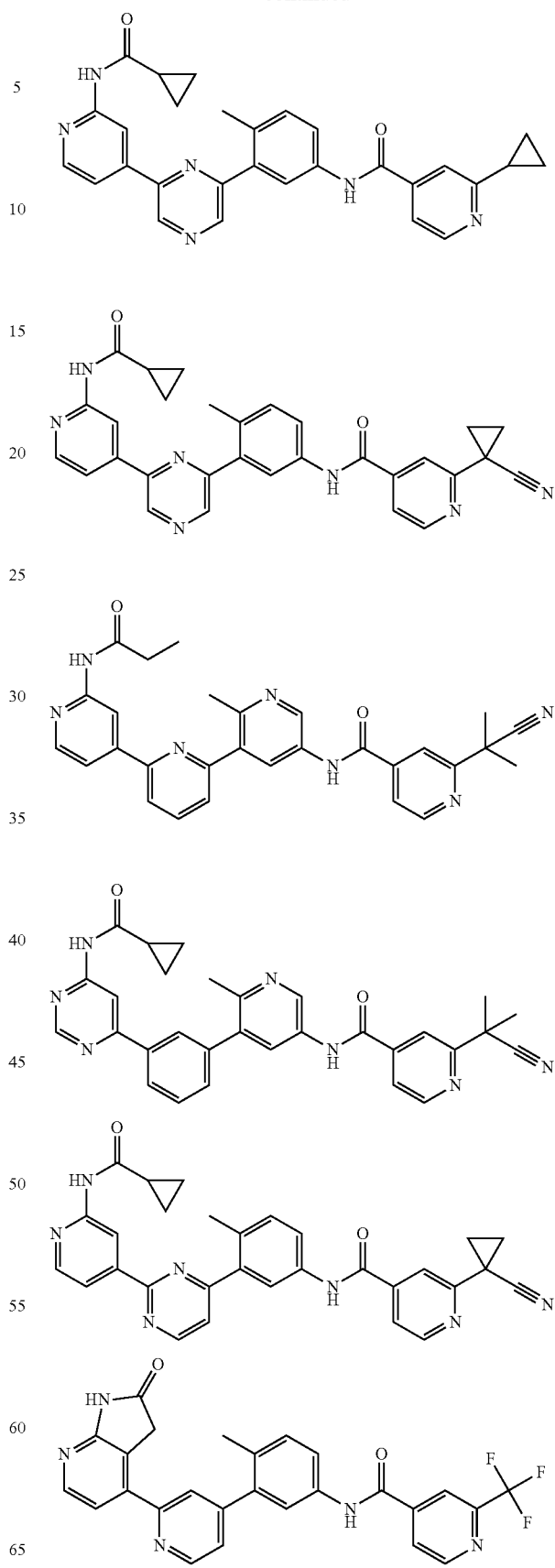

-continued
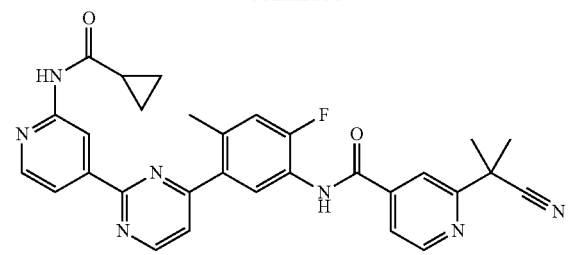
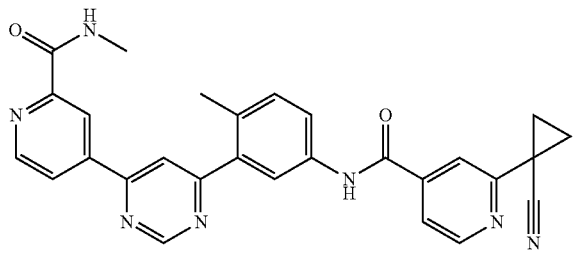
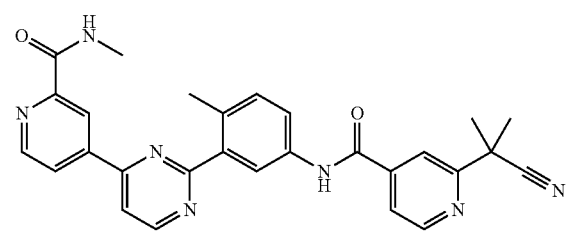
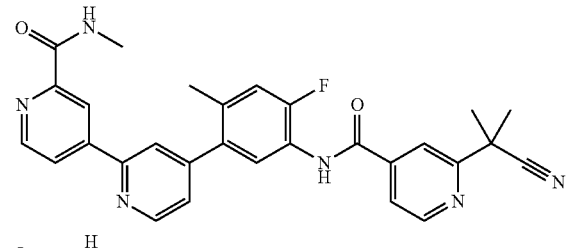
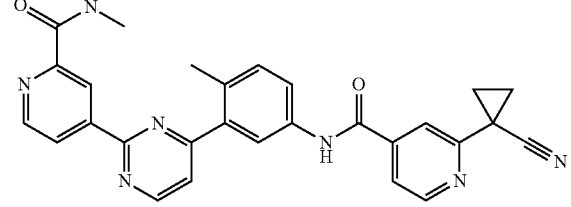
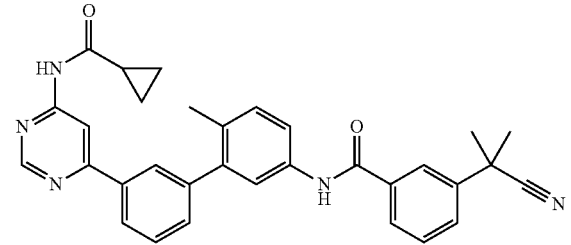
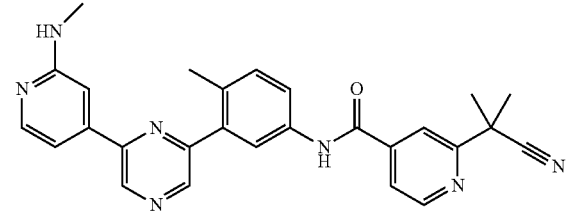
-continued
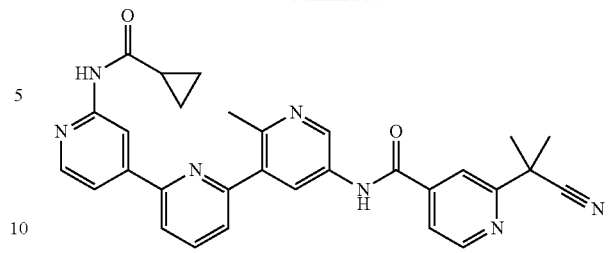
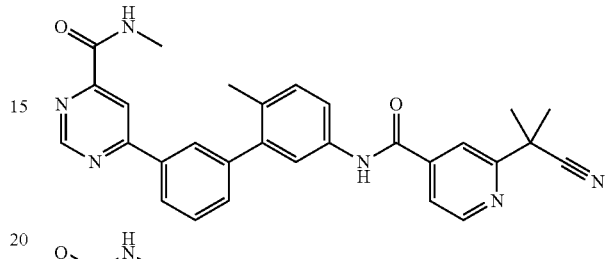
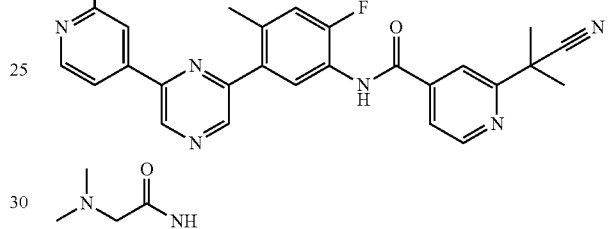
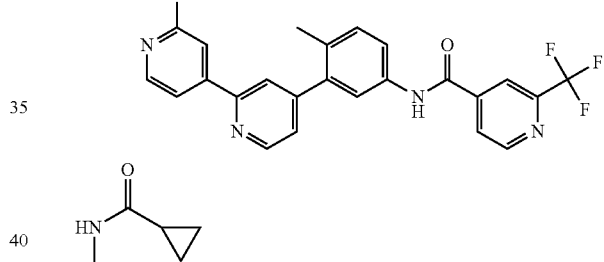
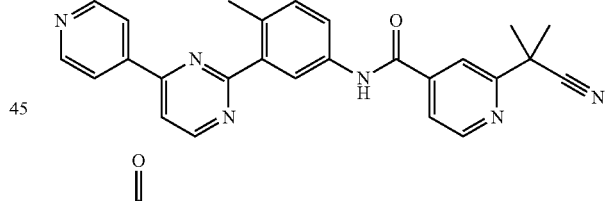
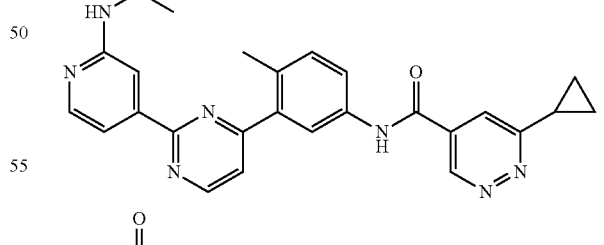
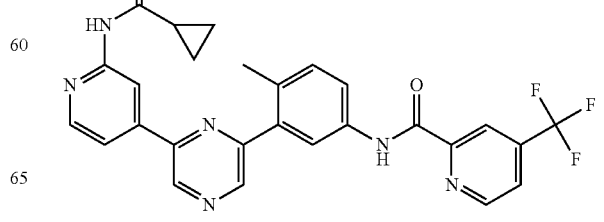

219
-continued
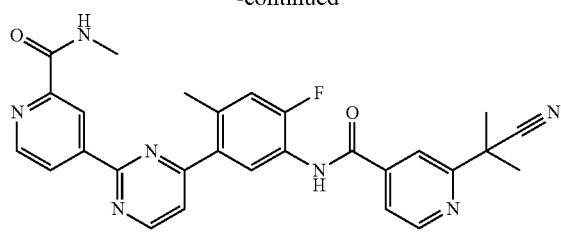
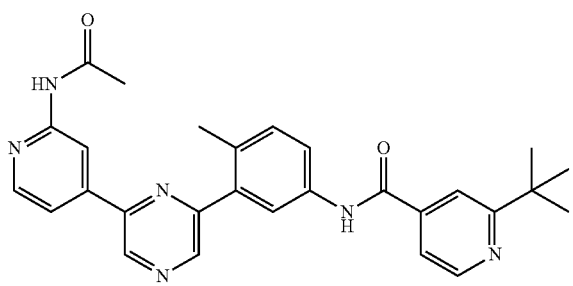
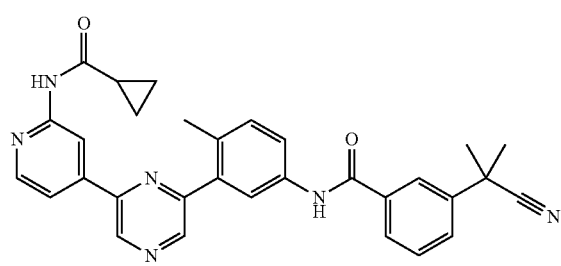
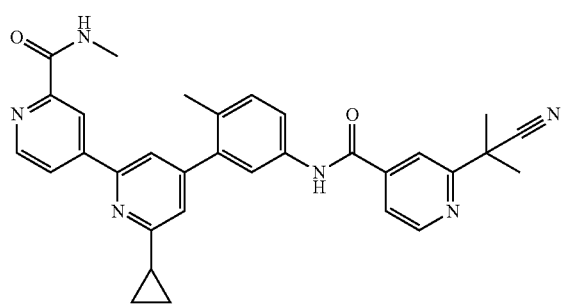
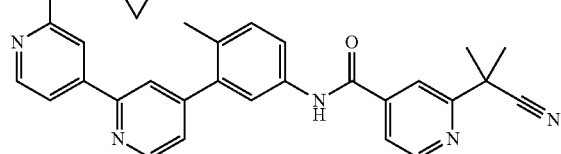
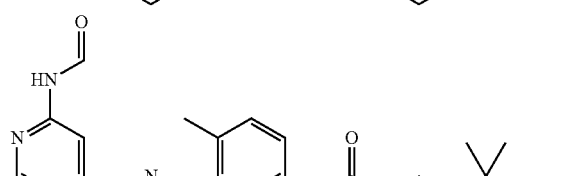
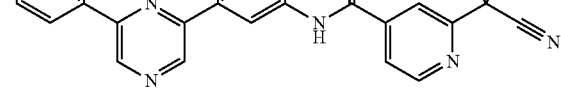
220
-continued
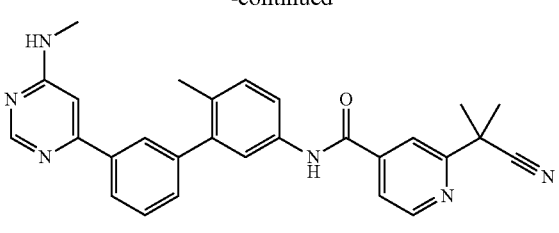
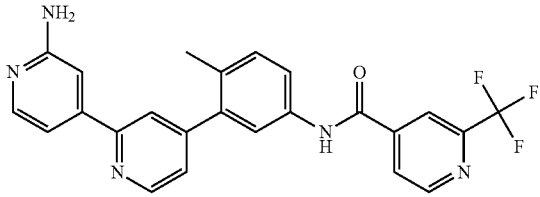
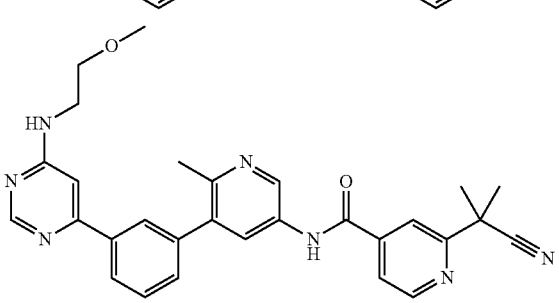
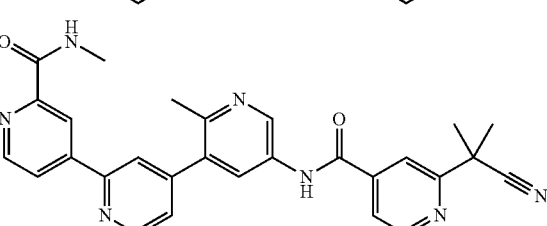
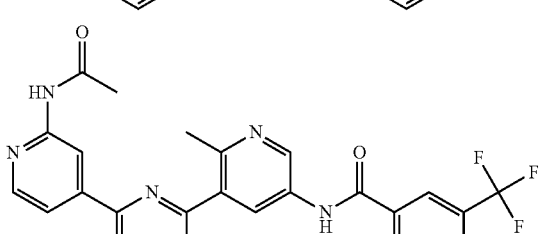
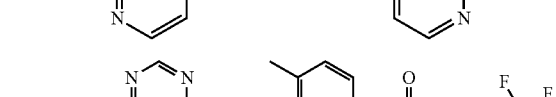
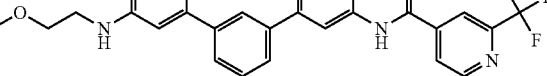
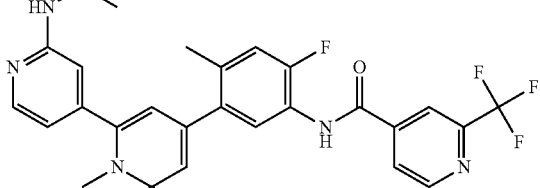

221
-continued
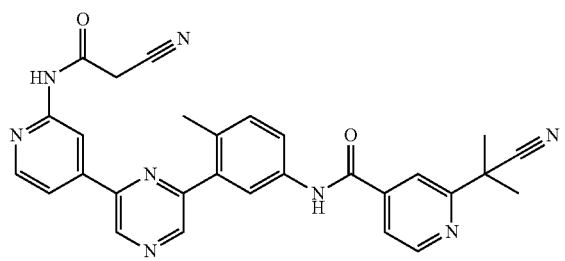
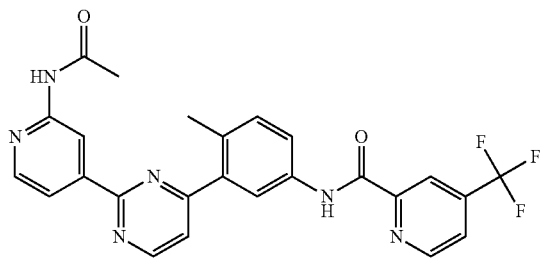
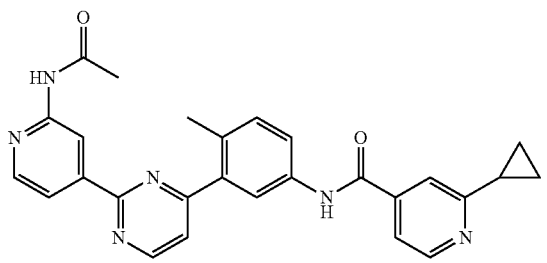
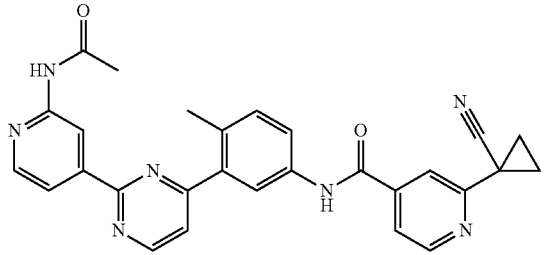
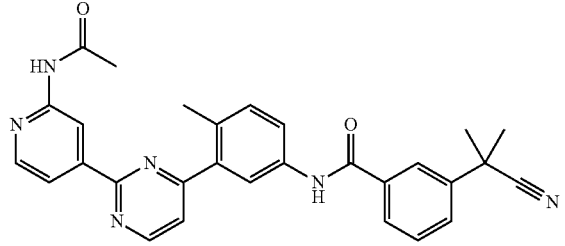
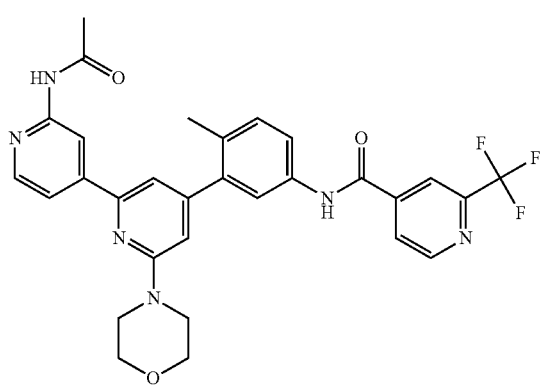
222
-continued
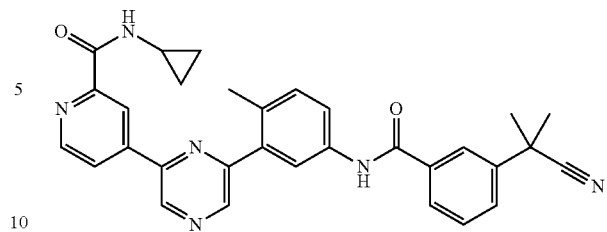
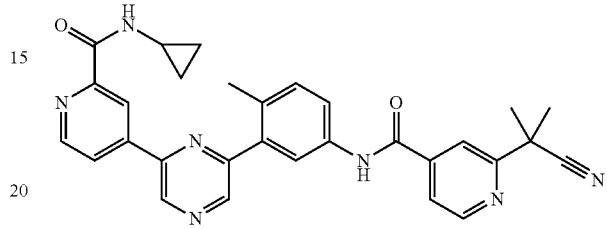
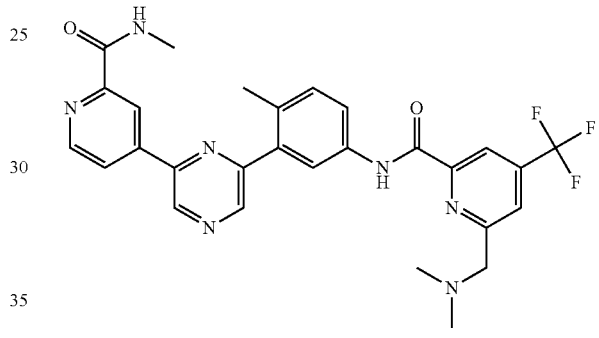
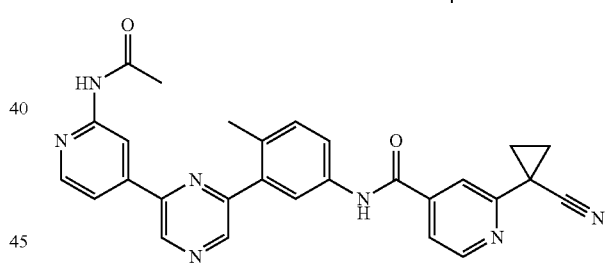
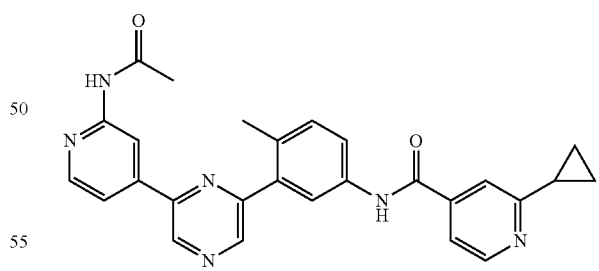
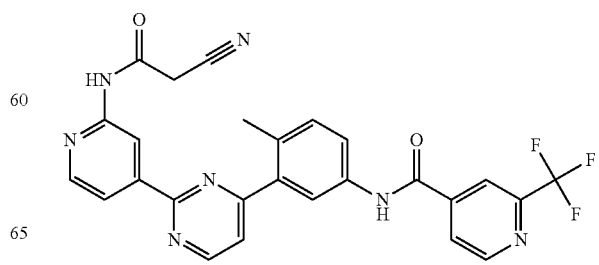

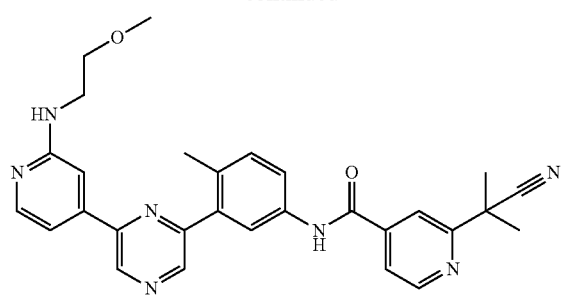
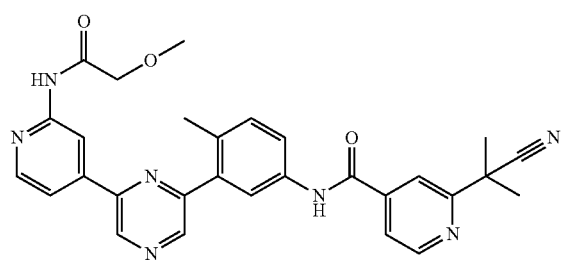
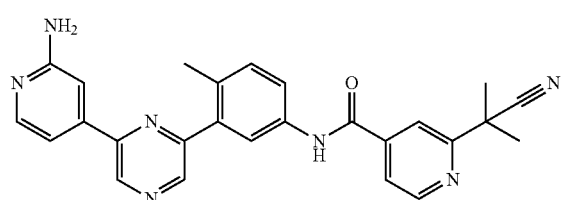
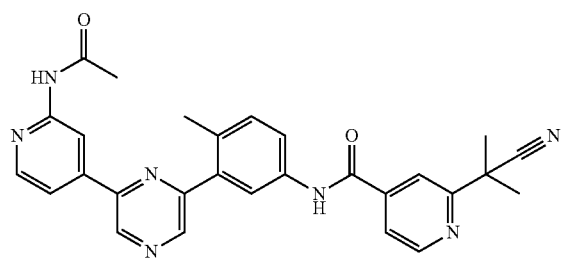
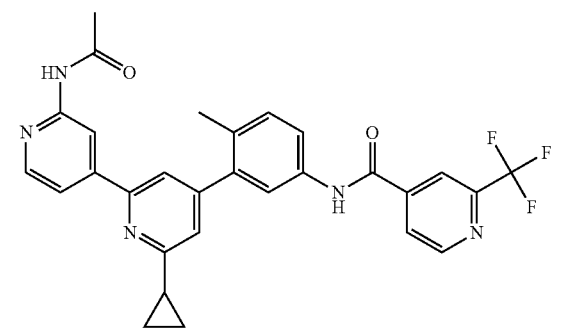
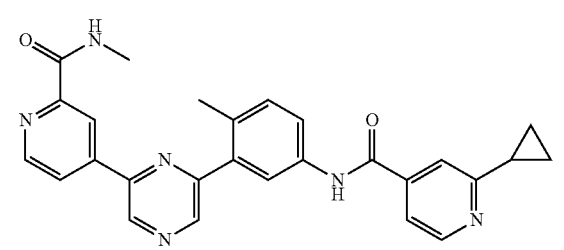
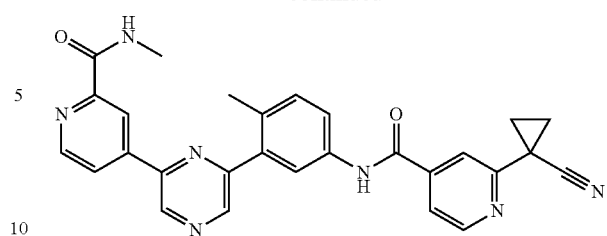
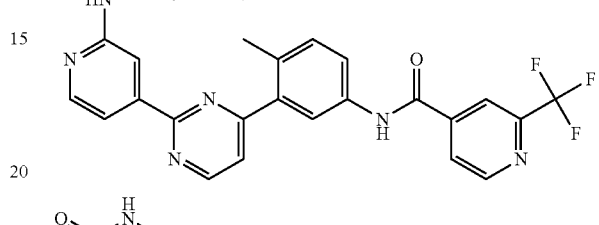
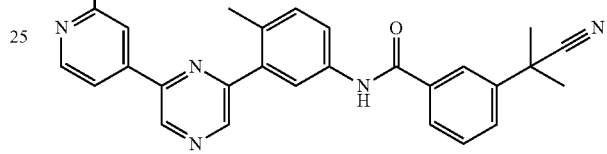
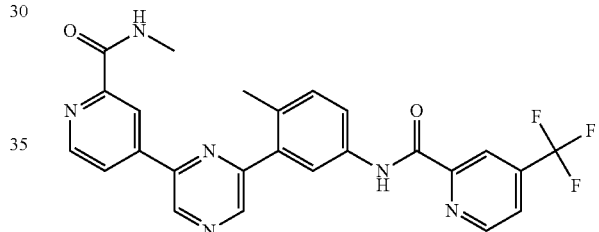
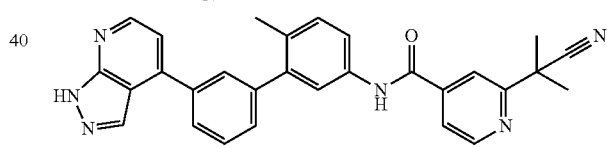
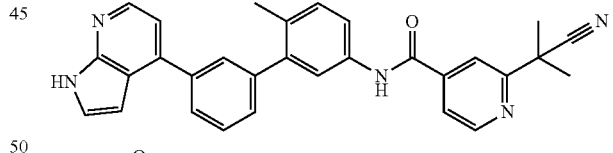
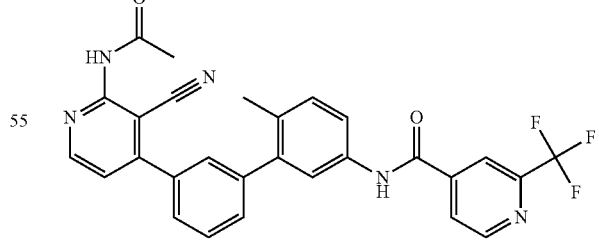
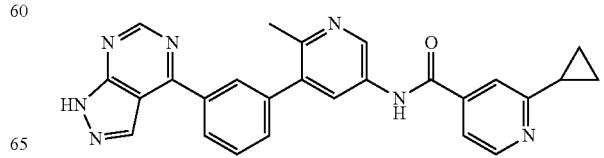

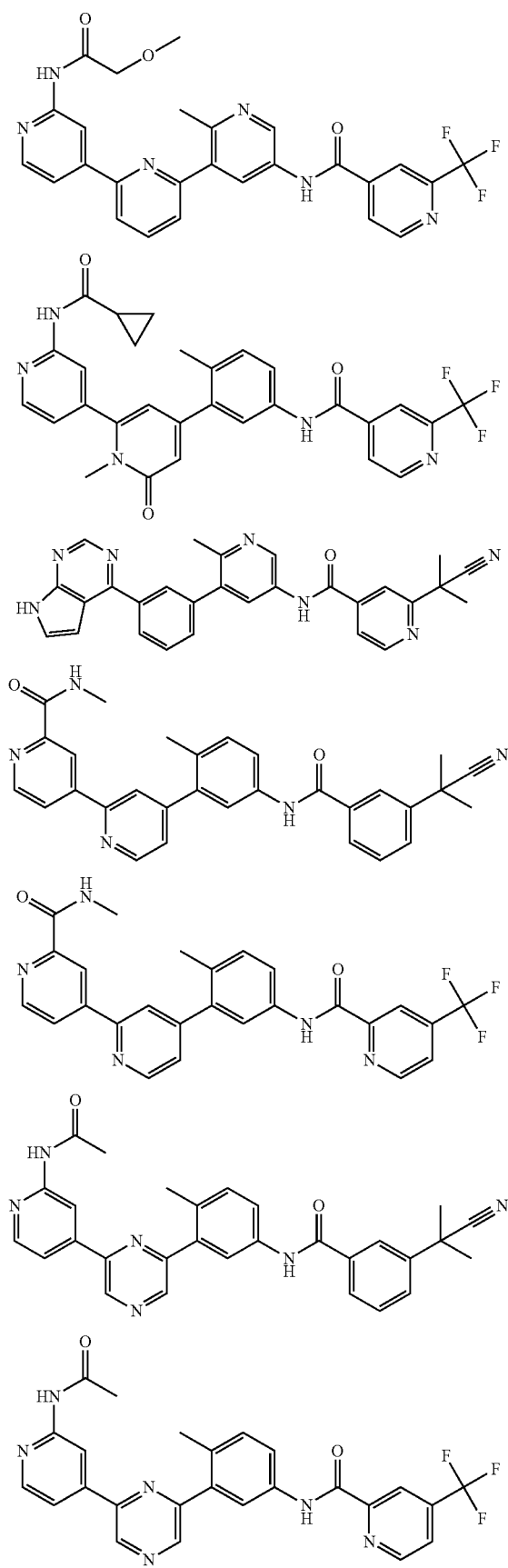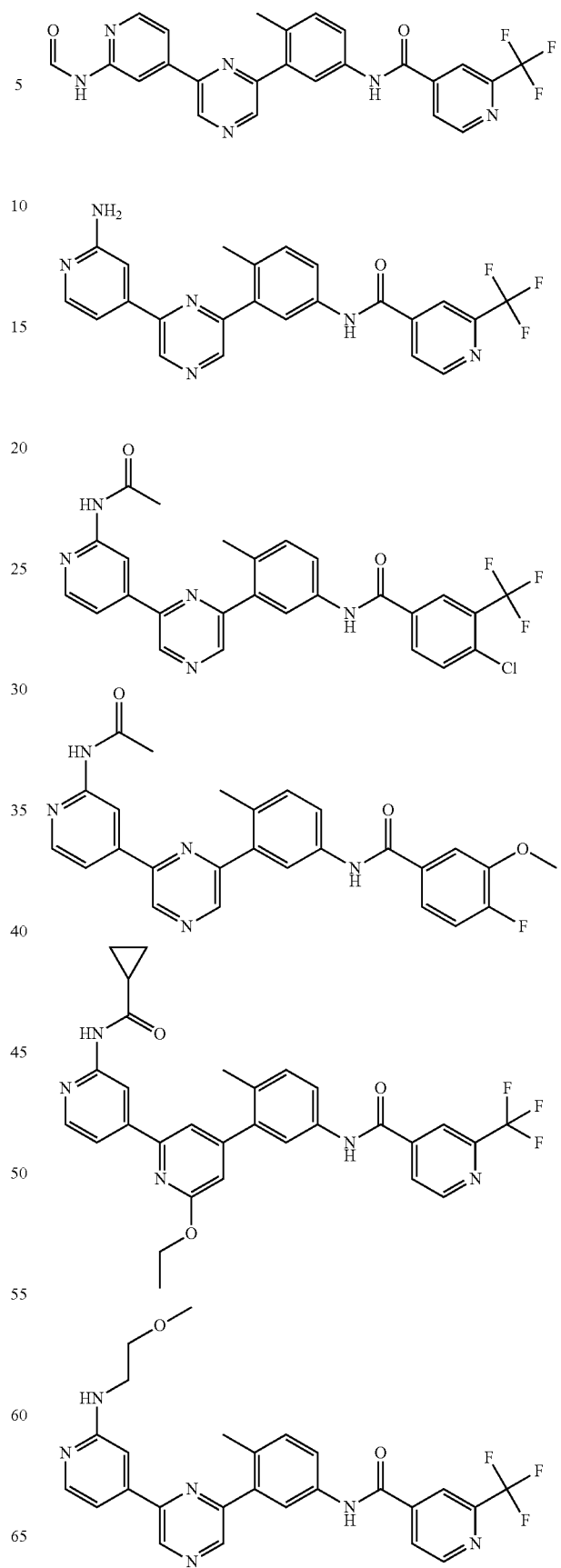

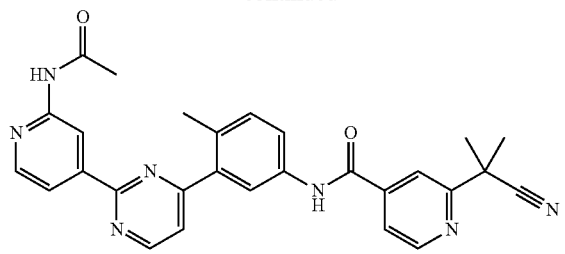
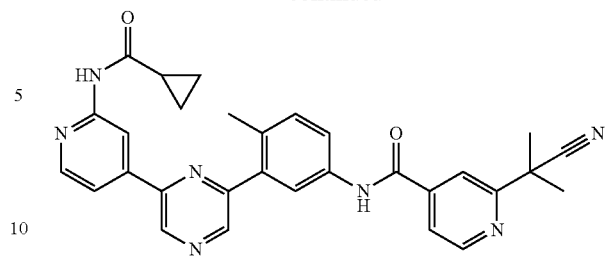
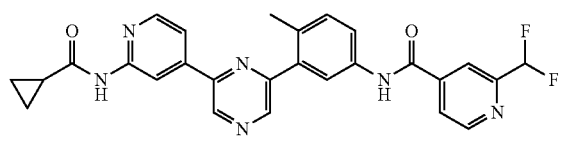
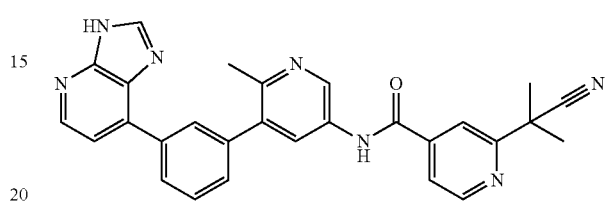
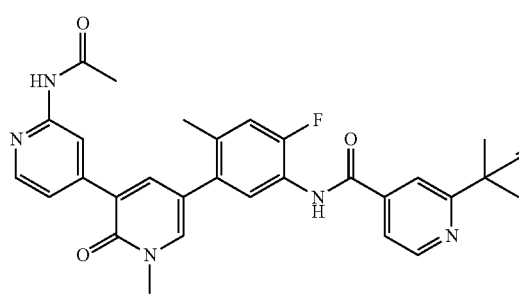
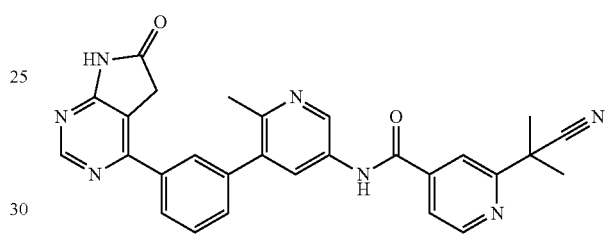
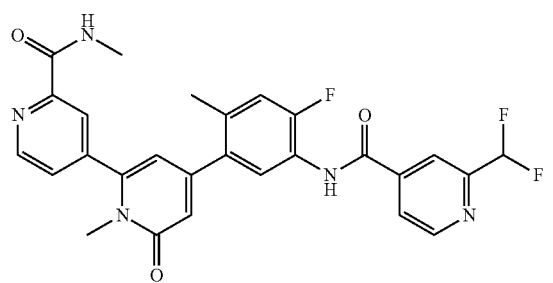
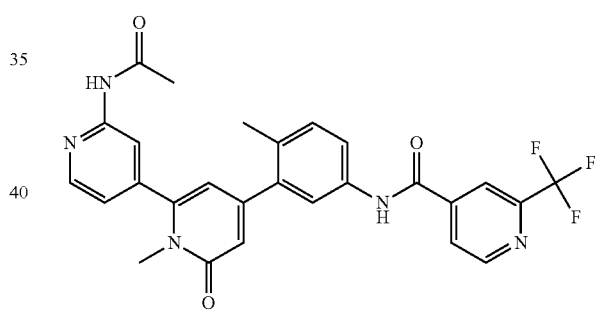
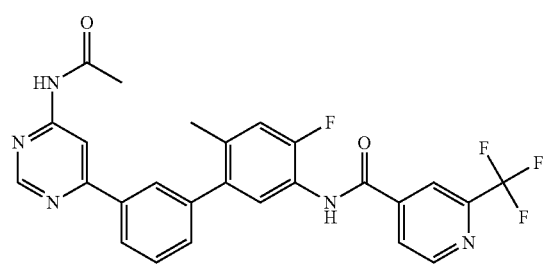
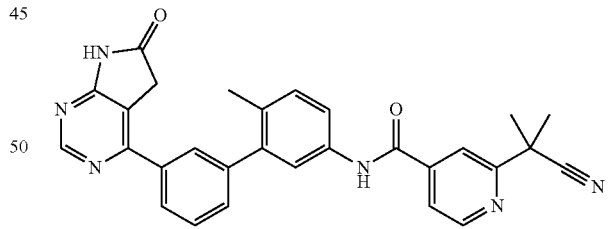
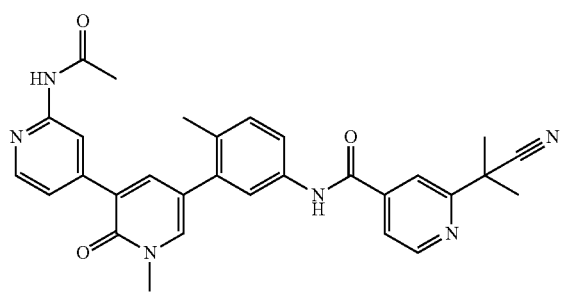
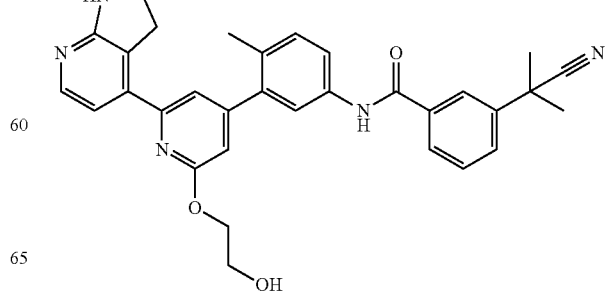

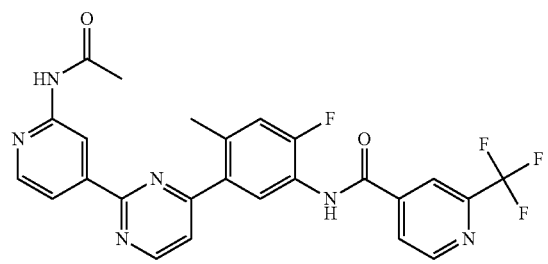
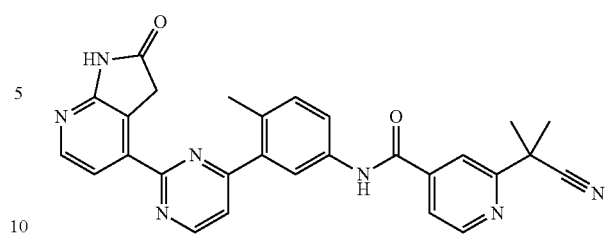
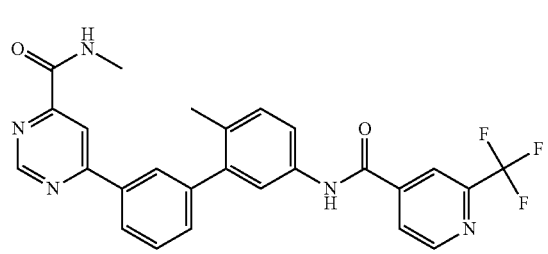
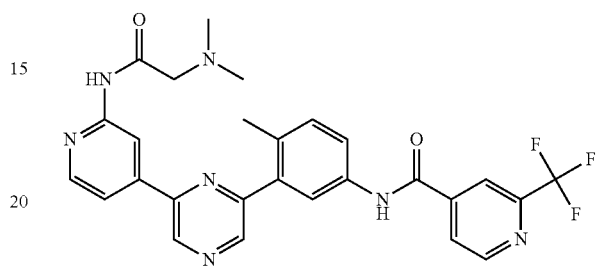
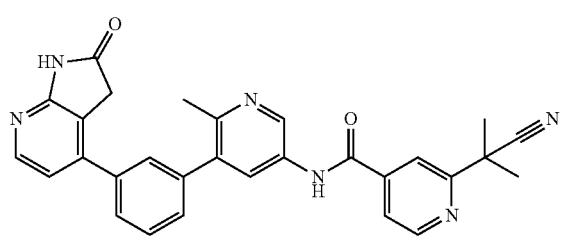
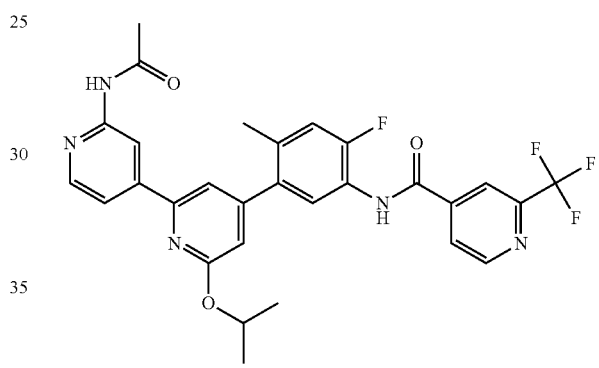
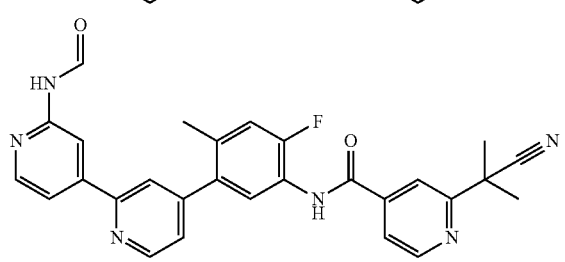
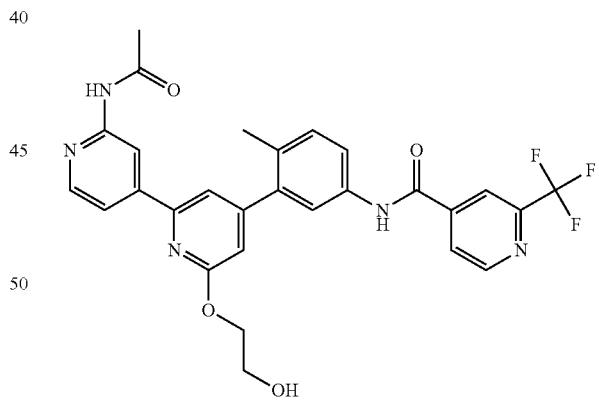
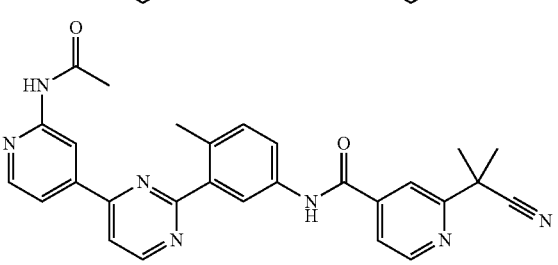
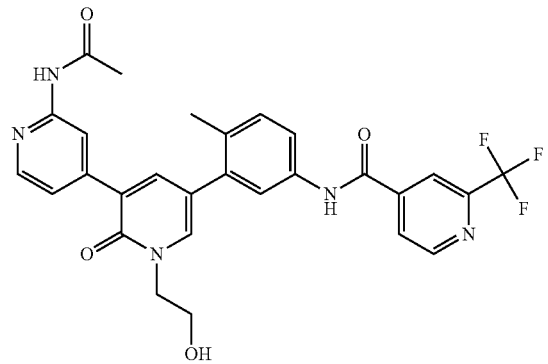
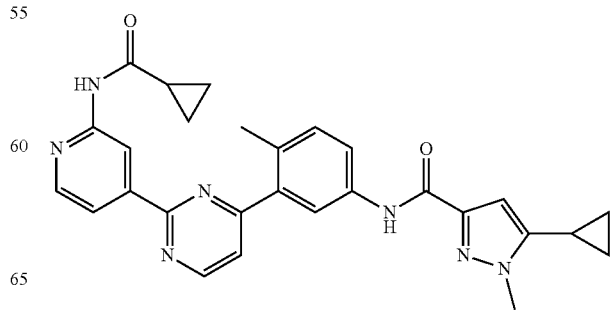

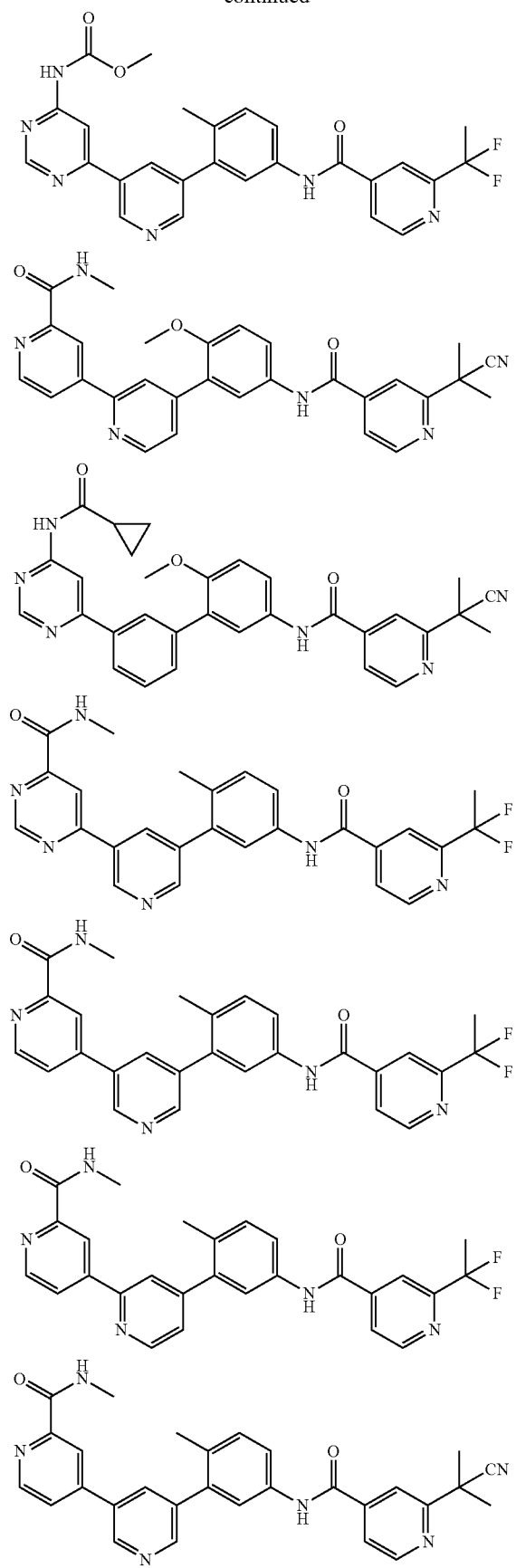
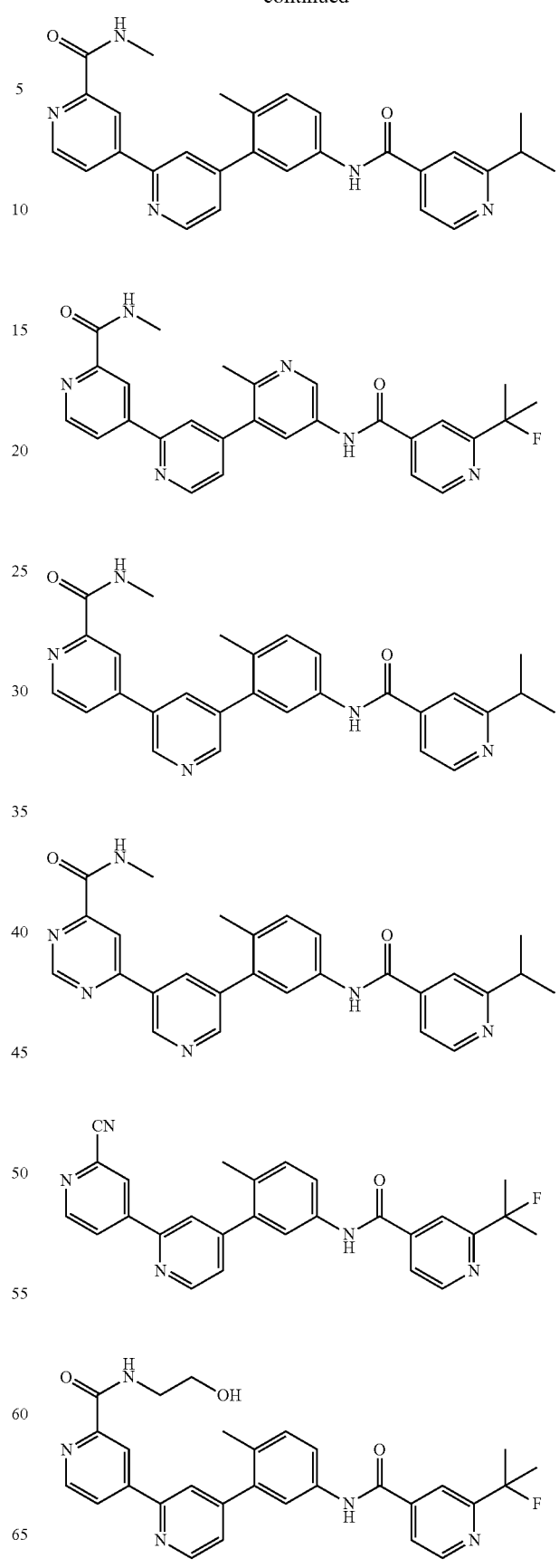

233
-continued
234
-continued
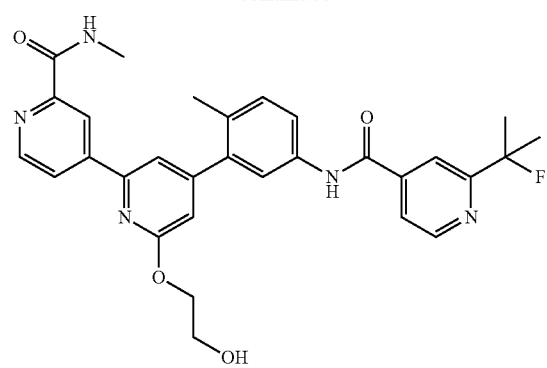
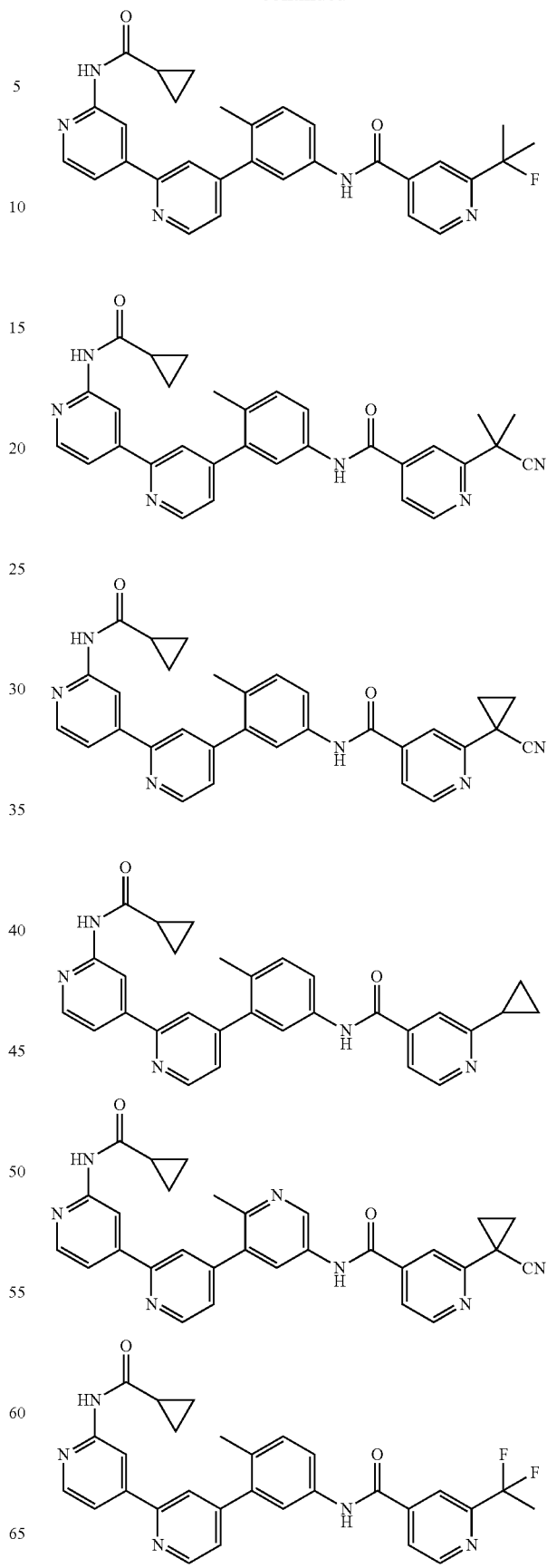

235
-continued
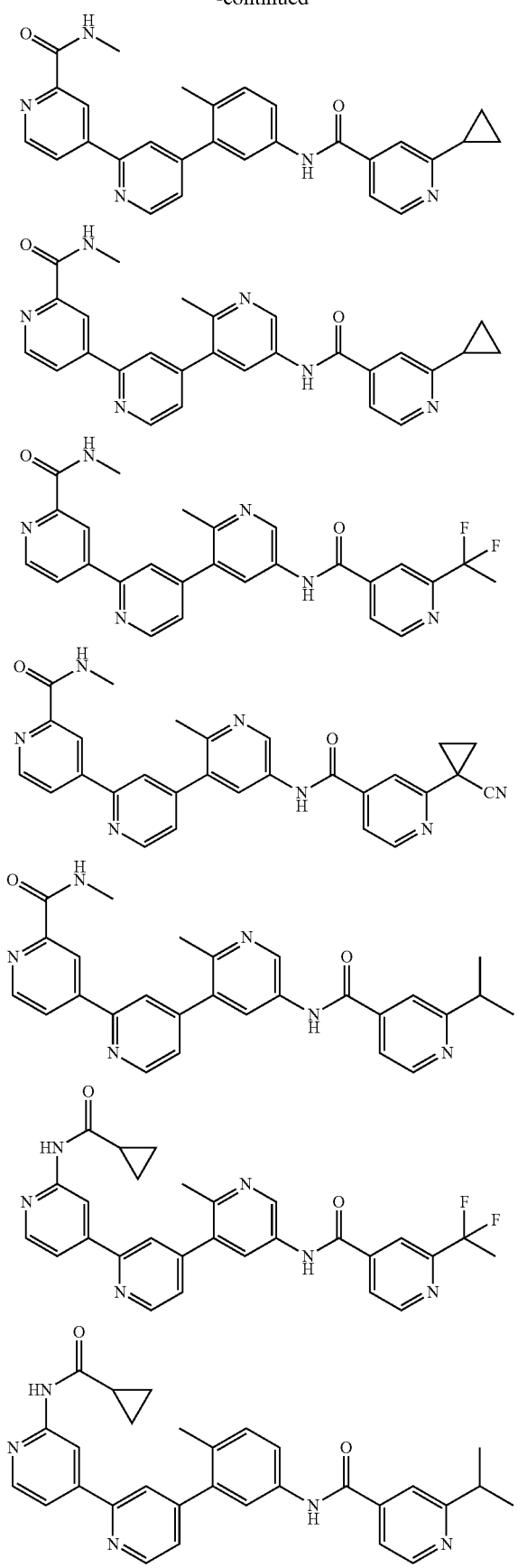
236
-continued
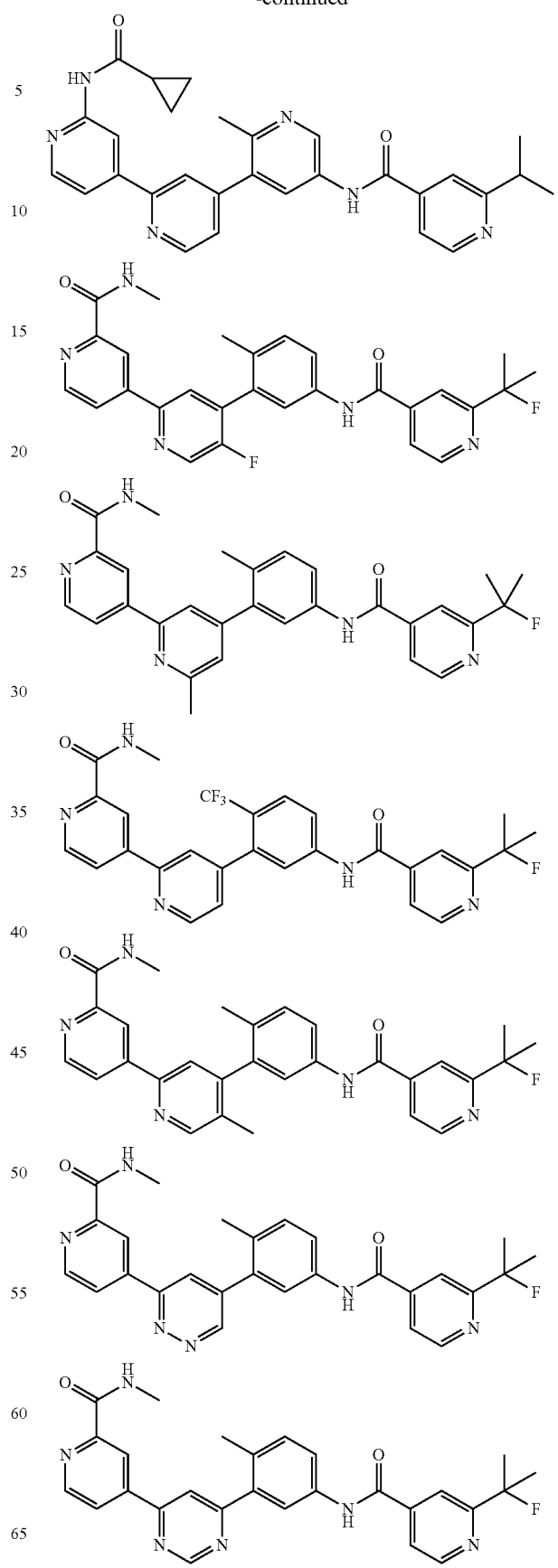

237
-continued
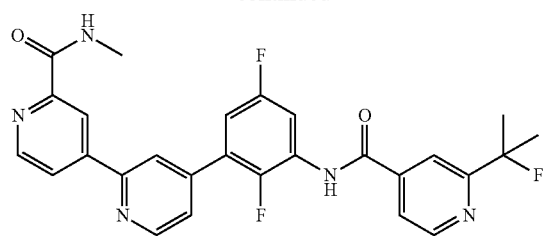
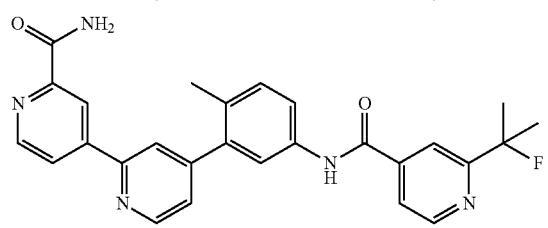
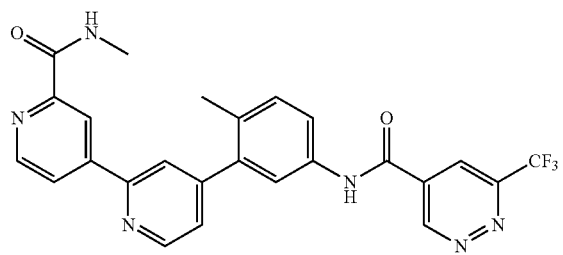
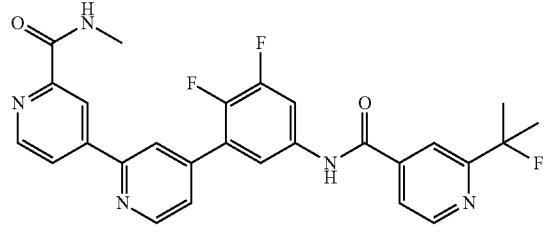
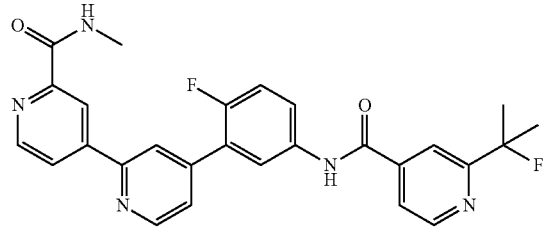
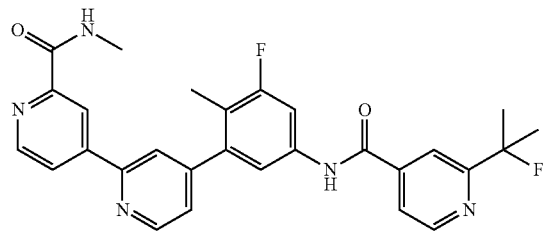
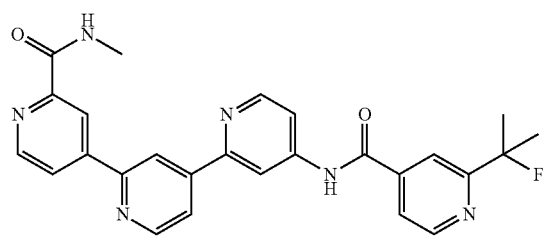
238
-continued
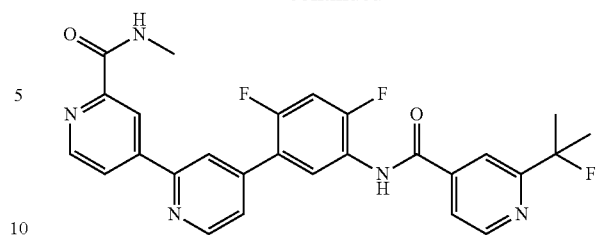
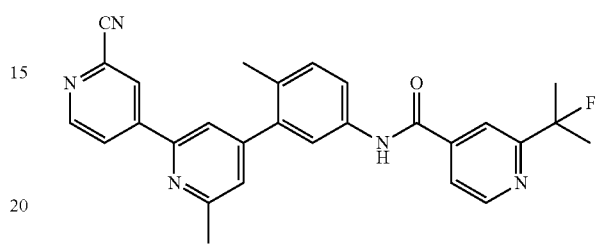
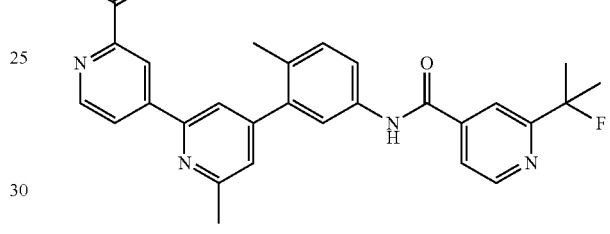
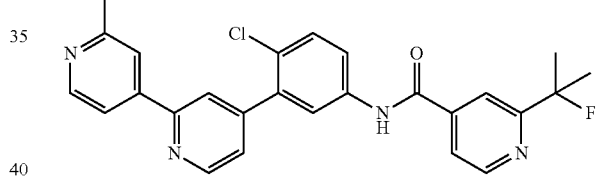
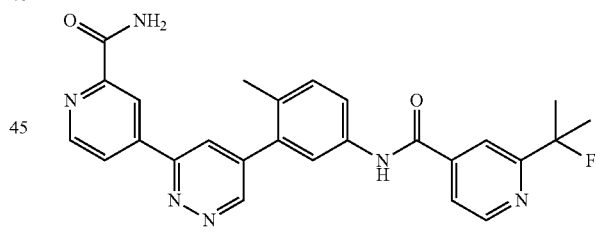
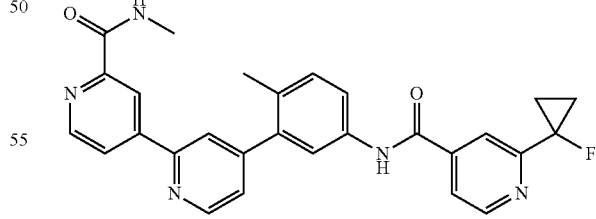

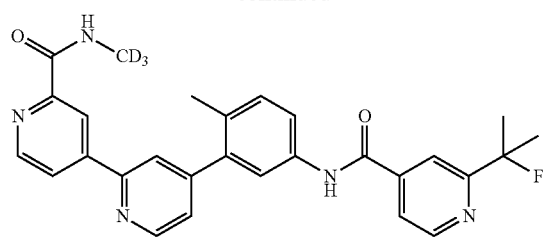
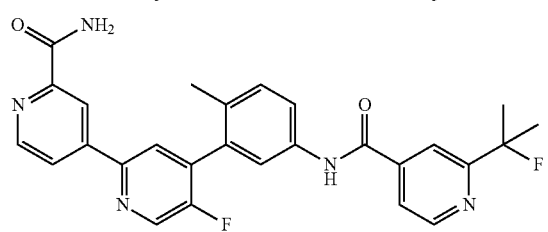
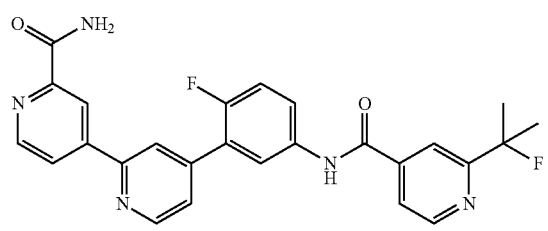
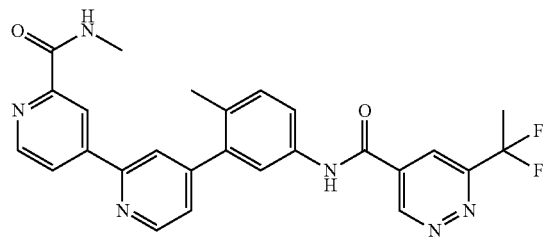

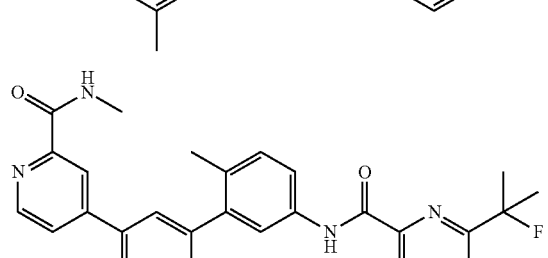
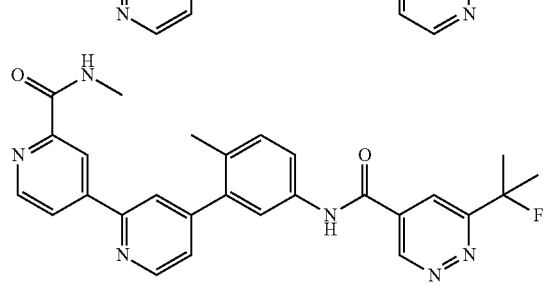
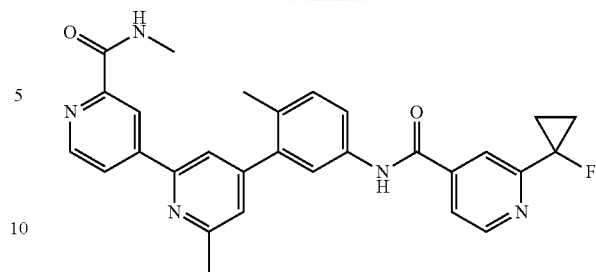
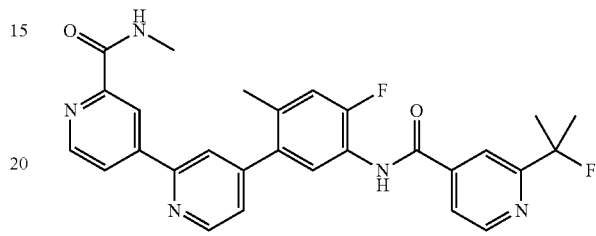
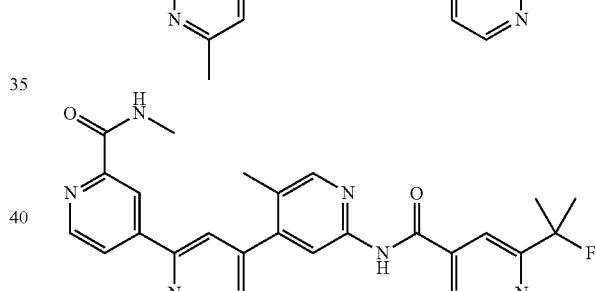
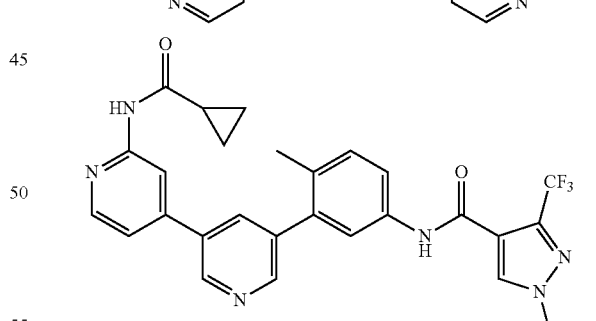
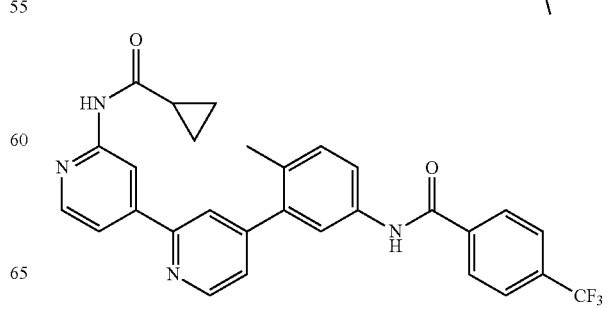

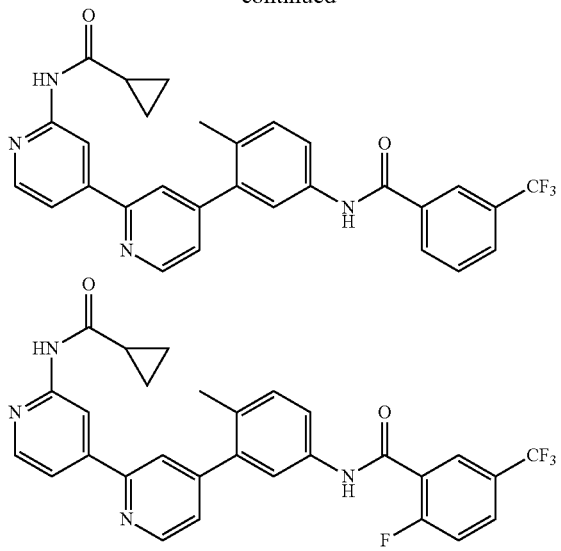

and pharmaceutically acceptable salts, enantiomers, stereoisomers, and tautomers thereof.

Methods of Treatment

Compounds described herein can act as RAF inhibitors, e.g., BRAF inhibitors or CRAF inhibitors, and are therefore useful in the treatment of diseases and disorders in patients in need thereof, such as cancer. Exemplary cancers include, but are not limited to, melanoma, multiple myeloma, thyroid cancer, ovarian cancer, colorectal cancer, colon cancer, pancreatic cancer, lung cancer, bladder cancer, gastrointestinal stromal tumors, solid tumors, blood-borne cancers, acute myelogenous leukemia (AML), or other cancers caused by activation of the RAS→RAF→MEK→ERK signaling pathway. In some embodiments, a cancer described herein is a BRAF V600X driven cancer, an atypical BRAF mutated cancer, a BRAF fusion cancer, a CRAF fusion cancer, or a RAS mutant cancer. In some embodiments, the cancer has a BRAF oncogenic mutation. In some embodiments, the cancer has a RAS oncogenic mutation. In some embodiments, the RAS oncogenic mutation is RAS Q61R or Q61K mutation. In some embodiments, the cancer has a NF1 oncogenic mutation. In some embodiments, the lung cancer is non-small lung cancer (NSCL). In some embodiments, the colorectal cancer is colon cancer. In some embodiments, the colorectal cancer is rectal cancer.

The compounds provided herein may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound provided herein may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result is achieved.

Combination Therapy

Compounds described herein, e.g., a compound of Formula I as defined herein (or a compound of Formula I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T), can be administered in combination with one or more additional therapeutic agents to treat a disorder described herein, such as a cancer described herein. For example, provided in the present disclosure is a pharmaceutical composition comprising a compound described herein, e.g., a compound of Formula I as defined herein (or a compound of Formula I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T), one or more additional therapeutic agents, and a pharmaceutically acceptable excipient. In some embodiments, a compound of Formula I as defined herein (or a compound of Formula I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T) and one additional therapeutic agent is administered. In some embodiments, a compound of Formula I as defined herein (or a compound of Formula I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T) and two additional therapeutic agents are administered. In some embodiments, a compound of Formula I as defined herein (or a compound of Formula I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T) and three additional therapeutic agents are administered. Combination therapy can be achieved by administering two or more therapeutic agents, each of which is formulated and administered separately. For example, a compound of Formula I as defined herein (or a compound of Formula I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T) and an additional therapeutic agent can be formulated and administered separately. Combination therapy can also be achieved by administering two or more therapeutic agents in a single formulation, for example a pharmaceutical composition comprising a compound of Formula I (or a compound of Formula I-A, I-AA, I-AB, I-AC, I-B, I-B, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T) as one therapeutic agent and one or more additional therapeutic agents such as a MAPK pathway inhibitor or chemotherapeutic agent. For example, a compound of Formula I as defined herein (or a compound of Formula I-A, I-AA, I-AB, I-AC, I-B, I-BA, I-C, I-CA, I-D, I-DA, I-DB, I-E, I-EA, I-EB, I-F, I-FA, I-G, I-GA, I-H, I-HA, I-J, I-JA, I-K, I-KA, I-L, I-LA, I-M, I-N, I-NA, I-O, I-O, I-P, I-PA, I-Q, I-QA, I-R, I-RA, I-S, I-SA-i, I-SA-ii, or I-T) and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y—Y—X, X-X-Y-Y, etc.

In some embodiments, compounds described herein are combined with other agents including MAPK pathway inhibitors. In some embodiments, the other agent is an inhibitor of RAS. In some embodiments, the other agent is an inhibitor of RAS. In some embodiments, the other agent is an inhibitor of oncogenic KRAS. In some embodiments, the other agent is an inhibitor of KRAS G12C. In some embodiments, the other agent is an inhibitor of RAS. In some embodiments, the other agent is an inhibitor of KRAS G12D. In some embodiments, the other agent is a MEK inhibitor. In some embodiments the other agent is an ERK inhibitor.

In some embodiments, compounds described herein are combined with an immunomodulatory agent. In some embodiments, the immunomodulatory enhances the adaptive immune response. In some embodiments, the immunomodulatory enhances the activity of antigen-presenting cells. In some embodiments, the immunomodulatory agent enhances the anti-tumor activity of myeloid cells including macrophages. In some embodiments, the immunomodulatory enhances the anti-tumor activity of Natural Killer cells. In some embodiments, the immunomodulatory agent enhances the activity of effector T Cells, including cytotoxic T Cells.

In some embodiments, the one or more additional therapeutic agents that may be administered in combination with a compound provided herein can be a MAPK pathway inhibitor. Such MAPK pathway inhibitors include, for example, MEK inhibitors, ERK inhibitors, and Ras inhibitors.

Exemplary MEK inhibitors include, but are not limited to, trametinib, selumetinib, cobimetinib, binimetinib, and pharmaceutically acceptable salts thereof. Exemplary ERK inhibitors include, but are not limited to, include, but are not limited to, ulixertinib, SCH772984, LY3214996, ravoxertinib, VX-11e, ASN-007, GDC-0994, MK-8353, ASTX-029, LTT462, KO-947, and pharmaceutically acceptable salts thereof. Exemplary Ras inhibitors include, but are not limited to, AMG-510, MRTX849, ARS-1620, ARS-3248, LY3499446, and pharmaceutically acceptable salts thereof.

In some embodiments, the additional therapeutic agents can be immunomodulatory agents including but not limited to anti-PD-1 or anti-PDL-1 therapeutics including pembrolizumab, nivolumab, pidilizumab, cemiplimab, atezolizumab, durvalumab, BMS-936559, or avelumab. In some embodiments, the additional therapeutic agents can be anti-TIM3 (anti-HAVcr2) therapeutics including but not limited to TSR-022 or MBG453, anti-LAG3 therapeutics including but not limited to relatlimab, LAG525, or TSR-033, anti-4-1BB (anti-CD37, anti-TNFRSF9), CD40 agonist therapeutics including but not limited to SGN-40, CP-870,893 or RO7009789, anti-CD47 therapeutics including but not limited to Hu5F9-G4, anti-CD20 therapeutics, anti-CD38 therapeutics, STING agonists including but not limited to ADU-S100, MK-1454, ASA404, or amidobenzimidazoles. In some embodiments, the additional therapeutic agents can be anti-CTLA4 agents including ipilimumab, tremelimumab. In some embodiments, the additional therapeutic agents can be hypomethylating agents including but not limited to azacytidine or decitabine, other immunomodulatory therapeutics including but not limited to epidermal growth factor inhibitors, statins, metformin, angiotensin receptor blockers, thalidomide, lenalidomide, pomalidomide, prednisone, or dexamethasone. In some embodiments, the additional therapeutic agents can be immunotherapeutic agents including targeted therapeutic agents, cancer vaccines, and CAR-T cell therapy.

The compounds described herein may be administered in combination with other therapeutic agents known to treat cancers. Such other therapeutic agents include radiation therapy, anti-tubulin agents, DNA alkylating agents, DNA synthesis-inhibiting agents, DNA intercalating agents, anti-estrogen agents, anti-androgens, steroids, anti-EGFR agents, kinase inhibitors, mTOR inhibitors, PI3 kinase inhibitors, cyclin-dependent kinase inhibitors, CD4/CD6 kinase inhibitors, topoisomerase inhibitors, Histone Deacetylase (HDAC) inhibitors, DNA methylation inhibitors, anti-HER2 agents, anti-angiogenic agents, proteasome inhibitors, PARP (poly ADP ribose polymerase) inhibitors, cell cycle regulating kinase inhibitors, thalidomide, lenalidomide, antibody-drug-conjugates (ADCs).

In an embodiment, the additional therapeutic agents can be chemotherapeutic agents including but not limited to an anti-tubulin agents (for example, paclitaxel, paclitaxel protein-bound particles for injectable suspension including but not limited to nab-paclitaxel, eribulin, docetaxel, ixabepilone, vincristine, auristatins, or maytansinoids), vinorelbine, DNA-alkylating agents (including but not limited to cisplatin, carboplatin, oxaliplatin, cyclophosphamide, ifosfamide, temozolomide), DNA intercalating agents or DNA topoisomerase inhibitors (including but not limited to anthracyclines such as doxorubicin, pegylated liposomal doxorubicin, daunorubicin, idarubicin, mitoxantrone, or epirubicin, camptothecins such as topotecan, irinotecan, or exatecan), 5-fluorouracil, capecitabine, cytarabine, decitabine, 5-aza cytadine, gemcitabine and methotrexate.

In some embodiments, the additional therapeutic agents can be kinase inhibitors including but not limited to erlotinib, gefitinib, neratinib, afatinib, osimertinib, lapatanib, crizotinib, brigatinib, ceritinib, alectinib, lorlatinib, everolimus, temsirolimus, abemaciclib, LEE011, palbociclib, cabozantinib, ripretinib, sunitinib, pazopanib, sorafenib, regorafenib, sunitinib, axitinib, dasatinib, imatinib, nilotinib, idelalisib, ibrutinib, BLU-667, Loxo 292, larotrectinib, and quizartinib, In some embodiments, the additional therapeutic agents can be anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, talazoparib, and rucaparib, topoisomerase I inhibitors including but not limited to irinotecan, camptothecin, exatecan, and topotecan, topoisomerase II inhibitors including but not limited to anthracyclines, etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNep and 5-aza-2'-deoxycytidine, proteasome inhibitors including but not limited to bortezomib and carfilzomib, biological agents including but not limited to trastuzumab, ado-trastuzumab, pertuzumab, cetuximab, and panitumumab.

In some embodiments, the additional therapeutic agents can be anti-angiogenic agents including but not limited to bevacizumab, rebastinib, aflibercept, and AMG386.

In some embodiments, the additional therapeutic agents can be antibody-drug-conjugates (ADCs) including but not limited to ADCs containing DM1, DM4, MMAE, MMAF, or camptothecin payloads, brentuximab vedotin and trastuzumab emtansine, radiotherapy, therapeutic vaccines including but not limited to sipuleucel-T.

In some embodiments, the additional therapeutic agent can be autophagy inhibitors, inhibitors of vesicular trafficking, including but not limited to ULK inhibitors such as ULK1 inhibitors, ULK2 inhibitors, ULK1/ULK2 inhibitors, VPS34 inhibitors, PPT1 inhibitors, or lysosomal blocking agents. In some embodiments, the additional therapeutic agent can be DCC-3116, SAR405, SB02024, hydroxychloroquine, chloroquine, and LYS05.

In some embodiments, the additional therapeutic agent can be EGFR inhibitors including, but not limited to, cetuximab, osimertinib, and afatinib, and pharmaceutically acceptable salts thereof.

In some embodiments, the additional therapeutic agent is selected from a luteinizing hormone-releasing hormone (LHRH) analog, including goserelin and leuprolide.

In some embodiments, the additional therapeutic agent is selected from the group consisting of selected from the group consisting of everolimus, trabectedin, abraxane, TLK 286, AV-299, DN-101, pazopanib, GSK690693, RTA 744, ON 0910.Na, AZD 6244 (ARRy-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, AZD 2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRx-0402, lucanthone, LY 317615, neuradiab, vitespan, Rta 744, alanosine (Sdx 102), talampanel, atrasentan, XR 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258, 3-[5-(methylsulfonylpiperadinemethyl)-indolylj-quinolone, vatalanib, AG-013736, AVE-0005, the acetate salt of [D-Ser(tBu) 6, Azgly 10](pyro-Glu-His-Trp-Ser-Tyr-D-Ser(tBu)-Leu-Arg-Pro-Azgly-NH2 acetate [$C_{59}H_{84}N_{18}O_{14}$—($C_2H_4O_2$)$_x$ where x=1 to 2.4](SEQ ID NO: 5), goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714; TAK-165, HKI-272, erlotinib, lapatanib, canertinib, ABX-EGF antibody, erbitux, EKB-569, PKI-166, GW-572016, ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, ipilumumab, and mixtures thereof.

Pharmaceutical Compositions and Kits

Another aspect of this disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which contains one or more of the compounds described herein, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound provided herein, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous, or organic solvents, or mixtures thereof, and powders. Liquid dosage forms for oral administration include pharmaceutically acceptable emulsions, microemulsions, solutions, suspensions, syrups, and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another embodiment, provided are enteral pharmaceutical formulations including a disclosed compound and an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5.

Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives described herein.

Advantageously, provided herein are kits for use by a e.g., a consumer in need of treatment of cancer. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and synthetic procedures known in the art. In the description of the synthetic methods described below it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

The following abbreviation are used in this disclosure and have the following definitions: "ADP" is adenosine diphosphate, "Ag$_2$CO$_3$" is silver acetate, "aq" is aqueous, "ATP" is adenosine triphosphate, "Ar" is argon gas, "Boc" is t-butylcarbonate, "BSA" is bovine serum albumin, "conc" is concentrated, "Cs$_2$CO$_3$" is cesium carbonate, "CuI" is copper (I) iodide, "DCM" is dichloromethane, "DIEA" is N,N-diisopropylethylamine, "DMF" is N,N-dimethylformamide, "dppf" is 1,1'-bis(diphenylphosphino)ferrocene, "DMSO-d$_6$" is dimethylsulfoxide-deuterium, "EDC" is 1-ethyl-3-(3-dimethylaminopropyl)carbodiimide, "ESI" is electrospray ionization, "EtOAc" is ethyl acetate, "EtOH" is ethanol, "GST" is glutathione S-transferase, "h" is hour or hours, "HATU" is hexafluorophosphate azabenzotriazole tetramethyl uronium, "H$_2$" is hydrogen gas, "HCl" is hydrochloric acid, "H$_2$O" is water, "IC$_{50}$" is half maximal inhibitory concentration, "K$_2$CO$_3$" is potassium carbonate, "KOAc" is potassium acetate, "K$_3$PO$_4$" is potassium phosphate, "LiOH" is lithium hydroxide, "mCPBA" is meta-Chloroperoxybenzoic acid, "MeCN" is acetonitrile, "MeOH" is methanol, "MgSO$_4$" is magnesium sulfate, "MHz" is megahertz, "min" is minute or minutes, "MS" is mass spectrometry, "m/z" is mass/charge number, "NaCN" is sodium cyanide, "NADH" is nicotinamide adenine dinucleotide, "NaH" is sodium hydride, "NaHCO$_3$" is sodium bicarbonate, "NaOEt" is sodium methoxide, "Na$_2$SO$_4$" is sodium sulfate, "NH$_4$Cl" is ammonium chloride, "NH$_4$OH" is ammonium hydroxide, "NMR" is nuclear magnetic resonance, "OMs" is O-mesylate, "PBS" is phosphate buffered saline, "Pd" is palladium, "Pd/C" is palladium on carbon, "Pd(OAc)$_2$" is palladium (II) acetate, "rt" is room temperature which is also known as "ambient temp," which will be understood to consist of a range of normal laboratory temperatures ranging from 15-25° C., "sat'd." is saturated, "SFC" is supercritical fluid chromatography, "SM" is starting material, "S$_N$Ar" is nucleophilic aromatic substitution, "TCFH" is chloro-N,N,N',N'-tetramethylformamidinium hexafluorophosphate, "T$_3$P" is 1-propanephosphonic acid anhydride, "TBAF" is tetrabutyl ammonium fluoride, "TEA" is triethylamine, "TFA" is trifluoroacetic acid, "THF" is tetrahydrofuran, "Xantphos" is 4,5-bis(diphenylphosphino)-9,9-dimethylxanthene, "X-Phos" is 2-dicyclohexylphosphino-2',4',6'-triisopropylbiphenyl and "ZnCl$_2$" is zinc chloride.

General Chemistry

Exemplary compounds described herein are available by the general synthetic methods illustrated in the Schemes below, intermediate preparations, and the accompanying Examples.

Synthetic Schemes

Scheme 1

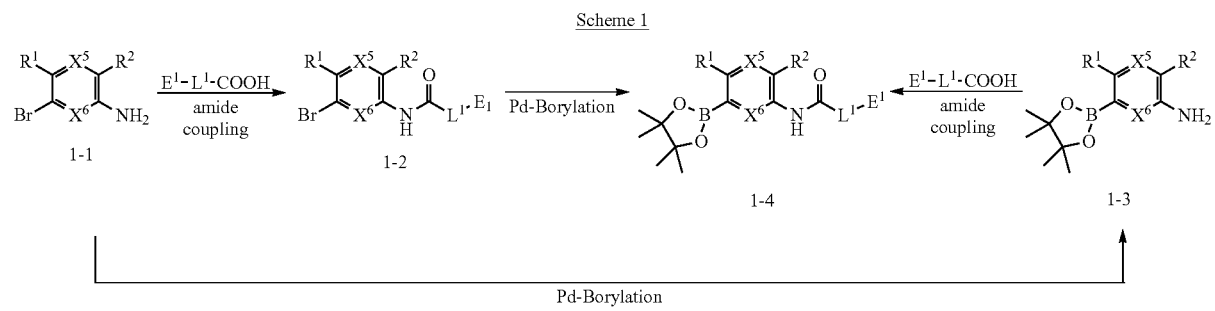

Scheme 1 illustrates an exemplary preparation of boronates 1-4. Amines 1-1 react with carboxylic acids E$^1$-L$^1$-COOH (commercially available or synthesized by those skilled in the art) to afford amides 1-2. Compounds 1-2 upon borylation provide boronates 1-4. Borylation is a well-documented reaction to those skilled in the art (for example, Pd (0) catalyzed reaction with bis(pinacolato)diboron). Alternatively, boronates 1-4 can be prepared by amide coupling reaction of 1-3 (commercially available or synthesized by Pd-catalyzed borylation from 1-1) with acids E$^1$-L$^1$-COOH in the presence of coupling reagents such as T3P, TCFH, HATU, and EDC.

Scheme 2

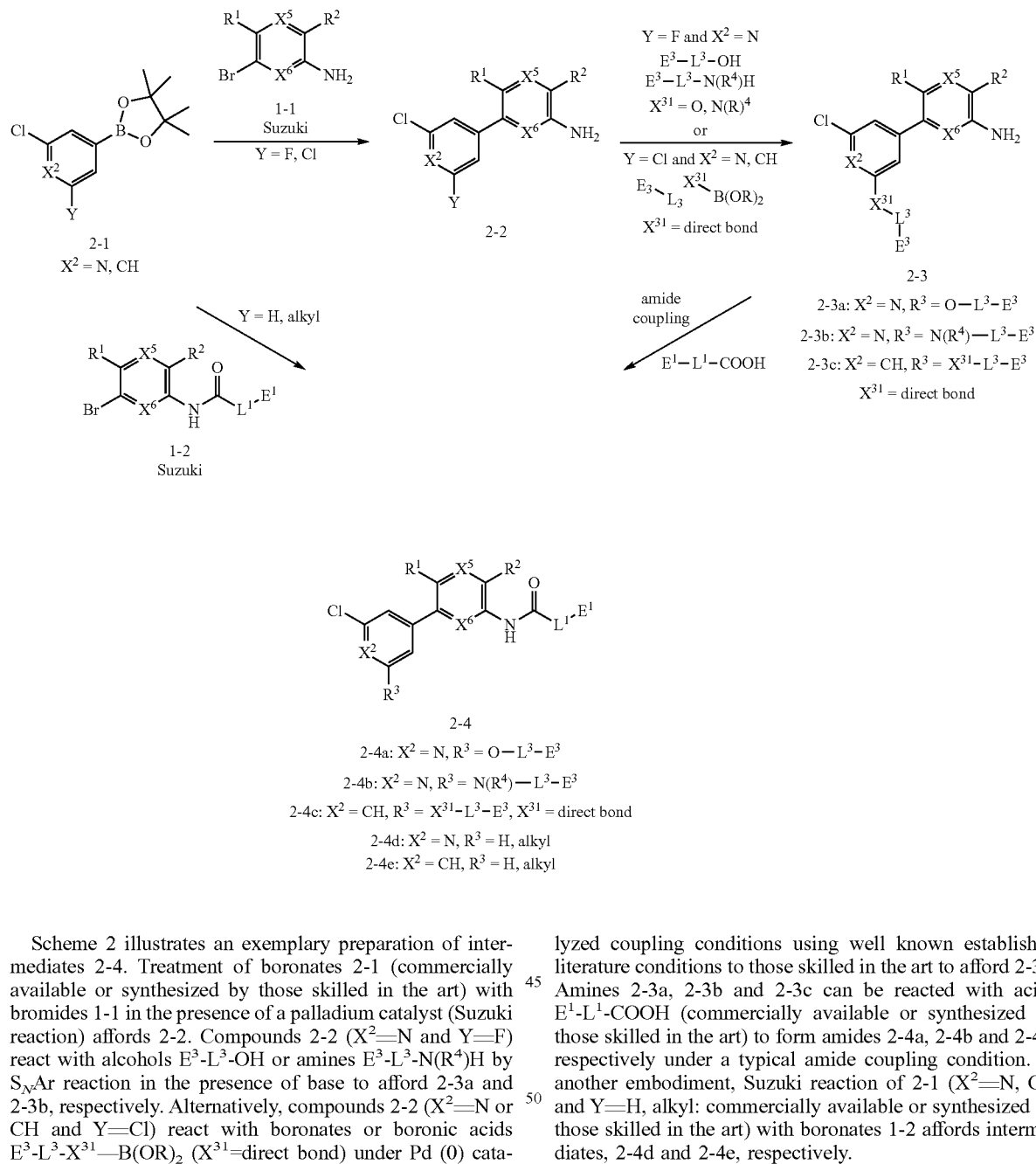

Scheme 2 illustrates an exemplary preparation of intermediates 2-4. Treatment of boronates 2-1 (commercially available or synthesized by those skilled in the art) with bromides 1-1 in the presence of a palladium catalyst (Suzuki reaction) affords 2-2. Compounds 2-2 ($X^2$=N and Y=F) react with alcohols $E^3$-$L^3$-OH or amines $E^3$-$L^3$-N($R^4$)H by $S_NAr$ reaction in the presence of base to afford 2-3a and 2-3b, respectively. Alternatively, compounds 2-2 ($X^2$=N or CH and Y=Cl) react with boronates or boronic acids $E^3$-$L^3$-$X^{31}$—B(OR)$_2$ ($X^{31}$=direct bond) under Pd (0) catalyzed coupling conditions using well known established literature conditions to those skilled in the art to afford 2-3c. Amines 2-3a, 2-3b and 2-3c can be reacted with acids $E^1$-$L^1$-COOH (commercially available or synthesized by those skilled in the art) to form amides 2-4a, 2-4b and 2-4c, respectively under a typical amide coupling condition. In another embodiment, Suzuki reaction of 2-1 ($X^2$=N, CH and Y=H, alkyl: commercially available or synthesized by those skilled in the art) with boronates 1-2 affords intermediates, 2-4d and 2-4e, respectively.

Scheme 3

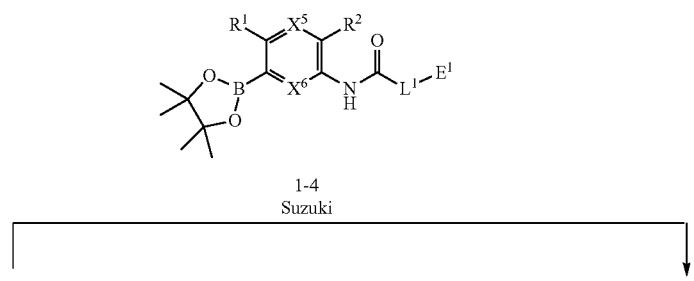

-continued

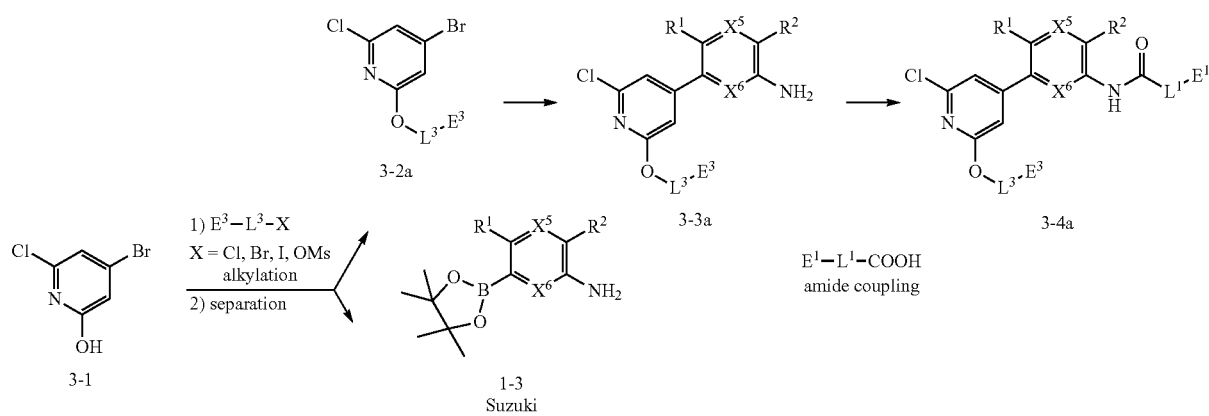

$L^2 = L^3$ and $E^2 = E^3$

Scheme 3 illustrates an exemplary preparation of intermediates 3-4a and 3-4b. 4-bromo-6-chloropyridin-2-ol (3-1) reacts with alkylating reagents $E^3$-$L^3$-X (X=Cl, Br, I, OMs) in the presence of base such as $Ag_2CO_3$ in an aprotic solvent like toluene to produce a mixture of O-alkylated (3-2a) and N-alkylated (3-2b) compounds which can be separated by a suitable method such as SFC purification, crystallization or chromatography. Each of 3-2a and 3-2b reacts with boronates 1-3 under Suzuki reaction conditions to afford 3-3a and 3-3b, respectively. Amide coupling reaction of 3-3a and 3-3b with carboxylic acids $E^1$-$L^1$-COOH affords 3-4a and 3-4b, respectively. In another embodiment, Suzuki reaction of 3-2a and 3-2b with boronates 1-4 affords 3-4a and 3-4b, respectively.

Scheme 4

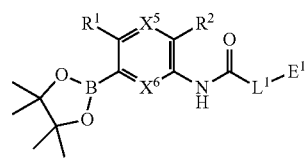

1-4
Suzuki

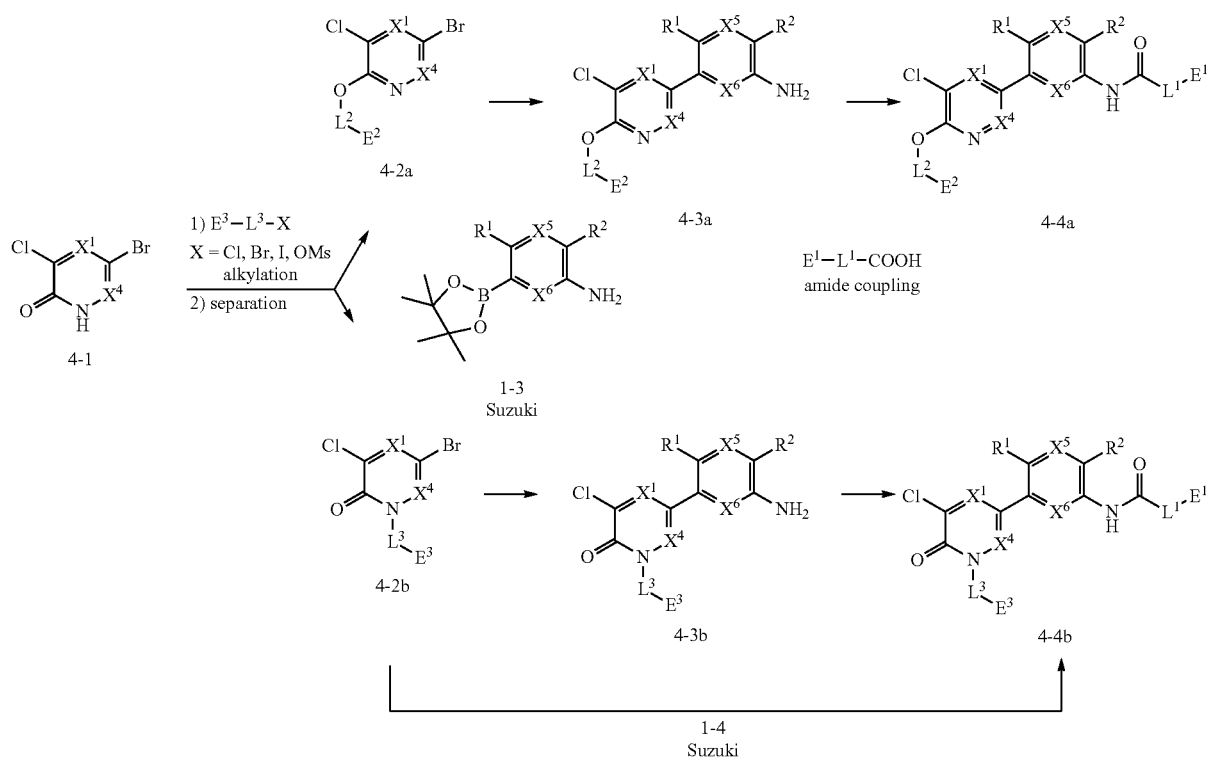

$L^2 = L^3$ and $E^2 = E^3$

Scheme 4 illustrates an exemplary preparation of intermediates 4-4a and 4-4b. In a similar manner as described in scheme 3, 4-1 reacts with alkylating reagents $E^3$-$L^3$-X (X=Cl, Br, I, OMs) to produce a mixture of O-alkylated (4-2a) and N-alkylated (4-2b) compounds which can be separated by a suitable method well known to those skilled in the art. Suzuki reaction of 4-2a and 4-2b with boronates 1-3 affords 4-3a and 4-3b, respectively. Finally, each of 4-3a and 4-3b upon treatment with carboxylic acids $E^1$-$L^1$-COOH under amide coupling conditions affords 4-4a and 4-4b, respectively. In another embodiment, Suzuki reaction of 4-2a and 4-2b with boronates 1-4 affords 4-4a and 4-4b, respectively.

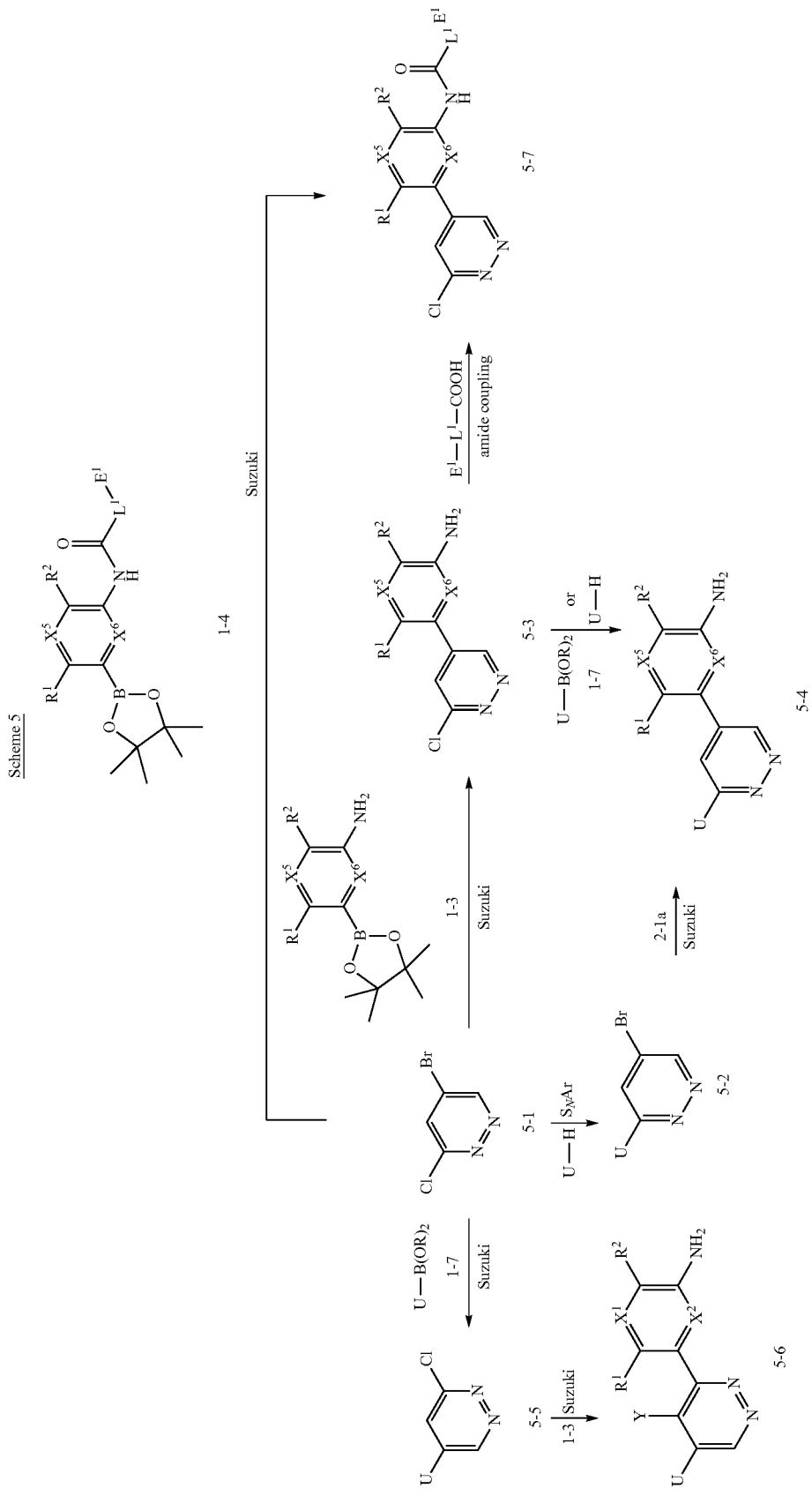

Scheme 5 illustrates an exemplary preparation of pyridazine intermediates 5-4, 5-6 and 5-7. 5-Bromo-3-chloropyridazine 5-1 reacts with alcohols or amines U—H to afford 5-2 by $S_N$Ar reaction. U-substituted bromides 5-2 react with boronates 1-3 to afford 5-4 by Pd catalyzed Suzuki reactions. Alternatively, the treatment of 5-bromo-3-chloropyridazine 5-1 with boronates 1-3 under Suzuki reaction conditions affords 5-3. Chlorides 5-3 react with boronates or boronic acids U—B(OR)$_2$ 1-7 to provide 5-4 by Pd (0) catalyzed Suzuki reaction. Chlorides 5-3 react with carboxylic acids $E^1$-$L^1$-COOH under amide coupling conditions to afford intermediates 5-7. Alternatively intermediates 5-7 can be directly prepared from 5-1 with boronates 1-4 by Suzuki reaction. The treatment of 5-bromo-3-chloropyridazine 5-1 with boronates or boronic acids U—B(OR)$_2$ 1-7 under Suzuki reaction conditions affords 5-5. U-substituted chlorides 5-5 react with boronates 1-3 to provide 5-6 by Pd (0) catalyzed Suzuki reaction.

mercially available or synthesized by those skilled in the art) by Suzuki reaction to afford 6-4.

Scheme 7

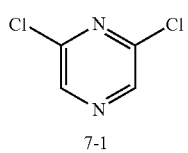
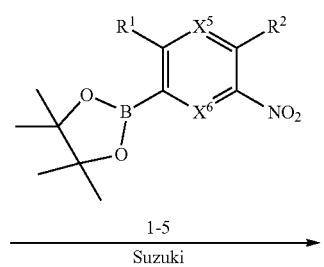

Scheme 6

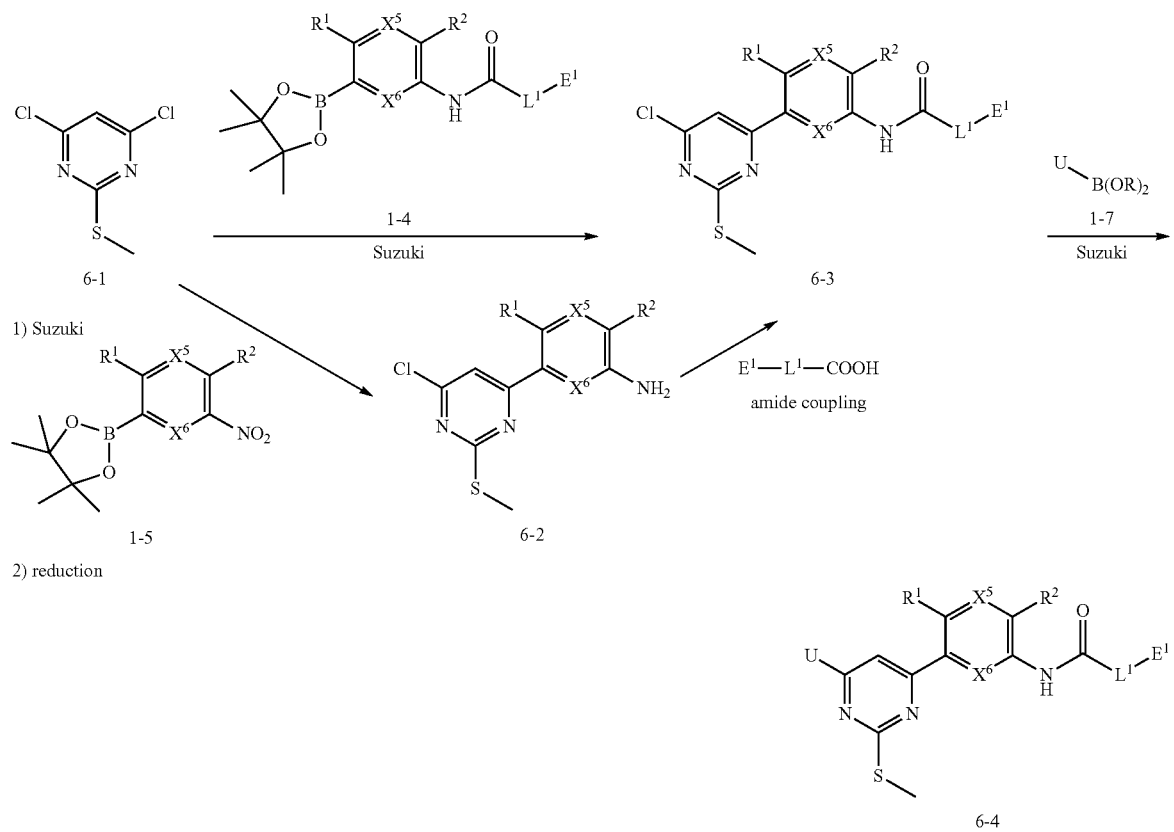

Scheme 6 illustrates an exemplary preparation of intermediates 6-4. 4,6-Dichloro-2-(methylthio)pyrimidine (6-1) reacts with boronates 1-5 in the presence of a palladium catalyst (Suzuki reaction), followed by nitro reduction of the resulting intermediate under mild reducing conditions (zinc or iron metal with ammonium chloride) to afford 6-2. Compounds 6-2 upon treatment with carboxylic acids $E^1$-$L^1$-COOH under amide coupling conditions afford 6-3. Alternatively, 6-3 can be directly prepared from 6-1 with boronates 1-4 by Suzuki reaction. Finally, chlorides 6-3 react with boronates or boronic acids U—B(OR)$_2$ 1-7 (com- -continued

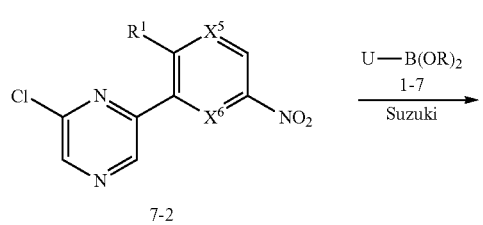

Scheme 7 illustrates an exemplary preparation of compounds of Formula I. 2,6-Dichloropyrazine (7-1) reacts with boronates 1-5 by Suzuki reaction to afford 7-2 which can be subjected to another Suzuki reaction with boronates or boronic acids U—B(OR)₂ 1-7 to furnish 7-3. Finally, nitro reduction of 7-3 under mild reducing conditions (zinc or iron metal with ammonium chloride) affords the corresponding amines which can be reacted with carboxylic acids $E^1$-L-COOH under amide coupling conditions to afford compounds of Formula I.

Scheme 8 illustrates an exemplary preparation of compounds of Formula I. Compounds either 2,4-dichloropyrimidine or 4-bromo-2-chloropyrimidine (8-1) react with boronates 1-4 by Suzuki reaction to afford 8-2a which can be subjected to another Suzuki reaction with boronates or boronic acids U—B(OR)₂ 1-7 to furnish compounds of Formula I. In a similar manner, compounds either 2,4-dichloropyrimidine or 4-bromo-2-chloropyrimidine (8-1) react with boronates or boronic acids U—B(OR)₂ 1-7 by Suzuki reaction to afford 8-2a which can be subjected to another Suzuki reaction with boronates 1-4 to furnish compounds of Formula I.

Scheme 9

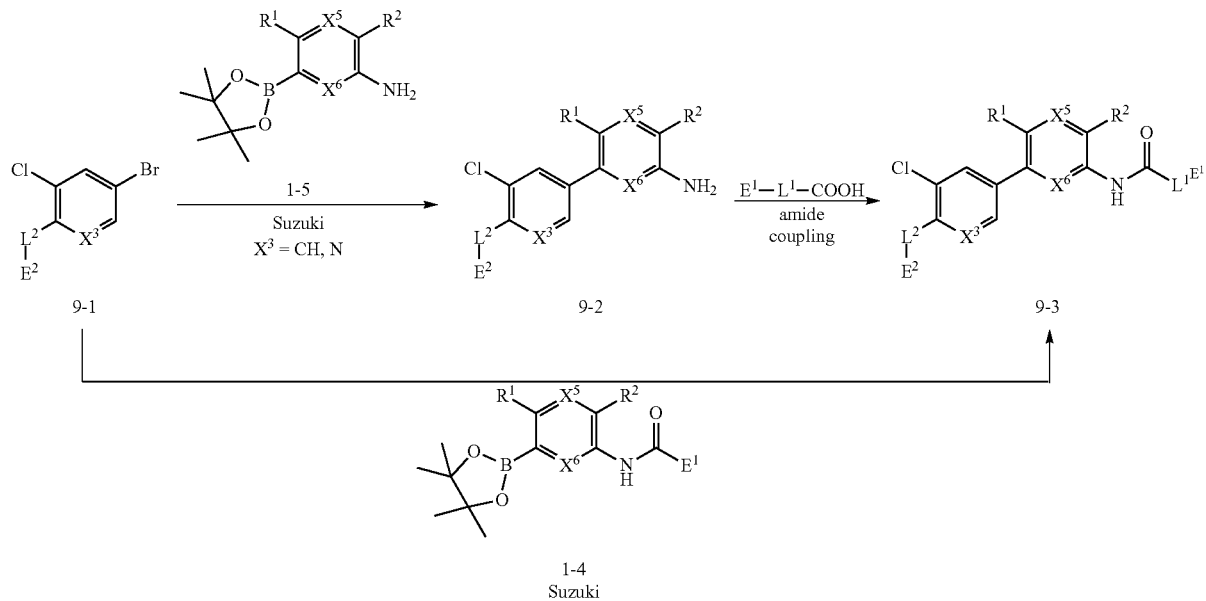

Scheme 9 illustrates an exemplary preparation of intermediates 9-3. Treatment of bromides 9-1 (commercially available or synthesized by those skilled in the art) with boronates 1-5 (commercially available or synthesized by those skilled in the art) in the presence of a palladium catalyst (Suzuki reaction) affords amines 9-2. Amines 9-2 react with carboxylic acids $E^1$-$L^1$-COOH under amide coupling conditions to those skilled in the art to afford 9-3. In another embodiment, bromides 9-1 react with boronates 1-4 by Suzuki reaction to afford 9-3.

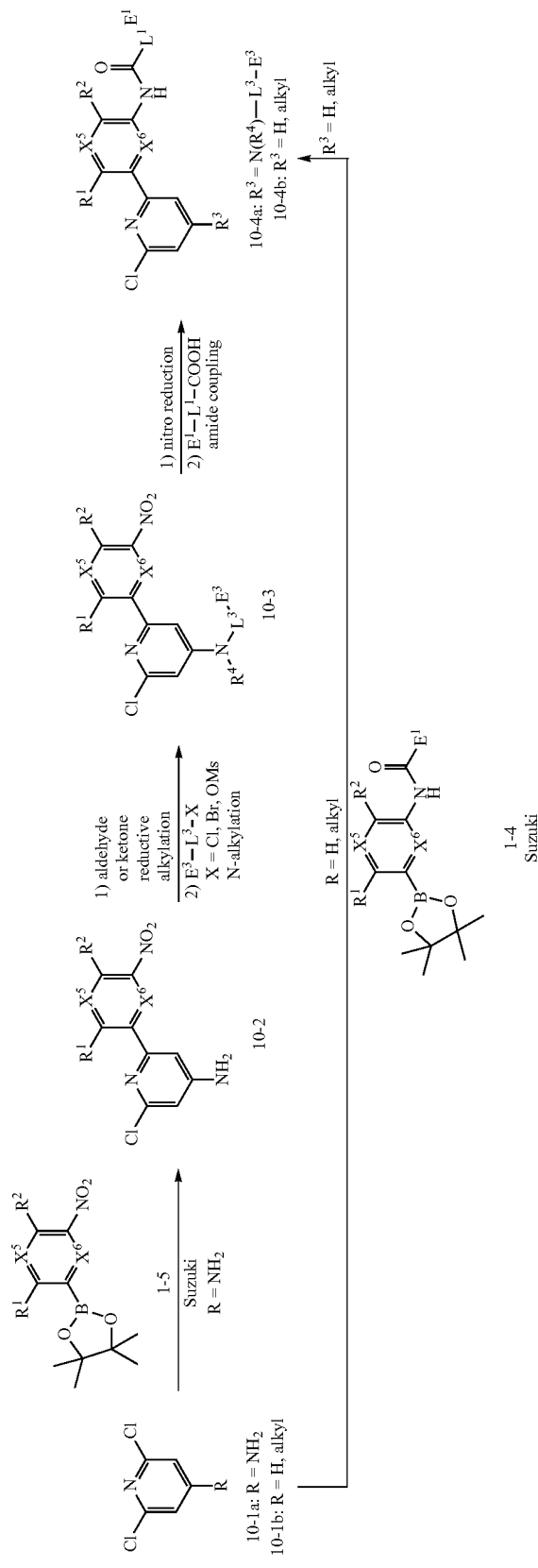
Scheme 10

Scheme 10 illustrates an exemplary preparation of intermediates 10-4. Treatment of 2,6-dichloropyridin-4-amine (10-1a, R=NH$_2$) with boronates 1-5 (commercially available or synthesized by those skilled in the art) in the presence of a palladium catalyst (Suzuki reaction) affords 10-2. Treatment of 10-2 with aldehydes or ketones to introduce R$^4$ by reductive alkylation known to those skilled in the art gives the R$^4$ substituted secondary amines. N-alkylation of the secondary amines with different alkylating reagents (E$^3$-L$^3$-X: X=Cl, Br, OMs) in the presence of base affords 10-3. Nitro reduction of 10-3 under mild reducing conditions (zinc or iron metal with ammonium chloride) affords amines which are reacted with carboxylic acids E$^1$-L$^1$-COOH under amide coupling conditions to those skilled in the art to afford 10-4a (R$^3$=N(R$^4$)-L$^3$-E$^3$). In another embodiment, commercially available 10-1b (R=H, alkyl) reacts with boronates 1-4 by Suzuki reaction to afford 10-4b (R$^3$=H, alkyl).

Scheme 11

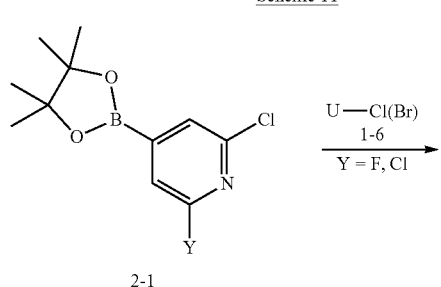

2-1

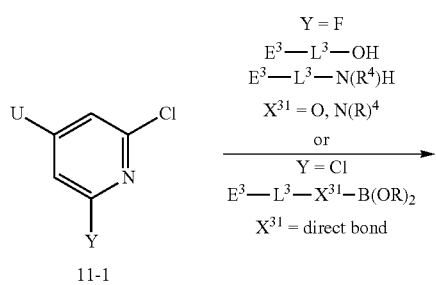

11-1

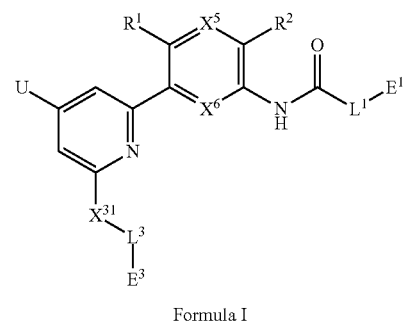

11-2

11-2a: X$^{31}$ = O, NR$^4$
11-2b: X$^{31}$ = direct bond

Formula I

Scheme 11 illustrates an exemplary preparation of compounds of Formula I. Treatment of boronates 2-1 (commercially available or synthesized by those skilled in the art) with chloride or bromides 1-6 (commercially available or synthesized by those skilled in the art) in the presence of a palladium catalyst (Suzuki reaction) affords 11-1. Compound 11-1 (Y=F) reacts with alcohols E$^3$-L$^3$-OH or amines E$^3$-L$^3$-N(R$^4$)H by S$_N$Ar reaction in the presence of base to afford 11-2a. Alternatively, compound 11-1 (Y=Cl) reacts with boronates or boronic acids E$^3$-L$^3$-X$^{31}$—B(OR)$_2$ (X$^{31}$=direct bond) under Pd (0) catalyzed coupling conditions using well known established literature conditions to those skilled in the art to afford 11-2b. Finally, chlorides 11-2 can be reacted with boronates 1-4 by Suzuki reaction to afford compounds of Formula I.

Scheme 12

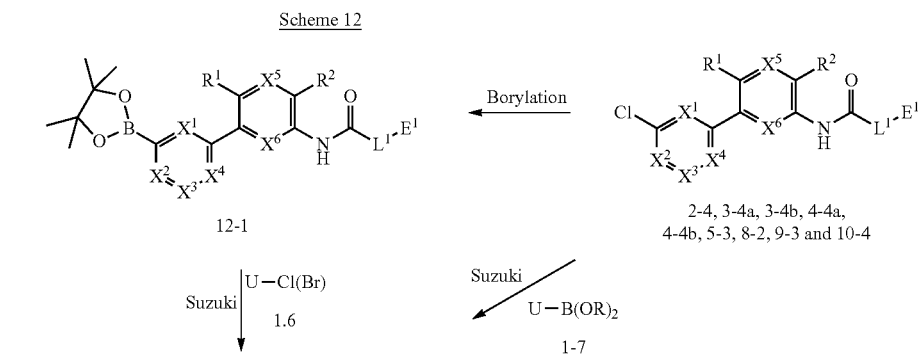

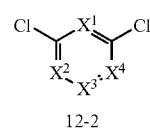

12-2

-continued

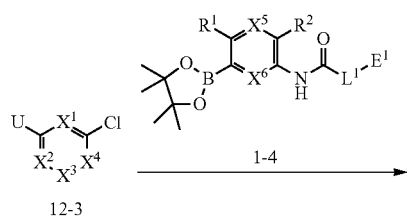

12-3

1-4

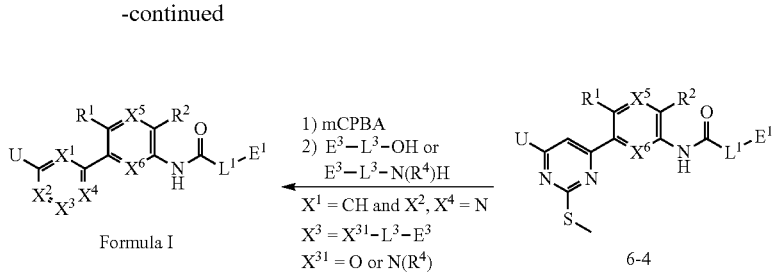

Formula I 1) mCPBA
2) $E^3-L^3$-OH or
$E^3-L^3$-N($R^4$)H $X^1$ = CH and $X^2$, $X^4$ = N
$X^3$ = $X^{31}$-$L^3$-$E^3$
$X^{31}$ = O or N($R^4$)

6-4

Scheme 12 illustrates an exemplary preparation of compounds of Formula I. Compounds of Formula I can be prepared by Suzuki reaction of chlorides (2-4, 3-4a, 3-4b, 4-4a, 4-4b, 5-3, 8-2, 9-4 and 10-4) with boronates or boronic acids U—B(OR)$_2$ 1-7 (commercially available or synthesized by those skilled in the art). Alternatively, chlorides (2-4, 3-4a, 3-4b, 4-4a, 4-4b, 5-3, 8-2, 9-4 and 10-4) can be converted boronates 12-1 by borylation under Pd(0) conditions. Boronates 12-1 react with U-substituted chlorides (or bromides) 1.6 (commercially available or synthesized by those skilled in the art) by Suzuki reaction to afford compounds of Formula I. Dichlorides 12-2 (commercially available or synthesized by those skilled in the art) react with boronates or boronic acids U—B(OR)$_2$ 1-7 (commercially available or synthesized by those skilled in the art) under Suzuki conditions to afford intermediates 12-3. Finally, compounds of Formula I can be prepared by Suzuki reaction of chlorides (12-3) with boronates 1-4. In another embodiment, sulfides 6.4 are converted to compounds of Formula I according to a well-documented reaction sequence: an oxidation reaction using conditions known in the art such as mCPBA in DCM, followed by substitution reaction of the resulting intermediate with commercially available alcohols $E^3$-$L^3$-OH or amines $E^3$-$L^3$-N($R^4$)H.

Scheme 13

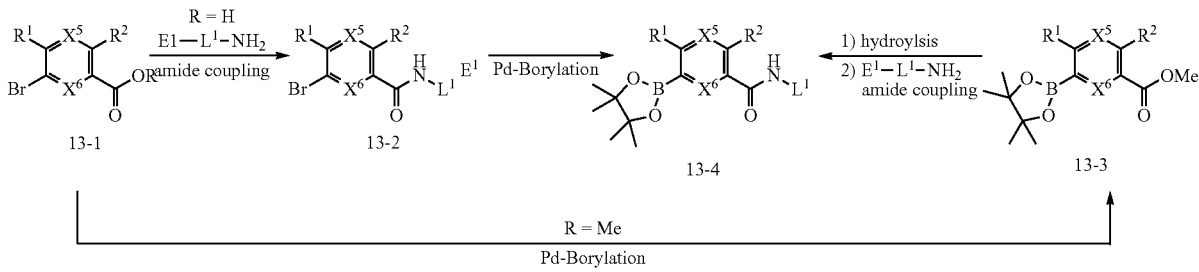

Scheme 13 illustrates an exemplary preparation of key intermediates 13-4. Carboxylic acids 13-1 (R=H, commercially available or synthesized by those skilled in the art) reacts with amines $E^1$-L-NH$_2$ (commercially available or synthesized by those skilled in the art) by standard amide bond formation conditions which is known in the literature to afford 13-2. Bromides 13-2 convert to boronates 13-4 by Pd-catalyzed borylation. In another embodiment, 13-4 can be prepared from 13-3 (prepared by Pd-catalyzed borylation of 13-1 (R=Me)) by hydrolysis, followed by amide coupling reaction of the resulting intermediate with amines $E^1$-NH$_2$.

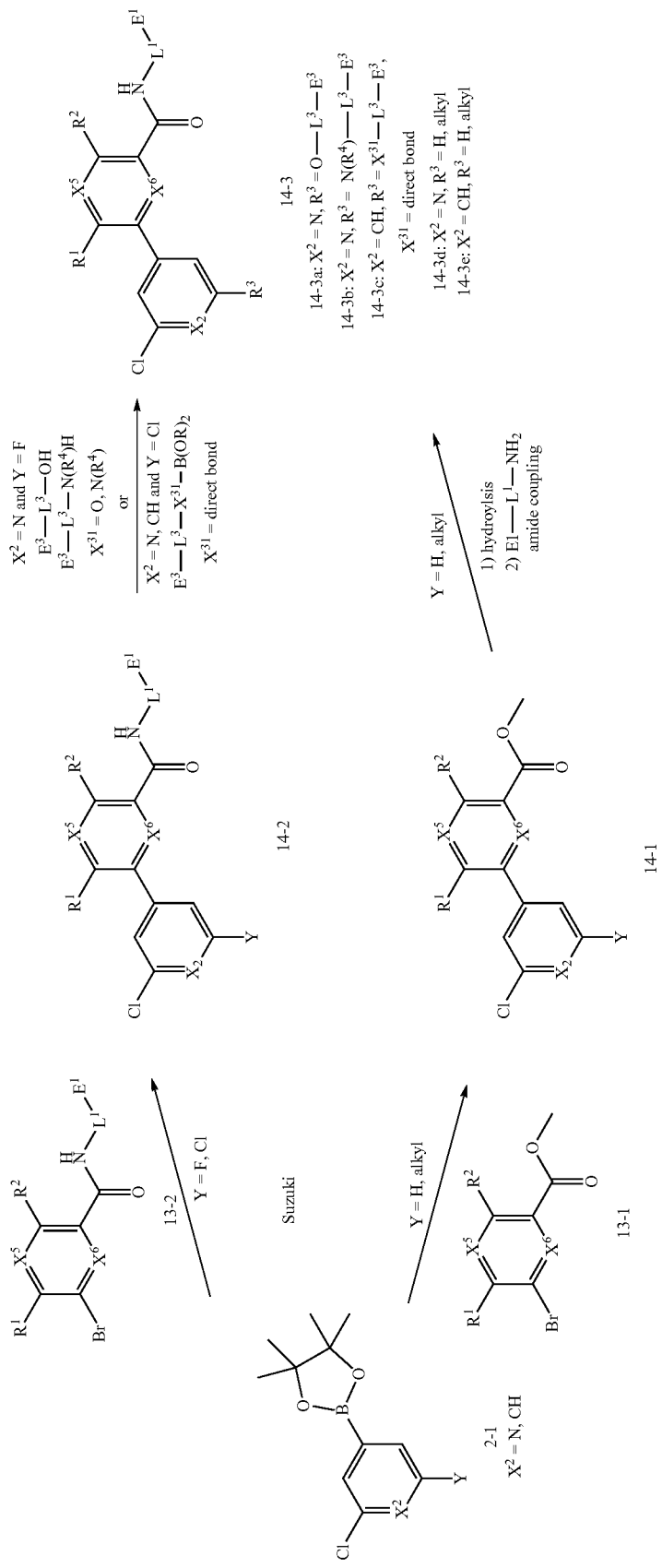

Scheme 14 illustrates an exemplary preparation of intermediates 14-3. Treatment of boronates 2-1 (commercially available or synthesized by those skilled in the art) with bromides 13-2 in the presence of a palladium catalyst (Suzuki reaction) affords 14-2. Compounds 14-2 ($X^2$=N and Y=F) react with alcohols $E^3$-$L^3$-OH or amines $E^3$-$L^3$-N($R^4$)H by $S_NAr$ reaction in the presence of base to afford 14-3a and 14-3b, respectively. Alternatively, compounds 14-2 ($X^2$=N or CH and Y=Cl) react with boronates or boronic acids $E^3$-$L^3$-$X^{31}$—B(OR)$_2$ ($X^{31}$=direct bond) under Pd (0) catalyzed coupling conditions using well known established literature conditions to those skilled in the art to afford 14-3c. In another embodiment, Suzuki reaction of 2-1 ($X^2$=N or CH and Y=H or alkyl, commercially available) with bromides 13-1 affords 14-1. Hydrolysis of 14-1, followed by amide coupling reaction of the resulting intermediate with amines $E^1$-$L^1$-$NH_2$ affords intermediates 14-3d and 14-3e.

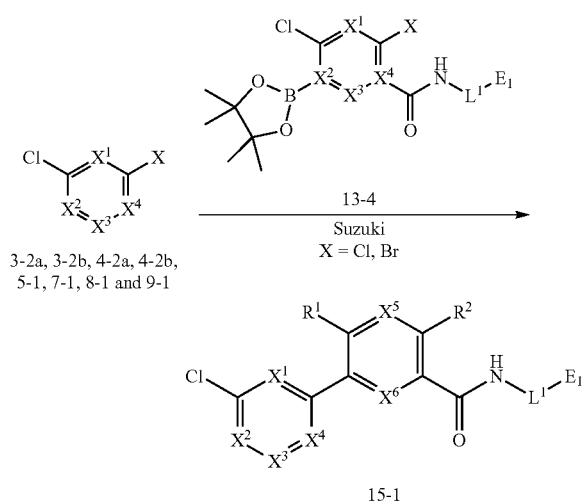

Scheme 15

Scheme 15 illustrates an exemplary preparation of intermediates 15-1. Compounds 3-2a, 3-2b, 4-2a, 4-2b, 5-1, 7-1, 8-1, and 9-1 react with boronates 13-4 in the presence of a palladium catalyst (Suzuki reaction) to afford 15-1.

Scheme 16

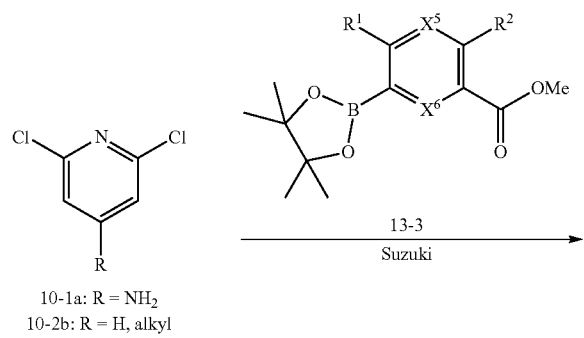

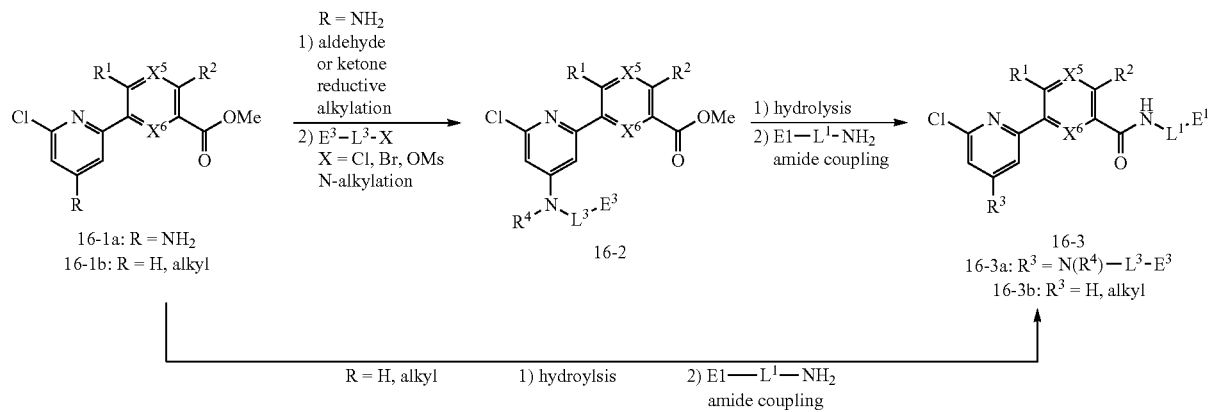

Scheme 16 illustrates an exemplary preparation of intermediates 16-3. Each of 10-1a and 10-1b reacts with boronates 13-3 (commercially available or synthesized by those skilled in the art) in the presence of a palladium catalyst (Suzuki reaction) to afford 16-1a and 16-1b, respectively. Treatment of 16-1a (R=$NH_2$) with aldehydes or ketones to introduce $R^4$ by reductive alkylation conditions known to those skilled in the art gives the $R^4$ substituted secondary amines. N-alkylation of the secondary amines with different alkylating reagents ($E^3$-$L^3$-X: X=Cl, Br, OMs) in the presence of base affords 16-2. Hydrolysis of 16-2 affords the corresponding acids which react with amines $E^1$-$L^1$-$NH_2$ under amide coupling conditions to afford 16-3a. In a similar manner, hydrolysis of 16-1b (R=H, alkyl), followed by amide coupling reaction of the resulting intermediate with amines $E^1$-$L^1$-$NH_2$ affords 16-3b.

Scheme 17 illustrates an exemplary preparation of intermediates 17-3. 4,6-Dichloro-2-(methylthio)pyrimidine (6-1) reacts with boronates 13-3 in the presence of a palladium catalyst (Suzuki reaction) to afford 17-1. Hydrolysis of 17-1, followed by amide coupling reaction of the resulting intermediate with amines $E^1$-$L^1$-$NH_2$ affords 17-2. Alternatively, 17-2 can be directly prepared from 6-1 with boronates 13-4 by Suzuki reaction. Chlorides 17-2 react with boronates or boronic acids U—$B(OR)_2$ 1-7 (commercially available or synthesized by those skilled in the art) by Suzuki reaction to afford 17-3.

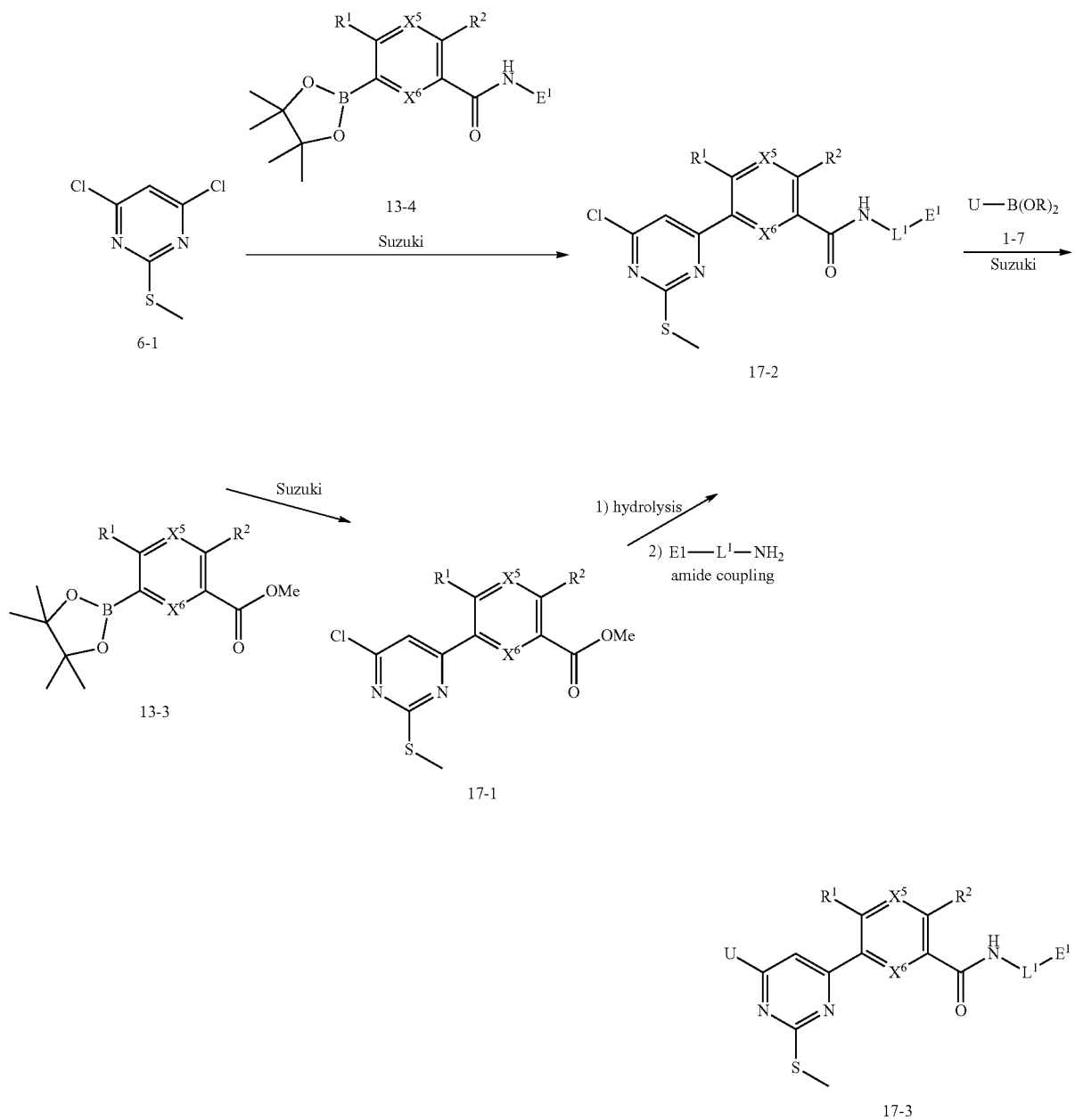

Scheme 17

Scheme 18

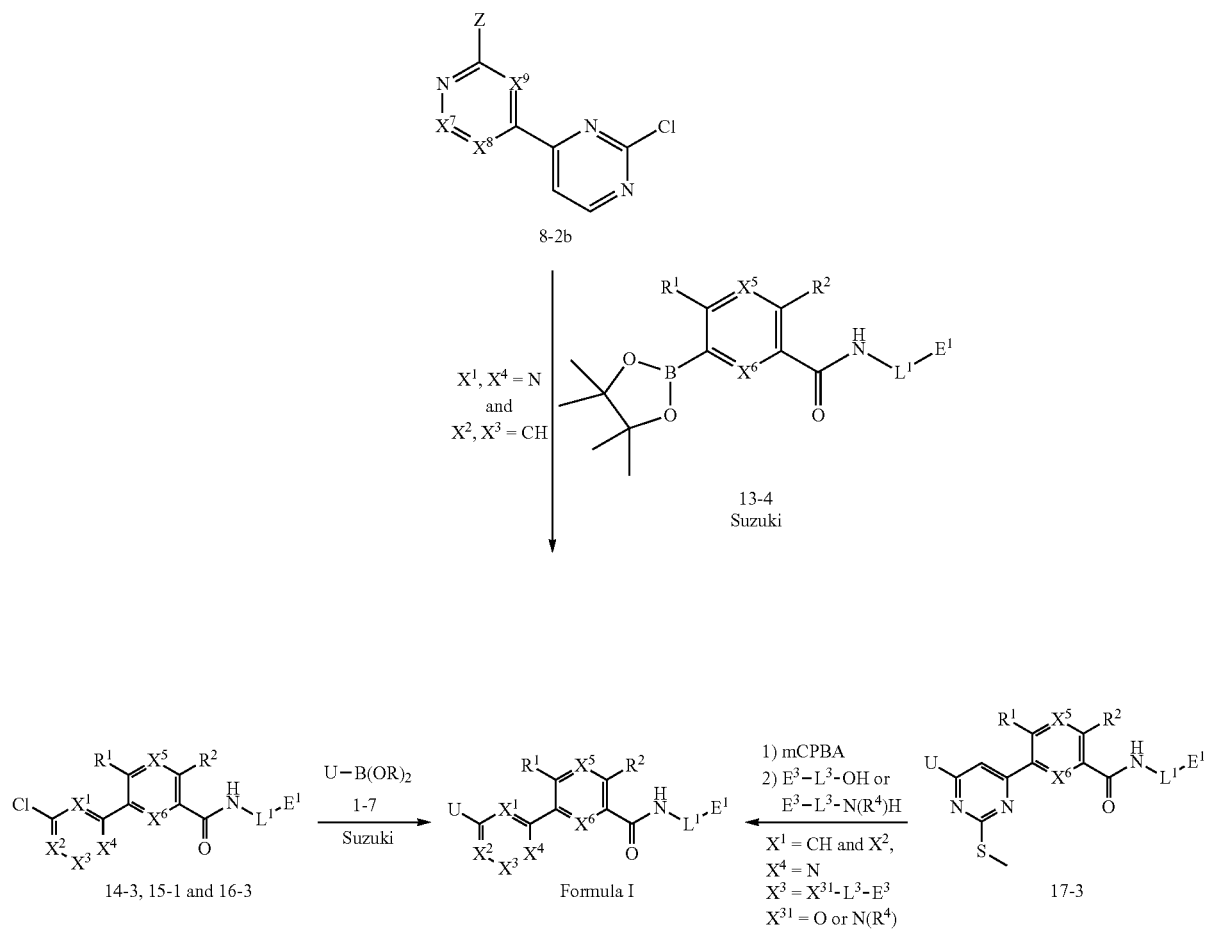

Scheme 18 illustrates an exemplary preparation of compounds of Formula I. Compounds of Formula I can be prepared by Suzuki reaction of chlorides (14-3, 15-1 and 16-3) with boronates or boronic acids U—B(OR)$_2$ 1-7 (commercially available or synthesized by those skilled in the art). Compound 8-2b ($X^1$, $X^4$=N and $X^2$, $X^3$=CH) reacts with boronates 13-4 in the presence of a palladium catalyst (Suzuki reaction) to afford compounds of Formula I. In another embodiment, sulfides 17-3 are converted to compounds of Formula I according to a well-documented reaction sequence: an oxidation reaction using conditions known in the art such as mCPBA in DCM, followed by substitution reaction of the resulting intermediate with commercially available alcohols $E^3$-$L^3$-OH or amines $E^3$-$L^3$-N(R$^4$)H.

Preparation of Intermediates

Using the synthetic procedures and methods described herein and methods known to those skilled in the art, the following compounds were made:

General Method A: Borylation

Intermediate A1: tert-butyl methyl(4-(4,4,5,5-tetramethyl-1,3,2-dioxaborolan-2-yl)pyridin-2-yl)carbamate

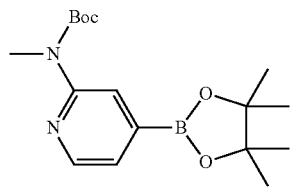

A mixture of tert-butyl (4-bromopyridin-2-yl)(methyl) carbamate (0.82 g, 2.9 mmol), 4,4,4',4',5,5,5',5'-octamethyl-2,2'-bi(1,3,2-dioxaborolane) (0.87 g, 3.4 mmol) and KOAc (0.84 g, 8.6 mmol) in DMF (15 mL) was allowed to stir at rt. The reaction mixture was sparged with Ar for 10 min. Pd(dppf)Cl$_2$·DCM adduct (0.12 g, 0.14 mmol) was added and the reaction mixture was sealed and heated to 80° C. overnight. The reaction was cooled to rt and diluted with EtOAc (30 mL). The organic layer was separated and washed with brine (30 mL), dried over anhydrous $Na_2SO_4$, filtered, and concentrated under reduced pressure to afford a brown oil. The brown oil was treated with hexanes (20 mL) and the solid was filtered. The filtrate was concentrated to dryness under vacuum to afford tert-butyl methyl(4-(4,4,5,5-tetramethyl-1,3,2-dioxaborolan-2-yl)pyridin-2-yl)carbamate (1.09 g, 100% yield) as a brown solid. $^1$H NMR (400 MHz, DMSO-$d_6$): δ 8.40 (d, J=4.8 Hz, H), 7.90 (s, 1H), 7.27 (d, J=4.8 Hz, 18), 3.29 (s, 3H), 1.48 (s, 9H), 1.30 (s, 12H); MS (ESI) m/z: 335.2 (M+H$^+$).

Using the General Method A above, the following Intermediates of Table A were prepared.

TABLE A

| Ex. No. | Product | Yield (%) | $^1$H NMR (400 or 500 MHZ, DMSO-$d_6$): δ | MS (m/z: M + H$^+$) |
|---|---|---|---|---|
| A2 | | crude | No Data | 299.2 |
| A3 | | crude | 10.7 (s, 1H), 8.28 (m, 2H), 7.22 (d, J = Hz, 1H), 1.15 (s, 12H), 1.06 (brs, 1H), 0.86 (m, 4H). | 288.9 |
| A4 | | crude | No Data | 224.0 (boronic acid) |
| A5 | | crude | 10.4 (s, 1H), 8.31 (brs, 1H), 7.92 (s, 1H), 7.23 (d, J = 5.2 Hz, 1H), 2.09 (s, 3H), 1.30 (s, 12H). | 263.3 |

TABLE A-continued

| Ex. No. | Product | Yield (%) | ¹H NMR (400 or 500 MHZ, DMSO-$d_6$): δ | MS (m/z: M + H⁺) |
|---|---|---|---|---|
| A6 | | 57 | 8.78 (d, J = 5.6 Hz, 1H), 8.66 (d, J = 4.7 Hz, 1H), 8.22 (s, 1H), 7.73 (dd, J = 1.2 and 4.7 Hz, 1H), 2.81 (d, J = 4.9 Hz, 3H), 1.32 (s, 12H). | No Data |
| A7 | | crude | 10.5 (brs, 1H), 9.28 (d, J = 9.6 Hz, 1H), 8.29 (m, 2H), 7.28 (m, 1H), 1.30 (s, 12H). | 249.7 |
| A8 | | crude | 8.09 (m, 1H), 6.78 (s, 1H), 6.60 (d, J = 5.2 Hz, 1H), 6.57 (brm, 1H), 3.41 (brm, 4H), 3.24 (s, 3H), 1.27 (s, 12H). | 279.3 |
| A9 | | crude | 8.74 (d, J = 4.0 Hz, 1H), 8.64 (d, J = 4.4 Hz, 1H), 8.21 (s, 1H), 7.74 (d, J = 4.4 Hz, 1H), 2.88-2.95 (m, 1H), 1.32 (s, 12H), 0.68 (m, 4H). | 206.9 (boronic acid) |
| A10 | | 91 | 9.35 (s, 1H), 8.35 (d, J = 4.8 Hz, 1H), 8.33 (s, 1H), 7.31 (d, J = 4.8 Hz, 1H), 3.31 (s, 3H), 1.37 (s, 6H), 1.29 (s, 12H). | 321.3 |

TABLE A-continued

| Ex. No. | Product | Yield (%) | ¹H NMR (400 or 500 MHZ, DMSO-d₆): δ | MS (m/z: M + H⁺) |
|---|---|---|---|---|
| A11 | (structure) | crude | No Data | 305.3 |
| A12 | (structure) | crude | No Data | 234.2 (boronic acid) |
| A13 | (structure) | crude | 9.51 (s, 1H), 8.34 (d, J = 4.8 Hz, 1H), 8.27 (s, 1H), 7.28 (d, J = 4.8 Hz, 1H), 1.41 (s, 3H), 1.30 (s, 12H), 1.12 (m, 2H), 0.66 (m, 2H). | 303.1 |
| A14 | (structure) | crude | 10.3 (s, 1H), 8.40 (d, J = 4.8 Hz, 1H), 8.17 (s, 1H), 7.34 (d, J = 4.8 Hz, 1H), 1.72 (m, 2H), 1.69 (m, 2H), 1.30 (s, 12H). | 314.3 |
| A15 | (structure) | Crude | 8.81 (brm, 1H), 8.66 (d, J = 4.4 Hz, 1H), 8.22 (s, 1H), 7.74 (d, J = 4.8 Hz, 1H), 3.32 (m, 2H), 1.32 (s, 12H), 1.15 (t, J = 7.2 Hz, 3H). | 195.1 (boronic acid) |

TABLE A-continued

| Ex. No. | Product | Yield (%) | ¹H NMR (400 or 500 MHZ, DMSO-d₆): δ | MS (m/z: M + H⁺) |
|---|---|---|---|---|
| A16 | | 42 | 10.2 (s, 1H), 8.28 (dd, J = 1.0 and 4.7 Hz, 1H), 8.10 (d, J = 1.0 Hz, 1H), 7.20 (d, J = 0.9 Hz, 1H), 3.66 (s, 3H), 1.30 (s, 12H). | No Data |
| A17 | | crude | No Data | 179.0 |
| A18 | | crude | No Data | 286.2 (boronic acid) |
| A19 | | crude | No Data | No Data |
| A20 | | crude | No Data | 248.2 (boronic acid) |

TABLE A-continued

| Ex. No. | Product | Yield (%) | ¹H NMR (400 or 500 MHZ, DMSO-d₆): δ | MS (m/z: M + H⁺) |
|---|---|---|---|---|
| A21 | (pyridine with C(O)NH-CH₂CH₂-OCH₃ at 2-position and Bpin at 4-position) | Crude | 8.68 (brs, 1H), 8.67 (d, J = 4.8 Hz, 1H), 8.23 (s, 1H), 7.75 (d, J = 4.4 Hz, 1H), 3.47 (m, 4H), 3.26 (s, 3H), 1.16 (s, 12H). | 306.8 |
| A22 | (1-SEM-pyrazolo[3,4-b]pyridine with Bpin) | 60 | 8.63 (d, J = 4.4 Hz, 1H), 7.92 (s, 1H), 7.50 (d, J = 4.4 Hz, 1H), 5.79 (s, 2H), 3.52-3.59 (m, 2H), 1.37 (s, 12H), 0.79-0.88 (m, 2H), 0.08 (s, 9H). | 376.1 |
| A23 | (pyridine-2-carboxamide with NH-CH₂CH₂-OH and 4-Bpin) | crude | No Data | 293.0 |
| A24 | (pyridine-2-carboxamide with N-Boc-azetidin-3-yl and 4-Bpin) | crude | No Data | 404.0 |
| A25 | (pyridine-2-carboxamide with NH-CH₂-CN and 4-Bpin) | crude | No Data | 206.0 (boronic acid) |

TABLE A-continued

| Ex. No. | Product | Yield (%) | $^1$H NMR (400 or 500 MHZ, DMSO-$d_6$): δ | MS (m/z: M + H$^+$) |
|---|---|---|---|---|
| A26 | (structure) | 40 | 8.69 (m, 1H), 8.63 (d, J = 5.2 Hz, 1H), 8.02 (d, J = 2.0 Hz, 1H), 7.77 (dd, J = 2.0 and 5.2 Hz, 1H), 3.39 (m, 2H), 2.41 (m, 2H), 2.17 (s, 6H), 1.16 (s, 12H). | 238.0 |
| A27 | (structure) | crude | No Data | 184.0 (boronic acid) |

General Method B: Suzuki Coupling Reaction

Intermediate B1:
3-(2,6-dichloropyridin-4-yl)-4-methylaniline

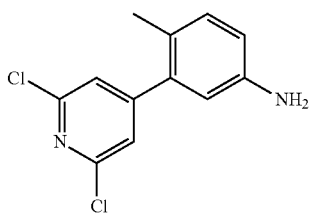 [SMILES: Cc1ccc(N)cc1-c1cc(Cl)nc(Cl)c1]

A solution of 2,6-dichloro-4-iodopyridine (2.0 g, 7.3 mmol), and 4-methyl-3-(4,4,5,5-tetramethyl-1,3,2-dioxaborolan-2-yl)aniline (2.0 g, 8.8 mmol) in 1,4-dioxane (50 mL) was treated with K$_2$CO$_3$ (2.0 N, 7.3 mL, 15 mmol). The reaction mixture was sparged with Ar for 2 min and then Pd(dppf)Cl$_2$ (0.3 g, 0.37 mmol) was added. The reaction mixture was heated at 80° C. for 20 h and then cooled to rt. The solution was filtered through a pad of celite and washed with EtOAc (50 mL). The filtrate was washed with brine and the organic layer was dried over anhydrous Na$_2$SO$_4$, filtered, and concentrated under reduced pressure to obtain the crude. The crude was purified by silica gel column chromatography (0 to 70% EtOAc/hexanes) to obtain 3-(2,6-dichloropyridin-4-yl)-4-methylaniline (1.7 g, 92% yield) as a light brown solid. MS (ESI) m/z: 253.0 (M+H$^+$).

Using the General Method B above, the 'following Intermediates of Table B were prepared.

TABLE B

| Ex. No. | Product | Yield (%) | $^1$H NMR (400 or 500 MHz, DMSO-$d_6$): δ | MS (m/z: M + H$^+$) |
|---|---|---|---|---|
| B2 | (structure) | 76 | 8.41 (d, J = 5.1 Hz, 1H), 7.42 (d, J = 1.4 Hz, 1H), 7.35 (dd, J = 1.5 and 5.1 Hz, 1H), 6.96 (d, J = 8.2 Hz, 1H), 6.56 (dd, J = 2.4 and 8.1 Hz, 1H), 6.46 (d, J = 2.4 Hz, 1H), 5.03 (s, 2H), 2.06 (s, 3H). | 219.2 |
| B3 | (structure) | 65 | 7.44 (s, 1H), 7.21 (s, 1H), 6.97 (d, J = 8.0 Hz, 1H), 6.58 (dd, J = 2.4 and 8.4 Hz, 1H), 6.48 (brs, 1H), 5.00 (brs, 2H), 2.08 (s, 3H). | 237.2 |

TABLE B-continued

| Ex. No. | Product | Yield (%) | $^1$H NMR (400 or 500 MHz, DMSO-$d_6$): δ | MS (m/z: M + H$^+$) |
|---|---|---|---|---|
| B4 | | 50 | 7.44 (s, 1H), 7.22 (s, 1H), 7.00 (d, J = 12.4 Hz, 1H), 6.70 (d, J = 9.2 Hz, 1H), 5.10 (brs, 2H), 2.11 (s, 3H). | 255.0 |
| B5 | | 96 | 7.54 (s, 1H), 7.30 (s, 1H), 7.20 (d, J = 8.6 Hz, 1H), 6.66 (dd, J = 2.8 and 8.6 Hz, 1H), 6.61 (d, J = 2.7 Hz, 1H), 5.48 (s, 2H). | 257.0 |
| B6 | | 57 | 6.92 (d, J = 8.0 Hz, 1H), 6.54 (d, J = 4.0 Hz, 1H), 6.44 (d, J = 4.0 Hz, 2H), 6.26 (s, 1H), 5.00 (brs, 2H), 3.58 (s, 3H), 2.08 (s, 3H). | 248.8 |
| B7 | | 26 | 6.95 (d, J = 8.0 Hz, 1H), 6.88 (s, 1H), 6.58 (m, 1H), 6.43 (d, J = 2.0 Hz, 1H), 5.00 (s, 2H), 3.66 (s, 3H), 1.95 (s, 3H). | 250.2 |
| B8 | | 44 | 7.60 (s, 1H), 7.20 (brs, 1H), 7.11 (d, J = 7.6 Hz, 1H), 6.63 (dd, J = 2.0 and 8.0 Hz, 1H), 6.51 (s, 1H), 3.66 (s, 3H), 2.22 (s, 3H). (in CDCl$_3$, NH$_2$ protons are missing) | 248.8 |
| B9 | | 71 | 7.25 (s, 1H), 7.12 (s, 1H), 6.95 (d, J = 8.4 Hz, 1H), 6.54 (m, 1H), 6.48 (s, 1H), 5.00 (brs, 2H), 2.14 (m, 1H), 2.08 (s, 3H), 1.02 (m, 2H), 0.88 (m, 2H). | 259.2 |
| B10 | | 36 | 8.34 (d, J = 2.5 Hz, 1H), 8.27 (m, 1H), 7.74 (s, 1H), 7.66 (d, J = 8.5 Hz, 1H), 2.56 (s, 3H), 2.51 (s, 3H). | 296.0 |

TABLE B-continued

| Ex. No. | Product | Yield (%) | ¹H NMR (400 or 500 MHz, DMSO-d$_6$): δ | MS (m/z: M + H⁺) |
|---|---|---|---|---|
| B11 | | 56 | 8.42 (d, J = 5.1 Hz, 1H), 7.43 (s, 1H), 7.35 (dd, J = 1.4 and 5.1 Hz, 1H), 6.97 (d, J = 12.4 Hz, 1H), 6.66 (d, J = 9.2 Hz, 1H), 5.09 (s, 2H), 2.08 (s, 3H). | 237.0 |
| B12 | | 89 | 7.37-7.45 (m, 2H), 7.30 (s, 1H), 7.24 (d, J = 7.6 Hz, 1H), 6.92 (d, J = 8.0 Hz, 1H), 6.50 (dd, J = 8.0, 2.4 Hz, 1H), 6.43 (d, J = 2.4 Hz, 1H), 4.93 (brs, 2H), 2.03 (s, 3H). | 217.9 |
| B13 | | 90 | 8.48 (d, J = 5.1 Hz, 1H), 7.93 (d, J = 8.1 Hz, 1H), 7.79 (s, 1H), 7.60 (s, 1H), 7.51 (d, J = 8.0 Hz, 1H), 7.47 (d, J = 5.1 Hz, 1H), 3.84 (s, 3H), 2.31 (s, 3H). | 262.2 |
| B14 | | 60 | 8.46 (d, J = 4.8 Hz, 1H), 7.91 (s, 1H), 7.52 (s, 1H), 7.42 (d, J = 5.2 Hz, 1H), 6.81 (s, 1H), 5.2 (brs, 2H), 2.31 (s, 3H). | 219.8 |
| B15 | | 56 | 7.38 (s, 1H), 7.36 (s, 1H), 7.01 (m, 1H), 6.72 (dd, J = 2.8 and 6.4 Hz, 1H), 6.65 (m, 1H), 5.1 (brs, 2H), 2.51 (s, 3H). | 236.8 |
| B16 | | 60 | No Data | 263.0 |
| B17 | | 49 | No Data | 464.0 |
| B18 | | 59 | 8.91 (d, J = 5.1 Hz, 1H), 8.31 (d, J = 7.8 Hz, 1H), 7.89 (d, J = 5.1 Hz, 1H), 7.68 (d, J = 12.4 Hz, 1H), 2.51 (s, 3H). | 268.0 |

TABLE B-continued

| Ex. No. | Product | Yield (%) | ¹H NMR (400 or 500 MHz, DMSO-$d_6$): δ | MS (m/z: M + H⁺) |
|---|---|---|---|---|
| B19 | | 52 | 7.74 (d, J = 2.0 Hz, 1H), 7.57 (d, J = 2.4 Hz, 1H), 6.90 (d, J = 8.0 Hz, 1H), 6.47 (dd, J = 2.0 and 8.0 Hz, 1H), 6.43 (d, J = 2.4 Hz, 1H), 5.90 (brs, 2H), 4.90 (t, J = 5.6 Hz, 1H), 4.05 (t, J = 5.2 Hz, 2H), 3.66 (m, 2H), 2.09 (s, 3H). | 279.3 |
| B20 | | 63 | 8.76 (s, 1H), 8.74 (s, 1H), 6.99 (d, J = 8.0 Hz, 1H), 6.71 (s, 1H), 6.63 (m, 1H), 5.0 (brs, 2H), 2.18 (s, 3H). | 219.8 |
| B21 | | 41 | 7.73 (s, 2H), 6.89 (d, J = 12.4 Hz, 1H), 6.61 (d, J = 9.6 Hz, 1H), 4.9 (brs, 2H), 3.54 (s, 3H), 2.09 (s, 3H). | 266.9 |
| B22 | | 97 | No Data | 236.0 |
| B23 | | 28 | 6.92 (d, J = 12.0 Hz, 1H), 6.64 (d, J = 8.0 Hz, 1H), 6.45 (d, J = 1.6 Hz, 1H), 6.24 (d, J = 1.6 Hz, 1H), 5.0 (brs, 2H), 3.58 (s, 3H), 2.11 (s, 3H). | 266.9 |
| B24 | | 63 | No Data | 250.0 |
| B25 | | 70 | 8.91 (d, J = 5.1 Hz, 1H), 8.34 (d, J = 2.5 Hz, 1H), 8.28 (dd, J = 2.5 and 8.4 Hz, 1H), 7.92 (d, J = 5.1 Hz, 1H), 7.68 (d, J = 8.5 Hz, 1H), 2.51 (s, 3H). | 250.0 |

TABLE B-continued

| Ex. No. | Product | Yield (%) | $^1$H NMR (400 or 500 MHz, DMSO-$d_6$): δ | MS (m/z: M + H$^+$) |
|---|---|---|---|---|
| B26 | | 20 | No Data | 268.0 |
| B27 | | 48 | 9.18 (s, 1H), 8.36 (d, J = 2.5 Hz, 1H), 8.28 (dd, J = 2.5 and 8.5 Hz, 1H), 8.10 (s, 1H), 7.68 (t, J = 9.0 Hz, 1H), 2.51 (s, 3H). | 250.0 |
| B28 | | 59 | No Data | 238.0 |
| B29 | | 73 | 7.86 (d, J = 2.8 Hz, 1H), 7.42-7.49 (m, 2H), 7.38 (s, 1H), 7.30 (m, 1H), 6.77 (d, J = 2.4 Hz, 1H), 5.18 (brs, 2H), 2.22 (s, 3H). | 218.9 |
| B30 | | 60 | 7.94 (t, J = 7.6 Hz, 1H), 7.91 (d, J = 2.4 Hz, 1H), 7.56 (d, J = 7.6 Hz, 1H), 7.50 (t, J = 8.0 Hz, 1H), 6.99 (d, J = 2.8 Hz, 1H), 5.22 (brs, 2H), 2.33 (s, 3H). | 219.9 |
| B31 | | 25 | 8.83 (d, J = 5.2 Hz, 1H), 8.05 (d, J = 5.6 Hz, 1H), 7.77 (d, J = 5.2 Hz, 1H), 7.11 (d, J = 2.4 Hz, 1H), 5.36 (brs, 2H), 2.39 (s, 3H). | 220.9 |
| B32 | | 28 | 7.57 (s, 1H), 6.97 (d, J = 8.4 Hz, 1H), 6.71 (d, J = 2.4 Hz, 1H), 6.60 (dd, J = 2.4 and 8.0 Hz, 1H), 5.08 (brs, 2H), 2.22 (s, 3H), 2.21 (m, 1H), 1.17 (m, 2H), 1.11 (m, 2H). | 259.9 |
| B33 | | 72 | 8.47 (d, J = 5.2 Hz, 1H), 7.59 (s, 1H), 7.52 (d, J = 5.2 Hz, 1H), 7.03 (m, 1H), 6.74 (m, 1H), 6.67 (m, 1H), 5.17 (brs, 2H). | 222.9 |

TABLE B-continued

| Ex. No. | Product | Yield (%) | ¹H NMR (400 or 500 MHz, DMSO-$d_6$): δ | MS (m/z: M + H⁺) |
|---|---|---|---|---|
| B34 | | 80 | 7.21 (s, 1H), 7.08 (s, 1H), 7.05 (s, 1H), 6.91 (d, J = 8.4 Hz, 1H), 6.48 (dd, J = 2.4 and 8.0 Hz, 1H), 6.41 (d, J = 2.4 Hz, 1H), 4.91 (brs, 2H), 2.36 (s, 3H), 2.03 (s, 3H). | 231.9 |
| B35 | | 60 | 7.30 (brs, 1H), 7.05 (brd, J = 13.2 Hz, 1H), 6.92 (brt, J = 8.4 Hz, 2H), 6.48-6.53 (m, 1H), 6.42 (brm, 1H), 4.92 (brs, 2H), 2.08 (s, 3H), 2.02 (m, 1H), 0.96 (m, 2H), 0.79 (m, 2H). | 258.1 |
| B36 | | 48 | 7.21 (brs, 2H), 6.95 (brd, J = 8.0 Hz, 1H), 6.55 (dd, J = 2.0 and 8.0 Hz, 1H), 6.44 (brd, J = 2.4 Hz, 1H), 5.01 (brs, 2H), 2.48 (s, 3H), 2.06 (s, 3H). | 233.1 |
| B37 | | 54 | 7.84 (d, J = 2.4 Hz, 1H), 7.12 (s, 2H), 6.98 (s, 1H), 6.77 (m, 1H), 5.16 (brs, 2H), 2.22 (s, 3H), 2.01 (m, 1H), 0.92 (m, 2H), 0.76 (m, 2H). | 259.0 |
| B38 | | 58 | 7.91 (t, J = 7.6 Hz, 1H), 7.46 (d, J = 5.2 Hz, 1H), 7.44 (d, J = 5.2 Hz, 1H), 6.94 (d, J = 8.4 Hz, 1H), 6.64 (brd, J = 2.4 Hz, 1H), 6.55 (dd, J = 2.4 and 8.0 Hz, 1H), 4.98 (brs, 2H), 2.14 (s, 3H). | 219.1 |
| B39 | | 70 | 8.40 (d, J = 5.2 Hz, 1H), 7.53 (d, J = 0.8 Hz, 1H), 7.47 (dd, J = 1.2 and 5.2 Hz, 1H), 6.90 (d, J = 8.8 Hz, 1H), 6.67 (d, J = 2.8 Hz, 1H), 6.65 (s, 1H), 4.82 (brs, 2H), 3.66 (s, 3H). | 234.9 |
| B40 | | 78 | 7.51 (d, J = 4.0 Hz, 4H), 7.45 (m, 1H), 6.64 (m, 2H), 6.28 (brs, 2H). | 229.1 |

TABLE B-continued

| Ex. No. | Product | Yield (%) | $^1$H NMR (400 or 500 MHz, DMSO-$d_6$): δ | MS (m/z: M + H$^+$) |
|---|---|---|---|---|
| B41 | | 62 | 8.53 (d, J = 5.2 Hz, 1H), 7.64 (s, 1H), 7.59 (s, 1H), 7.54 (d, J = 1.6 Hz, 1H), 6.71 (d, J = 2.0 Hz, 1H), 6.69 (s, 1H), 6.39 (br s, 2H). | 230.0 |
| B42 | | 48 | No Data | 234.2 |
| B43 | | 91 | 8.02 (d, J = 2.4 Hz, 1H), 7.82 (d, J = 2.0 Hz, 1H), 6.93 (d, J = 8.4 Hz, 1H), 6.52 (dd, J = 2.4 and 8.0 Hz, 1H), 6.44 (d, J = 2.4 Hz, 1H), 4.93 (brs, 2H), 4.41 (q, J = 6.8 Hz, 2H), 2.05 (s, 3H), 1.37 (t, J = 6.8Hz, 3H). | 263.0 |
| B44 | | 77 | No Data | 251.0 |
| B45 | | 62 | 9.29 (d, J = 2.8 Hz, 1H), 8.38 (d, J = 2.8 Hz, 1H), 7.63 (s, 1H), 7.66 (m, 2H), 7.49 (m, 1H), 2.56 (s, 3H). | 248.9 |
| B49 | | 55 | No Data | 268.0 |
| B50 | | 59 | 9.48 (d, J = 2.0 Hz, 1H), 8.42 (m, 2H), 8.30 (m, 1H), 7.69 (d, J = 8.4 Hz, 1H), 2.40 (s, 3H). | 250.0 |
| B51 | | 91 | No Data | 220.0 |

TABLE B-continued

| Ex. No. | Product | Yield (%) | ¹H NMR (400 or 500 MHz, DMSO-d$_6$): δ | MS (m/z: M + H⁺) |
|---|---|---|---|---|
| B52 | | 55 | 9.42 (d, J = 2.4 Hz, 1H), 8.16 (d, J = 2.0 Hz, 1H), 7.97 (d, J = 2.4 Hz, 1H), 7.04 (d, J = 2.4 Hz, 1H), 5.31 (s, 2H), 2.32 (s, 3H). | 221.0 |
| B53 | | crude | 8.34 (d, J = 1.9 Hz, 1H), 7.80 (d, J = 1.9 Hz, 1H), 6.95 (d, J = 8.1 Hz, 1H), 6.54 (dd, J = 2.4 and 8.1 Hz, 1H), 6.45 (d, J = 2.5 Hz, 1H), 5.00 (s, 2H), 2.58 (s, 3H), 2.05 (s, 3H). | 233.0 |
| B54 | | 87 | No Data | 237.0 |
| B55 | | 62 | No Data | 251.0 |
| B56 | | 25 | 9.53 (d, J = 2.4 Hz, 1H), 8.12 (q, J = 3.2 Hz, 1H), 8.49 (dt, J = 7.2, 2.8 Hz, 1H), 8.43 (t, J = 2.0 Hz, 1H), 7.76 (t, J = 9.6 Hz, 1H). | 254.1 |
| B57 | | 72 | No Data | 219.0 |
| B58 | | 66 | No Data | 220.2 |
| B59 | | crude | No Data | 241.0 |

TABLE B-continued

| Ex. No. | Product | Yield (%) | ¹H NMR (400 or 500 MHz, DMSO-$d_6$): δ | MS (m/z: M + H⁺) |
|---|---|---|---|---|
| B60 | 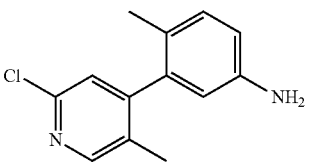 [SMILES: Cc1ccc(N)cc1-c1cc(Cl)ncc1C] | 84 | No Data | 233.0 |
| B61 | 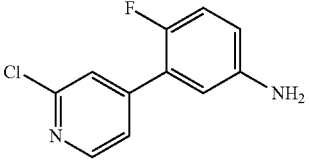 [SMILES: Nc1ccc(F)c(-c2ccnc(Cl)c2)c1] | 49 | 8.47 (d, J = 5.2 Hz, 1H), 7.58 (s, 1H), 7.52 (d, J = 5.2 Hz, 1H), 7.03 (dd, J = 8.8 and 10.9 Hz, 1H), 6.75 (dd, J = 2.8 and 6.6 Hz, 1H), 6.67 (m, 1H), 5.16(s, 2H). | 223.0 |
| B62 | 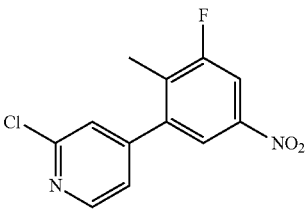 [SMILES: Cc1c(F)cc([N+](=O)[O-])cc1-c1ccnc(Cl)c1] | 52 | 8.55 (dd, J = 0.7 and 5.1 Hz, 1H), 8.21 (dd, J = 2.3 and 9.4 Hz, 1H), 8.04 (m, 1H), 7.70 (d, J = 1.5 Hz, 1H), 7.55 (dd, J = 1.5 and 5.1 Hz, 1H), 2.25 (d, J = 2.6 Hz, 3H). | 267.0 |
| B63 | 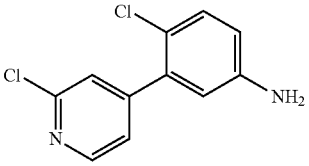 [SMILES: Nc1ccc(Cl)c(-c2ccnc(Cl)c2)c1] | 88 | No Data | 239.0 |
| B64 | 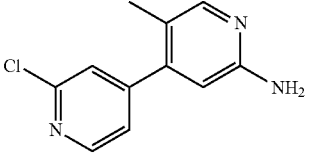 | 81 | No Data | 220.0 |

General Method C: Nitro Reduction

Intermediate B46: 3-(6-chloro-2-(methylthio)pyrimidin-4-yl)-4-methylaniline

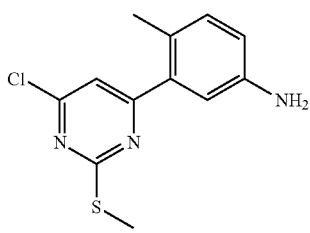 [SMILES: CSc1nc(Cl)cc(-c2cc(N)ccc2C)n1]

A solution of 4-chloro-6-(2-methyl-5-nitrophenyl)-2-(methylthio)pyrimidine (B10, 0.53 g, 1.8 mmol) in a mixture of THF (6 mL) and MeOH (3 mL) was treated with NH₄C₁ (0.096 g, 1.8 mmol) and zinc (1.17 g, 1.8 mmol). The reaction mixture was stirred at rt for 1.5 h. The reaction mixture was diluted with THE (15 mL) and filtered through a pad of celite. The filtrate was concentrated under reduced pressure and the residue was dissolved in EtOAc (30 mL). The solution was washed with brine and the organic layer was dried over anhydrous $Na_2SO_4$ and concentrated under reduced pressure to give 3-(6-chloro-2-(methylthio)pyrimidin-4-yl)-4-methylaniline (B46, 0.49 g, 102% yield) as an orange residue. MS (ESI) m/z: 266.0 (M+H⁺).

General Method D: Hydrolysis

Intermediate B47: 3-(2-chloropyridin-4-yl)-4-methylbenzoic acid

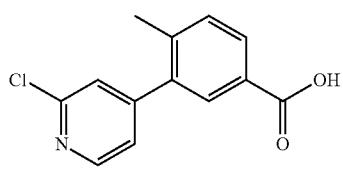 [SMILES: Cc1ccc(C(=O)O)cc1-c1ccnc(Cl)c1]

A mixture of methyl 3-(2-chloropyridin-4-yl)-4-methylbenzoate (B13, 0.32 g, 1.2 mmol) and LiOH (3.0 g, 71 mmol) in a mixture of 1,4-dioxane (3.0 mL) and water (3.0 mL) was heated to 60° C. for 2 h. The reaction mixture was cooled to rt and diluted with water (30 mL). conc-HCl was added until the reaction mixture pH=2. The solution was treated with DCM (50 mL) and then washed with sat'd NaHCO₃ (aq, 50 mL). The organic layer was dried over anhydrous MgSO₄, filtered, and concentrated under reduced pressure to obtain 3-(2-chloropyridin-4-yl)-4-methylbenzoic acid (B47, 0.31 g, 100% yield) as a white solid. MS (ESI) m/z: 248.0 (M+H$^+$).

Using the General Method D above, the following Intermediates of Table C were prepared.

TABLE C

| Ex No. | SM | Product | Yield (%) | $^1$H NMR (400 or 500 MHZ, DMSO-d₆): δ | MS (m/z: M + H$^+$) |
|---|---|---|---|---|---|
| B48 | B16 | (structure) | 84 | 13.0 (brs, 1H), 8.91 (s, 1H), 8.82 (s, 1H), 8.03 (s, 1H), 7.96 (dd, J = 1.8 and 8.0 Hz, 1H), 7.50 (d, J = 8.0 Hz, 1H), 2.43 (s, 3H). | 249.0 |

General Method E: Aromatic Substitution Reaction-NaH as a Base

Intermediate C1: 3-(2-(2-((tert-butyldimethylsilyl)oxy)ethoxy)-6-chloropyridin-4-yl)-4-methylaniline

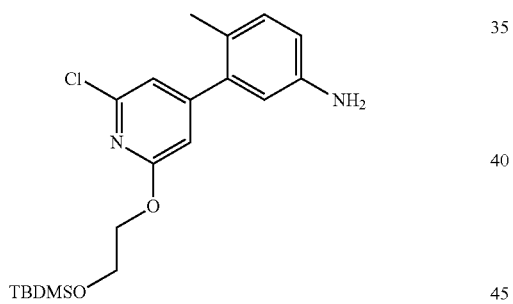

General Method F: Aromatic Substitution Reaction-Cs₂CO₃ as a Base

Intermediate C2: 3-(2-chloro-6-morpholinopyridin-4-yl)-4-methylaniline

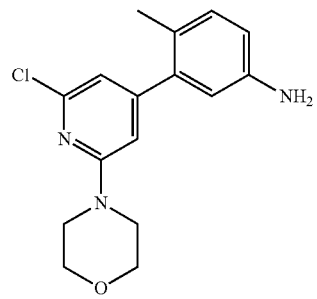 [SMILES: Cc1ccc(N)cc1-c1cc(Cl)nc(N2CCOCC2)c1]

A solution of 2-((tert-butyldimethylsilyl)oxy)ethan-1-ol (0.42 g, 2.4 mmol) in DMF (5.0 mL) was added with NaH (0.15 g, 3.8 mmol, 60% in mineral oil) portion wise under an ice-water bath and the reaction mixture was stirred at rt for 30 min. A solution of 3-(2-chloro-6-fluoropyridin-4-yl)-4-methylaniline (B3, 0.45 g, 1.9 mmol) in DMF (1 mL) was added into the reaction mixture and the reaction mixture was heated at 40° C. for 2 h. The reaction mixture was quenched with sat'd NaHCO₃ (aq, 20 mL) under an ice-water bath. The solution was extracted with DCM (4×25 mL) and the combined organics were dried over anhydrous Na₂SO₄, filtered and concentrated under reduced pressure. The crude was purified by silica gel column chromatography (5 to 40% EtOAc/hexanes) to obtain 3-(2-(2-((tert-butyldimethylsilyl)oxy)ethoxy)-6-chloropyridin-4-yl)-4-methylaniline (0.47 g, 62% yield). MS (ESI) m/z: 393.2 (M+H$^+$).

A solution of 3-(2-chloro-6-fluoropyridin-4-yl)-4-methylaniline (B3, 0.9 g, 3.6 mmol) in DMF (10 mL) was treated with Cs₂CO₃ (1.15 g, 3.6 mmol). Morpholine (0.9 mL, 10.7 mmol) was added and the reaction mixture was stirred at 90° C. overnight. The mixture was cooled to rt and then quenched with water (80 mL). The solution was extracted with EtOAc (2×70 mL) and the combined organics were washed with brine, dried over anhydrous MgSO₄, filtered, concentrated under reduced pressure. The crude was purified silica gel column chromatography (0 to 60%, EtOAc/hexanes) to afford 3-(2-chloro-6-morpholinopyridin-4-yl)-4-methylaniline (0.81 g, 75% yield) as a gummy mass. $^1$H NMR (500 MHz, DMSO-d₆): δ 6.92 (d, J=8.1 Hz, 1H), 6.63 (s, 1H), 6.59 (s, 1H), 6.52 (dd, J=2.4 and 8.1 Hz, 1H), 6.43 (d, J=2.4 Hz, 1H), 4.97 (s, 2H), 3.67 (t, J=4.8 Hz, 4H), 3.46 (t, J=4.8 Hz, 4H), 2.05 (s, 3H); MS (ESI) m/z: 304.2 (M+H$^+$).

General Method G: Suzuki Reaction

Intermediate C₃: ethyl 2'-acetamido-4-chloro-[2,4'-bipyridine]-6-carboxylate

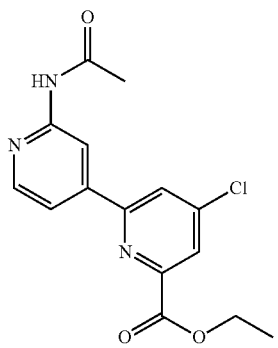 [SMILES: CCOC(=O)c1cc(Cl)cc(-c2ccnc(NC(C)=O)c2)n1]

A solution of ethyl 4,6-dichloropicolinate (3.0 g, 13.6 mmol) and N-(4-(4,4,5,5-tetramethyl-1,3,2-dioxaborolan-2-yl)pyridin-2-yl)acetamide (A5, 8.93 g, 34.1 mmol) in a mixture of 1,4-dioxane (45 mL) and water (5 mL) was treated with NaHCO$_3$ (2.3 g, 27.3 mmol). The reaction mixture was purged with nitrogen for 20 min and then PdCl$_2$(dppf)DCM adduct (0.55 g, 0.68 mmol) was added. The reaction mixture was heated at 90° C. for 6 h and then cooled to rt. The reaction mixture was diluted with EtOAc (30 mL) and the solution was filtered through a pad of celite. The filtrate was washed with water (50 mL) and the organic layer was dried over anhydrous Na$_2$SO$_4$, filtered and concentrated under reduced pressure. The crude was purified by silica gel column chromatography (0 to 60% EtOAc/heptane) to obtain ethyl 2'-acetamido-4-chloro-[2,4'-bipyridine]-6-carboxylate (0.8 g, 18% yield) as light brown solid. $^1$H NMR (400 MHz, DMSO-d$_6$): δ 10.6 (brs, 1H), 8.77 (s, 1H), 8.47 (d, J=6.0 Hz, 1H), 8.39 (s, 1H), 8.14 (brs, 1H), 7.80 (brs, 1H), 4.40 (m, 2H), 2.13 (s, 3H), 1.15 (m, 3H); MS (ESI) m/z: 320.2 (M+H$^+$).

Using the General Methods E, F, and G above, the following Intermediates of Table D were prepared.

TABLE D

| Ex. No. | SM | Product | Method | Yield (%) | $^1$H NMR (400 or 500 MHZ, DMSO-d$_6$): δ | MS (m/z: M + H$^+$) |
|---|---|---|---|---|---|---|
| C4 | B4 | | E | 76 | 6.99 (d, J = 1.1 Hz, 1H), 6.94 (d, J = 12.4 Hz, 1H), 6.66 (d, J = 1.1 Hz, 1H), 6.63 (d, J = 9.2 Hz, 1H), 5.08 (s, 2H), 4.33 (t, J = 4.8 Hz, 2H), 3.90 (t, J = 4.8 Hz, 2H), 2.06 (s, 3H), 0.83 (s, 9H), 0.02 (s, 6H). | 411.2 |
| C5 | B4 | | F | 95 | No Data | 335.2 |
| C6 | A5 | | G | 50 | No Data | 295.0 |

TABLE D-continued
| Ex. No. | SM | Product | Method | Yield (%) | $^1$H NMR (400 or 500 MHZ, DMSO-$d_6$): δ | MS (m/z: M + H$^+$) |
|---|---|---|---|---|---|---|
| C7 | A6 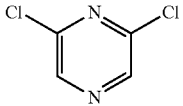 | 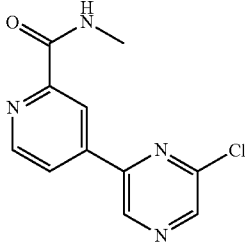 [SMILES: CNC(=O)c1cc(-c2cncc(Cl)n2)ccn1] | G | 65 | 9.48 (s, 1H), 8.93 (s, 1H), 8.88 (d, J = 5.6 Hz, 1H), 8.82 (d, J = 5.1 Hz, 1H), 8.67 (s, 1H), 8.30 (m, 1H), 2.85 (d, J = 4.8 Hz, 3H). | 249.2 |
| C8 | A5 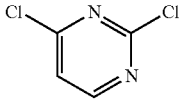 | 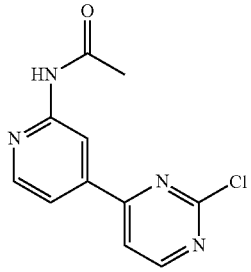 [SMILES: CC(=O)Nc1cc(-c2ccnc(Cl)n2)ccn1] | G | 27 | 10.7 (s, 1H), 8.94 (d, J = 5.2 Hz, 1H), 8.78 (s, 1H), 8.51 (d, J = 5.2 Hz, 1H), 8.16 (d, J = 5.2 Hz, 1H), 7.77 (m, 1H), 2.13 (s, 3H). | 249.2 |
| C9 | A3 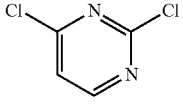 | 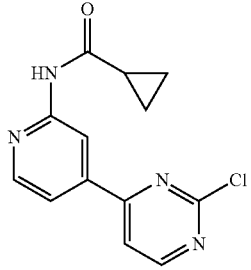 [SMILES: O=C(Nc1cc(-c2ccnc(Cl)n2)ccn1)C1CC1] | G | 85 | 11.1 (s, 1H), 8.93 (d, J = 5.2 Hz, 1H), 8.82 (s, 1H), 8.52 (d, J = 5.2 Hz, 1H), 8.17 (d, J = 5.2 Hz, 1H), 7.78 (dd, J = 1.6 and 5.2 Hz, 1H), 2.02 (m, 1H), 0.83 (m, 4H) | 275.2 |
| C10 | A6 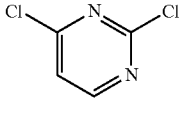 | 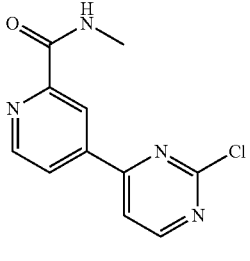 [SMILES: CNC(=O)c1cc(-c2ccnc(Cl)n2)ccn1] | G | 13 | 8.98 (d, J = 5.1 Hz, 1H), 8.92 (d, J = 5.1 Hz, 1H), 8.85 (d, J = 5.1 Hz, 1H), 8.78 (m, 1H), 8.38 (d, J = 5.2 Hz, 1H), 8.31 (dd, J = 5.2, 1.9 Hz, 1H), 2.84 (d, J = 4.7 Hz, 3H). | 249.2 |
| C11 | 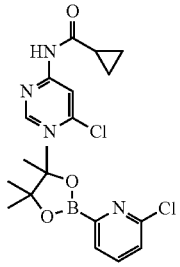 | 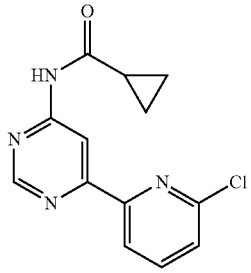 | G | 50 | 11.4 (s, 1H), 8.99 (d, J = 1.2 Hz, 1H), 8.94 (s, 1H), 8.39 (d, J = 7.6 Hz, 1H), 8.07 (t, J = 7.6 Hz, 1H), 7.70 (d, J = 8.0 Hz, 1H), 2.08 (m, 1H), 0.90 (m, 4H). | 275.1 |

TABLE D-continued
| Ex. No. | SM | Product | Method | Yield (%) | ¹H NMR (400 or 500 MHZ, DMSO-d₆): δ | MS (m/z: M + H⁺) |
|---|---|---|---|---|---|---|
| C12 | A3 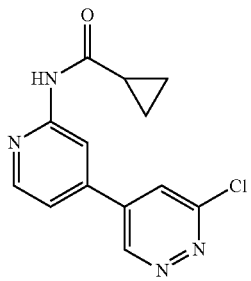 | 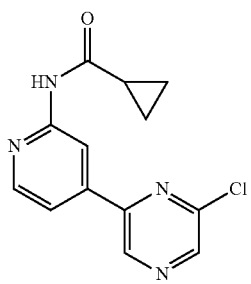 [SMILES: O=C(Nc1cc(-c2cncc(Cl)n2)ccn1)C1CC1] | G | 31 | No Data | 275.2 |
| C13 | A3 | 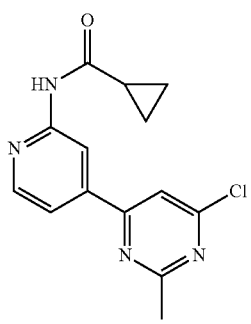 [SMILES: Cc1nc(Cl)cc(-c2ccnc(NC(=O)C3CC3)c2)n1] | G | 33 | 11.0 (s, 1H), 9.29 (s, 1H), 8.88 (s, 1H), 8.78 (s, 1H), 8.48 (d, J = 5.2 Hz, 1H), 7.79 (d, J = 1.2 and 5.2 Hz, 1H), 2.04 (m, 1H), 0.81-0.88 (m, 4H). | 275.2 |
| C14 | A3 | 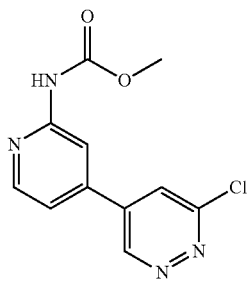 [SMILES: COC(=O)Nc1cc(-c2cnnc(Cl)c2)ccn1] | GG | 35 | 11.00 (s, 1H), 8.84 (s, 1H), 8.50 (d, J = 5.2 Hz, 1H), 8.12 (s, 1H), 7.82 (d, J = 5.2 Hz, 1H), 2.70 (s, 3H), 2.04 (m, 1H), 0.83-0.85 (m, 4H). | 289.2 |
| C15 | A16 | 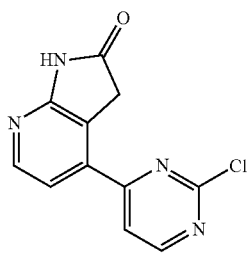 [SMILES: O=C1Cc2c(-c3ccnc(Cl)n3)ccnc2N1] | G | 67 | 10.6 (s, 1H), 9.61 (d, J = 1.9 Hz, 1H), 8.46 (dd, J = 0.8 and 5.2 Hz, 1H), 8.28 (d, J = 2.0 Hz, 1H), 8.22 (dd, 0.8 and 1.7 Hz, 1H), 7.58 (dd, J = 1.7 and 5.2 Hz, 1H), 3.70 (s, 3H). | 265.0 |
| C17 | A17 | | G | 25 | 11.3 (s, 1H), 8.96 (d, J = 5.2 Hz, 1H), 8.26 (d, J = 5.9 Hz, 1H), 8.16 (d, J = 5.3 Hz, 1H), 7.56 (d, J = 5.6 Hz, 1H), 3.93 (s, 2H). | 247.0 |

TABLE D-continued

| Ex. No. | SM | Product | Method | Yield (%) | ¹H NMR (400 or 500 MHZ, DMSO-d₆): δ | MS (m/z: M + H⁺) |
|---|---|---|---|---|---|---|
| C18 | A6 | | G | 34 | 8.85 (brd, J = 4.8 Hz, 1H), 8.79 (dd, J = 0.8 and 5.2 Hz, 1H), 8.58 (d, J = 4.8 Hz, 1H), 8.36 (d, J = 1.2 Hz, 1H), 8.06 (d, J = 2.0 Hz, 1H), 8.04 (m, 1H), 7.91 (dd, J = 1.6 and 5.2 Hz, 1H), 2.86 (d, J = 4.8 Hz, 3H). | 248.1 |
| C19 | | | G | 71 | No Data | 249.0 |
| C20 | | | G | 59 | No Data | 234.0 |
| C21 | | | G | 84 | No Data | 275.0 |
| C22 | A16 | | G | 45 | 10.4 (brs, 1H), 8.94 (d, J = 5.2 Hz, 1H), 8.58 (s, 1H), 8.47 (d, J = 4.4 Hz, 1H), 8.18 (d, J = 5.2 Hz, 1H), 7.75 (dd, J = 5.2, 1.6 Hz, 1H), 3.71 (s, 3H). | 265.0 |

TABLE D-continued

| Ex. No. | SM | Product | Method | Yield (%) | ¹H NMR (400 or 500 MHZ, DMSO-$d_6$): δ | MS (m/z: M + H⁺) |
|---|---|---|---|---|---|---|
| C23 | | | G | 27 | 11.0 (brs, 1H), 9.13 (s, 1H), 8.93 (s, 1H), 8.79 (d, J = 1.6 Hz, 1H), 8.48 (s, 1H), 8.36 (s, 1H), 3.75 (s, 3H). | 264.8 |
| C24 | A16 | | G | 65 | 10.4 (s, 1H), 8.69 (s, 1H), 8.45 (d, J = 5.2 Hz, 1H), 8.14 (s, 1H), 7.78 (d, J = 5.2 Hz, 1H), 3.72 (s, 3H), 2.71 (s, 3H), | 278.8 |
| C25 | A6 | | G | 35 | 8.89 (brd, J = 4.4 Hz, 1H), 8.83 (br m, 1H), 8.75 (d, J = 1.2 Hz, 1H), 8.37 (s, 1H), 8.34 (dd, J = 2.0 and 5.2 Hz, 1H), 2.87 (d, J = 10.8 Hz, 3H), 2.49 (s, 3H). | 263.0 |

Preparation of Example C16: N-(4-chloro-6-(2-hydroxypropan-2-yl)-[2,4'-bipyridin]-2'-yl)acetamide

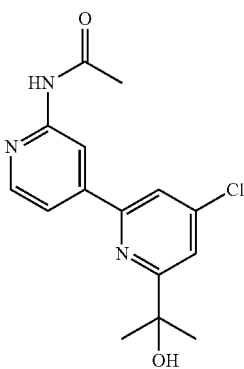 [SMILES: CC(=O)Nc1cc(-c2cc(Cl)cc(C(C)(C)O)n2)ccn1]

A solution of ethyl 2'-acetamido-4-chloro-[2,4'-bipyridine]-6-carboxylate (C3, 1.0 g, 3.1 mmol) in THF (50 mL) was stirred at −78° C. Methyl lithium (1.6 M in THF, 9.8 mL, 15.7 mmol) was added dropwise at −78° C. and then the reaction mixture was stirred −78° C. for 3 h. The reaction mixture was allowed to increase gradually to rt and then stirred at rt for 16 h. The reaction mixture was quenched with chilled water (20 mL) and the solution was extracted with EtOAc (3×60 mL). The combined organic extracts were dried over anhydrous $Na_2SO_4$, filtered and concentrated under reduced pressure. The crude was purified by silica gel column chromatography (0 to 80% EtOAc/heptane) to obtain N-(4-chloro-6-(2-hydroxypropan-2-yl)-[2,4'-bipyridin]-2'-yl)acetamide (C16, 0.3 g, 31% yield) as white solid. ¹H NMR (400 MHz, DMSO-$d_6$): δ 10.8 (brs, 1H), 8.85 (s, 1H), 8.47 (brs, 1H), 7.96 (s, 1H), 7.77 (brs, 2H), 5.4 (s, 1H), 2.13 (s, 3H), 1.50 (s, 6H); MS (ESI) m/z: 306.3 (M+H⁺).

General Method H: Suzuki Reaction

Intermediate D1: N-(4-(5-amino-2-methylphenyl)-6-(2-hydroxypropan-2-yl)-[2,4'-bipyridin]-2'-yl)acetamide

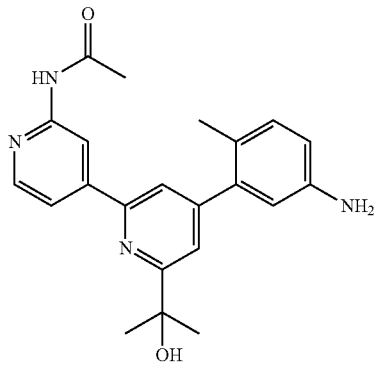 [SMILES: CC(=O)Nc1cc(-c2cc(-c3cc(N)ccc3C)cc(C(C)(C)O)n2)ccn1]

A solution of N-(4-chloro-6-(2-hydroxypropan-2-yl)-[2,4'-bipyridin]-2'-yl)acetamide (C16, 0.28 g, 0.91 mmol) and 4-methyl-3-(4,4,5,5-tetramethyl-1,3,2-dioxaborolan-2-yl)aniline (0.64 g, 2.75 mmol) in a mixture of 1,4-dioxane (6 mL) and water (1 mL) was treated with $K_2CO_3$ (0.38 g, 2.75 mmol). The reaction mixture was purged with nitrogen for 10 min. $PdCl_2$(dppf)DCM adduct (0.037 g, 0.045 mmol) was added and then the mixture was heated at 90° C. for 5 h. The reaction was cooled to rt and then diluted with EtOAc (30 mL). The solution was filtered through a pad of celite and washed with EtOAc (50 mL). The filtrate was washed with water (10 mL) and the organic layer was dried over anhydrous $Na_2SO_4$, filtered and concentrated under reduced pressure. The crude was purified by silica gel column chromatography (0 to 80% EtOAc/heptane) to obtain N-(4-(5-amino-2-methylphenyl)-6-(2-hydroxypropan-2-yl)-[2,4'-bipyridin]-2'-yl)acetamide (0.22 g, 64% yield) as light brown solid. $^1$H NMR (400 MHz, DMSO-$d_6$): δ 10.5 (brs, 1H), 8.82 (s, 1H), 8.39 (brs, 1H), 7.78 (m, 1H), 7.70 (s, 1H), 7.65 (s, 1H), 6.99 (d, J=8.0 Hz, 1H), 6.56 (m, 2H), 5.3 (s, 1H), 5.0 (brs, 2H), 2.11 (s, 6H), 1.55 (s, 6H); MS (ESI) m/z: 377.2 (M+H$^+$).

Using the General Method H above, the following Intermediates of Table E were prepared.

TABLE E

| Ex. No. | SM | Product | Yield (%) | $^1$H NMR (400 or 500 MHZ, DMSO-d6): δ | MS (m/z: M + H+) |
|---|---|---|---|---|---|
| D2 | A5 B8 | | 46 | 10.4 (s, 1H), 8.42 (s, 1H), 8.28 (brs, 1H), 7.91 (s, 1H), 7.65 (s, 1H), 7.49 (brs, 2H), 6.93 (d, J = 8.0 Hz, 1H), 6.49 (s, 1H), 4.90 (brs, 2H), 3.57 (s, 3H), 2.13 (s, 3H), 2.09 (s, 3H). | 349.3 |
| D3 | A3 B9 | | 44 | 10.9 (s, 1H), 8.75 (s, 1H), 8.38 (d, J = 5.2 Hz, 1H), 7.72 (m, 1H), 7.55 (s, 1H), 7.26 (s, 1H), 6.96 (m, 1H), 6.56 (m, 1H), 6.44 (s, 1H), 4.90 (brs, 2H), 2.20 (m, 1H), 2.09 (s, 3H), 1.98 (m, 1H), 1.02 (m, 4H), 0.85 (m, 4H). | 685.4 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D4 | A2 B9 | (structure) | 40 | 10.9 (brs, 1H), 8.30 (s, 1H), 7.73 (s, 1H), 7.63 (m, 2H), 7.73 (s, 1H), 7.98 (d, J = 8.0 Hz, 1H), 6.56 (dd, J = 2.4 and 8.0 Hz, 1H), 6.52 (s, 1H), 5.00 (brs, 2H), 2.22 (m, 1H), 2.10 (s, 3H), 1.98 (s, 3H), 1.02 (m, 2H), 1.09 (m, 2H). | 395.3 |
| D5 | A5 B17 | (structure) | 60 | No Data | 364.2 |
| D6 | D5 | (structure) Method C | 57 | No Data | 334.2 |
| D7 | B19 | (structure) | 59 | No Data | 379.0 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D8 | A5 B18 | | crude | No Data | 368.2 |
| D9 | D8 Method C | | 44 | No Data | 338.2 |
| D10 | A5 B2 | | 62 | 10.6 (brs, 1H), 8.82 (s, 1H), 8.75 (d, J = 5.2 Hz, 1H), 8.42 (d, J = 7.6 Hz, 1H), 7.87 (s, 1H), 7.78 (dd, J = 1.2 and 5.2 Hz, 1H), 7.42 (dd, J = 1.2 and 4.8 Hz, 1H), 6.99 (d, J = 8.0 Hz, 1H), 6.59 (dd, J = 2.4 and 8.4 Hz, 1H), 6.54 (d, J = 2.0 Hz, 1H), 5.00 (s, 2H), 2.12 (s, 3H), 2.08 (s, 3H). | 319.1 |
| D11 | A5 B20 | | 42 | 10.6 (s, 1H), 9.43 (s, 1H), 8.95 (s, 1H), 8.81 (s, 1H), 8.47 (d, J = 4.8 Hz, 1H), 7.84 (m, 1H), 7.03 (d, J = 8.0 Hz, 1H), 6.77 (d, J = 2.4 Hz, 1H), 6.63 (dd, J = 2.0 and 8.0 Hz, 1H), 5.0 (s, 2H), 2.29 (s, 3H), 2.12 (s, 3H). | 320.4 |
| D12 | A3 B20 | | 59 | 10.9 (s, 1H), 9.21 (s, 1H), 8.86 (s, 1H), 8.80 (s, 1H), 8.48 (d, J = 5.2 Hz, 1H), 7.83 (m, 1H), 7.02 (d, J = 8.4 Hz, 1H), 6.75 (d, J = 2.4 Hz, 1H), 6.64 (dd, J = 2.4 and 8.0 Hz, 1H), 5.00 (s, 2H), 2.23 (s, 3H), 2.02 (m, 1H), 0.85 (m, 4H). | 346.0 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D13 | A3 B2 | | 61 | 10.8 (brs, 1H), 8.83 (s, 1H), 8.75 (d, J = 5.2 Hz, 1H), 8.42 (d, J = 9.2 Hz, 1H), 7.86 (s, 1H), 7.78 (dd, J = 1.2 and 5.6 Hz, 1H), 7.42 (dd, J = 1.2 and 4.8 Hz, 1H), 6.99 (d, J = 8.0 Hz, 1H), 6.58 (dd, J = 2.4 and 8.0 Hz, 1H), 6.53 (d, J = 2.4 Hz, 1H), 5.0 (s, 2H), 2.10 (s, 3H), 2.02 (m, 1H), 0.83 (m, 4H). | 345.3 |
| D14 | A5 B21 | | 70 | 10.4 (brs, 1H), 8.41 (s, 1H), 8.28 (m, 1H), 7.85 (d, J = 2.8 Hz, 1H), 7.64 (d, J = 2.8 Hz, 1H), 7.44 (brs, 1H), 6.94 (d, J = 12.4 Hz, 1H), 6.67 (d, J = 9.6 Hz, 1H), 5.0 (s, 2H), 3.54 (s, 3H), 2.14 (s, 3H), 2.08 (s, 3H). | 367.0 |
| D15 | A5 B11 | | 84 | 10.5 (s, 1H), 8.81 (s, 1H), 8.76 (d, J = 5.2 Hz, 1H), 8.40 (d, J = 5.6 Hz, 1H), 7.87 (s, 1H), 7.78 (d, J = 5.6 Hz, 1H), 7.41 (d, J = 4.8 Hz, 1H), 7.00 (d, J = 12.4 Hz, 1H), 6.74 (d, J = 8.8 Hz, 1H), 5.00 (s, 2H), 2.13 (s, 3H), 2.12 (s, 3H). | 337.3 |
| D16 | A7 B11 | | 37 | 10.8 (brs, 1H), 9.34 (d, J = 10.0 Hz, 1H), 8.71 (brs, 1H), 8.37 (brs, 1H), 7.91 (m, 1H), 7.83 (s, 1H), 7.72 (s, 1H), 7.43 (d, J = 4.8 Hz, 1H), 6.99 (d, J = 12.4 Hz, 1H), 7.75 (d, J = 9.2 Hz, 1H), 5.00 (brs, 2H), 2.13 (s, 3H). | 323.3 |
| D17 | A6 B23 | | 87 | 8.87 (d, J = 4.0 Hz, 1H), 8.76 (d, J = 4.0 Hz, 1H), 8.09 (brs, 1H), 7.80 (dd, J = 1.6 and 5.2 Hz, 1H), 6.93 (d, J = 12.4 Hz, 1H), 6.70 (d, J = 9.2 Hz, 1H), 6.36 (d, J = 1.6 Hz, 1H), 6.18 (d, J = 2.0 Hz, 1H), 5.0 (brs, 2H), 3.26 (s, 3H), 2.84 (d, J = 5.2 Hz, 3H), 2.15 (s, 3H). | 367.0 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D18 | A6 B2 | | 64 | 8.83 (m, 1H), 8.78 (d, J = 5.0 Hz, 1H), 8.74 (m, 2 H), 8.30 (dd, J = 1.8 and 5.1 Hz, 1H), 8.07 (s, 1H), 7.45 (dd, J = 1.5 and 5.0 Hz, 1H), 6.99 (d, J = 8.1 Hz, 1H), 6.58 (dd, J = 2.4 and 8.1 Hz, 1H), 6.56 (d, J = 2.4 Hz, 1H), 5.03 (s, 2H), 2.85 (d, J = 4.8 Hz, 3H), 2.11 (s, 3H). | 319.2 |
| D19 | B20 | | 47 | 9.93 (s, 1H), 9.21 (s, 1H), 8.80 (s, 1H), 8.55 (s, 1H), 8.41 (d, J = 5.6 Hz, 1H), 7.77 (d, J = 5.6 Hz, 1H), 7.01 (d, J = 8.0 Hz, 1H), 6.76 (d, J = 2.4 Hz, 1H), 6.64 (dd, J = 2.4 and 8.4 Hz, 1H), 5.05 (brs, 2H), 2.24 (s 3H), 1.48 (s, 9H). | 378.0 |
| D20 | A6 B24 | | 84 | No Data | 350.2 |
| D21 | D20 | Method C | 82 | No Data | 320.2 |
| D22 | A8 B20 | | 30 | 9.12 (s, 1H), 8.75 (s, 1H), 8.12 (d, J = 6.0 Hz, 1H), 7.29 (s, 1H), 7.20 (brs, 1H), 7.00 (dd, J = 4.0 and 8.4 Hz, 1H), 6.81 (s, 1H), 6.75 (s, 1H), 6.63 (d, J = 7.6 Hz, 1H), 5.03 (brs, 2H), 3.47 (s, 4H), 3.27 (s, 3H), 2.23 (s, 3H). | 336.1 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D23 | A5 B25 | (structure: acetamido-pyridine-pyrimidine-methyl-nitrophenyl) | crude | No Data | 350.2 |
| D24 | D23 | (structure: acetamido-pyridine-pyrimidine-methyl-aminophenyl) Method C | 75 | 10.6 (s, 1H), 9.10 (s, 1H), 8.99 (d, J = 5.2 Hz, 1H), 8.47 (d, J = 5.1 Hz, 1H), 7.99 (d, J = 5.2 Hz, 1H), 7.63 (d, J = 5.2 Hz, 1H), 7.02 (d, J = 8.2 Hz, 1H), 6.80 (d, J = 2.3 Hz, 1H), 6.64 (m, 1H), 5.08 (s, 2H), 2.30 (s, 3H), 2.12 (s, 3H). | 320.2 |
| D25 | A5 B23 | (structure: acetamido-pyridine-pyridinone-fluoro-methyl-aminophenyl) | 44 | 10.7 (s, 1H), 8.43 (d, J = 5.2 Hz, 1H), 8.15 (s, 1H), 7.29 (d, J = 4.4 Hz, 1H), 6.92 (d, J = 12.4 Hz, 1H), 6.69 (d, J = 8.8 Hz, 1H), 6.34 (s, 1H), 6.11 (s, 1H), 5.03 (d, J = 8.0 Hz, 2H), 3.27 (s, 3H), 2.14 (s, 3H), 2.11 (s, 3H). | 367.0 |
| D26 | A9 B2 | (structure: cyclopropylamide-pyridine-pyridine-methyl-aminophenyl) | 78 | 8.79 (m, 2H), 8.74 (d, J = 0.8 Hz, 1H), 8.19 (d, J = 5.2 Hz, 1H), 8.31 (dd, J = 1.6 and 2.0 Hz, 1H), 8.08 (s, 1H), 7.45 (dd, J = 1.2 and 4.0 Hz, 1H), 7.00 (d, J = 8.4 Hz, 1H), 6.57 (m, 2H), 5.02 (brs, 2H), 2.91-2.98 (m, 1H), 2.12 (s, 3H), 0.74 (m, 4H). | 345.2 |
| D27 | A6 B14 | (structure: methylamide-pyridine-pyridine-methylpyridine-amine) | 61 | 8.85 (d, J = 4.8 Hz, 1H), 8.82 (d, J = 5.2 Hz, 1H), 8.77 (d, J = 1.2 Hz, 1H), 8.75 (d, J = 5.2 Hz, 1H), 8.32 (dd, J = 3.2 and 6.8 Hz, 1H), 8.18 (s, 1H), 7.94 (d, J = 2.4 Hz, 1H), 7.54 (m, 2H), 7.48 (m, 1H), 6.91 (d, J = 2.4 Hz, 1H), 2.85 (d, J = 4.8 Hz 3H), 2.30 (s, 3H). | 320.0 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D28 | A6 B9 | (structure) | 75 | 8.83 (brm, 1H), 8.71 (d, J = 5.2 Hz, 1H), 8.65 (s, 1H), 8.25 (m, 1H), 7.91 (s, 1H), 7.34 (s, 1H), 6.98 (d, J = 8.0 Hz, 1H), 6.55-6.61 (m, 2H), 5.01 (brs, 2H), 2.85 (d, J = 4.8 Hz, 3H), 2.25 (m, 1H), 2.12 (s, 3H), 1.02-1.09 (m, 4H). | 359.3 |
| D29 | A6 B18 | (structure) | 91 | No Data | 368.2 |
| D30 | D29 | (structure) Method C | 83 | 9.03 (d, J = 5.2 Hz, 1H), 8.95 (s, 1H), 8.87 (d, J = 5.5 Hz, 1H), 8.82 (d, J = 5.1 Hz, 1H), 8.47 (dd, J = 1.7 and 5.1 Hz, 1H), 7.69 (d, J = 5.2 Hz, 1H), 7.05 (m, 2H), 5.18 (s, 2H), 2.85 (d, J = 4.8 Hz, 3H), 2.32 (s, 3H). | No Data |
| D31 | A6 B26 | (structure) | 77 | No Data | 368.2 |
| D32 | D31 | (structure) Method C | 86 | No Data | 338.2 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D33 | A3 B30 | | 95 | 10.9 (s, 1H), 8.83 (s, 1H), 8.43 (d, J = 4.8 Hz, 1H), 8.04 (t, J = 7.6 Hz, 1H), 7.98 (d, J = 7.6 Hz, 1H), 7.92 (d, J = 7.6 Hz, 1H), 7.77 (t, J = 4.4 Hz, 1H), 7.59 (d, J = 7.6 Hz, 1H), 7.04 (d, J = 2.4 Hz, 1H), 5.22 (brs, 2H), 2.38 (s, 3H), 2.03 (m, 1H), 0.83 (m, 4H). | 346.1 |
| D34 | B30 | | 55 | 10.5 (s, 1H), 8.86 (s, 1H), 8.41 (d, J = 5.2 Hz, 1H), 8.04 (t, J = 7.6 Hz, 1H), 7.99 (d, J = 8.0 Hz, 1H), 7.93 (d, J = 2.0 Hz, 1H), 7.75 (d, J = 4.4 Hz, 1H), 7.60 (d, J = 7.2 Hz, 1H), 7.05 (d, J = 2.4 Hz, 1H), 5.24 (brs, 2H), 2.43 (q, J = 7.6 Hz, 2H), 2.39 (s, 3H), 1.10 (t, J = 7.6 Hz, 3H). | 334.2 |
| D35 | A6 B25 | | crude | No Data | 350.2 |
| D36 | D35 | Method C | 56 | No Data | 320.2 |
| D37 | A6 B11 | | 41 | No Data | 337.2 |

TABLE E-continued

| Ex. No. | SM | Product | Yield (%) | $^1$H NMR (400 or 500 MHZ, DMSO-d6): δ | MS (m/z: M + H+) |
|---|---|---|---|---|---|
| D38 | A6 B27 | (structure) | 71 | No Data | 350.2 |
| D39 | D38 | (structure) Method C | 51 | No Data | 320.2 |
| D40 | A6 B18 | (structure) | crude | No Data | 394.2 |
| D41 | D40 | (structure) Method C | 49 | No Data | 364.2 |
| D42 | A3 B25 | (structure) | crude | No Data | 376.2 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D43 | D42 | (structure) Method C | 62 | No Data | 346.2 |
| D44 | B12 | (structure) | 72 | 11.3 (s, 1H), 8.95 (s, 1H), 8.60 (s, 1H), 8.01 (d, J = 7.6 Hz, 1H), 7.91 (br s, 1H), 7.58 (t, J = 7.6 Hz, 1H), 7.47 (brd, J = 8.0 Hz, 1H), 6.95 (d, J = 8.0 Hz, 1H), 6.51 (brm, 2H), 4.93 (brs, 2H), 2.06 (s, 3H), 2.05 (m, 1H), 0.88 (m, 4H). | 345.1 |
| D45 | C11 | (structure) | 51 | 11.3 (s, 1H), 9.05 (s, 1H), 8.98 (s, 1H), 8.35 (d, J = 8.0 Hz, 1H), 8.04 (t, J = 8.0 Hz, 1H), 7.57 (brd, J = 9.2 Hz, 1H), 6.98 (d, J = 8.0 Hz, 1H), 6.66 (brs, 1H), 6.58 (brd, J = 8.0 Hz, 1H), 4.99 (brs, 2H), 2.25 (s, 3H), 2.06 (m, 1H), 0.88 (m, 4H). | 346.1 |
| D46 | C9 | (structure) | 25 | 11.0 (s, 1H), 9.03 (d, J = 5.2 Hz, 1H), 8.92 (s, 1H), 8.51 (d, J = 5.2 Hz, 1H), 7.97 (d, J = 5.6 Hz, 1H), 7.85 (d, J = 5.2 Hz, 1H), 7.15 (d, J = 2.0 Hz, 1H), 6.99 (d, J = 8.4 Hz, 1H), 6.63 (dd, J = 2.8 and 8.4 Hz, 1H), 5.02 (brs, 2H), 2.39 (s, 3H), 2.04 (m, 1H), 0.84 (m, 4H). | 346.1 |
| D47 | C10 | (structure) | 85 | 9.18 (d, J = 5.3 Hz, 1H), 8.92 (brm, 1H), 8.88 (d, J = 5.2 Hz, 1H), 8.79 (s, 1H), 8.74 (d, J = 8.0 Hz, 1H), 8.40 (dd, J = 1.8 and 5.1 Hz, 1H), 8.34 (d, J = 5.4 Hz, 1H), 7.70 (d, J = 12.4 Hz, 1H), 2.86 (d, J = 4.8 Hz, 3H), 2.76 (s, 3H). | 368.2 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D48 | D47 | (structure) | crude | No Data | 338.2 |
| D49 | C9 | (structure) | 58 | 11.0 (s, 1H), 9.14 (d, J = 5.3 Hz, 1H), 8.96 (s, 1H), 8.73 (d, J = 8.1 Hz, 1H), 8.54 (dd, J = 0.8 and 5.2 Hz, 1H), 8.13 (d, J = 5.3 Hz, 1H), 7.88 (dd, J = 1.6 and 5.2 Hz, 1H), 7.70 (d, J = 12.5 Hz, 1H), 2.76 (s, 3H), 2.05 (m, 1H), 0.81-0.87 (m, 4H). | 394.2 |
| D50 | D49 | (structure) | crude | No Data | 364.2 |
| D51 | A3 B14 | (structure) | 63 | No Data | 346.2 |
| D52 | A6 B43 | (structure) | 29 | 8.81 (q, J = 4.8 Hz, 1H), 8.67 (d, J = 5.2 Hz, 1H), 8.31 (s, 1H), 8.18 (d, J = 2.0 Hz, 1H), 7.87 (m, 2H), 6.95 (d, J = 8.8 Hz, 1H), 6.52 (m, 2H), 4.93 (brs, 2H), 4.44 (q, J = 6.8 Hz, 2H), 2.83 (d, J = 4.8 Hz, 3H), 2.10 (s, 3H), 1.34 (t, J = 7.2 Hz, 3H). | 363.0 |

TABLE E-continued

| Ex. No. | SM | Product | Yield (%) | $^1$H NMR (400 or 500 MHZ, DMSO-d6): δ | MS (m/z: M + H+) |
|---|---|---|---|---|---|
| D53 | A6 B15 | | 56 | 8.85 (brq, J = 5.6 Hz, 1H), 8.74 (d, J = 5.2 Hz, 1H), 8.71 (d, J = 1.2 Hz, 1H), 8.27 (dd, J = 1.6 and 5.2 Hz, 1H), 8.02 (s, 1H), 7.49 (s, 1H), 7.04 (td, J = 2.0 and 8.8 Hz, 1H), 6.81 (dd, J = 2.8 and 6.8 Hz, 1H), 6.66 (dt, J = 3.2 and 8.4 Hz, 1H), 5.13 (brs, 2H), 2.85 (d, J = 4.8 Hz, 3H), 2.64 (s, 3H). | 337.0 |
| D54 | C13 | | 54 | 10.9 (s, 1H), 9.21 (s, 1H), 8.83 (s, 1H), 8.80 (s, 1H), 8.48 (d, J = 5.2 Hz, 1H), 7.84 (dd, J = 1.2 and 4.8 Hz, 1H), 7.03 (d, J = 12.4 Hz, 1H), 6.97 (d, J = 9.2 Hz, 1H), 5.12 (brs, 2H), 2.22 (s, 3H), 2.14 (m, 1H), 0.79-0.89 (m, 4H). | 364.1 |
| D55 | A3 B44 | | 78 | No Data | 377.2 |
| D56 | D55 | | 59 | No Data | 347.2 |
| D57 | C9 | | 44 | 11.1 (s, 1H), 9.40 (d, J = 2.7 Hz, 1H), 9.20 (d, J = 5.3 Hz, 1H), 9.02 (d, J = 2.6 Hz, 1H), 8.98 (d, J = 1.6 Hz, 1H), 8.55 (d, J = 5.1 Hz, 1H), 8.19 (d, J = 5.2 Hz, 1H), 7.91 (dd, J = 1.6 and 5.2 Hz, 1H), 2.98 (s, 3H), 2.05 (m, 1H), 0.82-0.87 (m, 4H). | 377.2 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D58 | D57 | | 90 | No Data | 347.2 |
| D59 | B45 | | 55 | 11.3 (s, 1H), 9.30 (d, J = 2.4 Hz, 1H), 8.96 (s, 1H), 8.61 (s, 1H), 8.42 (d, J = 2.4 Hz, 1H), 8.15 (m, 1H), 8.11 (s, 1H), 7.70 (d, J = 2.4 Hz, 1H), 7.69 (s, 1H), 2.58 (s, 3H), 2.07 (m, 1H), 0.86-0.92 (m, 4H). | 376.2 |
| D60 | D59 | | 67 | 11.3 (s, 1H), 8.95 (s, 1H), 8.60 (s, 1H), 8.04 (d, J = 8.0 Hz, 1H), 7.95 (s, 1H), 7.88 (d, J = 2.4 Hz, 1H), 7.62 (t, J = 7.6 Hz, 1H), 7.53 (d, J = 8.0 Hz, 1H), 6.84 (d, J = 2.4 Hz, 1H), 5.20 (brs, 2H), 2.25 (s, 3H), 2.07 (m, 1H), 0.86-0.92 (m, 4H). | 346.0 |
| D61 | C14 | | 38 | 11.0 (s, 1H), 9.38 (d, J = 2.4 Hz, 1H), 8.91 (s, 1H), 8.77 (d, J = 2.4 Hz, 1H), 8.52 (d, J = 5.2 Hz, 1H), 8.27 (s, 1H), 7.90 (d, J = 5.2 Hz, 1H), 2.80 (s, 3H), 2.75 (s, 3H), 2.06 (m, 1H), 0.83-0.86 (m, 4H). | 391.0 |
| D62 | D61 | | 73 | 11.0 (s, 1H), 8.89 (s, 1H), 8.48 (s, 1H), 7.98 (d, J = 13.2 Hz, 2H), 7.86 (s, 1H), 7.13 (s, 1H), 5.30 (s, 2H), 2.75 (s, 3H), 2.49 (s, 3H), 2.04 (m, 1H), 0.84-0.87 (m, 4H). | 361.3 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D63 | C12 | | 24 | 11.03 (s, 1H), 9.54 (s, 1H), 8.43-8.61 (m, 2H), 8.00 (s, 1H), 7.65 (d, J = 5.5 Hz, 1H), 7.02 (d, J = 12.3 Hz, 1H), 6.95 (d, J = 9.3 Hz, 1H), 5.12 (s, 2H), 2.17 (s, 3H), 2.07 (m, 1H), 0.86-0.80 (m, 4H). | 364.2 |
| D64 | C15 | | 71 | No Data | 354.2 |
| D65 | A3 B11 | | 67 | 10.88 (s, 1H), 8.83 (s, 1H), 8.74 (d, J = 5.2 Hz, 1H), 8.41 (d, J = 5.2 Hz, 1H), 7.86 (s, 1H), 7.78 (dd, J = 4.0, 1.2 Hz, 1H), 7.42 (d, J = 4.8 Hz, 1H), 7.00 (d, J = 12.0 Hz, 1H), 6.73 (d, J = 9.2 Hz, 1H), 5.09 (s, 2H), 2.12 (s, 3H), 2.02 (m, 1H), 0.81-0.84 (m, 4H). | 363.3 |
| D66 | A16 B11 | | 54 | 10.28 (s, 1H), 8.75 (d, J = 4.8 Hz, 1H), 8.59 (s, 1H), 8.36 (d. J = 4.8 Hz, 1H), 7.88 (s, 1H), 7.74 (d, J = 4.8 Hz, 1H), 7.42 (d, J = 4.8Hz, 1H), 7.00 (d, J = 12.4 Hz, 1H), 6.74 (d, J = 9.2 Hz, 1H), 5.09 (s, 2H), 3.69 (s, 3H), 2.13 (s, 3H). | 353.0 |
| D67 | A16 B28 | | 60 | 10.35 (s, 1H), 9.00 (d, J = 5.2 Hz, 1H), 8.88 (s, 1H), 8.44 (d, J = 4.8 Hz, 1H), 7.96 (d, J = 4.8 Hz, 1H), 7.65 (d, J = 4.8 Hz, 1H), 7.06 (d, J = 4.4 Hz, 1H), 7.02 (s, 1H), 5.17 (s, 2H), 3.70 (s, 3H), 2.33 (s, 3H). | 354.0 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D68 | A16 B51 | (structure) | 35 | No Data | 336.2 |
| D69 | C15 | (structure) | 22 | 10.44 (s, 1H), 9.59 (s, 1H), 8.45 (d, J = 5.1 Hz, 1H), 8.27 (s, 1H), 8.15 (d, J = 15.9 Hz, 1H), 7.97 (s, 1H), 7.62 (d, J = 5.3 Hz, 1H), 7.10 (s, 1H), 5.29 (s, 2H), 3.69 (s, 3H), 2.33 (s, 3H). | 337.0 |
| D70 | A6 B52 | (structure) | 46 | 9.75 (d, J = 2.0 Hz, 1H), 8.89 (d, J = 4.4 Hz, 1H), 8.83 (d, J = 4.8 Hz, 1H), 8.52 (s, 1H), 8.36 (s, 1H), 8.34 (d, J = 2.0 Hz, 1H), 7.98 (d, J = 2.4 Hz, 1H), 7.14 (d, J = 2.4 Hz, 1H), 5.30 (s, 2H), 2.86 (d, J = 6.0 Hz, 3H), 2.32 (s, 3H). | 321.1 |
| D71 | A16 B14 | (structure) | 71 | 10.28 (s, 1H), 8.77 (d, J = 5.0 Hz, 1H), 8.60 (t, J = 1.1 Hz, 1H), 8.36 (d, J = 5.3 Hz, 1H), 7.96 (d, J = 1.2 Hz, 1H), 7.92 (d, J = 2.6 Hz, 1H), 7.75 (dd, J = 5.2, 1.6 Hz, 1H), 7.48 (dd, J = 5.0, 1.5 Hz, 1H), 6.88 (d, J = 2.7 Hz, 1H), 5.26 (s, 2H), 3.69 (s, 3H), 2.28 (s, 3H). | 336.0 |
| D72 | A6 B50 | (structure) | crude | No Data | No Data |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D73 | D72 | | 20 | 9.70 (d, J = 2.0 Hz, 1H), 8.87 (q, J= 4.8 Hz, 1H), 8.82 (dd, J = 5.2, 0.4 Hz, 1H), 8.50 (d, J = 0.8 Hz, 1H), 8.21 (d, J = 2.4 Hz, 1H), 8.19 (dd, J = 4.8, 1.6 Hz, 1H), 7.03 (d, J = 8.0 Hz, 1H), 6.77 (d, J = 2.4 Hz, 1H), 6.64 (dd, J = 8.0, 2.4 Hz, 1H), 5.05 (br s, 2H), 2.86 (br d, J = 4.8 Hz, 3H), 2.18 (s, 3H). | 320.3 |
| D74 | C12 | | 54 | 11.01 (s, 1H), 9.54 (d, J = 2.0 Hz, 1H), 8.53 (d, J = 1.2 Hz, 1H), 8.50 (d, J = 5.2 Hz, 1H), 7.97 (d, J = 2.0 Hz, 1H), 7.66 (dd, J = 5.2, 2.0 Hz, 1H), 7.02 (d, J = 8.4 Hz, 1H), 6.73 (d, J = 2.4 Hz, 1H), 6.64 (dd, J = 8.0, 2.4 Hz, 1H), 5.04 (s, 2H), 2.15 (s, 3H), 2.05 (m, 1H), 0.81-0.85 (m, 4H). | 346.1 |
| D75 | A3 B52 | | 56 | 11.03 (s, 1H), 9.58 (s, 1H), 8.54 (s, 1H), 8.51 (d, J = 3.6 Hz, 1H), 8.11 (s, 1H), 7.98 (s, 1H), 7.66 (s, 1H), 7.10 (s, 1H), 5.30 (s, 2H), 2.33 (s, 3H), 2.04 (m, 1H), 0.84-0.87 (m, 4H). | 347.3 |
| D76 | A17 B2 | | 8 | No Data | 317.2 |
| D77 | A21 B50 | reduction with Fe | 54 | 9.71 (s, 1H), 8.82 (d, J = 4.8 Hz, 1H), 8.80 (s, 1H), 8.51 (s, 1H), 8.22 (s, 2H), 7.03 (d, J = 8.4 Hz, 1H), 6.77 (s, 1H), 6.65 (d, J = 7.6 Hz, 1H), 5.04 (brs, 2H) 3.50 (brm, 4H), 3.28 (s, 3H), 2.10 (s, 3H). | 364.2 |

TABLE E-continued
| Ex. No. | SM | Product | Yield (%) | $^1$H NMR (400 or 500 MHZ, DMSO-d6): δ | MS (m/z: M + H+) |
|---|---|---|---|---|---|
| D78 | A19 B50 | 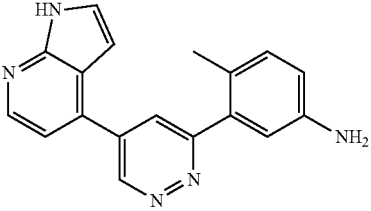 reduction with Fe | 65 | 9.61 (s, 1H), 8.38 (d, J = 5.2 Hz, 1H), 8.03 (s, 1H), 7.65 (s, 1H), 7.47 (d, J = 5.2 Hz, 1H), 7.03 (d, J = 8.4 Hz, 1H), 6.83 (s, 1H), 6.75 (s, 2H), 6.63 (m, 1H), 5.05 (brs, 2H), 2.21 (s, 3H). | 301.9 |
| D79 | A9 B50 | 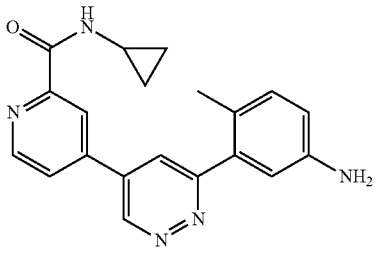 reduction with Fe | 36 | No Data | 346.1 |
| D80 | C18 | 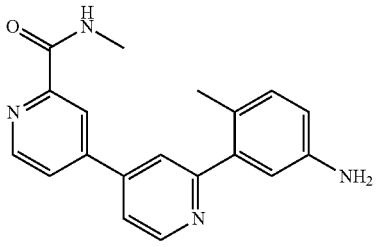 [SMILES: CNC(=O)c1cc(-c2nccc(-c3cc([N+](=O)[O-])ccc3C)n2)ccn1] reduction with Fe | 34 | 8.87 (m, 1H), 8.74-8.79 (m, 2H), 8.37 (s, 1H), 8.07 (m, 1H), 7.84 (d, J = 3.6 Hz, 1H), 7.80 (m, 1H), 6.98 (m, 1H), 6.73 (m, 1H), 6.56 (dd, J = 8.0, 2.4 Hz, 1H), 4.97 (br s, 2H), 2.85 (d, J = 4.8 Hz, 3H), 2.18 (s, 3H). | 319.3 |
| D81 | C19 | 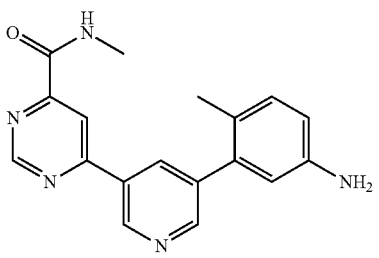 [SMILES: CNC(=O)c1cc(-c2cncc(-c3cc(N)ccc3C)c2)ncn1] | 97 | 9.40 (s, 1H), 9.37 (d, J = 2.1 Hz, 1H), 9.06 (q, J = 4.9 Hz, 1H), 8.70 (d, J = 2.1 Hz, 1H), 8.62 (s, 1H), 8.50 (m, 1H), 6.99 (d, J = 8.0 Hz, 1H), 6.59 (d, J = 8.0 Hz, 1H), 6.53 (s, 1H), 5.02 (s, 2H), 2.86 (d, J = 4.8 Hz, 3H), 2.10 (s, 3H). | 320.2 |
| D82 | C20 | 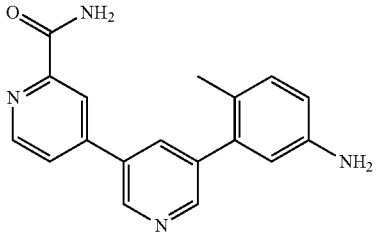 [SMILES: Cc1ccc(N)cc1-c1cncc(-c2ccnc(C(N)=O)c2)c1] | crude | No Data | 350.0 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D83 | A16 B54 | (structure) | 75 | 10.3 (s, 1H), 8.90 (s, 1H), 8.60 (s, 1H), 8.37 (m, 1H), 8.18 (s, 1H), 8.00 (s, 1H), 7.49 (m, 1H), 7.01 (d, J = 12.3 Hz, 1H), 6.75 (d, J = 9.1 Hz, 1H), 5.08 (s, 2H), 3.69 (s, 3H), 2.12 (s, 3H). | 353.2 |
| D84 | A16 B55 | (structure) | 83 | 10.3 (s, 1H), 8.55 (d, J = 1.6 Hz, 1H), 8.34 (d, J = 5.2 Hz, 1H), 7.71 (dd, J = 1.6 and 5.2 Hz, 1H), 7.68 (s, 1H), 7.27 (d, J = 1.3 Hz, 1H), 6.98 (d, J = 12.3 Hz, 1H), 6.72 (d, J = 9.2 Hz, 1H), 5.07 (s, 2H), 3.69 (s, 3H), 2.60 (s, 3H), 2.12 (s, 3H). | |
| D85 | A16 B56 | (structure) reduction with Fe | 65 | No Data | 340.0 |
| D86 | A16 B25 | (structure) reduction with Fe | crude | No Data | 336.2 |
| D87 | C21 | (structure) | 84 | 11.4 (s, 1H), 9.16 (d, J = 2.1 Hz, 1H), 9.00 (d, J = 1.2 Hz, 1H), 8.68 (d, J = 2.0 Hz, 1H), 8.63 (s, 1H), 8.23 (t, J = 2.4 Hz, 1H), 7.00 (d, J = 8.1 Hz, 1H), 6.58 (dd, J = 2.4 and 8.1 Hz, 1H), 6.53 (d, J = 2.4 Hz, 1H), 5.03 (s, 2H), 2.05-2.10 (m, 4H), 0.85-0.95 (m, 4H). | 346.2 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D88 | A22 B50 | 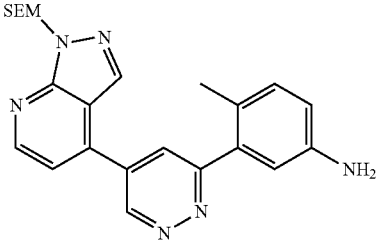 reduction with Fe | 12 | 9.71 (d, J = 2.0 Hz, 1H), 8.77 (d, J = 4.8 Hz, 1H), 8.60 (s, 1H), 8.19 (d, J = 2.0 Hz, 1H), 7.76 (d, J = 4.8 Hz, 1H), 7.04 (d, J = 8.0 Hz, 1H), 6.82 (d, J = 2.0 Hz, 1H), 6.65 (dd, J = 2.4 and 8.0 Hz, 1H), 5.86 (s, 2H), 5.06 (s, 2H), 3.64 (t, J = 8.0 Hz, 2H), 2.23 (s, 3H), 0.85 (d, J = 2.0 Hz, 2H), 0.04 (s, 9H). | 433.1 |
| D89 | A16 C1 | 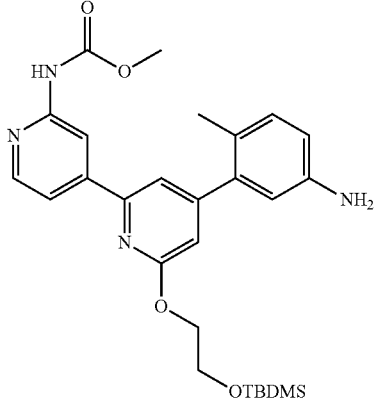 [SMILES: COC(=O)Nc1cc(-c2cc(-c3cc(N)ccc3C)cc(OCCO[Si](C)(C)C(C)(C)C)n2)ccn1] | 63 | 10.25 (s, 1H), 8.55 (s, 1H), 8.34 (d, J = 5.2 Hz, 1H), 7.71 (d, J = 5.2 Hz, 1H), 7.48 (s, 1H), 6.97 (d, J = 8.4 Hz, 1H), 6.74 (s, 1H), 6.57 (dd, J = 8.0, 2.4 Hz, 1H), 6.51 (d, J = 2.4 Hz, 1H), 5.02 (s, 2H), 4.51 (t, J = 4.4 Hz, 2H), 4.02 (t, J = 4.8 Hz, 2H), 3.69 (s, 3H), 2.09 (s, 3H), 0.86 (s, 9H), 0.05 (s, 6H). | 509.1 |
| D90 | A16 B29 | 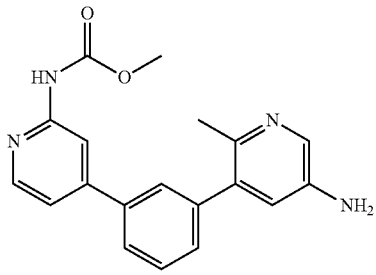 [SMILES: COC(=O)Nc1cc(-c2cccc(-c3cc(N)cnc3C)c2)ccn1] | 46 | 10.3 (s, 1H), 8.32 (d, J = 5.6 Hz, 1H), 8.16 (s, 1H), 7.87 (d, J = 2.8 Hz, 1H), 7.71 (d, J = 8.0 Hz, 1H), 7.60 (m, 2H), 7.41-7.46 (m, 2H), 6.84 (d, J = 2.8 Hz, 1H), 5.18 (s, 2H), 3.70 (s, 3H), 2.26 (s, 3H). | 335.2 |
| D91 | C29 | 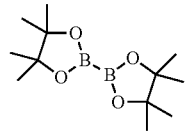 | 44 | 10.8 (s, 1H), 8.89 (s, 1H), 8.37 (s, 1H), 8.05 (d, J = 7.6 Hz, 1H), 7.97 (s, 1H), 7.88 (d, J = 2.4 Hz, 1H), 7.63 (t, J = 7.6 Hz, 1H), 7.54 (d, J = 7.6 Hz, 1H), 6.85 (d, J = 2.4 Hz, 1H), 5.19 (s, 2H), 3.74 (s, 3H), 2.26 (s, 3H). | 336.2 |
| D92 | C23 |  | 38 | 9.19 (m, 2H), 8.88 (s, 1H), 8.66 (s, 1H), 8.32 (s, 1H), 8.23 (s, 1H), 7.00 (d, J = 8.4 Hz, 1H), 6.57 (d, J = 7.2 Hz, 1H), 6.54 (s, 1H) 5.02 (br s, 2H), 3.71 (s, 3H), 2.09 (s, 3H). | 336.0 |
| D93 | C21 |  | 79 | No Data | 347.2 |
| D94 | B57 | 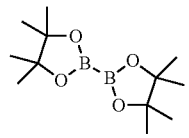 | 42 | 9.29 (d, J = 2.0 Hz, 1H), 9.13 (d, J = 0.8 Hz, 1H), 8.69 (d, J = 2.0 Hz, 1H), 8.41 (t, J = 2.0 Hz, 1H), 8.35 (d, J = 1.2 Hz, 1H), 7.00 (d, J = 8.0 Hz, 1H), 6.58 (dd, J = 8.4, 6.4 Hz, 1H), 6.54 (d, J = 2.0 Hz, 1H), 5.03 (s, 2H), 2.04 (s, 3H), 1.48 (s, 9H). NH proton missing. | 375.9 negative |
| D95 | A6 B57 |  | 66 | No Data | 319.2 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D96 | A3 B57 | | 76 | No Data | 345.2 |
| D97 | B57 | | 50 | 11.0 (s, 1H), 9.17 (2.0 Hz, 1H), 9.00 (s, 1H), 8.68 (d, J = 1.6 Hz, 1H), 8.66 (s, 1H), 8.25 (s, 1H), 7.00 (d, J = 8.0 Hz, 1H), 6.57 (d, J = 8.0 Hz, 1H), 6.54 (s, 1H), 5.04 (s, 2H), 2.78-2.85 (m, 1H), 2.10 (s, 3H), 1.11 (d, J = 8.4 Hz, 6H). | 348.2 |
| D98 | C21 | | 39 | No Data | 364.2 |
| D99 | C25 | | 38 | 8.90 (d, J = 4.0 Hz, 1H), 8.80 (m, 2H), 8.39 (dd, J = 1.2 and 5.2 Hz, 1H), 8.12 (s, 1H), 7.02 (d, J = 8.0 Hz, 1H), 6.80 (d, J = 2.4 Hz, 1H), 6.64 (dd, J = 2.0 and 8.0 Hz, 1H), 5.06 (s, 2H), 2.86 (d, J = 4.8 Hz, 3H), 2.78 (s, 3H), 2.24 (s, 3H). | 334.0 |
| D100 | A17 B57 | | 19 | No Data | 347.0 |
| D101 | A3 B58 | | 44 | 11.0 (s, 1H), 8.91 (d, J = 2.0 Hz, 1H), 8.65 (s, 1.6 Hz, 1H), 8.45 (s, 1H), 8.43 (d, J = 5.2 Hz, 1H), 8.05 (t, J = 2.4 Hz, 1H), 7.91 (d, J = 2.8 Hz, 1H), 7.54 (dd, J = 1.2 and 5.2 Hz, 1H), 6.88 (d, J = 2.8 Hz, 1H), 5.25 (s, 2H), 2.27 (s, 3H), 2.02 (m, 1H), 0.83 (m, 4H). | 346.0 |

TABLE E-continued

| Ex. No. | SM | Product | Yield (%) | $^1$H NMR (400 or 500 MHZ, DMSO-d6): δ | MS (m/z: M + H+) |
|---|---|---|---|---|---|
| D102 | A16 B57 | | 60 | 10.4 (s, 1H), 8.89 (d, J = 5.0 Hz, 1H), 8.61 (d, J = 2.0 Hz, 1H), 8.53 (d, J = 4.0 Hz, 1H), 8.18 (s, 1H), 7.99 (s, 1H), 7.50 (m, 1H), 6.95 (d, J = 8.0 Hz, 1H), 6.56 (s, 2H), 5.02 (s, 2H), 3.69 (s, 3H), 2.11 (s, 3H). | 335.1 |
| D103 | A6 C1 | | 25 | 8.83 (d, J = 5.2 Hz, 1H), 8.72 (d, J = 5.2 Hz, 1H), 8.66 (s, 1H), 8.27 (d, J = 5.2 Hz, 1H), 7.68 (s, 1H), 6.98 (d, J = 8.0 Hz, 1H), 6.78 (s, 1H), 6.58 (dd, J = 2.0 and 8.0 Hz, 1H), 6.53 (s, 1H), 5.02 (s, 2H), 4.53 (t, J = 4.4 Hz, 2H), 4.01 (t, J = 4.8 Hz, 2H), 2.85 (d, J = 4.4 Hz, 3H), 2.10 (s, 3H), 0.84 (s, 9H), 0.05 (s, 6H). | 493.0 |
| D104 | A6 B59 | | 53 | No Data | 341.2 |
| D105 | A6 B61 | | 22 | 8.89 (q, J = 4.4 Hz, 1H), 8.83 (d, J = 5.2 Hz, 1H), 8.76 (d, J = 5.1 Hz, 1H), 8.73 (m, 1H), 8.31 (dd, J = 1.8 and 5.1 Hz, 1H), 8.23 (s, 1H), 7.62 (dt, J = 1.7 and 5.1 Hz, 1H), 7.06 (dd, J = 8.8 and 10.8 Hz, 1H), 6.85 (dd, J = 2.8 and 6.7 Hz, 1H), 6.69 (m, 1H), 5.17 (s, 2H), 2.86 (d, J = 4.8 Hz, 3H). | 323.0 |
| D106 | A6 B62 H$_2$/ Pd-C | | 34 | 8.84 (q, J = 4.4 Hz, 1H), 8.80 (d, J = 6.0 Hz, 1H), 8.76 (d, J = 1.2 Hz, 1H), 8.74 (d, J = 4.8 Hz, 1H), 8.32 (dd, J = 1.8 and 5.1 Hz, 1H), 8.10 (s, 1H), 7.46 (dd, J = 1.5 and 4.8 Hz, 1H), 6.39-6.48 (m, 2H), 5.37 (s, 2H), 2.86 (d, J = 4.8 Hz, 3H), 1.99 (d, J = 2.0 Hz, 3H). | 337.0 |

TABLE E-continued

| Ex. No. | SM | Product | Yield (%) | ¹H NMR (400 or 500 MHZ, DMSO-d6): δ | MS (m/z: M + H+) |
|---|---|---|---|---|---|
| D107 | A6 B36 | (structure) | 69 | 8.82-8.88 (m, 1H), 8.68-8.75 (m, 2H), 8.27 (dd, J = 1.9 and 5.2 Hz, 1H), 7.87 (s, 1H), 7.31 (s, 1H), 6.98 (d, J = 8.1 Hz, 1H), 6.51-6.60 (m, 2H), 5.02 (s, 2H), 2.84 (d, J = 4.8 Hz, 3H), 2.62 (s, 3H), 2.11 (s, 3H). | 333.2 |
| D108 | A27 B36 | (structure) | 45 | No Data | 336.2 |

General Method I: Amide Coupling Reaction with Acyl Chloride

Intermediate E1: N-(5-bromo-2-fluoro-4-methylphenyl)-2-(trifluoromethyl)isonicotinamide

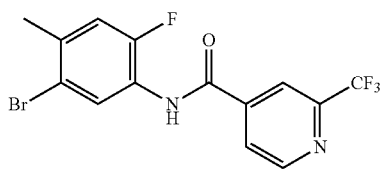 [SMILES: Cc1cc(F)c(NC(=O)c2ccnc(C(F)(F)F)c2)cc1Br]

A solution of 2-(trifluoromethyl)isonicotinic acid (1.40 g, 7.4 mmol) in anhydrous THF (25 mL) under Ar was cooled to 0° C. DMF (0.076 mL, 0.98 mmol) was added and then oxalyl dichloride (0.84 mL, 9.8 mmol) was added dropwise. The reaction mixture was stirred at 0° C. for 1 h while slowly warming to rt. The mixture was concentrated to almost complete dryness (approximately 1 mL left) and then the residue was dissolved in anhydrous THF (15 mL). The solution was stirred at 0° C. under Ar. A solution of 5-bromo-2-fluoro-4-methylaniline (1.0 g, 4.9 mmol) and DIEA (1.88 mL, 10.8 mmol) in anhydrous THF (10 mL) was added dropwise at 0° C. into a solution of 2-(trifluoromethyl) isonicotinoyl chloride in THF. The reaction mixture was stirred at 0° C. for 10 min and then warmed to rt slowly for 1 h. The mixture was quenched with sat'd NaHCO₃ (aq, 50 mL) and then the solution was extracted with EtOAc (3×30 mL). The combined organics were washed with brine (50 mL), dried over anhydrous Na₂SO₄, filtered and concentrated under reduced pressure. The crude was purified silica gel column chromatography (0 to 5%, DCM/MeOH) to give N-(5-bromo-2-fluoro-4-methylphenyl)-2-(trifluoromethyl) isonicotinamide (1.29 g, 70% yield) as a white solid. MS (ESI) m/z: 377.0 (M+H⁺) and 379.0.

Using the General Method I above, the following Intermediates of Table F were prepared.

TABLE F

| Ex. No. | SM1 | SM2 | Product | Yield (%) | ¹H NMR (400 or 500 MHz, DMSO-d₆): δ | MS (m/z: M + H⁺) |
|---|---|---|---|---|---|---|
| E2 | (structure) | (structure) | (structure) | 57 | No Data | 358.0 360.0 |
| E3 | (structure) | (structure) | (structure) | crude | No Data | 407.2 |

TABLE F-continued

| Ex. No. | SM1 | SM2 | Product | Yield (%) | $^1$H NMR (400 or 500 MHz, DMSO-d$_6$): δ | MS (m/z: M + H$^+$) |
|---|---|---|---|---|---|---|
| E4 | 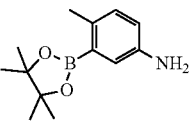 | 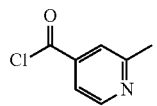 | 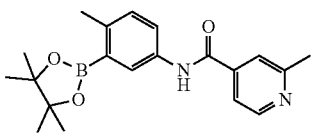 | crude | 10.4 (s, 1H), 8.61 (d, J = 5.2 Hz, 1H), 7.94 (s, 1H), 7.86 (d, J = 8.4 Hz, 1H), 7.75 (s, 1H), 7.66 (d, J = 5.1 Hz, 1H), 7.17 (d, J = 8.4 Hz, 1H), 2.56 (s, 3H), 2.43 (s, 3H), 1.30 (s, 12H). | No Data |
| E5 | 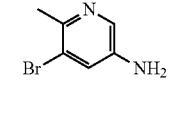 | 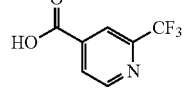 | 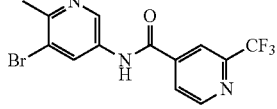 | 89 | 10.9 (s, 1H), 9.01 (d, J = 4.8 Hz, 1H), 8.79 (brs, 1H), 8.46 (s, 1H), 8.37 (s, 1H), 8.19 (d, J = 4.8 Hz, 1H), 2.56 (s, 3H). | 360.0 |
| E6 | 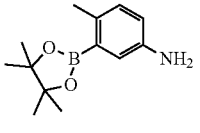 | 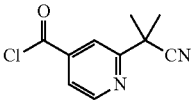 | 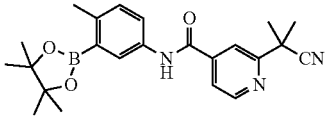 [SMILES: Cc1ccc(NC(=O)c2ccnc(C(C)(C)C#N)c2)cc1B1OC(C)(C)C(C)(C)O1] | crude | 10.5 (s, 1H), 8.78 (d, J = 5.1 Hz, 1H), 8.03 (s, 1H), 7.93 (m, 1H), 7.87 (m, 2H), 7.17 (m, 1H), 2.44 (s, 3H), 1.76 (s, 6H), 1.30 (s, 12H). | 406.0 |
| E7 | 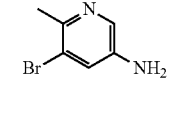 | 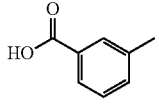 | 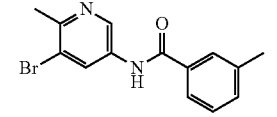 [SMILES: Cc1cccc(C(=O)Nc2cnc(C)c(Br)c2)c1] | 75 | 10.5 (s, 1H), 8.80 (s, 1H), 8.46 (s, 1H), 7.78 (brs, 1H), 7.75 (t, J = 4.8 Hz, 1H), 7.44 (brs, 2H), 2.54 (s, 3H), 2.40 (s, 3H). | 306.8 |
| E8 | E5 | 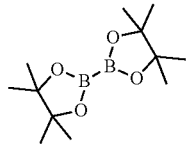 | 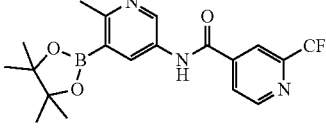  Method A | 60 | 10.8 (s, 1H), 8.97 (d, J = 2.8 Hz, 1H), 8.41 (s, 1H), 8.33 (d, J = 2.8 Hz, 1H), 8.21 (d, J = 4.8 Hz, 1H), 7.43-7.56 (m, 1H), 2.62 (s, 3H), 1.33 (s, 12H). | 408.0 |
| E9 | 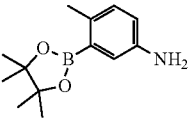 | 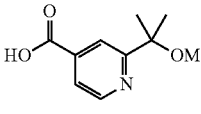 | 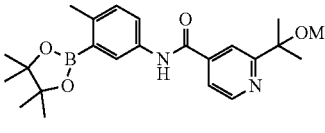 | crude | No Data | 411.1 |
| E10 | 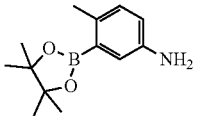 | 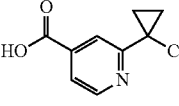 | 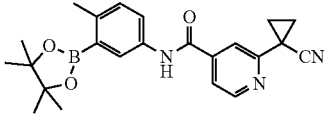 [SMILES: Cc1ccc(NC(=O)c2ccnc(C3(C#N)CC3)c2)cc1B1OC(C)(C)C(C)(C)O1] | 28 | No Data | 404.0 |
| E11 | 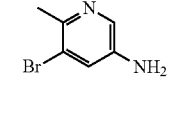 | 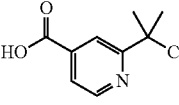 | 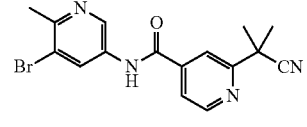 [SMILES: Cc1ncc(NC(=O)c2ccnc(C(C)(C)C#N)c2)cc1Br] | 91 | 10.8 (s, 1H), 8.83 (dd, J = 0.8 and 5.0 Hz, 1H), 8.78 (d, J = 2.3 Hz, 1H), 8.44 (d, J = 2.2 Hz, 1H), 8.01 (s, 1H), 7.87 (dd, J = 1.6 and 5.0 Hz, 1H), 2.56 (s, 3H), 1.76 (s, 6H). | No Data |
| E12 | E11 | 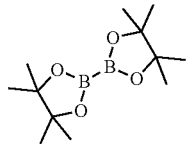 | 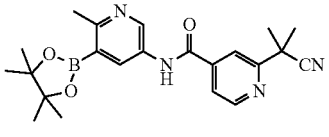  Method A | 81 | 10.7 (s, 1H), 8.97 (d, J = 2.7 Hz, 1H), 8.82 (dd, J = 0.8 and 5.0 Hz, 1H), 8.32 (d, J = 2.7 Hz, 1H), 8.06 (s, 1H), 7.90 (dd, J = 1.5 and 5.0 Hz, 1H), 2.62 (s, 3H), 1.77 (s, 6H), 1.33 (s, 12H). | No Data |

TABLE F-continued

| Ex. No. | SM1 | SM2 | Product | Yield (%) | $^1$H NMR (400 or 500 MHz, DMSO-$d_6$): δ | MS (m/z: M + H$^+$) |
|---|---|---|---|---|---|---|
| E13 | | | | 50 | 10.5 (s, 1H), 8.73 (d, J = 4.8 Hz, 1H), 8.05 (s, 1H), 7.95 (d, J = 2.0 Hz, 1H), 7.87 (dd, J = 2.0 and 8.0 Hz, 1H), 7.83 (dd, J = 1.6 and 5.2 Hz, 1H), 7.19 (d, J = 8.4 Hz, 1H), 2.44 (s, 3H), 1.71 (d, J = 22.4 Hz, 6H), 1.31 (s, 12H). | 399.3 |
| E14 | | | | 100 | No Data | 405.0 407.0 |
| E15 | | | | 100 | 10.8 (s, 1H), 8.75 (dt, J = 1.0 and 5.1 Hz, 1H), 7.99 (dt, J = 1.0 and 2.1 Hz, 1H), 7.85-7.94 (m, 2H), 7.77 (dd, J = 1.6 and 5.1 Hz, 1H), 1.68 (d, J = 22.2 Hz, 6H) | No Data |
| E16 | | | | crude | | |
| E17 | | | | crude | No Data | 373.0 375.0 |
| E18 | | | | crude | No Data | 355.0 357.0 |

General Method J: Amide Coupling Reaction with HATU

Intermediate F1: N-(3-(2-chloropyridin-4-yl)-4-methylphenyl)-2-(trifluoromethyl)isonicotinamide

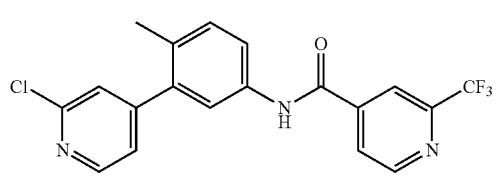 [SMILES: Cc1ccc(NC(=O)c2ccnc(C(F)(F)F)c2)cc1-c1ccnc(Cl)c1]

A solution of 2-(trifluoromethyl)isonicotinic acid (2.63 g, 14 mmol) in DMF (34 mL) was treated with HATU (5.23 g, 14 mmol) and DIEA (3.61 mL, 21 mmol). The reaction mixture was stirred for 10 min and then 3-(2-chloropyridin-4-yl)-4-methylaniline (B2, 1.50 g, 6.9 mmol) was added. The reaction was then stirred at rt for 4 h. and then cooled to rt. The reaction mixture was quenched with ice water (100 mL) and allowed to stir for 90 min. The yellow solid was filtered and dissolved in MeOH. The solution was concentrated under reduced pressure to afford a yellow oil. The yellow oil was purified by silica gel column chromatography (0 to 50% EtOAc/hexanes) to afford N-(3-(2-chloropyridin-4-yl)-4-methylphenyl)-2-(trifluoromethyl)isonicotinamide (1.49 g, 55% yield) as a yellow solid. $^1$H NMR (500 MHz, DMSO-$d_6$): δ 10.7 (s, 1H), 8.99 (d, J=5.0 Hz, 1H), 8.49 (d, J=5.1 Hz, 1H), 8.36 (s, 1H), 8.18 (d, J=5.0 Hz, 1H), 7.78 (dd, J=2.2 and 8.3 Hz, 1H), 7.70 (d, J=2.2 Hz, 1H), 7.55 (s, 1H), 7.46 (d, J=5.1 Hz, 1H), 7.37 (d, J=8.3 Hz, 1H), 2.24 (s, 3H); MS (ESI) m/z: 392.0 (M+H$^+$).

General Method K: Amide Coupling Reaction with T3P

Intermediate F2: N-(3-(6-chloro-1-methyl-2-oxo-1,2-dihydropyridin-4-yl)-4-methylphenyl)-2-(trifluoromethyl)isonicotinamide

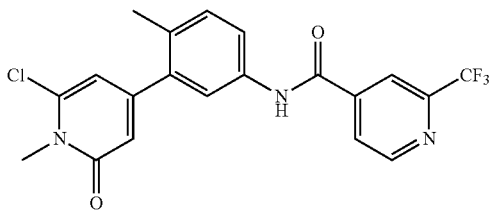 [SMILES: Cc1ccc(NC(=O)c2ccnc(C(F)(F)F)c2)cc1-c1cc(Cl)n(C)c(=O)c1]

A solution of 4-(5-amino-2-methylphenyl)-6-chloro-1-methylpyridin-2(1H)-one (B6, 0.6 g, 2.4 mmol) and 2-(trifluoromethyl)isonicotinic acid (0.55 g, 7.2 mmol) in THF (12 mL), was treated with DIEA (1.2 g, 9.6 mmol). T3P (50% in EtOAc, 4.6 mL, 7.2 mmol) was added and the reaction mixture was stirred at rt for 6 h. The reaction mixture was quenched with water (12 mL) and the solution was extracted with EtOAc (3×30 mL). The combined organic extracts were washed with brine (30 mL), dried over anhydrous Na$_2$SO$_4$, filtered, and concentrated under reduced pressure to afford N-(3-(6-chloro-1-methyl-2-oxo-1,2-dihydropyridin-4-yl)-4-methylphenyl)-2-(trifluoromethyl)isonicotinamide (0.95 g, 93% yield) as brown solid. $^1$H NMR (500 MHz, DMSO-d$_6$): δ 10.7 (s, 1H), 8.99 (d, J=4.8 Hz, 1H), 8.35 (s, 1H), 8.19 (d, J=4.0 Hz, 1H)), 7.74 (d, J=8.0 Hz, 1H), 7.68 (d, J=2.0 Hz, 1H), 7.33 (d, J=8.0 Hz, 1H), 6.55 (s, 1H), 6.35 (s, 1H), 3.61 (s, 3H), 2.27 (s, 3H); MS (ESI) m/z: 422.0 (M+H$^+$).

General Method L: Amide Coupling Reaction with Acyl Chloride

Intermediate F3: N-(3-(2-chloropyridin-4-yl)-4-methylphenyl)-3-methylbenzamide

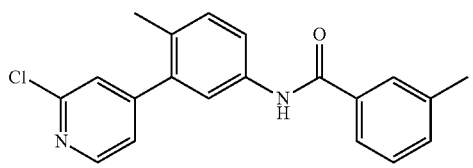 [SMILES: Cc1cccc(C(=O)Nc2ccc(C)c(-c3ccnc(Cl)c3)c2)c1]

A mixture of DMF (0.071 mL, 0.91 mmol) and 3-methylbenzoic acid (0.75 g, 5.5 mmol) in THF (15 mL) was cooled to 0° C. Oxalyl chloride (0.80 mL, 9.1 mmol) was added dropwise and the reaction mixture was stirred for 30 min under the same conditions. The mixture was concentrated to dryness and then THF (20 mL) was added and concentrated (repeat twice). A mixture of 3-(2-chloropyridin-4-yl)-4-methylaniline (B2, 1.0 g, 4.6 mmol) and DIEA (1.8 mL, 10.1 mmol) in THF (30 mL) was cooled to 0° C. and the solution of the acid chloride in THF (20 mL) was added into the amine solution. The reaction mixture was stirred under the same condition for 30 min. The reaction mixture was concentrated under reduced pressure and the residue was treated with sat'd NaHCO$_3$ (aq, 50 mL) and DCM (30 mL). The aq. layer was extracted with DCM (2×30 mL). The combined organic extracts were dried over anhydrous MgSO$_4$, filtered, and concentrated under reduced pressure to obtain N-(3-(2-chloropyridin-4-yl)-4-methylphenyl)-3-methylbenzamide (1.54 g, crude). $^1$H NMR (500 MHz, DMSO-d$_6$): δ 10.3 (s, 1H), 8.48 (d, J=5.1 Hz, 1H), 7.75 (m, 4H), 7.54 (s, 1H), 7.45 (dd, J=1.5 and 5.1 Hz, 1H), 7.39 (m, 2H), 7.32 (d, J=8.3 Hz, 1H), 2.39 (s, 3H), 2.23 (s, 3H); MS (ESI) m/z: 337.0 (M+H$^+$).

General Method M: Suzuki Reaction

Intermediate F4: N-(3-(2,6-dichloropyridin-4-yl)-4-methylphenyl)-2-(trifluoromethyl)isonicotinamide

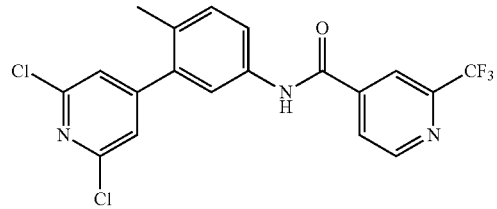 [SMILES: Cc1ccc(NC(=O)c2ccnc(C(F)(F)F)c2)cc1-c1cc(Cl)nc(Cl)c1]

A mixture of 2,6-dichloro-4-(4,4,5,5-tetramethyl-1,3,2-dioxaborolan-2-yl)pyridine (1.53 g, 5.6 mmol), N-(3-bromo-4-methylphenyl)-2-(trifluoromethyl)isonicotinamide (E2, 2.0 g, 5.6 mmol) and K$_2$CO$_3$ (1.54 g, 11 mmol) in a mixture of 1,4-dioxane (25 mL) and water (3 mL) was sparged with Ar for 2 min. Pd(dppf)Cl$_2$ (0.10 g, 0.14 mmol) was added and then sparged with Ar again for 2 min. The reaction mixture was heated to 85° C. for 2 h and then cooled to rt. The reaction mixture was diluted with DCM (100 mL) and the solution was filtered through a pad of celite. The filtrate was treated with sat'd NaHCO$_3$ (aq, 125 mL) and then the organic layer was dried over anhydrous MgSO$_4$, filtered, and concentrated under reduced pressure to yield a brown solid. The crude was purified by silica gel column chromatography (0 to 50% EtOAc/hexanes) to obtain N-(3-(2,6-dichloropyridin-4-yl)-4-methylphenyl)-2-(trifluoromethyl)isonicotinamide (2.22 g, 93% yield) as a tan solid. MS (ESI) m/z: 426.0 (M+H$^+$).

Using the General Methods J, K, L and M above, the following Intermediates of Table G were prepared.

TABLE G

| Ex. No. | SM | Product | Method | Yield (%) | ¹H NMR (400 or 500 MHz, DMSO-d₆): δ | MS (m/z: M + H⁺) |
|---|---|---|---|---|---|---|
| F5 | C1 | | J | 69 | No Data | 566.2 |
| F6 | E2 | | M | 45 | No Data | 406.0 |
| F7 | E1 | | M | 40 | No Data | 424.0 |
| F8 | B29 | | J | crude | No Data | 346.2 |
| F9 | C2 | | J | 93 | 10.7 (s, 1H), 8.98 (d, J = 5.0 Hz, 1H), 8.36 (s, 1H), 8.18 (d, J = 5.0 Hz, 1H), 7.75 (d, J = 8.4 Hz, 1H), 7.64 (s, 1H), 7.33 (d, J = 8.4 Hz, 1H), 6.73 (s, 1H), 6.69 (s, 1H), 3.68 (t, J = 4.7 Hz, 4H), 3.49 (t, J = 4.7 Hz, 4H), 2.23 (s, 3H). | 477.2 |
| F10 | B14 | | K | 45 | No Data | 392.2 |
| F11 | B7 | | J | 41 | 10.7 (s, 1H), 8.99 (d, J = 8.0 Hz, 1H), 8.35 (s, 1H), 8.18 (d, J = 8.0 Hz, 1H), 7.77 (d, J = 8.0 Hz, 1H), 7.66 (s, 1H), 7.38 (d, J = 8.0 Hz, 1H), 7.02 (s, 1H), 3.69 (s, 3H), 2.15 (s, 3H). | 421.3 (M − H⁺) |
| F12 | B3 | | J | 52 | 10.7 (s, 1H), 9.00 (d, J = 5.2 Hz, 1H), 8.36 (s, 1H), 8.19 (d, J = 4.8 Hz, 1H), 7.81 (d, J = 8.0 Hz, 1H), 7.67 (d, J = 8.8 Hz, 1H), 7.55 (m, 1H), 7.35 (m, 1H), 7.20 (s, 1H), 2.26 (s, 3H). | 408.0 (M − H⁺) |

TABLE G-continued

| Ex. No. | SM | Product | Method | Yield (%) | ¹H NMR (400 or 500 MHz, DMSO-d₆): δ | MS (m/z: M + H⁺) |
|---|---|---|---|---|---|---|
| F13 | B4 | | J | 53 | 10.7 (s, 1H), 9.01 (d, J = 5.2 Hz, 1H), 8.36 (s, 1H), 8.19 (d, J = 5.2 Hz, 1H), 7.64 (d, J = 7.6 Hz, 1H), 7.57 (s, 1H), 7.41 (d, J = 11.2 Hz, 1H), 7.34 (s, 1H), 2.31 (s, 3H). | 426.0 (M − H⁻) |
| F14 | B11 | | L | crude | No Data | 410.0 |
| F15 | B2 | | J | 58 | No Data | 391.2 |
| F16 | B29 | | direct amid coupling with LiHMDS | 91 | No Data | 364.2 |
| F17 | B16 | Using oxalyl chloride | L | crude | 10.6 (s, 1H), 8.66 (d, J = 5.6 Hz, 1H), 8.52 (d, J = 5.1 Hz, 1H), 8.28 (d, J = 2.0 Hz, 1H), 8.05 (m, 1H), 7.98 (m, 1H), 7.94 (d, J = 1.9 Hz, 1H), 7.65 (d, J = 7.0 Hz, 1H), 7.55 (m, 2H), 2.35 (s, 3H). | 392.0 |
| F18 | E2 | | M | 53 | 10.8 (s, 1H), 8.96 (t, J = 5.0 Hz, 1H), 8.84 (d, J = 5.2 Hz, 1H), 8.36 (s, 1H), 8.18 (d, J = 5.0 Hz, 1H), 7.93 (d, J = 2.2 Hz, 1H), 7.85 (dd, J = 2.2 and 8.4 Hz, 1H), 7.76 (d, J = 5.2 Hz, 1H), 7.39 (d, J = 8.4 Hz, 1H), 2.38 (s, 3H). | 393.0 |
| F19 | E2 | | M | 91 | No Data | 391.0 |
| F20 | E2 | | M | 35 | 10.8 (s, 1H), 8.99 (d, J = 5.0 Hz, 1H), 8.88 (s, 1H), 8.82 (s, 1H), 8.38 (s, 1H), 8.20 (d, J = 5.1 Hz, 1H), 7.91 (d, J = 2.3 Hz, 1H), 7.86 (dd, J = 2.3 and 8.3 Hz, 1H), 7.40 (d, J = 8.4 Hz, 1H), 2.37 (s, 3H). | 393.0 |
| F21 | B14 | | J | 75 | 10.9 (s, 1H), 9.01 (d, J = 4.8 Hz, 1H), 8.90 (s, 1H), 8.54 (d, J = 5.2 Hz, 1H), 8.38 (s, 1H), 8.21 (d, J = 4.8 Hz, 1H), 8.10 (s, 1H), 7.65 (s, 1H), 7.53 (m, 1H), 2.45 (s, 3H). | 393.1 |

TABLE G-continued

| Ex. No. | SM | Product | Method | Yield (%) | ¹H NMR (400 or 500 MHz, DMSO-d₆): δ | MS (m/z: M + H⁺) |
|---|---|---|---|---|---|---|
| F22 | B14 | | J | 65 | 10.7 (s, 1H), 8.92 (s, 1H), 8.53 (d, J = 5.2 Hz, 1H), 8.33 (s, 1H), 8.28 (d, J = 7.6 Hz, 1H), 8.11 (s, 1H), 7.99 (d, J = 7.6 Hz, 1H), 7.81 (m, 1H), 7.65 (s, 1H), 7.54 (m, 1H), 2.44 (s, 3H). | 392.1 |
| F23 | B2 | | J | crude | No Data | 338.2 |
| F24 | B2 | Using oxalyl chloride | L | crude | 10.7 (s, 1H), 8.90 (d, J = 5.1 Hz, 1H), 8.49 (d, J = 5.1 Hz, 1H), 8.17 (s, 1H), 8.05 (d, J = 5.1 Hz, 1H), 7.79 (dd, J = 2.3 and 8.7 Hz, 1H), 7.71 (d, J = 2.2 Hz, 1H), 7.55 (s, 1H), 7.46 (d, J = 5.2 Hz, 1H), 7.37 (d, J = 8.4 Hz, 1H), 7.07 (t, J = 54.4 Hz, 1H), 2.24 (s, 3H). | 374.0 |
| F25 | E4 | | M | 71 | 10.5 (s, 1H), 9.15 (s, 1H), 8.63 (d, J = 5.2 Hz, 1H), 7.96 (d, J = 2.3 Hz, 1H), 7.91 (s, 1H), 7.83 (dd, J = 2.3 and 8.3 Hz, 1H), 7.73 (s, 1H), 7.65 (d, J = 5.2 Hz, 1H), 7.36 (d, J = 8.4 Hz, 1H), 2.57 (s, 3H), 2.38 (s, 3H). | 339.2 |
| F26 | B15 | | J | 96 | 10.8 (s, 1H), 9.01 (d, J = 4.8 Hz, 1H), 8.37 (s, 1H), 8.20 (d, J = 4.4 Hz, 1H), 8.01 (brs, 1H), 7.99 (brs, 1H), 7.47 (m, 3H), 2.53 (s, 3H). | 410.0 |
| F27 | E5 | | M | 69 | 10.9 (s, 1H), 9.01 (d, J = 4.8 Hz, 1H), 8.86 (brs, 1H), 8.38 (s, 1H), 8.21 (brs, 1H), 8.05 (s, 1H), 7.50 (m, 3H), 7.42 (m, 1H), 2.42 (s, 3H). | 392.3 |
| F28 | E3 | | M | 61 | 10.6 (s, 1H), 8.99 (d, J = 4.8 Hz, 1H), 8.36 (s, 1H), 8.18 (brs, 1H), 8.12 (d, J = 2.4 Hz, 1H), 7.95 (s, 1H), 7.74 (dd, J = 2.4 and 8.4 Hz, 1H), 7.66 (s, 1H), 7.34 (d, J = 8.4 Hz, 1H), 4.44 (q, J = 6.8 Hz, 2H), 2.24 (s, 3H), 1.38 (t, J = 6.8 Hz, 3H). | 436.0 |
| F29 | B48 | | J | 59 | 10.4 (s, 1H), 8.96 (s, 1H), 8.84 (s, 1H), 8.08 (s, 1H), 8.05 (s, 1H), 7.98 (dd, J = 1.9 and 8.0 Hz, 1H), 7.57 (s, 1H), 7.52 (d, J = 8.0 Hz, 1H), 4.47 (m, 1H), 2.44 (s, 3H), 1.40 (d, J = 6.7 Hz, 6H). | 356.2 |

TABLE G-continued

| Ex. No. | SM | Product | Method | Yield (%) | ¹H NMR (400 or 500 MHz, DMSO-d₆): δ | MS (m/z: M + H⁺) |
|---|---|---|---|---|---|---|
| F30 | E6 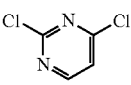 | 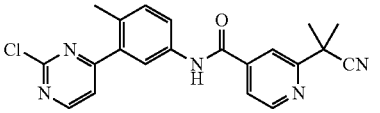 [SMILES: Cc1ccc(NC(=O)c2ccnc(C(C)(C)C#N)c2)cc1-c1ccnc(Cl)n1] | M | 41 | 10.7 (s, 1H), 8.86 (d, J = 5.1 Hz, 1H), 8.81 (d, J = 5.1 Hz, 1H), 8.02 (s, 1H), 7.94 (d, J = 2.2 Hz, 1H), 7.87 (m, 2H), 7.79 (d, J = 5.2 Hz, 1H), 7.40 (d, J = 8.4 Hz, 1H), 2.39 (s, 3H), 1.76 (s, 6H). | No Dada |
| F31 | B47 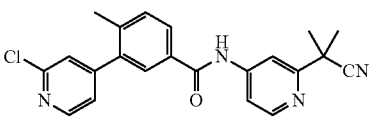 | 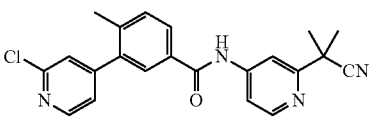 Using CDI | J | 6 | No Data | 391.2 |
| F32 | B11 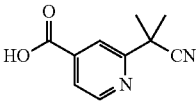 | 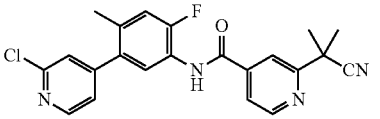 [SMILES: Cc1cc(F)c(NC(=O)c2ccnc(C(C)(C)C#N)c2)cc1-c1ccnc(Cl)c1] | J | 78 | No Data | 409.0 |
| F33 | E3 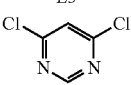 | 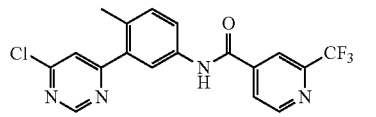 [SMILES: Cc1ccc(NC(=O)c2ccnc(C(F)(F)F)c2)cc1-c1cc(Cl)ncn1] | M | 64 | 10.8 (s, 1H), 8.99 (d, J = 5.0 Hz, 1H), 8.86 (d, J = 5.2 Hz, 1H), 8.38 (s, 1H), 8.20 (d, J = 5.0 Hz, 1H), 7.95 (d, J = 2.2 Hz, 1H), 7.88 (dd, J = 2.2 and 8.3 Hz, 1H), 7.79 (d, J = 5.2 Hz, 1H), 7.40 (d, J = 8.4 Hz, 1H), 2.39 (s, 3H). | 393.2 |
| F34 | B29 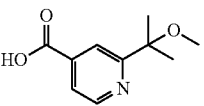 | 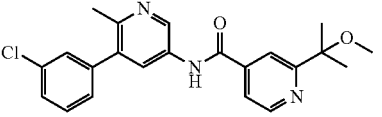 [SMILES: COC(C)(C)c1cc(C(=O)Nc2cnc(C)c(-c3cccc(Cl)c3)c2)ccn1] | J | 35 | 10.7 (s, 1H), 8.88 (d, J = 2.4 Hz, 1H), 8.74 (d, J = 5.2 Hz, 1H), 8.05 (d, J = 2.0 Hz, 1H), 8.03 (s, 1H), 7.77 (dd, J = 1.2 and 5.2 Hz, 1H), 7.50-7.58 (m, 4H), 3.12 (s, 3H), 2.42 (s, 3H), 1.51 (s, 6H). | 396.2 |
| F35 | E7 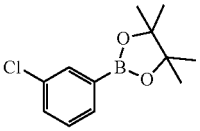 | 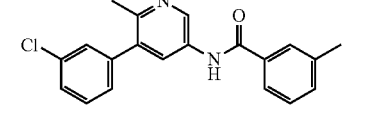 | M | 92 | 10.4 (s, 1H), 8.87 (s, 1H), 8.06 (s, 1H), 7.79 (s, 1H), 7.77 (m, 1H), 7.75 (m, 3H), 7.49 (m, 3H), 2.40 (s, 6H). | 337.0 |
| F36 | B30 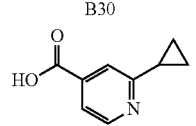 | 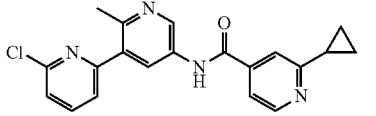 [SMILES: Cc1ncc(NC(=O)c2ccnc(C3CC3)c2)cc1-c1cccc(Cl)n1] | J | 48 | 10.7 (s, 1H), 8.95 (s, 1H), 8.60 (d, J = 4.8 Hz, 1H), 8.27 (s, 1H), 8.15 (brs, 1H), 8.02 (t, J = 7.6 Hz, 1H), 7.78 (s, 1H), 7.69 (d, J = 7.6 Hz, 1H), 7.57 (m, 1H), 2.54 (s, 3H), 2.19-2.28 (m, 1H), 0.98-1.04 (m, 4H). | 365.0 |
| F37 | B2 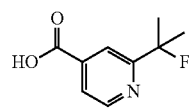 | 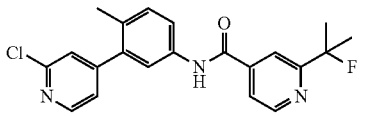 | | 62 | 10.61 (s, 1H), 8.76 (d, J = 5.2 Hz, 1H), 8.49 (d, J = 5.2 Hz, 1H), 8.02 (s, 1H), 7.82 (m, 2H), 7.71 (s, 1H), 7.56 (s, 1H), 7.45 (d, J = 5.2 Hz, 1H), 7.36 (d, J = 8.4 Hz, 1H), 2.24 (s, 3H), 1.70 (d, J = 22.4 Hz, 6H). | 383.9 |

TABLE G-continued

| Ex. No. | SM | Product | Method | Yield (%) | ¹H NMR (400 or 500 MHz, DMSO-d₆): δ | MS (m/z: M + H⁺) |
|---|---|---|---|---|---|---|
| F38 | B22 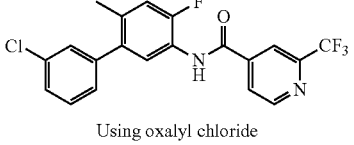 | 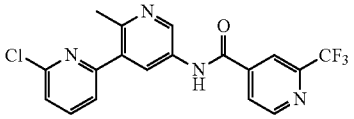 [SMILES: Cc1ncc(NC(=O)c2ccnc(C(F)(F)F)c2)cc1-c1cccc(Cl)n1] Using oxalyl chloride | L | 89 | 10.6 (s, 1H), 8.99 (d, J = 5.0 Hz, 1H), 8.35 (s, 1H), 8.18 (d, J = 5.0 Hz, 1H), 7.45-7.53 (m, 3H), 7.41 (s, 1H), 7.31 (m, 2H), 2.24 (s, 3H). | 409.2 |
| F39 | E8 | | M | 67 | 11.0 (s, 1H), 9.01 (d, J = 5.2 Hz, 1H), 8.94 (d, J = 2.4 Hz, 1H), 8.41 (s, 1H), 8.25 (d, J = 2.4 Hz, 1H), 8.22 (d, J = 4.8 Hz, 1H), 8.02 (t, J = 7.6 Hz, 1H), 7.71 (d, J = 7.6 Hz, 1H), 7.59 (d, J = 7.6 Hz, 1H), 2.54 (s, 3H). | 392.9 |
| F40 | E2 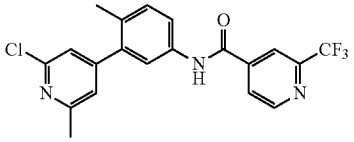 | | M | 45 | No Data | 406.0 |
| F41 | E8 | | M | 50 | 11.0 (s, 1H), 9.01 (brm, 2H), 8.92 (d, J = 5.2 Hz, 1H), 8.41 (s, 1H), 8.37 (d, J = 2.4 Hz, 1H), 8.23 (d, J = 5.2 Hz, 1H), 7.91 (d, J = 5.2 Hz, 1H), 2.60 (s, 3H). | 393.8 |
| F42 | B20 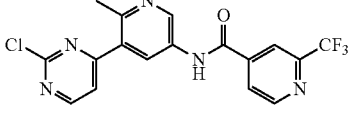 | | L | 76 | 10.7 (s, 1H), 8.89 (s, 1H), 8.82 (brm, 1H), 8.80 (s, 1H), 8.02 (s, 1H), 7.85-7.91 (m, 3H), 7.40 (d, J = 8.4 Hz, 1H), 2.38 (s, 3H), 1.77 (s, 6H). | 392.0 |
| F43 | B12 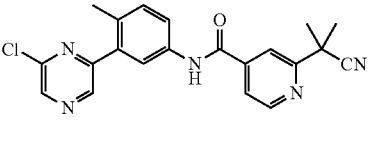 | | L | 80 | 10.3 (s, 1H), 8.04 (brm, 1H), 7.94 (d, J = 8.0 Hz, 1H), 7.74 (m, 2H), 7.66 (d, J = 2.0 Hz, 1H), 7.59 (t, J = 8.0 Hz, 1H), 7.47 (m, 2H), 7.42 (brm, 1H), 7.35 (m, 1H), 7.30 (d, J = 8.4 Hz, 1H), 2.21 (s, 3H), 1.74 (s, 6H). | 389.0 |
| F44 | B29 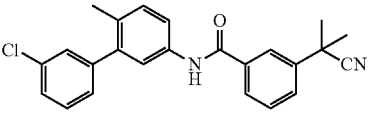 | | L | 89 | 10.8 (s, 1H), 8.86 (t, J = 2.4 Hz, 1H), 8.83 (d, J = 5.2 Hz, 1H), 8.03 (m, 2H), 7.89 (d, J = 4.8 Hz, 1H), 7.50-7.56 (m, 3H), 7.43 (dd, J = 1.6 and 6.4 Hz, 1H), 2.32 (s, 3H), 1.76 (s, 6H). | 391.0 |
| F45 | B31 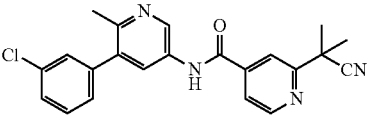 | | L | 50 | 10.9 (s, 1H), 9.00 (d, J = 2.0 Hz, 1H), 8.91 (d, J = 5.2 Hz, 1H), 8.83 (m, 1H), 8.36 (brm, 1H), 8.05 (s, 1H), 7.91 (d, J = 5.2 Hz, 2H), 2.60 (s, 3H), 1.77 (s, 6H). | 393.0 |
| F46 | B32 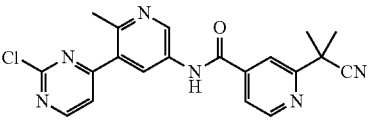 | 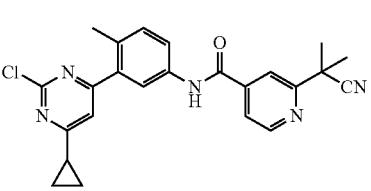 [SMILES: Cc1ccc(NC(=O)c2ccnc(C(C)(C)C#N)c2)cc1-c1cc(C2CC2)nc(Cl)n1] | J | 56 | 10.7 (brs, 1H), 8.81 (d, J = 4.8 Hz, 1H), 8.02 (s, 1H), 7.85-7.95 (m, 3H), 7.69 (s, 1H), 7.38 (d, J = 8.0 Hz, 1H), 2.38 (s, 3H), 2.26 (m, 1H), 1.77 (s, 6H), 1.25 (m, 2H), 1.17 (m, 2H). | 432.0 |

TABLE G-continued

| Ex. No. | SM | Product | Method | Yield (%) | ¹H NMR (400 or 500 MHz, DMSO-d₆): δ | MS (m/z: M + H⁺) |
|---|---|---|---|---|---|---|
| F47 | B14 | | J | 42 | No Data | 392.2 |
| F48 | B12 | | K | 45 | 10.4 (s, 1H), 8.19 (d, J = 6.8 Hz, 2H), 7.84 (s, 1H), 7.75 (dd, J = 2.0 and 8.0 Hz, 1H), 7.65 (d, J = 3.6 Hz, 1H), 7.50 (m, 2H), 7.42 (s, 1H), 7.35 (m, 2H), 3.56 (s, 2H), 2.25 (s, 3H), 2.18 (s, 6H). | 447.0 |
| F49 | B33 | | K | 78 | 10.7 (s, 1H), 8.82 (d, J = 5.2 Hz, 1H), 8.53 (d, J = 5.2 Hz, 1H), 8.02 (brm, 2H), 7.86-7.94 (m, 2H), 7.70 (brs, 1H), 6.61 (brd, J = 5.2 Hz, 1H), 7.44 (brt, J = 9.6 Hz, 1H), 1.76 (s, 6H). | 394.9 |
| F50 | B34 | | J | 80 | 10.5 (s, 1H), 8.81 (d, J = 5.2 Hz, 1H), 8.00 (s, 1H), 7.86 (d, J = 4.8 Hz, 1H), 7.70 (dd, J = 2.0 and 8.4 Hz, 1H), 7.63 (d, J = 2.4 Hz, 1H), 7.30 (brm, 2H), 7.21 (s, 1H), 7.15 (s, 1H), 2.37 (s, 3H), 2.32 (s, 3H), 1.76 (s, 6H). | 404.0 |
| F51 | B35 | | K | 74 | 10.6 (brs, 1H), 8.81 (d, J = 4.8 Hz, 1H), 8.01 (s, 1H), 7.85 (brm, 1H), 7.73 (brm, 1H), 7.66 (brm, 1H), 7.61 (s, 1H), 7.45 (d, J = 2.4 Hz, 1H), 7.33 (brm, 1H), 7.15 (brm, 1H), 2.23 (s, 3H), 2.02 (m, 1H), 1.76 (s, 6H), 1.00 (m, 2H), 0.77 (m, 2H). | 430.1 |
| F52 | B36 | | K | 28 | 10.6 (s, 1H), 8.81 (d, J = 5.2 Hz, 1H), 8.06 (s, 1H), 7.86 (m, 1H), 7.77 (brm, 1H), 7.67 (brs, 1H), 7.28-7.37 (m, 3H), 2.49 (s, 3H), 2.24 (s, 3H), 1.76 (s, 6H). | 405.2 |
| F53 | B37 | | K | 50 | 10.8 (brs, 1H), 8.83 (brm, 2H), 8.00 (m, 2H), 7.89 (d, J = 4.0 Hz, 1H), 7.51 (brm, 1H), 7.25 (brs, 1H), 7.10 (brm, 1H), 2.41 (s, 3H), 2.02 (m, 1H), 1.76 (s, 6H), 0.98 (m, 2H), 0.83 (m, 2H). | 431.0 |
| F54 | E6 | | M | 89 | 10.7 (s, 1H), 9.38 (d, J = 1.8 Hz, 1H), 8.82 (d, J = 5.0 Hz, 1H), 8.08 (d, J = 1.8 Hz, 1H), 8.01 (s, 1H), 7.87 (dd, J = 1.6 and 5.0 Hz, 1H), 7.82 (dd, J = 2.3 and 8.3 Hz, 1H), 7.76 (d, J = 2.3 Hz, 1H), 7.43 (d, J = 8.4 Hz, 1H), 2.30 (s, 3H), 1.77 (s, 6H). | 392.2 |

TABLE G-continued

| Ex. No. | SM | Product | Method | Yield (%) | ¹H NMR (400 or 500 MHz, DMSO-d₆): δ | MS (m/z: M + H⁺) |
|---|---|---|---|---|---|---|
| F55 | C1 | | K | 30 | 10.3 (s, 1H), 8.04 (s, 1H), 7.94 (d, J = 7.6 Hz, 1H), 7.75 (m, 2H), 7.69 (d, J = 2.0 Hz, 1H), 7.60 (t, J = 8.0 Hz, 1H), 7.33 (d, J = 8.4 Hz, 1H), 7.10 (s, 1H), 6.81 (s, 1H), 4.87 (t, J = 5.6 Hz, 1H), 4.31 (t, J = 4.8 Hz, 2H), 3.73 (q, J = 5.2 Hz, 2H), 2.24 (s, 3H), 1.74 (s, 6H). | 450.2 |
| F56 | C1 | | K | 28 | 10.3 (s, 1H), 8.04 (s, 1H), 7.93 (d, J = 6.8 Hz, 1H), 7.75 (m, 2H), 7.68 (brs, 1H), 7.60 (t, J = 8.0 Hz, 1H), 7.32 (d, J = 8.4 Hz, 1H), 7.11 (s, 1H), 6.79 (s, 1H), 4.37 (t, J = 4.8 Hz, 2H), 3.93 (t, J = 5.6 Hz, 2H), 2.23 (s, 3H), 1.74 (s, 6H), 0.84 (s, 9H), 0.05 (s, 6H). | 564.3 |
| F57 | B38 | | K | 56 | 10.6 (s, 1H), 8.80 (d, J = 5.2 Hz, 1H), 8.02 (s, 1H), 7.98 (d, J = 8.0 Hz, 1H), 7.87 (dd, J = 1.2 and 5.2 Hz, 1H), 7.79-7.94 (m, 2H), 7.59 (d, J = 7.6, Hz, 1H), 7.53 (d, J = 8.0 Hz, 1H), 7.35 (d, J = 8.0 Hz, 1H), 2.32 (s, 3H), 1.76 (s, 6H). | 391.0 |
| F58 | B39 | | K | 53 | 10.6 (s, 1H), 8.81 (d, J = 4.8 Hz, 1H), 8.46 (d, J = 5.2 Hz, 1H), 8.02 (s, 1H), 7.81-7.88 (m, 3H), 7.63 (s, 1H), 7.57 (d, J = 5.2 Hz, 1H), 7.24 (d, J = 8.8 Hz, 1H), 3.83 (s, 3H), 1.77 (s, 6H). | 407.0 |
| F59 | B2 | | K | 78 | 10.6 (s, 1H), 8.81 (d, J = 4.8 Hz, 1H), 8.50 (d, J = 5.2 Hz, 1H), 8.00 (s, 1H), 7.86 (d, J = 4.8 Hz, 1H), 7.77 (dd, J = 2.0 and 8.0 Hz, 1H), 7.70 (s, 1H), 7.56 (s, 1H), 7.47 (d, J = 4.8 Hz, 1H), 7.37 (d, J = 8.4 Hz, 1H), 2.22 (s, 3H), 1.76 (s, 6H). | 390.9 |
| F60 | B40 | | K | 51 | 11.0 (s, 1H), 8.84 (d, J = 4.8 Hz, 1H), 8.03 (m, 4H), 7.88 (dd, J = 1.6 and 5.2 Hz, 1H), 7.67 (d, J = 1.2 Hz, 1H), 7.56-7.62 (m, 3H), 1.77 (s, 6H). | 401.2 |
| F61 | B41 | | K | 40 | 11.1 (s, 1H), 8.86 (d, J = 4.8 Hz, 1H), 8.61 (d, J = 4.8 Hz, 1H), 8.08 (brm, 3H), 8.02 (s, 1H), 7.88 (dd, J = 1.6 and 5.2 Hz, 1H), 7.80 (s, 1H), 7.68 (m, 1H), 1.77 (s, 6H). | 402.0 |
| F62 | B29 | | J | 68 | 10.8 (s, 1H), 8.87 (brs, 1H), 8.78 (brm, 1H), 8.05 (s, 2H), 8.83 (d, J = 4.4 Hz, 1H), 7.51 (brm, 3H), 7.42 (brm, 1H), 2.41 (s, 3H), 1.71 (d, J = 22.0 Hz, 6H). | 384.3 |

TABLE G-continued

| Ex. No. | SM | Product | Method | Yield (%) | $^1$H NMR (400 or 500 MHz, DMSO-$d_6$): δ | MS (m/z: M + H$^+$) |
|---|---|---|---|---|---|---|
| F63 | B12 | | K | 72 | 10.4 (s, 1H), 8.56 (d, J = 4.8 Hz, 1H), 7.73 (s, 1H), 7.71 (d, J = 2.0 Hz, 1H), 7.66 (d, J = 2.0 Hz, 1H), 7.55 (dd, J = 1.2 and 4.0 Hz, 1H), 7.43-7.51 (m, 2H), 7.41 (s, 1H), 7.28-7.37 (m, 2H), 2.21 (s, 3H), 2.18 (m, 1H), 0.97-1.01 (m, 4H). | 363.2 |
| F64 | B42 | | direct amid coupling with LiHMDS | crude | No Data | 379.2 |
| F65 | B30 | | J | 50 | 10.7 (s, 1H), 8.94 (d, J = 2.4 Hz, 1H), 8.70 (d, J = 5.2 Hz, 1H), 8.24 (d, J = 2.4 Hz, 1H), 8.02 (t, J = 8.0 Hz, 1H), 7.77 (s, 1H), 7.69 (m, 2H), 7.58 (d, J = 8.0 Hz, 1H), 3.12 (m, 1H), 2.53 (s, 3H), 1.28 (d, J = 6.8 Hz, 6H). | 367.3 |
| F66 | B53 | | K | 55 | No Data | 398.2 |
| F67 | B54 | | K | crude | No Data | 382.0 |
| F68 | B54 | | K | 98 | No Data | 402.2 |
| F69 | B57 | | J (EDC) | 87 | 10.6 (s, 1H), 8.80 (d, J = 5.0 Hz, 1H), 8.66 (d, J = 2.4 Hz, 1H), 8.55 (d, J = 1.8 Hz, 1H), 8.01 (s, 1H), 7.99 (t, J = 2.2 Hz, 1H), 7.86 (dd, J = 1.5 and 5.1 Hz, 1H), 7.76 (m, 1H), 7.69 (d, J =2.3 Hz, 1H), 7.35 (d, J =8.3 Hz, 1H), 2.23 (s, 3H), 1.76 (s, 6H). | 391.2 |
| F70 | B12 | | L | 92 | 10.5 (s, 1H), 8.79 (d, J = 5.1 Hz, 1H), 8.00 (s, 1H), 7.85 (d, J = 5.1 Hz, 1H), 7.72 (dd, J = 2.4 and 8.1 Hz, 1H), 7.64 (s, 1H), 7.44-7.50 (m, 2 H), 7.41 (s, 1H), 7.29-7.34 (m, 2 H), 2.21 (s, 3 H), 1.75 (s, 6 H). | 390.2 |

TABLE G-continued

| Ex. No. | SM | Product | Method | Yield (%) | ¹H NMR (400 or 500 MHz, DMSO-d$_6$): δ | MS (m/z: M + H⁺) |
|---|---|---|---|---|---|---|
| F71 | E13 (2-chloro-4-bromo-5-fluoropyridine) | biaryl amide product | M | 99 | No Data | 385.2 |
| F72 | E13 (2-chloro-4-bromo-6-methylpyridine) | biaryl amide product | M | crude | No Data | 398.2 |
| F73 | E14 (2-chloropyridin-4-yl boronic acid) | CF$_3$ biaryl amide product | M | 57 | No Data | 438.0 |
| F74 | B60 (2-(2-fluoropropan-2-yl)isonicotinic acid) | biaryl amide product | L | 85 | No Data | 398.0 |
| F75 | E13 (3-chloro-5-bromopyridazine) | biaryl amide product | M | 99 | No Data | 385.2 |
| F76 | E13 (4,6-dichloropyrimidine) | biaryl amide product | M | 48 | 10.7 (s, 1H), 9.16 (d, J = 1.0 Hz, 1H), 8.76 (d, J = 5.0 Hz, 1H), 8.05 (d, J = 1.6 Hz, 1H), 7.97 (d, J = 2.3 Hz, 1H), 7.93 (d, J = 1.1 Hz, 1H), 7.82-7.89 (m, 2H), 7.38 (d, J = 8.4 Hz, 1H), 2.39 (s, 3H), 1.74 (s, 3H), 1.68 (s, 3H) | 385.0 |
| F77 | E15 (2-chloropyridin-4-yl boronic acid) | difluoro biaryl amide product | M | 39 | No Data | 406.2 |
| F78 | E16 (2-chloropyridin-4-yl boronic acid) | bipyridyl amide product | M | 74 | No Data | 371.0 |
| F79 | E17 (2-chloropyridin-4-yl boronic acid) | difluoro biaryl amide product | M | crude | No Data | 406.0 |
| F80 | B63 (2-(2-fluoropropan-2-yl)isonicotinic acid) | biaryl amide product | L | 38 | 10.79 (s, 1H), 8.77 (d, J = 5.0 Hz, 1H), 8.54 (d, J = 5.0 Hz, 1H), 8.04 (s, 1H), 7.91-7.96 (m, 2H), 7.83 (dd, J = 1.6 and 5.0 Hz, 1H), 7.65 (m, 2H), 7.55 (dd, J = 1.1 and 5.0 Hz, 1H), 1.70 (d, J = 22.0 Hz, 6H). | 404.0 |

TABLE G-continued

| Ex. No. | SM | Product | Method | Yield (%) | ¹H NMR (400 or 500 MHz, DMSO-d₆): δ | MS (m/z: M + H⁺) |
|---|---|---|---|---|---|---|
| F81 | E18 | | M | 40 | 10.71 (s, 1H), 8.76 (dd, J = 1.0 and 5.1 Hz, 1H), 8.52 (d, J = 5.2 Hz, 1H), 8.04 (m, 2H), 7.92 (m, 1H), 7.82 (dd, J = 1.6 and 5.1 Hz, 1H), 7.68 (s, 1H), 7.60 (m, 1H), 7.35 (m, 1H), 1.69 (d, J = 22.2 Hz, 6H). | 388.0 |
| F82 | B11 | | L | 39 | No Data | 402.0 |
| F83 | B64 | | J (EDC) | crude | No Data | 385.0 |

General Method N: Substitution Reaction

Example G1: N-(3-(2-chloro-6-ethoxypyridin-4-yl)-4-methylphenyl)-2-(trifluoromethyl)isonicotinamide

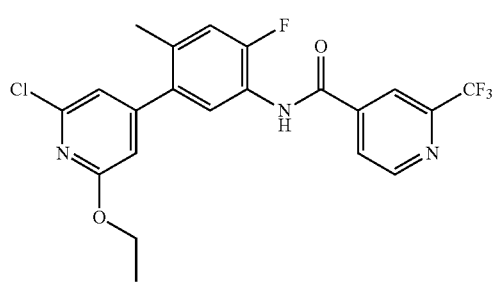 [SMILES: CCOc1cc(-c2cc(NC(=O)c3ccnc(C(F)(F)F)c3)c(F)cc2C)cc(Cl)n1]

A solution of N-(5-(2-chloro-6-fluoropyridin-4-yl)-2-fluoro-4-methylphenyl)-2-(trifluoromethyl) isonicotinamide (F13, 0.3 g, 0.70 mmol) in 1,4-dioxane (3.0 mL) was treated with NaOEt (21% in ethanol, 0.45 mL, 1.40 mmol). The reaction mixture was stirred at rt for 2.5 h. The reaction mixture was quenched with water (10 mL) and the solution was extracted with EtOAc (3×20 mL). The combined organic extracts were washed with brine (10 mL), dried over anhydrous Na₂SO₄, filtered and concentrated under reduced pressure to obtain N-(5-(2-chloro-6-ethoxypyridin-4-yl)-2-fluoro-4-methylphenyl)-2-(trifluoromethyl)isonicotinamide (0.25 g, 92% yield) as light brown solid. ¹H NMR (400 MHz, DMSO-d₆): δ 10.6 (s, 1H), 9.00 (d, J=4.8 Hz, 1H), 8.35 (s, 1H), 8.18 (d, J=4.4 Hz, 1H), 7.59 (d, J=8.0 Hz, 1H), 7.36 (d, J=11.6 Hz, 1H), 7.09 (s, 1H), 6.80 (s, 1H), 4.34 (q, J=7.2 Hz, 2H), 2.25 (s, 3H), 1.33 (t, J=7.2 Hz, 3H); MS (ESI) m/z: 454.1 (M+H⁺).

General Method O: Suzuki Reaction

Intermediate G2: N-(3-(2-chloro-6-cyclopropylpyridin-4-yl)-4-methylphenyl)-2-(trifluoromethyl)isonicotinamide

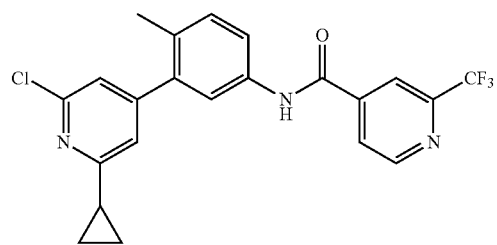 [SMILES: Cc1ccc(NC(=O)c2ccnc(C(F)(F)F)c2)cc1-c1cc(Cl)nc(C2CC2)c1]

A mixture of cyclopropylboronic acid (0.22 g, 2.5 mmol), N-(3-(2,6-dichloropyridin-4-yl)-4-methylphenyl)-2-(trifluoromethyl)isonicotinamide (F4, 1.0 g, 2.3 mmol) and K₃PO₄ (1.0 g, 4.7 mmol) in a mixture of toluene (10 mL) and water (1.2 mL) was sparged with Ar for 2 min. Pd(OAc)₂ (53 mg, 0.23 mmol) and tricyclohexylphosphane (0.10 g, 0.35 mmol) were added. The reaction mixture was heated to 90° C. for 3 h. The reaction was cooled to rt and then diluted with DCM (30 mL). The solution was filtered through a pad of celite and the filtrate was treated with sat'd NaHCO₃ (aq, 50 mL). The organic layer was dried over anhydrous MgSO₄, filtered, and concentrated under reduced pressure to yield a brown oil. The crude was purified silica gel column chromatography (0 to 50% EtOAc/hexanes) to afford N-(3-(2-chloro-6-cyclopropylpyridin-4-yl)-4-methylphenyl)-2-(trifluoromethyl)isonicotinamide (0.23 g, 23% yield) as a clear solid. ¹H NMR (500 MHz, DMSO-d₆): δ 10.7 (s, 1H), 8.99 (d, J=5.0 Hz, 1H), 8.36 (s, 1H), 8.18 (d, J=5.0 Hz, 1H), 7.77 (dd, J=2.2 and 8.4 Hz, 1H), 7.68 (d, J=2.2 Hz, 1H), 7.36 (m, 2H), 7.24 (s, 2H), 2.24 (s, 3H), 2.17 (m, H), 1.01 (m, 2H), 0.95 (i, 2H); MS (ESI) m/z: 432.0 (M+H).

Using the General Methods A, N and O above, the following Intermediates of Table H were prepared.

TABLE H
| Ex. No. | SM | Product | Method | Yield (%) | ¹H NMR (400 or 500 MHz, DMSO-d₆): δ | MS (m/z: M + H⁺) |
|---|---|---|---|---|---|---|
| G3 | F12 OH |  | N | 75 | 10.6 (s, 1H), 8.99 (d, J = 5.2 Hz, 1H), 8.36 (s, 1H), 8.18 (d, J = 4.4 Hz, 1H), 7.75 (dd, J = 2.0 and 8.4 Hz, 1H), 7.73 (s, 1H), 7.35 (d, J = 8.4 Hz, 1H), 7.08 (s, 1H), 6.79 (s, 1H), 4.31 (q, J = 6.8 Hz, 2H), 2.26 (s, 3H), 1.33 (t, J = 6.8 Hz, 3H). | 436.0 |
| G4 | F13 OH | 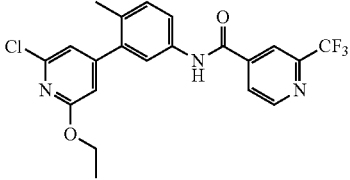 [SMILES: CCOc1cc(-c2cc(NC(=O)c3ccnc(C(F)(F)F)c3)ccc2C)cc(Cl)n1] | N | 90 | 10.7 (s, 1H), 9.00 (d, J = 4.8 Hz 1H), 8.39 (d, J = 15.0 Hz 1H), 8.18 (d, J = 4.0 Hz, 1H), 7.59 (d, J = 8.0 Hz, 1H), 7.36 (d, J = 11.2 Hz, 1H), 7.06 (s, 1H), 6.74 (s, 1H), 5.21 (m, 1H), 2.32 (s, 3H), 1.39 (d, J = 6.4 Hz, 6H). | 468.3 |
| G5 | F19 |  | A | crude | No Data | 387.0 (boronic acid) |
| G6 | C6 E3 | 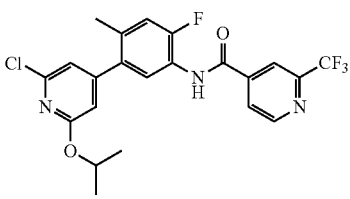 [SMILES: Cc1cc(F)c(NC(=O)c2ccnc(C(F)(F)F)c2)cc1-c1cc(Cl)nc(OC(C)C)c1] | O | 11 | No Data | 539.2 |
| G7 | F70 | 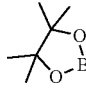 | A | crude | No Data | 482.0 |
| G8 | F38 | 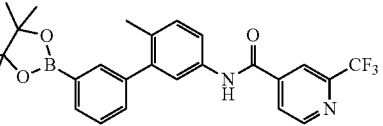 | A | crude | No Data | 501.0 |
| G9 | F43 | 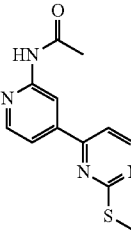 | A | 60 | No Data | 481.1 |
| G10 | F44 | 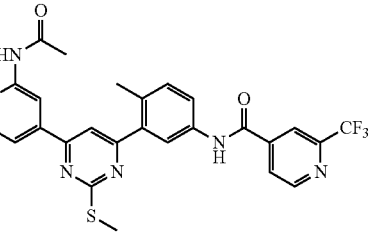 | A | crude | 10.8 (s, 1H), 8.88 (d, J = 2.4 Hz, 1H), 8.83 (d, J = 4.8 Hz, 1H), 8.03-8.11 (m, 2H), 7.94 (s, 1H), 7.88 (dd, J = 1.2 and 4.8 Hz, 1H), 7.73 (d, J = 7.2 Hz, 1H), 7.62 (m, 1H), 7.52 (t, J = 7.2 Hz, 1H), 2.41 (s, 3H), 1.76 (s, 6H), 1.30 (s, 12H). | 483.1 |

TABLE H-continued

| Ex. No. | SM | Product | Method | Yield (%) | ¹H NMR (400 or 500 MHz, DMSO-d₆): δ | MS (m/z: M + H⁺) |
|---|---|---|---|---|---|---|
| G11 | F48 | | A | crude | 10.4 (s, 1H), 8.19 (d, J = 7.2 Hz, 2H), 7.84 (s, 1H), 7.74 (m, 1H), 7.61 (s, 1H), 7.68 (d, J = 7.2 Hz, 1H), 7.47 (m, 1H), 7.42 (s, 2H), 7.29 (m, 1H), 3.56 (s, 2H), 2.20 (s, 3H), 2.18 (s, 6H), 1.30 (s, 12H). | 539.1 |
| G12 | F50 | | A | crude | No Data | 496.1 |
| G13 | F51 | | A | 41 | 10.5 (brs, 1H), 8.80 (d, J = 4.8 Hz, 1H), 8.00 (brm, 1H), 7.86 (br d, J = 4.8 Hz, 1H), 7.72 (m, 2H), 7.59 (d, J = 8.0 Hz, 1H), 7.37 (brs, 1H), 7.33 (t, J = 8.8 Hz, 1H), 7.15 (s, 1H), 2.25 (s, 3H), 2.02 (m, 1H), 1.76 (s, 6H), 1.30 (s, 12H), 0.96 (m, 2H), 0.70 (m, 2H). | 522.4 |
| G14 | F53 | | A | 38 | No Data | 523.1 |
| G15 | B57 | | A & J | crude | No Data | 483.1 |
| G16 | F58 | | A | 57 | 10.5 (s, 1H), 7.80 (d, J = 4.8 Hz, 1H), 8.01 (s, 1H), 7.88 (d, J = 1.6 Hz, 1H), 7.80 (dd, J = 2.4 and 8.8 Hz, 1H), 7.73 (s, 1H), 7.66 (m, 3H), 7.46 (t, J = 7.6 Hz, 1H), ), 7.15 (d, J = 9.2 Hz, 1H), 3.76 (s, 3H), 1.76 (s, 6H), 1.30 (s, 12H). | 498.3 |
| G17 | F60 | | A | 78 | 11.0 (s, 1H), 8.84 (d, J = 5.2 Hz, 1H), 8.07 (d, J = 1.6 Hz, 1H), 8.04 (dd, J = 2.0 and 8.4 Hz, 1H), 7.92-8.00 (m, 3H), 7.89 (dd, J = 1.2 and 5.2 Hz, 1H), 7.81 (s, 1H), 7.78 (m, 1H), 7.58 (t, J = 7.6 Hz, 1H), 1.77 (s, 6H), 1.31 (s, 12H). | 493.1 |
| G18 | F62 | | A | 79 | 10.7 (s, 1H), 8.89 (d, J = 2.4 Hz, 1H), 8.77 (d, J = 5.2 Hz, 1H), 8.09 (brs, 1H), 8.03 (d, J = 2.0 Hz, 1H), 7.84 (d, J = 4.8 Hz, 1H), 7.72 (d, J = 7.6 Hz, 1H), 7.64 (s, 1H), 7.61 (d, J = 7.6 Hz, 1H), 7.52 (t, J = 7.6 Hz, 1H), 2.41 (s, 3H), 1.71 | 476.4 |

TABLE H-continued
| Ex. No. | SM | Product | Method | Yield (%) | ¹H NMR (400 or 500 MHz, DMSO-d₆): δ | MS (m/z: M + H⁺) |
|---|---|---|---|---|---|---|
| | | | | | (d, J = 22.0 Hz, 6H), 1.31 (s, 12H). | |
| G19 | F63 | 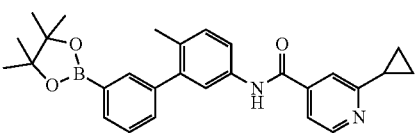 [SMILES: Cc1ccc(NC(=O)c2ccnc(C3CC3)c2)cc1-c1cccc(B2OC(C)(C)C(C)(C)O2)c1] | A | 80 | 10.4 (s, 1H), 8.56 (d, J = 4.8 Hz, 1H), 7.74 (br m, 2H), 7.68 (brd, J = 7.6 Hz, 1H), 7.64-7.71 (brm, 2H), 7.57 (brm, 1H), 7.45-7.55 (m, 2H), 7.29 (brd, J = 8.4 Hz, 1H), 2.19 (s, 3H), 2.18 (m, 1H), 1.30 (s, 12H), 0.98 (m, 4H). | 455.1 |
| G20 | F34 | 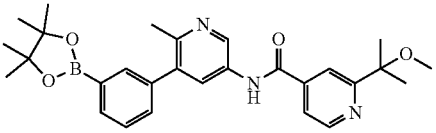 | A | Crude | 10.7 (s, 1H), 8.89 (d, J = 2.4 Hz, 1H), 8.74 (d, J = 4.8 Hz, 1H), 8.03 (brm, 2H), 7.95 (s, 1H), 7.88 (d, J = 5.2 Hz, 1H), 7.73 (d, J = 7.2 Hz, 1H), 7.62 (m, 1H), 7.48-7.55 (m, 1H), 3.12 (s, 3H), 2.32 (s, 3H), 1.51 (s, 6H), 1.31 (s, 12H). | 488.1 |
| G21 | F16 | 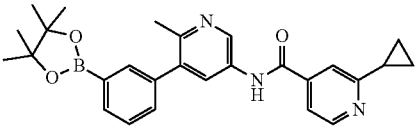 [SMILES: Cc1ncc(NC(=O)c2ccnc(C3CC3)c2)cc1-c1cccc(B2OC(C)(C)C(C)(C)O2)c1] | A | 89 | No Data | 456.2 |
| G22 | F10 | 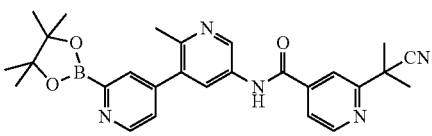 [SMILES: Cc1ncc(NC(=O)c2ccnc(C(C)(C)C#N)c2)cc1-c1ccnc(B2OC(C)(C)C(C)(C)O2)c1] | A | crude | No Data | 484.2 |
| G23 | F8 | 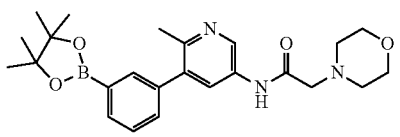 [SMILES: Cc1ncc(NC(=O)CN2CCOCC2)cc1-c1cccc(B2OC(C)(C)C(C)(C)O2)c1] | A | crude | No Data | 438.2 |
| G24 | F67 | 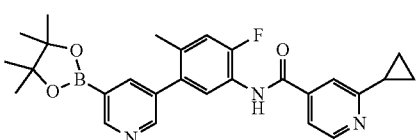 | A | crude | No Data | 392.2 (boronic acid) |
| G25 | F69 | 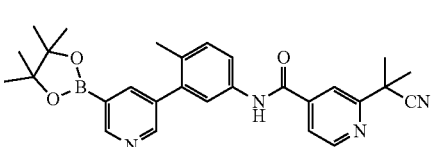 | A | crude | No Data | 401.2 (boronic acid) |

General Method P: Suzuki Reaction

Example 1a: N-(3-(2'-acetamido-6-(2-((tert-butyldiphenylsilyl)oxy)ethoxy)-[2,4'-bipyridin]-4-yl)-4-methylphenyl)-2-(trifluoromethyl)isonicotinamide

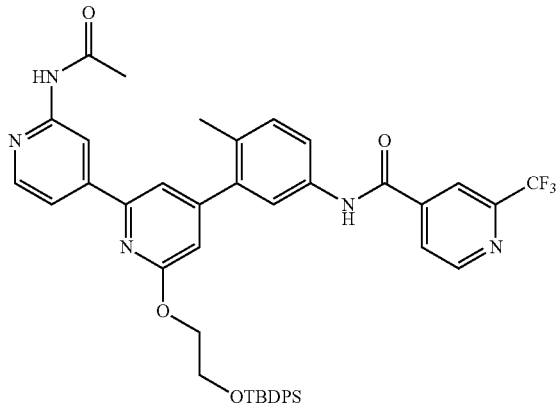

A solution of N-(3-(2-(2-((tert-butyldimethylsilyl)oxy)ethoxy)-6-chloropyridin-4-yl)-4-methylphenyl)-2-(trifluoromethyl)isonicotinamide (F5, 0.17 g, 0.30 mmol) and N-(4-(4,4,5,5-tetramethyl-1,3,2-dioxaborolan-2-yl)pyridin-2-yl)acetamide (A5, 0.12 g, 0.45 mmol) in a mixture of EtOH (3.0 mL) and toluene (3.0 mL) was treated with K$_2$CO$_3$ (2.0 N, 0.30 mL, 0.60 mmol). The reaction mixture was sparged with Ar for 2 min and then Xphos Pd G2 (24 mg, 0.03 mol) was added. The mixture was heated at 80° C. under Ar overnight. The reaction was cooled to rt and quenched with sat'd NaHCO$_3$ (aq, 30 mL). The solution was extracted with DCM (4×25 mL). The combined organics were dried over anhydrous Na$_2$SO$_4$, filtered, and concentrated under reduced pressure to afford a brown oil. The brown oil was purified by silica gel column chromatography (0 to 80% EtOAc/hexanes) to afford N-(3-(2'-acetamido-6-(2-((tert-butyldimethylsilyl)oxy)ethoxy)-[2,4'-bipyridin]-4-yl)-4-methylphenyl)-2-(trifluoromethyl)isonicotinamide (0.18 g, crude) as a yellow oil.

General Method Q: Deprotection

Example 1: N-(3-(2'-acetamido-6-(2-hydroxyethoxy)-[2,4'-bipyridin]-4-yl)-4-methylphenyl)-2-(trifluoromethyl)isonicotinamide

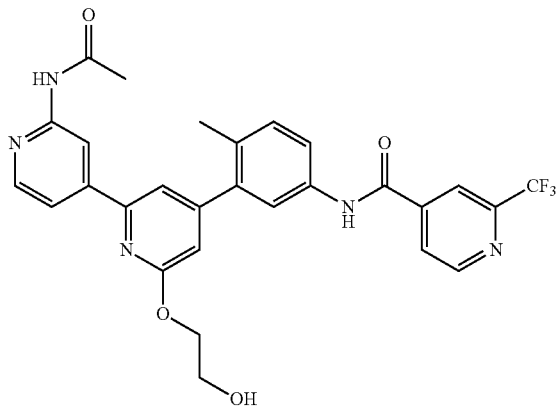 [SMILES: CC(=O)Nc1cc(-c2cc(-c3cc(NC(=O)c4ccnc(C(F)(F)F)c4)ccc3C)cc(OCCO)n2)ccn1]

A solution of N-(3-(2'-acetamido-6-(2-((tert-butyldimethylsilyl)oxy)ethoxy)-[2,4'-bipyridin]-4-yl)-4-methylphenyl)-2-(trifluoromethyl)isonicotinamide (1a, 0.18 g, 0.30 mmol) in THF (10 mL) was treated with TBAF (1.0 M in THF, 0.90 mL, 0.90 mmol). The reaction mixture was stirred at rt for 3 h. The reaction was concentrated under reduced pressure. The crude was purified by silica gel column chromatography (0 to 7% MeOH/DCM) to obtain N-(3-(2'-acetamido-6-(2-hydroxyethoxy)-[2,4'-bipyridin]-4-yl)-4-methylphenyl)-2-(trifluoromethyl)isonicotinamide (0.11 g, 68% yield) as a white solid. $^1$H NMR (500 MHz, DMSO-d$_6$): δ 10.7 (s, 1H), 10.6 (s, 1H), 8.98 (d, J=5.0 Hz, 1H), 8.80 (s, 1H), 8.40 (d, J=5.3 Hz, 1H), 8.37 (s, 1H), 8.19 (d, J=5.0 Hz, 1H), 7.78 (m, 2H), 7.74 (d, J=2.2 Hz, 1H), 7.56 (s, 1H), 7.38 (d, J=8.4 Hz, 1H), 6.89 (s, 1H), 4.88 (t, J=5.5 Hz, 1H), 4.46 (t, J=5.1 Hz, 2H), 3.81 (m, 2H), 2.28 (s, 3H), 2.11 (s, 3H); MS (ESI) m/z: 552.2 (M+H$^+$).

General Method R: Amide Coupling Reaction

Example 21: N-(3-(2'-acetamido-1-methyl-2-oxo-1,2-dihydro-[3,4'-bipyridin]-5-yl)-4-methylphenyl)-2-(trifluoromethyl)isonicotinamide

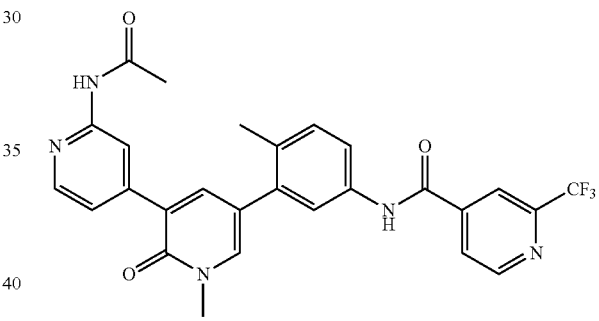

A solution of 2-(trifluoromethyl)isonicotinic acid (0.13 g, 0.69 mmol) in DMF (5 mL) was treated with DIEA (0.5 mL, 2.87 mmol). HATU (0.44 g, 1.15 mmol) was added and then the reaction mixture was stirred at rt for 15 min. N-(5-(5-amino-2-methylphenyl)-1-methyl-2-oxo-1,2-dihydro-[3,4'-bipyridin]-2'-yl)acetamide (D2, 0.2 g, 0.57 mmol) was added and the reaction mixture was stirred at rt for 5 h. The mixture was quenched with chilled water (10 mL) and the solution was extracted with EtOAc (4×30 mL). The combined organic extracts were dried over anhydrous Na$_2$SO$_4$, filtered and concentrated under reduced pressure. The crude was purified by silica gel column chromatography (0 to 100% EtOAc/heptane) to obtain N-(3-(2'-acetamido-1-methyl-2-oxo-1,2-dihydro-[3,4'-bipyridin]-5-yl)-4-methylphenyl)-2-(trifluoromethyl)isonicotinamide (0.055 g, 18% yield) as a pale yellow solid. $^1$H NMR (400 MHz, DMSO-d$_6$): δ 10.7 (s, 1H), 10.4 (s, 1H), 8.99 (d, J=4.8 Hz, 1H), 8.44 (s, 1H), 8.36 (s, 1H), 8.30 (d, J=5.2 Hz, 1H), 8.19 (d, J=4.4 Hz, 1H), 7.96 (brs, 1H), 7.72 (m, 3H), 7.48 (m, 1H), 7.34 (d, J=8.4 Hz, 1H), 3.60 (s, 3H), 2.31 (s, 3H), 2.08 (s, 3H); MS (ESI) m/z: 522.2 (M+H$^+$).

General Method S: Amide Coupling and Substitution

Example 39: N-(3-(2'-(2-cyanoacetamido)-[2,4'-bipyridin]-4-yl)-4-methylphenyl)-2-(trifluoromethyl)isonicotinamide

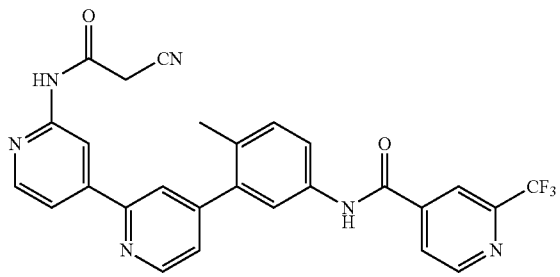 [SMILES: Cc1ccc(NC(=O)c2ccnc(C(F)(F)F)c2)cc1-c1ccnc(-c2ccnc(NC(=O)CC#N)c2)c1]

A solution of N-(3-(2'-amino-[2,4'-bipyridin]-4-yl)-4-methylphenyl)-2-(trifluoromethyl)isonicotinamide (16, 0.10 g, 0.22 mmol) in EtOAc (10 ml) was treated with sat'd NaHCO$_3$ (aq, 10 mL). 2-Chloroacetyl chloride (0.1 mL, 1.1 mmol) was added dropwise under an ice-water bath and then the reaction mixture was allowed to warm to rt. The reaction mixture was stirred at rt for 4 h. The aqueous layer was extracted with EtOAc (3×20 mL). The combined organics were dried over anhydrous Na$_2$SO$_4$, filtered and concentrated under reduced pressure to obtain N-(3-(2'-(2-chloroacetamido)-[2,4'-bipyridin]-4-yl)-4-methylphenyl)-2-(trifluoromethyl)isonicotinamide (0.11 g, crude).

A solution of N-(3-(2'-(2-chloroacetamido)-[2,4'-bipyridin]-4-yl)-4-methylphenyl)-2-(trifluoromethyl)isonicotinamide (0.11 g, 0.22 mmol) in DMSO (5 mL) was treated with NaCN (0.022 g, 0.45 mmol). The reaction mixture was stirred at rt for 1 h. The reaction mixture was quenched with sat'd NaHCO$_3$ (aq, 40 mL) and the solution was extracted with DCM (4×20 mL). The combined organics were dried over anhydrous Na$_2$SO$_4$, filtered and concentrated under reduced pressure to obtain N-(3-(2'-(2-cyanoacetamido)-[2,4'-bipyridin]-4-yl)-4-methylphenyl)-2-(trifluoromethyl)isonicotinamide (0.026 g, 23% yield) as a yellow solid. $^1$H NMR (400 MHz, DMSO-d$_6$): δ 11.0 (s, 1H), 10.8 (s, 1H), 8.98 (d, J=5.0 Hz, 1H), 8.82 (d, J=5.0 Hz, 1H), 8.79 (brs, 1H), 8.44 (d, J=5.0 Hz, 1H), 8.38 (s, 1H), 8.21 (d, J=5.0 Hz, 1H), 8.02 (s, 1H), 7.88 (dd, J=1.6 and 5.3 Hz, 1H), 7.82 (dd, J=2.2 and 8.3 Hz, 1H), 7.76 (d, J=2.2 Hz, 1H), 7.53 (dd, J=1.5 and 5.0 Hz, 1H), 7.40 (d, J=8.4 Hz, 1H), 4.02 (s, 2H), 2.29 (s, 3H); MS (ESI) m/z: 517.2 (M+H$^+$).

General Method T: Oxidation and Substitution

Example 41: N-(3-(6-(2-acetamidopyridin-4-yl)-2-(dimethylamino)pyrimidin-4-yl)-4-methylphenyl)-2-(trifluoromethyl)isonicotinamide

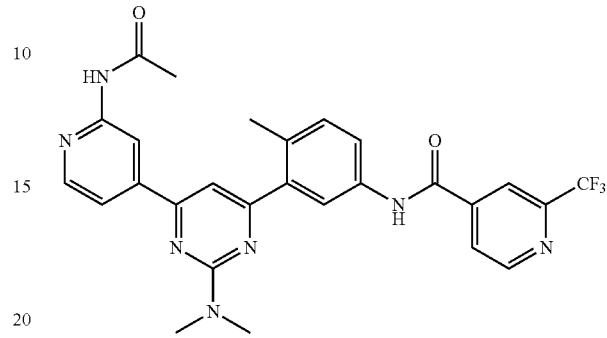

A suspended of N-(3-(6-(2-acetamidopyridin-4-yl)-2-(methylthio)pyrimidin-4-yl)-4-methylphenyl)-2-(trifluoromethyl)isonicotinamide (G6, 0.15 g, 0.27 mmol) in DCM (5 mL) was cooled to 0° C. and mi-CPBA (0.070 g, 0.30 mmol) was added. The mixture was warmed to rt and stirred at rt for 30 min. The reaction mixture was treated with sat'd NaHCO$_3$ solution (25 mL) and stirred for 15 min. The aqueous layer was extracted with DCM (2×25 mL) and the combined organics were dried over anhydrous Na$_2$SO$_4$, filtered and concentrated under reduced pressure to obtain N-(3-(6-(2-acetamidopyridin-4-yl)-2-(methylsulfinyl)pyrimidin-4-yl)-4-methylphenyl)-2-(trifluoromethyl)isonicotinamide (0.15 g, crude).

A solution of N-(3-(6-(2-acetamidopyridin-4-yl)-2-(methylsulfinyl)pyrimidin-4-yl)-4-methylphenyl)-2-(trifluoromethyl)isonicotinamide (0.15 g, 0.27 mmol) in THF (3 mL) was added dimethylamine (2 N in THF, 0.41 mL, 0.82 mmol). The reaction mixture was stirred at rt for 3 h. The solution was quenched with 5% Na$_2$SO$_3$ (aq, 30 mL) and the extracted with DCM (3×25 mL). The combined organic extracts were dried over anhydrous Na$_2$SO$_4$, filtered and concentrated under reduced pressure. The crude was purified by silica gel column chromatography (0 to 50%, EtOAc/hexanes) to obtain N-(3-(6-(2-acetamidopyridin-4-yl)-2-(dimethylamino)pyrimidin-4-yl)-4-methylphenyl)-2-(trifluoromethyl)isonicotinamide (0.034 g, 23% yield). $^1$H NMR (400 MHz, DMSO-d$_6$): δ 10.8 (s, 1H), 10.6 (s, 1H), 8.99 (d, J=5.0 Hz, 1H), 8.85 (s, 1H), 8.44 (d, J=5.2 Hz, 1H), 8.38 (s, 8H), 8.20 (d, J=5.0 Hz, 1H), 7.90 (d, J=2.3 Hz, 1H), 7.84 (dd, J=2.3 and 8.3 Hz, 1H), 7.80 (dd, J=1.6 and 5.2 Hz, 1H), 7.37 (d, J=8.3 Hz, 1H), 7.25 (s, 1H), 3.25 (s, 6H), 2.42 (s, 3H), 2.12 (s, 3H); MS (ESI) m/z: 536.2 (M+H$^+$).

Using the General Methods K, P, Q, R, S and T above, the following Intermediates of Table I were prepared.

TABLE I

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| 2 | A5 F14 | | P | 64 | 10.7 (s, 1H), 10.6 (s, 1H), 8.99 (d, J = 5.0 Hz, 1H), 8.81 (t, J = 5.0 Hz, 2H), 8.40 (d, J = 5.3 Hz, 1H), 8.37 (s, 1H), 8.19 (d, J = 5.0 Hz, 1H), 7.96 (s, 1H), 7.79 (dd, J = 1.6 and 5.3 Hz, 1H), 7.64 (d, J = 7.7 Hz, 1H), 7.51 (d, J = 5.0 | 510.2 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| | | | | | Hz, 1H), 7.40 (d, J = 11.4 Hz, 1H), 2.32 (s, 3H), 2.11 (s, 3H). | |
| 3 | A6 F1 | | P | 41 | 10.8 (s, 1H), 8.99 (d, J = 5.0 Hz, 1H), 8.85 (t, J = 5.0 Hz, 2H), 8.75 (m, 2H), 8.37 (s, 1H), 8.33 (dd, J = 1.8 and 5.1 Hz, 1H), 8.18 (m, 2H), 7.82 (dd, J = 2.3 and 8.3 Hz, 1H), 7.76 (d, J = 2.2 Hz, 1H), 7.54 (m, 1H), 7.40 (d, J = 8.4 Hz, 1H), 2.85 (d, J = 4.8 Hz, 3H), 2.29 (s, 3H). | 492.2 |
| 4 | A5 F7 | | P | 39 | 10.7 (s, 1H), 10.6 (s, 1H), 8.99 (d, J = 5.0 Hz, 1H), 8.76 (s, 1H), 8.39 (d, J = 5.3 Hz, 1H), 8.36 (s, 1H), 8.19 (d, J = 5.0 Hz, 1H), 7.76 (dd, J = 1.6 and 5.3 Hz, 1H), 7.74 (s, 1H), 7.61 (d, J = 7.7 Hz, 1H), 7.38 (s, 1H), 7.37 (s, 1H), 2.62 (s, 3H), 2.31 (s, 3H), 2.11 (s, 3H). | 524.2 |
| 5 | A5 F6 | | P | 57 | 10.7 (s, 1H), 10.6 (s, 1H), 8.98 (d, J = 5.0 Hz, 1H), 8.77 (s, 1H), 8.39 (d, J = 5.2 Hz, 1H), 8.37 (s, 1H), 8.19 (d, J = 5.0 Hz, 1H), 7.80 (dd, J = 2.3 and 8.3 Hz, 1H), 7.77 (dd, J = 1.6 and 5.3 Hz, 1H), 7.72 (m, 2H), 7.38 (m, 2H), 2.63 (s, 3H), 2.28 (s, 3H), 2.11 (s, 3H). | 506.2 |
| 6 | A5 F1 | | P | 28 | 10.8 (s, 1H), 10.6 (s, 1H), 8.98 (d, J = 5.0 Hz, 1H), 8.82 (t, J = 5.3 Hz, 2H), 8.41 (d, J = 5.3 Hz, 1H), 8.37 (s, 1H), 8.19 (d, J = 5.0 Hz, 1H), 7.97 (s, 1H), 7.80 (m, 2H), 7.74 (d, J = 2.2 Hz, 1H), 7.52 (dd, J = 1.5 and 5.0 Hz, 1H), 7.40 (d, J = 8.4 Hz, 1H), 2.28 (s, 3H), 2.11 (s, 3H). | 492.2 |
| 7 | A4 F14 | | P | 16 | 10.7 (s, 1H), 10.0 (s, 1H), 8.99 (d, J = 5.0 Hz, 1H), 8.86 (s, 1H), 8.82 (d, J = 5.0 Hz, 1H), 8.42 (d, J = 5.3 Hz, 1H), 8.37 (s, 1H), 8.19 (d, J = 5.0 Hz, 1H), 7.99 (s, 1H), 7.83 (d, J = 5.4 Hz, 1H), 7.64 (d, J = 7.7 Hz, 1H), 7.53 (d, J = 5.1 Hz, 1H), 7.40 (d, J = 11.3 Hz, 1H), 3.16 (s, 2H), 2.32 (s, 3H), 2.31 (s, 6H). | 553.2 |
| 8 | A5 G3 | | P | 30 | 10.7 (s, 1H), 10.6 (s, 1H), 8.99 (d, J = 5.2 Hz, 1H), 8.82 (s, 1H), 8.40 (d, J = 5.6 Hz, 1H), 8.37 (s, 1H), 8.19 (d, J = 4.8 Hz, 1H), 7.78 (m, 2H), 7.73 (d, J = 2.0 Hz, 1H), 7.55 (s, 1H), 7.38 (d, J = 8.4 Hz, 1H), 6.87 (s, 1H), 4.50 (m, 2H), 2.28 (s, 3H), 2.11 (s, 3H), 1.42 (t, J = 7.2 Hz, 3H). | 536.1 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 9 | A5 G1 | | P | 21 | 10.7 (s, 1H), 10.5 (s, 1H), 8.99 (d, J = 5.2 Hz, 1H), 8.81 (s, 1H), 8.39 (d, J = 5.2 Hz, 1H), 8.37 (s, 1H), 8.19 (d, J = 4.4 Hz, 1H), 7.77 (m, 1H), 7.62 (d, J = 7.6 Hz, 1H), 7.54 (s, 1H), 7.38 (d, J = 11.6 Hz, 1H), 6.87 (s, 1H), 4.49 (q, J = 7.2 Hz, 2H), 2.31 (s, 3H), 2.11 (s, 3H), 1.41 (t, J = 7.2 Hz, 3H). | 554.1 |
| 10 | A5 G4 | | P | 12 | 10.7 (s, 1H), 10.5 (s, 1H), 8.99 (d, J = 4.8 Hz, 1H), 8.83 (s, 1H), 8.38 (d, J = 5.2 Hz, 1H), 8.34 (s, 1H), 8.19 (d, J = 4.4 Hz, 1H), 7.76 (d, J = 5.2 Hz, 1H), 7.62 (d, J = 7.6 Hz, 1H), 7.52 (s, 1H), 7.37 (d, J = 11.2 Hz, 1H), 6.81 (s, 1H), 5.43 (m, 1H), 2.32 (s, 3H), 2.11 (s, 3H), 1.40 (d, J = 6.4 Hz, 6H). | 568.2 |
| 11 | A5 F2 | | P | 34 | 10.7 (s, 1H), 10.6 (s, 1H), 8.98 (d, J = 4.8 Hz, 1H), 8.44 (d, J = 5.2 Hz, 1H), 8.35 (s, 1H), 8.18 (d, J = 3.6 Hz, 2H), 7.75 (dd, J = 2.0 and 8.0 Hz, 1H), 7.71 (d, J = 1.6 Hz, 1H), 7.33 (m, 2H), 6.45 (d, J = 2.0 Hz, 1H), 6.20 (d, J = 1.6 Hz, 1H), 3.30 (s, 3H), 2.31 (s, 3H), 2.11 (s, 3H). | 522.1 |
| 12 | A3 G3 | | P | 20 | 10.8 (s, 1H), 10.7 (s, 1H), 8.99 (d, J = 5.2 Hz, 1H), 8.79 (s, 1H), 8.41 (d, J = 5.2 Hz, 1H), 8.37 (s, 1H), 8.19 (d, J = 4.8 Hz, 1H), 7.80 (m, 2H), 7.71 (d, J = 1.6 Hz, 1H), 7.52 (s, 1H), 7.38 (d, J = 8.4 Hz, 1H), 6.87 (s, 1H), 4.49 (q, J = 6.8 Hz, 2H), 2.23 (s, 3H), 2.02 (m, 1H), 1.39 (t, J = 6.8 Hz, 3H), 0.84 (m, 4H). | 562.1 |
| 13 | A3 F2 | | P | 23 | 11.0 (s, 1H), 10.6 (s, 1H), 8.98 (d, J = 5.2 Hz, 1H), 8.45 (d, J = 5.2 Hz, 1H), 8.35 (s, 1H), 8.18 (s, 2H), 7.75 (dd, J = 2.0 and 8.0 Hz, 1H), 7.69 (d, J = 2.0 Hz, 1H), 7.32 (m, 2H), 6.45 (d, J = 2.0 Hz, 1H), 6.19 (d, J = 1.6 Hz, 1H), 3.30 (s, 3H), 2.30 (s, 3H), 2.02 (m, 1H), 0.83 (m, 4H). | 548.1 |
| 14 | A5 G2 | | P | 39 | 10.7 (s, 1H), 10.6 (s, 1H), 8.98 (d, J = 5.0 Hz, 1H), 8.77 (s, 1H), 8.38 (m, 2H), 8.19 (d, J = 5.0 Hz, 1H), 7.80 (m, 2H), 7.72 (m, 2H), 7.67 (s, 1H), 7.38 (m, 2H), 2.28 (s, 3H), 2.27 (m, 1H), 2.11 (s, 3H), 1.10 (m, 2H), 1.04 (m, 2H). | 532.2 |

TABLE I-continued

| Ex. No. | SM | Product | Method | Yield (%) | $^1$H NMR (400 or 500 MHz, (DMSO-d$_6$): δ | MS (m/z: M + H$^+$) |
|---|---|---|---|---|---|---|
| 15 | A5 F9 | | P | 79 | 10.7 (s, 1H), 10.5 (s, 1H), 8.98 (d, J = 5.0 Hz, 1H), 8.77 (s, 1H), 8.36 (m, 2H), 8.19 (d, J = 5.0 Hz, 1H), 7.80 (dd, J = 2.2 and 8.3 Hz, 1H), 7.74 (d, J = 5.3 Hz, 1H), 7.69 (d, J = 2.2 Hz, 1H), 7.37 (d, J = 8.4 Hz, 1H), 7.24 (s, 1H), 6.88 (s, 1H), 3.74 (t, J = 4.7 Hz, 4H), 3.62 (t, J = 4.7 Hz, 4H), 2.27 (s, 3H), 2.10 (s, 3H). | 577.2 |
| 16 | F1 | | P & Q | 44 | 10.7 (s, 1H), 8.99 (d, J = 5.0 Hz, 1H), 8.76 (d, J = 5.0 Hz, 1H), 8.37 (s, 1H), 8.19 (d, J = 5.1 Hz, 1H), 8.01 (d, J = 5.4 Hz, 1H), 7.87 (s, 1H), 7.79 (d, J = 8.5 Hz, 1H), 7.74 (s, 1H), 7.46 (d, J = 5.0 Hz, 1H), 7.40 (d, J = 8.5 Hz, 1H), 7.24 (s, 1H), 7.19 (d, J = 5.4 Hz, 1H), 6.04 (s, 2H), 2.28 (s, 3H). | 450.2 |
| 17 | 16 | | S | 46 | 10.8 (s, 1H), 10.2 (brs, 1H), 8.99 (d, J = 5.0 Hz, 1H), 8.87 (s, 1H), 8.83 (d, J = 5.0 Hz, 1H), 8.43 (d, J = 5.3 Hz, 1H), 8.37 (s, 1H), 8.20 (d, J = 5.0 Hz, 1H), 8.01 (s, 1H), 7.86 (d, J = 5.3 Hz, 1H), 7.81 (m, 1H), 7.76 (s, 1H), 7.53 (d, J = 5.0 Hz, 1H), 7.41 (d, J = 8.4 Hz, 1H), 3.26 (brs, 2H), 2.41 (s, 6H), 2.29 (s, 3H). | 535.2 |
| 18 | A17 F1 | | P | 4 | 11.10 (s, 1H), 10.80 (s, 1H), 8.99 (d, J = 5.0Hz, 1H), 8.82 (s, 1H), 8.37 (s, 1H), 8.21 (d, J = 5.0 Hz, 1H), 8.18 (d, J = 5.6 Hz, 1H), 7.97 (s, 1H), 7.77-7.80 (m, 2H), 7.55 (d, J = 5.7 Hz, 1H), 7.49 (d, J = 5.1 Hz, 1H), 7.40 (d, J = 8.3 Hz, 1H), 3.93 (s, 2H), 2.30 (s, 3H). | 490.2 |
| 19 | A5 F15 | | P | 41 | 10.6 (s, 1H), 10.6 (s, 1H), 8.81 (m, 3H), 8.41 (d, J = 5.3 Hz, 1H), 7.99 (s, 1H), 7.98 (s, 1H), 7.86 (d, J = 5.1 Hz, 1H), 7.80 (m, 2H), 7.73 (d, J = 2.2 Hz, 1H), 7.52 (d, J = 5.0 Hz, 1H), 7.39 (d, J = 8.4 Hz, 1H), 2.28 (s, 3H), 2.11 (s, 3H), 1.75 (s, 6H). | 491.2 |
| 20 | A17 F40 | | P | 8 | 11.08 (s, 1H), 10.72 (s, 1H), 8.99 (d, J = 5.0 Hz, 1H), 8.36 (s, 1H), 8.15-8.19 (m, 2H), 7.76-7.78 (m, 2H), 7.74 (s, 1H), 7.53 (d, J = 5.6 Hz, 1H), 7.39 (d, J = 8.4 Hz, 1H), 7.34 (s, 1H), 3.94 (s, 2H), 2.63 (s, 3H), 2.29 (s, 3H). | 504.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 22 | C17 E6 | | P | 29 | 1H NMR (500 MHZ, DMSO) ? 11.25 (s, 1H), 10.68 (s, 1H), 9.12 (d, J = 5.2 Hz, 1H), 8.81 (d, J = 5.0 Hz, 1H), 8.36 (d, J = 2.4 Hz, 1H), 8.28 (d, J = 5.6 Hz, 1H), 8.06-8.02 (m, 2H), 7.89 (d, J = 5.0 Hz, 1H), 7.85 (dd, J = 8.3, 2.4 Hz, 1H), 7.65 (d, J = 5.6 Hz, 1H), 7.40 (d, J = 8.3 Hz, 1H), 4.01 (s, 2H), 2.56 (s, 3H), 1.77 (s, 6H). | 490.2 |
| 23 | D76 | | R (T3P) | 16 | 1H NMR (500 MHZ, DMSO) ? 11.13 (s, 1H), 10.64 (s, 1H), 8.83 (d, J = 5.0 Hz, 1H), 8.81 (d, J = 5.1 Hz, 1H), 8.19 (d, J = 5.6 Hz, 1H), 8.01 (s, 1H), 7.99 (s, 1H), 7.87 (dd, J = 5.0, 1.6 Hz, 1H), 7.78 (dd, J = 8.2, 2.3 Hz, 1H), 7.75 (d, J = 2.3 Hz, 1H), 7.56 (d, J = 5.6 Hz, 1H), 7.50 (dd, J = 4.9, 1.5 Hz, 1H), 7.40 (d, J = 8.3 Hz, 1H), 3.94 (s, 2H), 2.31 (s, 3H), 1.76 (s, 6H). | 489.2 |
| 24 | A5 F18 | | P | 20 | 10.8 (s, 1H), 10.6 (s, 1H), 9.12 (s, 1H), 9.08 (d, J = 5.2 Hz, 1H), 8.99 (d, J = 5.0 Hz, 1H), 8.48 (d, J = 5.2 Hz, 1H), 8.38 (s, 1H), 8.21 (d, J = 5.0 Hz, 1H), 8.01 (d, J = 3.6 Hz, 2H), 7.88 (dd, J = 2.3 and 8.3 Hz, 1H), 7.75 (d, J = 5.2 Hz, 1H), 7.44 (d, J = 8.4 Hz, 1H), 2.48 (s, 3H), 2.12 (s, 3H). | 493.2 |
| 25 | A6 F18 | | P | 67 | 10.8 (s, 1H), 9.11 (d, J = 5.1 Hz, 1H), 8.98 (m, 2H), 8.88 (d, J = 5.6 Hz, 1H), 8.84 (d, J = 5.1 Hz, 1H), 8.49 (d, J = 5.0 Hz, 1H), 8.38 (s, 1H), 8.21 (d, J = 5.0 Hz, 1H), 8.03 (d, J = 2.2 Hz, 1H), 7.88 (dd, J = 2.3 and 8.4 Hz, 1H), 7.80 (d, J = 5.2 Hz, 1H), 7.44 (d, J = 8.4 Hz, 1H), 2.85 (d, J = 4.8 Hz, 3H), 2.47 (s, 3H). | 493.2 |
| 26 | A5 F17 | | P | 49 | 10.9 (s, 1H), 10.6 (s, 1H), 8.85 (d, J = 4.3 Hz, 2H), 8.66 (d, J = 5.6 Hz, 1H), 8.41 (d, J = 5.3 Hz, 1H), 8.29 (d, J = 1.9 Hz, 1H), 8.06 (m, 2H), 7.99 (m, 2H), 7.81 (dd, J = 1.6 and 5.3 Hz, 1H), 7.58 (m, 2H), 2.38 (s, 3H), 2.11 (s, 3H). | 492.2 |
| 27 | A6 G2 | | P | 65 | 10.7 (s, 1H), 8.99 (d, J = 5.0 Hz, 1H), 8.82 (d, J = 5.5 Hz, 1H), 8.72 (d, J = 5.2 Hz, 1H), 8.67 (s, 1H), 8.37 (s, 1H), 8.26 (d, J = 5.2 Hz, 1H), 8.20 (d, J = 5.0 Hz, 1H), 7.90 (s, 1H), 7.80 (m, 1H), 7.74 (d, J = 2.2 Hz, 1H), 7.44 (s, 1H), 7.39 (d, J = 8.4 Hz, 1H), 2.84 (d, J = 4.8 Hz, 3H), | 532.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| | | | | | 2.29 (s, 4H), 1.12 (m, 2H), 1.07 (d, J = 8.0 Hz, 2H). | |
| 28 | A5 F19 | | P | 53 | 10.7 (s, 1H), 10.6 (s, 1H), 8.98 (d, J = 5.0 Hz, 1H), 8.42 (s, 1H), 8.37 (m, 2H), 8.19 (d, J = 5.0 Hz, 1H), 7.74 (m, 3H), 7.62 (m, 2H), 7.49 (d, J = 7.7 Hz, 1H), 7.46 (m, 1H), 7.35 (d, J = 8.3 Hz, 1H), 2.26 (s, 3H), 2.10 (s, 3H). | 491.2 |
| 29 | D11 | | R | 59 | 10.8 (s, 1H), 10.6 (s, 1H), 9.29 (s, 1H), 8.99 (d, J = 5.0 Hz, 1H), 8.92 (s, 1H), 8.87 (s, 1H), 8.48 (d, J = 5.2 Hz, 1H), 8.38 (s, 1H), 8.21 (d, J = 5.0 Hz, 1H), 7.97 (d, J = 2.2 Hz, 1H), 7.85 (m, 2H), 7.44 (d, J = 8.4 Hz, 1H), 2.44 (s, 3H), 2.11 (s, 3H). | 493.2 |
| 30 | A5 G5 | | P | 87 | 11.0 (s, 1H), 10.7 (s, 1H), 8.98 (d, J = 5.0 Hz, 1H), 8.94 (s, 1H), 8.60 (s, 1H), 8.37 (s, 1H), 8.19 (d, J = 5.0 Hz, 1H), 8.06 (d, J = 7.9 Hz, 1H), 8.01 (s, 1H), 7.77 (dd, J = 2.2 and 8.3 Hz, 1H), 7.71 (d, J = 2.2 Hz, 1H), 7.66 (t, J = 7.7 Hz, 1H), 7.58 (d, J = 7.7 Hz, 1H), 7.36 (d, J = 8.3 Hz, 1H), 2.25 (s, 3H), 2.16 (s, 3H). | 492.2 |
| 31 | A6 F17 | | P | 44 | 10.9 (s, 1H), 8.87 (d, J = 5.0 Hz, 1H), 8.84 (d, J = 5.6 Hz, 1H), 8.79 (s, 1H), 8.75 (d, J = 5.1 Hz, 1H), 8.66 (d, J = 5.6 Hz, 1H), 8.35 (dd, J = 1.8 and 5.1 Hz, 1H), 8.29 (m, 2H), 8.07 (d, J = 5.6 Hz, 1H), 8.00 (m, 2H), 7.62 (d, J = 5.0 Hz, 1H), 7.59 (d, J = 8.0 Hz, 1H), 2.85 (d, J = 4.8 Hz, 3H), 2.39 (s, 3H). | 492.2 |
| 32 | A5 F3 | | P | 55 | 10.6 (s, 1H), 10.3 (s, 1H), 8.86 (s, 1H), 8.83 (d, J = 5.0 Hz, 1H), 8.43 (d, J = 5.3 Hz, 1H), 7.98 (s, 1H), 7.82 (m, 2H), 7.77 (m, 3H), 7.53 (dd, J = 1.5 and 5.0 Hz, 1H), 7.41 (m, 2H), 7.36 (d, J = 8.4 Hz, 1H), 2.40 (s, 3H), 2.28 (s, 3H), 2.14 (s, 3H). | 437.2 |
| 33 | D1 | | R | 17 | 10.7 (s, 1H), 10.5 (s, 1H), 9.25 (s, 1H), 8.85 (s, 1H), 8.57 (dd, J = 1.2 and 8.0 Hz, 1H), 8.41 (d, J = 5.2 Hz, 1H), 8.11 (d, J = 8.4 Hz, 1H), 7.81 (m, 3H), 7.79 (brs, 1H), 7.72 (s, 1H), 7.40 (d, J = 8.4 Hz, 1H), 5.4 (s, 1H), 2.29 (s, 3H), 2.12 (s, 3H), 1.57 (s, 6H). | 550.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 34 | A5 F11 | (structure) | P | 20 | 10.6 (s, 1H), 10.4 (s, 1H), 8.98 (d, J = 4.8 Hz, 1H), 8.33 (s, 1H), 8.16 (d, J = 4.4 Hz, 1H), 8.12 (d, J = 7.2 Hz, 1H), 8.10 (s, 1H), 7.70 (dd, J = 2.0 and 8.0 Hz, 1H), 7.61 (s, 1H), 7.20 (d, J = 8.4 Hz, 1H), 6.93 (s, 1H), 6.69 (m, 1H), 3.80 (s, 3H), 2.03 (s, 3H), 1.96 (s, 3H). | 523.2 |
| 35 | F14 | (structure) | P | 37 | 10.7 (m, 2H), 9.99 (m, 3H), 8.37 (s, 2H), 8.19 (d, J = 4.8 Hz, 1H), 8.04 (m, 1H), 7.84 (brs, 1H), 7.73 (s, 1H), 7.65 (d, J = 7.6 Hz, 1H), 7.53 (d, J = 4.8 Hz, 1H), 7.40 (d, J = 11.2 Hz, 1H), 2.32 (s, 3H). | 496.0 |
| 36 | A5 F21 | (structure) | P | 40 | 10.9 (s, 1H), 10.5 (s, 1H), 9.02 (d, J = 5.2 Hz, 1H), 8.94 (d, J = 2.0 Hz, 1H), 8.87 (s, 1H), 8.85 (s, 1H), 8.43 (d, J = 5.2 Hz, 1H), 8.40 (s, 1H), 8.22 (d, J = 4.8 Hz, 1H), 8.15 (d, J = 2.0 Hz, 1H), 8.07 (s, 1H), 7.81 (d, J = 4.8 Hz, 1H) 7.60 (d, J = 4.8, 1H), 2.50 (s, 3H), 2.12 (s, 3H). | 493.0 |
| 37 | A5 F22 | (structure) | P | 28 | 10.7 (s, 1H), 10.5 (s, 1H), 8.95 (d, J = 2.0 Hz, 1H), 8.86 (s, 1H), 8.85 (s, 1H), 8.43 (d J = 5.2 Hz, 1H), 8.34 (s, 1H), 8.29 (d, J = 8.0 Hz, 1H), 8.16 (d, J = 2.0 Hz, 1H), 8.07 (s, 1H), 8.01 (d, J = 8.0 1H), 7.82 (m, 2H) 7.60 (d, J = 4.8, 1H), 2.48 (s, 3H), 2.12 (s, 3H). | 492.1 |
| 38 | (structure) F19 | (structure) | P | 61 | 10.7 (s, 1H), 8.98 (d, J = 5.0 Hz, 1H), 8.36 (s, 1H), 8.19 (d, J = 5.0 Hz, 1H), 7.97 (d, J = 5.4 Hz, 1H), 7.72 (m, 2H), 7.66 (d, J = 7.9 Hz, 1H), 7.57 (t, J = 7.6 Hz, 2H), 7.43 (d, J = 7.6 Hz, 1H), 7.35 (d, J = 8.3 Hz, 1H), 6.83 (dd, J = 1.6 and 5.4 Hz, 1H), 6.76 (s, 1H), 5.96 (s, 2H), 2.26 (s, 3H). | 449.2 |
| 40 | A6 F23 | (structure) | P | 11 | 10.5 (s, 1H), 8.85 (d, J = 5.0 Hz, 2H), 8.77 (s, 1H), 8.75 (d, J = 5.1 Hz, 1H), 8.63 (d, J = 5.2 Hz, 1H), 8.33 (dd, J = 1.8 and 5.1 Hz, 1H), 8.18 (s, 1H), 7.81 (d, J = 8.5 Hz, 1H), 7.75 (m, 2H), 7.65 (d, J = 5.3 Hz, 1H), 7.55 (d, J = 5.2 Hz, 1H), 7.38 (d, J = 8.4 Hz, 1H), 2.85 (d, J = 4.8 Hz, 3H), 2.56 (s, 3H), 2.28 (s, 3H). | 438.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 42 | A6 F21 | | P | 46 | 10.9 (s, 1H), 9.02 (d, J = 4.8 Hz, 1H), 8.94 (d, J = 2.0 Hz, 1H), 8.89 (d, J = 4.8 Hz, 1H), 8.85 (d, J = 4.8 Hz, 1H), 8.79 (s, 1H), 8.76 (d, J = 4.8 Hz, 1H), 8.4 (s, 1H), 8.34 (d, J = 3.6 Hz, 1H), 8.30 (s, 1H), 8.22 (d, J = 4.8 Hz, 1H), 8.17 (d, J = 2.0 Hz, 1H), 7.64 (d, J = 4.4 Hz, 1H), 2.85 (d, J = 4.8 Hz, 3H), 2.50 (s, 3H). | 493.1 |
| 43 | A17 F42 | | P | 28 | 11.20 (s, 1H), 10.68 (s, 1H), 9.28 (s, 1H), 8.93 (s, 1H), 8.82 (dd, J = 5.0, 0.9 Hz, 1H), 8.25 (d, J = 5.6 Hz, 1H), 8.04-7.98 (m, 2H), 7.88 (dd, J = 5.0, 1.6 Hz, 1H), 7.83 (dd, J = 8.3, 2.3 Hz, 1H), 7.64 (d, J = 5.6 Hz, 1H), 7.43 (d, J = 8.4 Hz, 1H), 3.96 (s, 2H), 2.42 (s, 3H), 1.77 (s, 6H). | 490.2 |
| 44 | F1 | | P | 65 | 10.8 (s, 1H), 8.99 (d, J = 5.0 Hz, 1H), 8.82 (d, J = 5.0 Hz, 1H), 8.70 (d, J = 5.4 Hz, 2H), 8.37 (s, 1H), 8.20 (d, J = 5.0 Hz, 1H), 8.13 (m, 3H), 7.81 (dd, J = 2.3 and 8.3 Hz, 1H), 7.76 (d, J = 2.2 Hz, 1H), 7.51 (dd, J = 1.5 and 5.0 Hz, 1H), 7.40 (d, J = 8.3 Hz, 1H), 2.29 (s, 3H). | 435.2 |
| 45 | F1 | | P | 71 | 10.8 (s, 1H), 9.54 (s, 2H), 9.29 (s, 1H), 9.01 (d, J = 5.0 Hz, 1H), 8.84 (d, J = 5.0 Hz, 1H), 8.39 (s, 1H), 8.21 (m, 2H), 7.81 (m, 2H), 7.52 (dd, J = 1.5 and 5.0 Hz, 1H), 7.42 (d, J = 8.3 Hz, 1H), 2.32 (s, 3H). | 436.2 |
| 46 | F1 | | P | 38 | 10.8 (s, 1H), 10.7 (d, J = 13.8 Hz, 1H), 9.37 (d, J = 10.1 Hz, 1H), 9.00 (d, J = 5.0 Hz, 1H), 8.84 (m, 1H), 8.42 (m, 2H), 8.24 (d, J = 5.0 Hz, 1H), 8.04 (m, 1H), 7.76-7.85 (m, 4H), 7.55 (d, J = 5.0 Hz, 1H), 7.42 (d, J = 8.3 Hz, 1H), 2.30 (s, 3H). | 478.2 |
| 47 | A6 F20 | | P | 5 | 10.8 (s, 1H), 9.49 (s, 1H), 8.99 (m, 2H), 8.89 (d, J = 5.4 Hz, 1H), 8.84 (d, J = 5.1 Hz, 1H), 8.78 (s, 1H), 8.39 (m, 2H), 8.23 (d, J = 5.0 Hz, 1H), 8.00 (d, J = 2.2 Hz, 1H), 7.90 (m, 1H), 7.47 (d, J = 8.4 Hz, 1H), 2.87 (d, J = 4.8 Hz, 3H), 2.45 (s, 3H). | 493.2 |
| 48 | A6 F24 | | P | 66 | 10.7 (s, 1H), 8.90 (d, J = 5.1 Hz, 1H), 8.84 (t, J = 4.7 Hz, 2H), 8.77 (s, 1H), 8.75 (d, J = 5.1 Hz, 1H), 8.33 (dd, J = 1.8 and 5.1 Hz, 1H), 8.19 (s, 2H), 8.06 (d, J = 5.1 Hz, 1H), 7.82 (dd, J = 2.2 and 8.3 Hz, 1H), 7.77 (d, J = 2.2 Hz, 1H), | 474.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | 7.55 (d, J = 5.0 Hz, 1H), 7.40 (d, J = 8.4 Hz, 1H), 7.07 (t, J = 54.8 Hz, 1H), 2.85 (d, J = 4.8 Hz, 3H), 2.29 (s, 3H). | |
| 49 | F15 | | P | 49 | 10.6 (s, 1H), 8.80 (m, 2H), 8.56 (d, J = 5.3 Hz, 1H), 8.10 (s, 1H), 8.02 (d, J = 10.5 Hz, 2H), 7.93 (d, J = 5.3 Hz, 1H), 7.86 (dd, J = 1.5 and 5.1 Hz, 1H), 7.79 (dd, J = 2.3 and 8.3 Hz, 1H), 7.73 (d, J = 2.2 Hz, 1H), 7.49 (dd, J = 1.5 and 5.0, Hz, 1H), 7.39 (d, J = 8.4 Hz, 1H), 2.55 (s, 3H) 2.28 (s, 3H), 1.75 (s, 6H). | 448.2 |
| 50 | D18 | | R | 43 | 10.6 (s, 1H), 8.84 (t, J = 4.7 Hz, 2H), 8.80 (d, J = 5.1 Hz, 1H), 8.77 (s, 1H), 8.75 (d, J = 5.1 Hz, 1H), 8.33 (dd, J = 1.8 and 5.1 Hz, 1H), 8.19 (s, 1H), 8.01 (s, 1H), 7.87 (d, J = 5.1 Hz, 1H), 7.80 (dd, J = 2.2 and 8.3 Hz, 1H), 7.74 (d, J = 2.2 Hz, 1H), 7.55 (dd, J = 1.5 and 5.0 Hz, 1H), 7.40 (d, J = 8.4 Hz, 1H), 2.85 (d, J = 4.8 Hz, 3H), 2.29 (s, 3H), 1.76 (s, 6H). | 491.2 |
| 51 | A6 F11 | | P | 23 | 10.7 (s, 1H), 8.98 (d, J = 4.8 Hz, 1H), 8.74 (d, J = 4.8 Hz, 1H), 8.48 (d, J = 5.2 Hz, 1H), 8.34 (s, 1H), 8.15 (d, J = 4.8 Hz, 1H), 7.94 (s, 1H), 7.72 (d, J = 8.4 Hz, 1H), 7.6 (brs, 1H), 7.21 (brs, 2H), 6.96 (s, 1H), 3.83 (s, 3H), 2.77 (d, J = 4.8 Hz, 3H), 1.90 (s, 3H). | 523.1 |
| 52 | A6 F22 | | P | 41 | 10.7 (s, 1H), 8.95 (brs, 1H), 8.90 (d, J = 5.2 Hz, 1H), 8.86 (d, J = 4.8 Hz, 1H), 8.79 (s, 1H), 8.77 (d, J = 5.2 Hz, 1H), 8.34 (brs, 2H), 8.30 (m, 2H), 8.17 (brs, 1H), 8.00 (d, J = 8.0 Hz, 1H), 7.8 (m, 1H), 7.64 (d, J = 4.8 Hz, 1H), 2.86 (d, J = 4.8 Hz, 3H), 2.49 (s, 3H). | 492.1 |
| 53 | F2 | | P & Q | 32 | 10.6 (s, 1H), 8.99 (d, J = 4.8 Hz, 1H), 8.35 (s, 1H), 8.19 (d, J = 4.8 Hz, 1H), 8.01 (d, J = 5.2 Hz, 1H), 7.74 (m, 2H), 7.33 (d, J = 8.4 Hz, 1H), 6.63 (m, 1H), 6.51 (s, 1H), 6.41 (s, 1H), 6.2 (brs, 2H), 6.14 (s, 1H), 3.31 (s, 3H), 2.30 (s, 3H). | 479.4 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 54 | A3 F1 | (structure) | P | 36 | 10.9 (s, 1H), 10.8 (s, 1H), 8.98 (d, J = 5.0 Hz, 1H), 8.85 (s, 1H), 8.80 (d, J = 5.0 Hz, 1H), 8.42 (d, J = 5.3 Hz, 1H), 8.37 (s, 1H), 8.20 (d, J = 5.1 Hz, 1H), 7.95 (s, 1H), 7.80 (m, 2H), 7.74 (d, J = 2.2 Hz, 1H), 7.51 (m, 1H), 7.40 (d, J = 8.4 Hz, 1H), 2.27 (s, 3H), 2.02 (m, 1H), 0.81 (m, 4H). | 518.2 |
| 55 | (structure) F15 | (structure) | P | 75 | 10.6 (s, 1H), 8.79 (m, 2H), 8.70 (d, J = 4.6 Hz, 2H), 8.13 (s, 3H), 8.01 (s, 1H), 7.86 (d, J = 5.0 Hz, 1H), 7.79 (d, J = 8.4 Hz, 1H), 7.74 (s, 1H), 7.51 (d, J = 4.2 Hz, 1H), 7.39 (m, 1H), 2.28 (s, 3H), 1.75 (d, J = 2.2 Hz, 6H). | 432.2 |
| 56 | (structure) F15 | (structure) | P & Q | 47 | 10.6 (s, 1H), 8.80 (d, J = 5.1 Hz, 1H), 8.75 (d, J = 5.0 Hz, 1H), 8.01 (t, J = 3.1 Hz, 2H), 7.85 (m, 2H), 7.78 (dd, J = 2.3 and 8.3 Hz, 1H), 7.73 (d, J = 2.2 Hz, 1H), 7.46 (dd, J = 1.5 and 5.0 Hz, 1H), 7.38 (d, J = 8.4 Hz, 1H), 7.24 (s, 1H), 7.18 (dd, J = 1.5 and 5.4 Hz, 1H), 6.01 (s, 2H), 2.28 (s, 3H), 1.75 (s, 6H). | 449.2 |
| 57 | 38 (structure) | (structure) | L | 79 | 10.7 (s, 1H), 10.1 (s, 1H), 8.98 (d, J = 5.0 Hz, 1H), 8.39 (m, 3H), 8.19 (d, J = 5.0 Hz, 1H), 7.73 (m, 3H), 7.64 (m, 2H), 7.50 (m, 2H), 7.36 (d, J = 8.3 Hz, 1H), 4.08 (s, 2H), 3.37 (s, 3H), 2.26 (s, 3H). | 521.2 |
| 58 | A3 F19 | (structure) | P | 73 | 10.8 (s, 1H), 10.6 (s, 1H), 8.92 (d, J = 5.0 Hz, 1H), 8.38 (s, 1H), 8.32 (d, J = 6.5 Hz, 2H), 8.14 (d, J = 5.0 Hz, 1H), 7.70 (m, 2H), 7.64 (d, J = 2.2 Hz, 1H), 7.56 (m, 2H), 7.40 (m, 2H), 7.29 (d, J = 8.4 Hz, 1H), 2.19 (s, 3H), 1.96 (m, 1H), 1.11 (m, 1H), 0.75 (m, 4H). | 217.2 |
| 59 | A5 F25 | (structure) | P | 66 | 10.7 (s, 1H), 10.6 (s, 1H), 9.43 (s, 1H), 8.93 (s, 1H), 8.63 (d, J = 5.2 Hz, 1H), 8.50 (d, J = 5.2 Hz, 1H), 8.24 (s, 1H), 7.99 (d, J = 2.2 Hz, 1H), 7.90 (d, J = 5.3 Hz, 1H), 7.86 (dd, J = 2.2 and 8.3 Hz, 1H), 7.74 (s, 1H), 7.66 (d, J = 5.2 Hz, 1H), 7.39 (d, J = 8.4 Hz, 1H), 2.56 (s, 3H), 2.41 (s, 3H), 2.13 (s, 3H). | 439.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 60 | A6 F25 | | P | 73 | 10.6 (s, 1H), 9.47 (s, 1H), 8.88 (d, J = 5.4 Hz, 1H), 8.84 (d, J = 6.2 Hz, 2H), 8.63 (d, J = 5.2 Hz, 1H), 8.46 (s, 1H), 8.43 (dd, J = 1.8 and 5.1 Hz, 1H), 8.01 (d, J = 2.2 Hz, 1H), 7.86 (dd, J = 2.2 and 8.3 Hz, 1H), 7.75 (s, 1H), 7.66 (d, J = 5.2 Hz, 1H), 7.39 (d, J = 8.4 Hz, 1H), 2.86 (d, J = 4.8 Hz, 3H), 2.57 (s, 3H), 2.43 (s, 3H). | 439.2 |
| 61 | 56 | | L | 90 | 10.7 (s, 1H), 10.1 (s, 1H), 8.85 (s, 1H), 8.83 (d, J = 5.0 Hz, 1H), 8.80 (d, J = 5.1 Hz, 1H), 8.43 (d, J = 5.3 Hz, 1H), 8.02 (d, J = 14.1 Hz, 2H), 7.85 (m, 2H), 7.82 (dd, J = 2.2 and 8.3 Hz, 1H), 7.75 (m, 1H), 7.53 (d, J = 5.0 Hz, 1H), 7.39 (d, J = 8.4 Hz, 1H), 4.09 (s, 2H), 3.38 (s, 3H), 2.28 (s, 3H), 1.76 (s, 6H). | 521.2 |
| 62 | 38 & NaCN | | L & S_N2 | 58 | 10.9 (s, 1H), 10.7 (s, 1H), 8.98 (d, J = 5.0 Hz, 1H), 8.41 (d, J = 5.3 Hz, 1H), 8.37 (s, 2H), 8.19 (d, J = 5.0 Hz, 1H), 7.76 (m, 2H), 7.71 (d, J = 2.2 Hz, 1H), 7.65 (m, 2H), 7.54 (d, J = 5.3 Hz, 1H), 7.50 (d, J = 7.7 Hz, 1H), 7.36 (d, J = 8.3 Hz, 1H), 4.01 (s, 2H), 2.26 (s, 3H). | 516.2 |
| 63 | 56 & NaCN | | L & S_N2 | 19 | 11.0 (s, 1H), 10.7 (s, 1H), 8.81 (d, J = 5.0 Hz, 1H), 8.79 (d, J = 4.9 Hz, 2H), 8.45 (d, J = 5.3 Hz, 1H), 8.03 (d, J = 8.9 Hz, 2H), 7.88 (d, J = 5.1 Hz, 2H), 7.82 (dd, J = 2.2 and 8.3 Hz, 1H), 7.76 (s, 1H), 7.47 (d, J = 5.1 Hz, 1H), 7.39 (d, J = 8.4 Hz, 1H), 4.02 (s, 2H), 2.28 (s, 3H), 1.76 (s, 6H). | 516.2 |
| 64 | A5 F27 | | P | 26 | 10.9 (s, 1H), 10.5 (s, 1H), 9.01 (d, J = 5.2 Hz, 1H), 8.88 (d, J = 2.4 Hz, 1H), 8.43 (s, 1H), 8.37 (m, 2H), 8.21 (d, J = 4.8 Hz, 1H), 8.11 (brs, 1H), 7.78 (d, J = 8.0 Hz, 1H), 7.72 (s, 1H), 7.67 (t, J = 7.6 Hz, 1H), 7.56 (d, J = 7.6 Hz, 1H), 7.48 (m, 1H), 2.47 (s, 3H), 2.11 (s, 3H). | 492.0 |
| 65 | A5 F26 | | P | 63 | 10.8 (s, 1H), 10.6 (s, 1H), 9.01 (d, J = 5.2 Hz, 1H), 8.77 (s, 1H), 8.42 (d, J = 5.2 Hz, 1H), 8.39 (s, 1H), 8.22 (d, J = 4.8 Hz, 1H), 8.04 (m, 1H), 7.93 (m, 2H), 7.77 (d, J = 5.2 Hz, 1H), 7.54 (s, 1H), 7.47 (t, J = 10.0 Hz, 1H), 2.65 (s, 3H), 2.12 (s, 3H). | 509.9 |

TABLE I-continued

| Ex No. | SM | Product | Method | Yield (%) | $^1$H NMR (400 or 500 MHz, (DMSO-$d_6$): δ | MS (m/z: M + H$^+$) |
|---|---|---|---|---|---|---|
| 66 | A6 F26 | | P | 30 | 10.8 (s, 1H), 9.01 (d, J = 5.2 Hz, 1H), 8.8 (m, 1H), 8.76 (d, J = 5.2 Hz, 1H), 8.73 (s, 1H), 8.40 (s, 1H), 8.29 (m, 1H), 8.23 (d, J = 4.8 Hz, 1H), 8.13 (s, 1H), 8.04 (m, 1H), 7.93 (m, 1H), 7.58 (s, 1H), 7.47 (t, J = 10.0 Hz, 1H), 2.86 (d, J = 5.2 Hz, 3H), 2.68 (s, 3H). | 510.0 |
| 67 | A6 F2 | | P | 12 | 10.6 (s, 1H), 8.99 (d, J = 5.2 Hz, 1H), 8.8 (m, 1H), 8.77 (d, J = 4.8 Hz, 1H), 8.35 (s, 1H), 8.19 (d, J = 4.8 Hz, 1H), 8.12 (brm, 1H), 7.84 (m, 1H), 7.76 (brm, 1H), 7.73 (m, 1H), 7.33 (d, J = 8.4 Hz, 1H), 6.47 (brs, 1H), 6.27 (brs, 1H), 3.29 (s, 3H), 2.83 (d, J = 4.8 Hz, 3H), 2.32 (s, 3H). | 522.0 |
| 68 | A5 F28 | | P | 42 | 10.7 (s, 1H), 10.6 (s, 1H), 8.99 (d, J = 5.2 Hz, 1H), 8.43 (s, 1H), 8.35 (m, 2H), 8.26 (d, J = 2.4 Hz, 1H), 8.19 (d, J = 4.8 Hz, 1H), 7.83 (brs, 1H), 7.74 (dd, J = 1.6 and 8.0 Hz, 1H), 7.70 (brs, 1H), 7.37 (m, 2H), 4.46 (q, J = 6.8 Hz, 2H), 2.28 (s, 3H), 2.10 (s, 3H), 1.36 (t, J = 6.8 Hz, 3H). | 536.0 |
| 69 | A6 F28 | | P | 42 | 10.7 (s, 1H), 8.99 (d, J = 5.2 Hz, 1H), 8.8 (m, 1H), 8.69 (d, J = 5.2 Hz, 1H), 8.37 (s, 1H), 8.33 (s, 1H), 8.29 (brs, 1H), 8.20 (d, J = 4.8 Hz, 1H), 7.97 (brs, 1H), 7.90 (m, 1H), 7.75 (d, J = 8.4 Hz, 1H), 7.71 (s, 1H), 7.36 (d, J = 8.4 Hz, 1H), 4.47 (q, J = 6.8 Hz, 2H), 2.84 (d, J = 4.8 Hz, 3H), 2.29 (s, 3H), 1.34 (t, J = 6.8 Hz, 3H). | 536.0 |
| 70 | A3 F27 | | P | 29 | 10.8 (s, 2H), 9.01 (d, J = 5.2 Hz, 1H), 8.89 (d, J = 2.4 Hz, 1H), 8.44 (s, 1H), 8.38 (brm, 2H), 8.21 (d, J = 4.8 Hz, 1H), 8.09 (brs, 1H), 7.78 (d, J = 7.6 Hz, 1H), 7.71 (s, 1H), 7.66 (t, J = 7.6 Hz, 1H), 7.55 (d, J = 7.6 Hz, 1H), 7.48 (m, 1H), 2.46 (s, 3H), 2.15 (m, 1H), 0.82 (m, 4H). | 518.0 |
| 71 | A3 F28 | | P | 25 | 10.8 (s, 1H), 10.6 (s, 1H), 8.99 (d, J = 5.2 Hz, 1H), 8.40 (s, 1H), 8.35 (m, 2H), 8.26 (d, J = 2.4 Hz, 1H), 8.19 (d, J = 4.8 Hz, 1H), 7.81 (brs, 1H), 7.76 (dd, J = 2.4 and 8.0 Hz, 1H), 7.68 (brs, 1H), 7.37 (m, 2H), 4.45 (q, J = 7.2 Hz, 2H), 2.27 (s, 3H), 2.02 (m, 1H), 1.34 (t, J = 7.2 Hz, 3H), 0.81 (brs, 4H). | 562.0 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 72 | A3 F26 | (structure) | P | 31 | 10.9 (s, 1H), 10.8 (s, 1H), 9.01 (d, J = 4.8 Hz, 1H), 8.80 (s, 1H), 8.43 (d, J = 5.2 Hz, 1H), 8.39 (s, 1H), 8.22 (d, J = 4.8 Hz, 1H), 8.04 (m, 1H), 7.94 (m, 2H), 7.78 (m, 1H), 7.54 (s, 1H) 7.47 (t, J = 9.2 Hz, 1H), 2.65 (s, 3H), 2.04 (m, 1H), 0.83 (m, 4H). | 536.0 |
| 73 | A6 F27 | (structure) | P | 35 | 10.9 (s, 1H), 9.02 (d, J = 5.2 Hz, 1H), 8.90 (s, 1H), 8.84 (brs, 1H), 8.71 (d, J = 5.2 Hz, 1H), 8.40 (s, 1H), 8.33 (s, 1H), 8.21 (d, J = 4.4 Hz, 1H), 8.12 (s, 1H), 7.99 (brs, 1H), 7.93 (d, J = 7.6 Hz, 1H), 7.89 (s, 1H), 7.69 (t, J = 7.6 Hz, 1H), 7.60 (d, J = 7.2 Hz, 1H), 2.85 (d, J = 4.4 Hz, 3H), 2.48 (s, 3H). | 491.9 |
| 74 | A6 F31 | (structure) | P | 20 | 10.7 (s, 1H), 8.87 (d, J = 5.0 Hz, 1H), 8.83 (t, J = 5.3 Hz, 1H), 8.80 (s, 1H), 8.75 (d, J = 5.2 Hz, 1H), 8.50 (d, J = 5.6 Hz, 1H), 8.35 (d, J = 5.2 Hz, 1H), 8.29 (s, 1H), 8.01 (t, J = 4.5 Hz, 3H), 7.85 (d, J = 5.6 Hz, 1H), 7.62 (m, 1H), 7.58 (d, J = 7.9 Hz, 1H), 2.85 (d, J = 4.8 Hz, 3H), 2.39 (s, 3H), 1.67 (s, 6H). | 491.2 |
| 75 | A5 F32 | (structure) | P | 51 | 10.6 (d, J = 6.2 Hz, 2H), 8.81 (t, J = 5.2 Hz, 3H), 8.40 (d, J = 5.3 Hz, 1H), 8.04 (s, 1H), 7.96 (s, 1H), 7.86 (d, J = 5.1 Hz, 1H), 7.79 (m, 1H), 7.61 (d, J = 7.7 Hz, 1H), 7.51 (d, J = 5.0 Hz, 1H), 7.39 (d, J = 11.3 Hz, 1H), 2.32 (s, 3H), 2.11 (s, 3H), 1.75 (s, 6H). | 509.2 |
| 76 | A3 F32 | (structure) | P | 32 | 10.9 (s, 1H), 10.6 (s, 1H), 8.83 (s, 1H), 8.80 (t, J = 6.0 Hz, 2H), 8.41 (d, J = 5.3 Hz, 1H), 8.04 (s, 1H), 7.95 (s, 1H), 7.86 (d, J = 5.0 Hz, 1H), 7.80 (dd, J = 1.6 and 5.3 Hz, 1H), 7.60 (d, J = 7.7 Hz, 1H), 7.51 (d, J = 5.0 Hz, 1H), 7.39 (d, J = 11.3 Hz, 1H), 2.68 (s, 3H), 2.02 (m, 1H), 1.75 (s, 6H), 0.81 (m, 4H). | 535.2 |
| 77 | (structure) G7 | (structure) | P | 33 | 11.3 (s, 1H), 10.6 (s, 1H), 8.95 (s, 1H), 8.79 (d, J = 5.1 Hz, 1H), 8.61 (s, 1H), 8.06 (d, J = 7.9 Hz, 1H), 8.00 (d, J = 6.8 Hz, 2H), 7.86 (d, J = 5.1 Hz, 1H), 7.76 (dd, J = 2.2 and 8.3 Hz, 1H), 7.68 (d, J = 2.2 Hz, 1H), 7.64 (t, J = 7.7 Hz, 1H), 7.56 (d, J = 7.7 Hz, 1H), 7.35 (d, J = 8.4 Hz, 1H), 2.24 (s, 3H), 2.06 (m, 1H), 1.75 (s, 6H), 0.88 (d, J = 6.2 Hz, 4H). | 517.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 78 | A6 F30 | | P | 81 | 10.7 (s, 1H), 9.11 (d, J = 5.2 Hz, 1H), 8.97 (s, 1H), 8.88 (d, J = 5.6 Hz, 1H), 8.84 (d, J = 5.1 Hz, 1H), 8.81 (d, J = 5.1 Hz, 1H), 8.49 (d, J = 5.0 Hz, 1H), 8.02 (m, 2H), 7.88 (t, J = 6.6 Hz, 2H), 7.80 (d, J = 5.2 Hz, 1H), 7.44 (d, J = 8.4 Hz, 1H), 2.85 (d, J = 4.8 Hz, 3H), 2.47 (s, 3H), 1.76 (s, 6H). | 492.2 |
| 79 | G7 | | P | 30 | 11.0 (s, 1H), 10.6 (s, 1H), 8.94 (s, 1H), 8.79 (d, J = 5.1 Hz, 1H), 8.59 (s, 1H), 8.06 (d, J = 7.9 Hz, 1H), 8.02 (s, 2H), 7.87 (d, J = 5.1 Hz, 1H), 7.76 (dd, J = 2.3 and 8.3 Hz, 1H), 7.70 (d, J = 2.2 Hz, 1H), 7.66 (t, J = 7.7 Hz, 1H), 7.57 (d, J = 7.7 Hz, 1H), 7.35 (d, J = 8.3 Hz, 1H), 2.25 (s, 3H), 2.16 (s, 3H), 1.76 (s, 6H). | 491.2 |
| 80 | G5 | | P | 58 | 11.3 (s, 1H), 10.7 (s, 1H), 8.98 (d, J = 5.0 Hz, 1H), 8.95 (s, 1H), 8.61 (s, 1H), 8.37 (s, 1H), 8.19 (d, J = 5.0 Hz, 1H), 8.07 (d, J = 7.9 Hz, 1H), 7.99 (s, 1H), 7.77 (dd, J = 2.2 and 8.3 Hz, 1H), 7.70 (d, J = 2.2 Hz, 1H), 7.64 (t, J = 7.7 Hz, 1H), 7.57 (d, J = 7.7 Hz, 1H), 7.36 (d, J = 8.4 Hz, 1H), 2.24 (s, 3H), 2.06 (m, 1H), 0.88 (d, J = 6.2 Hz, 4H). | 518.2 |
| 81 | A6 F29 | | P | 77 | 10.4 (s, 1H), 9.49 (s, 1H), 9.06 (s, 1H), 8.87 (d, J = 5.4 Hz, 1H), 8.82 (d, J = 5.1 Hz, 1H), 8.76 (s, 1H), 8.38 (d, J = 5.2 Hz, 1H), 8.16 (s, 1H), 8.06 (s, 1H), 8.01 (d, J = 8.1 Hz, 1H), 7.57 (m, 2H), 4.47 (m, 1H), 2.85 (d, J = 4.8 Hz, 3H), 2.51 (s, 3H), 1.40 (d, J = 6.7 Hz, 6H). | 456.2 |
| 82 | F30 | | P & Q | 38 | 10.7 (s, 1H), 9.01 (d, J = 5.1 Hz, 1H), 8.81 (d, J = 5.0 Hz, 1H), 8.07 (d, J = 5.3 Hz, 1H), 8.02 (s, 1H), 7.96 (d, J = 2.2 Hz, 1H), 7.86 (m, 2H), 7.69 (d, J = 5.2 Hz, 1H), 7.49 (s, 1H), 7.41 (m, 2H), 6.14 (s, 2H), 2.44 (s, 3H), 1.76 (s, 6H). | 450.2 |
| 83 | D6 | | R | 45 | 10.8 (s, 1H), 10.67 (s, 1H), 8.99 (d, J = 5.0 Hz, 1H), 8.87 (s, 1H), 8.48 (d, J = 5.2 Hz, 1H), 8.39 (s, 1H), 8.21 (d, J = 5.0 Hz, 1H), 8.01 (s, 1H), 7.93 (d, J = 2.2 Hz, 1H), 7.87 (m, 2H), 7.40 (d, J = 8.4 Hz, 1H), 2.78 (s, 3H), 2.41 (s, 3H), 2.13 (s, 3H). | 507.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 84 | A5 F33 | | P | 50 | 10.8 (s, 1H), 10.6 (s, 1H), 9.12 (s, 1H), 9.08 (d, J = 5.2 Hz, 1H), 8.99 (d, J = 5.0 Hz, 1H), 8.48 (d, J = 5.2 Hz, 1H), 8.38 (s, 1H), 8.21 (d, J = 5.0 Hz, 1H), 8.01 (s, 2H), 7.88 (d, J = 8.4 Hz, 1H), 7.75 (d, J = 5.2 Hz, 1H), 7.44 (d, J = 8.4 Hz, 1H), 2.48 (s, 3H), 2.12 (s, 3H). | 493.2 |
| 85 | A6 F33 | | P | 72 | 10.8 (s, 1H), 9.12 (d, J = 5.2 Hz, 1H), 8.99 (d, J = 5.0 Hz, 1H), 8.97 (s, 1H), 8.88 (d, J = 5.4 Hz, 1H), 8.84 (d, J = 5.1 Hz, 1H), 8.49 (dd, J = 1.7 and 5.0 Hz, 1H), 8.38 (s, 1H), 8.21 (d, J = 5.0 Hz, 1H), 8.03 (d, J = 2.3 Hz, 1H), 7.89 (dd, J = 2.3 and 8.3 Hz, 1H), 7.80 (d, J = 5.2 Hz, 1H), 7.45 (d, J = 8.4 Hz, 1H), 2.85 (d, J = 4.8 Hz, 3H), 2.47 (s, 3H). | 493.2 |
| 86 | C7 E6 | | P | 30 | 10.7 (s, 1H), 9.46 (s, 1H), 8.96 (s, 1H), 8.87 (d, J = 5.6 Hz, 1H), 8.81 (m, 2H), 8.76 (s, 1H), 8.37 (d, J = 5.1 Hz, 1H), 8.02 (s, 1H), 7.96 (s, 1H), 7.87 (t, J = 7.3 Hz, 2H), 7.43 (d, J = 8.4 Hz, 1H), 2.85 (d, J = 4.8 Hz, 3H), 2.43 (s, 3H), 1.76 (s, 6H). | 492.2 |
| 87 | A5 F29 | | P | 64 | 10.6 (s, 1H), 10.4 (s, 1H), 9.32 (s, 1H), 9.04 (s, 1H), 8.89 (s, 1H), 8.48 (d, J = 5.2 Hz, 1H), 8.15 (s, 1H), 8.06 (s, 1H), 8.00 (d, J = 8.1 Hz, 1H), 7.87 (d, J = 5.3 Hz, 1H), 7.57 (m, 2H), 4.47 (m, 1H), 2.53 (s, 3H), 2.11 (s, 3H), 1.40 (d, J = 6.7 Hz, 6H). | 456.2 |
| 88 | 82 | | L | 60 | 10.7 (s, 1H), 10.2 (s, 1H), 9.12 (s, 1H), 9.09 (d, J = 5.2 Hz, 1H), 8.81 (d, J = 5.1 Hz, 1H), 8.51 (d, J = 5.2 Hz, 1H), 8.06 (dd, J = 1.4 and 5.2 Hz, 1H), 8.02 (m, 2H), 7.87 (m, 2H), 7.77 (d, J = 5.2 Hz, 1H), 7.43 (d, J = 8.4 Hz, 1H), 4.10 (s, 2H), 3.38 (s, 3H), 1.76 (s, 6H). | 522.2 |
| 89 | D6 | | R | 39 | 10.7 (s, 2H), 8.87 (s, 1H), 8.80 (d, J = 5.1 Hz, 1H), 8.48 (d, J = 5.2 Hz, 1H), 8.02 (d, J = 6.7 Hz, 2H), 7.91 (d, J = 2.3 Hz, 1H), 7.87 (m, 3H), 7.40 (d, J = 8.4 Hz, 1H), 2.78 (s, 3H), 2.41 (s, 3H), 2.13 (s, 3H), 1.76 (s, 6H). | 506.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 90 | F20 | | P & Q | 73 | 10.7 (s, 1H), 9.19 (s, 1H), 8.99 (d, J = 5.2 Hz, 1H), 8.87 (s, 1H), 8.38 (s, 1H), 8.21 (d, J = 4.8 Hz, 1H), 8.08 (d, J = 6.0 Hz, 1H), 7.94 (s, 1H), 7.88 (dd, J = 2.4 and 8.4 Hz, 1H), 7.43 (d, J = 8.4 Hz, 1H), 7.25 (brm, 2H), 6.1 (brs, 2H), 2.41 (s, 3H). | 450.9 |
| 91 | A6 F35 | | P | 20 | 10.4 (s, 1H), 8.90 (s, 1H), 8.8 (m, 1H), 8.71 (d, J = 4.8 Hz, 1H), 8.33 (s, 1H), 8.13 (s, 1H), 7.99 (brs, 1H), 7.90 (m, 1H), 7.88 (s, 1H), 7.80 (s, 1H), 7.76 (brs, 1H), 7.68 (t, J = 8.0 Hz, 1H), 7.58 (d, J = 7.6 Hz, 1H), 7.45 (brs, 2H), 2.85 (d, J = 4.8 Hz, 3H), 2.40 (s, 3H), 2.32 (s, 3H). | 437.1 |
| 92 | C8 E3 | | P | 19 | 10.8 (s, 1H), 10.7 (s, 1H), 9.12 (d, J = 5.2 Hz, 1H), 8.99 (d, J = 5.0 Hz, 1H), 8.96 (s, 1H), 8.52 (d, J = 5.2 Hz, 1H), 8.40 (s, 1H), 8.36 (d, J = 2.3 Hz, 1H), 8.22 (d, J = 5.1 Hz, 1H), 8.06 (d, J = 5.3 Hz, 1H), 7.90 (dd, J = 2.3 and 8.3 Hz, 1H), 7.87 (d, J = 5.3 Hz, 1H), 7.41 (s, 1H), 7.40 (s, 1H), 2.62 (s, 3H), 2.13 (s, 3H). | 493.2 |
| 93 | C17 E11 | | P | 5 | 1H NMR (500 MHZ, DMSO) ? 11.27 (s, 1H), 10.90 (s, 1H), 9.17 (d, J = 5.3 Hz, 1H), 8.98 (d, J = 2.6 Hz, 1H), 8.85 (d, J = 5.1 Hz, 1H), 8.79 (d, J = 2.6 Hz, 1H), 8.29 (d, J = 5.6 Hz, 1H), 8.09 (d, J = 5.3 Hz, 1H), 8.06 (s, 1H), 7.92 (dd, J = 5.1, 1.5 Hz, 1H), 7.66 (d, J = 5.6 Hz, 1H), 4.01 (s, 2H), 2.78 (s, 3H), 1.78 (s, 6H). | 491.2 |
| 94 | F21 | HCl salt | P & Q | 77 | 13.8 (brs, 1H), 11.6 (brs, 1H), 9.12 (brs, 1H), 9.04 (d, J = 4.8 Hz, 1H), 8.56 (brs, 1H), 8.49 (s, 1H), 8.33 (d, J = 4.8 Hz, 1H), 8.10 (brs, 2H), 8.07 (d, J = 6.8 Hz, 1H), 7.91 (brs, 2H), 7.77 (t, J = 8.0 Hz, 1H), 7.71 (d, J = 8.0 Hz, 1H), 7.33 (s, 1H), 7.30 (d, J = 6.8 Hz, 1H), 2.60 (s, 3H). | 450.0 |
| 95 | dimethyl-amine | | L & S_N2 | 51 | 10.9 (s, 1H), 10.0 (s, 1H), 9.01 (d, J = 5.2 Hz, 1H), 8.88 (brs, 1H), 8.45 (s, 1H), 8.39 (brs, 2H), 8.21 (d, J = 4.8 Hz, 1H), 8.11 (s, 1H), 7.80 (d, J = 8.0 Hz, 1H), 7.74 (brs, 1H), 7.68 (t, J = 8.0 Hz, 1H), 7.57 (d, J = 7.6 Hz, 1H), 7.52 (dd, J = 5.2 Hz & 1.6 Hz, 1H), 3.15 (s, 2H), 2.47 (s, 3H), 2.31 (s, 6H). | 535.0 |

TABLE I-continued

| Ex No. | SM | Product | Method | Yield (%) | 1H NMR (400 or 500 MHz, (DMSO-d6): δ | MS (m/z: M + H+) |
|---|---|---|---|---|---|---|
| 96 | 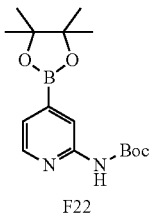 F22 | 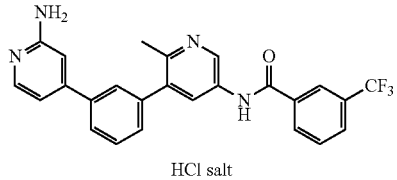 [SMILES: Cc1ncc(NC(=O)c2cccc(C(F)(F)F)c2)cc1-c1cccc(-c2ccnc(N)c2)c1] HCl salt | P & Q | 65 | 13.6 (brs, 1H), 11.1 (brs, 1H), 9.05 (s, 1H), 8.44 (brs, 1H), 8.38 (s, 1H), 8.35 (d, J = 8.0 Hz, 1H), 8.03 (m, 3H), 7.89 (brs, 2H), 7.82 (t, J = 8.0 Hz, 1H), 7.76 (t, J = 8.0 Hz, 1H), 7.70 (d, J = 7.2 Hz, 1H), 7.31 (brs, 2H), 2.56 (s, 3H). | 449.0 |
| 97 | 96 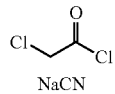 NaCN | 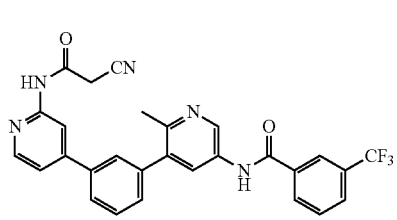 [SMILES: Cc1ncc(NC(=O)c2cccc(C(F)(F)F)c2)cc1-c1cccc(-c2ccnc(NC(=O)CC#N)c2)c1] | L & S<sub>N</sub>2 | 14 | 10.9 (s, 1H), 10.6 (s, 1H), 8.90 (s, 1H), 8.42 (d, J = 5.2 Hz, 1H), 8.37 (brs, 1H), 8.33 (brs, 1H), 8.29 (d, J = 8.0 Hz, 1H), 8.11 (s, 1H), 7.99 (d, J = 7.6 Hz, 1H), 7.80 (brs, 2H), 7.75 (s, 1H), 7.68 (t, J = 7.2 Hz, 1H), 7.57 (brs, 2H), 4.01 (s, 2H), 2.46 (s, 3H). | 515.9 |
| 98 | 90 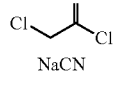 NaCN | 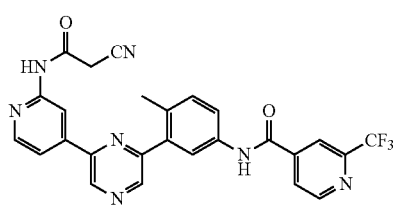 [SMILES: Cc1ccc(NC(=O)c2ccnc(C(F)(F)F)c2)cc1-c1cncc(-c2ccnc(NC(=O)CC#N)c2)n1] | L & S<sub>N</sub>2 | 41 | 11.0 (s, 1H), 10.8 (s, 1H), 9.33 (s, 1H), 8.99 (d, J = 5.2 Hz, 1H), 8.94 (s, 1H), 8.83 (brs, 1H), 8.54 (d, J = 5.2 Hz, 1H), 8.39 (s, 1H), 8.21 (d, J = 4.4 Hz, 1H), 7.99 (brs, 1H), 7.94 (dd, J = 5.2 Hz & 1.2 Hz, 1H), 7.88 (dd, J = 8.4 Hz & 2.4 Hz, 1H), 7.46 (d, J = 8.4 Hz, 1H), 4.02 (s, 2H), 2.46 (s, 3H). | 517.9 |
| 99 | 90 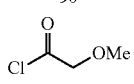 | 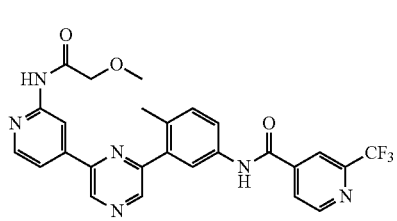 | L | 80 | 10.8 (s, 1H), 10.2 (s, 1H), 9.32 (s, 1H), 8.99 (d, J = 5.2 Hz, 1H), 8.94 (s, 1H), 8.88 (s, 1H), 8.52 (d, J = 5.2 Hz, 1H), 8.39 (s, 1H), 8.22 (d, J = 4.8 Hz, 1H), 7.98 (brs, 1H), 7.91 (dd, J = 5.2 Hz & 1.2 Hz, 1H), 7.89 (dd, J = 8.4 Hz & 2.0 Hz, 1H), 7.45 (d, J = 8.4 Hz, 1H), 4.10 (s, 2H), 3.37 (s, 3H), 2.45 (s, 3H). | 522.9 |
| 100 | 90 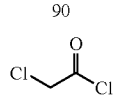 NHMe2 | 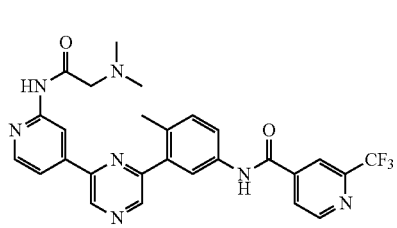 [SMILES: Cc1ccc(NC(=O)c2ccnc(C(F)(F)F)c2)cc1-c1cncc(-c2ccnc(NC(=O)CN(C)C)c2)n1] | L & S<sub>N</sub>2 | 30 | 10.8 (s, 1H), 10.0 (s, 1H), 9.32 (s, 1H), 8.99 (d, J = 4.8 Hz, 1H), 8.94 (s, 1H), 8.90 (s, 1H), 8.51 (d, J = 5.2 Hz, 1H), 8.38 (brs, 1H), 8.21 (d, J = 5.2 Hz, 1H), 7.98 (brs, 1H), 7.91 (dd, J = 5.2 Hz & 1.6 Hz, 1H), 7.88 (dd, J = 8.4 Hz & 2.0 Hz, 1H), 7.45 (d, J = 8.4 Hz, 1H), 3.16 (s, 2H), 2.45 (s, 3H), 2.31 (s, 6H). | 536.0 |
| 101 | A17 F30 | 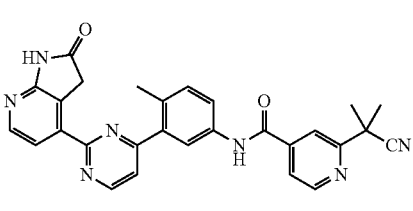 [SMILES: Cc1ccc(NC(=O)c2ccnc(C(C)(C)C#N)c2)cc1-c1ccnc(-c2ccnc3c2CC(=O)N3)n1] | P | 29 | 1H NMR (500 MHZ, DMSO) ? 11.18 (s, 1H), 10.74 (s, 1H), 9.09 (d, J = 5.1 Hz, 1H), 8.81 (d, J = 5.0 Hz, 1H), 8.25 (d, J = 5.5 Hz, 1H), 8.07 (d, J = 2.3 Hz, 1H), 8.03 (s, 1H), 7.88 (dd, J = 5.0, 1.5 Hz, 1H), 7.87-7.83 (m, 2H), 7.75 (d, J = 5.2 Hz, 1H), 7.42 (d, J = 8.4 Hz, 1 Hz), 3.97 (s, 2H), 2.44 (s, 3H), 1.76 (s, 6H). | 490.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 102 | D7 | | R | 27 | 10.7 (s, 1H), 10.4 (s, 1H), 8.98 (d, J = 4.8 Hz, 1H), 8.43 (s, 1H), 8.36 (s, 1H), 8.30 (d, J = 5.2 Hz, 1H), 8.19 (d, J = 4.8 Hz, 1H), 7.81 (d, J = 2.4 Hz, 1H), 7.73 (brs, 2H), 7.69 (brs, 1H), 7.49 (dd, J = 5.6 Hz & 1.6 Hz, 1H), 7.34 (d, J = 8.4 Hz, 1H), 4.9 (t, J = 5.2 Hz, 1H), 4.12 (t, J = 5.2 Hz, 2H), 3.73 (t, J = 5.2 Hz, 2H), 2.32 (s, 3H), 2.08 (s, 3H). | 551.9 |
| 103 | C8 E6 | | P | 42 | 10.7 (d, J = 8.4 Hz, 2H), 9.13 (d, J = 5.2 Hz, 1H), 8.98 (s, 1H), 8.82 (d, J = 5.0 Hz, 1H), 8.54 (d, J = 5.2 Hz, 1H), 8.35 (d, J = 2.3 Hz, 1H), 8.08 (d, J = 5.3 Hz, 1H), 8.06 (s, 1H), 7.90 (t, J = 7.0 Hz, 3H), 7.42 (d, J = 8.4 Hz, 1H), 2.64 (s, 3H), 2.15 (s, 3H), 1.78 (s, 6H). | 492.2 |
| 104 | D16 | | R | 30 | 10.6 (brs, 1H), 10.5 (s, 1H), 9.34 (brs, 1H), 8.82 (m, 2H), 8.38 (brs, 1H), 8.04 (s, 2H), 7.86 (m, 2H), 7.73 (s, 1H), 7.62 (d, J = 8.0 Hz, 1H), 7.53 (d, J = 5.2 Hz, 1H), 7.40 (d, J = 11.6 Hz, 1H), 2.33 (s, 3H), 1.76 (s, 6H). | 495.0 |
| 105 | A17 F10 | | P | 18 | 11.1 (s, 1H), 10.8 (s, 1H), 8.86 (d, J = 2.4 Hz, 1H), 8.84 (d, J = 5.0 Hz, 1H), 8.15 (d, J = 5.5 Hz, 1H), 8.10 (d, J = 2.4 Hz, 1H), 8.03 (s, 1H), 7.89 (dd, J = 1.5 and 5.0 Hz, 1H), 7.72-7.76 (m, 2H), 7.65 (t, J = 7.9 Hz, 1H), 7.53 (d, J = 7.6 Hz, 1H), 7.16 (d, J = 5.5 Hz, 1H), 3.83 (s, 2H), 2.49 (s, 3H), 1.77 (s, 6H). | 489.2 |
| 106 | G5 | | P | 23 | 10.8 (s, 1H), 9.36 (s, 1H), 9.05 (d, J = 5.4 Hz, 1H), 8.98 (d, J = 5.0 Hz, 1H), 8.52 (s, 1H), 8.38 (s, 1H), 8.29 (d, J = 7.8 Hz, 1H), 8.21 (m, 2H), 7.78 (dd, J = 2.2 and 8.3 Hz, 1H), 7.74 (d, J = 2.2 Hz, 1H), 7.68 (t, J = 7.7 Hz, 1H), 7.62 (d, J = 7.7 Hz, 1H), 7.36 (d, J = 8.3 Hz, 1H), 2.85 (d, J = 4.8 Hz, 3H), 2.26 (s, 3H). | 492.2 |
| 107 | D9 | | R | 5 | 10.8 (s, 1H), 10.6 (s, 1H), 9.11 (s, 1H), 9.07 (d, J = 5.2 Hz, 1H), 9.00 (d, J = 5.0 Hz, 1H), 8.48 (d, J = 5.2 Hz, 1H), 8.38 (s, 1H), 8.21 (d, J = 5.0 Hz, 1H), 8.00 (d, J = 5.2 Hz, 1H), 7.92 (d, J = 7.7 Hz, 1H), 7.77 (d, J = 5.2 Hz, 1H), 7.44 (d, J = 11.3 Hz, 1H), 2.54 (s, 3H), 2.12 (s, 3H). | 511.2 |

TABLE I-continued

| Ex. No. | SM | Product | Method | Yield (%) | ¹H NMR (400 or 500 MHz, (DMSO-d$_6$): δ | MS (m/z: M + H⁺) |
|---|---|---|---|---|---|---|
| 108 | A17 F55 | | P | 19 | 10.85 (s, 1H), 10.14 (s, 1H), 8.15 (d, J = 5.6 Hz, 1H), 8.05 (s, 1H), 7.94 (d, J = 7.2 Hz, 1H), 7.71-7.78 (m, 3H), 7.58 (t, J = 8.0 Hz, 1H), 7.55 (s, 1H), 7.50 (d, J = 5.6 Hz, 1H), 7.34 (d, J = 8.0 Hz, 1H), 6.83 (s, 1H), 4.63 (br s, 1H), 4.48 (t, J = 5.2 Hz, 2H), 3.96 (s, 2H), 3.82 (t, J = 4.8 Hz, 2H), 2.30 (s, 3H), 1.76 (s, 6H). at high Temp. | 548.4 |
| 109 | G7 | | P | 7 | 11.55 (s, 1H), 10.56 (s, 1H), 8.80 (d, J = 5.2 Hz, 1H), 8.77 (s, 1H), 8.01 (m, 3H), 7.86 (d, J = 4.8 Hz, 1H), 7.73 (br d, J = 8.4 Hz, 1H), 7.71 (br s, 1H), 7.64 (t, J = 8.0 Hz, 1H), 7.54 (d, J = 7.2 Hz, 1H), 7.35 (d, J = 8.0 Hz, 1H), 4.00 (s, 2H), 2.27 (s, 3H), 1.76 (s, 6H). | 489.2 |
| 110 | G10 | | P | 14 | 11.59 (s, 1H), 10.81 (s, 1H), 8.89 (d, J = 2.4 Hz, 1H), 8.84 (d, J = 5.0 Hz, 1H), 8.78 (s, 1H), 8.11 (d, J = 2.5 Hz, 1H), 8.06 (dd, J = 6.8, 1.5 Hz, 2H), 8.04 (d, J = 1.3 Hz, 1H), 7.90 (dd, J = 5.1, 1.5 Hz, 1H), 7.68 (t, J = 7.9 Hz, 1H), 7.62 (d, J = 7.6 Hz, 1H), 4.03 (s, 2H), 2.48 (s, 3H), 1.77 (s, 6H) | 490.2 |
| 111 | G10 | | P | 35 | 13.13 (s, 1H), 10.77 (s, 1H), 8.89 (d, J = 9.9 Hz, 1H), 8.82 (d, J = 5.0 Hz, 1H), 8.54-8.41 (m, 1H), 8.19-8.07 (m, 4H), 8.04 (s, 1H), 7.92 (d, J = 8.4 Hz, 1H), 7.89 (d, J = 5.0 Hz, 1H), 7.62 (t, J = 7.7 Hz, 1H), 7.49 (dt, J = 7.5, 1.4 Hz, 1H), 2.42 (s, 3H), 1.76 (s, 6H). | 474.2 |
| 112 | D12 | | R | 29 | 10.9 (s, 1H), 10.6 (s, 1H), 9.28 (s, 1H), 8.92 (s, 1H), 8.87 (s, 1H), 8.81 (d, J = 4.8 Hz, 1H), 8.50 (d, J = 5.2 Hz, 1H), 8.02 (s, 1H), 7.94 (brs, 1H), 7.87 (m, 3H), 7.44 (d, J = 8.4 Hz, 1H), 2.41 (s, 3H), 2.04 (m, 1H), 1.76 (s, 6H), 0.81 (m, 4H). | 518.0 |
| 113 | D2 | | R | 12 | 10.5 (s, 1H), 10.4 (s, 1H), 8.81 (d, J = 4.8 Hz, 1H), 8.44 (s, 1H), 8.30 (d, J = 4.8 Hz, 1H), 8.00 (s, 1H), 7.97 (s, 1H), 7.86 (d, J = 8.0 Hz, 1H), 7.74 (s, 1H), 7.70 (m, 2H), 7.49 (d, J = 8.0 Hz, 1H), 7.33 (d, J = 8.4 Hz, 1H), 3.60 (s, 3H), 2.31 (s, 3H), 2.11 (s, 3H), 1.76 (s, 6H). | 521.0 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 114 | G8 | | P | 22 | 11.0 (s, 1H), 10.7 (s, 1H), 8.98 (d, J = 5.0 Hz, 1H), 8.94 (d, J = 1.2 Hz, 1H), 8.59 (s, 1H), 8.37 (s, 1H), 8.19 (d, J = 5.0 Hz, 1H), 8.06 (d, J = 7.9 Hz, 1H), 7.99 (s, 1H), 7.65 (t, J = 7.7 Hz, 1H), 7.56 (m, 2H), 7.35 (d, J = 11.4 Hz, 1H), 2.28 (s, 3H), 2.16 (s, 3H). | 510.2 |
| 115 | D17 | | R | 19 | 10.6 (s, 1H), 8.91 (m, 2H), 8.77 (d, J = 4.8 Hz, 1H), 8.17 (s, 1H), 8.12 (s, 1H), 8.05 (d, J = 4.4 Hz, 1H), 7.8 (m, 1H), 7.67 (d, J = 7.2 Hz, 1H), 7.32 (d, J = 11.6 Hz, 1H), 7.08 (t, J = 54.8 Hz, 1H), 6.48 (d, J = 2.0 Hz, 1H), 6.28 (d, J = 2.0 Hz, 1H), 3.28 (brs, 3H), 2.83 (d, J = 4.8 Hz, 3H), 2.33 (s, 3H). | 522.0 |
| 116 | D14 | | R | 20 | 10.5 (brs, 1H), 10.4 (brs, 1H), 8.81 (d, J = 5.2 Hz, 1H), 8.43 (s, 1H), 8.29 (d, J = 5.6 Hz, 1H), 8.04 (s, 1H), 7.94 (d, J = 2.4 Hz, 1H), 7.85 (d, J = 5.2 Hz, 1H), 7.73 (d, J = 2.4 Hz, 1H), 7.54 (m, 1H), 7.48 (m, 1H), 7.33 (d, J = 11.2 Hz, 1H), 3.58 (s, 3H), 2.34 (s, 3H), 2.08 (s, 3H), 1.76 (s, 6H). | 539.0 |
| 117 | D12 | | R | 15 | 10.9 (s, 1H), 10.7 (s, 1H), 9.28 (s, 1H), 8.90 (m, 3H), 8.49 (d, J = 4.8 Hz, 1H), 8.19 (s, 1H), 8.07 (brs, 1H), 7.96 (s, 1H), 7.87 (brs, 2H), 7.43 (d, J = 8.8 Hz, 1H), 7.08 (t, J = 54.8 Hz, 1H), 2.41 (s, 3H), 2.04 (m, 1H), 0.82 (brm, 4H). | 500.9 |
| 118 | A5 F30 | | P | 40 | 10.7 (s, 1H), 10.6 (s, 1H), 9.12 (s, 1H), 9.09 (d, J = 5.2 Hz, 1H), 8.82 (d, J = 4.8 Hz, 1H), 8.48 (d, J = 4.8 Hz, 1H), 8.01 (m, 3H), 7.88 (m, 2H), 7.77 (d, J = 5.2 Hz, 1H), 7.43 (d, J = 8.8 Hz, 1H), 3.30 (s, 3H), 2.12 (s, 3H), 1.76 (s, 6H). | 492.0 |
| 119 | A8 F20 | | P | 20 | 10.7 (s, 1H), 9.20 (s, 1H), 9.00 (d, J = 4.8 Hz, 1H), 8.87 (s, 1H), 8.38 (s, 1H), 8.21 (d, J = 4.4 Hz, 1H), 8.13 (d, J = 5.6 Hz, 1H), 7.96 (s, 1H), 7.87 (d, J = 8.0 Hz, 1H), 7.43 (d, J = 8.4 Hz, 1H), 7.31 (s, 1H), 7.23 (d, J = 5.2 Hz, 1H), 6.80 (brs, 1H), 3.47 (brm, 4H), 3.27 (s, 3H), 2.42 (s, 3H). | 509.0 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| 120 | D11 | | R | 75 | 10.6 (s, 1H), 10.4 (s, 1H), 9.28 (s, 1H), 8.91 (s, 1H), 8.87 (s, 1H), 8.48 (d, J = 5.2 Hz, 1H), 7.97 (d, J = 2.3 Hz, 1H), 7.85 (m, 2H), 7.74 (dd, J = 2.1 and 8.3 Hz, 1H), 7.61 (m, 1H), 7.37 (m, 2H), 3.93 (s, 3H), 2.43 (s, 3H), 2.11 (s, 3H). | 472.2 |
| 121 | D11 | | R | 36 | 10.7 (s, 1H), 10.6 (s, 1H), 9.28 (s, 1H), 8.92 (s, 1H), 8.87 (s, 1H), 8.48 (d, J = 5.2 Hz, 1H), 8.42 (d, J = 2.1 Hz, 1H), 8.29 (dd, J = 2.1 and 8.4 Hz, 1H), 7.97 (d, J = 2.3 Hz, 1H), 7.92 (d, J = 8.4 Hz, 1H), 7.85 (m, 2H), 7.41 (d, J = 8.4 Hz, 1H), 2.43 (s, 3H), 2.11 (s, 3H). | 526.2 |
| 122 | F18 | | P & Q | | 10.8 (s, 1H), 9.02 (d, J = 5.1 Hz, 1H), 9.00 (d, J = 5.1 Hz, 1H), 8.38 (s, 1H), 8.21 (d, J = 5.0 Hz, 1H), 8.07 (d, J = 5.3 Hz, 1H), 7.98 (d, J = 2.3 Hz, 1H), 7.87 (dd, J = 2.3 and 8.3 Hz, 1H), 7.69 (d, J = 5.1 Hz, 1H), 7.50 (s, 1H), 7.41 (m, 2H), 6.15 (s, 2H), 2.44 (s, 3H). | |
| 123 | F20 | | P & Q | 10 | 10.79 (s, 1H), 10.76 (m, 1H), 9.35 (m, 1.6H), 8.99 (d, J = 5.0 Hz, 1H), 8.94 (s, 1H), 8.84 (br s, 0.4H), 8.50 (m, 0.4H), 8.47 (m, 0.6H), 8.38 (s, 1.4H), 8.21 (d, J = 5.0 Hz, 1H), 7.97 (d, J = 2.3 Hz, 1H), 7.88 (m, 2H), 7.74 (s, 0.6H), 7.44 (d, J = 8.4 Hz, 1H), 2.43 (s, 3H). rotamers | |
| 124 | D11 | | R | 53 | 10.9 (s, 1H), 10.6 (s, 1H), 9.28 (s, 1H), 9.03 (d, J = 5.1 Hz, 1H), 8.93 (s, 1H), 8.89 (s, 1H), 8.48 (d, J = 5.2 Hz, 1H), 8.35 (s, 1H), 8.16 (d, J = 2.3 Hz, 1H), 8.09 (d, J = 5.1 Hz, 1H), 8.01 (dd, J = 2.3 and 8.3 Hz, 1H), 7.87 (dd, J = 1.6 and 5.3 Hz, 1H), 7.42 (d, J = 8.4 Hz, 1H), 2.45 (s, 3H), 2.11 (s, 3H). | 493.2 |
| 125 | D11 | | R | 34 | 10.6 (s, 1H), 10.5 (s, 1H), 9.28 (s, 1H), 8.92 (s, 1H), 8.88 (s, 1H), 8.48 (d, J = 5.2 Hz, 1H), 8.07 (s, 1H), 7.96 (m, 2H), 7.86 (m, 2H), 7.75 (d, J = 7.9 Hz, 1H), 7.59 (t, J = 7.8 Hz, 1H), 7.40 (d, J = 8.4 Hz, 1H), 2.43 (s, 3H), 2.11 (s, 3H), 1.74 (s, 6H). | 491.2 |

TABLE I-continued

| Ex No. | SM | Product | Method | Yield (%) | $^1$H NMR (400 or 500 MHz, (DMSO-$d_6$): δ | MS (m/z: M + H$^+$) |
|---|---|---|---|---|---|---|
| 126 | D18 | | R | 71 | 10.9 (s, 1H), 9.02 (d, J = 5.1 Hz, 1H), 8.85 (d, J = 5.0 Hz, 2H), 8.78 (d, J = 1.7 Hz, 1H), 8.75 (d, J = 5.1 Hz, 1H), 8.33 (dd, J = 2.0 and 7.2 Hz, 2H), 8.19 (s, 1H), 8.08 (d, J = 5.1 Hz, 1H), 7.96 (m, 2H), 7.56 (dd, J = 1.5 and 5.0 Hz, 1H), 7.38 (d, J = 8.2 Hz, 1H), 2.85 (d, J = 4.8 Hz, 3H), 2.30 (s, 3H). | 492.2 |
| 127 | D18 | | R | 12 | 10.4 (s, 1H), 8.84 (d, J = 5.0 Hz, 2H), 8.77 (s, 1H), 8.75 (d, J = 5.1 Hz, 1H), 8.33 (dd, J = 1.8 and 5.1 Hz, 1H), 8.19 (s, 1H), 8.05 (s, 1H), 7.94 (d, J = 7.8 Hz, 1H), 7.81 (dd, J = 2.2 and 8.3 Hz, 1H), 7.75 (t, J = 2.3 Hz, 2H), 7.59 (t, J = 7.8 Hz, 1H), 7.55 (d, J = 5.0 Hz, 1H), 7.37 (d, J = 8.4 Hz, 1H), 2.85 (d, J = 4.8 Hz, 3H), 2.29 (s, 3H), 1.74 (s, 6H). | 490.2 |
| 128 | F39 | | P & Q | crude | No Data | 451.0 |
| 129 | G10 | | 1839-004-2 | 43 | 14.25 (s, 1H), 10.80 (s, 1H), 9.07 (s, 1H), 8.91 (d, J = 2.4 Hz, 1H), 8.83 (dd, J = 5.0, 0.8 Hz, 1H), 8.73 (d, J = 1.2 Hz, 1H), 8.38 (m, 1H), 8.30 (q, J = 1.5 Hz, 1H), 8.14 (d, J = 2.5 Hz, 1H), 8.03 (dd, J = 1.6, 0.9 Hz, 1H), 7.89 (dd, J = 5.1, 1.6 Hz, 1H), 7.81-7.70 (m, 2H), 2.48 (s, 3H), 1.76 (s, 6H). | 475.2 |
| 130 | 128 | | L | 24 | 11.0 (s, 1H), 10.12 (s, 1H), 9.01 (d, J = 5.2 Hz, 1H), 8.95 (t, J = 2.4 Hz, 1H), 8.86 (s, 1H), 8.47 (d, J = 5.2 Hz, 1H), 8.41 (s, 1H), 8.32 (d, J = 2.4 Hz, 1H), 8.23 (d, J = 4.8 Hz, 1H), 8.15 (t, J = 8.0 Hz, 1H), 8.09 (d, J = 7.6 Hz, 1H), 7.84 (dd, J = 1.2 and 5.2 Hz, 1H), 7.75 (d, J = 7.2 Hz, 1H), 4.09 (s, 2H), 3.37 (s, 3H), 2.63 (s, 3H). | 523.0 |
| 131 | G21 | | P | 23 | 14.25 (s, 1H), 10.67 (s, 1H), 9.07 (s, 1H), 8.91 (d, J = 2.4 Hz, 1H), 8.72 (s, 1H), 8.59 (dd, J = 5.1, 0.8 Hz, 1H), 8.38 (dt, J = 7.4, 1.7 Hz, 1H), 8.30 (d, J = 1.9 Hz, 1H), 8.15 (d, J = 2.5 Hz, 1H), 7.81-7.70 (m, 3H), 7.59 (dd, J = 5.1, 1.7 Hz, 1H), 2.21 (m, 1H), 1.05-0.93 (m, 4H). | 448.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 132 | G5 | | P | 37 | 10.9 (s, 1H), 10.7 (s, 1H), 8.97 (d, J = 5.0 Hz, 1H), 8.71 (d, J = 5.2 Hz, 1H), 8.36 (s, 1H), 8.18 (d, J = 5.0 Hz, 1H), 7.65-7.74 (m, 4 H), 7.57 (m, 3 H), 7.35 (d, J = 8.3 Hz, 1H), 2.27 (s, 3 H), 2.13 (s, 3H). | 516.2 |
| 133 | G9 | | P | 44 | 11.84 (s, 1H), 10.56 (s, 1H), 8.79 (d, J = 5.0 Hz, 1H), 8.29 (d, J = 4.9 Hz, 1H), 7.99 (s, 1H), 7.85 (dd, J = 5.1, 1.6 Hz, 1H), 7.79 (d, J = 7.7 Hz, 1H), 7.75-7.69 (m, 3H), 7.65 (t, J = 7.7 Hz, 1H), 7.56 (t, J = 3.0 Hz, 1H), 7.48 (d, J = 7.7 Hz, 1H), 7.35 (d, J = 8.1 Hz, 1H), 7.24 (d, J = 4.9 Hz, 1H), 6.62 (dd, J = 3.5, 1.8 Hz, 1H), 2.31 (s, 3H), 1.75 (s, 6H). | 472.2 |
| 134 | G9 | | P | 50 | 13.84 (s, 1H), 10.57 (s, 1H), 8.80 (d, J = 5.0 Hz, 1H), 8.59 (d, J = 4.8 Hz, 1H), 8.32 (d, J = 1.4 Hz, 1H), 7.99 (d, J = 1.3 Hz, 1H), 7.91 (dt, J = 7.8, 1.4 Hz, 1H), 7.86 (dd, J = 5.1, 1.5 Hz, 1H), 7.82-7.76 (m, 1H), 7.76-7.67 (m, 3H), 7.56 (dt, J = 7.7, 1.5 Hz, 1H), 7.43 (d, J = 4.8 Hz, 1H), 7.36 (d, J = 8.1 Hz, 1H), 2.31 (s, 3H), 1.75 (s, 6H). | 473.2 |
| 135 | D21 | | R | 44 | 10.94 (s, 1H), 9.46 (s, 1H), 9.03 (d, J = 5.1 Hz, 1H), 8.97 (s, 1H), 8.87 (d, J = 5.5 Hz, 1H), 8.82 (d, J = 5.1 Hz, 1H), 8.77 (d, J = 1.7 Hz, 1H), 8.38 (dd, J = 1.8 and 5.1 Hz, 1H), 8.35 (s, 1H), 8.18 (d, J = 2.3 Hz, 1H), 8.09 (d, J = 5.1 Hz, 1H), 8.02 (dd, J = 2.3 and 8.3 Hz, 1H), 7.42 (d, J = 8.4 Hz, 1H). 2.85 (d, J = 4.8 Hz, 3H). 2.44 (s, 3H). | 493.2 |
| 136 | D21 | | R | 31 | 10.44 (s, 1H), 9.46 (s, 1H), 8.96 (s, 1H), 8.87 (m, 1H), 8.82 (d, J = 5.1 Hz, 1H), 8.76 (d, J = 1.7 Hz, 1H), 8.37 (dd, J = 1,8 and 5.1 Hz, 1H), 8.06 (s, 1H), 7.97 (m, 2H), 7.86 (dd, J = 2.3 and 8.3 Hz, 1H), 7.75 (d, J = 7.9 Hz, 1H), 7.60 (t, J = 7.8 Hz, 1H), 7.41 (d, J = 8.4 Hz, 1H), 2.85 (d, J = 4.8 Hz, 3H), 2.42 (s, 3H), 1.74 (s, 6H). | 491.2 |
| 137 | 122 | | L | 48 | 10.8 (s, 1H), 10.2 (s, 1H), 9.12 (s, 1H), 9.10 (d, J = 5.2 Hz, 1H), 8.99 (d, J = 5.0 Hz, 1H), 8.51 (d, J = 5.2 Hz, 1H), 8.38 (s, 1H), 8.21 (d, J = 5.0 Hz, 1H), 8.06 (d, J = 5.2 Hz, 1H), 8.02 (d, J = 2.2 Hz, 1H), 7.88 (dd, J = 2.2 and 8.3 | 523.2 |

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| | | | | | Hz, 1H), 7.77 (d, J = 5.2 Hz, 1H), 7.44 (d, J = 8.4 Hz, 1H), 4.10 (s, 2H), 3.38 (s, 3H). | |
| 138 | D21 | | R | 19 | 10.7 (s, 1H), 9.47 (s, 1H), 8.97 (s, 1H), 8.87 (d, J = 5.4 Hz, 1H), 8.82 (d, J = 5.1 Hz, 1H), 8.76 (s, 1H), 8.70 (d, J = 5.1 Hz, 1H), 8.37 (dd, J = 1.8 and 5.1 Hz, 1H), 7.97 (d, J = 2.2 Hz, 1H), 7.94 (s, 1H), 7.86 (dd, J = 2.2 and 8.3 Hz, 1H), 7.80 (m, 1H), 7.43 (d, J = 8.4 Hz, 1H), 2.85 (d, J = 4.8 Hz, 3H), 2.43 (s, 3H), 1.87 (m, 2H), 1.76 (m, 2H). | 490.2 |
| 139 | D21 | | R | 15 | 10.6 (s, 1H), 9.46 (s, 1H), 8.96 (s, 1H), 8.87 (m, 1H), 8.82 (d, J = 5.1 Hz, 1H), 8.76 (s, 1H), 8.57 (d, J = 5.1 Hz, 1H), 8.37 (dd, J = 1.8 and 5.1 Hz, 1H), 7.98 (d, J = 2.2 Hz, 1H), 7.87 (dd, J = 2.2 and 8.3 Hz, 1H), 7.75 (s, 1H), 7.58 (d, J = 5.1 Hz, 1H), 7.42 (d, J = 8.4 Hz, 1H), 2.85 (d, J = 4.8 Hz, 3H), 2.42 (s, 3H), 2.17-2.24 (m, 1H), 0.94-1.01 (m, 4H). | 465.2 |
| 140 | D11 | | R | 52 | 10.7 (brs, 1H), 10.6 (brs, 1H), 9.29 (s, 1H), 8.93 (s, 1H), 8.88 (s, 1H), 8.81 (d, J = 4.8 Hz, 1H), 8.49 (m, 1H), 8.02 (s, 1H), 7.96 (s, 1H), 7.86 (m, 3H), 7.44 (d, J = 8.4 Hz, 1H), 2.44 (s, 3H), 2.12 (s, 3H), 1.76 (s, 6H). | 492.2 |
| 141 | D19 | | R & Q | 73 | 10.7 (s, 1H), 9.19 (s, 1H), 8.87 (s, 1H), 8.81 (d, J = 4.8 Hz, 1H), 8.07 (d, J = 6.0 Hz, 1H), 8.02 (s, 1H), 7.93 (brs, 1H), 7.87 (d, J = 5.2 Hz, 1H), 7.84 (m, 1H), 7.42 (d, J = 8.4 Hz, 1H), 7.24 (brs, 2H), 6.15 (brs, 2H), 2.41 (s, 3H), 1.76 (s, 6H). | 450.2 |
| 142 | 141 | | L | 58 | 10.7 (s, 1H), 10.2 (s, 1H), 9.32 (s, 1H), 8.94 (s, 1H), 8.88 (s, 1H), 8.81 (d, J = 4.8 Hz, 1H), 8.52 (s, 1H), 8.02 (s, 1H), 7.97 (s., 1H), 7.92 (d, J = 4.8 Hz, 1H), 7.88 (m, 2H), 7.44 (d, J = 8.4 Hz, 1H), 4.10 (s, 2H), 3.37 (s, 3H), 2.45 (s, 3H), 1.76 (s, 6H). | 522.3 |
| 143 | D22 | | R | 21 | 10.7 (s, 1H), 9.20 (s, 1H), 8.88 (s, 1H), 8.81 (d, J = 4.8 Hz, 1H), 8.13 (d, J = 5.6 Hz, 1H), 8.02 (s, 1H), 7.95 (d, J = 1.6 Hz, 1H), 7.88 (d, J = 5.2 Hz, 1H), 7.84 (m, 1H), 7.42 (d, J = 8.0 Hz, 1H), 7.33 (s, 1H), 7.25 (d, J = 5.2 Hz, 1H), 6.89 (brs, 1H), 3.48 (s, | 508.3 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | 4H), 3.27 (s, 3H), 2.42 (s, 3H), 1.76 (s, 6H). | |
| 144 | 122  NaCN | 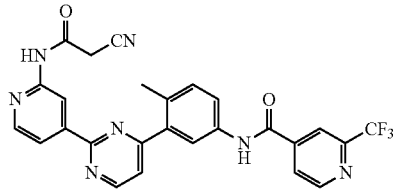 | L & S_N2 | 27 | 11.0 (s, 1H), 10.8 (s, 1H), 9.10 (d, J = 5.2 Hz, 1H), 9.07 (s, 1H), 8.99 (d, J = 5.0 Hz, 1H), 8.53 (d, J = 5.2 Hz, 1H), 8.38 (s, 1H), 8.21 (d, J = 5.0 Hz, 1H), 8.08 (dd, J = 1.4 and 5.2 Hz, 1H), 8.02 (d, J = 2.2 Hz, 1H), 7.87 (dd, J = 2.3 and 8.3 Hz, 1H), 7.77 (d, J = 5.2 Hz, 1H), 7.45 (d, J = 8.4 Hz, 1H), 4.02 (s, 2H). | 518.2 |
| 145 | D11 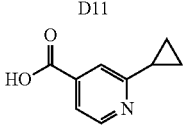 | 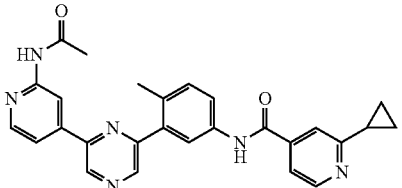 | R | 11 | 10.6 (s, 1H), 10.5 (s, 1H), 9.28 (s, 1H), 8.91 (s, 1H), 8.87 (s, 1H), 8.57 (d, J = 5.1 Hz, 1H), 8.48 (d, J = 5.2 Hz, 1H), 7.97 (d, J = 2.3 Hz, 1H), 7.86 (m, 2H), 7.75 (s, 1H), 7.57 (dd, J = 1.6 and 5.1 Hz, 1H), 7.41 (d, J = 8.4 Hz, 1H), 2.43 (s, 3H), 2.17-2.22 (m, 1H), 2.11 (s, 3H), 0.95-1.02 (m, 4H). | 465.2 |
| 146 | D11 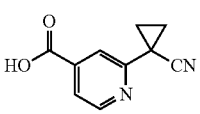 | 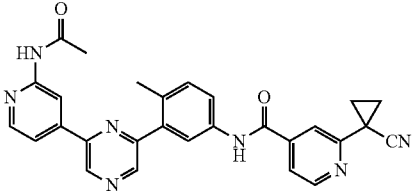 [SMILES: CC(=O)Nc1cc(-c2cncc(-c3cc(NC(=O)c4cccc(C(C)(C)C#N)c4)ccc3C)n2)ccn1] Using oxalyl chloride | L | 10 | 10.7 (s, 1H), 10.6 (s, 1H), 9.28 (s, 1H), 8.92 (s, 1H), 8.87 (s, 1H), 8.70 (d, J = 5.1 Hz, 1H), 8.48 (d, J = 5.2 Hz, 1H), 7.94 (m, 2H), 7.84 (m, 2H), 7.80 (dd, J = 1.5 and 5.1 Hz, 1H), 7.43 (d, J = 8.4 Hz, 1H), 2.44 (s, 3H), 2.11 (s, 3H), 1.87 (m, 2H), 1.76 (m, 2H). | 490.2 |
| 147 | D11 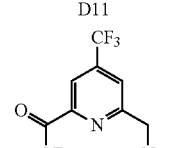 LiOH | 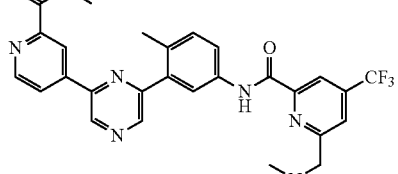 Using oxalyl chloride | L | 29 | 10.7 (s, 1H), 9.47 (s, 1H), 8.98 (s, 1H), 8.87 (d, J = 5.5 Hz, 1H), 8.82 (d, J = 5.1 Hz, 1H), 8.77 (s, 1H), 8.38 (d, J = 5.1 Hz, 1H), 8.22 (s, 1H), 8.11 (d, J = 2.2 Hz, 1H), 7.99 (m, 2H), 7.44 (d, J = 8.4 Hz, 1H), 3.81 (s, 2H), 2.85 (d, J = 4.8 Hz, 3H), 2.44 (s, 3H), 2.27 (s, 6H). | 550.2 |
| 148 | D12 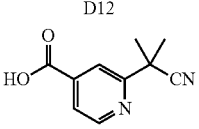 | 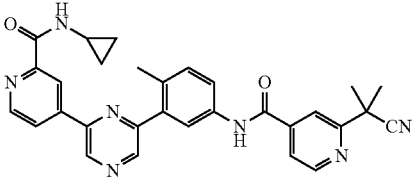 [SMILES: Cc1ccc(NC(=O)c2ccnc(C(C)(C)C#N)c2)cc1-c1cncc(-c2ccnc(C(=O)NC3CC3)c2)n1] | R | 43 | 10.7 (s, 1H), 9.47 (s, 1H), 8.97 (s, 1H), 8.82 (m, 1H), 8.80 (dd, J = 3.1 and 5.1 Hz, 2H), 8.75 (s, 1H), 8.37 (s, 1H), 8.02 (s, 1H), 7.97 (d, J = 2.2 Hz, 1H), 7.87 (m, 2H), 7.44 (d, J = 8.4 Hz, 1H), 2.93 (m, 1H), 2.43 (s, 3H), 1.76 (s, 6H), 0.70 (m, 4H). | 518.2 |
| 149 | D12 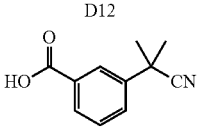 | 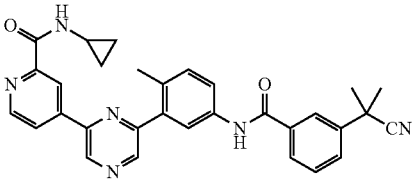 [SMILES: Cc1ccc(NC(=O)c2cccc(C(C)(C)C#N)c2)cc1-c1cncc(-c2ccnc(C(=O)NC3CC3)c2)n1] | R | 60 | 10.4 (s, 1H), 9.46 (s, 1H), 8.96 (s, 1H), 8.83 (d, J = 5.0 Hz, 1H), 8.80 (d, J = 5.1 Hz, 1H), 8.76 (s, 1H), 8.37 (dd, J = 1.8 and 5.1 Hz, 1H), 8.06 (s, 1H), 7.96 (m, 2H), 7.86 (dd, J = 2.2 and 8.3 Hz, 1H), 7.75 (d, J = 7.9 Hz, 1H), 7.60 (t, J = 7.8 Hz, 1H), 7.41 (d, | 517.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | J = 8.4 Hz, 1H), 2.93 (m, 1H), 2.42 (s, 3H), 1.74 (s, 6H), 0.70 (m, 4H). | |
| 150 | D24 | | R | 33 | 10.6 (s, 1H), 10.4 (s, 1H), 9.12 (s, 1H), 9.08 (d, J = 5.2 Hz, 1H), 8.48 (d, J = 5.2 Hz, 1H), 8.06 (s, 1H), 8.01 (m, 2H), 7.96 (d, J = 7.8 Hz, 1H), 7.86 (dd, J = 2.3 and 8.3 Hz, 1H), 7.75 (m, 2H), 7.60 (t, J = 7.8 Hz, 1H), 7.40 (d, J = 8.4 Hz, 1H), 2.47 (s, 3H), 2.12 (s, 3H), 1.74 (s, 6H). | 491.2 |
| 151 | D24 | | R | 32 | 10.7 (s, 1H), 10.6 (s, 1H), 9.12 (s, 1H), 9.08 (d, J = 5.2 Hz, 1H), 8.71 (d, J = 5.1 Hz, 1H), 8.48 (d, J = 5.2 Hz, 1H), 8.01 (m, 2H), 7.94 (s, 1H), 7.86 (dd, J = 2.3 and 8.3 Hz, 1H), 7.81 (d, J = 5.1 Hz, 1H), 7.76 (d, J = 5.2 Hz, 1H), 7.43 (d, J = 8.4 Hz, 1H), 2.47 (s, 3H), 2.12 (s, 3H), 1.88 (m, 2H), 1.77 (m, 2H) | 490.2 |
| 152 | D24 | | R | 39 | 10.6 (s, 1H), 10.6 (s, 1H), 9.12 (s, 1H), 9.08 (d, J = 5.2 Hz, 1H), 8.57 (d, J = 5.1 Hz, 1H), 8.48 (d, J = 5.2 Hz, 1H), 8.01 (m, 2H), 7.86 (dd, J = 2.2 and 8.3 Hz, 1H), 7.74 (m, 2H), 7.57 (m, 1H), 7.41 (d, J = 8.4 Hz, 1H), 2.47 (s, 3H), 2.21 (m, 1H), 2.12 (s, 3H), 0.95-1.02 (m, 4H). | 465.2 |
| 153 | D24 | | R | 60 | 11.0 (s, 1H), 10.6 (s, 1H), 9.12 (s, 1H), 9.08 (d, J = 5.2 Hz, 1H), 9.03 (d, J = 5.1 Hz, 1H), 8.48 (d, J = 5.2 Hz, 1H), 8.35 (s, 1H), 8.21 (d, J = 2.2 Hz, 1H), 8.09 (d, J = 5.1 Hz, 1H), 8.01 (m, 2H), 7.76 (d, J = 5.2 Hz, 1H), 7.41 (d, J = 8.4 Hz, 1H), 2.48 (s, 3H), 2.12 (s, 3H). | 493.2 |
| 154 | 141 NaCN | | L & SN2 | 16 | 11.0 (s, 1H), 10.7 (s, 1H), 9.33 (s, 1H), 8.94 (s, 1H), 8.83 (brs, 1H), 8.81 (d, J = 5.2 Hz, 1H), 8.54 (d, J = 5.2 Hz, 1H), 8.02 (s, 1H), 7.97 (s, 1H), 7.95 (dd, J = 1.2 and 4.0 Hz, 1H), 7.87 (m, 2H), 7.45 (d, J = 8.4 Hz, 1H), 4.02 (brs, 2H), 2.45 (s, 3H), 1.76 (s, 6H). | 517.3 |
| 155 | D25 | | R | 20 | 10.7 (s, 1H), 10.7 (s, 1H), 8.99 (d, J = 5.2 Hz, 1H), 8.44 (d, J = 5.2 Hz, 1H), 8.35 (s, 1H), 8.17 (m, 2H), 7.59 (m, 1H), 7.32 (m, 2H), 6.46 (d, J = 2.0 Hz, 1H), 6.21 (d, J = 1.6 Hz, 1H), 3.29 (s, 3H), 2.34 (s, 3H), 2.10 (s, 3H). | 540.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 156 | G5 | | P | 14 | 10.7 (s, 1H), 8.99 (d, J = 4.8 Hz, 1H), 8.50 (brs, 1H), 8.37 (s, 1H), 8.19 (d, J = 4.8 Hz, 1H), 7.98 (brm, 2H), 7.76 (dd, J = 2.4 and 8.4 Hz, 1H), 7.71 (s, 1H), 7.59 (t, J = 8.0, Hz, 1H), 7.49 (d, J = 7.6 Hz, 1H), 7.45 (m, 1H), 7.35 (d, J = 8.4 Hz, 1H), 7.07 (s, 1H), 3.50 (m, 4H), 3.27 (s, 3H), 2.26 (s, 3H). | 508.2 |
| 157 | A5 F41 | | P | 44 | 11.0 (s, 1H), 10.7 (s, 1H), 9.14 (m, 2H), 9.02 (d, J = 5.2 Hz, 1H), 9.00 (d, J = 2.4 Hz, 1H), 8.50 (d, J = 5.2 Hz, 1H), 8.43 (d, J = 2.4 Hz, 1H), 8.41 (s, 1H), 8.23 (d, J = 4.8 Hz, 1H), 8.03 (dd, J = 1.6 and 5.2 Hz, 1H), 7.87 (d, J = 5.2 Hz, 1H), 2.68 (s, 3H), 2.13 (s, 3H). | 493.9 |
| 158 | D27 | | R | 68 | 10.8 (s, 1H), 8.94 (brs, 1H), 8.89 (d, J = 4.8 Hz, 1H), 8.84 (m, 2H), 8.78 (s, 1H), 8.77 (d, J = 9.2 Hz, 1H), 8.34 (d, J = 4.4 Hz, 1H), 8.30 (s, 1H), 8.16 (s, 1H), 8.04 (s, 1H), 7.90 (d, J = 5.2 Hz, 1H), 7.64 (d, J = 4.8 Hz, 1H), 2.86 (d, J = 4.4 Hz, 3H), 2.50 (s, 3H), 1.77 (s, 6H). 3 hydrogens merged with solvent peak | 491.9 |
| 159 | G7 | | P | 6 | 10.6 (s, 1H), 8.80 (d, J = 4.8 Hz, 1H), 8.50 (s, 1H), 8.01 (s, 1H), 7.97 (brm, 2H), 7.87 (d, J = 5.2 Hz, 1H), 7.74 (brd, J = 8.0 Hz, 1H), 7.69 (s, 1H), 7.59 (t, J = 8.0 Hz, 1H), 7.48 (brm, 2H), 7.35 (d, J = 8.4 Hz, 1H), 7.07 (s, 1H), 3.48 (brm, 4H), 3.27 (s, 3H), 2.25 (s, 3H), 1.76 (s, 6H). | 507.2 |
| 160 | G7 | | P | 31 | 10.6 (s, 1H), 8.81 (d, J = 5.2 Hz, 1H), 8.50 (brs, 1H), 8.01 (br m, 3H), 7.86 (dd, J = 1.2 and 5.2 Hz, 1H), 7.75 (dd, J = 2.0 and 8.0 Hz, 1H), 7.69 (d, J = 1.2 Hz, 1H), 7.58 (t, J = 7.6 Hz, 1H), 7.49 (d, J = 7.6 Hz, 1H), 7.35 (brm, 2H), 6.98 (s, 1H), 2.85 (d, J = 4.4 Hz, 3H), 2.25 (s, 3H), 1.76 (s, 6H). | 463.2 |
| 161 | A7 F42 | | P | 35 | 10.8 (brm, 1H), 10.7 (s, 1H), 9.33 (brm, 1.5H), 8.94 (s, 1H), 8.87 (s, 0.4H), 8.11 (d, J = 5.2 Hz, 1H), 8.38-8.51 (m, 1.5H), 8.02 (s, 1H), 7.96 (s, 1H), 7.87 (brm, 3H), 7.75 (s, 0.6H), 7.44 (d, J = 8.4 Hz, 1H), 2.43 (s, 3H), 1.76 (s, 6H). rotamers | 478.0 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 162 | D26 | | R | 27 | 10.6 (s, 1H), 8.86 (d, J = 4.8 Hz, 1H), 8.81 (d, J = 4.8 Hz, 2H), 8.77 (s, 1H), 8.73 (d, J = 5.2 Hz, 1H), 8.33 (d, J = 4.4 Hz, 1H), 8.20 (s, 1H), 8.01 (s, 1H), 7.88 (d, J = 5.2 Hz, 1H), 8.01 (d, J = 8.4 Hz, 1H), 7.75 (s, 1H), 7.57 (d, J = 4.8 Hz, 1H), 7.41 (d, J = 8.4 Hz, 1H), 2.94 (m, 1H), 2.30 (s, 3H), 1.76 (s, 6H), 0.71 (brm, 4H). | 517.0 |
| 163 | D28 | | R | 29 | 10.6 (s, 1H), 8.84 (m, 1H), 8.81 (d, J = 4.8 Hz, 1H), 8.73 (d, J = 5.2 Hz, 1H), 8.68 (s, 1H), 8.28 (brd, J = 5.2 Hz, 1H), 8.01 (s, 1H), 7.91 (s, 1H), 7.88 (d, J = 4.8 Hz, 1H), 7.80 (m, 1H), 7.73 (brm, 1H), 7.46 (s, 1H), 7.39 (d, J = 8.4 Hz, 1H), 2.85 (d, J = 4.8 Hz, 3H), 2.30 (s, 1H), 2.27 (brm, 1H), 1.76 (s, 6H), 1.05-1.12 (m, 4H). | 531.3 |
| 164 | D12 | | R | 17 | 10.7 (s, 1H), 10.6 (s, 1H), 9.29 (s, 1H), 8.93 (s, 1H), 8.88 (s, 1H), 8.71 (d, J = 5.2 Hz, 1H), 8.48 (d, J = 5.2 Hz, 1H), 7.97 (s, 1H), 7.87 (m, 3H), 7.68 (d, J = 5.2 Hz, 1H), 7.42 (d, J = 8.4 Hz, 1H), 2.44 (s, 3H), 2.12 (s, 3H), 1.37 (s, 9H). | 481.0 |
| 165 | D11 | | R | 22 | 11.0 (s, 1H), 10.4 (s, 1H), 9.28 (s, 1H), 8.92 (s, 1H), 8.88 (s, 1H), 8.50 (d, J = 5.2 Hz, 1H), 8.06 (s, 1H), 7.96 (m, 2H), 7.86 (m, 2H), 7.75 (d, J = 8.0 Hz, 1H), 7.60 (t, J = 8.0 Hz, 1H), 7.41 (d, J = 8.4 Hz, 1H), 2.41 (s, 3H), 2.01 (m, 1H), 1.74 (s, 6H), 0.82 (m, 4H). | 517.2 |
| 166 | D30 | | L | 19 | 10.7 (s, 1H), 9.10 (d, J = 5.2 Hz, 1H), 8.96 (s, 1H), 8.88 (m, 1H), 8.84 (d, J = 5.0 Hz, 1H), 8.81 (d, J = 5.5 Hz, 1H), 8.49 (dd, J = 1.8 and 5.0 Hz, 1H), 8.06 (s, 1H), 7.89 (m, 2H), 7.82 (d, J = 5.2 Hz, 1H), 7.44 (d, J = 11.3 Hz, 1H), 2.85 (d, J = 4.8 Hz, 3H), 2.52 (s, 3H), 1.76 (s, 6H). | 510.2 |
| 167 | D12 | | R | 4 | 11.0 (s, 1H), 10.9 (s, 1H), 9.28 (s, 1H), 9.03 (d, J = 5.1 Hz, 1H), 8.92 (s, 1H), 8.89 (s, 1H), 8.49 (d, J = 5.2 Hz, 1H), 8.35 (s, 1H), 8.15 (d, J = 2.3 Hz, 1H), 8.10 (d, J = 5.1 Hz, 1H), 8.01 (dd, J = 2.3 and 8.3 Hz, 1H), 7.87 (dd, J = 1.5 and 5.3 Hz, 1H), 7.42 (d, J = 8.4 Hz, 1H), 2.42 (s, 3H) 2.03 (m, 1H), 0.80 (m, 4H). | 519.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 168 | D30 | | R | 11 | 10.8 (s, 1H), 10.7 (s, 1H), 9.39 (d, J = 2.0 Hz, 1H), 9.12 (s, 1H), 9.08 (d, J = 5.2 Hz, 1H), 8.48 (d, J = 5.2 Hz, 1H), 8.01 (d, J = 3.4 Hz, 2H), 7.93 (d, J = 2.1 Hz, 1H), 7.86 (dd, J = 2.2 and 8.3 Hz, 1H), 7.75 (d, J = 5.2 Hz, 1H), 7.43 (d, J = 8.4 Hz, 1H), 2.47 (s, 3H), 2.37 (m, 1H), 2.12 (s, 3H), 1.13-1.16 (m, 4H). | 466.2 |
| 169 | C9 E6 | | P | 64 | 11.0 (s, 1H), 10.7 (s, 1H), 9.11 (d, J = 5.3 Hz, 1H), 8.95 (s, 1H), 8.80 (d, J = 5.1 Hz, 1H), 8.53 (d, J = 5.2 Hz, 1H), 8.31 (d, J = 2.3 Hz, 1H), 8.06 (d, J = 5.3 Hz, 1H), 8.03 (s, 1H), 7.89 (m, 3H), 7.40 (d, J = 8.4 Hz, 1H), 2.58 (s, 3H), 2.03 (m, 1H), 1.76 (s, 6H), 0.82 (m, 4H). | 518.2 |
| 170 | D32 | | R | 35 | 10.7 (s, 1H), 9.48 (s, 1H), 8.99 (s, 1H), 8.83 (dd, J = 3.0 and 5.3 Hz, 3H), 8.76 (s, 1H), 8.38 (dd, J = 1.9 and 5.1 Hz, 1H), 8.07 (s, 1H), 7.87 (m, 2H), 7.46 (d, J = 11.3 Hz, 1H), 2.85 (d, J = 4.7 Hz, 3H), 2.48 (s, 3H), 1.77 (s, 6H). | 510.2 |
| 171 | G7 | | P | 25 | 10.6 (s, 1H), 9.37 (d, J = 0.8 Hz, 1H), 9.06 (q, J = 4.4 Hz, 1H), 8.80 (d, J = 5.2 Hz, 1H), 8.53 (d, J = 1.2 Hz, 1H), 8.30 (brd, J = 7.6 Hz, 1H), 8.24 (brs, 1H), 8.01 (brs, 1H), 7.87 (dd, J = 1.2 and 5.2 Hz, 1H), 7.76 (m, 1H), 7.75 (m, 1H), 7.71 (t, J = 7.6 Hz, 1H), 7.63 (brd, J = 7.6 Hz, 1H), 7.36 (d, J = 8.4 Hz, 1H), 2.87 (d, J = 4.8 Hz, 3H), 2.27 (s, 3H), 1.76 (s, 6H). | 491.2 |
| 172 | D33 | | R | 54 | 10.9 (s, 1H), 10.8 (s, 1H), 8.94 (d, J = 6.4 Hz, 1H), 8.84 (m, 2H), 8.45 (d, J = 5.2 Hz, 1H), 8.28 (m, 1H), 8.12 (t, J = 8.0 Hz, 1H), 8.05 (m, 2H), 7.90 (dd, J = 1.2 and 4.8 Hz, 1H), 7.79 (dd, J = 1.6 and 5.2 Hz, 1H), 7.73 (d, J = 7.2 Hz, 1H), 2.60 (s, 3H), 2.03 (m, 1H), 1.77 (s, 6H), 0.82 (m, 4H). | 518.3 |
| 173 | F42 | | P | 21 | 10.7 (s, 1H), 9.23 (s, 1H), 8.88 (s, 1H), 8.82 (d, J = 5.2 Hz, 1H), 8.15 (d, J = 5.2 Hz, 1H), 8.02 (s, 1H), 7.94 (d, J = 2.0 Hz, 1H), 7.88 (dd, J = 1.2 and 5.2 Hz, 1H), 7.84 (dd, J = 2.0 and 8.4 Hz, 1H), 7.42 (d, J = 8.4 Hz, 1H), 7.24 (m, 2H), 6.73 (q, J = 4.4 Hz, 1H), 2.83 (d, J = 4.4 Hz, 3H), 2.41 (s, 3H), 1.76 (s, 6H). | 464.1 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 174 | G9 | | P | 51 | 11.3 (s, 1H), 10.3 (s, 1H), 8.96 (s, 1H), 8.62 (s, 1H), 7.97-8.10 (m, 3H), 7.94 (d, J = 7.6 Hz, 1H), 7.75 (m, 2H), 7.70 (s, 1H), 7.65 (t, J = 7.6 Hz, 1H), 7.59 (m, 2H), 7.33 (d, J = 8.0 Hz, 1H), 2.24 (s, 3H), 2.07 (m, 1H), 1.74 (s, 6H), 0.89 (m, 4H). | 516.2 |
| 175 | D36 | | R | 29 | 10.8 (s, 1H), 9.11 (d, J = 5.1 Hz, 1H), 8.97 (s, 1H), 8.91 (m, 1H), 8.84 (d, J = 5.0 Hz, 1H), 8.70 (d, J = 5.0 Hz, 1H), 8.49 (dd, J = 1.8 and 5.1 Hz, 1H), 8.02 (d, J = 2.3 Hz, 1H), 7.94 (s, 1H), 7.87 (dd, J = 2.3 and 8.3 Hz, 1H), 7.79-7.82 (m, 2H), 7.43 (d, J = 8.3 Hz, 1H), 2.84 (d, J = 4.7 Hz, 3H), 2.46 (s, 3H), 1.88 (q, J = 4.4 Hz, 2H), 1.76 (q, J = 4.5 Hz, 2H). | 490.2 |
| 176 | D37 | | R | 21 | 10.6 (s, 1H), 8.88 (m, 1H), 8.85 (d, J = 5.0 Hz, 1H), 8.82 (d, J = 5.0 Hz, 1H), 8.77 (d, J = 1.8 Hz, 1H), 8.75 (d, J = 5.1 Hz, 1H), 8.34 (dd, J = 1.9 and 5.1 Hz, 1H), 8.20 (s, 1H), 8.05 (s, 1H), 7.88 (dd, J = 1.5 and 5.1 Hz, 1H), 7.64 (d, J = 7.7 Hz, 1H), 7.57 (dd, J = 1.6 and 5.0 Hz, 1H), 7.41 (d, J = 11.3 Hz, 1H), 2.85 (d, J = 4.7 Hz, 3H), 2.34 (s, 3H), 1.76 (s, 6H) | 509.2 |
| 177 | E6 C10 | | P | 59 | 10.7 (s, 1H), 9.15 (d, J = 5.2 Hz, 1H), 8.92 (brq, J = 4.8 Hz, 1H), 8.87 (d, J = 5.0 Hz, 1H), 8.78-8.83 (m, 2H), 8.40 (dd, J = 1.8 and 5.1 Hz, 1H), 8.33 (d, J = 2.3 Hz, 1H), 8.28 (d, J = 5.2 Hz, 1H), 8.03 (s, 1H), 7.87-7.92 (m, 2H), 7.41 (d, J = 8.4 Hz, 1H), 2.85 (d, J = 4.8 Hz, 3H), 2.60 (s, 3H), 1.76 (s, 6H). | 492.2 |
| 178 | D39 | | K | 5 | 10.7 (s, 1H), 9.48 (d, J = 1.3 Hz, 1H), 8.97 (brm, 1H), 8.82-8.89 (m, 2H), 8.72 (d, J = 5.0 Hz, 1H), 8.49 (s, 1H), 8.45 (dd, J = 1.9 and 5.0 Hz, 1H), 8.01 (d, J = 2.4 Hz, 1H), 7.95 (s, 1H), 7.87 (dd, J = 8.3, 2.4 Hz, 1H), 7.82 (dd, J = 1.6 and 5.1 Hz, 1H), 7.43 (d, J = 8.5 Hz, 1H), 2.86 (d, J = 4.8 Hz, 3H), 2.44 (s, 3H), 1.87-1.92 (m, 2H), 1.74-1.81 (m, 2H). | 490.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 179 | D41 | | R | 45 | 11.0 (s, 1H), 10.7 (s, 1H), 9.11 (s, 1H), 9.05 (d, J = 5.2 Hz, 1H), 8.81 (d, J = 5.0 Hz, 1H), 8.49 (d, J = 5.1 Hz, 1H), 8.06 (s, 1H), 8.00 (dd, J = 1.6 and 5.2 Hz, 1H), 7.85-7.90 (m, 2H), 7.77 (d, J = 5.2 Hz, 1H), 7.44 (d, J = 11.3 Hz, 1H), 2.52 (s, 3H), 2.03 (m, 1H), 1.76 (s, 6H), 0.78-0.86 (m, 4H). | 536.2 |
| 180 | D43 | | R | 43 | 11.0 (s, 1H), 10.7 (s, 1H), 9.12 (s, 1H), 9.07 (d, J = 5.1 Hz, 1H), 8.71 (d, J = 5.0 Hz, 1H), 8.49 (d, J = 5.2 Hz, 1H), 8.01 (dd, J = 1.5 and 5.2 Hz, 1H), 7.99 (d, J = 2.3 Hz, 1H), 7.93 (s, 1H), 7.86 (dd, J = 2.3 and 8.3 Hz, 1H), 7.80 (dd, J = 1.5 and 5.1 Hz, 1H), 7.75 (d, J = 5.1 Hz, 1H), 7.43 (d, J = 8.4 Hz, 1H), 2.45 (s, 3H), 2.03 (m, 1H), 1.88 (m, 2H), 1.77 (m, 2H), 0.77-0.87 (m, 4H). | 516.2 |
| 181 | G10 | | P | 37 | 11.4 (s, 1H), 10.8 (s, 1H), 8.97 (s, 1H), 8.90 (d, J = 2.4 Hz, 1H), 8.83 (d, J = 5.2 Hz, 1H), 8.62 (s, 1H), 8.10 (m, 2H), 8.06 (s, 1H), 8.04 (s, 1H), 7.89 (d, J = 5.2 Hz, 1H), 7.67 (m, 2H), 2.45 (s, 3H), 2.08 (m, 1H), 1.76 (s, 6H), 0.89 (m, 4H). | 518.3 |
| 182 | D34 | | K | 72 | 10.8 (s, 1H), 10.6 (s, 1H), 8.94 (d, J = 2.4 Hz, 1H), 8.87 (s, 1H), 8.83 (d, J = 5.2 Hz, 1H), 8.44 (d, J = 5.2 Hz, 1H), 8.30 (brd, J = 2.0 Hz, 1H), 8.13 (m, 1H), 8.06 (m. 2H), 7.91 (brd, J = 4.8 Hz, 1H), 7.79 (brd, J = 4.8 Hz, 1H), 7.74 (d, J = 7.6 Hz, 1H), 2.62 (s, 3H), 2.43 (q, J = 7.6 Hz, 2H), 1.77 (s, 6H), 1.07 (t, J = 7.6 Hz, 3H). | 506.1 |
| 183 | D12 | | K | 25 | 11.0 (s, 1H), 10.7 (s, 1H), 9.28 (s, 1H), 8.92 (s, 1H), 8.88 (s, 1H), 8.71 (d, J = 5.2 Hz, 1H), 8.50 (d, J = 4.8 Hz, 1H), 7.94 (brm, 2H), 7.86 (m, 2H), 7.80 (brd, J = 4.0 Hz, 1H), 7.43 (d, J = 8.4 Hz, 1H), 2.41 (s, 3H), 2.03 (m, 1H), 1.88 (m, 2H), 1.77 (m, 2H), 0.81 (m, 4H). | 516.2 |
| 184 | D12 | | K | 11 | 11.0 (s, 1H), 10.6 (s, 1H). 9.28 (s, 1H), 8.91 (s, 1H), 8.88 (s, 1H), 8.57 (d, J = 5.2 Hz, 1H). 8.50 (d, J = 5.2 Hz, 1H). 7.96 (m, 1H). 7.86 (brm, 2H), 7.75 (s, 1H), 7.58 (dd, J= 1.2 and 5.2 Hz, 1H). 7.41 (d, J = 8.4 Hz, 1H), 2.41 (s, 3H), 2.21 (m, 1H), 2.03 (m, 1H), 0.99 (m, 4H), 0.83 (m, 4H). | 491.3 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 185 | D12 | | K | 7 | 11.0 (s, 1H), 10.6 (s, 1H), 9.28 (s, 1H), 8.92 (s, 1H), 8.88 (s, 1H), 8.50 (d, J = 5.6 Hz, 1H), 8.21 (brd, J = 7.2 Hz, 2H), 7.94 (d, J = 2.0 Hz, 1H), 7.84-7.91 (m, 3H), 7.42 (d, J = 8.4 Hz, 1H), 3.56 (s, 2H), 2.41 (s, 3H), 2.18 (s, 6H), 2.03 (m, 1H), 0.81 (m, 4H). | 575.3 |
| 186 | D43 | | K | 56 | 11.0 (s, 1H), 10.7 (s, 1H), 9.12 (s, 1H), 9.07 (d, J = 5.1 Hz, 1H), 8.76 (d, J = 5.0 Hz, 1H), 8.49 (d, J = 5.1 Hz, 1H), 8.04 (s, 1H), 8.00-8.03 (m, 2H), 7.88 (dd, J = 2.3 and 8.3 Hz, 1H), 7.84 (dd, J = 1.7 and 5.0 Hz, 1H), 7.75 (d, J = 5.2 Hz, 1H), 7.42 (d, J = 8.4 Hz, 1H), 2.45 (s, 3H), 2.03 (m, 1H), 1.70 (d, J = 20 Hz, 6H), 0.77-0.86 (m, 4H). | 511.2 |
| 187 | C9 E10 | | P | 63 | 11.03 (s, 1H), 10.7 (s, 1H), 9.12 (d, J = 5.3 Hz, 1H), 8.96 (s, 1H), 8.71 (d, J = 5.2 Hz, 1H), 8.54 (d, J = 5.2 Hz, 1H), 8.32 (s, 1H), 8.08 (m, 1H), 7.95 (s, 1H), 7.85-7.92 (m, 2H), 7.82 (d, J = 5.2 Hz, 1H), 7.40 (d, J = 8.6 Hz, 1H), 2.59 (s, 3H), 2.04 (m, 1H), 1.92-1.84 (m, 2H), 1.76-1.79 (m, 2H), 0.82-0.85 (m, 4H). | 516.2 |
| 188 | D43 | | K | 62 | 11.0 (brm, 2H), 9.13 (s, 1H), 9.07 (d, J = 5.1 Hz, 1H), 9.03 (d, J = 5.0 Hz, 1H), 8.49 (d, J = 5.1 Hz, 1H), 8.35 (s, 1H), 8.20 (d, J = 2.3 Hz, 1H), 8.10 (dd, J = 1.8 and 5.1 Hz, 1H), 8.00-8.04 (m, 2H), 7.76 (d, J = 5.1 Hz, 1H), 7.41 (d, J = 8.4 Hz, 1H), 2.47 (s, 3H), 2.04 (m, 1H), 0.78-0.86 (m, 4H). | 519.2 |
| 189 | D43 | | K | 66 | 11.0 (s, 1H), 10.8 (s, 1H), 9.12 (s, 1H), 9.07 (d, J = 5.2 Hz, 1H), 8.90 (d, J = 5.0 Hz, 1H), 8.49 (dd, J = 0.5 and 5.5 Hz, 1H), 8.19 (s, 1H), 8.07 (d, J = 1.6 Hz, 1H), 7.99-8.04 (m, 2H), 7.88 (dd, J = 8.3, 2.3 Hz, 1H), 7.75 (d, J = 5.1 Hz, 1H), 7.43 (d, J = 8.4 Hz, 1H), 7.09 (t, J = 54 Hz, 1H), 2.46 (s, 3H), 2.05 (m, 1H), 0.77-0.87 (m, 4H). | 501.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 190 | D43 | | K | 60 | 11.0 (s, 1H), 10.7 (s, 1H), 9.12 (s, 1H), 9.07 (d, J = 5.1 Hz, 1H), 8.72 (d, J = 5.0 Hz, 1H), 8.49 (d, J = 5.2 Hz, 1H), 7.98-8.04 (m, 3H), 7.88 (dd, J = 2.3 and 8.3 Hz, 1H), 7.77 (dd, J = 1.7 and 5.1 Hz, 1H), 7.75 (d, J = 5.2 Hz, 1H), 7.42 (d, J = 8.4 Hz, 1H), 3.11 (s, 3H), 2.45 (s, 3H), 2.04 (m, 1H), 1.50 (s, 6H), 0.77-0.87 (m, 4H). | 523.2 |
| 191 | G7 | | P | 57 | 10.6 (s, 1H), 9.87 (d, J = 2.4 Hz, 1H), 9.33 (brq, J = 5.5 Hz, 1H), 8.81 (d, J = 5.0 Hz, 1H), 8.45 (d, J = 2.4 Hz, 1H), 8.00-8.05 (m, 2H), 7.98 (t, J = 1.9 Hz, 1H), 7.87 (dd, J = 1.6 and 5.0 Hz, 1H), 7.75 (dd, J = 2.3 and 8.3 Hz, 1H), 7.67-7.73 (m, 2H), 7.58 (d, J = 7.8 Hz, 1H), 7.36 (d, J = 8.4 Hz, 1H), 2.89 (d, J = 4.7 Hz, 3H), 2.28 (s, 3H), 1.76 (s, 6H). | 491.2 |
| 192 | G10 | | P | 29 | 10.8 (s, 1H), 8.89 (d, J = 2.0 Hz, 1H), 8.84 (m, 2H), 8.71 (d, J = 5.2 Hz, 1H), 8.33 (s, 1H), 8.10 (d, J = 1.6 Hz, 1H), 8.04 (brs, 1H), 8.00 (brd, J = 4.8 Hz, 1H), 7.93 (d, J = 7.6 Hz, 1H), 7.89 (m, 2H), 7.69 (m, 1H), 7.59 (brd, J = 7.6 Hz, 1H), 2.85 (d, J = 4.4 Hz, 3H), 2.47 (s, 3H), 1.76 (s, 6H). | 491.3 |
| 193 | A3 F45 | | P | | 11.0 (s, 1H), 10.9 (s, 1H), 9.13 (s, 1H), 9.12 (d, J = 5.2 Hz, 1H), 9.00 (brs, 1H), 8.84 (d, J = 5.2 Hz, 1H), 8.51 (d, J = 4.8 Hz, 1H), 8.40 (brs, 1H), 8.05 (s, 1H), 8.03 (brd, J = 4.8 Hz, 1H), 7.91 (brd, J = 5.2 Hz, 1H), 7.86 (d, J = 5.2 Hz, 1H), 2.66 (s, 3H), 2.03 (m, 1H), 1.77 (s, 6H), 0.83 (m, 4H). | 519.3 |
| 194 | A6 F45 | | P | | 10.9 (s, 1H), 9.17 (d, J = 5.2 Hz, 1H), 9.01 (brd, J = 2.0 Hz, 1H), 8.98 (s, 1H), 8.91 (brq, J = 4.8 Hz, 1H), 8.85 (m, 2H), 8.51 (dd, J = 3.6 and 6.4 Hz, 1H), 8.44 (brd J = 2.0 Hz, 1H), 8.06 (s, 1H), 7.92 (m, 2H), 2.86 (d, J = 4.8 Hz, 3H), 2.67 (s, 3H), 1.77 (s, 6H). | 493.1 |
| 195 | A5 F45 | | P | | 10.9 (brs, 1H), 10.7 (brs, 1H), 9.13 (s, 2H), 8.99 (s, 1H), 8.84 (brd, J = 4.0 Hz, 1H), 8.50 (brd, J = 4.4 Hz, 1H), 8.42 (s, 1H), 8.04 (m, 2H), 7.89 (dd, J = 3.6 and 16.4 Hz, 2H), 2.68 (s, 3H), 2.13 (s, 3H), 1.77 (s, 6H). | 493.1 |

TABLE I-continued

| Ex No. | SM | Product | Method | Yield (%) | $^1$H NMR (400 or 500 MHz, (DMSO-$d_6$): δ | MS (m/z: M + H$^+$) |
|---|---|---|---|---|---|---|
| 196 | A6 F46 | | P | 43 | 10.7 (s, 1H), 8.90 (s, 1H), 8.87 (m, 1H), 8.81 (d, J = 4.8 Hz, 2H), 8.44 (dd, J = 3.6 and 6.4 Hz, 1H), 8.03 (s, 1H), 7.97 (d, J = 2.0 Hz, 1H), 7.89 (d, J = 5.2 Hz, 1H), 7.86 (dd, J = 1.6 and 8.4 Hz, 1H), 7.71 (s, 1H), 7.42 (d, J = 8.4 Hz, 1H), 2.85 (d, J = 4.8 Hz, 3H), 2.45 (s, 3H), 2.35 (m, 1H), 1.77 (s, 6H), 1.28 (m, 2H), 1.21 (m, 2H). | 532.3 |
| 197 | G7 | | P | 77 | 10.6 (s, 1H), 10.1 (s, 1H), 8.97 (d, J = 1.2 Hz, 1H), 8.79 (dd, J = 0.9 and 5.0 Hz, 1H), 8.59 (d, J = 1.2 Hz, 1H), 8.08 (dt, J = 1.4 and 7.9 Hz, 1H), 8.04-7.98 (m, 2H), 7.86 (dd, J = 1.5 and 5.1 Hz, 1H), 7.76 (dd, J = 2.3 and 8.3 Hz, 1H), 7.69 (d, J = 2.3 Hz, 1H), 7.65 (t, J = 7.7 Hz, 1H), 7.57 (dt, J = 1.4 and 7.6 Hz, 1H), 7.35 (d, J = 8.4 Hz, 1H), 2.24 (s, 3H), 1.75 (s, 6H), 1.43 (s, 3H), 1.19 (m, 2H), 0.71 (m, 2H). | 531.2 |
| 198 | C9 E12 | | P | 64 | 11.0 (s, 1H), 10.9 (s, 1H), 9.15 (dd, J = 1.2 and 5.3 Hz, 1H), 9.02 (d, J = 2.6 Hz, 1H), 8.97 (s, 1H), 8.84 (d, J = 5.0 Hz, 1H), 8.75 (d, J = 2.6 Hz, 1H), 8.55 (d, J = 5.2 Hz, 1H), 8.12 (dd, J = 1.8 and 5.3 Hz, 1H), 8.07 (s, 1H), 7.92 (brd, J = 7.0 Hz, 1H), 7.90 (d, J = 5.2 Hz, 1H), 2.81 (s, 3H), 2.05 (m, 1H), 1.78 (s, 6H), 0.88-0.81 (m, 4H). | 516.2 |
| 199 | C10 E12 | | P | 49 | 10.9 (s, 1H), 9.20 (d, J = 5.3 Hz, 1H), 9.03 (d, J = 2.5 Hz, 1H), 8.94 (brm, 1H), 8.89 (d, J = 5.0 Hz, 1H), 8.84 (d, J = 5.0 Hz, 1H), 8.82 (s, 1H), 8.78 (d, J = 2.6 Hz, 1H), 8.42 (dd, J = 1.7 and 5.1 Hz, 1H), 8.34 (d, J = 5.3 Hz, 1H), 8.07 (s, 1H), 7.93 (dd, J = 1.5 and 5.1 Hz, 1H), 2.86 (d, J = 4.8 Hz, 3H), 2.83 (s, 3H), 1.78 (s, 6H). | 493.2 |
| 200 | G7 | | P | 39 | 11.0 (d, J = 4.2 Hz, 1H), 10.6 (s, 1H), 9.04 (d, J = 1.2 Hz, 1H), 8.79 (d, J = 5.0 Hz, 1H), 8.58 (d, J = 1.3 Hz, 1H), 8.10 (d, J = 7.8 Hz, 1H), 8.03 (d, J = 2.0 Hz, 1H), 8.00 (s, 1H), 7.86 (dd, J = 1.4 and 5.1 Hz, 1H), 7.75 (dd, J = 2.3 and 8.3 Hz, 1H), 7.69 (d, J = 2.2 Hz, 1H), 7.66 (t, J = 7.7 Hz, 1H), 7.59 (d, J = 7.6 Hz, 1H), 7.35 (d, J = 8.3 Hz, 1H), 2.24 (s, 3H), 1.75 (s, 6H), 1.54-1.44 (m, 2H), 1.42-1.35 (m, 2H). | 535.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 201 | G10 | | P | 34 | 10.8 (s, 1H), 9.89 (s, 1H), 9.34 (m, 1H), 8.89 (d, J = 2.4 Hz, 1H), 8.84 (d, J = 5.0 Hz, 1H), 8.48 (d, J = 2.3 Hz, 1H), 8.12 (d, J = 2.5 Hz, 1H), 8.09-8.06 (m, 2H), 8.04 (s, 1H), 7.90 (dd, J = 1.5 and 5.0 Hz, 1H), 7.73 (m, 1H), 7.65 (m, 1H), 2.89 (d, J = 4.7 Hz, 3H), 2.48 (s, 3H), 1.77 (s, 6H). | 492.2 |
| 202 | G11 | | P | 10 | 11.3 (s, 1H), 10.5 (s, 1H), 8.96 (d, J = 0.8 Hz, 1H), 8.62 (d, J = 0.8 Hz, 1H), 8.20 (brs, 1H), 8.18 (brs, 1H), 8.07 (brm, 1H), 8.00 (brm, 1H), 7.83 (brs, 1H), 7.79 (dd, J = 6.0 and 10.8 Hz, 1H), 7.69 (m, 1H), 7.65 (t, J = 7.6 Hz, 1H), 7.57 (m, 1H), 7.34 (d, J = 8.4 Hz, 1H), 3.56 (s, 2H), 2.24 (s, 3H), 2.18 (s, 6H), 2.07 (m, 1H), 0.89 (m, 4H). | 574.4 |
| 203 | D44 | | K | 21 | 11.3 (s, 1H), 10.6 (s, 1H), 8.96 (s, 1H), 8.70 (d, J = 4.8 Hz, 1H), 8.61 (s, 1H), 8.07 (d, J = 7.2 Hz, 1H), 8.00 (s, 1H), 7.92 (s, 1H), 7.75 (m, 2H), 7.69 (s, 1H), 7.65 (t, J = 7.6 Hz, 1H), 7.57 (d, J = 7.2 Hz, 1H), 7.35 (d, J = 8.0 Hz, 1H), 2.24 (s, 3H), 2.07 (m, 1H), 1.87 (m, 2H), 1.77 (m, 2H), 0.88 (m, 4H). | 515.4 |
| 204 | G10 | | P | 40 | 10.8 (s, 1H), 9.35 (s, 1H), 8.90 (d, J = 2.4 Hz, 1H), 8.82 (d, J = 4.8 Hz, 1H), 8.78 (m, 1H), 8.53 (s, 1H), 8.35 (brm, 1H), 8.32 (brs, 1H), 8.12 (d, J = 2.4 Hz, 1H), 8.04 (s, 1H), 7.90 (dd, J = 1.2 and 4.0 Hz, 1H), 7.72 (m, 1H), 7.67 (m, 1H0, 2.86 (d, J = 4.8 Hz, 3H), 2.47 (s, 3H), 1.77 (s, 6H). at high temp | 492.4 |
| 205 | A6 F49 | | P | 32 | 10.8 (s, 1H), 8.90 (d, J = 5.2 Hz, 1H), 8.87 (d, J = 4.8 Hz, 1H), 8.84 (d, J = 5.2 Hz, 1H), 8.78 (d, J = 5.2 Hz, 1H), 8.75 (brm, 1H), 8.33 (m, 2H), 8.08 (dd, J = 2.8 and 7.2 Hz, 1H), 8.04 (s, 1H), 7.93 (m, 1H), 7.90 (dd, J = 1.2 and 4.8 Hz, 1H), 7.72 (brd, J = 4.8 Hz, 1H), 7.48 (m, 1H), 2.85 (d, J = 4.8 Hz, 3H), 1.77 (s, 6H). at high temp | 495.3 |
| 206 | A11 F15 | | P | 47 | 10.6 (s, 1H), 9.90 (s, 1H), 8.81 (m, 3H), 8.44 (d, J = 5.2 Hz, 1H), 8.00 (d, J = 7.6 Hz, 2H), 7.85 (m, 2H), 7.81 (dd, J = 8.0, 1.2 Hz, 1H), 7.73 (brm, 1H), 7.52 (brd, J = 4.0 Hz, 1H), 7.40 (d, J = 8.4 Hz, 1H), 2.28 (s, 3H), 1.76 (s, 6H), 1.25(s, 9H). | 533.4 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| 207 | G10 | | P & Q | 31 | 11.0 (brs, 1H), 8.99 (d, J = 2.0 Hz, 1H), 8.83 (d, J = 4.0 Hz, 1H) 8.66 (s, 1H), 8.33 (d, J = 2.0 Hz, 1H), 8.12 (s, 1H), 8.00 (m, 2H), 7.93 (dd, J = 1.2 and 4.8 Hz, 1H), 7.67-7.78 (m, 2H), 7.11 (s, 1H), 2.54 (s, 3H), 1.78 (s, 6H). at high temperature | 450.3 |
| 208 | G10 | | P | 25 | 10.8 (s, 1H), 9.98 (s, 1H), 9.00 (d, J = 1.2 Hz, 1H), 8.91 (d, J = 2.4 Hz, 1H), 8.82 (dd, J = 5.1, 0.9 Hz, 1H), 8.61 (d, J = 1.3 Hz, 1H), 8.15 (dt, J = 7.5, 1.7 Hz, 1H), 8.12-8.08 (m, 2H), 8.05 (m, 1H), 7.90 (dd, J = 1.6 and 5.1 Hz, 1H), 7.74-7.62 (m, 2H), 3.26 (s, 3H), 2.45 (s, 3H), 1.76 (s, 6H), 1.40 (s, 6H). | 550.2 |
| 209 | A10 F47 | | P | 28 | 10.9 (s, 1H), 9.50 (s, 1H), 8.94 (d, J = 2.5 Hz, 1H), 8.90-8.86 (m, 2H), 8.84 (dd, J = 0.8 and 5.0 Hz, 1H), 8.46 (dd, J = 0.8 and 5.3 Hz, 1H), 8.16-8.12 (m, 2H), 8.05 (dd, J = 0.9 and 1.5 Hz, 1H), 7.90 (m, 2H), 7.62 (dd, J = 1.6 and 5.0 Hz, 1H), 3.30 (s, 3H), 1.77 (s, 6H), 1.41 (s, 6H). | 550.2 |
| 210 | G7 | | P | 66 | 10.6 (s, 1H), 10.48 (s, 1H), 8.97 (s, 1H), 8.79 (d, J = 5.0 Hz, 1H), 8.64 (s, 1H), 8.09 (d, J = 6.8 Hz, 1H), 8.04-7.99 (m, 2H), 7.86 (d, J = 1.5 Hz, 1H), 7.76 (dd, J = 8.3, 2.3 Hz, 1H), 7.70 (d, J = 2.3 Hz, 1H), 7.65 (t, J = 7.7 Hz, 1H), 7.57 (d, J = 7.6 Hz, 1H), 7.36 (d, J = 8.3 Hz, 1H), 2.25 (s, 3H), 1.75 (s, 6H), 1.25 (s, 9H). | 533.2 |
| 211 | G7 | | P | 69 | 10.6 (s, 1H), 9.98 (s, 1H), 8.99 (s, 1H), 8.79 (d, J = 5.1 Hz, 1H), 8.61 (s, 1H), 8.11 (d, J = 7.8 Hz, 1H), 8.06-7.99 (m, 2H), 7.86 (d, J = 1.5 Hz, 1H), 7.76 (dd, J = 2.3 and 8.3 Hz, 1H), 7.70 (d, J = 2.3 Hz, 1H), 7.66 (t, J = 7.7 Hz, 1H), 7.61-07.56 (m, 1H), 7.36 (d, J = 8.3 Hz, 1H), 3.25 (s, 3H), 2.25 (s, 3H), 1.75 (s, 6H), 1.39 (s, 6H). | 549.2 |
| 212 | G12 | | P | 17 | 11.3 (s, 1H), 10.5 (s, 1H), 8.94 (s, 1H), 8.80 (d, J = 4.8 Hz, 1H), 8.60 (s, 1H), 8.01 (s, 1H), 7.87 (m, 2H), 7.80 (s, 1H), 7.75 (dd, J = 2.4 and 8.0 Hz, 1H), 7.67 (brm, 1H), 7.38 (s, 1H), 7.34 (d, J = 8.4 Hz, 1H), 2.47 (s, 3H), 2.24 (s, 3H), 2.07 (m, 1H), 1.76 (s, 6H), 0.88 (m, 4H). | 531.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 213 | G10 | | P | 15 | 10.8 (s, 1H), 10.5 (s, 1H), 8.98 (s, 1H), 8.91 (d, J = 2.4 Hz, 1H), 8.82 (d, J = 5.0 Hz, 1H), 8.65 (s, 1H), 8.06-8.16 (m, 3H), 8.04 (s, 1H), 7.90 (d, J = 1.3 Hz, 1H), 7.62-7.72 (m, 2H), 2.45 (s, 3H), 1.76 (s, 6H), 1.25 (s, 9H). | 534.2 |
| 214 | D18 | | K | 43 | 10.7 (s, 1H), 8.86-8.90 (m, 1H), 8.85 (d, J = 5.0 Hz, 1H), 8.78 (m, 1H), 8.72-8.76 (m, 2H), 8.34 (dd, J = 1.8 and 5.2 Hz, 1H), 8.20 (s, 1H), 8.03 (s, 1H), 7.80-7.86 (m, 2H), 7.77 (m, 1H), 7.56 (dd, J = 1.5 and 5.0 Hz, 1H), 7.39 (d, J = 8.4 Hz, 1H), 2.84 (d, J = 4.8 Hz, 3H), 2.29 (s, 3H), 1.69 (d, J = 22.5 Hz, 6H). | 484.2 |
| 215 | D18 | | K | 28 | 10.7 (s, 1H), 9.38 (m, 1H), 8.88 (m, 1H), 8.85 (d, J = 5.0 Hz, 1H), 8.77 (s, 1H), 8.75 (d, J = 5.2 Hz, 1H), 8.34 (dd, J = 1.8 and 5.2 Hz, 1H), 8.19 (s, 1H), 7.90 (d, J = 2.0 Hz, 1H), 7.79 (dd, J = 2.3 and 8.3 Hz, 1H), 7.74 (d, J = 2.2 Hz, 1H), 7.55 (d, J = 1.5 Hz, 1H), 7.40 (d, J = 8.3 Hz, 1H), 2.84 (d, J = 4.8 Hz, 3H), 2.36 (m, 1H), 2.29 (s, 3H), 1.11-1.19 (m, 4H). | 465.2 |
| 216 | G13 | | P | 15 | 11.3 (s, 1H), 10.6 (s, 1H), 8.94 (d, J = 1.2 Hz, 1H), 8.80 (d, J = 5.2 Hz, 1H), 8.58 (d, J = 1.2 Hz, 1H), 8.01 (brs, 1H), 7.86 (dd, J = 1.2 and 5.2 Hz, 1H), 7.76 (m, 2H), 7.72 (brm, 1H), 7.65 (brm, 1H), 7.34 (d, J = 8.4 Hz, 1H), 7.23 (brm, 1H), 2.23 (s, 3H), 2.16 (m, 1H), 2.07 (m, 1H), 1.76 (s, 6H), 1.04 (m, 2H), 0.88 (m, 4H), 0.80 (m, 2H). | 557.4 |
| 217 | A6 F52 | | P | 40 | 10.6 (s, 1H), 8.85 (q, J = 4.4 Hz, 1H), 8.81 (d, J = 4.8 Hz, 1H), 8.75 (d, J = 0.8 Hz, 1H), 8.74 (d, J = 4.8 Hz, 1H), 8.30 (dd, J = 3.6 and 6.8 Hz, 1H), 8.01 (s, 1H), 7.99 (s, 1H), 7.87 (dd, J = 3.6 and 6.4 Hz, 1H), 7.79 (dd, J = 6.0 and 10.8 Hz, 1H), 7.73 (d, J = 2.0 Hz, 1H), 7.42 (s, 1H), 7.39 (d, J = 8.4 Hz, 1H), 2.85 (d, J = 4.8 Hz, 3H), 2.67 (s, 3H), 2.29 (s, 3H), 1.76 (s, 6H). | 505.4 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 218 | G14 | | P | 18 | 11.3 (s, 1H), 10.8 (s, 1H), 8.95 (d, J = 0.8 Hz, 1H), 8.90 (d, J = 2.4 Hz, 1H), 8.83 (d, J = 5.2 Hz, 1H), 8.58 (d, J = 1.2 Hz, 1H), 8.05 (d, J = 2.4 Hz, 1H), 8.04 (s, 1H), 7.89 (dd, J = 1.6 and 5.2 Hz, 1H), 7.81 (brm, 1H), 7.78 (brm, 1H), 7.30 (brs, 1H), 2.43 (s, 3H), 2.15 (m, 1H), 2.08 (m, 1H), 1.76 (s, 6H), 1.04 (m, 2H), 0.88 (m, 4H), 0.81 (m, 2H). | 558.4 |
| 219 | A12 F47 | | P | 27 | 10.9 (s, 1H), 10.8 (d, J = 2.9 Hz, 1H), 8.94 (d, J = 2.4 Hz, 1H), 8.87 (d, J = 5.0 Hz, 1H), 8.84 (d, J = 5.0 Hz, 1H), 8.80 (d, J = 1.5 Hz, 1H), 8.52 (d, J = 5.2 Hz, 1H), 8.13-8.16 (m, 2H), 8.05 (s, 1H), 7.95 (dd, J = 1.6 and 5.3 Hz, 1H), 7.90 (dd, J = 1.5 and 5.1 Hz, 1H), 7.63 (dd, J = 1.5 and 5.0 Hz, 1H), 2.49 (s, 3H), 1.77 (s, 6H), 1.71 (s, 6H) | 545.2 |
| 220 | D45 | | K | 15 | 11.3 (s, 1H), 10.6 (s, 1H), 9.06 (d, J = 0.8 Hz, 1H), 9.00 (d, J = 1.2 Hz, 1H), 8.70 (br d, J = 5.2 Hz, 1H), 8.41 (d, J = 7.6 Hz, 1H), 8.12 (t, J = 7.6 Hz, 1H), 7.93 (br s, 1H), 7.87 (br m, 1H), 7.78-7.83 (br m, 2H), 7.70 (d, J = 8.8 Hz, 1H), 7.39 (d, J = 8.4 Hz, 1H), 2.49 (s, 3H), 2.06 (m, 1H), 1.89 (m, 2H), 1.77 (m, 2H), 0.86 (m, 4H). | 516.3 |
| 221 | A8 F30 | | P | 27 | 10.68 (s, 1H), 9.02 (d, J = 5.2 Hz, 1H), 8.81 (d, J = 5.2 Hz, 1H), 8.12 (d, J = 5.2 Hz, 1H), 8.02 (s, 1H), 7.99 (d, J = 1.6 Hz, 1H), 7.88 (br d, J = 4.0 Hz, 1H), 7.84 (dd, J = 8.4, 2.0 Hz, 1H), 7.71 (d, J = 5.2 Hz, 1H), 7.57 (s, 1H), 7.42 (m, 2H), 6.90 (br s, 1H), 3.48 (br m, 4H), 3.27 (s, 3H), 2.46 (s, 3H), 1.77 (s, 6H). | 508.4 |
| 222 | A3 F44 | | P | 46 | 10.9 (s, 1H), 10.8 (s, 1H), 8.89 (d, J = 2.5 Hz, 1H), 8.83 (dd, J = 0.8 and 5.0 Hz, 1H), 8.45 (dd, J = 0.8 and 1.7 Hz, 1H), 8.39 (dd, J = 0.7 and 5.3 Hz, 1H), 8.08 (d, J = 2.5 Hz, 1H), 8.03 (dd, J = 0.9 and 1.5 Hz, 1H), 7.89 (dd, J = 1.6 and 5.1 Hz, 1H), 7.79 (m, 1H), 7.71 (t, J = 1.8 Hz, 1H), 7.66 (t, J = 7.7 Hz, 1H), 7.56 (dt, J = 7.8, 1.3 Hz, 1H), 7.48 (dd, J = 1.7 and 5.3 Hz, 1H), 2.46 (s, 3H), 1.97-2.07 (m, 1H), 1.77 (s, 6H), 0.74-0.89 (m, 4H). | 517.2 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| 223 | A3 F43 | | P | 64 | 10.9 (s, 1H), 10.6 (s, 1H), 8.79 (d, J = 5.0 Hz, 1H), 8.44 (s, 1H), 8.38 (d, J = 5.2 Hz, 1H), 8.00 (s, 1H), 7.85 (d, J = 4.0 Hz, 1H), 7.74 (dd, J = 2.2 and 8.3 Hz, 2H), 7.69-7.65 (m, 1H), 7.59-7.64 (m, 2H), 7.44-7.50 (m, 2H), 7.36 (m, 1H), 2.24 (s, 3H), 1.98-2.06 (m, 1H), 1.75 (s,6H), 0.76-0.83 (m, 4H). | 516.2 |
| 224 | G15 | | P | 20 | 11.4 (s, 1H), 10.6 (s, 1H), 9.22 (d, J = 2.0 Hz, 1H), 9.01 (d, J = 0.8 Hz, 1H), 8.81 (d, J = 5.2 Hz, 1H), 8.78 (d, J = 2.0 Hz, 1H), 8.65 (d, J = 0.8 Hz, 1H), 8.33 (t, J = 2.0 Hz, 1H), 8.01 (s, 1H), 7.87 (dd, J = 1.2 and 4.8 Hz, 1H), 7.81 (dd, J = 1.6 and 8.0 Hz, 1H), 7.72 (brm, 1H), 7.40 (d, J = 8.4 Hz, 1H), 2.27 (s, 3H), 2.08 (m, 1H), 1.76 (s, 6H), 0.89 (m, 4H). | 518.4 |
| 225 | G10 | | P | 28 | 10.9 (s, 1H), 10.8 (s, 1H), 8.91 (s, 2H), 8.82 (brd, J = 4.8 Hz, 1H), 8.39 (s, 1H), 8.06-8.15 (m, 3H), 8.04 (s, 1H), 7.90 (brd, J = 4.8 Hz, 1H), 7.70 (brt, J = 7.6 Hz, 1H), 7.65 (brd, J = 7.6 Hz, 1H), 3.73 (s, 3H), 2.46 (s, 3H), 1.77 (s, 6H). | 508.3 |
| 226 | C11 E12 | | P | 77 | 11.4 (s, 1H), 10.9 (s, 1H), 9.09 (d, J = 1.3 Hz, 1H), 9.02 (d, J = 1.2 Hz, 1H), 8.95 (d, J = 2.4 Hz, 1H), 8.84 (d, J = 5.0 Hz, 1H), 8.46 (d, J = 7.9 Hz, 1H), 8.28 (d, J = 2.5 Hz, 1H), 8.17 (t, J = 7.8 Hz, 1H), 8.05 (d, J = 1.1 Hz, 1H), 7.91 (dd, J = 1.5 and 5.0 Hz, 1H), 7.81 (d, J = 7.7 Hz, 1H), 2.59 (s, 3H), 2.06 (m, 1H), 1.77 (s, 6H), 0.85-0.88 (m, 4H). | 519.2 |
| 227 | G10 | | P | 10 | 10.8 (s, 1H), 8.89 (d, J = 2.5 Hz, 1H), 8.84 (d, J = 5.0 Hz, 1H), 8.52 (s, 1H), 7.95-8.29 (m, 2H), 7.90 (dd, J = 1.5 and 5.1 Hz, 1H), 7.63 (t, J = 7.9 Hz, 1H), 7.57 (dt, J = 7.6, 1.5 Hz, 1H), 7.39 (s, 1H), 7.00 (s, 1H), 2.86 (d, J = 4.8 Hz, 3H), 2.46 (s, 3H), 1.77 (s, 6H). | 494.2 |
| 228 | A11 F47 | | P | 51 | 10.7 (s, 1H), 9.95 (d, J = 3.5 Hz, 1H), 8.94 (d, J = 2.4 Hz, 1H), 8.82-8.88 (m, 3H), 8.45 (d, J = 5.2 Hz, 1H), 8.14 (d, J = 2.5 Hz, 1H), 8.11 (s, 1H), 8.05 (d, J = 1.5 Hz, 1H), 7.88-7.93 (m, 1H), 7.86 (dd, J = 1.6 and 5.2 Hz, 1H), 7.61 (dd, J = 1.6 and 5.0 Hz, 1H), 2.49 (s, 3H), 1.77 (s,6H), 1.26 (s, 9H). | 534.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 229 | D43 | | K | 56 | 11.0 (s, 1H), 10.6 (s, 1H), 9.12 (s, 1H), 9.06 (d, J = 5.1 Hz, 1H), 8.57 (d, J = 5.1 Hz, 1H), 8.49 (d, J = 5.2 Hz, 1H), 7.99-8.04 (m, 2H), 7.86 (dd, J = 2.3 and 8.3 Hz, 1H), 7.72-7.78 (m, 2H), 7.58 (dd, J = 1.7 and 5.1 Hz, 1H), 7.41 (d, J = 8.4 Hz, 1H), 2.45 (s, 3H), 2.21 (m, 1H), 2.03 (m, 1H), 0.93-1.04 (m, 4H), 0.77-0.87 (m, 4H). | 491.2 |
| 230 | A3 F54 | | P | 78 | 11.0 (s, 1H), 10.7 (s, 1H), 9.43 (d, J = 2.0 Hz, 1H), 8.95 (s, 1H), 8.82 (d, J = 5.0 Hz, 1H), 8.51 (d, J = 5.2 Hz, 1H), 8.29 (d, J = 2.1 Hz, 1H), 8.02 (s, 1H), 7.82-7.91 (m, 3H), 7.79 (d, J = 2.3 Hz, 1H), 7.44 (d, J = 8.4 Hz, 1H), 2.32 (s, 3H), 2.05 (m, 1H), 1.76 (s, 6H), 0.83-0.85 (m, 4H). | 518.2 |
| 231 | A6 F55 | | P | 66 | 10.4 (s, 1H), 8.84 (q, J = 4.4 Hz, 1H), 8.74 (d, J = 5.2 Hz, 1H), 8.70 (d, J = 0.8 Hz, 1H), 8.30 (dd, J = 2.0 and 5.2 Hz, 1H), 8.05 (s, 1H), 7.95 (d, J = 8.0 Hz, 1H), 7.79 (m, 2H), 7.75 (m, 2H), 7.60 (t, J = 8.0 Hz, 1H), 7.36 (d, J = 8.4 Hz, 1H), 6.93 (s, 1H), 4.92 (t, J = 5.6 Hz, 1H), 4.49 (t, J = 5.2 Hz, 2H), 3.82 (q, J = 5.2 Hz, 2H), 2.84 (d, J = 4.8 Hz, 3H), 2.29 (s, 3H), 1.74 (s, 6H). | 550.4 |
| 232 | D46 | | K | 47 | 11.0 (s, 1H), 10.7 (s, 1H), 9.11 (d, J = 5.2 Hz, 1H), 8.95 (s, 1H), 8.75 (d, J = 4.8 Hz, 1H), 8.53 (d, J = 5.2 Hz, 1H), 8.34 (d, J = 2.0 Hz, 1H), 8.04-8.08 (m, 2H), 7.93-7.86 (m, 2H), 7.85 (dd, J = 1.6 and 5.2 Hz, 1H), 7.39 (d, J = 8.4 Hz, 1H), 2.58 (s, 3H), 2.04 (m, 1H), 1.71 (d, J = 22.0 Hz, 6H), 0.84 (m, 4H). | 511.4 |
| 233 | D45 | | K | 11 | 11.3 (s, 1H), 10.6 (s, 1H), 9.06 (d, J = 0.8 Hz, 1H), 9.00 (d, J = 1.2 Hz, 1H), 8.01 (d, J = 5.2 Hz, 1H), 8.41 (d, J = 7.6 Hz, 1H), 8.12 (t, J = 8.0 Hz, 1H), 8.02 (brs, 1H), 7.88 (m, 2H), 7.80 (dd, J = 2.0 and 8.4 Hz, 1H), 7.71 (d, J = 7.6 Hz, 1H), 7.39 (d, J = 8.4 Hz, 1H), 2.38 (s, 3H), 2.05 (m, 1H), 1.76 (s, 6H), 0.86 (m, 4H). | 518.4 |

TABLE I-continued

| Ex No. | SM | Product | Method | Yield (%) | ¹H NMR (400 or 500 MHz, (DMSO-d$_6$): δ | MS (m/z: M + H$^+$) |
|---|---|---|---|---|---|---|
| 234 | A6 F57 | | P | 36 | 10.6 (s, 1H), 8.87 (q, J = 4.4 Hz, 1H), 8.80 (d, J = 5.2 Hz, 1H), 8.77 (d, J = 5.2 Hz, 1H), 8.73 (s, 1H), 8.30 (dd, J = 5.2, 1.6 Hz, 1H), 8.21 (d, J = 7.6 Hz, 1H), 8.11 (t, J = 8.0 Hz, 1H), 8.02 (s, 1H), 7.86-7.92 (m, 2H), 7.80 (dd, J = 8.4, 2.0 Hz, 1H), 7.68 (d, J = 7.6 Hz, 1H), 7.39 (d, J = 8.4 Hz, 1H), 2.84 (d, J = 4.8 Hz, 3H), 2.40 (s, 3H), 1.76 (s, 6H). | 491.4 |
| 235 | G15 | | P | 10 | 10.6 (s, 1H), 9.45 (d, J = 2.4 Hz, 1H), 9.43 (d, J = 1.2 Hz, 1H), 9.08 (q, J = 4.4 Hz, 1H), 8.81 (m, 2H), 8.67 (d, J = 0.8 Hz, 1H), 8.63 (m, 1H), 8.02 (s, 1H), 7.87 (dd, J = 1.2 and 5.2 Hz, 1H), 7.80 (dd, J = 2.0 and 8.4 Hz, 1H), 7.75 (m, 1H), 7.40 (d, J = 8.4 Hz, 1H), 2.83 (d, J = 4.8 Hz, 3H), 2.29 (s, 3H), 1.76 (s, 6H). | 492.3 |
| 236 | D43 | | R (EDC) | 15 | 11.0 (s, 1H), 10.1 (s, 1H), 9.12 (s, 1H), 9.06 (d, J = 5.2 Hz, 1H), 8.49 (d, J = 5.2 Hz, 1H), 8.06 (s, 1H), 8.02 (d, J = 4.8 Hz, 1H), 7.89 (d, J = 6.8 Hz, 1H), 7.73 (d, J = 5.2 Hz, 1H), 7.34 (d, J = 8.4 Hz, 1H), 6.40 (s, 1H), 3.94 (s, 3H), 2.43 (s, 3H), 2.05 (m, 1H), 1.94 (m, 1H), 0.97-0.99 (m, 2H), 0.81-0.84 (m, 4H), 0.69-0.70 (m, 2H). | 494.2 |
| 237 | A10 F59 | | P | 19 | 10.6 (s, 1H), 9.48 (s, 1H), 8.85 (s, 1H), 8.82 (d, J = 4.8 Hz, 1H), 8.80 (d, J = 4.8 Hz, 1H), 8.45 (d, J = 5.2 Hz, 1H), 8.02 (brs, 1H), 8.01 (brs, 1H), 7.89 (brd, J = 4.8 Hz, 1H), 7.86 (brd, J = 4.8 Hz, 1H), 7.80 (brd, J = 8.4 Hz, 1H), 7.74 (brm, 1H), 7.54 (brd, J = 4.4 Hz, 1H), 7.40 (brd, J = 8.4 Hz, 1H), 3.29 (s, 3H), 2.28 (s, 3H), 1.76 (s, 6H), 1.40 (s, 6H). | 549.4 |
| 238 | D92 | | R (EDC) | 49 | 11.0 (brs, 1H), 10.71 (brs, 1H), 9.24 (s, 1H), 8.95 (s, 1H), 8.88 (d, J = 4.8 Hz, 1H), 8.78 (s, 1H), 8.43 (s, 1H), 8.36 (s, 1H), 8.19 (s, 1H), 8.04 (d, J = 4.8 Hz, 1H), 7.82 (d, J = 8.4 Hz, 1H), 7.76 (s, 1H), 7.40 (d, J = 8.4 Hz, 1H), 3.74 (s, 3H), 2.28 (s, 3H), 2.05 (t, J = 18.8 Hz, 3H). | 505.1 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 239 | D46 | | K | 26 | 11.0 (s, 1H), 10.6 (s, 1H), 9.11 (d, J = 5.2 Hz, 1H), 8.94 (s, 1H), 8.72 (d, J = 5.2 Hz, 1H), 8.53 (d, J = 5.2 Hz, 1H), 8.32 (d, J = 2.0 Hz, 1H), 8.05 (d, J = 5.2 Hz, 1H), 8.03 (s, 1H), 7.85-7.93 (m, 2H), 7.79 (dd, J = 1.2 and 4.8 Hz, 1H), 7.39 (d, J = 8.4 Hz, 1H), 3.12 (s, 3H), 2.58 (s, 3H), 2.05 (m, 1H), 1.51 (s, 6H), 0.81-0.87 (m, 4H). | 523.4 |
| 240 | G17 | | P | 44 | 11.4 (s, 1H), 11.0 (s, 1H), 8.99 (s, 1H), 8.54 (d, J = 5.2 Hz, 1H), 8.65 (s, 1H), 8.25 (s, 1H), 8.18 (brd, J = 7.6 Hz, 1H), 8.05-8.10 (m, 2H), 8.00-8.05 (m, 2H), 7.90 (dd, J = 1.2 and 5.2 Hz, 1H), 7.80 (brd, J = 8.0 Hz, 1H), 7.75 (t, J = 7.6 Hz, 1H), 2.08 (m, 1H), 1.77 (s, 6H), 0.89 (m, 4H). | 528.4 |
| 241 | A14 F30 | | P | 24 | 10.7 (s, 1H), 10.5 (s, 1H), 9.08 (d, J = 5.2 Hz, 1H), 8.97 (s, 1H), 8.81 (d, J = 5.2 Hz, 1H), 8.56 (d, J = 5.2 Hz, 1H), 8.10 (dd, J = 1.2 and 5.2 Hz, 1H), 8.02 (brs, 1H), 8.00 (brd, J = 2.0 Hz, 1H), 7.85-7.91 (m, 2H), 7.77 (d, J = 5.2 Hz, 1H), 7.44 (d, J = 8.4 Hz, 1H), 2.47 (s, 3H), 1.77 (s, 6H), 1.75 (m, 2H), 1.70 (m, 2H). | 543.4 |
| 242 | D48 | | K | 44 | 10.7 (s, 1H), 9.15 (d, J = 5.2 Hz, 1H), 8.93 (brm, 1H), 8.87 (d, J = 5.1 Hz, 1H), 8.82 (d, J = 5.6 Hz, 1H), 8.80 (d, J = 1.8 Hz, 1H), 8.40 (dd, J = 1.8 and 5.1 Hz, 1H), 8.28 (d, J = 5.3 Hz, 1H), 8.22 (d, J = 8.0 Hz, 1H), 8.08 (s, 1H), 7.90 (dd, J = 1.6 and 5.0 Hz, 1H), 7.42 (d, J = 11.4 Hz, 1H), 2.86 (d, J = 4.7 Hz, 3H), 2.67 (s, 3H), 1.77 (s, 6H). | 510.2 |
| 243 | G7 | | P | 23 | 10.6 (s, 1H), 10.2 (d, J = 4.3 Hz, 1H), 9.01 (d, J = 1.2 Hz, 1H), 8.79 (d, J = 5.1 Hz, 1H), 8.59 (d, J = 1.2 Hz, 1H), 8.10 (dt, J = 1.5 and 7.9 Hz, 1H), 8.03 (d, J = 1.9 Hz, 1H), 8.00 (s, 1H), 7.86 (dd, J = 1.5 and 5.1 Hz, 1H), 7.75 (dd, J = 2.3 and 8.3 Hz, 1H), 7.69 (d, J = 2.3 Hz, 1H), 7.66 (t, J = 7.7 Hz, 1H), 7.58 (dt, J = 1.5 and 7.8 Hz, 1H), 7.35 (d, J = 8.4 Hz, 1H), 3.35 (s, 3H), 2.24 (s, 3H), 1.75 (s, 6H), 1.22-1.27 (m, 4H). | 547.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 244 | D50 | | K | 47 | 11.0 (s, 1H), 10.6 (s, 1H), 9.10 (d, J = 5.2 Hz, 1H), 8.96 (s, 1H), 8.82 (d, J = 5.0 Hz, 1H), 8.53 (d, J = 5.2 Hz, 1H), 8.22 (d, J = 8.0 Hz, 1H), 8.04-8.09 (m, 2H), 7.86-7.90 (m, 2H), 7.41 (d, J = 11.2 Hz, 1H), 2.66 (s, 3H), 2.04 (m, 1H), 1.77 (s, 6H), 0.80-0.85 (m, 4H). | 536.2 |
| 245 | C12 E6 | | P | 22 | 11.1 (s, 1H), 10.7 (s, 1H), 9.63 (d, J = 2.2 Hz, 1H), 8.81 (d, J = 5.0 Hz, 1H), 8.56 (s, 1H), 8.52 (d, J = 5.2 Hz, 1H), 8.14 (d, J = 2.3 Hz, 1H), 8.03 (s, 1H), 7.92 (d, J = 2.3 Hz, 1H), 7.85-7.90 (m, 2H), 7.69 (dd, J = 1.7 and 5.2 Hz, 1H), 7.44 (d, J = 8.4 Hz, 1H), 2.35 (s, 3H), 2.04 (q, J = 6.3 Hz, 1H), 1.77 (s, 6H), 0.84 (d, J = 6.2 Hz, 4H). | 518.2 |
| 246 | C10 E13 | | P | 30 | 10.7 (s, 1H), 9.15 (d, J = 5.2 Hz, 1H), 8.90 (brq, J = 4.8 Hz, 1H), 8.87 (d, J = 5.2 Hz, 1H), 8.81 (s, 1H), 8.75 (d, J = 4.8 Hz, 1H), 8.40 (brd, J = 3.6 Hz, 1H), 8.36 (d, J = 1.6 Hz, 1H), 8.27 (d, J = 5.2 Hz, 1H), 8.06 (s, 1H), 7.91 (dd, J = 1.6 and 8.0 Hz, 1H), 7.85 (brd, J = 4.0 Hz, 1H), 7.40 (d, J = 8.4 Hz, 1H), 2.85 (d, J = 4.8 Hz, 3H), 2.60 (s, 3H), 1.71 (d, J = 22.4 Hz, 6H). | 485.4 |
| 247 | A6 F61 | | P | 16 | 10.8 (brs, 1H), 8.96 (d, J = 5.2 Hz, 1H), 8.84-8.90 (m, 2H), 8.80 (d, J = 5.2 Hz, 1H), 8.78 (brs, 1H), 8.45 (s, 1H), 8.33 (dd, J = 1.6 and 4.8 Hz, 1H), 8.15 (brs, 1H), 8.08-8.14 (m, 2H), 8.03 (s, 1H), 7.91 (brd, J = 5.2 Hz, 1H), 7.77 (dd, J = 1.2 and 5.2 Hz, 1H), 2.85 (d, J = 4.8 Hz, 3H), 1.77 (s, 6H) | 502.3 |
| 248 | A13 F30 | | P | 24 | 10.7 (s, 1H), 9.68 (s, 1H), 9.07 (d, J = 5.2 Hz, 1H), 9.05 (s, 1H), 8.81 (d, J = 5.2 Hz, 1H), 8.51 (d, J = 5.2 Hz, 1H), 8.05 (dd, J = 1.2 and 5.2 Hz, 1H), 8.02 (s, 1H), 7.99 (d, J = 1.6 Hz, 1H), 7.84-7.90 (m, 2H), 7.76 (d, J = 5.2 Hz, 1H), 7.44 (d, J = 8.4 Hz, 1H), 2.46 (s, 3H), 1.77 (s, 6H), 1.44 (s, 3H), 1.15 (m, 2H), 0.68 (m, 2H). | 532.4 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 249 | G18 | | P | 45 | 11.4 (s, 1H), 10.8 (s, 1H), 8.97 (s, 1H), 8.91 (d, J = 2.0 Hz, 1H), 8.77 (d, J = 4.8 Hz, 1H), 8.62 (s, 1H), 8.08-8.13 (m, 2H), 8.06 (s, 2H), 7.84 (dd, J = 1.2 and 4.0 Hz, 1H), 7.69 (t, J = 7.6 Hz, 1H), 7.64 (brd, J = 7.6 Hz, 1H), 2.44 (s, 3H), 2.08 (m, 1H), 1.71 (d, J = 22.0 Hz, 6H), 0.88 (m, 4H). | 511.4 |
| 250 | D43 | | K | 19 | 11.0 (s, 1H), 10.8 (s, 1H), 9.39 (d, J = 2.0 Hz, 1H), 9.12 (s, 1H), 9.07 (d, J = 5.2 Hz, 1H), 8.49 (d, J = 5.2 Hz, 1H), 8.01 (dd, J = 1.5 and 5.2 Hz, 1H), 7.98 (d, J = 2.3 Hz, 1H), 7.91 (d, J = 2.1 Hz, 1H), 7.85 (dd, J = 2.3 and 8.3 Hz, 1H), 7.74 (d, J = 5.1 Hz, 1H), 7.43 (d, J = 8.4 Hz, 1H), 2.45 (s, 3H), 2.37 (m, 1H), 2.05 (m, 1H), 1.09-1.20 (m, 4H), 0.76-0.87 (m, 4H). | 492.2 |
| 251 | A3 F47 | | P | 44 | 10.9 (s, 1H), 10.9 (s, 1H), 8.94 (d, J = 2.4 Hz, 1H), 8.87 (s, 1H), 8.84 (dd, J = 3.6 and 5.0 Hz, 2H), 8.44 (d, J = 5.2 Hz, 1H), 8.13 (d, J = 2.5 Hz, 1H), 8.07 (s, 1H), 8.04 (s, 1H), 7.89 (m, 1H), 7.83 (dd, J = 1.6 and 5.3 Hz, 1H), 7.60 (dd, J = 1.6 and 5.0 Hz, 1H), 2.48 (s, 3H), 2.04 (m, 1H), 1.77 (s, 6H), 0.83 (m, 4H). | 518.2 |
| 252 | D50 | | K | 18 | 11.0 (s, 1H), 10.7 (s, 1H), 9.39 (d, J = 2.0 Hz, 1H), 9.09 (d, J = 5.3 Hz, 1H), 8.95 (s, 1H), 8.52 (d, J = 5.2 Hz, 1H), 8.27 (d, J = 8.1 Hz, 1H), 8.06 (d, J = 5.3 Hz, 1H), 7.92 (d, J = 2.1 Hz, 1H), 7.87 (dd, J = 1.6 and 5.3 Hz, 1H), 7.41 (d, J = 11.4 Hz, 1H), 2.65 (s, 3H), 2.39 (m, 1H), 2.02 (m, 1H), 1.10-1.18 (m, 4H), 0.78-0.85 (m, 4H). | 510.2 |
| 253 | D51 | | K | 67 | 10.9 (s, 1H), 10.7 (s, 1H), 8.94 (d, J = 2.4 Hz, 1H), 8.87 (s, 1H), 8.84 (d, J = 5.0 Hz, 1H), 8.60 (d, J = 5.0 Hz, 1H), 8.44 (d, J = 5.2 Hz, 1H), 8.15 (d, J = 2.4 Hz, 1H), 8.07 (s, 1H), 7.83 (dd, J = 1.6 and 5.2 Hz, 1H), 7.78 (s, 1H), 7.60 (d, J = 1.3 Hz, 2H), 2.47 (s, 3H), 2.23 (m, 1H), 2.04 (m, 1H), 0.94-1.05 (m, 4H), 0.78-0.88 (m, 4H). | 491.2 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| 254 | (structure: 6-cyclopropylpyridazine-3-carboxylic acid) | (structure) | K | 75 | 11.0 (s, 1H), 10.9 (s, 1H), 9.41 (d, J = 2.0 Hz, 1H), 8.92 (d, J = 2.4 Hz, 1H), 8.87 (s, 1H), 8.84 (d, J = 4.9 Hz, 1H), 8.44 (d, J = 5.3 Hz, 1H), 8.15 (d, J = 2.4 Hz, 1H), 8.07 (s, 1H), 7.95 (d, J = 2.1 Hz, 1H), 7.83 (dd, J = 1.6 and 5.2 Hz, 1H), 7.60 (dd, J = 1.6 and 5.0 Hz, 1H), 2.48 (s, 3H), 2.38 (m, 1H), 2.04 (m, 1H), 1.10-1.24 (m, 4H), 0.78-0.88 (m, 4H). | 492.2 |
| 255 | G19 (structure) | (structure) | P | 51 | 11.3 (s, 1H), 10.4 (s, 1H), 8.96 (s, 1H), 8.61 (s, 1H), 8.56 (d, J = 4.8 Hz, 1H), 8.06 (brd, J = 7.6 Hz, 1H), 7.99 (brs, 1H), 7.76 (dd, J = 8.4, 2.0 Hz, 1H), 7.74 (brs, 1H), 7.70 (brm, 1H), 7.64 (brt, J = 7.6 Hz, 1H), 7.56 (brd, J = 6.4 Hz, 2H), 7.33 (d, J = 8.4 Hz, 1H), 2.23 (s, 3H), 2.19 (m, 1H), 2.07 (m, 1H), 0.94-1.09 (m, 4H), 0.83-0.91 (m, 4H). | 490.5 |
| 256 | A3 F64 | (structure) | P | 51 | 11.0 (s, 1H), 10.7 (s, 1H), 8.89 (d, J = 2.5 Hz, 1H), 8.61 (d, J = 2.3 Hz, 1H), 8.59 (d, J = 5.0 Hz, 1H), 8.42 (d, J = 5.1 Hz, 1H), 8.17 (s, 1H), 8.10 (d, J = 2.4 Hz, 1H), 7.76 (s, 1H), 7.74 (d, J = 2.2 Hz, 1H), 7.58 (dd, J = 1.7 and 5.1 Hz, 1H), 7.25 (dd, J = 1.6 and 5.2 Hz, 1H), 2.52 (s, 3H), 2.46 (s, 3H), 2.21 (m, 1H), 2.02 (m, 1H), 0.95-1.04 (m, 4H), 0.80-0.82 (m, 4H). | 505.2 |
| 257 | A3 F30 | (structure) | P | 64 | 10.9 (s, 1H), 10.7 (s, 1H), 9.12 (s, 1H), 9.06 (d, J = 5.1 Hz, 1H), 8.81 (d, J = 5.1 Hz, 1H), 8.49 (d, J = 5.2 Hz, 1H), 8.00 (m, 2H), 7.98 (d, J = 2.3 Hz, 1H), 7.85-7.89 (m, 2H), 7.74 (d, J = 5.2 Hz, 1H), 7.43 (d, J = 8.4 Hz, 1H), 2.46 (s, 3H), 2.03 (m, 1H), 1.76 (s, 6H), 0.78-0.85 (m, 4H). | 518.2 |
| 258 | G7 (structure) | (structure) | P, Q & reductive alkylation with HCOH | 49 | 10.6 (s, 1H), 8.80 (d, J = 4.8 Hz, 1H), 8.50 (s, 1H), 8.01 (s, 1H), 7.98 (m, 2H), 7.87 (m, 2H), 7.74 (m, 1H), 7.70 (brm, 1H), 7.59 (t, J = 7.6 Hz, 1H), 7.48 (d, J = 7.6 Hz, 1H), 7.35 (d, = 8.4 Hz, 1H), 6.98 (s, 1H), 4.47 (brm, 1H), 3.64 (m, 2H), 2.89 (m, 2H), 2.26 (s, 3H), 2.25 (s, 3H), 1.76 (s, 6H). at high temp | 518.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 259 | D53 | | K | 30 | 10.8 (s, 1H), 8.87 (q, J = 4.8 Hz, 1H), 8.84 (d, J = 4.8 Hz, 1H), 8.76 (d, J = 5.2 Hz, 1H), 8.73 (d, J = 0.8 Hz, 1H), 8.30 (dd, J = 1.6 and 5.2 Hz, 1H), 8.14 (s, 1H), 8.06 (m, 1H), 8.04 (s, 1H), 7.93 (m, 1H), 7.90 (d, J = 5.2 Hz, 1H), 7.58 (s, 1H), 7.47 (t, J = 9.6 Hz, 1H), 2.86 (d, J = 4.8 Hz, 3H), 2.68 (s, 3H), 1.77 (s, 6H). | 509.2 |
| 260 | D52 | | K | 35 | 10.6 (s, 1H), 8.83 (q J = 4.4 Hz, 1H), 8.80 (d, J = 4.8 Hz, 1H), 8.69 (d, J = 5.2 Hz, 1H), 8.33 (s, 1H), 8.29 (d, J = 2.0 Hz, 1H), 8.00 (s, 1H), 7.97 (d, J = 2.0 Hz, 1H), 7.89 (dd, J = 1.6 and 5.2 Hz, 1H), 7.78 (d, J = 4.8 Hz, 1H), 7.75 (dd, J = 2.0 and 8.0 Hz, 1H), 7.70 (s, 1H), 7.35 (d, J = 8.4 Hz, 1H), 4.47 (q, J = 7.2 Hz, 2H), 2.83 (d, J = 4.8 Hz, 3H), 2.29 (s, 3H), 1.76 (s, 6H), 1.35 (t, J = 6.8 Hz, 3H). | 535.2 |
| 261 | 82, NaCN | | L & SN2 | 8 | 11.0 (s, 1H), 10.7 (s, 1H), 9.09 (d, J = 5.2 Hz, 1H), 9.07 (s, 1H), 8.81 (d, J = 5.0 Hz, 1H), 8.53 (d, J = 5.1 Hz, 1H), 8.08 (dd, J = 1.5 and 5.2 Hz, 1H), 8.01 (m, 2H), 7.88 (dd, J = 1.5 and 5.1 Hz, 1H), 7.85 (dd, J = 2.3 and 8.3 Hz, 1H), 7.78 (d, J = 5.2 Hz, 1H), 7.44 (d, J = 8.4 Hz, 1H), 4.02 (s, 2H), 1.76 (s, 6H). | 517.2 |
| 262 | D41 | | K | 27 | 11.0 (s, 1H), 10.7 (s, 1H), 9.12 (s, 1H), 9.05 (d, J = 5.2 Hz, 1H), 8.71 (d, J = 5.0 Hz, 1H), 8.49 (d, J = 5.1 Hz, 1H), 8.00 (dd, J = 1.5 and 5.2 Hz, 1H), 7.97 (s, 1H), 7.86 (d, J = 7.8 Hz, 1H), 7.80 (d, J = 1.5 Hz, 1H), 7.77 (d, J = 5.1 Hz, 1H), 7.44 (d, J = 11.3 Hz, 1H), 2.51 (s, 3H), 1.99-2.09 (m, 1H), 1.88 (m, 2H), 1.77 (m, 2H), 0.77-0.87 (m, 4H). | 534.2 |
| 263 | D41 | | K | 48 | 11.0 (s, 1H), 10.8 (s, 1H), 9.39 (d, J = 2.0 Hz, 1H), 9.11 (s, 1H), 9.06 (d, J = 5.2 Hz, 1H), 8.49 (d, J = 5.2 Hz, 1H), 8.00 (dd, J = 1.5 and 5.1 Hz, 1H), 7.90-7.93 (m, 2H), 7.76 (d, J = 5.2 Hz, 1H), 7.44 (d, J = 11.4 Hz, 1H), 2.51 (s, 3H), 2.39 (m, 1H), 2.03 (m, 1H), 1.11-1.20 (m, 4H), 0.78-0.86 (m, 4H). | 510.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 264 | D18 | | K | 43 | 10.6 (s, 1H), 8.88 (m, 1H), 8.85 (d, J = 5.0 Hz, 1H), 8.78 (s, 1H), 8.75 (d, J = 5.2 Hz, 1H), 8.72 (d, J = 5.1 Hz, 1H), 8.34 (dd, J = 1.8 and 5.2 Hz, 1H), 8.20 (s, 1H), 8.01 (s, 1H), 7.83 (dd, J = 2.3 and 8.2 Hz, 1H), 7.74-7.79 (m, 2H), 7.56 (d, J = 1.5 Hz, 1H), 7.39 (d, J = 8.4 Hz, 1H), 3.10 (s, 3H), 2.84 (d, J = 4.7 Hz, 3H), 2.29 (s, 3H), 1.50 (s, 6H). | 496.2 |
| 265 | D18 | | K | 63 | 10.6 (s, 1H), 8.85 (m, 2H), 8.78 (d, J = 5.2 Hz, 1H), 8.71 (d, J = 5.2 Hz, 1H), 8.33 (dd, J = 1.6 and 5.2 Hz, 1H), 8.20 (s, 1H), 7.93 (s, 1H), 7.80 (m, 2H), 7.76 (brs, 1H), 7.56 (brd, J = 4.8 Hz, 1H), 7.40 (d, J = 8.4 Hz, 1H), 2.85 (d, J = 4.8 Hz, 3H), 2.30 (s, 3H), 1.88 (m, 2H), 1.76 (m, 2H). | 489.4 |
| 266 | A15 F15 | | P | 31 | 10.6 (s, 1H), 8.88 (t, J = 6.0 Hz, 1H), 8.86 (d, J = 4.8 Hz, 1H), 8.81 (d, J = 5.2 Hz, 1H), 8.77 (brs, 1H), 8.75 (d, J = 5.2 Hz, 1H), 8.33 (dd, J = 1.2 and 5.2 Hz, 1H), 8.20 (s, 1H), 8.01 (s, 1H), 7.87 (brd, J = 4.8 Hz, 1H), 7.80 (dd, J = 1.6 and 8.0 Hz, 1H), 7.75 (d, J = 2.0 Hz, 1H), 7.56 (brd, J = 4.0 Hz, 1H), 7.40 (d, J = 8.4 Hz, 1H), 3.37 (q, J = 7.2 Hz, 2H), 2.30 (s, 3H), 1.76 (s, 6H), 1.14 (t, J = 7.2 Hz, 3H). | 505.4 |
| 267 | G7 | Side product | P | 24 | 10.6 (s, 1H), 8.80 (d, J = 5.1 Hz, 1H), 8.44 (d, J = 1.1 Hz, 1H), 8.00 (s, 1H), 7.94-7.98 (m, 2H), 7.86 (dd, J = 1.5 and 5.0 Hz, 1H), 7.74 (dd, J = 2.3 and 8.3 Hz, 1H), 7.69 (d, J = 2.3 Hz, 1H), 7.58 (t, J = 7.6 Hz, 1H), 7.49 (dt, J = 1.4 and 7.7 Hz, 1H), 7.34 (d, J = 8.4 Hz, 1H), 6.95 (d, J = 1.1 Hz, 1H), 6.92 (s, 2H), 2.25 (s, 3H), 1.75 (s, 6H) | 449.2 |
| 268 | C10 E9 | | P | 24 | 10.6 (s, 1H), 9.15 (d, J = 5.2 Hz, 1H), 8.90 (brq, J = 4.8 Hz, 1H), 8.87 (d, J = 4.8 Hz, 1H), 8.81 (d, J = 1.2 Hz, 1H), 8.72 (d, J = 5.2 Hz, 1H), 8.40 (dd, J = 1.6 and 5.2 Hz, 1H), 8.35 (d, J = 2.4 Hz, 1H), 8.27 (d, J = 5.6 Hz, 1H), 8.03 (brs, 1H), 7.91 (dd, J = 2.0 and 8.0 Hz, 1H), 7.80 (dd, J = 1.6 and 5.2 Hz, 1H), 7.40 (d, J = 8.4 Hz, 1H), 3.12 (s, 3H), 2.85 (d, J = 4.8 Hz, 3H), 2.60 (s, 3H), 1.51 (s, 6H). | 497.5 |

TABLE I-continued

| Ex No. | SM | Product | Method | Yield (%) | $^1$H NMR (400 or 500 MHz, (DMSO-$d_6$): δ | MS (m/z: M + H$^+$) |
|---|---|---|---|---|---|---|
| 269 | A3 F65 | 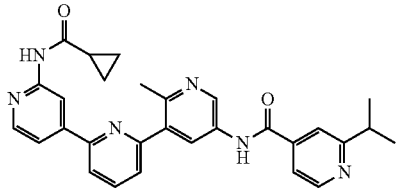 [SMILES: Cc1ncc(NC(=O)c2ccnc(C(C)C)c2)cc1-c1cccc(-c2ccnc(NC(=O)C3CC3)c2)n1] | P | 20 | 10.9 (s, 1H), 10.7 (s, 1H), 8.93 (d, J = 2.0 Hz, 1H), 8.85 (s, 1H), 8.70 (d, J = 5.2 Hz, 1H), 8.44 (d, J = 5.2 Hz, 1H), 8.29 (d, J = 2.0 Hz, 1H), 8.12 (t, J = 7.6 Hz, 1H), 8.05 (d, J = 7.6 Hz, 1H), 7.76-7.80 (m, 2H), 7.67-7.74 (m, 2H), 3.13 (m, 1H), 2.59 (s, 3H), 2.03 (m, 1H), 1.28 (d, J = 6.8 Hz, 6H), 0.79-0.85 (m, 4H). | 493.4 |
| 270 | A3 F36 | 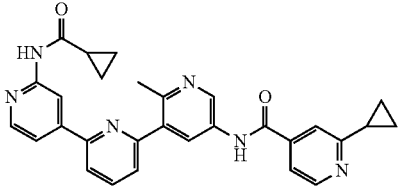 [SMILES: Cc1ncc(NC(=O)c2ccnc(C3CC3)c2)cc1-c1cccc(-c2ccnc(NC(=O)C3CC3)c2)n1] | P | 23 | 10.9 (s, 1H), 10.7 (s, 1H), 8.93 (s, 1H), 8.94 (s, 1H), 8.60 (brd, J = 4.8 Hz, 1H), 8.45 (brd, J = 5.2 Hz, 1H), 8.29 (s, 1H), 8.11 (brt, J = 7.6 Hz, 1H), 8.05 (brd, J = 8.0 Hz, 1H), 7.89 (brm, 2H), 7.72 (d, J = 7.6 Hz, 1H), 7.60 (brd, J = 4.4 Hz, 1H), 2.59 (s, 3H), 2.22 (m, 1H), 2.04 (m, 1H), 0.98-1.08 (m, 4H), 0.79-0.89 (m, 4H). | 491.4 |
| 271 | D54 | 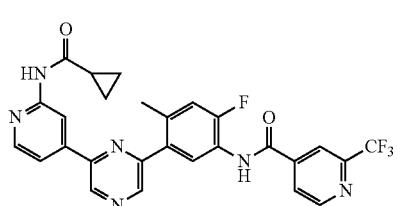 | K | 45 | 11.0 (s, 1H), 10.8 (s, 1H), 9.27 (s, 1H), 9.00 (d, J = 5.2 Hz, 1H), 8.92 (s, 1H), 8.86 (s, 1H), 8.49 (d, J = 5.2 Hz, 1H), 8.38 (s, 1H), 8.21 (brd, J = 4.8 Hz, 1H), 7.84-7.90 (brm, 2H), 7.45 (d, J = 11.6 Hz, 1H), 2.46 (s, 3H), 2.04 (m, 1H), 0.78-0.88 (m, 4H). | 537.4 |
| 272 | D46 | 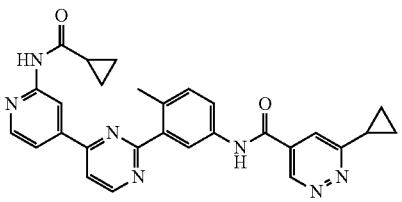 | direct amid coupling with LiHMDS | 52 | 11.0 (s, 1H), 10.8 (s, 1H), 9.40 (d, J = 2.1 Hz, 1H), 9.12 (d, J = 5.3 Hz, 1H), 8.95 (dd, J = 0.8 and 1.6 Hz, 1H), 8.54 (dd, J = 0.8 and 5.2 Hz, 1H), 8.32 (d, J = 2.4 Hz, 1H), 8.07 (d, J = 5.3 Hz, 1H), 7.92 (d, J = 2.1 Hz, 1H), 7.90-7.86 (m, 2H), 7.41 (d, J = 8.3 Hz, 1H), 2.59 (s, 3H), 2.38 (m, 1H), 2.03 (m, 1H), 1.19-1.13 (m, 4H), 0.87-0.81 (m, 4H). | 491.2 |
| 273 | D56 | 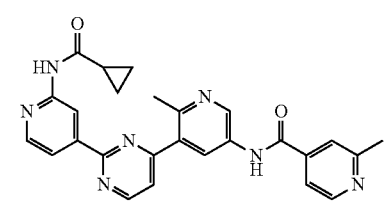 [SMILES: Cc1cc(C(=O)Nc2cnc(C)c(-c3ccnc(-c4ccnc(NC(=O)C5CC5)c4)n3)c2)ccn1] | R | 55 | 11.0 (s, 1H), 10.8 (s, 1H), 9.10-9.17 (m, 2H), 9.01 (d, J = 2.5 Hz, 1H), 8.68 (dd, J = 0.8 and 5.1 Hz, 1H), 8.52 (dd, J = 0.8 and 5.3 Hz, 1H), 8.43 (d, J = 2.5 Hz, 1H), 8.04 (dd, J = 1.5 and 5.2 Hz, 1H), 7.87 (d, J = 5.2 Hz, 1H), 7.79 (m, 1H), 7.70 (dd, J = 1.7 and 5.3 Hz, 1H), 2.66 (s, 3H), 2.60 (s, 3H), 2.05 (m, 1H), 0.85 (m, 4H) | 466.2 |
| 274 | G20 | 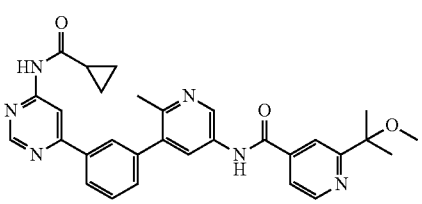 [SMILES: COC(C)(C)c1cc(C(=O)Nc2cnc(C)c(-c3cccc(-c4cc(NC(=O)C5CC5)ncn4)c3)c2)ccn1] | P | 43 | 11.3 (s, 1H), 10.7 (s, 1H), 8.97 (s, 1H), 8.92 (d, J = 2.0 Hz, 1H), 8.73 (d, J = 4.8 Hz, 1H), 8.62 (s, 1H), 8.10 (brm, 2H), 8.06 (brs, 1H), 8.04 (brs, 1H), 7.78 (brd, J = 4.8 Hz, 1H), 7.68 (brt, J = 7.6 Hz, 1H), 7.64 (brd, J = 7.6 Hz, 1H), 3.12 | 523.4 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| | | | | | (s, 3H), 2.44 (s, 3H), 2.08 (m, 1H), 1.51 (s, 6H), 0.86-0.92 (m, 4H). | |
| 275 | D54 | | K | 72 | 11.0 (s, 1H), 10.7 (s, 1H), 9.27 (s, 1H), 8.92 (s, 1H), 8.91 (d, J = 5.2 Hz, 1 H), 8.87 (s, 1H), 8.49 (d, J = 5.2 Hz, 1H), 8.20 (s, 1H), 8.07 (d, J = 4.8 Hz, 1H), 7.82-7.88 (m, 2H), 7.43 (d, J = 11.6 Hz, 1H), 7.09 (t, J = 54.8 Hz, 1H), 2.45 (s, 3H), 2.05 (m, 1H), 0.79-0.85 (m, 4H). | 519.4 |
| 276 | D54 | | K | 41 | 11.0 (s, 1H), 10.6 (s, 1H), 9.27 (s, 1H), 8.92 (s, 1H), 8.87 (s, 1H), 8.77 (d, J = 5.2 Hz, 1H), 8.49 (d, J = 5.2 Hz, 1H), 8.06 (brs, 1H), 7.84-7.88 (m, 2H), 7.81 (d, J = 8.0 Hz, 1H), 7.43 (d, J = 11.6 Hz, 1H), 2.46 (s, 3H), 2.04 (m, 1H), 1.71 (d, J = 22.4 Hz, 6H), 0.79-0.85 (m, 4H). | 529.4 |
| 277 | D56 | | K | 42 | 11.0 (s, 1H), 10.8 (s, 1H), 9.13 (q, J = 0.8 Hz, 1H), 9.11 (d, J = 5.2 Hz, 1H), 8.99 (d, J = 2.4 Hz, 1H), 8.60 (d, J = 0.8 Hz, 1H), 8.50 (dd, J = 0.8 and 5.2 Hz, 1H), 8.41 (d, J = 2.5 Hz, 1H), 8.02 (dd, J = 1.6 and 5.2 Hz, 1H), 7.85 (d, J = 5.2 Hz, 1H), 7.78 (q, J = 0.9 Hz, 1H), 7.60 (dd, J = 1.7 and 5.1 Hz, 1H), 2.65 (s, 3H), 2.21 (m, 1H), 2.04 (m, 1H), 0.93-1.06 (m, 4H), 0.77-0.89 (m, 4H). | 492.2 |
| 278 | D56 | | K | 19 | 11.0 (s, 1H), 10.9 (s, 1H), 9.42 (d, J = 2.1 Hz, 1H), 9.08-9.15 (m, 2H), 8.98 (d, J = 2.5 Hz, 1H), 8.50 (dd, J = 0.8 and 5.2 Hz, 1H), 8.40 (d, J = 2.4 Hz, 1H), 8.02 (dd, J = 1.5 and 5.2 Hz, 1H), 7.94 (d, J = 2.1 Hz, 1H), 7.85 (d, J = 5.1 Hz, 1H), 2.65 (s, 3H), 2.33-2.47 (m, 1H), 1.98-2.09 (m, 1H), 1.08-1.25 (m, 4H), 0.78-0.86 (m, 4H). | 493.2 |
| 279 | D60 | | K | 31 | 11.0 (s, 1H), 9.79 (s, 1H), 8.93 (s, 1H), 8.84 (d, J = 2.0 Hz, 1H), 8.58 (s, 1H), 8.41 (s, 1H), 8.09 (d, J = 7.6 Hz, 1H), 8.04 (s, 1H), 8.00 (m, 2H), 7.67 (t, J = 7.6 Hz, 1H), 7.59 (brd, J = 7.2 Hz, 1H), 2.42 (s, 3H), 2.10 (m, 1H), 1.58 (s, 9H), 0.83-0.98 (m, 4H). at high Temp. | 496.4 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 280 | D60 | | R | 26 | 11.4 (s, 1H), 10.9 (s, 1H), 8.97 (s, 1H), 8.93 (m, 2H), 8.62 (s, 1H), 8.21 (s, 1H), 8.06-8.11 (m, 4H), 7.69 (t, J = 7.6 Hz, 1H), 7.65 (d, J = 7.6 Hz, 1H), 7.09 (t, J = 54.4 Hz, 1H), 2.45 (s, 3H), 2.08 (m, 1H), 0.85-0.92 (m, 4H). | 501.3 |
| 281 | D56 | | K | 27 | 10.9 (s, 1H), 10.8 (s, 1H), 9.08 (dd, J = 0.9 and 1.6 Hz, 1H), 9.05 (d, J = 5.1 Hz, 1H), 9.01 (d, J = 2.5 Hz, 1H), 8.80 (s, 1H), 8.44 (dd, J = 0.8 and 5.2 Hz, 1H), 8.42 (d, J = 2.5 Hz, 1H), 7.97 (dd, J = 1.6 and 5.2 Hz, 1H), 7.78 (d, J = 5.1 Hz, 1H), 4.87 (m, 1H), 2.58 (s, 3H), 1.99 (m, 1H), 1.48 (d, J = 6.7 Hz, 6H), 0.71-0.80 (m, 4H). | 484.2 |
| 282 | G10 | | P | 16 | 10.8 (s, 1H), 10.3 (s, 1H), 8.89 (d, J = 2.4 Hz, 1H), 8.82 (dd, J = 0.8 and 5.1 Hz, 1H), 8.34 (d, J = 0.7 Hz, 1H), 8.17 (m, 1H), 8.09 (d, J = 2.5 Hz, 1H), 8.04 (m, 1H), 7.89 (dd, J = 1.6 and 5.0 Hz, 1H), 7.79 (m, 1H), 7.72 (t, J = 1.8 Hz, 1H), 7.66 (t, J = 7.7 Hz, 1H), 7.55 (m, 1H), 7.44 (dd, J = 1.7 and 5.2 Hz, 1H), 3.68 (s, 3H), 2.46 (s, 3H), 1.76 (s, 6H). | 507.2 |
| 283 | D56 | | R | 7 | 11.0 (s, 1H), 10.1 (s, 1H), 9.14 (t, J = 1.2 Hz, 1H), 9.12 (d, J = 5.2 Hz, 1H), 8.95 (d, J = 2.4 Hz, 1H), 8.52 (dd, J = 0.8 and 5.2 Hz, 1H), 8.50 (s, 1H), 8.34 (d, J = 2.5 Hz, 1H), 8.06 (s, 1H), 8.03 (dd, J = 1.5 and 5.2 Hz, 1H), 7.85 (d, J = 5.2 Hz, 1H), 2.64 (s, 3H), 2.06 (m, 1H), 1.57 (s, 9H), 0.79-0.90 (m, 4H). | 497.2 |
| 284 | D44 | | R | 13 | 11.3 (s, 1H), 10.6 (s, 1H), 9.37 (d, J = 2.0 Hz, 1H), 8.96 (s, 1H), 8.61 (s, 1H), 8.07 (brd, J = 8.0 Hz, 1H), 7.99 (brs, 1H), 7.89 (d, J = 2.0 Hz, 1H), 7.74 (dd, J = 2.0 and 6.8 Hz, 1H), 7.68 (d, J = 2.0Hz, 1H), 7.65 (t, J = 8.0 Hz, 1H), 7.57 (brd, J = 7.2 Hz, 1H), 7.36 (d, J = 8.4 Hz, 1H), 2.37 (m, 1H), 2.24 (s, 3H), 2.07 (m, 1H), 1.11-1.20 (m, 4H), 0.83-0.89 (m, 4H). | 491.4 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 285 | D58 | | R | 21 | 11.0 (s, 1H), 10.8 (s, 1H), 9.14 (d, J = 5.2 Hz, 1H), 9.02 (d, J = 2.4 Hz, 1H), 8.95 (s, 1H), 8.85 (s, 1H), 8.81 (d, J = 2.4 Hz, 1H), 8.54 (d, J = 5.2 Hz, 1H), 8.10 (d, J = 5.6 Hz, 1H), 7.91 (dd, J = 1.6 and 5.2 Hz, 1H), 4.93 (m, 1H), 2.76 (s, 3H), 2.04 (m, 1H), 1.54 (d, J = 6.8 Hz, 6H), 0.80-0.88 (m, 4H). | 484.4 |
| 286 | D62 | | R | 65 | 11.0 (s, 1H), 10.9 (s, 1H), 8.99 (s, 1H), 8.92 (s, 1H), 8.73 (d, J = 4.8 Hz, 1H), 8.50 (d, J = 4.8 Hz, 1H), 8.34 (s, 1H), 8.15 (s, 1H), 7.98 (s, 1H), 7.88 (d, J = 4.4 Hz, 1H), 7.83 (d, J = 4.4 Hz, 1H), 2.79 (s, 3H), 2.61 (s, 3H), 2.04 (m, 1H), 1.87-1.92 (m, 2H), 1.76-1.79 (m, 2H), 0.82-0.87 (m, 4H). | 531.4 |
| 287 | D62 | | R | 34 | 11.0 (s, 1H), 10.7 (s, 1H), 8.98 (d, J = 2.0 Hz, 1H), 8.91 (s, 1H), 8.59 (d, J = 5.2 Hz, 1H), 8.50 (d, J = 4.8 Hz, 1H), 8.35 (d, J = 2.0 Hz, 1H), 8.13 (s, 1H), 7.87 (brd, J = 5.2 Hz, 1H), 7.78 (s, 1H), 7.60 (brd, J = 4.8 Hz, 1H), 2.79 (s, 3H), 2.60 (s, 3H), 2.22 (m, 1H), 2.03 (m, 1H), 0.98-1.04 (m, 4H), 0.82-0.87 (m, 4H). | 506.4 |
| 288 | G21 | | P | 9 | 10.7 (s, 1H), 10.3 (s, 1H), 8.89 (d, J = 2.4 Hz, 1H), 8.58 (d, J = 0.7 Hz, 1H), 8.33 (d, 1H), 8.17 (d, J = 1.8 Hz, 1H), 8.10 (d, J = 2.4 Hz, 1H), 7.75-7.81 (m, 2H), 7.72 (t, J = 1.8 Hz, 1H), 7.66 (t, J = 7.7 Hz, 1H), 7.58 (dd, J = 1.7 and 5.2 Hz, 1H), 7.55 (m, 1H), 7.44 (dd, J = 1.6 and 5.2 Hz, 1H), 3.68 (s, 3H), 2.45 (s, 3H), 2.20 (m, 1H), 0.94-1.04 (m, 4H). | 480.2 |
| 289 | G10 | | P | 33 | 10.8 (s, 1H), 8.88 (d, J = 2.4 Hz, 1H), 8.82 (dd, J = 0.8 and 5.0 Hz, 1H), 8.32 (d, J = 5.2 Hz, 1H), 8.09-8.15 (m, 2H), 8.07 (d, J = 2.5 Hz, 1H), 8.03 (s, 1H), 7.89 (dd, J = 1.5 and 5.0 Hz, 1H), 7.62 (m, 1H), 7.57 (m, 1H), 7.22 (d, J = 5.2 Hz, 1H), 6.67 (s, 2H), 2.44 (s, 3H), 1.76 (s, 6H). | 450.2 |
| 290 | G10 | | P | 52 | 10.8 (s, 1H), 10.5 (s, 1H), 8.89 (d, J = 2.5 Hz, 1H), 8.82 (dd, J = 0.8 and 5.0 Hz, 1H), 8.69 (d, J = 5.3 Hz, 1H), 8.25-8.31 (m, 2H), 8.09 (d, J = 2.5 Hz, 1H), 8.03 (m, 1H), 7.89 (dd, J = 1.5 and 5.2 Hz, 1H), 7.81 (d, J = 5.3 Hz, 1H), 7.68 (t, J = 7.6 Hz, | 508.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | 1H), 7.62 (dt, J = 1.5 and 7.6 Hz, 1H), 3.67 (s, 3H), 2.45 (s, 3H), 1.76 (s, 6H) | |
| 291 | D60 | | R | 29 | 11.3 (s, 1H), 10.7 (s, 1H), 8.97 (s, 1H), 8.90 (d, J = 1.2 Hz, 1H), 8.62 (s, 1H), 8.59 (d, J = 4.8 Hz, 1H), 8.09 (brm, 2H), 8.05 (brs, 1H), 7.77 (s, 1H), 7.62-7.72 (m, 2H), 7.59 (brd, J = 4.4 Hz, 1H), 2.44 (s, 3H), 2.21 (m, 1H), 2.08 (m, 1H), 0.96-1.06 (m, 4H), 0.85-0.90 (m, 4H). | 491.1 |
| 292 | D60 | | direct amid coupling with LiHMDS | 27 | 11.3 (s, 1H), 10.7 (s, 1H), 8.96 (d, J = 1.6 Hz, 2H), 8.83 (s, 1H), 8.62 (d, J = 0.8 Hz, 1H), 8.15 (d, J = 2.0 H, 1H), 8.09 (brd, J = 8.0 Hz, 1H), 8.04 (brs, 1H), 7.68 (t, J = 7.6 Hz, 1H), 7.63 (brd, J = 7.6 Hz, 1H), 4.91 (m, 1H), 2.42 (s, 3H), 2.08 (m, 1H), 1.54 (d, J = 6.4 Hz, 6H), 0.86-0.92 (m, 4H). | 483.4 |
| 293 | D58 | | K | 11 | 11.0 (s, 1H), 10.9 (s, 1H), 9.15 (d, J = 5.2 Hz, 1H), 9.01 (d, J = 2.0 Hz, 1H), 8.96 (s, 1H), 8.72-8.76 (m, 2H), 8.54 (d, J = 5.2 Hz, 1H), 8.11 (d, J = 5.2 Hz, 1H), 7.98 (s, 1H), 7.89 (brd, J = 5.2 Hz, 1H), 7.84 (brd, J = 5.2 Hz, 1H), 2.81 (s, 3H), 2.04 (m, 1H), 1.86-1.92 (m, 2H), 1.75-1.80 (m, 2H), 0.80-0.87 (m, 4H). | 517.4 |
| 294 | D58 | | direct amid coupling with LiHMDS | 20 | 11.0 (s, 1H), 10.9 (brm, 1H), 9.42 (d, J = 2.0 Hz, 1H), 9.15 (d, J = 5.2 Hz, 1H), 9.00 (d, J = 2.4 Hz, 1H), 8.96 (s, 1H), 8.75 (d, J = 2.4 Hz, 1H), 8.54 (d, J = 5.2 Hz, 1H), 8.11 (d, J = 5.6 Hz, 1H), 7.94 (d, J = 2.0 Hz, 1H), 7.89 (dd, J = 1.2 and 5.2 Hz, 1H), 2.81 (s, 3H), 2.37 (m, 1H), 2.05 (m, 1H), 1.17-1.20 (m, 4H), 0.80-0.88 (m, 4H). | 493.4 |
| 295 | D58 | | R | 38 | 11.0 (s, 1H), 10.8 (s, 1H), 9.15 (brd, J = 5.2 Hz, 1H), 9.03 (brs, 1H), 8.96 (s, 1H), 8.81 (brs, 1H), 8.61 (brd, J = 4.8 Hz, 1H), 8.54 (d, J = 5.2 Hz, 1H), 8.12 (brd, J = 4.8 Hz, 1H), 7.89 (brd, J = 2.0 Hz, 1H), 7.80 (s, 1H), 7.63 (brd, J = 4.8 Hz, 1H), 2.82 (s, 3H), 2.25 (m, 1H), 2.05 (m, 1H), 0.97-1.05 (m, 4H), 0.80-0.90 (m, 4H). | 492.1 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 296 | D58 | | K | 42 | 11.0 (s, 1H), 10.79 (s, 1H), 9.15 (brd, J = 4.8 Hz, 1H), 9.01 (brs, 1H), 8.96 (brs, 1H), 8.78 (brs, 1H), 8.67 (brd, J = 5.2 Hz, 1H), 8.54 (brd, J = 4.8 Hz, 1H), 8.11 (brd, J = 5.2 Hz, 1H), 7.89 (brd, J = 4.4 Hz, 1H), 7.80 (s, 1H), 7.71 (brm, 1H), 2.80 (s, 3H), 2.59 (s, 3H), 2.05 (m, 1H), 0.82-0.89 (m, 4H). | 466.4 |
| 297 | G22 | | P | 21 | 10.8 (s, 1H), 10.24 (s, 1H), 8.87 (d, J = 2.4 Hz, 1H), 8.79 (dd, J = 5.0 and 11.0 Hz, 2H), 8.58 (m, 1H), 8.32 (d, J = 5.2 Hz, 1H), 8.08 (d, J = 2.4 Hz, 1H), 8.03 (t, J = 1.1 Hz, 1H), 7.98 (t, J = 1.2 Hz, 1H), 7.83 (dd, J = 1.5 and 5.0 Hz, 1H), 7.72 (dd, J = 1.6 and 5.2 Hz, 1H), 7.54 (dd, J = 1.6 and 5.0 Hz, 1H), 3.63 (s, 3H), 2.50 (s, 3H), 1.71 (s, 6H). | 508.2 |
| 298 | D63 | | K | 44 | 11.0 (s, 1H), 10.6 (s, 1H), 9.60 (d, J = 2.2 Hz, 1H), 8.81 (d, J = 5.0 Hz, 1H), 8.54 (d, J = 1.6 Hz, 1H), 8.51 (d, J = 5.2 Hz, 1H), 8.13 (d, J = 2.2 Hz, 1H), 8.05 (s, 1H), 7.87 (dd, J = 1.6 and 5.0 Hz, 1H), 7.81 (d, J = 7.7 Hz, 1H), 7.68 (dd, J = 1.7 and 5.2 Hz, 1H), 7.42 (d, J = 11.3 Hz, 1H), 2.38 (s, 3H), 2.04 (m, 1H), 1.76 (s, 6H), 0.79-0.86 (m, 4H). | 536.2 |
| 299 | D64 | | K | 11 | 10.3 (s, 1H), 10.4 (s, 1H), 9.62 (d, J = 2.1 Hz, 1H), 8.81 (d, J = 5.0 Hz, 1H), 8.46 (d, J = 5.2 Hz, 1H), 8.28 (s, 1H), 8.16 (d, J = 2.2 Hz, 1H), 8.05 (s, 1H), 7.87 (dd, J = 5.1, 1.6 Hz, 1H), 7.82 (d, J = 7.8 Hz, 1H), 7.65 (dd, J = 1.6 and 5.2 Hz, 1H), 7.43 (d, J = 11.3 Hz, 1H), 3.70 (s, 3H), 2.40 (s, 3H), 1.76 (s, 6H). | 526.2 |
| 300 | D65 | | K | 32 | 10.9 (s, 1H), 10.6 (s, 1H ), 8.84 (brs, 1H), 8.79 (brd, J = 4.8 Hz, 1H), 8.76, (brd, J = 4.8 Hz, 1H), 8.42 (brd, J = 5.2 Hz, 1H), 8.04 (brs, 1H), 7.95 (brs, 1H), 7.81 (brt, J = 4.8 Hz, 2H), 7.59 (brd, J = 7.6 Hz, 1H), 7.51 (brd, J = 4.8 Hz, 1H), 7.38 (d, J = 11.6 Hz, 1H), 2.31 (s, 3H), 2.03 (brm, 1H), 1.70 (d, J = 22.0 Hz, 6H), 0.79-0.84 (m, 4H). | 528.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 301 | G10 | | P | 46 | 10.8 (s, 1H), 8.88 (d, J = 2.4 Hz, 1H), 8.82 (d, J = 5.0 Hz, 1H), 8.70 (d, J = 5.1 Hz, 1H), 8.35 (d, J = 1.9 Hz, 1H), 8.18 (s, 1H), 8.09 (d, J = 2.5 Hz, 1H), 8.03 (s, 1H), 8.00 (dd, J = 1.9 and 5.1 Hz, 1H), 7.92 (m, 1H), 7.87-7.90 (m, 2H), 7.72 (s, 1H), 7.68 (t, J = 7.7 Hz, 1H), 7.58 (m, 1H), 2.47 (s, 3H), 1.76 (s, 6H). | 477.2 |
| 302 | D66 | | K | 17 | 10.6 (s, 1H), 10.3 (s, 1H), 8.81 (d, J = 5.2 Hz, 1H), 8.76 (d, J = 5.2 Hz, 1H), 8.62 (s, 1H), 8.37 (d, J = 5.2 Hz, 1H), 8.05 (s, 1H), 7.98 (s, 1H), 7.82 (dd, J = 1.2 and 5.2 Hz, 1H), 7.77 (dd, J = 1.2 and 5.2 Hz, 1H), 7.59 (d, J = 8.0 Hz, 1H), 7.52 (dd, J = 1.6 and 5.2 Hz, 1H), 7.39 (d, J = 11.6 Hz, 1H), 3.69 (s, 3H), 2.32 (s, 3H), 1.70 (d, J = 22.0 Hz, 6H). | 518.1 |
| 303 | D67 | | K | 20 | 10.6 (s, 1H), 10.4 (s, 1H), 9.08 (d, J = 5.2 Hz, 1H), 8.90 (s, 1H), 8.82 (d, J = 5.2 Hz, 1H), 8.45 (d, J = 5.2 Hz, 1H), 8.06 (s, 1H), 7.98 (dd, J = 4.0 and 6.4 Hz, 1H), 7.89 (d, J = 1.5 Hz, 1H), 7.88 (s, 1H), 7.78 (d, J = 5.2 Hz, 1H), 7.45 (d, J = 11.2 Hz, 1H), 3.70 (s, 3H), 2.54 (s, 3H), 1.77 (s, 6H). | 526.1 |
| 304 | D67 | | K | 14 | 10.6 (s, 1H), 10.4 (s, 1H), 9.07 (d, J = 5.2 Hz, 1H), 8.90 (s, 1H), 8.77 (d, J = 4.8 Hz, 1H), 8.45 (d, J = 5.2 Hz, 1H), 8.06 (s, 1H), 7.98 (dd, J = 4.0 and 6.0 Hz, 1H), 7.87 (d, J = 8.0 Hz, 1H), 7.84 (dd, J = 5.6 and 8.0 Hz, 1H), 7.78 (d, J = 5.2 Hz, 1H), 7.43 (d, J = 11.2 Hz, 1H), 3.69 (s, 3H), 2.54 (s, 3H), 1.73 (d, J = 22.0 Hz, 6H). | 519.1 |
| 305 | D68 | | K | 42 | 10.7 (s, 1H), 10.5 (s, 1H), 9.63 (d, J = 2.2 Hz, 1H), 8.80 (dd, J = 0.8 and 5.0 Hz, 1H), 8.46 (m, 1H), 8.29 (d, J = 1.5 Hz, 1H), 8.15 (d, J = 2.2 Hz, 1H), 8.02 (t, J = 1.2 Hz, 1H), 7.93 (d, J = 2.3 Hz, 1H), 7.84-7.90 (m, 2H), 7.64 (dd, J = 1.7 and 5.2 Hz, 1H), 7.43 (d, J = 8.4 Hz, 1H), 3.70 (s, 3H), 2.35 (s, 3H), 1.76 (s, 6H) | 508.2 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| 306 | D69 | | K | 9 | 9.63 (d, J = 2.2 Hz, 1H), 8.87 (s, 1H), 8.73 (d, J = 5.0 Hz, 1H), 8.46 (dd, J = 0.8 and 5.0 Hz, 1H), 8.35 (d, J = 2.5 Hz, 1H), 8.29 (dd, J = 0.8 and 1.7 Hz, 1H), 8.23 (d, J = 2.2 Hz, 1H), 8.07 (s, 1H), 7.90 (dd, J = 1.5 and 5.0 Hz, 1H), 7.64 (dd, J = 1.7 and 5.2 Hz, 1H), 3.69 (s, 3H), 2.51 (s, 3H), 1.74 (s, 6H). | 509.2 |
| 307 | D65 | | K | 6 | 10.9 (s, 1H), 10.7 (brs, 1H), 8.91 (d, J = 4.8 Hz, 1H), 8.84 (s, 1H), 8.80 (d, J = 4.8 Hz, 1H), 8.42 (d, J = 5.2 Hz, 1H), 8.19 (s, 1H), 8.06 (brd, J = 4.8 Hz, 1H), 7.96 (s, 1H), 7.81 (dd, J = 1.6 and 5.2 Hz, 1H), 7.62 (d, J = 7.6 Hz, 1H), 7.51 (dd, J = 1.2 and 5.2 Hz, 1H), 7.39 (d, J = 11.6 Hz, 1H), 7.06 (brt, J = 54.8 Hz, 1H), 2.31 (s, 3H), 2.03 (m, 1H), 0.79-0.87 (m, 4H). | 518.2 |
| 308 | D66 | | K | 7 | 10.6 (s, 1H), 10.3 (s, 1H), 8.81 (d, J = 5.2 Hz, 2H), 8.62, (s, 1H), 8.37 (d, J = 5.2 Hz, 1H), 8.05 (s, 1H), 7.98 (s, 1H), 7.87 (dd, J = 1.2 and 5.2 Hz, 1H), 7.77 (dd, J = 1.6 and 5.6 Hz, 1H), 7.61 (d, J = 7.6 Hz, 1H), 7.52 (dd, J = 1.2 and 4.8 Hz, 1H), 7.40 (d, J = 11.2 Hz, 1H), 3.69 (s, 3H), 2.34 (s, 3H), 1.76 (s, 6H). | 525.4 |
| 309 | D70 | | R (TCFH) | 34 | 10.9 (s, 1H), 9.82 (d, J = 2.0 Hz, 1H), 9.00 (d, J = 2.4 Hz, 1H), 8.89 (brq, J = 4.8 Hz, 1H), 8.85 (brd, J = 5.6 Hz, 1H), 8.79 (d, J = 5.2 Hz, 1H), 8.56 (d, J = 1.2 Hz, 1H), 8.48 (d, J = 2.4 Hz, 1H), 8.40 (d, J = 2.4 Hz, 1H), 8.22 (dd, J = 3.2 and 6.8 Hz, 1H), 8.08 (brs, 1H), 7.86 (dd, J = 3.4 and 6.8 Hz, 1H), 2.86 (d, J = 4.8 Hz, 3H), 1.71 (d, J = 22.4 Hz, 6H). 3Hs are under solvents | 486.2 |
| 310 | D75 | | R (TCFH) | 56 | 11.0 (s, 1H), 10.9 (s, 1H), 9.65 (d, J = 2.4 Hz, 1H), 9.00 (d, J = 2.4 Hz, 1H), 8.79 (d, J = 5.2 Hz, 1H), 8.56 (s, 1H), 8.53 (d, J = 5.2 Hz, 1H), 8.36 (d, J = 2.4 Hz, 1H), 8.26 (d, J = 2.0 Hz, 1H), 8.08 (s, 1H), 7.85 (dd, J = 3.6 and 8.0 Hz, 1H), 7.68 (dd, J = 4.4 and 5.2 Hz, 1H), 2.54 (s, 3H), 2.05 (m, 1H), 1.71 (d, J = 22.0 Hz, 6H), 0.85 (m, 4H). | 512.2 |

TABLE I-continued

| Ex No. | SM | Product | Method | Yield (%) | $^1$H NMR (400 or 500 MHz, (DMSO-$d_6$): δ | MS (m/z: M + H$^+$) |
|---|---|---|---|---|---|---|
| 311 | D68 | | K | 15 | 10.5 (s, 1H), 10.4 (s, 1H), 9.62 (d, J = 2.2 Hz, 1H), 8.46 (dd, J = 0.8 and 5.2 Hz, 1H), 8.29 (dd, J = 0.8 and 1.7 Hz, 1H), 8.15 (d, J = 2.2 Hz, 1H), 8.06 (t, J = 1.9 Hz, 1H), 7.93-7.98 (m, 2H), 7.87 (dd, J = 2.3 and 8.3 Hz, 1H), 7.74 (m, 1H), 7.65 (dd, J = 1.6 and 5.2 Hz, 1H), 7.59 (t, J = 7.8 Hz, 1H), 7.41 (d, J = 8.4 Hz, 1H), 3.70 (s, 3H), 2.34 (s, 3H), 1.74 (s, 6H). | 507.2 |
| 312 | D71 | | R | 75 | 11.0 (s, 1H), 10.3 (s, 1H), 9.01 (d, J = 5.0 Hz, 1H), 8.93 (d, J = 2.4 Hz, 1H), 8.85 (m, 1H), 8.63 (dd, J = 0.8 and 1.7 Hz, 1H), 8.39 (d, J = 1.3 Hz, 1H), 8.37 (dd, J = 0.8 and 5.2 Hz, 1H), 8.20 (dd, J = 1.6 and 5.0 Hz, 1H), 8.14 (d, J = 2.5 Hz, 1H), 8.07 (d, J = 1.3 Hz, 1H), 7.77 (dd, J = 1.6 and 5.2 Hz, 1H), 7.59 (dd, J = 1.6 and 5.0 Hz, 1H), 3.66-3.71 (m, 3H). | 509.2 |
| 313 | D71 | | R | 34 | 10.9 (s, 1H), 10.3 (s, 1H), 8.93 (d, J = 2.4 Hz, 1H), 8.92 (d, J = 5.1 Hz, 1H), 8.85 (d, J = 5.0 Hz, 1H), 8.63 (s, 1H), 8.37 (d, J = 5.3 Hz, 1H), 8.20 (s, 1H), 8.14 (d, J = 2.4 Hz, 1H), 8.08 (s, 2H), 7.78 (m, 1H), 7.59 (d, J = 5.5 Hz, 1H), 6.90-7.24 (m, 1H), 3.68 (s, 3H). | 491.2 |
| 314 | D73 | | R | 47 | 10.7 (s, 1H), 9.79 (s, 1H), 8.87 (q, J = 4.8 Hz, 1H), 8.84 (d, J = 5.2 Hz, 1H), 8.81 (d, J = 5.2 Hz, 1H), 8.53 (d, J = 0.8 Hz, 1H), 8.36 (d, J = 2.4 Hz, 1H), 8.21 (dd, J = 1.6 and 4.8 Hz, 1H), 8.03 (s, 1H), 7.94 (d, J = 2.4 Hz, 1H), 7.87 (m, 2H), 7.44 (d, J = 8.4 Hz, 1H), 2.86 (d, J = 4.8 Hz, 3H), 2.37 (s, 3H), 1.76 (s, 6H). | 492.4 |
| 315 | D74 | | R | 26 | 11.0 (s, 1H), 10.7 (s, 1H), 9.61 (d, J = 2.0 Hz, 1H), 8.76 (d, J = 5.2 Hz, 1H), 8.56 (s, 1H), 8.52 (d, J = 5.2 Hz, 1H), 8.12 (d, J = 2.0 Hz, 1H), 8.04 (brs, 1H), 7.93 (d, J = 1.6 Hz, 1H), 7.89 (dd, J = 2.4 and 6.4 Hz, 1H), 7.83 (dd, J = 1.2 and 3.6 Hz, 1H), 7.68 (dd, J = 1.6 and 3.6 Hz, 1H), 7.42 (d, J = 8.4 Hz, 1H), 2.34 (s, 3H), 2.04 (m, 1H), 1.71 (d, J = 22.4 Hz, 6H), 0.84 (m, 4H). | 511.4 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 316 | D70 | | R (TCFH) | 28 | 10.9 (s, 1H), 9.83 (s, 1H), 8.99 (d, J = 2.4 Hz, 1H), 8.89 (q, J = 4.8 Hz, 1H), 8.85 (d, J = 2.4 Hz, 1H), 8.83 (d, J = 2.4 Hz, 1H), 8.56 (d, J = 1.2 Hz, 1H), 8.48 (d, J = 2.4, 1H), 8.38 (d, J = 2.4 Hz, 1H), 8.22 (dd, J = 1.6 and 3.2 Hz, 1H), 8.06, (s, 1H), 7.91 (dd, J = 3.6, 1.6 Hz, 1H), 2.86 (d, J = 4.8 Hz, 3H), 2.57 (s, 3H), 1.77 (s, 6H). | 493.3 |
| 317 | D70 | | R | 17 | 10.8 (s, 1H), 9.83 (s, 1H), 8.98 (d, J = 2.4 Hz, 1H), 8.89 (q, J = 4.8 Hz, 1H), 8.84 (d, J = 4.4 Hz, 1H), 8.60 (d, J = 4.8, Hz, 1H), 8.56 (d, J = 1.2, Hz, 1H), 8.48 (d, J = 2.0 Hz, 1H), 8.39 (d, J = 3.6 Hz, 1H), 8.22 (dd, J = 1.6 and 3.2 Hz, 1H), 7.78 (brs, 1H), 7.60 (dd, J = 1.6 and 3.6 Hz, 1H), 2.86 (d, J = 4.8 Hz, 3H), 2.56, (s, 3H), 2.22 (m, 1H), 0.83-0.86 (m, 4H). | 466.4 |
| 318 | D70 | | R (TCFH) | 29 | 11.0 (s, 1H), 9.83 (d, J = 2.0 Hz, 1H), 9.01 (d, J = 4.8 Hz, 1H), 8.99 (d, J = 2.4 Hz, 1H), 8.89 (q, J = 4.8 Hz, 1H), 8.85 (d, J = 5.2 Hz, 1H), 8.56 (d, J = 1.2 Hz, 1H), 8.49 (d, J = 2.0 Hz, 1H), 8.42 (brs, 1H), 8.40 (d, J = 2.4 Hz, 1H), 8.22 (m, 2H), 2.86 (d, J = 4.8 Hz, 3H), 2.57 (s, 3H), | 494.3 |
| 319 | D74 | | R (TCFH) | 31 | 11.0 (s, 1H), 10.6 (s, 1H), 9.62 (d, J = 2.0 Hz, 1H), 8.72 (d, J = 5.2 Hz, 1H), 8.56 (s, 1H), 8.52 (d, J = 5.2, Hz, 1H), 8.12 (d, J = 2.4 Hz, 1H), 8.02 (s, 1H), 7.93 (d, J = 2.0 Hz, 1H), 7.89 (dd, J = 2.0 and 6.0 Hz, 1H), 7.77 (dd, J = 1.6 and 3.2 Hz, 1H), 7.68 (dd, J = 1.6 and 3.2 Hz, 1H), 7.42 (d, J = 8.4 Hz, 1H), 3.11 (s, 3H), 2.34 (s, 3H), 2.04 (m, 1H), 1.51 (s, 6H), 0.84 (m, 4H). | 523.4 |
| 320 | D74 | | R (TCFH) | 22 | 10.0 (s, 1H), 10.5 (s, 1H), 9.60 (d, J = 2.0 Hz, 1H), 8.79 (s, 1H), 8.56 (s, 1H), 8.52 (d, J = 5.2, Hz, 1H), 8.10 (d, J = 2.0 Hz, 1H), 8.00 (d, J = 2.4 Hz, 1H), 7.91 (dd, J = 2.4 and 6.0 Hz, 1H), 7.67 (dd, J = 1.6 and 3.6 Hz, 1H), 7.37 (d, J = 8.4 Hz, 1H), 4.91 (m, 1H), 2.32 (s, 3H), 2.05 (m, 1H), 1.54 (d, J = 6.4 Hz, 6H), 0.83-0.85 (m, 4H). | 483.4 |

TABLE I-continued

| Ex No. | SM | Product | Method | Yield (%) | $^1$H NMR (400 or 500 MHz, (DMSO-$d_6$): δ | MS (m/z: M + H$^+$) |
|---|---|---|---|---|---|---|
| 321 | D74 | | R (TCFH) | 25 | 11.0 (s, 1H), 9.87 (s, 1H), 9.60 (d, J = 2.0 Hz, 1H), 8.55 (brs, 1H), 8.52 (d, J = 5.2 Hz, 1H), 8.46 (s, 1H), 8.11 (d, J = 2.4 Hz, 1H), 8.01 (s, 1H), 7.84 (m, 2H), 7.67 (dd, J = 1.6 and 3.6 Hz, 1H), 7.36 (d, J = 8.0 Hz, 1H), 2.31 (s, 3H), 2.04 (m, 1H), 1.55 (s, 9H), 0.84 (m, 4H). | 496.4 |
| 322 | D70 | | R | 38 | 10.6 (s, 1H), 9.82 (s, 1H), 8.99 (s, 1H), 8.88 (brm, 1H), 8.85 (d, J = 4.8 Hz, 1H), 8.56 (s, 1H), 8.48(s, 1H), 8.38 (s, 1H), 8.23 (d, J = 4.0 Hz, 1H), 7.70 (s, 1H), 7.63 (s, 2H), 3.96 (s, 3H), 2.86 (d, J = 4.0 Hz, 3H), 2.56 (s, 3H). | 489.2 |
| 323 | D71 | | K | 40 | 10.8 (s, 1H), 10.3 (s, 1H), 8.94 (d, J = 2.4 Hz, 1H), 8.84 (dd, J = 0.8 and 5.0 Hz, 1H), 8.77 (m, 1H), 8.63 (dd, J = 0.8 and 1.6 Hz, 1H), 8.37 (dd, J = 0.8 and 5.3 Hz, 1H), 8.14 (d, J = 2.5 Hz, 1H), 8.08 (d, J = 1.4 Hz, 1H), 8.05 (d, J = 1.9 Hz, 1H), 7.83 (dd, J = 1.7 and 5.0 Hz, 1H), 7.77 (dd, J = 1.6 and 5.3 Hz, 1H), 7.59 (dd, J = 1.6 and 5.0 Hz, 1H), 3.68 (s, 3H), 2.47 (s, 3H), 1.72 (s, 3H), 1.67 (s, 3H). | 501.2 |
| 324 | D70 | | R | 17 | 10.1 (s, 1H), 9.81 (dd, J = 0.6 and 2.2 Hz, 1H), 8.93 (d, J = 2.4 Hz, 1H), 8.89 (q, J = 4.8 Hz, 1H), 8.84 (d, J = 5.1 Hz, 1H), 8.54 (dt, J = 0.7 and 1.7 Hz, 1H), 8.46 (d, J = 2.2 Hz, 1H), 8.44 (s, 1H), 8.31 (d, J = 2.5 Hz, 1H), 8.21 (dd, J = 5.1, 1.9 Hz, 1H), 8.01 (s, 1H), 3.82 (m, 1H), 2.85 (d, J = 4.8 Hz, 3H), 2.53 (s, 3H), 1.05-1.13 (m, 2H), 0.96-1.05 (m, 2H). | 455.2 |
| 325 | D73 | | R | 24 | 10.7 (s, 1H), 9.78 (d, J = 2.0 Hz, 1H), 8.88 (q, J = 4.0 Hz, 1H), 8.83 (d, J = 5.2 Hz, 1H), 8.76 (d, J = 5.2 Hz, 1H), 8.53 (d, J = 1.2 Hz, 1H), 8.35 (d, J = 2.0 Hz, 1H), 8.21 (dd, J = 2.0 and 5.2 Hz, 1H), 8.05 (s, 1H), 7.96 (d, J = 2.4 Hz, 1H), 7.88 (dd, J = 2.4 and 8.4 Hz, 1H), 7.84 (dd, J = 1.6 and 5.2 Hz, 1H), 7.42 (d, J = 8.4 Hz, 1H), 2.86 (d, J = 4.8 Hz, 3H), 2.36 (s, 3H), 1.70 (d, J = 22.4 Hz, 6H). | 485.3 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 326 | D73 | | R | 24 | 10.5 (s, 1H), 9.78 (d, J = 2.4 Hz, 1H), 8.88 (q, J = 4.8 Hz, 1H), 8.83 (d, J = 4.8 Hz, 1H), 8.57 (d, J = 5.2 Hz, 1H), 8.53 (s, 1H), 8.34 (d, J = 2.0 Hz, 1H), 8.21 (dd, J = 1.6 and 5.2 Hz, 1H), 7.96 (d, J = 2.4 Hz, 1H), 7.86 (dd, J = 2.0 and 8.0 Hz, 1H), 7.76 (s, 1H), 7.58 (dd, J = 1.2 and 5.2 Hz, 1H), 7.41 (d, J = 8.4 Hz, 1H), 2.86 (d, J = 4.8 Hz, 3H), 2.36 (s, 3H), 2.18-2.24 (m, 1H), 0.95-1.03 (m, 4H). | 465.3 |
| 327 | D73 | | R | 23 | 10.8 (s, 1H), 9.78 (d, J = 2.4 Hz, 1H), 8.91 (d, J = 5.2 Hz, 1H), 8.87 (q, J = 4.8 Hz, 1H), 8.85 (d, J = 5.2 Hz, 1H), 8.53 (d, J = 1.2 Hz, 1H), 8.35 (d, J = 2.0 Hz, 1H), 8.22 (m, 2H), 8.08 (brd, J = 4.8 Hz, 1H), 7.97 (d, J = 2.0 Hz, 1H), 7.88 (dd, J = 2.0 and 8.4 Hz, 1H), 7.43 (d, J = 8.4 Hz, 1H), 7.08 (t, J = 54.8 Hz, 1H), 2.86 (d, J = 4.8 Hz, 3H), 2.37 (s, 3H). | 475.3 |
| 328 | D73 | | R | 26 | 10.6 (s, 1H), 9.78 (d, J = 2.0 Hz, 1H), 8.88 (q, J = 4.4 Hz, 1H), 8.83 (d, J = 5.2 Hz, 1H), 8.72 (d, J = 4.8 Hz, 1H), 8.53 (d, J = 1.2 Hz, 1H), 8.36 (d, J = 2.0 Hz, 1H), 8.21 (dd, J = 1.6 and 5.2 Hz, 1H), 8.03 (s, 1H), 7.96 (d, J = 2.0 Hz, 1H), 7.88 (dd, J = 1.6 and 5.2 Hz, 1H), 7.77 (dd, J = 1.6 and 5.2 Hz, 1H), 7.42 (d, J = 8.4 Hz, 1H), 3.12 (s, 3H), 2.86 (d, J = 4.8 Hz, 3H), 2.36 (s, 3H), 1.51 (s, 6H). | 497.3 |
| 329 | D73 | | R | 22 | 10.6 (s, 1H), 9.78 (s, 1H), 8.88 (q, J = 4.4 Hz, 1H), 8.83 (d, J = 5.2 Hz, 1H), 8.53 (d, J = 0.8 Hz, 1H), 8.35-8.40 (m, 3H), 8.21 (dd, J = 2.0 and 5.2 Hz, 1H), 7.94 (d, J = 2.4 Hz, 1H), 7.87 (dd, J = 2.4 and 8.4 Hz, 1H), 7.71 (m, 1H), 7.42 (d, J = 8.4 Hz, 1H), 2.86 (d, J = 4.8 Hz, 3H), 2.36 (s, 3H). | 510.3 |
| 330 | D73 | | R | 17 | 11.0 (s, 1H), 9.82 (d, J = 2.0 Hz, 1H), 8.99 (d, J = 2.0 Hz, 1H), 8.94 (d, J = 4.8 Hz, 1H), 8.88 (d, J = 4.8 Hz, 1H), 8.85 (q, J = 4.8 Hz, 1H), 8.56 (s, 1H), 8.48 (d, J = 2.0 Hz, 1H), 8.40 (d, J = 2.4 Hz 1H), 8.22 (m, 2H), 8.11 (d, J = 4.8 Hz, 1H), 7.09 (t, J = 54.8 Hz, 1H), 2.86 (d, J = 4.8 Hz, 3H), 2.57 (s, 3H). | 476.3 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 331 | D74 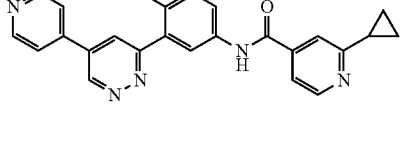 | 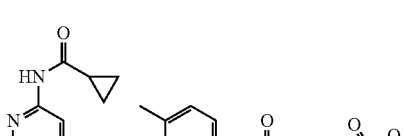 | R | 32 | 11.0 (s, 1H), 10.5 (s, 1H), 9.61 (d, J = 2.0 Hz, 1H), 8.57 (d, J = 5.2 Hz, 1H), 8.55 (s, 1H), 8.52 (d, J = 4.8 Hz, 1H), 8.11 (d, J = 2.0 Hz, 1H), 7.93 (brs, 1H), 7.87 (brd, J = 8.4 Hz, 1H), 7.75 (brs, 1H), 7.68 (brd, J = 5.2, 1.6 Hz, 1H), 7.58 (brd, J = 4.8 Hz, 1H), 7.41 (d, J = 8.4 Hz, 1H), 2.24 (s, 3H), 2.20 (m, 1H), 2.05 (m, 1H), 0.97-0.99 (m, 4H), 0.83-0.85 (m, 4H). | 491.3 |
| 332 | D74 | | R | 53 | 11.0 (s, 1H), 10.9 (s, 1H), 9.61 (d, J = 2.0 Hz, 1H), 9.00 (d, J = 5.2 Hz, 1H), 8.55 (s, 2H), 8.52 (d, J = 5.2, Hz, 1H), 8.23 (dd, J = 1.6 and 5.2 Hz, 1H), 8.13 (d, J = 2.4, Hz, 1H), 7.94 (d, J = 2.0 Hz, 1H), 7.89 (dd, J = 2.0 and 8.4 Hz, 1H), 7.68 (dd, J = 1.6 and 5.2 Hz, 1H), 7.44 (d, J = 8.4 Hz, 1H), 3.35 (s, 3H), 2.34 (s, 3H), 2.05 (m, 1H), 0.83-0.85 (m, 4H). | 529.3 |
| 333 | D70 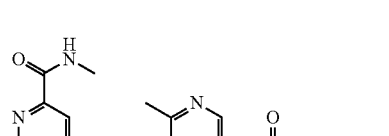 | | R | 26 | 10.4 (s, 1H), 9.80 (d, J = 2.0 Hz, 1H), 8.86 (q, J = 4.8 Hz, 1H), 8.84 (d, J = 4.8 Hz, 1H), 8.76 (d, J = 2.4 Hz, 1H), 8.54 (d, J = 1.2 Hz, 1H), 8.43 (d, J = 2.0 Hz, 1H), 8.22 (d, J = 2.4 Hz, 1H), 8.20 (dd, J = 2.0 and 5.2 Hz, 1H), 2.86 (d, J = 4.8 Hz, 3H), 2.55 (m, 3H), 1.89 (m, 2H), 1.33 (s, 6H). 3Hs are under solvents | 444.3 |
| 334 | D58 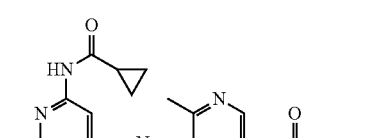 | | R (TCFH) | 38 | 11.0 (s, 1H), 10.2 (s, 1H), 9.11 (d, J = 5.2 Hz, 1H), 8.94 (s, 1H), 8.79 (d, J = 2.0 Hz, 1H), 8.58 (d, J = 2.4 Hz, 1H), 8.53 (d, J = 5.2 Hz, 1H), 8.08 (d, J = 5.2 Hz, 1H), 7.87 (brd, J = 5.2 Hz, 1H), 3.09 (m, 1H), 2.83 (t, J = 8.8 Hz, 1H), 2.74 (s, 3H), 2.59 (m, 1H), 2.40 (m, 2H), 2.25 (s, 3H), 2.01-2.08 (m, 3H), 0.80-0.89 (m, 4H). | 458.2 |
| 335 | D58 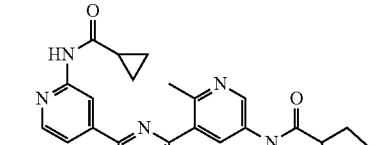 | | R | 39 | 11.0 (s, 1H), 10.3 (s, 1H), 9.12 (d, J = 5.2 Hz, 1H), 8.94 (s, 1H), 8.79 (d, J = 2.4 Hz, 1H), 8.60 (d, J = 2.4 Hz, 1H), 8.53 (d, J = 5.2 Hz, 1H), 8.08 (d, J = 5.2 Hz, 1H), 7.87 (dd, J = 1.2 and 5.2 Hz, 1H), 3.95 (t, J = 8.0 Hz, 1H), 3.69-3.81 (m, 3H), 3.19 (m, 1H), 2.75 (s, 3H), 2.01-2.13 (m, 3H), 0.80-0.88 (m, 4H). | 445.3 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 336 | D56 | | R | 59 | 11.0 (s, 1H), 10.3 (s, 1H), 9.13 (t, J = 1.2 Hz, 1H), 9.10 (d, J = 5.1 Hz, 1H), 8.80 (d, J = 2.5 Hz, 1H), 8.51 (dd, J = 0.8 and 5.2 Hz, 1H), 8.29 (d, J = 2.5 Hz, 1H), 8.02 (dd, J = 1.5 and 5.2 Hz, 1H), 7.82 (d, J = 5.2 Hz, 1H), 3.92 (m, 2H), 3.29-3.43 (m, 2H), 2.66 (m, 1H), 2.61 (s, 3H), 2.05 (m, 1H), 1.60-1.79 (m, 4H), 0.81-0.87 (m, 4H). | 459.2 |
| 337 | D56 | | R | 52 | 11.0 (s, 1H), 10.4 (s, 1H), 9.12 (m, 1H), 9.08 (d, J = 5.2 Hz, 1H), 8.78 (d, J = 2.5 Hz, 1H), 8.49 (dd, J = 0.8 and 5.2 Hz, 1H), 8.26 (d, J = 2.5 Hz, 1H), 8.00 (dd, J = 1.6 and 5.2 Hz, 1H), 7.81 (d, J = 5.1 Hz, 1H), 3.94 (t, J = 8.2 Hz, 1H), 3.66-3.82 (m, 3H), 3.12-3.24 (m, 1H), 2.60 (s, 3H), 1.98-2.16 (m, 3H), 0.77-0.89 (m, 4H). | 445.2 |
| 338 | D58 | | K | 24 | 11.2 (s, 1H), 10.2 (s, 1H), 9.12 (d, J = 5.3 Hz, 1H), 8.95 (dd, J = 0.8 and 1.6 Hz, 1H), 8.78 (d, J = 2.6 Hz, 1H), 8.58 (d, J = 2.5 Hz, 1H), 8.54 (dd, J = 0.8 and 5.2 Hz, 1H), 8.09 (d, J = 5.3 Hz, 1H), 7.88 (dd, J = 1.6 and 5.2 Hz, 1H), 4.32 (s, 2H), 4.22 (s, 2H), 2.74 (s, 3H), 2.30 (m, 1H), 2.02-2.15 (m, 3H), 1.74-1.81 (m, 2H), 1.39-1.49 (m, 4H), 0.82-0.87 (m, 4H). | 499.2 |
| 339 | D58 | | K | 40 | 11.0 (s, 1H), 10.2 (s, 1H), 9.12 (d, J = 5.3 Hz, 1H), 8.95 (dd, J = 0.8 and 1.7 Hz, 1H), 8.80 (d, J = 2.6 Hz, 1H), 8.61 (d, J = 2.5 Hz, 1H), 8.54 (dd, J = 0.8 and 5.2 Hz, 1H), 8.09 (d, J = 5.3 Hz, 1H), 7.88 (dd, J = 1.6 and 5.2 Hz, 1H), 3.88-3.94 (m, 2H), 3.34-3.38 (m, 2H), 2.75 (s, 3H), 2.62 (m, 1H), 2.05 (m, 1H), 1.62-1.77 (m, 4H), 0.81-0.88 (m, 4H). | 459.2 |
| 340 | D43 | | R | 50 | 11.0 (s, 1H), 9.37 (s, 1H), 9.11 (s, 1H), 9.03 (d, J = 5.1 Hz, 1H), 8.48 (d, J = 5.2 Hz, 1H), 7.99 (dd, J = 1.5 and 5.2 Hz, 1H), 7.85 (d, J = 2.3 Hz, 1H), 7.67-7.73 (m, 2H), 7.30 (d, J = 8.4 Hz, 1H), 2.40 (s, 3H), 2.03 (m, 1H), 1.79-1.95 (m, 14H), 0.77-0.87 (m, 4H). | 507.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 341 | D43 | | R | 55 | 11.0 (s, 1H), 10.0 (s, 1H), 9.11 (s, 1H), 9.03 (d, J = 5.2 Hz, 1H), 8.48 (d, J = 5.2 Hz, 1H), 7.99 (dd, J = 1.5 and 5.2 Hz, 1H), 7.85 (d, J = 2.3 Hz, 1H), 7.69 (d, J = 5.1 Hz, 1H), 7.63 (dd, J = 2.3 and 8.3 Hz, 1H), 7.30 (d, J = 8.4 Hz, 1H), 3.23 (s, 3H), 3.09 (m, 1H), 2.39 (s, 3H), 2.24-2.33 (m, 1H), 1.99-2.11 (m, 3H), 1.81-1.89 (m, 2H), 1.38-1.51 (m, 2H), 1.05-1.19 (m, 2H), 0.77-0.87 (m, 4H). | 486.2 |
| 342 | D33 | | R | 36 | 10.9 (s, 1H), 9.53 (s, 1H), 8.83 (d, J = 1.6 Hz, 1H), 8.77 (d, J = 2.5 Hz, 1H), 8.43 (d, J = 5.2 Hz, 1H), 8.13 (d, J = 2.5 Hz, 1H), 8.08 (t, J = 7.8 Hz, 1H), 8.02 (d, J = 7.8 Hz, 1H), 7.76 (dd, J = 1.6 and 5.2 Hz, 1H), 7.65 (m, 1H), 2.52 (s, 3H), 2.04 (m, 1H), 1.89-1.92 (m, 6H), 1.80-1.82 (m, 6H), 0.77-0.86 (m, 4H). | 507.2 |
| 343 | D33 | | R | 47 | 10.9 (s, 1H), 10.2 (s, 1H), 8.83 (d, J = 1.6 Hz, 1H), 8.71 (d, J = 2.4 Hz, 1H), 8.43 (d, J = 5.2 Hz, 1H), 8.14 (d, J = 2.5 Hz, 1H), 8.08 (t, J = 7.8 Hz, 1H), 8.03 (d, J = 7.8 Hz, 1H), 7.77 (dd, J = 1.7 and 5.3 Hz, 1H), 7.66 (d, J = 7.6 Hz, 1H), 3.23 (s, 3H), 3.09 (tt, J = 4.1 and 10.8 Hz, 1H), 2.52 (s, 3H), 2.24-2.35 (m, 1H), 1.98-2.10 (m, 3H), 1.84-1.91 (m, 2H), 1.45 (m, 2H), 1.06-1.17 (m, 2H), 0.81 (m, 4H). | 486.2 |
| 344 | D44 | | K | 32 | 11.3 (s, 1H), 9.89 (s, 1H), 8.95 (d, J = 0.8 Hz, 1H), 8.60 (d, J = 0.8 Hz, 1H), 8.04 (brd, J = 8.0 H, 1H), 7.95 (brm, 1H), 7.62 (t, J = 7.6 Hz, 1H), 7.54 (brm, 2H), 7.51 (d, J = 1.6 Hz, 1H), 7.24 (d, J = 8.4 Hz, 1H), 3.03 (m, 1H), 2.80 (t, J = 8.4 Hz, 1H), 2.56-2.61 (m, 1H), 2.42-2.48 (m, 1H), 2.35 (m, 1H), 2.23 (s, 3H), 2.18 (s, 3H), 2.07 (m, 1H), 1.93-1.99 (m, 2H), 0.84-0.92 (m, 4H). | 456.4 |
| 345 | D44 | | K | 21 | 11.3 (s, 1H), 10.0 (s, 1H), 8.95 (s, 1H), 8.60 (s, 1H), 8.05 (d, J = 7.6 Hz, 1H), 7.95 (s, 1H), 7.62 (t, J = 7.6 Hz, 1H), 7.50-7.60 (brm, 3H), 7.25 (d, J = 8.0 Hz, 1H), 3.92 (t, J = 7.6 Hz, 1H), 3.67-3.78 (m, 3H), 3.13 (m, 1H), 2.19 (s, 3H), 2.04-2.09 (m, 3H), 0.84-0.92 (m, 4H). | 443.4 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 346 | D44 | | K | 28 | 11.3 (s, 1H), 9.66 (s, 1H), 8.95 (s, 1H), 8.60 (s, 1H), 8.04 (d, J = 7.6 Hz, 1H), 7.95 (s, 1H), 7.59-7.70 (m, 3H), 7.52 (brd, J = 8.0 Hz, 1H), 7.25 (d, J = 8.8 Hz, 1H), 4.08 (dd, J = 10.0, 2.8 Hz, 1H), 3.92 (brd, J = 11.6 Hz, 1H), 3.62 (td, J = 2.4 and 11.2 Hz, 1H), 2.92 (brd, J = 10.8 Hz, 1H), 2.61 (d, J = 11.2 Hz, 1H), 2.21 (s, 3H), 2.20 (s, 3H), 1.98-2.09 (m, 3H), 0.86-0.92 (m, 4H). | 472.4 |
| 347 | D60 | | K | 30 | 11.3 (s, 1H), 10.1 (s, 1H), 8.96 (s, 1H), 8.66 (d, J = 1.2 Hz, 1H), 8.60 (s, 1H), 8.08 (d, J = 7.6 Hz, 1H), 8.00 (s, 1H), 7.97 (s, 1H), 7.65 (t, J = 7.6 Hz, 1H), 7.58 (d, J = 7.6 Hz, 1H), 3.23 (s, 3H), 3.10 (m, 1H), 2.38 (s, 3H), 2.30 (m, 1H), 2.01-2.10 (brm, 3H), 1.87 (brm, 2H), 1.44 (brm, 2H), 1.10-1.20 (m, 2H), 0.84-0.89 (m, 4H). | 486.4 |
| 348 | D60 | | R | 30 | 11.3 (s, 1H), 10.1 (s, 1H), 8.96 (s, 1H), 8.67 (d, J = 2.4 Hz, 1H), 8.61 (s, 1H), 8.08 (brd, J = 8.0 Hz, 1H), 8.01 (s, 1H), 7.98 (d, J = 2.0 Hz, 1H), 7.66 (t, J = 7.6 Hz, 1H), 7.59 (brd, J = 7.6 Hz, 1H), 3.66 (dd, J = 4.4 and 11.2 Hz, 1H), 3.58 (td, J = 2.4 and 12.0 Hz, 1H), 2.77 (tt, J = 3.6 and 12.0 Hz, 1H), 2.39 (s, 3H), 2.08 (m, 1H), 1.64-1.69 (m, 2H), 1.49-1.60 (m, 1H), 1.43 (t, J = 12.8 Hz, 1H), 1.19 (s, 3H), 1.14 (s, 3H), 0.85-0.93 (m, 4H). | 486.4 |
| 349 | D60 | | R | 26 | 11.3 (s, 1H), 10.1 (s, 1H), 8.96 (s, 1H), 8.67 (d, J = 2.0 Hz, 1H), 8.61 (s, 1H), 8.08 (brd, J = 7.6 Hz, 1H), 8.00 (brs, 1H), 7.98 (d, J = 2.0 Hz, 1H), 7.66 (t, J = 7.6 Hz, 1H), 7.59 (brd, J = 7.6 Hz, 1H), 3.90 (m, 2H), 3.35 (m, 2H), 2.58-2.63 (m, 1H), 2.39 (s, 3H), 2.08 (m, 1H), 1.61-1.73 (m, 4H), 0.86-0.92 (m, 4H). | 458.4 |
| 350 | D60 | | K & deprotection with TFA | 48 | 11.3 (s, 1H), 9.87 (s, 1H), 8.96 (s, 1H), 8.81 (d, J = 2.4 Hz, 1H), 8.61 (s, 1H), 8.08 (brd, J = 7.6 Hz, 1H), 8.04 (d, J = 2.0 Hz, 1H), 8.01 (brm, 1H), 7.66 (brt, J = 7.6 Hz, 1H), 7.59 (brd, J = 7.6 Hz, 1H), 4.01 (dd, J = 2.8 and 10.0 Hz, 1H), 3.88 (brd, J = 10.8 Hz, 1H), 3.56 (td, J = 4.0 and 10.8 Hz, 1H), 3.05 (dd, J = 2.4 and 12.4 Hz, 1H), 2.63-2.73 (m, 3H), 2.39 (s, 3H), 2.08 | 459.4 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | (m, 1H), 1.85 (brs, 1H), 0.86-0.94 (m, 4H). | |
| 351 | D60 | | R | 15 | 11.3 (s, 1H), 10.1 (s, 1H), 8.96 (s, 1H), 8.67 (d, J = 2.0 Hz, 1H), 8.61 (s, 1H), 8.08 (brd, J = 7.6 Hz, 1H), 8.00 (brs, 1H), 7.96 (brd, J = 2.4 Hz, 1H), 7.66 (brt, J = 7.6 Hz, 1H), 7.59 (brd, J = 7.6 Hz, 1H), 3.08 (m, 1H), 2.83 (t, J = 8.8 Hz, 1H), 2.61 (m, 1H), 2.45 (m, 1H), 2.39 (m, 3H), 2.38 (m, 1H), 2.25 (s, 3H), 2.08 (m, 1H), 1.97-2.02 (m, 2H), 0.86-0.92 (m, 4H). | 457.4 |
| 352 | D60 | | R | 56 | 11.33 (s, 1H), 10.27 (s, 1H), 8.96 (s, 1H), 8.67 (d, J = 2.0 Hz, 1H), 8.61 (s, 1H), 8.08 (brd, J = 7.6 Hz, 1H), 8.01 (brs, 1H), 7.97 (d, J = 2.0 Hz, 1H), 7.66 (brt, J = 7.6 Hz, 1H), 7.59 (brd, J = 7.6 Hz, 1H), 3.93 (t, J = 8.0 Hz, 1H), 3.67-3.79 (m, 3H), 3.16 (m, 1H), 2.39 (s, 3H), 2.06-2.11 (m, 3H), 0.87-0.93 (m, 4H). | 444.4 |
| 353 | G23 | | P | 25 | 12.4 (s, 1H), 10.4 (s, 1H), 9.33 (d, J = 2.5 Hz, 1H), 9.20 (d, J = 1.2 Hz, 1H), 9.15 (d, J = 1.3 Hz, 1H), 8.46 (dt, J = 1.0 and 2.4 Hz, 1H), 8.38 (d, J = 2.5 Hz, 1H), 8.28 (m, 1H), 7.51-7.56 (m, 2H), 3.62-3.68 (m, 4H), 3.31 (s, 2H), 2.63 (s, 3H), 2.50-2.57 (m, 4H), 2.25 (m, 1H), 1.24-1.32 (m, 2H), 0.87-0.97 (m, 2H). solvent: pyridine-d5 | 473.2 |
| 354 | D58 | | K | 49 | 11.2 (s, 1H), 10.3 (s, 1H), 9.12 (d, J = 5.3 Hz, 1H), 8.95 (dd, J = 0.8 and 1.6 Hz, 1H), 8.77 (d, J = 2.5 Hz, 1H), 8.59 (d, J = 2.6 Hz, 1H), 8.54 (dd, J = 0.8 and 5.2 Hz, 1H), 8.09 (d, J = 5.3 Hz, 1H), 7.88 (dd, J = 1.6 and 5.2 Hz, 1H), 2.67-2.79 (m, 5H), 2.60-2.63 (m, 2H), 2.29-2.43 (m, 2H), 2.05 (m, 1H), 0.80-0.89 (m, 4H). | 479.2 |
| 355 | D58 | | K | 42 | 11.0 (s, 1H), 10.3 (s, 1H), 9.12 (d, J = 5.3 Hz, 1H), 8.95 (dd, J = 0.8 and 1.7 Hz, 1H), 8.76 (d, J = 2.6 Hz, 1H), 8.58 (d, J = 2.6 Hz, 1H), 8.54 (dd, J = 0.8 and 5.2 Hz, 1H), 8.09 (d, J = 5.3 Hz, 1H), 7.88 (dd, J = 1.6 and 5.2 Hz, 1H), 4.69 (dd, J = 6.0 and 7.9 Hz, 2H), 4.36 (t, J = 6.2 Hz, 2H), 2.79 (d, J = 7.8 Hz, 2H), 2.74 (s, 3H), 2.06 (m, 1H), 0.81-0.89 (m, 4H). | 445.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 356 | D60 | | R | 37 | 11.3 (s, 1H), 10.2 (s, 1H), 8.96 (s, 1H), 8.63 (d, J = 2.0 Hz, 1H), 8.60 (s, 1H), 8.08 (brd, J = 7.6 Hz, 1H), 7.99 (brs, 1H), 7.94 (brd, J = 1.2 Hz, 1H), 7.65 (brt, J = 7.6 Hz, 1H), 7.58 (brd, J = 7.2 Hz, 1H), 4.67 (m, 2H), 4.34 (m, 2H), 2.77 (d, J = 7.6 Hz, 2H), 2.38 (s, 3H), 2.08 (m, 1H), 1.25 (m, 1H), 0.86-0.92 (m, 4H). | 444.3 |
| 357 | D18 | | K | 19 | 10.1 (s, 1H), 8.79-8.87 (m, 2H), 8.71-8.78 (m, 2H), 8.31 (m, 1H), 8.14 (m, 1H), 7.54-7.61 (m, 2H), 7.50 (dd, J = 1.5 and 5.0 Hz, 1H), 7.29 (d, J = 8.9 Hz, 1H), 2.85 (d, J = 0.7 Hz, 3H), 2.24 (s, 3H), 1.81-1.90 (m, 2H), 1.32 (s, 6H). | 442.2 |
| 358 | D18 | | K | 25 | 9.73 (s, 1H), 8.79-8.87 (m, 2H), 8.70-8.79 (m, 2H), 8.31 (m, 1H), 8.17-8.11 (m, 1H), 7.62-7.76 (m, 2H), 7.51 (dt, J = 1.7 and 5.0 Hz, 1H), 7.29 (d, J = 1.7 Hz, 1H), 4.05 (d, J = 1.8 Hz, 2H), 3.35 (dd, J = 1.8 and 7.0 Hz, 2H), 2.84 (dd, J = 1.8 and 4.9 Hz, 3H), 2.24 (s, 3H), 1.10 (m, 1H), 0.41-0.53 (m, 2H), 0.12-1.28 (m, 2H). | 431.2 |
| 359 | D69 | | R | 28 | 10.4 (s, 1H), 10.1 (brs, 1H), 9.64 (d, J = 2.0 Hz, 1H), 8.86 (d, J = 2.4 Hz, 1H), 8.48 (d, J = 5.2 Hz, 1H), 8.29 (s, 1H), 8.25 (d, J = 2.0 Hz, 1H), 8.23 (d, J = 2.0 Hz, 1H), 7.64 (d, J = 4.0 Hz, 1H), 3.71 (s, 3H), 3.41 (brm, 2H), 2.66 (brm, 4H), 1.78 (brm, 4H). 3Hs are under solvents | 448.3 |
| 360 | D68 | | K | 27 | 10.4 (s, 1H), 9.77 (s, 1H), 9.60 (d, J = 2.2 Hz, 1H), 8.45 (dd, J = 0.8 and 5.2 Hz, 1H), 8.27 (dd, J = 0.8 and 1.7 Hz, 1H), 8.09 (s, 1H), 7.83 (d, J = 2.3 Hz, 1H), 7.72 (dd, J = 2.3 and 8.3 Hz, 1H), 7.63 (dd, J = 5.2, 1.6 Hz, 1H), 7.33 (d, J = 8.4 Hz, 1H), 4.06 (s, 2H), 3.69 (s, 3H), 3.36 (d, J = 6.9 Hz, 2H), 2.30 (s, 3H), 1.11 (m, 1H), 0.41-0.54 (m, 2H), 0.12-0.28 (m, 2H). | 448.2 |
| 361 | D69 | | K | 6 | 11.0 (s, 1H), 10.5 (s, 1H), 9.74 (d, J = 2.1 Hz, 1H), 9.07 (d, J = 2.5 Hz, 1H), 8.85 (d, J = 5.1 Hz, 1H), 8.55 (d, J = 5.2 Hz, 1H), 8.45 (d, J = 2.5 Hz, 1H), 8.37 (d, J = 1.6 Hz, 1H), 8.36 (d, J = 2.2 Hz, 1H), 8.15 (s, 1H), 7.93 (dd, J = | 502.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | 1.6 and 5.1 Hz, 1H), 7.72 (dd, J = 1.6 and 5.3 Hz, 1H), 3.77 (s, 3H), 2.62 (s, 3H), 1.80 (s, 3H), 1.76 (s, 3H). | |
| 362 | D69 | | K | 8 | 10.8 (s, 1H), 10.5 (s, 1H), 9.68 (d, J = 2.2 Hz, 1H), 9.00 (d, J = 2.4 Hz, 1H), 8.61 (d, J = 5.0 Hz, 1H), 8.49 (d, J = 5.2 Hz, 1H), 8.39 (d, J = 2.5 Hz, 1H), 8.32 (d, J = 1.6 Hz, 1H), 8.30 (d, J = 2.2 Hz, 1H), 7.80 (d, J = 1.6 Hz, 1H), 7.66 (dd, J = 1.6 and 5.2 Hz, 1H), 7.62 (dd, J = 1.7 and 5.0 Hz, 1H), 3.72 (s, 3H), 2.56 (s, 3H), 2.23 (m, 1H), 0.95-1.07(m, 4H). | 482.2 |
| 363 | D69 | | K | 8 | 10.9 (s, 1H), 10.4 (s, 1H), 9.61 (d, J = 2.2 Hz, 1H), 8.94 (d, J = 2.4 Hz, 1H), 8.87 (d, J = 5.0 Hz, 1H), 8.42 (d, J = 5.2 Hz, 1H), 8.33 (d, J = 2.4 Hz, 1H), 8.24 (d, J = 1.6 Hz, 1H), 8.23 (d, J = 2.2 Hz, 1H), 8.17 (s, 1H), 8.04 (d, J = 5.0 Hz, 1H), 7.59 (dd, J = 1.6 and 5.2 Hz, 1H), 6.89-7.19 (m, 1H), 3.64 (s, 3H), 2.50 (s, 3H). | 492.2 |
| 364 | D72 | | R | 49 | 10.8 (s, 1H), 9.78 (d, J = 2.4 Hz, 1H), 8.99 (d, J = 2.8 Hz, 1H), 8.88 (q, J = 4.8 Hz, 1H), 8.83 (d, J = 4.4 Hz, 1H), 8.53 (d, J = 1.2 Hz, 1H), 8.39 (s, 1H), 8.36 (d, J = 2.0 Hz, 1H), 8.21 (m, 2H), 7.96 (d, J = 2.0 Hz, 1H), 7.88 (dd, J = 2.0 and 8.0 Hz, 1H), 7.44 (d, J = 8.4 Hz, 1H), 2.86 (d, J = 4.8 Hz, 3H), 2.37 (s, 3H). | 493.3 |
| 365 | D77 | | K | 22 | 10.3 (s, 1H), 9.78 (d, J = 2.0 Hz, 1H), 8.84 (d, J = 4.8 Hz, 1H), 8.81 (m, 1H), 8.55 (d, J = 1.2 Hz, 1H), 8.35 (d, J = 2.0 Hz, 1H), 8.23 (dd, J = 2.0 and 8.0 Hz, 1H), 7.96 (d, J = 2.0 Hz, 1H), 7.87 (dd, J = 8.0, 2.0 Hz, 1H), 7.72 (brd, J = 8.0 Hz, 1H), 7.64 (brs, 1H), 7.39 (m, 2H), 7.29 (brd, J = 7.6 Hz, 1H), 3.50 (m, 4H), 3.28 (s, 3H), 2.35 (s, 3H) 2.01 (m, 1H), 0.96-1.02 (m, 2H), 0.75-0.80 (m, 2H). | 508.4 |
| 366 | D72 | | R | 66 | 10.4 (s, 1H), 9.77 (d, J = 2.4 Hz, 1H), 8.88 (q, J = 4.4 Hz, 1H), 8.83 (d, J = 5.2 Hz, 1H), 8.82 (s, 1H), 8.53 (d, J = 1.6 Hz, 1H), 8.33 (d, J = 2.0 Hz, 1H), 8.21 (dd, J = 1.6 and 4.8 Hz, 1H), 8.03 (d, J = 2.0 Hz, 1H), 7.90 (dd, J = 2.4 and 8.4 Hz, 1H), 7.38 (d, J = 8.4 Hz, 1H), 2.86 (d, | 471.3 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | J = 4.8 Hz, 3H), 2.35 (s, 3H), 1.66 (s, 9H). | |
| 367 | D74 | | R | 60 | 11.0 (s, 1H), 10.8 (s, 1H), 9.61 (d, J = 2.0 Hz, 1H), 8.55 (s, 1H), 8.51 (d, J = 5.2 Hz, 1H), 8.12 (d, J = 2.4 Hz, 1H), 7.91 (d, J = 2.0 Hz, 1H), 7.84 (dd, J = 2.0 and 8.0 Hz, 1H), 7.68 (dd, J = 1.6 and 5.2 Hz, 1H), 7.41 (d, J = 8.4 Hz, 1H), 7.30 (s, 1H), 2.33 (s, 3H) 2.05 (m, 1H), 1.32 (s, 9H), 0.84 (m, 4H). | 497.3 |
| 368 | D69 | | R | 20 | 10.4 (s, 1H), 10.2 (s, 1H), 9.64 (d, J = 2.0 Hz, 1H), 8.76 (d, J = 2.4 Hz, 1H), 8.47 (d, J = 5.2 Hz, 1H), 8.29 (s, 1H), 8.24 (s, 1H), 8.23 (d, J = 2.0 Hz, 1H), 7.64 (dd, J = 1.2 and 5.2 Hz, 1H), 3.71 (s, 3H), 2.35 (d, J = 7.6 Hz, 2H), 2.24 (m, 1H), 1.72-1.80 (m, 2H), 1.56-1.64 (m, 2H), 1.46-1.55 (m, 2H), 1.13-1.22 (m, 2H). 3Hs are under solvents | 447.3 |
| 369 | D78 | | R | 15 | 12.0 (s, 1H), 10.6 (s, 1H), 9.68 (d, J = 2.4 Hz, 1H), 8.81 (d, J = 5.2 Hz, 1H), 8.40 (d, J = 4.8 Hz, 1H), 8.18 (d, J = 2.0 Hz, 1H), 8.02 (s, 1H), 7.98 (d, J = 2.0 Hz, 1H), 7.87 (m, 2H), 7.69 (t, J = 3.2 Hz, 1H), 7.50 (d, J = 4.8 Hz, 1H), 7.44 (d, J = 8.4 Hz, 1H), 6.77 (m, 1H), 2.41 (s, 3H) 1.76 (s, 6H). | 474.3 |
| 370 | D74 | | R | 36 | 11.0 (s, 1H), 9.98 (s, 1H), 9.59 (d, J = 2.0 Hz, 1H), 8.54 (s, 1H), 8.51 (d, J = 5.2 Hz, 1H), 8.06 (d, J = 2.4 Hz, 1H), 7.77 (d, J = 2.0 Hz, 1H), 7.66 (m, 2H), 7.31 (d, J = 8.4 Hz, 1H), 3.97 (dd, J = 3.6 and 11.6 Hz, 1H), 3.36 (m, 1H), 3.01 (m, 1H), 2.58 (m, 1H), 2.28 (s, 3H) 2.04 (m, 1H), 1.76 (brd, J = 12.8 Hz, 1H), 1.53-1.68 (m, 3H), 1.32 (m, 1H), 0.83-0.89 (m, 10H). | 500.4 |
| 371 | A6 F66 | | P | 9 | 10.6 (s, 1H), 8.86 (q, J = 4.8 Hz, 1H), 8.70-8.76 (m, 2H), 8.58 (d, J = 2.2 Hz, 1H), 8.05 (m, 1H), 8.01 (s, 1H), 7.69-7.83 (m, 5H), 7.34 (d, J = 8.3 Hz, 1H), 2.84 (d, J = 4.8 Hz, 3H), 2.51 (s, 3H), 2.27 (s, 3H), 1.69 (d, J = 22.3 Hz, 6H). | 498.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 372 | D79 | | R | 25 | 10.7 (s, 1H), 9.78 (d, J = 2.4 Hz, 1H), 8.85 (d, J = 4.8 Hz, 1H), 8.82 (s, 1H), 8.81 (s, 1H), 8.52 (brs, 1H), 8.36 (d, J = 2.0 Hz, 1H), 8.21 (dd, J = 1.6 and 5.2 Hz, 1H), 8.03 (s, 1H), 7.95 (d, J = 1.6 Hz, 1H), 7.87 (m, 2H), 7.44 (d, J = 8.4 Hz, 1H), 2.95 (m, 1H), 2.37 (s, 3H) 1.77 (s, 6H), 0.70-0.85 (m, 4H). | 518.3 |
| 373 | D74 | | R | 14 | 11.0 (s, 1H), 9.72 (s, 1H), 9.60 (d, J = 2.4 Hz, 1H), 8.55 (s, 1H), 8.51 (d, J = 5.2 Hz, 1H), 8.40 (s, 1H), 8.10 (d, J = 2.4 Hz, 1H), 7.85 (d, J = 2.0 Hz, 1H), 7.78 (dd, J = 2.0 and 8.0 Hz, 1H), 7.68 (dd, J = 1.6 and 5.2 Hz, 1H), 7.34 (d, J = 8.4 Hz, 1H), 4.43 (m, 1H), 2.35 (s, 3H) 2.30 (s, 3H), 2.04 (m, 1H), 1.42 (d, J = 6.8 Hz, 6H), 0.84 (m, 4H). | 496.3 |
| 374 | D70 | | R (TCFH) | 13 | 10.3 (s, 1H), 9.80 (d, J = 2.0 Hz, 1H), 8.89 (q, J = 4.8 Hz, 1H), 8.83 (d, J = 4.8 Hz, 1H), 8.76 (d, J = 2.8 Hz, 1H), 8.54 (d, J = 1.2 Hz, 1H), 8.43 (d, J = 2.0 Hz, 1H), 8.23 (d, J = 2.4 Hz, 1H), 8.20 (dd, J = 0.8 and 4.8 Hz, 1H), 2.85 (d, J = 4.8 Hz, 3H), 2.50-2.62 (m, 2H), 2.09 (dt, J = 22.8, 7.2 Hz, 2H), 0.96 (m, 2H), 0.60-0.66 (m, 2H). 3Hs are under solvents | 435.4 |
| 375 | D68 | | R (T3P) | 10 | 10.7 (s, 1H), 10.4 (s, 1H), 9.63 (d, J = 2.2 Hz, 1H), 8.75 (d, J = 5.0 Hz, 1H), 8.46 (d, J = 5.2 Hz, 1H), 8.29 (d, J = 1.5 Hz, 1H), 8.15 (d, J = 2.2 Hz, 1H), 8.04 (s, 1H), 7.95 (d, J = 2.3 Hz, 1H), 7.88 (dd, J = 2.3 and 8.3 Hz, 1H), 7.83 (d, J = 5.1 Hz, 1H), 7.64 (dd, J = 1.6 and 5.2 Hz, 1H), 7.42 (d, J = 8.3 Hz, 1H), 3.70 (s, 3H), 2.35 (s, 3H), 1.72 (s, 3H), 1.68 (s, 3H). | 501.2 |
| 376 | D80 | | R (T3P) | 25 | 10.6 (s, 1H), 8.89 (q, J = 4.8 Hz, 1H), 8.85 (d, J = 8.0 Hz, 1H), 8.79 (dd, J = 5.2 and 6.8 Hz, 2H), 8.41 (d, J = 1.2 Hz, 1H), 8.10 (dd, J = 1.6 and 5.2 Hz, 1H), 8.02 (s, 1H), 7.98 (s, 1H), 7.88 (m, 3H), 7.81 (dd, J = 2.0 and 8.0 Hz, 1H), 7.37 (d, J = 8.4 Hz, 1H), 2.85 (d, J = 4.8 Hz, 3H), 2.37 (s, 3H), 1.76 (s, 6H). | 491.3 |

TABLE I-continued

| Ex No. | SM | Product | Method | Yield (%) | $^1$H NMR (400 or 500 MHz, (DMSO-$d_6$): δ | MS (m/z: M + H$^+$) |
|---|---|---|---|---|---|---|
| 377 | D75 | | R | 15 | 11.0 (s, 1H), 9.98 (s, 1H), 9.59 (d, J = 2.0 Hz, 1H), 8.55 (s, 1H), 8.51 (d, J = 5.2 Hz, 1H), 8.09 (d, J = 2.0 Hz, 1H), 7.97 (d, J = 1.6 Hz, 1H), 7.88 (d, J = 8.4 Hz, 1H), 7.68 (d, J = 4.4 Hz, 1H), 7.33 (d, J = 8.4 Hz, 1H), 6.40 (s, 1H), 3.93 (s, 3H), 2.31 (s, 3H) 2.05 (m, 1H), 1.93 (m, 1H), 0.99 (m, 2H), 0.97 (m, 4H), 0.69 (m, 2H). | 494.3 |
| 378 | D80 | | R | 41 | 10.6 (s, 1H), 8.87 (q, J = 4.8 Hz, 1H), 8.85 (d, J = 8.4 Hz, 1H), 8.78 (d, J = 4.8 Hz, 1H), 8.75 (d, J = 4.8 Hz, 1H), 8.41 (d, J = 1.2 Hz, 1H), 8.10 (dd, J = 1.6 and 4.8 Hz, 1H), 8.04 (s, 1H), 7.98 (s, 1H), 7.90 (d, J = 2.0 Hz, 1H), 7.88 (dd, J = 1.6 and 5.2 Hz, 1H), 7.84 (m, 2H), 7.35 (d, J = 8.4 Hz, 1H), 2.85 (d, J = 4.8 Hz, 3H), 2.37 (s, 3H), 1.70 (d, J = 22.0 Hz, 6H). | 484.3 |
| 379 | D81 | | R (T3P) | 29 | 10.6 (s, 1H), 9.45 (d, J = 2.1 Hz, 1H), 9.42 (s, 1H), 9.07 (q, J = 4.8 Hz, 1H), 8.81 (d, J = 2.1 Hz, 1H), 8.75 (d, J = 5.0 Hz, 1H), 8.66 (s, 1H), 8.62 (m, 1H), 8.03 (s, 1H), 7.78-7.85 (m, 2H), 7.76 (m, 1H), 7.39 (d, J = 8.3 Hz, 1H), 2.86 (d, J = 4.8 Hz, 3H), 2.28 (s, 3H), 1.70 (d, J = 22.3 Hz, 6H). | 485.2 |
| 380 | D82 | | R (T3P) | 8 | 10.6 (s, 1H), 9.08 (d, J = 2.2 Hz, 1H), 8.75 (m, 2H), 8.72 (d, J = 2.0 Hz, 1H), 8.40 (s, 1H), 8.28 (t, J = 2.2 Hz, 1H), 8.20 (s, 1H), 8.08 (dd, J = 1.9 and 5.2 Hz, 1H), 8.03 (s, 1H), 7.78-7.85 (m, 2H), 7.72-7.77 (m, 2H), 7.38 (d, J = 8.3 Hz, 1H), 2.28 (s, 3H), 1.70 (d, J = 22.2 Hz, 6H). | 470.2 |
| 381 | D82 | | R (EDC) | 20 | 10.1 (s, 1H), 9.07 (d, J = 2.2 Hz, 1H), 8.74 (d, J = 5.1 Hz, 1H), 8.70 (d, J = 2.0 Hz, 1H), 8.49 (s, 1H), 8.40 (s, 1H), 8.27 (s, 1H), 8.20 (s, 1H), 8.16 (s, 1H), 8.07 (dd, J = 1.9 and 5.2 Hz, 1H), 7.72-7.79 (m, 2H), 7.68 (d, J = 2.3 Hz, 1H), 7.33 (d, J = 8.4 Hz, 1H), 5.24 (q, J = 9.1 Hz, 2H), 2.26 (s, 3H). | 481.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 382 | D81 | | R (EDC) | 17 | 10.1 (s, 1H), 9.44 (d, J = 2.1 Hz, 1H), 9.42 (s, 1H), 9.07 (q, J = 4.8 Hz, 1H), 8.79 (d, J = 2.1 Hz, 1H), 8.65 (s, 1H), 8.61 (m, 1H), 8.48 (s, 1H), 8.15 (s, 1H), 7.75 (dd, J = 2.2 and 8.3 Hz, 1H), 7.69 (d, J = 2.2 Hz, 1H), 7.34 (d, J = 8.3 Hz, 1H), 5.24 (q, J = 9.1 Hz, 2H), 2.86 (d, J = 4.8 Hz, 3H), 2.26 (s, 3H). | 496.0 |
| 383 | D81 | | R (EDC) | 33 | 10.5 (s, 1H), 9.43 (d, J = 2.1 Hz, 1H), 9.41 (s, 1H), 9.06 (q, J = 4.8 Hz, 1H), 8.76 (d, J = 2.1 Hz, 1H), 8.64 (s, 1H), 8.58 (t, J = 2.2 Hz, 1H), 7.84 (s, 1H), 7.62 (d, J = 2.2 Hz, 1H), 7.53 (dd, J = 2.3 and 8.3 Hz, 1H), 7.33 (d, J = 8.3 Hz, 1H), 5.26 (s, 2H), 2.96 (m, 1H), 2.86 (d, J = 4.8 Hz, 3H), 2.24 (s, 3H), 1.22 (d, J = 6.9 Hz, 6H). | 471.2 |
| 384 | D83 | | R (EDC) | 12 | 10.5 (s, 1H), 10.3 (s, 1H), 8.88 (d, J = 2.1 Hz, 1H), 8.70 (d, J = 5.0 Hz, 1H), 8.63 (d, J = 2.0 Hz, 1H), 8.32 (d, J = 5.2 Hz, 1H), 8.13 (d, J = 1.5 Hz, 1H), 8.03 (t, J = 2.3 Hz, 1H), 7.99 (s, 1H), 7.76 (dd, J = 1.6 and 5.1 Hz, 1H), 7.53 (d, J = 7.7 Hz, 1H), 7.46 (dd, J = 1.6 and 5.2 Hz, 1H), 7.32 (d, J = 11.3 Hz, 1H), 3.63 (s, 3H), 2.25 (s, 3H), 1.66 (s, 3H), 1.62 (s, 3H). | 518.2 |
| 385 | G10 | | P | 51 | 10.78 (s, 1H), 8.89 (d, J = 2.4 Hz, 1H), 8.85-8.79 (m, 1H), 8.65 (s, 1H), 8.24-8.17 (m, 2H), 8.13 (d, J = 2.5 Hz, 1H), 8.12 (br s, 1H), 8.03 (t, J = 1.2 Hz, 1H), 7.89 (dd, J = 5.1, 1.6 Hz, 1H), 7.79-7.72 (m, 2H), 7.24 (dd, J = 4.7, 1.3 Hz, 1H), 7.13 (dd, J = 4.6, 2.6 Hz, 1H), 2.45 (s, 3H), 1.76 (s, 6H). | 474.2 |
| 386 | D84 | | R (EDC) | 25 | 10.6 (s, 1H), 10.26 (s, 1H), 8.75 (d, J = 5.0 Hz, 1H), 8.57 (d, J = 1.4 Hz, 1H), 8.35 (d, J = 5.2 Hz, 1H), 8.04 (s, 1H), 7.81 (m, 1H), 7.76 (s, 1H), 7.73 (dd, J = 1.5 and 5.2 Hz, 1H), 7.56 (d, J = 7.7 Hz, 1H), 7.34-7.40 (m, 2H), 3.69 (s, 3H), 2.62 (s, 3H), 2.31 (s, 3H), 1.72 (s, 3H), 1.67 (s, 3H) | 532.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 387 109 79 | D79 | | R | 9 | 11.0 (s, 1H), 10.3 (s, 1H), 9.61 (d, J = 2.0 Hz, 1H), 8.82 (d, J = 2.8 Hz, 1H), 8.55 (d, J = 0.8 Hz, 1H), 8.51 (m, 2H), 8.12 (d, J = 2.4 Hz, 1H), 7.83 (m, 2H), 7.67 (dd, J = 1.6 and 3.6 Hz, 1H), 7.40 (m, 1H), 3.60 (s, 3H), 2.33 (s, 3H), 2.04 (m, 1H), 0.81-0.86 (m, 4H). | 549.3 |
| 388 | D79 | Pure cis or trans | R & SFC purification | 11 | 11.0 (s, 1H), 10.0 (s, 1H), 9.59 (d, J = 2.4 Hz, 1H), 8.54 (s, 1H), 8.51 (d, J = 0.8 Hz, 1H), 8.51 (d, J = 5.2 Hz, 1H), 8.07 (d, J = 2.4 Hz, 1H), 7.77 (d, J = 2.0 Hz, 1H), 7.67 (m, 2H), 7.31 (d, J = 8.4 Hz, 1H), 3.97 (dd, J = 3.2 and 10.4 Hz, 1H), 3.36 (m, 1H), 3.01 (m, 1H), 2.58 (m, 1H), 2.28 (s, 3H), 2.05 (m, 1H), 1.76 (m, 1H), 1.53-1.67 (m, 3H), 1.33 (m, 1H), 0.83-0.89 (m, 10H). | 500.3 |
| 389 | D79 | Pure cis or trans | R & SFC purification | 12 | 11.0 (s, 1H), 10.0 (s, 1H), 9.59 (d, J = 2.4 Hz, 1H), 8.54 (s, 1H), 8.51 (d, J = 5.2 Hz, 1H), 8.07 (d, J = 2.4 Hz, 1H), 7.77 (d, J = 2.0 Hz, 1H), 7.67 (m, 2H), 7.31 (d, J = 8.4 Hz, 1H), 3.97 (dd, J = 3.2 and 10.0 Hz, 1H), 3.36 (m, 1H), 3.01 (m, 1H), 2.58 (m, 1H), 2.28 (s, 3H), 2.04 (m, 1H), 1.76 (m, 1H), 1.56-1.67 (m, 3H), 1.32 (m, 1H), 0.83-0.89 (m, 10H). | 500.3 |
| 390 | D85 | | R (T3P) | 5 | 10.8 (s, 1H), 10.5 (s, 1H), 9.66 (d, J = 2.0 Hz, 1H), 8.83 (d, J = 5.2 Hz, 1H), 8.48 (m, 2H), 8.34 (brm, 1H), 8.31 (brs, 1H), 8.03-8.08 (m, 2H), 7.91 (dd, J = 4.8, 1.2 Hz, 1H), 7.63 (dd, J = 5.2, 1.2 Hz, 1H), 7.51 (dd, J = 9.2 and 10.8 Hz, 1H), 3.72 (s, 3H), 1.78 (s, 6H). | 512.4 |
| 391 | D86 | | R (EDC) | 15 | 10.7 (s, 1H), 10.4 (s, 1H), 9.10 (dd, J = 1.0 and 5.2 Hz, 1H), 8.92 (s, 1H), 8.78 (d, J = 5.0 Hz, 1H), 8.46 (d, J = 5.2 Hz, 1H), 8.06 (s, 1H), 8.03 (s, 1H), 8.00 (d, J = 1.3 Hz, 1H), 7.90 (dd, J = 2.3 and 8.3 Hz, 1H), 7.85 (d, J = 1.4 Hz, 1H), 7.77 (d, J = 5.1 Hz, 1H), 7.44 (d, J = 8.3 Hz, 1H), 3.71 (s, 3H), 2.49 (s, 3H), 1.72 (d, J = 20.0 Hz, 6H). | 501.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 392 | D80 | | R (TCFH) | 35 | 10.0 (s, 1H), 8.87 (q, J = 4.4 Hz, 1H), 8.82 (d, J = 5.2 Hz, 1H), 8.77 (d, J = 4.8 Hz, 1H), 8.39 (s, 1H), 8.07 (dd, J = 1.6 and 5.2 Hz, 1H), 7.92 (s, 1H), 7.86 (dd, J = 1.2 and 4.8 Hz, 1H), 7.72 (d, J = 2.0 Hz, 1H), 7.59 (dd, J = 2.0 and 8.0 Hz, 1H), 7.25 (d, J = 8.4 Hz, 1H), 2.85 (d, J = 4.8 Hz, 3H), 2.54 (m, 2H), 2.31 (s, 3H), 2.06 (m, 2H), 0.90-0.98 (m, 2H), 0.59-0.65 (m, 2H). | 433.3 |
| 393 | D81 | | R | 37 | 10.6 (s, 1H), 9.45 (d, J = 2.1 Hz, 1H), 9.42 (s, 1H), 9.07 (brq, J = 4.8 Hz, 1H), 8.80 (d, J = 2.0 Hz, 1H), 8.70 (d, J = 5.1 Hz, 1H), 8.66 (s, 1H), 8.62 (t, J = 2.2 Hz, 1H), 7.93 (s, 1H), 7.77-7.82 (m, 2H), 7.75 (m, 1H), 7.39 (d, J = 8.2 Hz, 1H), 2.86 (d, J = 4.7 Hz, 3H), 2.28 (s, 3H), 1.84-1.90 (m, 2H), 1.73-1.79 (m, 2H). | 490.2 |
| 394 | D87 | | R (EDC) | 38 | 11.4 (s, 1H), 10.6 (s, 1H), 9.21 (d, J = 2.1 Hz, 1H), 9.01 (s, 1H), 8.77 (d, J = 2.1 Hz, 1H), 8.75 (d, J = 5.1 Hz, 1H), 8.64 (d, J = 1.4 Hz, 1H), 8.33 (m, 1H), 8.03 (s, 1H), 7.79-7.84 (m, 2H), 7.74 (d, J = 2.2 Hz, 1H), 7.38 (d, J = 8.3 Hz, 1H), 2.26 (s, 3H), 2.07 (m, 1H), 1.72 (s, 3H), 1.67 (s, 3H), 0.85-0.74 (m, 4H) | 511.2 |
| 395 | D87 | | R (EDC) | 38 | 11.4 (s, 1H), 10.6 (s, 1H), 9.21 (d, J = 2.1 Hz, 1H), 9.00 (d, J = 1.3 Hz, 1H), 8.76 (d, J = 2.1 Hz, 1H), 8.70 (d, J = 5.1 Hz, 1H), 8.64 (s, 1H), 8.32 (m, 1H), 7.92 (s, 1H), 7.76-7.82 (m, 2H), 7.73 (d, J = 2.3 Hz, 1H), 7.39 (d, J = 8.3 Hz, 1H), 2.26 (s, 3H), 2.08 (p, J = 6.1 Hz, 1H), 1.87 (q, J = 4.4 Hz, 2H), 1.76 (q, J = 4.5 Hz, 2H), 0.85-0.93 (m, 4H). | 516.2 |
| 396 | D87 | | R (EDC) | 65 | 11.4 (s, 1H), 10.48 (s, 1H), 9.21 (d, J = 2.1 Hz, 1H), 9.01 (s, 1H), 8.76 (d, J = 2.1 Hz, 1H), 8.64 (s, 1H), 8.56 (d, J = 5.0 Hz, 1H), 8.32 (t, J = 2.3 Hz, 1H), 7.80 (dd, J = 8.3, 2.3 Hz, 1H), 7.74 (d, J = 2.0 Hz, 2H), 7.56 (dt, J = 1.2 and 5.2 Hz, 1H), 7.37 (d, J = 8.3 Hz, 1H), 2.25 (s, 3H), 2.19 (td, J = 4.1 and 8.1 Hz, 1H), 2.06 (m, 1H), 0.93-1.04 (m, 4H), 0.86-0.93 (m, 4H). | 491.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 397 | D87 | | R (EDC) | 40 | 11.4 (s, 1H), 10.8 (s, 1H), 9.23 (m, 1H), 8.96-9.08 (m, 2H), 8.78 (d, J = 2.0 Hz, 1H), 8.65 (s, 1H), 8.38 (s, 1H), 8.34 (d, J = 2.4 Hz, 1H), 8.20 (d, J = 5.0 Hz, 1H), 7.82 (dd, J = 2.3 and 8.3 Hz, 1H), 7.74 (d, J = 2.3 Hz, 1H), 7.41 (d, J = 8.3 Hz, 1H), 2.27 (s, 3H), 2.10 (m, 1H), 0.88-0.95 (m, 4H). | 519.2 |
| 398 | G24 | | P | 10 | 11.4 (s, 1H), 10.4 (s, 1H), 9.23 (d, J = 2.1 Hz, 1H), 9.02 (s, 1H), 8.77 (d, J = 2.1 Hz, 1H), 8.65 (s, 1H), 8.58 (d, J = 5.1 Hz, 1H), 8.33 (d, J = 2.4 Hz, 1H), 7.76 (s, 1H), 7.62-7.57 (m, 2H), 7.38 (d, J = 11.3 Hz, 1H), 2.30 (s, 3H), 2.22 (m, 1H), 2.09 (m, 1H), 0.94-1.05 (m, 4H), 0.88-0.94 (m, 4H). | 509.2 |
| 399 | A3 F68 | | P | 68 | 11.0 (s, 1H), 10.6 (s, 1H), 8.93 (brs, 1H), 8.76 (d, J = 5.0 Hz, 1H), 8.69 (brs, J = 1.5 Hz, 1H), 8.46 (s, 1H), 8.43 (d, J = 5.1 Hz, 1H), 8.08 (s, 1H), 8.05 (s, 1H), 7.82 (d, J = 5.0 Hz, 1H), 7.58 (d, J = 7.7 Hz, 1H), 7.56 (d, J = 1.6 Hz, 1H), 7.38 (d, J = 11.3 Hz, 1H), 2.30 (s, 3H), 2.04 (m, 1H), 1.70 (d, J = 25.0 Hz, 6H), 0.83 (m, 4H). | 528.2 |
| 400 | D88 | | R & deprotection with HCl | 52 | 9.71 (s, 1H), 8.73 (d, J = 4.0 Hz, 1H), 8.50 (d, J = 3.6 Hz, 1H), 8.46 (s, 1H), 8.29 (s, 1H), 8.03 (d, J = 12.8 Hz, 3H), 7.88 (d, J = 7.6 Hz, 1H), 7.85 (d, J = 3.6 Hz, 1H), 7.41 (m, 2H), 2.42 (s, 3H), 1.70 (d, J = 22.0 Hz, 6H). at high temp, NH is missing | 468.3 |
| 401 | D89 | | R & deprotection with HCl | 89 | 10.60 (brs, 1H), 10.3 (brs, 1H), 8.74 (d, J = 4.4 Hz, 1H), 8.58 (s, 1H), 8.35 (d, J = 4.8 Hz, 1H), 8.03 (s, 1H), 7.79-7.82 (m, 2H), 7.70-7.75 (m, 2H), 7.58 (s, 1H), 7.36 (d, J = 8.0 Hz, 1H), 6.89 (s, 1H), 4.89 (br m, 1H), 4.47 (br m, 2H), 3.81 (brm, 2H), 3.69 (s, 3H), 2.28 (s, 3H), 1.69 (d, J = 22.0 Hz, 6H). | 560.1 |
| 402 | D90 | | R (EDC) | 44 | 10.8 (brs, 1H), 10.3 (s, 1H), 8.89 (d, J = 2.0 Hz, 1H), 8.77 (d, J = 4.8 Hz, 1H), 8.34 (d, J = 5.2 Hz, 1H), 8.18 (s, 1H), 8.10 (d, J = 2.0 Hz, 1H), 8.06 (s, 1H), 7.84 (d, J = 4.0 Hz, 1H), 7.79 (d, J = 7.6 Hz, 1H), 7.73 (s, 1H), 7.67 (t, J = 7.6 Hz, 1H), 7.56 (d, J = 7.6 Hz, 1H), 7.44 (d, J = 4.8 Hz, 1H), | 500.3 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | 3.68 (s, 3H), 2.46 (s, 3H), 1.70 (d, J = 22.4 Hz, 6H). | |
| 403 | C22 E13 | | P | 12 | 10.7 (brs, 1H), 10.43 (brs, 1H), 9.12 (d, J = 5.2 Hz, 1H), 8.75 (d, J = 5.2 Hz, 1H), 8.73 (s, 1H), 8.48 (d, J = 5.2 Hz, 1H), 8.36 (d, J = 2.4 Hz, 1H), 8.08 (d, J = 5.2 Hz, 1H), 8.06 (s, 1H), 7.90 (dd, J = 2.4 and 8.4 Hz, 1H), 7.85 (m, 2H), 7.40 (d, J = 8.4 Hz, 1H), 3.70 (s, 3H), 3.61 (s, 3H), 1.71 (d, J = 22.0 Hz, 6H). | 501.2 |
| 404 | D91 | | R (EDC) | 50 | 10.8 (brs, 2H), 8.91 (m, 2H), 8.77 (d, J = 4.8 Hz, 1H), 8.39 (s, 1H), 8.06-8.12 (m, 4H), 7.84 (d, J = 4.4 Hz, 1H), 7.64-7.72 (m, 2H), 3.73 (s, 3H), 2.50 (s, 3H), 1.70 (d, J = 22.0 Hz, 6H). | 501.1 |
| 405 | D92 | | R (EDC) | 61 | 11.0 (s, 1H), 10.6 (s, 1H), 9.23 (s, 1H), 8.95 (s, 1H), 8.70 (d, J = 4.8 Hz, 1H), 8.43 (s, 1H), 8.46 (s, 1H), 8.36 (s, 1H), 7.93 (s, 1H), 7.80 (m, 2H), 7.75 (s, 1H), 7.40 (d, J = 8.4 Hz, 1H), 3.74 (s, 3H), 2.28 (s, 3H), 1.87 (brm, 2H), 1.76 (brm, 2H). | 506.2 |
| 406 | G24 | | P | 16 | 11.4 (s, 1H), 10.8 (s, 1H), 9.25 (d, J = 2.0 Hz, 1H), 9.01 (s, 1H), 8.94 (d, J = 2.4 Hz, 1H), 8.83 (d, J = 2.1 Hz, 1H), 8.77 (d, J = 5.1 Hz, 1H), 8.65 (s, 1H), 8.42 (s, 1H), 8.14 (d, J = 2.4 Hz, 1H), 8.06 (s, 1H), 7.85 (d, J = 1.5 Hz, 1H), 2.46 (s, 3H), 2.16 (m, 1H), 1.70 (d, J = 22.3 Hz, 6H), 0.84-0.94 (m, 4H). | 512.2 |
| 407 | F44 | | P | 15 | 10.8 (s, 1H), 8.85 (d, J = 2.4 Hz, 1H), 8.82 (d, J = 5.0 Hz, 1H), 8.61 (d, J = 6.9 Hz, 1H), 8.10 (d, J = 2.4 Hz, 1H), 8.02 (s, 1H), 7.87 (dd, J = 1.5 and 5.0 Hz, 1H), 7.84 (s, 1H), 7.74 (d, J = 7.7 Hz, 1H), 7.64-7.71 (m, 3H), 7.49 (d, J = 7.6 Hz, 1H), 7.31 (dd, J = 9.1, 6.7 Hz, 1H), 6.97 (t, J = 6.8 Hz, 1H), 2.39 (s, 3H)1.75 (s, 6H). | 473.2 |
| 408 | A6 F68 | | P | 17 | 10.6 (s, 1H), 9.08 (d, J = 2.2 Hz, 1H), 8.86 (d, J = 4.9 Hz, 1H), 8.76 (m, 2H), 8.73 (d, J = 2.0 Hz, 1H), 8.40 (d, J = 1.9 Hz, 1H), 8.28 (t, J = 2.2 Hz, 1H), 8.09 (dd, J = 1.9 and 5.2 Hz, 1H), 8.06 (s, 1H), 7.84 (m, 1H), 7.63 (d, J = 7.8 Hz, 1H), 7.39 (d, J = 11.4 Hz, 1H), 2.86 (d, J = 4.9 Hz, 3H), 2.33 (s, 3H), 1.71 (d, J = 25.0 Hz, 6H). | 502.2 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| 409 | D68 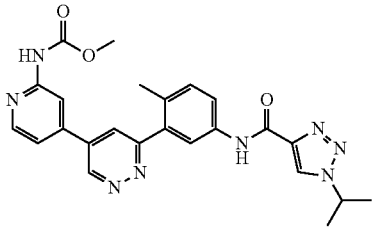 | 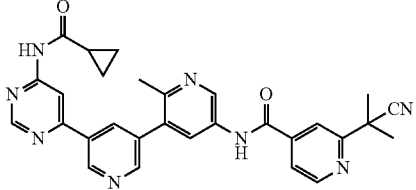 [SMILES: Cc1ncc(NC(=O)c2ccnc(C(C)(C)C#N)c2)cc1-c1cncc(-c2cc(NC(=O)C3CC3)ncn2)c1] | R | 15 | 10.5 (s, 1H), 10.4 (s, 1H), 9.62 (d, J = 2.2 Hz, 1H), 8.80 (s, 1H), 8.46 (d, J = 5.2 Hz, 1H), 8.29 (d, J = 1.5 Hz, 1H), 8.13 (d, J = 2.2 Hz, 1H), 8.02 (d, J = 2.3 Hz, 1H), 7.90 (dd, J = 2.3 and 8.3 Hz, 1H), 7.64 (m, 1H), 7.37 (d, J = 8.4 Hz, 1H), 4.91 (m, 1H), 3.70 (s, 3H), 2.33 (s, 3H), 1.53 (d, J = 6.7 Hz, 6H). | 473.2 |
| 410 | D93 | | R | 9 | 11.4 (s, 1H), 10.9 (s, 1H), 9.25 (d, J = 2.1 Hz, 1H), 9.01 (s, 1H), 8.94 (d, J = 2.4 Hz, 1H), 8.80-8.85 (m, 2H), 8.65 (s, 1H), 8.41 (m, 1H), 8.14 (d, J = 2.4 Hz, 1H), 8.05 (s, 1H), 7.90 (d, J = 5.1 Hz, 1H), 2.46 (s, 3H), 2.08 (m, 1H), 1.76 (s, 6H), 0.85-0.94 (m, 4H). | 519.2 |
| 411 | D94 | | R & Q | 29 | 10.5 (s, 1H), 9.13 (brs, 1H), 8.78 (brs, 1H), 8.74 (d, J = 4.8 Hz, 1H), 8.65 (s, 1H), 8.32 (s, 1H), 8.03 (s, 1H), 7.83 (m, 1H), 7.74-7.79 (m, 2H), 7.39 (d, J = 8.0 Hz, 1H), 7.15 (s, 1H), 2.28 (s, 3H), 1.72 (d, J = 22.0 Hz, 6H). NH proton is missing. @ high temp | 443.1 |
| 412 | D87 | | R (EDC) | 72 | 11.4 (s, 1H), 10.5 (s, 1H). 9.20 (d, J = 2.0 Hz, 1H), 9.00 (s, 1H), 8.78 (s, 1H), 8.75 (d, J = 2.1 Hz, 1H), 8.64 (s, 1H), 8.3 l(m, 1H). 7.85 (dd, J = 2.3 and 8.2 Hz, 1H), 7.82 (d, J = 2.2 Hz, 1H), 7.33 (d, J = 8.3 Hz, 1H), 4.90(m, 1H), 2.24 (s, 3H), 2.08 (h, J = 6.1 Hz, 1H), 1.53 (d, J = 6.7 Hz, 6H), 0.84-0.94 (m, 4H). | 483.2 |
| 413 | D95 | | R (EDC) | 28 | 10.6 (s, 1H), 9.07 (d, J = 2.2 Hz, 1H), 8.85 (q, J = 4.8 Hz, 1H), 8.75 (m, 2H), 8.72 (s, 1H), 8.38 (s, 1H), 8.28 (t, J = 2.2 Hz, 1H), 8.07 (dd, J = 1.9 and 5.1 Hz, 1H), 8.03 (s, 1H), 7.81 (m, 2H), 7.75 (d, J = 2.3 Hz, 1H), 7.38 (d, J = 8.3 Hz, 1H), 2.84 (d, J = 4.7 Hz, 3H), 2.28 (s, 3H), 1.70 (d, J = 22.1 Hz, 6H). | 484.2 |
| 414 | D92 | | R (EDC) | 19 | 11.0 (brs, 1H), 10.6 (brs, 1H), 9.23 (s, 1H), 8.95 (s, 1H), 8.81 (d, J = 5.2 Hz, 1H), 8.79 (s, 1H), 8.42 (s, 1H), 8.36 (s, 1H), 8.08 (s, 1H), 7.88 (d, J = 4.4 Hz, 1H), 7.80 (d, J = 8.0 Hz, 1H), 7.74 (s, 1H), 7.40 (d, J = 8.0 Hz, 1H), 3.74 (s, 3H), 2.25 (s, 3H), 1.73 (s, 6H). | 508.1 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 415 | D90 | | R | 37 | 10.7 (s, 1H), 10.3 (s, 1H), 8.66 (s, 1H), 8.33 (brd, J = 4.0 Hz, 1H), 8.16 (s, 1H), 7.94 (s, 1H), 7.86 (s, 1H), 7.77 (brd, J = 7.2, 1H), 7.60-7.70 (m, 2H), 7.51 (brd, J = 8.0 Hz, 1H), 7.42 (brd, J = 5.2 Hz, 1H), 5.30 (s, 2H), 3.68 (s, 3H), 2.97 (m. 1H), 2.42 (s, 3H), 1.23 (d, J = 6.4 Hz, 6H). | 486.2 |
| 416 | C24 E13 | | P | 10 | 10.7 (s, 1H), 10.4 (s, 1H), 8.76 (d, J = 5.2 Hz, 1H), 8.68 (s, 1H), 8.45 (d, J = 5.2 Hz, 1H), 8.05 (m, 2H), 7.93 (d, J = 2.4 Hz, 1H), 7.89 (dd, J = 2.4 and 8.4 Hz, 1H), 7.85 (m, 1H), 7.83 (m, 1H), 7.39 (d, J = 8.4 Hz, 1H), 3.71 (s, 3H) 2.79 (s, 3H), 2.41 (s, 3H), 1.70 (d, J = 22.4 Hz, 6H). | 515.1 |
| 417 | D96 | | R (EDC) | 45 | 11.0 (s, 1H), 10.6 (s, 1H), 8.94 (d, J = 2.0 Hz, 1H), 8.75 (d, J = 4.8 Hz, 1H), 8.69 (d, J = 1.6 Hz, 1H), 8.46 (s, 1H), 8.43 (d, J = 5.2 Hz, 1H), 8.08 (brs, 1H), 8.03 (s, 1H), 7.79-7.84 (m, 2H), 7.74 (brs, 1H), 7.55 (dd, J = 1.6 and 3.6 Hz, 1H), 7.38 (d, J = 8.4 Hz, 1H), 2.26 (s, 3H), 2.04 (m, 1H), 1.70 (d, J = 22.0 Hz, 6H), 0.82 (m, 4H). | 510.2 |
| 418 | D83 | | R (EDC) | 49 | 11.0 (s, 1H), 10.6 (s, 1H), 8.93 (d, J = 2.0 Hz, 1H), 8.81 (d, J = 5.2 Hz, 1H), 8.68 (d, J = 1.6 Hz, 1H), 8.45 (s, 1H), 8.43 (d, J = 5.2 Hz, 1H), 8.06 (brs, 1H), 8.04 (s, 1H), 7.87 (d, J = 4.4 Hz, 1H), 7.59 (d, J = 7.6 Hz, 1H), 7.56 (dd, J = 1.2 and 5.2 Hz, 1H), 7.39 (d, J = 11.2 Hz, 1H), 2.30 (s, 3H), 2.03 (m, 1H), 1.76 (s, 6H), 0.82 (m, 4H). | 535.1 |
| 419 | D87 | | R (EDC) | 20 | 11.4 (s, 1H), 10.7 (s, 1H), 9.22 (d, J = 2.0 Hz, 1H), 9.01 (d, J = 0.8 Hz, 1H), 8.88 (d, J = 5.2 Hz, 1H), 8.77 (d, J = 2.0 Hz, 1H), 8.65 (d, J = 0.8 Hz, 1H), 8.34 (t, J = 2.0 Hz, 1H), 8.13 (s, 1H), 8.02 (d, J = 5.2 Hz, 1H), 8.82 (dd, J = 2.0 and 8.0 Hz, 1H), 7.74 (d, J = 2.0 Hz, 1H), 7.40 (d, J = 8.4 Hz, 1H), 2.27 (s, 3H), 2.07 (m, 1H), 2.05 (t, J = 19.2 Hz, 3H), 0.89 (m, 4H). | 515.1 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 420 | D97 | | R | 38 | 11.1 (s, 1H), 10.6 (s, 1H), 9.24 (s, 1H), 9.01 (s, 1H), 8.81 (d, J = 4.8 Hz, 1H), 8.78 (brs, 1H), 8.69 (s, 1H), 8.36 (s, 1H), 8.01 (s, 1H), 7.88 (d, J = 4.8 Hz, 1H), 7.80 (brd, J = 8.0 Hz, 1H), 7.74 (s, 1H), 7.40 (d, J = 8.4 Hz, 1H), 2.81 (m, 1H), 2.27 (s, 3H), 1.76 (s, 6H), 1.12 (d, J = 6.8 Hz, 6H). | 520.1 |
| 421 | D87 | | R (EDC) | 54 | 11.4 (s, 1H), 10.7 (s, 1H), 9.21 (d, J = 1.2 Hz, 1H), 9.01 (s, 1H), 8.75 (d, J = 1.2 Hz, 1H), 8.64 (s, 1H), 8.31 (brs, 1H), 7.77 (m, 2H), 7.35 (d, J = 8.0 Hz, 1H), 6.61 (s, 1H), 2.25 (s, 3H), 2.21 (m, 1H), 2.08 (m, 1H), 1.13-1.17 (m, 2H), 0.97 (m, 2H), 0.90 (m, 4H). | 481.1 |
| 422 115 28 | D94 | | R & Q | 42 | 10.7 (s, 1H), 9.10 (s, 1H), 8.81 (m, 2H), 8.75 (s, 1H), 8.52 (brs, 2H), 8.32 (s, 1H), 8.03 (s, 1H), 7.87 (m, 1H), 7.81 (s, 1H) 7.74 (brd, J = 6.4 Hz, 1H), 7.41 (brd, J = 7.2 Hz, 1H), 7.12 (s, 1H), 2.28 (s, 3H), 1.76 (s, 6H). | 450.2 |
| 423 | D98 | | R (EDC) | 6 | 11.3 (s, 1H), 10.5 (s, 1H), 9.15 (s, 1H), 8.94 (s, 1H), 8.69 (d, J = 4.8 Hz, 2H), 8.58 (s, 1H), 8.25 (s, 1H), 7.98 (s, 1H), 7.76 (d, J = 5.1 Hz, 1H), 7.52 (d, J = 7.6 Hz, 1H), 7.32 (d, J = 11.3 Hz, 1H), 2.23 (s, 3H), 2.02 (m, 1H), 1.63 (d, J = 20 Hz, 6H), 0.84 (m, 4H). | 529.2 |
| 424 | D98 | | R (EDC) | 8 | 11.3 (s, 1H), 10.5 (s, 1H), 9.15 (s, 1H), 8.94 (s, 1H), 8.74 (d, J = 5.0 Hz, 1H), 8.70 (d, J = 2.1 Hz, 1H), 8.58 (d, J = 1.4 Hz, 1H), 8.26 (s, 1H), 7.98 (s, 1H), 7.80 (d, J = 5.0 Hz, 1H), 7.53 (d, J = 7.7 Hz, 1H), 7.33 (d, J = 11.3 Hz, 1H), 2.23 (s, 3H), 2.01 (m, 1H), 1.70 (s, 6H), 0.83 (m, 4H). | 536.2 |
| 425 | D92 | | R (EDC) | 33 | 11.0 (s, 1H), 10.6 (s, 1H), 9.23 (d, J = 2.0 Hz, 1H), 8.95 (d, J = 0.8 Hz, 1H), 8.78 (s, 1H), 8.75 (d, J = 5.2 Hz, 1H), 8.43 (s, 1H), 8.36 (t, J = 1.6 Hz, 1H), 8.03 (s, 1H), 7.82 (m, 2H), 7.76 (d, J = 2.0 Hz, 1H), 7.39 (d, J = 8.4 Hz, 1H), 3.74 (s, 3H) 2.28 (s, 3H), 1.70 (d, J = 22.0 Hz, 6H). | 501.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 426 | D94 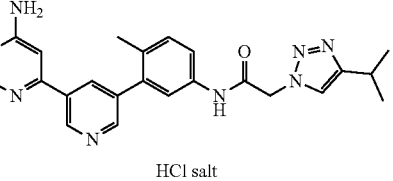 HCl salt | R & Q | 7 | 10.5 (s, 1H), 9.13 (d, J = 2.0 Hz, 1H), 8.66 (d, J = 2.4 Hz, 1H), 8.48 (s, 1H), 8.25 (t, J = 2.4 Hz, 1H), 7.85 (s, 1H), 7.60 (d, J = 2.4 Hz, 1H), 7.52 (dd, J = 2.0 and 9.4 Hz, 1H), 7.33 (d, J = 9.4 Hz, 1H), 7.01 (s, 3H), 5.26 (s, 2H), 2.97 (m, 1H), 2.23 (s, 3H), 1.23 (d, J = 6.8 Hz, 6H). | 429.2 |
| 427 | D30 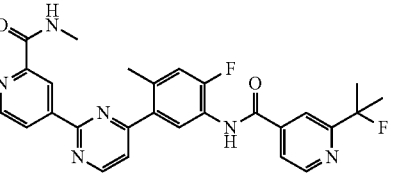 | R (EDC) | 16 | 10.7 (s, 1H), 9.11 (d, J = 5.2 Hz, 1H), 8.96 (s, 1H), 8.90 (q, J = 5.2 Hz, 1H), 8.85 (d, J = 4.8 Hz, 1H), 8.77 (d, J = 4.8 Hz, 1H), 8.49 (dd, J = 2.0 and 8.4 Hz, 1H), 8.06 (brs, 1H), 7.88 (d, J = 8.0 Hz, 1H), 7.84 (m, 2H), 7.44 (d, J = 11.2 Hz, 1H), 2.86 (d, J = 4.8 Hz, 3H), 1.71 (d, J = 22.4 Hz, 6H). 3Hs are under solvents | 503.2 |
| 428 | D99 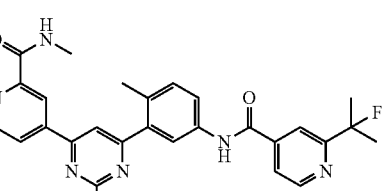 | R (EDC) | 33 | 10.69 (s, 1H), 8.90 (q, J = 4.8 Hz, 1H), 8.82 (m, 2H), 8.76 (d, J = 4.8 Hz, 1H), 8.40 (dd, J = 1.2 and 5.2 Hz, 1H), 8.25 (s, 1H), 8.05 (s, 1H), 7.95 (d, J = 1.6 Hz, 1H), 7.88 (dd, J = 1.6 amd 8.0 Hz, 1H), 7.85 (d, J = 5.2 Hz, 1H), 7.40 (d, J = 9.4 Hz, 1H), 2.86 (d, J = 4.8 Hz, 3H), 2.82 (s, 3H), 2.42 (s, 3H), 1.70 (d, J = 22.4 Hz, 6H). | 499.2 |
| 429 | D87 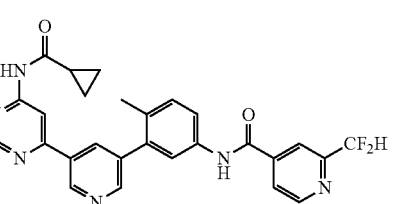 | R (EDC) | 53 | 11.2 (s, 1H), 10.7 (s, 1H), 9.22 (d, J = 1.6 Hz, 1H), 9.01 (d, J = 0.8 Hz, 1H), 8.90 (d, J = 4.8 Hz, 1H), 8.77 (d, J = 2.0 Hz, 1H), 8.65 (s, 1H), 8.33 (t, J = 2.0 Hz, 1H), 8.19 (s, 1H), 8.06 (brd, J = 4.4 Hz, 1H), 7.82 (dd, J = 1.6 and 8.0 Hz, 1H), 7.75 (d, J = 2.0 Hz, 1H), 7.40 (d, J = 8.4 Hz, 1H), 7.08 (t, J = 54.8 Hz, 1H), 2.27 (s, 3H) 2.08 (m, 1H), 089 (m, 4H). | 501.2 |
| 430 | D87 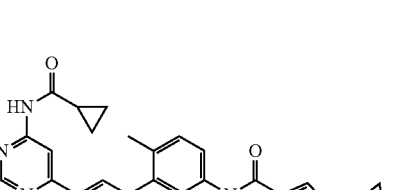 | R (EDC) | 24 | 11.4 (s, 1H), 9.84 (s, 1H), 9.21 (s, 1H), 9.01 (s, 1H), 8.75 (s, 1H), 8.64 (s, 1H), 8.39 (s, 1H), 8.32 (s, 1H), 7.97, (s, 1H), 7.74 (d, J = 7.6 Hz, 1H), 7.65 (s, 1H), 7.32 (d, J = 8.4 Hz, 1H), 3.80 (m, 1H). 2.21 (s, 3H) 2.08 (m, 1H), 1.14 (brm, 2H), 1.01 (m, 2H), 0.89 (m, 4H). | 480.2 |
| 431 | D87 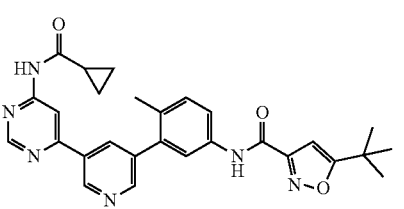 | R (EDC) | 49 | 11.3 (brs, 1H), 10.8 (brs, 1H), 9.21 (s, 1H), 9.00 (s, 1H), 8.75 (s, 1H), 8.64 (s, 1H), 8.32 (s, 1H), 7.78 (d, J = 9.4 Hz, 1H), 7.75 (s, 1H), 7.36 (d, J = 8.0 Hz, 1H), 6.67 (s, 1H), 2.25 (s, 3H), 2.08 (m, 1H), 1.34 (s, 9H), 0.88-0.99 (m, 4H). | 497.3 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 432 | D100 | | R (EDC) | 18 | 11.2 (s, 1H), 10.6 (s, 1H), 8.89 (d, J = 2.0 Hz, 1H), 8.75 (d, J = 4.8 Hz, 1H), 8.67 (d, J = 5.0 Hz, 1H), 8.18 (d, J = 5.6 Hz, 1H), 8.13 (s, 1H), 8.02 (s, 1H), 7.76-7.83 (m, 3H), 7.38 (d, J = 8.0 Hz, 1H), 7.23 (d, J = 5.6 Hz, 1H), 3.87 (s, 2H), 2.28 (s, 3H) 1.70 (d, J = 22.0 Hz, 6H). | 482.1 |
| 433 | D101 | | R (EDC) | 44 | 11.0 (brs, 1H), 10.8 (brs, 1H), 8.97 (d, J = 2.0 Hz, 1H), 8.93 (d, J = 2.4 Hz, 1H), 8.78 (d, J = 4.8 Hz, 1H), 8.76 (d, J = 2.0 Hz, 1H), 8.47 (s, 1H), 8.44 (d, J = 5.2 Hz, 1H), 8.18 (brt, J = 1.8 Hz, 1H), 8.14 (d, J = 2.4 Hz, 1H), 8.06 (s, 1H), 7.85 (dd, J = 1.2 and 4.2 Hz, 1H), 7.56 (dd, J = 1.2 and 5.2 Hz, 1H), 2.46 (s, 3H), 2.04 (m, 1H), 1.71 (d, J = 22.4 Hz, 6H), 0.82 (m, 4H). | 511.2 |
| 434 | D87 | | R (EDC) | 24 | 11.4 (s, 1H), 10.5 (s, 1H), 9.22 (d, J = 2.0 Hz, 1H), 9.01 (d, J = 1.2 Hz, 1H), 8.78 (d, J = 2.0 Hz, 1H), 8.69 (d, J = 5.2 Hz, 1H), 8.65 (d, J = 0.8 Hz, 1H), 8.35 (t, J = 2.0 Hz, 1H), 7.80 (dd, J = 2.0 and 7.5 Hz, 1H), 7.78 (s, 1H), 7.74 (d, J = 2.0 Hz, 1H), 7.71 (d, J = 4.8 Hz, 1H), 7.39 (d, J = 8.4 Hz, 1H), 3.13 (m, 1H), 2.32 (s, 3H), 2.08 (m, 1H), 1.28 (d, J = 6.8 Hz, 6H), 0.90 (m, 4H). | 493.3 |
| 435 | D102 | | R (EDC) | 30 | 10.6 (s, 1H), 10.4 (s, 1H), 8.95 (s, 1H), 8.75 (d, J = 4.8 Hz, 1H), 8.70 (s, 1H), 8.38 (d, J = 5.2 Hz, 1H), 8.20 (s, 1H), 8.10 (s, 1H), 8.03 (s, 1H), 7.81 (m, 2H), 7.75 (s, 1H), 7.52 (d, J = 4.4 Hz, 1H), 7.39 (d, J = 8.0 Hz, 1H), 3.69 (s, 3H), 2.21 (s, 3H), 1.70 (d, J = 22.0 Hz, 6H). | 500.2 |
| 436 | D46 | | R (EDC) | 63 | 11.0 (s, 1H), 10.0 (s, 1H), 9.09 (d, J = 5.2 Hz, 1H), 8.93 (s, 1H), 8.53 (d, J = 5.2 Hz, 1H), 8.36 (d, J = 2.0 Hz, 1H), 8.04 (d, J = 5.2 Hz, 1H), 7.88 (dd, J = 1.6 and 5.2 Hz, 1H), 7.81 (dd, J = 2.4 and 8.4 Hz, 1H), 7.30 (d, J = 8.4 Hz, 1H), 6.41 (s, 1H), 3.94 (s, 3H), 2.04 (s, 1H), 1.94 (s, 1H), 0.99 (m, 2H), 0.84 (m, 4H), 0.69 (m, 2H). | 494.3 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 437 | A6 F58 | | P | 26 | 10.6 (s, 1H), 8.85 (brm, 1H), 8.82 (m, 2H), 8.76 (d, J = 4.8 Hz, 1H), 8.73 (s, 1H), 8.30 (brd, J = 5.2 Hz, 1H), 8.25 (s, 1H), 8.03 (s, 1H), 7.82-7.87 (m, 3H), 7.67 (brd, J = 4.8 Hz, 1H), 7.26 (d, J = 8.8 Hz, 1H), 3.84 (s, 3H), 2.85 (d, J = 4.4 Hz, 3H), 1.77 (s, 6H). | 507.4 |
| 438 | G16 | | P | 26 | 11.3 (s, 1H), 10.5 (s, 1H), 8.96 (d, J = 0.8 Hz, 1H), 8.80 (d, J = 5.2 Hz, 1H), 8.60 (d, J = 0.8 Hz, 1H), 8.16 (brm, 1H), 7.98-8.04 (m, 2H), 7.87 (dd, J = 5.2, 1.2 Hz, 1H), 7.83 (dd, J = 8.8, 2.4 Hz, 1H), 7.75 (brd, J = 2.4 Hz, 1H), 7.68 (brd, J = 7.6 Hz, 1H), 7.61 (t, J = 8.0 Hz, 1H), 7.19 (d, J = 8.8 Hz, 1H), 3.80 (s, 3H), 2.08 (m, 1H), 1.76 (s, 6H), 0.88 (m, 4H). | 533.4 |
| 439 | D81 | | R (T3P) | 50 | 10.7 (s, 1H), 9.44 (d, J = 2.1 Hz, 1H), 9.42 (d, J = 1.3 Hz, 1H), 9.07 (q, J = 4.8 Hz, 1H), 8.87 (d, J = 5.0 Hz, 1H), 8.80 (d, J = 2.1 Hz, 1H), 8.66 (d, J = 1.3 Hz, 1H), 8.62 (t, J = 2.2 Hz, 1H), 8.19 (s, 1H), 8.04 (dd, J = 1.6 and 5.0 Hz, 1H), 7.81 (dd, J = 2.3 and 8.3 Hz, 1H), 7.77 (d, J = 2.2 Hz, 1H), 7.39 (d, J = 8.4 Hz, 1H), 2.86 (d, J = 4.9 Hz, 3H), 2.28 (s, 3H), 2.04 (t, J = 19.1 Hz, 3H). | 489.2 |
| 440 | D95 | | R (T3P) | 52 | 10.7 (s, 1H), 9.08 (d, J = 2.0 Hz, 1H), 8.86 (m, 2H), 8.75 (d, J = 4.8 Hz, 1H), 8.72 (d, J = 1.6 Hz, 1H), 8.39 (s, 1H), 8.29 (t, J = 2.0 Hz, 1H), 8.19 (s, 1H), 8.08 (dd, J = 4.8, 1.6, Hz, 1H), 8.04 (brd, J = 4.8 Hz, 1H), 7.82 (dd, J = 2.0 and 8.0 Hz, 1H), 7.76 (d, J = 2.0 Hz, 1H), 7.40 (d, J = 8.4 Hz, 1H), 2.85 (d, J = 4.8 Hz, 3H), 2.29 (s, 3H), 2.05 (t, J = 19.2 Hz, 3H). | 488.2 |
| 441 | D18 | | R (T3P) | 34 | 10.7 (s, 1H), 8.88 (d, J = 9.2 Hz, 1H), 8.87 (m, 2H), 8.77 (d, J = 1.2 Hz, 1H), 8.76 (d, J = 5.2 Hz, 1H), 8.34 (dd, J = 1.6 and 5.2 Hz, 1H), 8.20 (s, 2H), 8.03 (brd, J = 4.8 Hz, 1H), 7.84 (dd, J = 2.0 and 8.4 Hz, 1H) 7.77 (d, J = 2.0 Hz, 1H), 7.57 (dd, J = 1.2 and 4.8 Hz, 1H), 7.40 (d, J = 8.4 Hz, 1H), 2.86 (d, J = 4.8 Hz, 3H), 2.30 (s, 3H), 2.05 (t, J = 19.4 Hz, 3H). | 488.1 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 442 | D95 | | R (T3P) | 79 | 10.6 (s, 1H), 9.08 (d, J = 2.2 Hz, 1H), 8.84-8.88 (brm, 1H), 8.81 (d, J = 5.0 Hz, 1H), 8.71-8.76 (m, 2H), 8.39 (d, J = 1.8 Hz, 1H), 8.28 (t, J = 2.2 Hz, 1H), 8.08 (dd, J = 1.9 and 5.2 Hz, 1H), 8.02 (d, J = 1.5 Hz, 1H), 7.88 (dd, J = 1.5 and 5.1 Hz, 1H), 7.79 (dd, J = 2.3 and 8.3 Hz, 1H), 7.75 (d, J = 2.2 Hz, 1H), 7.40 (d, J = 8.3 Hz, 1H), 2.85 (d, J = 4.8 Hz, 3H), 2.29 (s, 3H), 1.77 (s, 6H). | 491.2 |
| 443 | D18 | | R (T3P) | 52 | 10.5 (s, 1H), 8.86 (m, 2H), 8.79 (s, 1H), 8.76 (d, J = 5.0 Hz, 1H), 8.68 (d, J = 4.9 Hz, 1H), 8.34 (d, J = 5.0 Hz, 1H), 8.20 (s, 1H), 7.82 (brd, J = 8.2 Hz, 1H), 7.77 (s, 1H), 7.75 (s, 1H), 7.68 (d, J = 5.0 Hz, 1H), 7.56 (d, J = 4.8 Hz, 1H), 7.39 (d, J = 8.3 Hz, 1H), 3.12 (m, 1H), 2.86 (d, J = 4.9 Hz, 3H), 2.30 (s, 3H), 1.28 (d, J = 7.0 Hz 6H). | 466.2 |
| 444 | D27 | | R | 50 | 10.8 (s, 1H), 8.95 (d, J = 2.4 Hz, 1H), 8.88 (d, J = 5.0 Hz, 1H), 8.85 (q, J = 4.9 Hz, 1H), 8.79 (s, 1H), 8.74-8.79 (m, 2H), 8.34 (dd, J = 1.8 and 5.1 Hz, 1H), 8.30 (d, J = 1.5 Hz, 1H), 8.17 (d, J = 2.5 Hz, 1H), 8.07 (s, 1H), 7.85 (dd, J = 1.6 and 5.0 Hz, 1H), 7.63 (dd, J = 1.5 and 4.9 Hz, 1H), 2.85 (d, J = 4.8 Hz, 3H), 1.70 (d, J = 22.1 Hz, 6H). 3Hs are under solvents | 485.2 |
| 445 | D95 | | R (T3P) | 52 | 10.5 (s, 1H), 9.08 (d, J = 2.2 Hz, 1H), 8.84-8.88 (brm, 1H), 8.75 (d, J = 5.1 Hz, 1H), 8.73 (d, J = 2.0 Hz, 1H), 8.68 (d, J = 5.1 Hz, 1H), 8.39 (d, J = 1.8 Hz, 1H), 8.28 (t, J = 2.2 Hz, 1H), 8.08 (dd, J = 1.9 and 5.2 Hz, 1H), 7.80 (dd, J = 2.3 and 8.2 Hz, 1H), 7.73-7.76 (m, 2H), 7.67 (dd, J = 1.6 and 5.1 Hz, 1H), 7.39 (d, J = 8.3 Hz, 1H), 3.11 (m, 1H), 2.85 (d, J = 4.8 Hz, 3H), 2.29 (s, 3H), 1.28 (d, J = 6.9 Hz, 6H). | 466.2 |
| 446 | D81 | | R | 16 | 10.5 (s, 1H), 9.44 (d, J = 2.2 Hz, 1H), 9.42 (d, J = 1.3 Hz, 1H), 9.06 (q, J = 4.8 Hz, 1H), 8.80 (d, J = 2.1 Hz, 1H), 8.67 (dd, J = 0.8 and 5.1 Hz, 1H), 8.66 (d, J = 1.4 Hz, 1H), 8.62 (t, J = 2.2 Hz, 1H), 7.80 (dd, J = 2.3 and 8.3 Hz, 1H), 7.76 (d, J = 2.3 Hz, 1H), 7.74 (s, 1H), 7.67 (dd, J = 1.7 and | 467.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | 5.1 Hz, 1H), 7.38 (d, J = 8.3 Hz, 1H), 3.10 (m, 1H), 2.86 (d, J = 4.9 Hz, 3H), 2.27 (s, 3H), 1.27 (d, J = 6.9 Hz, 6H). | |
| 447 | F37 | | P | 58 | 10.6 (brs, 1H), 8.89 (d, J = 5.2 Hz, 1H), 8.86 (d, J = 6.0 Hz, 1H), 8.81 (d, J = 0.8 Hz, 1H), 8.76 (d, J = 5.2 Hz, 1H), 8.52 (dd, J = 1.6 and 5.2 Hz, 1H), 8.32 (s, 1H), 8.03 (s, 1H), 7.82 (m, 2H), 7.77 (d, J = 2.0 Hz, 1H), 7.59 (dd, J = 1.2 and 4.8 Hz, 1H), 7.40 (d, J = 8.0 Hz, 1H), 2.29 (s, 3H), 1.70 (d, J = 22.0 Hz, 6H). | 452.2 |
| 448 | A23 F37 | | P | 38 | 10.6 (s, 1H), 8.86 (d, J = 5.2 Hz, 1H), 8.79 (brs, 1H), 8.73-8.78 (m, 3H), 8.35 (dd, J = 1.6 and 5.2 Hz, 1H), 8.21 (s, 1H), 8.04 (s, 1H), 7.83 (m, 2H), 7.76 (d, J = 2.0 Hz, 1H), 7.57 (dd, J = 1.2 and 5.2 Hz, 1H), 7.39 (d, J = 8.4 Hz, 1H), 4.81 (t, J = 5.6 Hz, 1H), 3.55 (m, 2H), 3.42 (m, 2H), 2.29 (s, 3H), 1.70 (d, J = 22.0 Hz, 6H). | 514.2 |
| 449 | D103 | | R & Q | 14 | 10.6 (s, 1H), 8.83 (brq, J = 4.0 Hz, 1H), 8.74 (m, 2H), 8.70 (s, 1H), 8.31 (d, J = 4.4 Hz, 1H), 8.03 (s, 1H), 7.72-7.86 (m, 4H), 7.37 (d, J = 8.0 Hz, 1H), 6.93 (s, 1H), 4.91 (brt, J = 4.0 Hz, 1H), 4.50 (brt, J = 4.8 Hz, 2H), 3.82 (m, 2H), 2.85 (d, J = 4.4 Hz, 3H), 2.89 (s, 3H), 1.70 (d, J = 22.0 Hz, 6H). | 544.3 |
| 450 | A24 F37 | | P, Q & reductive alkylation HCOH | 10 | 10.6 (brs, 1H), 9.13 (d, J = 4.0 Hz, 1H), 8.85 (d, J = 4.8 Hz, 1H), 8.75-8.78 (m, 3H), 8.36 (dd, J = 2.0 and 5.4 Hz, 1H), 8.20 (s, 1H), 8.03 (s, 1H), 7.81-7.83 (m, 2H), 7.76 (d, J = 2.0 Hz, 1H), 7.56 (dd, J = 1.2 and 4.8 Hz, 1H), 7.39 (d, J = 8.4 Hz, 1H), 4.49 (m, 1H), 3.56 (t, J = 7.2 Hz, 2H), 3.07 (t, J = 6.6 Hz, 2H), 2.29 (s, 3H), 2.25 (s, 3H), 1.70 (d, J = 22.4 Hz, 6H). | 539.2 |
| 451 | A25 F37 | | P | 8 | 10.6 (brs, 1H), 9.56 (t, J = 5.6 Hz, 1H), 8.87 (d, J = 4.8 Hz, 1H), 8.30 (d, J = 1.2 Hz, 1H), 8.81 (d, J = 5.2 Hz, 1H), 8.76 (d, J = 5.2 Hz, 1H), 8.42 (dd, J = 1.6 and 4.8 Hz, 1H), 8.25 (brs, 1H), 8.04 (brs, 1H), 7.83 (m, 1H), 7.82 (d, J = 1.6 Hz, 1H), 7.77 (d, J = 2.0 Hz, 1H), 7.58 (dd, J = 1.6 and 5.2 Hz, 1H), 7.40 (d, J = 8.4 Hz, 1H), 4.34 (d, J = | 509.3 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| | | | | | 6.0 Hz, 2H), 2.29 (s, 3H), 1.70 (d, J = 22.4Hz, 6H). | |
| 452 | 447 | | CH$_3$NH$_2$ | 11 | 10.7 (s, 1H), 9.54 (brs, 2H), 8.92 (m, 2H), 8.89 (d, J = 4.8 Hz, 1H), 8.76 (d, J = 5.2 Hz, 1H), 8.52 (brd, J = 5.2 Hz, 1H), 8.26 (s, 1H), 8.03 (s, 1H), 7.80-7.83 (m, 2H), 7.79 (dd, J = 2.0 and 8.4 Hz, 1H), 7.61 (dd, J = 1.6 and 5.2 Hz, 1H), 7.41 (d, J = 8.0 Hz, 1H), 3.06 (s, 3H), 2.29 (s, 3H), 1.70 (d, J = 22.0 Hz, 6H) | 483.3 |
| 453 | A26 F37 | | P | 16 | 10.6 (s, 1H), 8.86 (d, J = 4.8 Hz, 1H), 8.79 (d, J = 1.2 Hz, 1H), 8.76 (t, J = 5.2 Hz, 2H), 8.70 (t, J = 5.6 Hz, 1H), 8.36 (dd, J = 1.6 and 5.2 Hz, 1H), 8.21 (s, 1H), 8.04 (s, 1H), 7.80-7.85 (m, 2H), 7.77 (d, J = 2.0 Hz, 1H), 7.56 (dd, J = 1.2 and 4.8 Hz, 1H), 7.39 (d, J = 9.6 Hz, 1H), 3.42 (q, J = 6.0 Hz, 2H), 2.44 (t, J = 6.4 Hz, 2H), 2.30 (s, 3H), 2.19 (s, 6H), 1.70 (d, J = 22.0 Hz, 6H). | 541.3 |
| 454 | D51 | | R | 44 | 10.9 (s, 1H), 10.8 (s, 1H), 8.96 (d, J = 2.5 Hz, 1H), 8.89 (m, 1H), 8.85 (dd, J = 2.0 and 5.0 Hz, 1H), 8.79 (d, J = 5.0 Hz, 1H), 8.44 (d, J = 5.2 Hz, 1H), 8.15 (d, J = 2.4 Hz, 1H), 8.07 (dt, J = 1.3 and 2.4 Hz, 2H), 7.84 (m, 2H), 7.60 (dd, J = 1.6 and 4.9 Hz, 1H), 2.48 (s, 3H), 2.04 (m, 1H), 1.72 (d, J = 24.0 Hz, 6H), 0.84 (m, 4H). | 511.2 |
| 455 | D13 | | R | 75 | 10.9 (s, 1H), 10.6 (s, 1H), 8.86 (s, 1H), 8.81 (d, J = 5.0 Hz, 1H), 8.76 (d, J = 5.1 Hz, 1H), 8.43 (d, J = 5.3 Hz, 1H), 8.03 (s, 1H), 7.96 (s, 1H), 7.81-7.85 (m, 3H), 7.74 (d, J = 2.3 Hz, 1H), 7.52 (dd, J = 1.5 and 5.0 Hz, 1H), 7.39 (d, J = 8.4 Hz, 1H), 2.28 (s, 3H), 2.04 (m, 1H), 1.70 (d, J = 22.5 Hz, 6H), 0.83 (m, 4H). | 510.2 |
| 456 | D13 | | R | 46 | 10.9 (s, 1H), 10.6 (s, 1H), 8.85 (s, 1H), 8.82 (s, 1H), 8.81 (s, 1H), 8.43 (d, J = 5.3 Hz, 1H), 8.01 (s, 1H), 7.96 (s, 1H), 7.87 (dd, J = 1.5 and 5.1 Hz, 1H), 7.78-7.84 (m, 2H), 7.73 (d, J = 2.3 Hz, 1H), 7.52 (dd, J = 1.6 and 4.9 Hz, 1H), 7.40 (d, J = 8.4 Hz, 1H), 2.28 (s, 3H), 2.04 (m, 1H), 1.76 (s, 6H), 0.78-0.88 (m, 4H). | 517.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 457 | D13 | | R | 58 | 10.9 (s, 1H), 10.6 (s, 1H), 8.86 (d, J = 1.7 Hz, 1H), 8.81 (d, J = 5.1 Hz, 1H), 8.72 (dd, J = 0.5 and 5.5 Hz, 1H), 8.43 (d, J = 0.5 and 5.3 Hz, 1H), 8.13 (s, 1H), 7.97 (s, 1H), 7.94 (s, 1H), 7.78-7.84 (m, 2H), 7.73 (d, J = 2.3 Hz, 1H), 7.52 (dd, J = 1.6 and 5.0 Hz, 1H), 7.40 (d, J = 8.4 Hz, 1H), 2.28 (s, 3H), 2.04 (m, 1H), 1.88 (dd, J = 4.4 and 8.5 Hz, 2H), 1.78 (dd, J = 4.4 and 8.5 Hz, 2H), 0.78-0.88 (m, 4H). | 515.2 |
| 458 | D13 | | R | 63 | 10.9 (s, 1H), 10.5 (s, 1H), 8.86 (s, 1H), 8.81 (d, J = 4.9 Hz, 1H), 8.57 (d, J = 5.2 Hz, 1H), 8.43 (d, J = 5.2 Hz, 1H), 7.96 (s, 1H), 7.78-7.84 (m, 2H), 7.74 (m, 2H), 7.57 (dd, J = 1.7 and 5.1 Hz, 1H), 7.51 (dd, J = 1.5 and 4.9 Hz, 1H), 7.38 (d, J = 8.4 Hz, 1H), 2.27 (s, 3H), 2.21 (m, 1H), 2.04 (m, 1H), 0.93-1.05 (m, 4H), 0.78-0.88 (m, 4H). | 490.2 |
| 459 | D13 | | R | 37 | 10.9 (s, 1H), 10.7 (s, 1H), 8.89 (d, J = 5.0 Hz, 1H), 8.86 (s, 1H), 8.81 (d, J = 5.0 Hz, 1H), 8.43 (d, J = 5.3 Hz, 1H), 8.19 (s, 1H), 8.04 (dd, J = 1.6 and 5.0 Hz, 1H), 7.97 (s, 1H), 7.81-7.85 (m, 2H), 7.75 (d, J = 2.3 Hz, 1H), 7.52 (dd, J = 1.6 and 5.0 Hz, 1H), 7.40 (d, J = 8.4 Hz, 1H), 2.28 (s, 3H), 2.02-2.07 (m, 1H), 2.06 (t, J = 19.6 Hz, 3H), 0.83 (m, 4H). | 514.2 |
| 460 | D18 | | R | 46 | 10.5 (s, 1H), 8.86 (m, 2H), 8.76 (brs, 1H), 8.74 (d, J = 5.2 Hz, 1H), 8.57 (d, J = 5.1 Hz, 1H), 8.34 (dd, J = 1.8 and 5.2 Hz, 1H), 8.19 (s, 1H), 7.81 (dd, J = 2.3 and 8.1 Hz, 1H), 7.76 (d, J = 2.0 Hz, 1H), 7.73 (s, 1H), 7.57 (m, 2H), 7.39 (d, J = 8.3 Hz, 1H), 2.86 (d, J = 4.8 Hz, 3H), 2.29 (s, 3H), 2.21 (m, 1H), 0.99 (m, 4H). | 464.2 |
| 461 | D51 | | R | 29 | 10.9 (s, 1H), 10.86 (s, 1H), 8.93 (d, J = 2.4 Hz, 1H), 8.87 (brs, 1H), 8.84 (d, J = 4.0 Hz, 1H), 8.74 (dd, J = 0.9 and 5.1 Hz, 1H), 8.44 (dd, J = 0.8 and 5.2 Hz, 1H), 8.14 (d, J = 2.4 Hz, 1H), 8.07 (brs, 1H), 7.97 (brt, J = 1.2 Hz, 1H), 7.82 (m, 2H), 7.60 (dd, J = 1.6 and 5.0 Hz, 1H), 2.48 (s, 3H), 2.04 (m, 1H), 1.89 (m, 2H), 1.77 (m, 2H), 0.78-0.88 (m, 4H). | 516.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 462 | D27 | | R | 14 | 10.7 (s, 1H), 8.93 (d, J = 2.4 Hz, 1H), 8.88 (d, J = 5.0 Hz, 1H), 8.84 (q, J = 4.8 Hz, 1H), 8.78 (d, J = 1.8 Hz, 1H), 8.76 (d, J = 5.1 Hz, 1H), 8.59 (d, J = 5.1 Hz, 1H), 8.34 (dd, J = 1.9 and 5.1 Hz, 1H), 8.29 (s, 1H), 8.17 (d, J = 2.4 Hz, 1H), 7.77 (s, 1H), 7.63 (dd, J = 1.5 and 4.9 Hz, 1H), 7.59 (dd, J = 1.6 and 5.1 Hz, 1H), 2.85 (d, J = 4.8 Hz, 3H), 2.21 (m, 1H), 0.94-1.05 (m, 4H), 3Hs are under solvents. | 465.2 |
| 463 | D27 | | R | 70 | 10.9 (s, 1H), 8.94 (d, J = 2.4 Hz, 1H), 8.90 (d, J = 5.1 Hz, 1H), 8.88 (d, J = 5.0 Hz, 1H), 8.84 (q, J = 4.8 Hz, 1H), 8.78 (m, 1H), 8.76 (d, J = 5.1 Hz, 1H), 8.34 (dd, J = 1.8 and 5.1 Hz, 1H), 8.29 (s, 1H), 8.22 (s, 1H), 8.17 (d, J = 2.5 Hz, 1H), 8.05 (dd, J = 1.6 and 5.0 Hz, 1H), 7.63 (dd, J = 1.5 and 5.0 Hz, 1H), 2.85 (d, J = 4.8 Hz, 3H), 2.49 (s, 3H), 2.05 (t, J = 19.1 Hz, 3H), 3Hs are under solvents. | 489.2 |
| 464 | D27 | | R | 40 | 10.9 (s, 1H), 8.92 (d, J = 2.4 Hz, 1H), 8.88 (d, J = 5.0 Hz, 1H), 8.84 (q, J = 4.8 Hz, 1H), 8.78 (m, 1H), 8.76 (d, J = 5.1 Hz, 1H), 8.73 (d, J = 5.1 Hz, 1H), 8.34 (dd, J = 1.8 and 5.1 Hz, 1H), 8.30 (s, 1H), 8.16 (d, J = 2.4 Hz, 1H), 7.97 (s, 1H), 7.81 (dd, J = 1.6 and 5.1 Hz, 1H), 7.63 (dd, J = 1.6 and 5.0 Hz, 1H), 2.85 (d, J = 4.8 Hz, 3H), 1.85-1.92 (m, 2H), 1.74-1.80 (m, 2H), 3Hs are under solvents. | 490.2 |
| 465 | D27 | | R | 31 | 10.7 (s, 1H), 8.93 (d, J = 2.4 Hz, 1H), 8.88 (d, J = 4.9 Hz, 1H), 8.84 (q, J = 4.8 Hz, 1H), 8.78 (d, J = 1.7 Hz, 1H), 8.76 (d, J = 5.1 Hz, 1H), 8.70 (d, J = 5.0 Hz, 1H), 8.34 (dd, J = 1.9 and 5.1 Hz, 1H), 8.29 (s, 1H), 8.16 (d, J = 2.4 Hz, 1H), 7.76 (s, 1H), 7.69 (dd, J = 1.7 and 5.0 Hz, 1H), 7.63 (dd, J = 1.6 and 4.9 Hz, 1H), 3.12 (m, 1H), 2.85 (d, J = 4.8 Hz, 3H), 2.49 (s, 3H), 1.28 (d, J = 6.8 Hz, 6H). | 467.2 |
| 466 | D51 | | R | 42 | 10.92 (s, 1H), 10.91 (s, 1H), 8.96 (d, J = 2.4 Hz, 1H), 8.91 (d, J = 3.6 Hz, 1H), 8.87 (m, 1H), 8.85 (d, J = 5.0 Hz, 1H), 8.44 (dd, J = 0.8 and 5.2 Hz, 1H), 8.23 (brs, 1H), 8.15 (d, J = 2.4 Hz, 1H), 8.03-8.09 (m, 2H), 7.83 (dd, J = 1.6 and | 515.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| | | | | | 5.3 Hz, 1H), 7.60 (dd, J = 1.6 and 5.0 Hz, 1H), 2.49 (s, 3H), 2.06 It, J = 19.0 Hz, 3H), 2.05 (m, 1H), 0.81-0.88 (m, 4H). | |
| 467 | D13 | | R | 34 | 10.9 (s, 1H), 10.5 (s, 1H), 8.86 (s, 1H), 8.81 (d, J = 4.9 Hz, 1H), 8.68 (d, J = 5.2 Hz, 1H), 8.43 (d, J = 5.2 Hz, 1H), 7.96 (s, 1H), 7.82 (m, 1H), 7.81 (m, 1H), 7.73 (m, 2H), 7.67 (dd, J = 1.6 and 5.1 Hz, 1H), 7.52 (dd, J = 1.5 and 5.0 Hz, 1H), 7.38 (d, J = 8.4 Hz, 1H), 3.12 (m, 1H), 2.27 (s, 3H), 2.04 (m, 1H), 1.28 (d, J = 6.9 Hz, 6H), 0.78-0.88 (m, 4H). | 492.2 |
| 468 | D51 | | R | 27 | 10.9 (s, 1H), 10.7 (s, 1H), 8.95 (d, J = 2.4 Hz, 1H), 8.88 (brs, 1H), 8.85 (d, J = 5.0 Hz, 1H), 8.71 (d, J = 5.1 Hz, 1H), 8.44 (br d, J = 5.3 Hz, 1H), 8.15 (d, J = 2.5 Hz, 1H), 8.07 (brs, 1H), 7.83 (dd, J = 1.6 and 5.3 Hz, 1H), 7.77 (brs, 1H), 7.70 (dd, J = 1.7 and 5.1 Hz, 1H), 7.60 (dd, J = 1.5 and 5.0 Hz, 1H), 3.14 (m, 1H), 2.48 (s, 3H), 2.05 (m, 1H), 1.29 (d, J = 6.8 Hz, 6H), 0.80-0.87 (m, 4H). | 493.2 |
| 469 | A6 F71 | | P | 60 | 10.6 (s, 1H), 8.87 (d, J = 1.1 Hz, 1H), 8.82 (q, J = 4.8 Hz, 1H), 8.73 (m, 3H), 8.29 (m, 2H), 8.02 (d, J = 2.0 Hz, 1H), 7.83 (m, 2H), 7.78 (d, J = 2.2 Hz, 1H), 7.40 (d, J = 8.4 Hz, 1H), 2.84 (d, J = 4.8 Hz, 3H), 2.18 (s, 3H), 1.68 (d, J = 22.1 Hz, 6H). | 502.2 |
| 470 | A6 F72 | | P | 54 | 10.6 (s, 1H), 8.83 (d, J = 5.0 Hz, 1H), 8.69-8.77 (m, 3H), 8.29 (dd, J = 1.8 and 5.1 Hz, 1H), 8.02 (s, 1H), 7.98 (s, 1H), 7.77-7.84 (m, 2H), 7.73 (d, J = 2.2 Hz, 1H), 7.33-7.43 (m, 2H), 2.84 (d, J = 4.8 Hz, 3H), 2.65 (s, 3H), 2.28 (s, 3H), 1.97 (s, 1H), 1.68 (d, J = 22.2 Hz, 6H), 1.16 (t, J = 7.1 Hz, 1H), 1.05 (s, 1H). | 498.2 |
| 471 | A6 F73 | | P | 56 | 11.0 (s, 1H), 8.87 (dd, J = 10.9, 5.0 Hz, 2H), 8.81-8.74 (m, 3H), 8.31 (m, 1H), 8.24 (s, 1H), 8.17 (m, 1H), 8.05 (s, 1H), 7.90-7.99 (m, 2H), 7.84 (dd, J = 1.6 and 5.1 Hz, 1H), 7.55 (d, J = 4.9 Hz, 1H), 2.86 (d, J = 4.8 Hz, 3H), 1.70 (d, J = 22.2 Hz, 6H). | 538.0 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 472 | A6 F74 | | P | 63 | 10.6 (s, 1H), 8.82 (q, J = 4.7 Hz, 1H), 8.71-8.77 (m, 3H), 8.70 (d, J = 5.1 Hz, 1H), 8.29 (dd, J = 1.8 and 5.1 Hz, 1H), 8.00 (d, J = 11.7 Hz, 2H), 7.75-7.84 (m, 2H), 7.60 (d, J = 2.3 Hz, 1H), 7.38 (d, J = 8.4 Hz, 1H), 2.84 (d, J = 4.8 Hz, 3H), 2.13 (s, 3H), 2.04 (s, 3H), 1.69 (d, J = 22.1 Hz, 6H). | 498.2 |
| 473 | A6 F75 | | P | 11 | 10.7 (s, 1H), 9.44 (d, J = 1.9 Hz, 1H), 8.88 (q, J = 4.7 Hz, 1H), 8.83 (m, 2H), 8.75 (d, J = 5.0 Hz, 1H), 8.51 (d, J = 2.0 Hz, 1H), 8.41 (dd, J = 1.8 and 5.1 Hz, 1H), 8.03 (s, 1H), 7.83 (m, 3H), 7.42 (d, J = 8.4 Hz, 1H), 2.85 (d, J = 4.8 Hz, 3H), 2.32 (s, 3H), 7.68 (d, J = 22.2 Hz, 6H). | 485.2 |
| 474 | A6 F76 | | P | 66 | 10.7 (s, 1H), 9.46 (d, J = 1.3 Hz, 1H), 8.87 (q, J = 4.8 Hz, 1H), 8.83 (d, J = 4.8 Hz, 2H), 8.75 (dt, J = 1.0 and 5.1 Hz, 1H), 8.45 (d, J = 1.3 Hz, 1H), 8.42 (m, 1H), 8.04 (t, J = 1.3 Hz, 1H), 8.00 (d, J = 2.3 Hz, 1H), 7.88 (dd, J = 2.3 and 8.3 Hz, 1H), 7.83 (dd, J = 1.6 and 5.1 Hz, 1H), 7.39 (d, J = 8.4 Hz, 1H), 2.85 (d, J = 4.8 Hz, 3H), 2.42 (s, 3H), 1.69 (d, J = 22.2 Hz, 6H). | 485.2 |
| 475 | D104 | | R | 21 | 10.8 (s, 1H), 8.89 (d, J = 5.1 Hz, 1H), 8.84 (m, 1H), 8.77 (m, 3H), 8.38 (s, 1H), 8.34 (dd, J = 1.9 and 5.0 Hz, 1H), 8.04 (s, 1H), 7.83 (dd, J = 1.6 and 5.1 Hz, 1H), 7.76 (m, 2H), 7.66 (m, 1H), 2.85 (d, J = 4.8 Hz, 3H), 1.70 (d, J = 22.2 Hz, 6H). | 506.2 |
| 476 | 447 | | K₂CO₃ H₂O₂ | 100 | 10.6 (s, 1H), 8.84 (d, J = 5.0 Hz, 1H), 8.78 (s, 1H), 8.75 (d, J = 5.1 Hz, 2H), 8.33 (dd, J = 1.8 and 5.2 Hz, 1H), 8.19 (s, 2H), 8.03 (s, 1H), 7.80-7.84 (m, 2H), 7.76 (d, J = 2.2 Hz, 1H), 7.71 (s, 1H), 7.55 (m, 1H), 7.39 (d, J = 8.3 Hz, 1H), 2.29 (s, 3H), 1.70 (d, J = 22.1 Hz, 6H). | 470.2 |
| 477 | D18 | | R | 63 | 10.9 (s, 1H), 9.91 (d, J = 2.2 Hz, 1H), 8.84 (t, J = 5.5 Hz, 2H), 8.71-8.78 (m, 2H), 8.68 (d, J = 2.1 Hz, 1H), 8.32 (d, J = 5.0 Hz, 1H), 8.18 (s, 1H), 7.80 (d, J = 8.4 Hz, 1H), 7.74 (s, 1H), 7.55 (d, J = 5.0 Hz, 1H), 7.42 (d, J = 8.4 Hz, 1H), 2.84 (d, J = 5.1 Hz, 3H), 2.29 (s, 3H). | 493.0 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 478 | A6 F77 | | P | 25 | 10.9 (s, 1H), 8.91 (d, J = 5.0 Hz, 1H), 8.84 (q, J = 4.8 Hz, 1H), 8.72-8.80 (m, 3H), 8.37 (s, 1H), 8.32 (dd, J = 1.8 and 5.1 Hz, 1H), 8.08 (m, 1H), 8.05 (s, 1H), 7.83 (dd, J = 1.8 and 5.1 Hz, 2H), 7.72 (d, J = 4.9 Hz, 1H), 2.84 (d, J = 4.8 Hz, 3H), 1.70 (d, J = 22.2 Hz, 6H). | 506.0 |
| 479 | D105 | | R (T3P) | 54 | 10.8 (s, 1H), 8.89 (d, J = 5.2 Hz, 1H), 8.86 (q, J = 4.4 Hz, 1H), 8.73-8.81 (m, 3H), 8.31-8.36 (m, 2H), 8.10 (dd, J = 2.8 and 6.8 Hz, 1H), 8.06 (s, 1H), 7.99-7.93 (m, 1H), 7.85 (dd, J = 1.6 and 5.1 Hz, 1H), 7.72 (br d, J = 5.1 Hz, 1H), 7.46 (dd, J = 10.4, 9.0 Hz, 1H), 2.86 (d, J = 4.8 Hz, 3H), 1.71 (d, J = 22.1 Hz, 6H). | 488.0 |
| 480 | D106 | | R (T3P) | 39 | 10.8 (s, 1H), 8.87 (d, J = Hz, 1H), 8.84 (q, J = 4.4 Hz, 1H), 8.73-8.80 (m, 3H), 8.34 (dd, J = 1.8 and 5.2 Hz, 1H), 8.23 (s, 1H), 8.04 (s, 1H), 7.86 (dd, J = 2.0 and 12.0 Hz, 1H), 7.83 (dd, J = 1.6 and 5.2 Hz, 1H), 7.59 (br s 1H), 7.57 (dd, J = 1.2 and 4.8 Hz, 1H), 2.86 (d, J = 4.8 Hz, 3H), 2.18 (d, J = 2.1 Hz, 3H), 1.70 (d, J = 22.2 Hz, 6H). | 502.2 |
| 481 | A6 F78 | | P | 27 | 11.1 (s, 1H), 8.93 (d, J = 5.1 Hz, 1H), 8.88 (q, J = 4.5 Hz, 1H), 8.82 (d, J = 5.1 Hz, 1H), 8.79 (d, J = 5.1 Hz, 1H), 8.75 (m, 1H), 8.74 (s, 1H), 8.67 (s, 1H), 8.50 (brs, 1H), 8.35 (dd, J = 1.8 and 5.1 Hz, 1H), 8.05-8.12 (m, 2H), 7.99 (dd, J = 1.8 and 5.5 Hz, 1H), 7.89 (dd, J = 1.6 and 5.0 Hz, 1H), 2.87 (d, J = 4.8 Hz, 3H), 1.73 (d, J = 22.2 Hz, 6H). | 471.0 |
| 482 | A6 F79 | | P | 31 | 10.7 (s, 1H), 8.88 (d, J = 5.0 Hz, 1H), 8.86 (q, J = 4.4 Hz, 1H), 8.74-8.82 (m, 3H), 8.32-8.38 (m, 2H), 8.09 (s, 1H), 8.05 (t, J = 7.2 Hz, 1H), 7.85 (dd, J = 1.6 and 5.0 Hz, 1H), 7.73 (m, 1H), 7.67 (t, J = 10.4 Hz, 1H), 2.86 (d, J = 4.8 Hz, 3H), 1.72 (d, J = 22.8 Hz, 6H). | 506.2 |
| 483 | F72 | | P | 53 | 10.63 (s, 1H), 8.87 (d, J = 0.8 Hz, 1H), 8.78 (s, 1H), 8.77 (d, J = 3.6 Hz, 1H), 8.50 (dd, J = 1.8 and 5.2 Hz, 1H), 8.13 (s, 1H), 8.05 (s, 1H), 7.83 (dd, J = 1.2 and 4.0 Hz, 1H), 7.81 (dd, J = 2.0 and 6.4 Hz, 1H), 7.77 (d, J = 2.3 Hz, 1H), 7.45 (s, 1H), 7.39 (d, J = | 466.2 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| | | | | | 8.4 Hz, 1H), 2.67 (s, 3H), 2.30 (s, 3H), 1.71 (d, J = 22.1 Hz, 6H). | |
| 484 | 483 | | K₂CO₃ H₂O₂ | 74 | 10.65 (s, 1H), 8.78 (d, J = 1.8 Hz, 1H), 8.76 (d, J = 4.0 Hz, 1H), 8.74 (d, J = 4.0 Hz, 1H), 8.32 (dd, J = 1.8 and 5.2 Hz, 1H), 8.19 (d, J = 2.7 Hz, 1H), 8.04 (s, 1H), 7.99 (s, 1H), 7.80-7.85 (m, 2H), 7.75 (d, J = 2.3 Hz, 1H), 7.73 (d, J = 2.7 Hz, 1H), 7.42 (s, 1H), 7.38 (d, J = 8.4 Hz, 1H), 2.67 (s, 3H), 2.29 (s, 3H), 1.70 (d, J = 22.1 Hz, 6H). | 484.2 |
| 485 | A6 F80 | | P | 36 | 10.81 (s, 1H), 8.90 (d, J = 5.1 Hz, 1H), 8.86 (q, J = 4.4 Hz, 1H), 8.74-8.79 (m, 3H), 8.33 (m, 1H), 8.29 (s, 1H), 8.04 (s, 1H), 7.94-8.00 (m, 2H), 7.83 (dd, J = 1.6 and 5.1 Hz, 1H), 7.68 (d, J = 6.4 Hz, 1H), 7.65 (dd, J = 1.6 and 4.0 Hz, 1H), 2.85 (d, J = 4.0 Hz, 3H), 1.70 (d, J = 22.2 Hz, 6H). | 504.0 |
| 486 | F75 | | P And then K₂CO₃ H₂O₂ | 36 | 10.74 (s, 1H), 9.46 (s, 1H), 8.88 (s, 1H), 8.85 (d, J = 4.0 Hz, 1H), 8.76 (d, J = 5.1 Hz, 1H), 8.54 (d, J = 2.1 Hz, 1H), 8.45 (m, 1H), 8.25 (s, 1H), 8.05 (s, 1H), 7.83-7.92 (m, 3H), 7.77 (s, 1H), 7.43 (d, J = 8.3 Hz, 1H), 2.34 (s, 3H), 1.71 (d, J = 22.2 Hz, 6H). | 471.2 |
| 487 | D18 | | R | 54 | 10.66 (s, 1H), 8.84-8.88 (m, 2H), 8.79 (d, J = 0.8 Hz, 1H), 8.76 (d, J = 3.6 Hz, 1H), 8.71 (d, J = 3.6 Hz, 1H), 8.35 (dd, J = 1.8 and 1.8 Hz, 1H), 8.21 (s, 1H), 8.10 (s, 1H), 7.85 (dd, J = 2.3 and 8.3 Hz, 1H), 7.76-7.82 (m, 2H), 7.57 (dd, J = 1.6 and 5.0 Hz, 1H), 7.40 (d, J = 8.3 Hz, 1H), 2.87 (d, J = 4.8 Hz, 3H), 2.31 (s, 3H), 1.54-1.64 (m, 2H), 1.37-1.44 (m, 2H). | 482.0 |
| 488 | F76 | | P And then K₂CO₃ H₂O₂ | 81 | 10.69 (s, 1H), 9.48 (d, J = 1.3 Hz, 1H), 8.82-8.87 (m, 2H), 8.76 (d, J = 5.0 Hz, 1H), 8.48 (d, J = 0.8 Hz, 1H), 8.44 (dd, J = 1.6 and 4.4 Hz, 1H), 8.24 (s, 1H), 8.12 (s, 1H), 8.06 (s, 1H), 8.01 (d, J = 1.8 Hz, 1H), 7.89 (dd, J = 2.3 and 8.3 Hz, 1H), 7.85 (dd, J = 1.6 and 5.1 Hz, 1H), 7.79 (s, 1H), 7.41 (d, J = 8.4 Hz, 1H), 2.44 (s, 3H), 1.70 (d, J = 22.1 Hz, 6H). | 471.0 |

TABLE I-continued

| Ex No. | SM | Product | Method | Yield (%) | ¹H NMR (400 or 500 MHz, (DMSO-d₆): δ | MS (m/z: M + H⁺) |
|---|---|---|---|---|---|---|
| 489 | A27 F37 | (structure) | | 30 | 10.63 (s, 1H), 8.85 (d, J = 5.0 Hz, 1H), 8.82 (s, 1H), 8.78 (d, J = 1.8 Hz, 1H), 8.75 (d, J = 1.8 Hz, 2H), 8.34 (dd, J = 1.8 and 5.1 Hz, 1H), 8.20 (s, 1H), 8.04 (s, 1H), 7.80-7.86 (m, 2H), 7.77 (d, J = 2.3 Hz, 1H), 7.56 (dd, J = 1.5 and 5.1 Hz, 1H), 7.39 (d, J = 8.4 Hz, 1H), 2.29 (s, 3H), 1.70 (d, J = 22.1 Hz, 6H). | 487.2 |
| 490 | (structure) F71 | (structure) | P And then K₂CO₃ H₂O₂ | 30 | 10.66 (s, 1H), 8.87 (s, 1H), 8.74-8.78 (m, 3H), 8.28-8.34 (m, 2H), 8.19 (s, 1H), 8.02 (s, 1H), 7.84 (dd, J = 2.4 and 6.0 Hz, 1H), 7.80 (dd, J = 1.2 and 4.0 Hz, 1H), 7.77 (d, J = 2.3 Hz, 1H), 7.72 (s, 1H), 7.41 (d, J = 8.4 Hz, 1H), 2.18 (s, 3H), 1.68 (d, J = 22.2 Hz, 6H). | 488.2 |
| 491 | (structure) F81 | (structure) | P And then K₂CO₃ H₂O₂ | 40 | 10.84 (s, 1H), 8.87 (d, J = 5.1 Hz, 1H), 8.75 (m, 3H), 8.35 (m, 2H), 8.27 (m, 1H), 8.11 (dd, J = 2.7 and 7.0 Hz, 1H), 8.04 (d, J = 1.6 Hz, 1H), 7.97 (m, 1H), 7.88 (dd, J = 1.6 and 5.1 Hz, 1H), 7.71 (m, 2H), 7.44 (dd, J = 9.0 and 10.5 Hz, 1H), 1.70 (d, J = 22.3 Hz, 6H). | 474.0 |
| 492 | D18 (structure) | (structure) | R | 68 | 10.85 (s, 1H), 9.72 (d, J = 2.0 Hz, 1H), 8.79 (m, 2H), 8.66-8.73 (m, 2H), 8.41 (d, J = 2.1 Hz, 1H), 8.27 (dd, J = 1.9 and 5.1 Hz, 1H), 8.13 (d, J = 1.5 Hz, 1H), 7.76 (dd, J = 2.3 and 8.3 Hz, 1H), 7.70 (d, J = 2.3 Hz, 1H), 7.50 (dd, J = 1.5 and 5.0 Hz, 1H), 7.36 (d, J = 8.4 Hz, 1H), 2.79 (d, J = 4.9 Hz, 3H), 2.24 (s, 3H), 2.13 (t, J = 19.4 Hz, 3H). | 489.0 |
| 493 | A27 F72 | (structure) | P | 18 | 10.60 (s, 1H), 8.80 (s, 1H), 8.71-8.78 (m, 3H), 8.29 (dd, J = 1.9 and 5.2 Hz, 1H), 8.02 (s, 1H), 7.98 (s, 1H), 7.77-7.84 (m, 2H), 7.74 (d, J = 2.3 Hz, 1H), 7.40 (s, 1H), 7.36 (d, J = 8.4 Hz, 1H), 2.65 (s, 3H), 2.28 (s, 3H), 1.69 (d, J = 22.0 Hz, 3H). | 501.2 |
| 494 | D18 (structure) | (structure) | R | 53 | 10.51 (s, 1H), 9.14 (d, J = 5.0 Hz, 1H), 8.80-8.87 (m, 2H), 8.77 (dd, J = 0.8 and 1.9 Hz, 1H), 8.74 (dd, J = 0.8 and 5.2 Hz, 1H), 8.33 (dd, J = 1.9 and 5.2 Hz, 1H), 8.20 (dd, J = 0.9 and 1.6 Hz, 1H), 8.04 (d, J = 5.0 Hz, 1H), 7.91 (dd, J = 2.3 and 8.3 Hz, 1H), 7.82 (d, J = 2.3 Hz, 1H), 7.56 (dd, J = 1.5 and 5.0 Hz, 1H), 7.41 (d, J = 8.4 Hz, 1H), 2.84 (d, J = 4.8 Hz, | 485.2 |

TABLE I-continued

| Ex No. | SM | Product | Method | Yield (%) | $^1$H NMR (400 or 500 MHz, (DMSO-d$_6$): δ | MS (m/z: M + H$^+$) |
|---|---|---|---|---|---|---|
| | | | | | 3H), 2.29 (s, 3H), 1.82 (d, J = 22.0 Hz, 6H). | |
| 495 | D18 | | R | 44 | 10.84 (s, 1H), 9.60 (d, J = 2.1 Hz, 1H), 8.81-8.87 (m, 2H), 8.76 (dd, J = 0.8 and 1.9 Hz, 1H), 8.74 (dd, J = 0.8 and 5.2 Hz, 1H), 8.32 (dd, J = 1.8 and 5.2 Hz, 1H), 8.28 (m, 1H), 8.18 (dd, J = 0.9 and 1.6 Hz, 1H), 7.81 (dd, J = 2.3 and 8.3 Hz, 1H), 7.75 (d, J = 2.3 Hz, 1H), 7.55 (dd, J = 1.5 and 5.0 Hz, 1H), 7.40 (d, J = 8.4 Hz, 1H), 2.84 (d, J = 4.8 Hz, 3H), 2.29 (s, 3H), 1.81 (d, J = 22.0Hz, 6H). | 485.2 |
| 496 | D107 | | R | 62 | 10.63 (s, 1H), 8.83 (q, J = 4.8 Hz, 1H), 8.75 (d, J = 0.9 Hz, 1H), 8.72 (d, J = 0.8 Hz, 1H), 8.69 (d, J = 1.1 Hz, 1H), 8.30 (dd, J = 1.8 and 5.2 Hz, 1H), 8.08 (s, 1H), 7.99 (s, 1H), 7.81 (dd, J = 2.3 and 8.3 Hz, 1H), 7.73-7.79 (m, 2H), 7.41 (s, 1H), 7.37 (d, J = 8.4 Hz, 1H), 2.85 (d, J = 4.9 Hz, 3H), 2.66 (s, 3H), 2.28 (s, 3H), 1.51-1.63 (m, 2H), 1.35-1.43 (m, 2H). | 496.2 |
| 497 | A6 F82 | | P | 50 | 10.53 (s, 1H), 8.78 (dd, J = 5.0 and 0.8 Hz, 2H), 8.69 (m, 3H), 8.27 (dd, J = 1.8 and 5.1 Hz, 1.2 H), 8.12 (dd, J = 0.9 and 1.6 Hz, 1H), 7.99 (q, J = 4.8 Hz, 1H), 7.76 (dd, J = 1.7 and 5.1 Hz, 1H), 7.56 (d, J = 7.7 Hz, 1H), 7.49 (dd, J = 1.6 and 5.0 Hz, 1H), 7.33 (d, J = 11.3 Hz, 1H), 2.79 (d, J = 4.8 Hz, 3H), 2.27 (s, 3H), 1.64 (d, J = 22.2 Hz, 6H). | 502.2 |
| 498 | D108 | | R | 64 | 10.65 (s, 1H), 8.83 (s, 1H), 8.75 (m, 1H), 8.67-8.73 (m, 2H), 8.30 (dd, J = 1.8 and 5.2 Hz, 1H), 8.08 (s, 1H), 7.99 (s, 1H), 7.78-7.85 (m, 1H), 7.73-7.78 (m, 2H), 7.34-7.44 (m, 2H), 2.66 (s, 3H), 2.28 (s, 3H), 1.51-1.64 (m, 2H), 1.34-1.44 (m, 2H). | 499.2 |
| 499 | A6 F83 | | P | 55 | 11.35 (s, 1H), 8.90 (d, J = 5.0 Hz, 1H), 8.83 (d, J = 4.9 Hz, 1H), 8.75 (m, 3H), 8.43 (s, 1H), 8.33 (dd, J = 1.9 and 5.1 Hz, 1H), 8.27 (s, 1H), 8.17 (s, 1H), 8.05 (d, J = 1.8 Hz, 1H), 7.85 (dd, J = 1.7 and 5.1 Hz, 1H), 7.61 (dd, J = 1.5 and 5.0 Hz, 1H), 2.84 (d, J = 4.8 Hz, 3H), 2.27 (s, 3H), 1.69 (d, J = 22.1 Hz, 6H). | 485.2 |

TABLE I-continued

| Ex No. | SM | Product | Method | Yield (%) | ¹H NMR (400 or 500 MHz, (DMSO-d$_6$): δ | MS (m/z: M + H⁺) |
|---|---|---|---|---|---|---|
| 500 | D13 | | R (T3P) | 30 | 10.95 (s, 1H), 10.16 (s, 1H), 8.94 (d, J = 2.0 Hz, 1H), 8.67 (d, J = 1.8 Hz, 1H), 8.52 (s, 1H), 8.46 (s, 1H), 8.43 (d, J = 5.4 Hz, 1H), 8.06 (t, J = 1.8 Hz, 1H), 7.68 (dd, J = 2.0 and 8.3 Hz, 1H), 7.64 (d, J = 2.0 Hz, 1H) 7.55 (dd, J = 1.4 and 5.3 Hz, 1H), 7.34 (d, J = 8.4 Hz, 1H), 3.98 (s, 3H), 2.24 (s, 3H), 2.04 (m, 1H), 0.79-0.87 (m, 4H). | 521.1 |
| 501 | D13 | | R | 93 | 10.91 (s, 1H), 10.53 (s, 1H), 8.84 (m, 1H), 8.79 (d, J = 5.0 Hz, 1H), 8.42 (m, 1H), 8.14 (d, J = 8.0 Hz, 2H), 7.87-7.97 (m, 3H), 7.80 (m, 2H), 7.75 (d, J = 2.3 Hz, 1H), 7.50 (dd, J = 1.5 and 5.0 Hz, 1H), 7.37 (d, J = 8.3 Hz, 1H), 2.26 (s, 3H), 2.02 (m, 1H), 0.76-0.87 (m, 4H). | 517.2 |
| 502 | D13 | | R | 32 | 10.91 (s, 1H), 10.53 (s, 1H), 8.85 (s, 1H), 8.79 (d, J = 5.0 Hz, 1H), 8.41 (d, J = 5.2 Hz, 1H), 8.30 (s, 1H), 8.26 (d, J = 7.9 Hz, 1H), 7.96 (m, 2H), 7.71-7.85 (m, 4H), 7.51 (dd, J = 1.5 and 5.0 Hz, 1H), 7.36 (d, J = 8.4 Hz, 1H), 2.26 (s, 3H), 2.02 (m, 1H), 0.75-0.88 (m, 4H). | 517.2 |
| 503 | D13 | | R | 55 | 10.91 (s, 1H), 10.67 (s, 1H), 8.85 (d, J = 1.6 Hz, 1H), 8.79 (d, J = 5.0 Hz, 1H), 8.41 (d, J = 5.3 Hz, 1H), 8.06 (dd, J = 2.4 and 6.3 Hz, 1H), 7.96 (d, J = 10.6 Hz, 2H), 7.80 (dd, J = 1.6 and 5.2 Hz, 1H), 7.66-7.75 (m, 2H), 7.61 (t, J = 9.1 Hz, 1H), 7.49 (dd, J = 5.1, 1.5 Hz, 1H), 7.36 (d, J = 8.3 Hz, 1H), 2.25 (s, 3H), 2.03 (m, 1H), 0.76-0.88 (m, 4H). | 535.2 |

Biochemical Assay for A-Raf (1)

Activity of A-Raf kinase (SEQ. ID No: 1) was determined spectroscopically using a coupled pyruvate kinase/lactate dehydrogenase assay that continuously monitors the ATP hydrolysis-dependent oxidation of NADH (e.g., Schindler et al., Science, 2000, 289, 1938-1942). Assays were conducted in 384-well plates (100 μL final volume) using 5.55 nM A-Raf (Sigma), 1.5 units pyruvate kinase, 2.1 units lactate dehydrogenase, 1 mM phosphoenol pyruvate, 0.28 mM NADH, 30.1 nM MEK (SignalChem), and 1 mM ATP in assay buffer (100 mM Tris, pH 7.5, 15 mM MgCl$_2$, 0.5 mM DTT, 0.1% octyl-glucoside, 0.002% (w/v) BSA, and 0.002% Triton X-100). Inhibition of A-Raf was measured by adding serial diluted test compound (final assay concentration of 1% DMSO). A decrease in absorption at 340 nm was monitored continuously for 6 h at 30° C. on a multi-mode microplate reader (BioTek). The reaction rate was calculated using the 4 to 5 h time frame. The reaction rate at each concentration of compound was converted to percent inhibition using controls (i.e., reaction with no test compound and reaction with a known inhibitor) and IC$_{50}$ values were calculated by fitting a four-parameter sigmoidal curve to the data using Prism (GraphPad software).

Biochemical Assay for A-Raf (2)

Activity of A-Raf kinase (SEQ. ID No: 1) was determined spectroscopically using a coupled pyruvate kinase/lactate dehydrogenase assay that continuously monitors the ATP hydrolysis-dependent oxidation of NADH (e.g., Schindler et al., Science, 2000, 289, 1938-1942). Assays were conducted in 384-well plates (25 μL final volume) using 20 nM A-Raf (Eurofins), 1.5 units pyruvate kinase, 2.1 units lactate dehydrogenase, 1 mM phosphoenol pyruvate, 0.7 mM NADH, 100 nM MEK (SignalChem), and 1 mM ATP in assay buffer (100 mM Tris, pH 7.5, 15 mM MgCl$_2$, 0.5 mM DTT, 0.1% octyl-glucoside, 0.002% (w/v) BSA, and 0.002% Triton X-100). Inhibition of A-Raf was measured by adding serial diluted test compound (final assay concentration of 1% DMSO). A decrease in absorption at 340 nm was monitored hourly for 4 h at 30° C. on a multi-mode microplate reader (BioTek). The reaction rate was calculated using the 3 to 4 h time frame. The reaction rate at each concentration of compound was converted to percent inhibition using controls (i.e., reaction with no test compound and reaction with a known inhibitor) and $IC_{50}$ values were calculated by fitting a four-parameter sigmoidal curve to the data using Prism (GraphPad software).

A-Raf protein sequence residues 273-end containing Y301D and Y302D mutations with N-terminal GST-tag
(SEQ. ID No: 1)
MSPILGYWKIKGLVQPTRLLLEYLEEKYEEHLYERDEGDKWRNKKFELGLE

FPNLPYYIDGDVKLTQSMAIIRYIADKHNMLGGCPKERAEISMLEGAVLDI

RYGVSRIAYSKDFETLKVDFLSKLPEMLKMFEDRLCHKTYLNGDHVTHPDF

MLYDALDVVLYMDPMCLDAFPKLVCFKKRIEAIPQIDKYLKSSKYIAWPLQ

GWQATFGGGDHPPKSDLEVLFQGPEFKSPAEQRERKSLADDKKKVKNLGYR

DSGDDWEVPPSEVQLLKRIGTGSFGTVFRGRWHGDVAVKVLKVSQPTAEQA

QAFKNEMQVLRKTRHVNILLFMGFMTRPGFAIITQWCEGSSLYHHLHVADT

RFDMVQLIDVARQTAQGMDYLHAKNIIHRDLKSNNIFLHEGLTVKIGDFGL

ATVKTRWSGAQPLEQPSGSVLWMAAEVIRMQDPNPYSFQSDVYAYGVVLYE

LMTGSLPYSHIGCRDQIIFMVGRGYLSPDLSKISSNCPKAMRRLLSDCLKF

QREERPLFPQILATIELLQRSLPKIERSASEPSLHRTQADELPACLLSAAR

LVP

Biochemical Assay for B-Raf (1)

Activity of B-Raf kinase (SEQ. ID NO: 2) was determined spectroscopically using a coupled pyruvate kinase/lactate dehydrogenase assay that continuously monitors the ATP hydrolysis-dependent oxidation of NADH (e.g., Schindler et al., Science, 2000, 289, 1938-1942). Assays were conducted in 384-well plates (100 µL final volume) using 0.13 nM B-Raf (Sigma), 1.5 units pyruvate kinase, 2.1 units lactate dehydrogenase, 1 mM phosphoenol pyruvate, 0.28 mM NADH, 30.1 nM MEK (SignalChem), and 1 mM ATP in assay buffer (100 mM Tris, Ph 7.5, 15 mM $MgCl_2$, 0.5 mM DTT, 0.1% octyl-glucoside, 0.002% (w/v) BSA, and 0.002% Triton X-100). Inhibition of B-Raf was measured by adding serial diluted test compound (final assay concentration of 1% DMSO). A decrease in absorption at 340 nm was monitored continuously for 6 h at 30° C. on a multi-mode microplate reader (BioTek). The reaction rate was calculated using the 4 to 5 h time frame. The reaction rate at each concentration of compound was converted to percent inhibition using controls (i.e., reaction with no test compound and reaction with a known inhibitor) and $IC_{50}$ values were calculated by fitting a four-parameter sigmoidal curve to the data using Prism (GraphPad software).

Biochemical Assay for B-Raf (2)

Activity of B-Raf kinase (SEQ. ID NO: 2) was determined spectroscopically using a coupled pyruvate kinase/lactate dehydrogenase assay that continuously monitors the ATP hydrolysis-dependent oxidation of NADH (e.g., Schindler et al., Science, 2000, 289, 1938-1942). Assays were conducted in 384-well plates (25 µL final volume) using 2 nM B-Raf (Sigma), 1.5 units pyruvate kinase, 2.1 units lactate dehydrogenase, 1 mM phosphoenol pyruvate, 0.7 mM NADH, 50 nM MEK (SignalChem), and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of B-Raf was measured by adding serial diluted test compound (final assay concentration of 1% DMSO). A decrease in absorption at 340 nm was monitored hourly for 4 h at 30° C. on a multi-mode microplate reader (BioTek). The reaction rate was calculated using the 2 to 3 h time frame. The reaction rate at each concentration of compound was converted to percent inhibition using controls (i.e., reaction with no test compound and reaction with a known inhibitor) and $IC_{50}$ values were calculated by fitting a four-parameter sigmoidal curve to the data using Prism (GraphPad software).

B-Raf protein sequence residues 416-766 with N-terminal GST-tag
(SEQ. ID NO: 2)
LQKSPGPQRERKSSSSSEDRNRMKTLGRRDSSDDWEIPDGQITVGQRIGSG

SFGTVYKGKWHGDVAVKMLNVTAPTPQQLQAFKNEVGVLRKTRHVNILLFM

GYSTKPQLAIVTQWCEGSSLYHHLHIIETKFEMIKLIDIARQTAQGMDYLH

AKSIIHRDLKSNNIFLHEDLTVKIGDFGLATVKSRWSGSHQFEQLSGSILW

MAPEVIRMQDKNPYSFQSDVYAFGIVLYELMTGQLPYSNINNRDQIIFMVG

RGYLSPDLSKVRSNCPKAMKRLMAECLKKKRDERPLFPQILASIELLARSL

PKIHRSASEPSLNRAGFQTEDFSLYACASPKTPIQAGGYGAFPVH

Biochemical Assay for C-Raf (1)

Activity of C-Raf kinase (SEQ. ID NO: 3) was determined spectroscopically using a coupled pyruvate kinase/lactate dehydrogenase assay that continuously monitors the ATP hydrolysis-dependent oxidation of NADH (e.g., Schindler et al., Science, 2000, 289, 1938-1942). Assays were conducted in 384-well plates (100 µL final volume) using 0.43 nM C-Raf (Sigma), 1.5 units pyruvate kinase, 2.1 units lactate dehydrogenase, 1 mM phosphoenol pyruvate, 0.28 mM NADH, 30.1 nM MEK (SignalChem), and 1 mM ATP in assay buffer (100 mM Tris, Ph 7.5, 15 mM $MgCl_2$, 0.5 mM DTT, 0.1% octyl-glucoside, 0.002% (w/v) BSA, and 0.002% Triton X-100). Inhibition of C-Raf was measured by adding serial diluted test compound (final assay concentration of 1% DMSO). A decrease in absorption at 340 nm was monitored continuously for 6 h at 30° C. on a multi-mode microplate reader (BioTek). The reaction rate was calculated using the 4 to 5 h time frame. The reaction rate at each concentration of compound was converted to percent inhibition using controls (i.e., reaction with no test compound and reaction with a known inhibitor) and $IC_{50}$ values were calculated by fitting a four-parameter sigmoidal curve to the data using Prism (GraphPad software).

Biochemical Assay for C-Raf (2)

Activity of C-Raf kinase (SEQ. ID NO: 3) was determined spectroscopically using a coupled pyruvate kinase/lactate dehydrogenase assay that continuously monitors the ATP hydrolysis-dependent oxidation of NADH (e.g., Schindler et al., Science, 2000, 289, 1938-1942). Assays were conducted in 384-well plates (25 µL final volume) using 3.84 nM C-Raf (Eurofins), 1.5 units pyruvate kinase, 2.1 units lactate dehydrogenase, 1 mM phosphoenol pyruvate, 0.7 mM NADH, 50 nM MEK (SignalChem), and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of C-Raf was measured by adding serial diluted test compound (final assay concentration of 1% DMSO). A decrease in absorption at 340 nm was monitored hourly for 4 h at 30° C. on a multi-mode microplate reader (BioTek). The reaction rate was calculated using the 2 to 3 h time frame. The reaction rate at each concentration of compound was converted to percent inhibition using controls (i.e., reaction with no test compound and reaction with a known inhibitor) and IC$_{50}$ values were calculated by fitting a four-parameter sigmoidal curve to the data using Prism (GraphPad software).

```
C-Raf residues 306-end; Y340D, Y341D with N-
terminal GST-tag
                                      (SEQ. ID NO: 3)
QPKTPVPAQRERAPVSGTQEKNKIRPRGQRDSSDDWEIEASEVMLSTRIGS

GSFGTVYKGKWHGDVAVKILKVVDPTPEQFQAFRNEVAVLRKTRHVNILLF

MGYMTKDNLAIVTQWCEGSSLYKHLHVQETKFQMFQLIDIARQTAQGMDYL

HAKNIIHRDMKSNNIFLHEGLTVKIGDFGLATVKSRWSGSQQVEQPTGSVL

WMAPEVIRMQDNNPFSFQSDVYSYGIVLYELMTGELPYSHINNRDQIIFMV

GRGYASPDLSKLYKNCPKAMKRLVADCVKKVKEERPLFPQILSSIELLQHS

LPKINRSASEPSLHRAAHTEDINACTLTTSPRLPVF
```

Biochemical Assay for B-Raf (V600E) (1)

Activity of B-Raf (V600E) (SEQ. ID NO: 4) kinase was determined spectroscopically using a coupled pyruvate kinase/lactate dehydrogenase assay that continuously monitors the ATP hydrolysis-dependent oxidation of NADH (e.g., Schindler et al., Science, 2000, 289, 1938-1942). Assays were conducted in 384-well plates (100 µL final volume) using 0.03 nM B-Raf (SignalChem), 1.5 units pyruvate kinase, 2.1 units lactate dehydrogenase, 1 mM phosphoenol pyruvate, 0.28 mM NADH, 30.1 nM MEK (SignalChem), and 1 mM ATP in assay buffer (100 mM Tris, Ph 7.5, 15 mM MgCl$_2$, 0.5 mM DTT, 0.1% octyl-glucoside, 0.002% (w/v) BSA, and 0.002% Triton X-100). Inhibition of B-Raf (V600E) was measured by adding serial diluted test compound (final assay concentration of 1% DMSO). A decrease in absorption at 340 nm was monitored continuously for 6 h at 30° C. on a multi-mode microplate reader (BioTek). The reaction rate was calculated using the 3 to 4 h time frame. The reaction rate at each concentration of compound was converted to percent inhibition using controls (i.e., reaction with no test compound and reaction with a known inhibitor) and IC$_{50}$ values were calculated by fitting a four-parameter sigmoidal curve to the data using Prism (GraphPad software).

Biochemical Assay for B-Raf (V600E) (2)

Activity of B-Raf (V600E) (SEQ. ID NO: 4) kinase was determined spectroscopically using a coupled pyruvate kinase/lactate dehydrogenase assay that continuously monitors the ATP hydrolysis-dependent oxidation of NADH (e.g., Schindler et al., Science, 2000, 289, 1938-1942). Assays were conducted in 384-well plates (25 µL final volume) using 0.5 nM B-Raf (deCode), 1.5 units pyruvate kinase, 2.1 units lactate dehydrogenase, 1 mM phosphoenol pyruvate, 0.7 mM NADH, 100 nM MEK (SignalChem), and 1 mM ATP in assay buffer (100 mM Tris, pH 7.5, 15 mM MgCl$_2$, 0.5 mM DTT, 0.1% octyl-glucoside, 0.002% (w/v) BSA, and 0.002% Triton X-100). Inhibition of B-Raf (V600E) was measured by adding serial diluted test compound (final assay concentration of 1% DMSO). A decrease in absorption at 340 nm was monitored hourly for 4 h at 30° C. on a multi-mode microplate reader (BioTek). The reaction rate was calculated using the 3 to 4 h time frame. The reaction rate at each concentration of compound was converted to percent inhibition using controls (i.e., reaction with no test compound and reaction with a known inhibitor) and IC$_{50}$ values were calculated by fitting a four-parameter sigmoidal curve to the data using Prism (GraphPad software).

```
B-Raf (V600E) residues 416-766 with a N-terminal
GST-tag
                                      (SEQ. ID NO: 4)
LQKSPGPQRERKSSSSSEDRNRMKTLGRRDSSDDWEIPDGQITVGQRIGSG

SFGTVYKGKWHGDVAVKMLNVTAPTPQQLQAFKNEVGVLRKTRHVNILLFM

GYSTKPQLAIVTQWCEGSSLYHHLHIIETKFEMIKLIDIARQTAQGMDYLH

AKSIIHRDLKSNNIFLHEDLTVKIGDFGLATEKSRWSGSHQFEQLSGSILW

MAPEVIRMQDKNPYSFQSDVYAFGIVLYELMTGQLPYSNINNRDQIIFMVG

RGYLSPDLSKVRSNCPKAMKRLMAECLKKKRDERPLFPQILASIELLARSL

PKIHRSASEPSLNRAGFQTEDFSLYACASPKTPIQAGGYGAFPVH
```

TABLE J

Inhibition of biochemical activity of BRAF, CRAF, ARAF and BRAF V600E kinases by exemplary compounds ("Exp. No.").

| Ex. No. | ARAF (1) IC$_{50}$ | BRAF (1) IC$_{50}$ | CRAF (1) IC$_{50}$ | BRAF VE (1) IC$_{50}$ | ARAF (2) IC$_{50}$ | BRAF (2) IC$_{50}$ | CRAF (2) IC$_{50}$ | BRAF VE (2) IC$_{50}$ |
|---|---|---|---|---|---|---|---|---|
| 1 | ++++ | + | + | + | | | | |
| 2 | +++ | + | + | + | | | | |
| 3 | ++++ | + | + | + | | | | |
| 4 | ++++ | + | + | + | | | | |
| 5 | ++++ | + | + | + | | | | |
| 6 | ++ | + | + | + | | | | |
| 7 | ++++ | + | + | + | | | | |
| 8 | ++++ | + | + | + | | | | |
| 9 | ++++ | ++ | + | + | | | | |
| 10 | ++++ | ++ | ++ | + | | | | |
| 11 | ++++ | ++ | + | + | | | | |
| 12 | ++++ | + | + | + | | | | |
| 13 | ++++ | + | + | + | | | | |
| 14 | ++++ | + | + | + | | | | |
| 15 | ++++ | + | + | + | | | | |
| 16 | ++++ | + | + | + | | | | |
| 17 | ++++ | + | + | + | | | | |
| 18 | ++++ | + | + | + | | | | |

TABLE J-continued

Inhibition of biochemical activity of BRAF, CRAF, ARAF and BRAF V600E kinases by exemplary compounds ("Exp. No.").

| Ex. No. | ARAF (1) IC$_{50}$ | BRAF (1) IC$_{50}$ | CRAF (1) IC$_{50}$ | BRAF VE (1) IC$_{50}$ | ARAF (2) IC$_{50}$ | BRAF (2) IC$_{50}$ | CRAF (2) IC$_{50}$ | BRAF VE (2) IC$_{50}$ |
|---|---|---|---|---|---|---|---|---|
| 19 | +++ | + | + | + | | | | |
| 20 | ++++ | + | + | + | | | | |
| 21 | ++++ | + | + | + | | | | |
| 22 | ++++ | + | + | + | | | | |
| 23 | ++++ | + | + | + | | | | |
| 24 | +++ | + | + | + | | | | |
| 25 | ++++ | + | + | + | | | | |
| 26 | ++++ | + | + | + | | | | |
| 27 | ++++ | ++ | ++ | + | | | | |
| 28 | +++ | + | + | + | | | | |
| 29 | ++++ | + | + | + | | | | |
| 30 | +++ | + | + | + | | | | |
| 31 | ++++ | ++ | + | + | | | | |
| 32 | +++ | + | + | + | | | | |
| 33 | ++++ | ++++ | ++ | + | | | | |
| 34 | ++++ | ++++ | ++++ | ++++ | | | | |
| 35 | ++++ | + | + | + | | | | |
| 36 | ++++ | + | + | + | | | | |
| 37 | ++++ | + | + | + | | | | |
| 38 | ++++ | + | + | + | | | | |
| 39 | ++++ | + | + | + | | | | |
| 40 | ++++ | + | + | + | | | | |
| 41 | ++++ | + | + | + | | | | |
| 42 | ++++ | ++ | + | + | | | | |
| 43 | ++++ | + | + | + | | | | |
| 44 | ++++ | + | + | + | | | | |
| 45 | ++++ | + | + | + | | | | |
| 46 | ++++ | + | + | + | | | | |
| 47 | ++++ | + | + | + | | | | |
| 48 | ++++ | + | + | + | | | | |
| 49 | ++++ | ++ | + | + | | | | |
| 50 | ++++ | + | + | + | | | | |
| 51 | ++++ | ++++ | ++++ | ++++ | | | | |
| 52 | ++++ | ++ | + | + | | | | |
| 53 | ++++ | +++ | ++ | + | | | | |
| 54 | ++++ | + | + | + | | | | |
| 55 | ++++ | + | + | + | | | | |
| 56 | ++++ | + | + | + | | | | |
| 57 | ++++ | + | + | + | | | | |
| 58 | ++++ | + | + | + | | | | |
| 59 | ++++ | + | + | + | | | | |
| 60 | ++++ | ++ | + | + | | | | |
| 61 | ++++ | + | + | + | | | | |
| 62 | ++ | + | + | + | | | | |
| 63 | +++ | + | + | + | | | | |
| 64 | ++++ | + | + | + | | | | |
| 65 | ++++ | + | + | + | | | | |
| 66 | ++++ | ++++ | + | + | | | | |
| 67 | ++++ | ++++ | +++ | + | | | | |
| 68 | ++++ | + | + | + | | | | |
| 69 | ++++ | ++ | ++ | + | | | | |
| 70 | +++ | + | + | + | | | | |
| 71 | ++++ | ++ | ++ | + | | | | |
| 72 | ++++ | + | + | + | | | | |
| 73 | ++++ | ++ | + | + | | | | |
| 74 | ++++ | +++ | ++ | + | | | | |
| 75 | ++++ | + | + | + | | | | |
| 76 | ++++ | + | + | + | | | | |
| 77 | ++++ | + | + | + | | | | |
| 78 | ++++ | ++ | + | + | | | | |
| 79 | ++++ | + | + | + | | | | |
| 80 | ++++ | + | + | + | | | | |
| 81 | ++++ | ++ | ++ | + | | | | |
| 82 | ++++ | + | + | + | | | | |
| 83 | ++++ | + | + | + | | | | |
| 84 | ++++ | + | + | + | | | | |
| 85 | ++++ | + | + | + | | | | |
| 86 | ++++ | ++ | + | + | | | | |
| 87 | ++++ | + | + | + | | | | |
| 88 | ++++ | + | + | + | | | | |
| 89 | ++++ | ++ | + | + | | | | |
| 90 | ++++ | ++ | + | + | | | | |
| 91 | ++++ | + | + | + | | | | |

TABLE J-continued

Inhibition of biochemical activity of BRAF, CRAF, ARAF and BRAF V600E kinases by exemplary compounds ("Exp. No.").

| Ex. No. | ARAF (1) IC$_{50}$ | BRAF (1) IC$_{50}$ | CRAF (1) IC$_{50}$ | BRAF VE (1) IC$_{50}$ | ARAF (2) IC$_{50}$ | BRAF (2) IC$_{50}$ | CRAF (2) IC$_{50}$ | BRAF VE (2) IC$_{50}$ |
|---|---|---|---|---|---|---|---|---|
| 92 | ++ | + | + | + | | | | |
| 93 | ++++ | ++++ | +++ | ++ | | | | |
| 94 | ++++ | ++ | + | + | | | | |
| 95 | ++++ | + | + | + | | | | |
| 97 | +++ | + | + | + | | | | |
| 98 | ++ | + | + | + | | | | |
| 99 | ++++ | + | + | + | | | | |
| 100 | ++++ | + | + | + | | | | |
| 101 | ++++ | + | + | + | | | | |
| 102 | ++++ | ++ | ++ | + | | | | |
| 103 | +++ | + | + | + | | | | |
| 104 | ++++ | + | + | + | | | | |
| 105 | ++++ | ++ | + | + | | | | |
| 106 | ++++ | ++ | + | + | | | | |
| 107 | +++ | + | + | + | | | | |
| 108 | ++++ | + | + | + | | | | |
| 109 | ++++ | + | + | + | | | | |
| 110 | ++++ | ++ | ++ | + | | | | |
| 111 | ++++ | +++ | ++ | + | | | | |
| 112 | +++ | + | + | + | | | | |
| 113 | ++++ | ++ | + | + | | | | |
| 114 | ++++ | + | + | + | | | | |
| 115 | ++++ | ++++ | ++++ | ++ | | | | |
| 116 | ++++ | ++ | ++ | + | | | | |
| 117 | ++++ | + | + | + | | | | |
| 118 | +++ | + | + | + | | | | |
| 119 | ++++ | ++ | ++ | + | | | | |
| 120 | ++++ | + | + | + | | | | |
| 121 | ++++ | + | + | + | | | | |
| 122 | ++++ | + | + | + | | | | |
| 123 | ++++ | + | + | + | | | | |
| 124 | ++++ | + | + | + | | | | |
| 125 | ++++ | + | + | + | | | | |
| 126 | ++++ | ++ | + | + | | | | |
| 127 | ++++ | + | + | + | | | | |
| 129 | ++++ | + | + | + | | | | |
| 130 | ++++ | + | + | + | | | | |
| 131 | ++++ | + | + | + | | | | |
| 132 | ++++ | ++ | + | + | | | | |
| 133 | ++++ | ++ | ++ | + | | | | |
| 134 | ++++ | + | + | + | | | | |
| 135 | ++++ | + | + | + | | | | |
| 136 | ++++ | + | + | + | | | | |
| 137 | ++++ | + | + | + | | | | |
| 138 | ++++ | + | + | + | | | | |
| 139 | ++++ | + | + | + | | | | |
| 140 | +++ | + | + | + | | | | |
| 141 | ++++ | ++ | + | + | | | | |
| 142 | ++++ | + | + | + | | | | |
| 143 | ++++ | ++ | + | + | | | | |
| 144 | ++ | + | + | + | | | | |
| 145 | +++ | + | + | + | | | | |
| 146 | +++ | + | + | + | | | | |
| 147 | ++++ | +++ | ++ | + | | | | |
| 148 | ++++ | ++ | ++ | + | | | | |
| 149 | ++++ | ++ | ++ | + | | | | |
| 150 | ++ | + | + | + | | | | |
| 151 | ++ | + | + | + | | | | |
| 152 | +++ | + | + | + | | | | |
| 153 | ++ | + | + | + | | | | |
| 154 | ++ | + | + | + | | | | |
| 155 | ++++ | ++ | ++ | + | | | | |
| 156 | ++++ | ++ | + | + | | | | |
| 157 | ++++ | + | + | + | | | | |
| 158 | ++++ | ++ | ++ | + | | | | |
| 159 | ++++ | ++ | + | + | | | | |
| 160 | ++++ | + | + | + | | | | |
| 161 | +++ | + | + | + | | | | |
| 162 | ++++ | ++ | ++ | + | | | | |
| 163 | ++++ | ++ | ++ | + | | | | |
| 164 | ++ | + | + | + | | | | |
| 165 | ++ | + | + | + | | | | |
| 166 | ++++ | ++ | ++ | + | | | | |

TABLE J-continued

Inhibition of biochemical activity of BRAF, CRAF, ARAF and BRAF V600E kinases by exemplary compounds ("Exp. No.").

| Ex. No. | ARAF (1) IC$_{50}$ | BRAF (1) IC$_{50}$ | CRAF (1) IC$_{50}$ | BRAF VE (1) IC$_{50}$ | ARAF (2) IC$_{50}$ | BRAF (2) IC$_{50}$ | CRAF (2) IC$_{50}$ | BRAF VE (2) IC$_{50}$ |
|---|---|---|---|---|---|---|---|---|
| 167 | ++++ | + | + | + | | | | |
| 168 | ++++ | + | + | + | | | | |
| 169 | ++ | + | + | + | | | | |
| 170 | ++++ | ++ | ++ | + | | | | |
| 171 | ++++ | + | + | + | | | | |
| 172 | ++++ | + | + | + | | | | |
| 173 | ++++ | ++ | + | + | | | | |
| 174 | ++++ | + | + | + | | | | |
| 175 | ++++ | + | + | + | | | | |
| 176 | ++++ | ++ | + | + | | | | |
| 177 | ++++ | ++ | + | + | | | | |
| 178 | ++++ | + | + | + | | | | |
| 179 | +++ | + | + | + | | | | |
| 180 | ++ | + | + | + | | | | |
| 181 | ++++ | + | + | + | | | | |
| 182 | ++++ | ++ | + | + | | | | |
| 183 | ++ | + | + | + | | | | |
| 184 | ++ | + | + | + | | | | |
| 185 | ++ | + | + | + | | | | |
| 186 | +++ | + | + | + | | | | |
| 187 | ++ | + | + | + | | | | |
| 188 | ++++ | + | + | + | | | | |
| 189 | +++ | + | + | + | | | | |
| 190 | +++ | + | + | + | | | | |
| 191 | ++++ | ++ | + | + | | | | |
| 192 | ++++ | ++ | + | + | | | | |
| 193 | ++++ | + | + | + | | | | |
| 194 | ++++ | +++ | ++ | + | | | | |
| 195 | ++++ | + | + | + | | | | |
| 196 | ++++ | ++ | ++ | + | | | | |
| 197 | ++++ | +++ | ++ | + | | | | |
| 198 | ++++ | + | + | + | | | | |
| 199 | ++++ | +++ | ++ | + | | | | |
| 200 | ++++ | ++ | + | + | | | | |
| 201 | ++++ | +++ | ++ | + | | | | |
| 202 | ++++ | + | + | + | | | | |
| 203 | ++++ | + | + | + | | | | |
| 204 | ++++ | ++ | ++ | + | | | | |
| 205 | ++++ | ++ | + | + | | | | |
| 206 | ++++ | ++ | ++ | + | | | | |
| 207 | ++++ | ++ | + | + | | | | |
| 208 | ++++ | ++++ | +++ | ++ | | | | |
| 209 | ++++ | ++++ | +++ | ++ | | | | |
| 210 | ++++ | +++ | +++ | + | | | | |
| 211 | ++++ | +++ | +++ | + | | | | |
| 212 | ++++ | + | + | + | | | | |
| 213 | ++++ | ++++ | +++ | + | | | | |
| 214 | ++++ | ++ | + | + | | | | |
| 215 | ++++ | + | + | + | | | | |
| 216 | ++++ | ++ | ++ | + | | | | |
| 217 | ++++ | ++ | + | + | | | | |
| 218 | ++++ | ++ | + | + | | | | |
| 219 | ++++ | ++ | ++ | + | | | | |
| 220 | ++++ | ++ | ++ | + | | | | |
| 221 | ++++ | + | + | + | | | | |
| 222 | +++ | + | + | + | | | | |
| 223 | +++ | + | + | + | | | | |
| 224 | +++ | + | + | + | | | | |
| 225 | ++++ | + | + | + | | | | |
| 226 | ++++ | ++++ | +++ | ++ | | | | |
| 227 | ++++ | ++ | ++ | + | | | | |
| 228 | ++++ | ++ | ++ | + | | | | |
| 229 | ++ | + | + | + | | | | |
| 230 | ++++ | + | + | + | | | | |
| 231 | ++++ | + | + | + | | | | |
| 232 | ++ | + | + | + | | | | |
| 233 | ++++ | ++ | + | + | | | | |
| 234 | ++++ | + | + | + | | | | |
| 235 | ++++ | ++ | + | + | | | | |
| 237 | ++++ | ++ | ++ | + | | | | |
| 239 | +++ | + | + | + | | | | |
| 240 | ++++ | ++ | + | + | | | | |
| 241 | ++++ | + | + | + | | | | |

TABLE J-continued

Inhibition of biochemical activity of BRAF, CRAF, ARAF and BRAF V600E kinases by exemplary compounds ("Exp. No.").

| Ex. No. | ARAF (1) IC$_{50}$ | BRAF (1) IC$_{50}$ | CRAF (1) IC$_{50}$ | BRAF VE (1) IC$_{50}$ | ARAF (2) IC$_{50}$ | BRAF (2) IC$_{50}$ | CRAF (2) IC$_{50}$ | BRAF VE (2) IC$_{50}$ |
|---|---|---|---|---|---|---|---|---|
| 242 | ++++ | ++ | ++ | + | | | | |
| 243 | ++++ | +++ | ++ | + | | | | |
| 244 | ++ | + | + | + | | | | |
| 245 | +++ | + | + | + | | | | |
| 246 | ++++ | ++ | + | + | | | | |
| 247 | ++++ | ++++ | ++ | + | | | | |
| 248 | ++++ | ++ | + | + | | | | |
| 249 | +++ | + | + | + | | | | |
| 250 | ++++ | + | + | + | | | | |
| 251 | ++++ | + | + | + | | | | |
| 252 | ++++ | + | + | + | | | | |
| 253 | ++++ | + | + | + | | | | |
| 254 | ++++ | + | + | + | | | | |
| 255 | ++++ | + | + | + | | | | |
| 256 | ++++ | + | + | + | | | | |
| 257 | +++ | + | + | + | | | | |
| 258 | ++++ | ++ | ++ | + | | | | |
| 259 | ++++ | ++ | + | + | | | | |
| 260 | ++++ | ++ | + | + | | | | |
| 261 | ++ | + | + | + | | | | |
| 262 | +++ | + | + | + | | | | |
| 263 | ++++ | + | + | + | | | | |
| 264 | ++++ | ++ | + | + | | | | |
| 265 | ++++ | + | + | + | | | | |
| 266 | ++++ | ++ | + | + | | | | |
| 267 | ++++ | + | + | + | | | | |
| 268 | ++++ | ++ | ++ | + | | | | |
| 269 | ++++ | + | + | + | | | | |
| 270 | ++++ | + | + | + | | | | |
| 271 | +++ | + | + | + | | | | |
| 272 | ++++ | + | + | + | | | | |
| 273 | ++++ | ++ | + | + | | | | |
| 274 | ++++ | + | + | + | | | | |
| 275 | +++ | + | + | + | | | | |
| 276 | ++ | + | + | + | | | | |
| 277 | ++++ | + | + | + | | | | |
| 278 | ++++ | + | + | + | | | | |
| 279 | ++++ | + | + | + | | | | |
| 280 | ++++ | + | + | + | | | | |
| 281 | ++++ | + | + | + | | | | |
| 282 | ++++ | + | + | + | | | | |
| 283 | ++++ | + | + | + | | | | |
| 284 | +++ | + | + | + | | | | |
| 285 | ++++ | + | + | + | | | | |
| 286 | ++++ | + | + | + | | | | |
| 287 | ++++ | + | + | + | | | | |
| 288 | ++++ | + | + | + | | | | |
| 289 | ++++ | ++ | ++ | + | | | | |
| 290 | ++++ | +++ | ++ | + | | | | |
| 291 | ++++ | + | + | + | | | | |
| 292 | ++++ | + | + | + | | | | |
| 293 | ++++ | + | + | + | | | | |
| 294 | ++++ | + | + | + | | | | |
| 295 | ++++ | + | + | + | | | | |
| 296 | ++++ | ++ | ++ | + | | | | |
| 297 | ++++ | + | + | + | | | | |
| 298 | ++++ | + | + | + | | | | |
| 299 | ++++ | + | + | + | | | | |
| 300 | ++++ | + | + | + | | | | |
| 301 | ++++ | + | + | + | | | | |
| 302 | ++++ | + | + | + | | | | |
| 303 | ++++ | + | + | + | | | | |
| 304 | ++++ | + | + | + | | | | |
| 305 | ++++ | + | + | + | | | | |
| 306 | ++++ | ++ | ++ | ++ | | | | |
| 307 | +++ | + | + | + | | | | |
| 308 | ++++ | + | + | + | | | | |
| 309 | ++++ | ++++ | ++ | ++ | | | | |
| 310 | ++++ | + | + | + | | | | |
| 311 | ++++ | + | + | + | | | | |
| 312 | ++++ | + | + | +++ | | | | |
| 313 | ++++ | + | + | ++++ | | | | |
| 314 | ++++ | ++ | ++ | + | | | | |

TABLE J-continued

Inhibition of biochemical activity of BRAF, CRAF, ARAF and BRAF V600E kinases by exemplary compounds ("Exp. No.").

| Ex. No. | ARAF (1) IC$_{50}$ | BRAF (1) IC$_{50}$ | CRAF (1) IC$_{50}$ | BRAF VE (1) IC$_{50}$ | ARAF (2) IC$_{50}$ | BRAF (2) IC$_{50}$ | CRAF (2) IC$_{50}$ | BRAF VE (2) IC$_{50}$ |
|---|---|---|---|---|---|---|---|---|
| 315 | +++ | + | + | + | | | | |
| 316 | ++++ | +++ | ++ | ++ | | | | |
| 317 | ++++ | +++ | ++ | ++++ | | | | |
| 318 | ++++ | +++ | ++ | ++++ | | | | |
| 319 | ++++ | + | + | + | | | | |
| 320 | ++++ | + | + | ++ | | | | |
| 321 | ++++ | + | + | + | | | | |
| 322 | ++++ | ++++ | ++++ | ++++ | | | | |
| 323 | ++++ | + | + | + | | | | |
| 324 | ++++ | ++++ | ++++ | ++++ | | | | |
| 325 | ++++ | ++ | ++ | + | | | | |
| 326 | ++++ | ++ | + | ++ | | | | |
| 327 | ++++ | ++ | + | +++ | | | | |
| 328 | ++++ | +++ | ++ | + | | | | |
| 329 | ++++ | +++ | + | + | | | | |
| 330 | ++++ | +++ | ++ | ++++ | | | | |
| 331 | ++++ | + | + | + | | | | |
| 332 | ++++ | + | + | + | | | | |
| 333 | ++++ | ++++ | ++++ | ++++ | | | | |
| 334 | ++++ | ++++ | ++++ | ++++ | | | | |
| 335 | ++++ | ++++ | ++++ | ++++ | | | | |
| 336 | ++++ | ++++ | ++++ | +++ | | | | |
| 337 | ++++ | ++++ | ++++ | ++++ | | | | |
| 338 | ++++ | ++++ | ++++ | +++ | | | | |
| 339 | ++++ | ++++ | ++++ | ++ | | | | |
| 340 | ++++ | ++++ | ++ | + | | | | |
| 341 | ++++ | ++ | + | + | | | | |
| 342 | ++++ | ++++ | ++++ | ++++ | | | | |
| 343 | ++++ | ++++ | +++ | ++ | | | | |
| 344 | ++++ | ++++ | +++ | ++ | | | | |
| 345 | ++++ | ++++ | ++ | + | | | | |
| 346 | ++++ | + | + | + | | | | |
| 347 | ++++ | +++ | ++ | + | | | | |
| 348 | ++++ | ++ | + | + | | | | |
| 349 | ++++ | ++++ | +++ | ++ | | | | |
| 350 | ++++ | ++++ | ++++ | ++++ | | | | |
| 351 | ++++ | ++++ | ++++ | +++ | | | | |
| 352 | ++++ | ++++ | ++++ | +++ | | | | |
| 353 | ++++ | ++++ | +++ | ++ | | | | |
| 354 | ++++ | +++ | ++ | + | | | | |
| 355 | ++++ | ++++ | ++++ | ++++ | | | | |
| 356 | ++++ | ++++ | ++++ | +++ | | | | |
| 357 | ++++ | ++ | + | +++ | | | | |
| 358 | ++++ | + | + | +++ | | | | |
| 359 | ++++ | ++++ | ++++ | ++++ | | | | |
| 360 | ++++ | +++ | ++ | ++++ | | | | |
| 361 | ++++ | ++ | + | ++ | | | | |
| 362 | ++++ | ++ | + | ++++ | | | | |
| 363 | ++++ | +++ | ++ | ++++ | | | | |
| 364 | ++++ | ++ | ++ | ++ | | | | |
| 365 | ++++ | ++ | ++ | +++ | | | | |
| 366 | ++++ | ++ | ++ | ++ | | | | |
| 367 | ++++ | + | + | + | | | | |
| 368 | ++++ | ++++ | ++++ | ++++ | | | | |
| 369 | ++++ | + | + | + | | | | |
| 370 | ++++ | + | + | + | | | | |
| 371 | ++++ | ++ | ++ | + | | | | |
| 372 | ++++ | ++++ | +++ | ++ | | | | |
| 373 | ++++ | + | + | ++ | | | | |
| 374 | ++++ | ++++ | ++++ | ++++ | | | | |
| 375 | ++++ | + | + | + | | | | |
| 376 | ++++ | ++ | + | + | | | | |
| 377 | ++++ | + | + | + | | | | |
| 378 | ++++ | ++ | + | + | | | | |
| 379 | ++++ | ++ | + | + | | | | |
| 380 | ++++ | + | + | + | | | | |
| 381 | ++++ | ++ | + | ++ | | | | |
| 382 | ++++ | ++ | + | ++ | | | | |
| 383 | ++++ | ++ | ++ | ++++ | | | | |
| 384 | ++++ | + | + | + | | | | |
| 385 | ++++ | ++ | ++ | + | | | | |
| 386 | ++++ | ++ | + | + | | | | |
| 387 | ++++ | + | + | + | | | | |

TABLE J-continued

Inhibition of biochemical activity of BRAF, CRAF, ARAF and BRAF V600E kinases by exemplary compounds ("Exp. No.").

| Ex. No. | ARAF (1) IC$_{50}$ | BRAF (1) IC$_{50}$ | CRAF (1) IC$_{50}$ | BRAF VE (1) IC$_{50}$ | ARAF (2) IC$_{50}$ | BRAF (2) IC$_{50}$ | CRAF (2) IC$_{50}$ | BRAF VE (2) IC$_{50}$ |
|---|---|---|---|---|---|---|---|---|
| 388 | ++++ | + | + | ++ | | | | |
| 389 | ++++ | + | + | ++ | | | | |
| 390 | ++++ | + | + | ++ | | | | |
| 391 | ++++ | + | + | + | | | | |
| 392 | ++++ | +++ | ++ | ++++ | | | | |
| 393 | ++++ | + | + | + | | | | |
| 394 | ++ | + | + | + | | | | |
| 395 | +++ | + | + | + | | | | |
| 396 | ++ | + | + | + | | | | |
| 397 | ++++ | + | + | + | | | | |
| 398 | ++++ | + | + | + | | | | |
| 399 | +++ | + | + | + | | | | |
| 400 | ++++ | + | + | ++ | | | | |
| 401 | ++++ | + | + | + | | | | |
| 402 | ++++ | + | + | + | | | | |
| 403 | ++++ | + | + | + | | | | |
| 404 | ++++ | ++ | + | + | | | | |
| 405 | ++++ | + | + | + | | | | |
| 406 | +++ | + | + | + | | | | |
| 407 | ++++ | +++ | ++ | ++ | | | | |
| 408 | ++++ | ++ | + | + | | | | |
| 409 | ++++ | ++ | ++ | +++ | | | | |
| 410 | ++++ | + | + | + | | | | |
| 411 | ++++ | + | + | + | | | | |
| 412 | ++ | + | + | + | | | | |
| 413 | ++++ | + | + | + | | | | |
| 414 | ++++ | + | + | + | | | | |
| 415 | ++++ | +++ | ++ | ++++ | | | | |
| 416 | ++++ | + | + | + | | | | |
| 417 | ++ | + | + | + | | | | |
| 418 | +++ | + | + | + | | | | |
| 419 | +++ | + | + | + | | | | |
| 420 | ++++ | + | + | + | | | | |
| 421 | ++++ | + | + | + | | | | |
| 422 | ++++ | ++ | + | + | | | | |
| 423 | ++++ | + | + | + | | | | |
| 424 | +++ | + | + | + | | | | |
| 425 | ++++ | + | + | + | | | | |
| 426 | ++++ | ++++ | +++ | ++++ | | | | |
| 427 | ++++ | ++ | + | + | | | | |
| 428 | ++++ | ++ | ++ | + | | | | |
| 429 | ++ | + | + | + | | | | |
| 430 | +++ | + | + | + | | | | |
| 431 | ++ | + | + | + | | | | |
| 432 | ++++ | + | + | + | | | | |
| 433 | ++++ | + | + | + | | | | |
| 434 | ++ | + | + | + | | | | |
| 435 | ++++ | + | + | + | | | | |
| 436 | +++ | + | + | + | | | | |
| 437 | ++++ | ++ | + | + | | | | |
| 438 | ++++ | + | + | + | | | | |
| 439 | | | | | ++++ | + | + | + |
| 440 | | | | | ++++ | + | + | + |
| 441 | | | | | +++ | + | + | + |
| 442 | | | | | ++++ | + | + | + |
| 443 | | | | | +++ | + | + | + |
| 444 | | | | | ++++ | ++ | + | + |
| 445 | | | | | +++ | + | + | + |
| 446 | | | | | ++++ | + | + | + |
| 447 | | | | | ++++ | ++ | + | ++ |
| 448 | | | | | ++++ | ++ | + | + |
| 449 | | | | | ++++ | ++ | + | + |
| 450 | | | | | ++++ | ++ | ++ | + |
| 451 | | | | | ++++ | + | + | + |
| 452 | | | | | ++++ | + | + | + |
| 453 | | | | | ++++ | + | + | + |
| 454 | | | | | +++ | + | + | + |
| 455 | | | | | ++ | + | + | + |
| 456 | | | | | ++ | + | + | + |
| 457 | | | | | ++ | + | + | + |
| 458 | | | | | ++ | + | + | + |
| 459 | | | | | ++ | + | + | + |
| 460 | | | | | +++ | + | + | + |

TABLE J-continued

Inhibition of biochemical activity of BRAF, CRAF, ARAF and BRAF V600E kinases by exemplary compounds ("Exp. No.").

| Ex. No. | ARAF (1) IC$_{50}$ | BRAF (1) IC$_{50}$ | CRAF (1) IC$_{50}$ | BRAF VE (1) IC$_{50}$ | ARAF (2) IC$_{50}$ | BRAF (2) IC$_{50}$ | CRAF (2) IC$_{50}$ | BRAF VE (2) IC$_{50}$ |
|---|---|---|---|---|---|---|---|---|
| 461 | | | | | ++ | + | + | + |
| 462 | | | | | ++++ | ++ | + | ++ |
| 463 | | | | | ++++ | ++ | + | + |
| 464 | | | | | ++ | ++ | + | + |
| 465 | | | | | ++++ | ++ | + | + |
| 466 | | | | | +++ | + | + | + |
| 467 | | | | | ++ | + | + | + |
| 468 | | | | | ++ | + | + | + |
| 469 | | | | | ++++ | + | + | + |
| 470 | | | | | ++++ | ++ | + | + |
| 471 | | | | | ++ | ++++ | ++++ | ++++ |
| 472 | | | | | ++++ | +++ | +++ | + |
| 473 | | | | | ++++ | ++ | + | + |
| 474 | | | | | +++ | + | + | + |
| 475 | | | | | ++++ | ++++ | ++++ | ++++ |
| 476 | | | | | +++ | + | + | + |
| 477 | | | | | ++++ | + | + | ++ |
| 478 | | | | | ++++ | ++ | ++ | + |
| 479 | | | | | ++ | ++ | + | ++ |
| 480 | | | | | ++++ | ++ | ++ | + |
| 481 | | | | | ++++ | ++++ | +++ | ++++ |
| 482 | | | | | +++ | ++ | + | + |
| 483 | | | | | ++++ | ++ | + | ++ |
| 484 | | | | | +++ | + | + | + |
| 485 | | | | | ++++ | ++ | + | + |
| 486 | | | | | ++++ | ++ | + | + |
| 487 | | | | | ++ | + | + | + |
| 488 | | | | | +++ | + | + | + |
| 489 | | | | | ++ | + | + | + |
| 490 | | | | | ++++ | ++ | + | + |
| 491 | | | | | ++++ | + | + | + |
| 492 | | | | | ++++ | + | + | + |
| 493 | | | | | ++++ | ++ | + | + |
| 494 | | | | | ++++ | ++ | + | + |
| 495 | | | | | +++ | + | + | + |
| 496 | | | | | ++++ | ++ | + | + |
| 497 | | | | | ++++ | ++ | ++ | + |
| 498 | | | | | ++++ | ++ | ++ | + |
| 499 | | | | | ++++ | ++ | + | + |
| 500 | | | | | ++++ | + | + | + |
| 501 | | | | | ++++ | + | + | ++ |
| 502 | | | | | ++ | + | + | + |
| 503 | | | | | ++ | + | + | + |

For Table J, "+" refers to an IC$_{50}$ less than or equal to 100 nM; "++" refers to an IC$_{50}$ greater than 100 nM and less than or equal to 500 nM; "+++" refers to an IC$_{50}$ greater than 500 nM and less than or equal to 1000 nM; and "++++" refers to an IC$_{50}$ greater than 1000 nM and less than or equal to 10000 nM.

A375 Cell Proliferation Assay (1)

A375 cells (catalog (#CRL-1619) are obtained from the American Type Culture Collect (ATTC, Manassas, VA). Briefly, cells were grown in DMEM High Glucose supplemented with 10% characterized fetal bovine serum (Invitrogen, Carlsbad, CA) and 1% Penicillin/Streptomycin/L-Glutamine at 37° C., 5% CO$_2$, and 95% humidity. Cells are expanded until reaching 70-95% confluency at which point they are sub-cultured or harvested for assay use. A serial dilution of test compound is dispensed into a 96-well black clear bottom plate in triplicate. Two thousand five hundred cells are added per well in 200 µL complete growth medium in the 96-well plate. Plates are incubated for 67-72 h at 37° C., 5% CO$_2$, and 95% humidity. At the end of the incubation, 40 µL of a 440 µM solution of resazurin (Sigma, St. Louis, MO) in PBS is added to each well of the plate and plates are incubated for an additional 5-6 h at 37° C., 5% CO$_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate IC$_{50}$ values.

A375 Cell Proliferation Assay (2)

A375 cells (catalog (#CRL-1619) are obtained from the American Type Culture Collect (ATTC, Manassas, VA). Briefly, cells were grown in DMEM High Glucose supplemented with 10% characterized fetal bovine serum (Invitrogen, Carlsbad, CA) and 1% Penicillin/Streptomycin/L-Glutamine at 37° C., 5% CO$_2$, and 95% humidity. Cells are expanded until reaching 70-95% confluency at which point they are sub-cultured or harvested for assay use. Using the Beckman Coulter Echo 650, a serial dilution of test compound is dispensed into a 384-well black clear bottom plate in triplicate. Six hundred twenty-five cells are added per well in 50 µL complete growth medium in the 384-well plate. Plates are incubated for 67-72 h at 37° C., 5% CO$_2$, and 95% humidity. At the end of the incubation, 10 µL of a 440 µM solution of resazurin (Sigma, St. Louis, MO) in PBS is added to each well of the plate and plates are incubated for an additional 3-6 h at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values.

WM3928 Cell Proliferation Assay (1)

WM3928 cells (#WM3928-01-0001) are obtained from Rockland Immunochemicals Inc (Gilbertsville, PA). Briefly, cells were grown in MCDB 153 medium (Sigma, #M7403, St. Louis, MO) supplemented with 20% Leibovitz's L-15 (ThermoFisher #11415-064, Waltham, MA), 2% heat inactivated fetal bovine serum (ThermoFisher, #A3840001, Waltham, MA), 5 µg/mL Insulin (Bovine Pancreas) (Sigma, #I0516, St. Louis, MO), 1.68 mM Calcium Chloride (Sigma, #C-34006, St. Louis, MO) and 1% Penicillin/Streptomycin/L-Glutamine (ThermoFisher #10378016, Waltham, MA) at 37° C., 5% $CO_2$, and 95% humidity. Cells are expanded until reaching 70-95% confluency at which point they are sub-cultured or harvested for assay use. A serial dilution of test compound is dispensed into a 96-well black clear bottom plate in triplicate. Three thousand cells are added per well in 200 µL complete growth medium in the 96-well plate. Plates are incubated for 67-72 hours at 37° C., 5% $CO_2$, and 95% humidity. At the end of the incubation, 40 µL of a 440 µM solution of resazurin (Sigma, #199303, St. Louis, MO) in PBS is added to each well of the plate and plates are incubated for an additional 6-7 hours at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values.

WM3928 Cell Proliferation Assay (2)

WM3928 cells (#WM3928-01-0001) are obtained from Rockland Immunochemicals Inc (Gilbertsville, PA). Briefly, cells were grown in MCDB 153 medium (Sigma, #M7403, St. Louis, MO) supplemented with 20% Leibovitz's L-15 (ThermoFisher #11415-064, Waltham, MA), 2% heat inactivated fetal bovine serum (ThermoFisher, #A3840001, Waltham, MA), 5 µg/mL Insulin (Bovine Pancreas) (Sigma, #I0516, St. Louis, MO), 1.68 mM Calcium Chloride (Sigma, #C-34006, St. Louis, MO) and 1% Penicillin/Streptomycin/L-Glutamine (ThermoFisher #10378016, Waltham, MA) at 37° C., 5% $CO_2$, and 95% humidity. Cells are expanded until reaching 70-95% confluency at which point they are sub-cultured or harvested for assay use. Using the Beckman Coulter Echo 650, a serial dilution of test compound is dispensed into a 384-well black clear bottom plate in triplicate. Seven hundred fifty cells are added per well in 50 µL complete growth medium in the 384-well plate. Plates are incubated for 67-72 hours at 37° C., 5% $CO_2$, and 95% humidity. At the end of the incubation, 10 µL of a 440 µM solution of resazurin (Sigma, #199303, St. Louis, MO) in PBS is added to each well of the plate and plates are incubated for an additional 3-6 hours at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values.

WM3629 Cell Proliferation Assay (1)

WM3629 cells (#WM3629-01-0001) are obtained from Rockland Immunochemicals Inc (Gilbertsville, PA). Briefly, cells were grown in MCDB 153 medium (Sigma, #M7403, St. Louis, MO) supplemented with 20% Leibovitz's L-15 (ThermoFisher #11415-064, Waltham, MA), 2% heat inactivated fetal bovine serum (ThermoFisher, #A3840001, Waltham, MA), 5 µg/mL Insulin (Bovine Pancreas) (Sigma, #I0516, St. Louis, MO), 1.68 mM Calcium Chloride (Sigma, #C-34006, St. Louis, MO) and 1% Penicillin/Streptomycin/L-Glutamine (ThermoFisher #10378016, Waltham, MA) at 37° C., 5% $CO_2$, and 95% humidity. Cells are expanded until reaching 70-95% confluency at which point they are subcultured or harvested for assay use. A serial dilution of test compound is dispensed into a 96-well black clear bottom plate in triplicate. Four thousand five hundred cells are added per well in 200 µL complete growth medium in the 96-well plate. Plates are incubated for 67-72 hours at 37° C., 5% $CO_2$, and 95% humidity. At the end of the incubation, 40 µL of a 440 µM solution of resazurin (Sigma, #199303, St. Louis, MO) in PBS is added to each well of the plate and plates are incubated for an additional 6-7 hours at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values.

WM3629 Cell Proliferation Assay (2)

WM3629 cells (#WM3629-01-0001) are obtained from Rockland Immunochemicals Inc (Gilbertsville, PA). Briefly, cells were grown in MCDB 153 medium (Sigma, #M7403, St. Louis, MO) supplemented with 20% Leibovitz's L-15 (ThermoFisher #11415-064, Waltham, MA), 2% heat inactivated fetal bovine serum (ThermoFisher, #A3840001, Waltham, MA), 5 µg/mL Insulin (Bovine Pancreas) (Sigma, #I0516, St. Louis, MO), 1.68 mM Calcium Chloride (Sigma, #C-34006, St. Louis, MO) and 1% Penicillin/Streptomycin/L-Glutamine (ThermoFisher #10378016, Waltham, MA) at 37° C., 5% $CO_2$, and 95% humidity. Cells are expanded until reaching 70-95% confluency at which point they are sub-cultured or harvested for assay use. Using the Beckman Coulter Echo 650, a serial dilution of test compound is dispensed into a 384-well black clear bottom plate in triplicate. One thousand one hundred twenty-five cells are added per well in 50 µL complete growth medium in the 384-well plate. Plates are incubated for 67-72 hours at 37° C., 5% $CO_2$, and 95% humidity. At the end of the incubation, 10 µL of a 440 µM solution of resazurin (Sigma, #199303, St. Louis, MO) in PBS is added to each well of the plate and plates are incubated for an additional 3-6 hours at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values.

H2405 Cell Proliferation Assay (1)

H2405 cells (catalog #CRL-5994) are obtained from the American Type Culture Collect (ATTC, Manassas, VA). Briefly, cells were grown in RPMI 1640 supplemented with 5% characterized fetal bovine serum (Invitrogen, Carlsbad, CA) and 1% Penicillin/Streptomycin/L-Glutamine at 37° C., 5% $CO_2$, and 95% humidity. Cells are expanded until reaching 70-95% confluency at which point they are sub-cultured or harvested for assay use. A serial dilution of test compound is dispensed into a 96-well black clear bottom plate in triplicate. Three thousand cells are added per well in 200 µL complete growth medium in the 96-well plate. Plates are incubated for 67-72 h at 37° C., 5% $CO_2$, and 95% humidity. At the end of the incubation, 40 µL of a 440 µM solution of resazurin (Sigma, St. Louis, MO) in PBS is added to each well of the plate and plates are incubated for an additional 5-6 h at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values.

H2405 Cell Proliferation Assay (2)

H2405 cells (catalog #CRL-5994) are obtained from the American Type Culture Collect (ATTC, Manassas, VA). Briefly, cells were grown in RPMI 1640 supplemented with 5% characterized fetal bovine serum (Invitrogen, Carlsbad, CA) and 1% Penicillin/Streptomycin/L-Glutamine at 37° C., 5% $CO_2$, and 95% humidity. Cells are expanded until reaching 70-95% confluency at which point they are sub-cultured or harvested for assay use. A serial dilution of test compound is dispensed into a 384-well black clear bottom plate in triplicate. Seven hundred fifty cells are added per well in 50 μL complete growth medium in the 384-well plate. Plates are incubated for 67-72 h at 37° C., 5% $CO_2$, and 95% humidity. At the end of the incubation, 10 μL of a 440 μM solution of resazurin (Sigma, St. Louis, MO) in PBS is added to each well of the plate and plates are incubated for an additional 5-6 h at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values MiaPaca-2 Cell Proliferation Assay (1)

Miapaca-2 cells (catalog #CRL-1420) are obtained from the American Type Culture Collect (ATTC, Manassas, VA). Briefly, cells were grown in DMEM supplemented with 10% characterized fetal bovine serum (Invitrogen, Carlsbad, CA), 2.5% New Zealand sourced horse serum and 1% Penicillin/Streptomycin/L-Glutamine at 37° C., 5% $CO_2$, and 95% humidity. Cells are expanded until reaching 70-95% confluency at which point they are sub-cultured or harvested for assay use. A serial dilution of test compound is dispensed into a 96-well black clear bottom plate in triplicate. Three thousand cells are added per well in 200 μL complete growth medium in the 96-well plate. Plates are incubated for 67-72 h at 37° C., 5% $CO_2$, and 95% humidity. At the end of the incubation, 40 μL of a 440 μM solution of resazurin (Sigma, St. Louis, MO) in PBS is added to each well of the plate and plates are incubated for an additional 5-6 h at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values.

MiaPaca-2 Cell Proliferation Assay (2)

Miapaca-2 cells (catalog #CRL-1420) are obtained from the American Type Culture Collect (ATTC, Manassas, VA). Briefly, cells were grown in DMEM supplemented with 10% characterized fetal bovine serum (Invitrogen, Carlsbad, CA), 2.5% New Zealand sourced horse serum and 1% Penicillin/Streptomycin/L-Glutamine at 37° C., 5% $CO_2$, and 95% humidity. Cells are expanded until reaching 70-95% confluency at which point they are sub-cultured or harvested for assay use. A serial dilution of test compound is dispensed into a 384-well black clear bottom plate in triplicate. Seven hundred fifty cells are added per well in 50 μL complete growth medium in the 384-well plate. Plates are incubated for 67-72 h at 37° C., 5% $CO_2$, and 95% humidity. At the end of the incubation, 10 μL of a 440 μM solution of resazurin (Sigma, St. Louis, MO) in PBS is added to each well of the plate and plates are incubated for an additional 5-6 h at 37° C., 5% $CO_2$, and 95% humidity. Plates are read on a Synergy2 or equivalent reader (Biotek, Winooski VT) using an excitation of 540 nm and an emission of 600 nm. Data is analyzed using Prism software (GraphPad, San Diego, CA) to calculate $IC_{50}$ values.

MiaPaca-2 Combination Cell proliferation Assay (1)

Miapaca-2 cells (catalog #CRL-1420) are obtained from the American Type Culture Collect (ATCC, Manassas, VA). Briefly, cells were grown in DMEM supplemented with 10% characterized fetal bovine serum (Invitrogen, Carlsbad, CA), 2.5% New Zealand sourced horse serum and 1% Penicillin/Streptomycin/L-Glutamine at 37° C., 5% $CO_2$, and 95% humidity. Cells are expanded until reaching 70-95% confluency at which point they are subcultured or harvested for assay use. A serial dilution of test compound was dispensed into multiple 96-well black clear bottom plates in triplicate. A serial dilution of complete growth medium containing cobimetinib was prepared at twice the final concentration and 100 μL was dispensed across the test compound titration in triplicate. Three thousand cells are added per well in 100 μL complete growth medium in each 96-well plate. Plates are incubated for 67-72 hours at 37° C., 5% $CO_2$, and 95% humidity. At the end of the incubation, 40 μL of a 440 μM solution of resazurin (Sigma, St. Louis, MO) in PBS is added to each well of the plate and plates are incubated for an additional 5-7 hours at 37° C., 5% $CO_2$, and 95% humidity. Plates are read on a Synergy2 or equivalent reader (Biotek, Winooski VT) using an excitation of 540 nm and an emission of 600 nm. Drug synergy was assessed via BLISS analysis in the Combenefit software (Cancer Research UK Cambridge Institute, Cambridge, UK). Data is analyzed using Prism software (Graphpad, San Diego, CA) to calculate $IC_{50}$ values. Shifts in test compound $IC_{50}$ values are reported from top-constrained combination therapy curves.

MiaPaca-2 Combination Cell Proliferation Assay (2)

Miapaca-2 cells (catalog #CRL-1420) are obtained from the American Type Culture Collect (ATCC, Manassas, VA). Briefly, cells were grown in DMEM supplemented with 10% characterized fetal bovine serum (Invitrogen, Carlsbad, CA), 2.5% New Zealand sourced horse serum and 1% Penicillin/Streptomycin/L-Glutamine at 37° C., 5% $CO_2$, and 95% humidity. Cells are expanded until reaching 70-95% confluency at which point they are subcultured or harvested for assay use. Using the Beckman Coulter Echo 650, a threefold, 8-point serial dilution of compound was spotted column wise into a 384 well black, clear bottom, tissue culture treated plate. Likewise, a threefold, 8-point serial dilution of cobimetinib was spotted row wise into the 384 well black, clear bottom plate containing compound. DMSO concentration was constant across all wells at 0.4%. Seven hundred fifty cells are added per well in 50 μL complete growth medium in each 384-well plate. Plates are incubated for 67-72 hours at 37° C., 5% $CO_2$, and 95% humidity. At the end of the incubation, 10 μL of a 440 μM solution of resazurin (Sigma, St. Louis, MO) in PBS is added to each well of the plate and plates are incubated for an additional 4-6 hours at 37° C., 5% $CO_2$, and 95% humidity. Plates are read on a Synergy2 or equivalent reader (Biotek, Winooski VT) using an excitation of 540 nm and an emission of 600 nm. Drug synergy was assessed via BLISS analysis in the Combenefit software (Cancer Research UK Cambridge Institute, Cambridge, UK). Data is analyzed using Prism software (Graphpad, San Diego, CA) to calculate $IC_{50}$ values. Shifts in test compound $IC_{50}$ values are reported from top-constrained combination therapy curves.

TABLE K

Inhibition of cell proliferation in A375 (1), H2405 (1), WM3928 (1), WM3629 (1), MiaPaca-2 (1), and combination with cobimetinib in MiaPaca-2 (1) by exemplary compounds ("Ex. No.").

| Ex. No. | A375 (1) IC$_{50}$ | H2405 (1) IC$_{50}$ | WM3928 (1) IC$_{50}$ | WM3629 (1) IC$_{50}$ | MiaPaca2 (1) IC$_{50}$ | MiaPaca-2 Combo (1) IC$_{50}$ |
|---|---|---|---|---|---|---|
| 1 | + | | | | ++ | + |
| 2 | ++ | | | | ++++ | + |
| 3 | ++ | ++ | | | ++++ | ++ |
| 4 | ++ | | | | ++++ | + |
| 5 | ++ | | + | | ++++ | |
| 6 | + | + | | | ++++ | |
| 7 | +++ | | | | ++++ | ++ |
| 8 | + | | | | ++++ | |
| 9 | ++ | | | | | |
| 10 | + | | + | | | |
| 11 | ++++ | | | | ++++ | |
| 12 | ++ | ++ | | | ++++ | ++ |
| 13 | ++++ | | | | ++++ | |
| 14 | + | | | | ++++ | |
| 15 | + | + | | | ++++ | + |
| 16 | ++++ | ++++ | ++++ | | ++++ | |
| 17 | ++ | | | | ++++ | |
| 18 | ++++ | | | | ++++ | |
| 19 | + | + | | | ++ | + |
| 20 | ++++ | | | | ++++ | |
| 21 | ++++ | | | | ++++ | |
| 22 | ++++ | | + | | ++++ | |
| 23 | + | ++ | + | | ++++ | ++ |
| 24 | + | | + | | ++++ | + |
| 25 | +++ | | +++ | | ++++ | + |
| 26 | ++ | | | | ++++ | + |
| 27 | + | + | + | | ++++ | +++ |
| 28 | + | | | | ++++ | + |
| 29 | ++ | + | + | | ++++ | + |
| 30 | + | + | + | | ++++ | + |
| 31 | ++++ | | | | ++++ | |
| 32 | +++ | | | | ++++ | |
| 35 | +++ | | | | ++++ | |
| 36 | +++ | | | | ++++ | |
| 37 | + | | | | ++++ | |
| 38 | ++++ | | | | | |
| 39 | +++ | | | | ++++ | ++ |
| 40 | ++++ | | | | ++++ | |
| 41 | ++ | + | + | | ++++ | + |
| 42 | ++++ | +++ | ++++ | | ++++ | |
| 43 | +++ | | + | | ++++ | ++ |
| 44 | ++++ | | | | | |
| 45 | ++++ | | | | | |
| 46 | ++++ | | | | ++++ | |
| 47 | ++++ | | | | ++++ | ++ |
| 48 | +++ | ++ | +++ | | ++++ | + |
| 49 | +++ | | | | ++++ | |
| 50 | + | + | + | | ++++ | + |
| 52 | ++ | + | ++ | + | ++++ | |
| 53 | ++++ | ++++ | | | | |
| 54 | ++ | + | + | | ++++ | + |
| 55 | +++ | | | | ++++ | |
| 56 | ++ | +++ | +++ | | ++++ | |
| 57 | ++ | | | | ++++ | |
| 58 | ++ | + | ++ | | ++++ | |
| 59 | ++++ | | | | ++++ | |
| 60 | ++++ | | | | ++++ | |
| 61 | + | | | | ++++ | + |
| 62 | ++ | | | | ++++ | ++ |
| 63 | ++ | + | | | ++++ | ++ |
| 64 | ++ | | | | ++++ | |
| 65 | +++ | | | | ++++ | |
| 66 | ++++ | | | | | |
| 68 | + | ++ | + | | ++++ | + |
| 69 | ++ | ++ | + | + | ++++ | |
| 70 | ++ | | | | ++++ | |
| 71 | ++ | + | + | | ++++ | |
| 72 | ++++ | | ++ | | ++++ | |
| 73 | ++++ | | | | ++++ | |
| 74 | ++ | ++ | ++ | | ++++ | + |
| 75 | + | | | | ++++ | |
| 76 | + | | | | ++++ | |
| 77 | + | + | + | + | ++++ | + |
| 78 | + | | + | | ++++ | + |
| 79 | + | | | | ++++ | + |
| 80 | + | + | ++ | + | ++++ | + |
| 81 | ++++ | ++++ | | | | |
| 82 | +++ | +++ | ++++ | | ++++ | |
| 83 | ++ | | | | ++++ | |
| 84 | ++ | | | | ++++ | |
| 85 | ++++ | ++ | ++++ | | ++++ | |
| 86 | + | + | + | | ++++ | + |
| 87 | +++ | | | | ++++ | |
| 88 | + | | + | | ++++ | + |
| 89 | ++ | | + | | ++++ | + |
| 90 | ++++ | | | | ++++ | |
| 91 | ++++ | | | | | |
| 92 | ++ | | | | ++++ | |
| 94 | ++++ | | | | ++++ | |
| 95 | +++ | | | | | |
| 97 | ++ | | + | | ++++ | |
| 98 | +++ | | | | ++++ | |
| 99 | +++ | | | | ++++ | |
| 100 | ++ | | | | ++++ | |
| 101 | +++ | | ++ | | ++++ | |
| 102 | ++++ | | | | ++++ | |
| 103 | + | + | + | | ++++ | + |
| 104 | + | + | + | | ++++ | + |
| 105 | ++++ | | ++ | | ++++ | |
| 106 | +++ | | | | ++++ | |
| 107 | ++ | | | | ++++ | |
| 108 | + | + | + | | ++++ | |
| 109 | ++ | | + | | ++++ | |
| 110 | ++++ | | +++ | | ++++ | |
| 111 | ++++ | ++++ | ++++ | | ++++ | |
| 112 | + | + | + | | ++++ | + |
| 113 | ++ | | ++ | | ++++ | |
| 114 | + | | + | | ++++ | |
| 115 | | | | | | |
| 116 | ++ | | | | | |
| 117 | ++ | | + | | ++++ | + |
| 118 | + | | + | | ++++ | + |
| 120 | ++++ | | | | ++++ | |
| 121 | ++ | | | | | |
| 122 | ++++ | ++++ | ++++ | | ++++ | |
| 123 | ++ | | ++ | | ++++ | |
| 124 | + | + | + | | ++++ | + |
| 125 | + | + | + | | +++ | |
| 127 | + | | | | ++++ | + |
| 129 | +++ | ++ | ++ | | ++++ | |
| 130 | ++++ | ++ | | | | |
| 131 | ++++ | ++++ | ++++ | | ++++ | |
| 132 | +++ | | ++ | | ++++ | |
| 133 | ++++ | +++ | | | | |
| 134 | ++ | ++ | + | | ++++ | ++ |
| 135 | +++ | | | | ++++ | |
| 136 | + | | | | ++++ | |
| 138 | ++ | | | | ++++ | ++ |
| 139 | ++++ | | | | ++++ | |
| 140 | + | | + | | +++ | |
| 141 | ++++ | | | | ++++ | |
| 142 | + | | | | ++++ | |
| 143 | ++++ | | | | ++++ | |
| 144 | +++ | | | | | |
| 145 | | | + | | ++++ | |
| 146 | + | | + | | ++++ | |
| 148 | ++++ | | +++ | | ++++ | |
| 149 | ++++ | | | | | |
| 150 | + | | + | | ++++ | |
| 151 | + | | + | | ++++ | |
| 152 | ++ | | + | | ++++ | |
| 153 | + | | | | ++++ | |
| 154 | + | | + | | ++++ | |
| 155 | ++++ | | | | | |

TABLE K-continued

Inhibition of cell proliferation in A375 (1), H2405 (1), WM3928 (1), WM3629 (1), MiaPaca-2 (1), and combination with cobimetinib in MiaPaca-2 (1) by exemplary compounds ("Ex. No.").

| Ex. No. | A375 (1) IC$_{50}$ | H2405 (1) IC$_{50}$ | WM3928 (1) IC$_{50}$ | WM3629 (1) IC$_{50}$ | MiaPaca2 (1) IC$_{50}$ | MiaPaca-2 Combo (1) IC$_{50}$ |
|---|---|---|---|---|---|---|
| 156 | ++++ | | +++ | | ++++ | |
| 157 | ++++ | | ++ | | ++++ | |
| 158 | + | | ++ | | ++++ | + |
| 159 | +++ | | ++ | | ++++ | |
| 160 | ++ | | + | | ++++ | ++ |
| 161 | + | | + | | ++++ | |
| 162 | ++ | ++ | ++ | | ++++ | |
| 163 | + | + | + | | | |
| 164 | + | | | | ++ | |
| 166 | ++ | +++ | | | ++++ | |
| 168 | +++ | | +++ | | ++++ | |
| 169 | + | | + | | ++++ | |
| 171 | + | ++ | + | | ++++ | |
| 172 | + | | + | | ++++ | + |
| 173 | +++ | | | | ++++ | |
| 174 | + | | + | | ++++ | |
| 175 | ++ | | + | | ++++ | + |
| 176 | + | ++ | + | | ++++ | |
| 177 | ++ | | + | | ++++ | |
| 178 | ++ | ++ | + | + | ++++ | |
| 179 | + | | + | | ++++ | |
| 180 | + | + | + | + | ++++ | |
| 181 | + | + | + | + | ++++ | + |
| 182 | ++ | | + | | ++++ | |
| 184 | + | | + | | ++++ | + |
| 185 | + | + | + | | | |
| 186 | + | + | + | + | ++++ | |
| 187 | + | ++ | + | + | ++++ | |
| 189 | ++ | ++ | + | | ++++ | ++ |
| 190 | + | | + | | ++++ | |
| 191 | + | + | + | | | |
| 192 | + | ++ | + | | ++++ | |
| 193 | + | + | + | | ++++ | + |
| 194 | +++ | | ++ | | ++++ | |
| 195 | ++ | | | | | |
| 196 | + | ++ | ++ | | | |
| 197 | + | | + | | ++++ | ++ |
| 198 | + | + | + | | ++++ | + |
| 199 | ++++ | ++ | ++++ | | | |
| 200 | + | | + | | ++++ | |
| 201 | ++ | ++ | ++ | | | |
| 202 | ++ | ++ | + | | ++++ | |
| 203 | + | | + | | ++++ | |
| 204 | ++ | ++ | ++ | | ++++ | |
| 205 | ++ | | ++ | | | |
| 207 | ++++ | ++++ | | | | |
| 210 | | | | | | ++ |
| 211 | | | | | | |
| 212 | + | + | | + | ++++ | |
| 213 | | | ++ | | ++++ | |
| 214 | + | ++ | + | + | ++++ | ++ |
| 215 | +++ | | +++ | | ++++ | |
| 216 | + | | + | | ++++ | |
| 217 | + | ++ | ++ | | | |
| 218 | + | ++ | + | | ++++ | |
| 219 | ++ | | ++ | | ++++ | |
| 220 | ++++ | | ++++ | | ++++ | |
| 221 | ++++ | ++++ | +++ | | ++++ | |
| 222 | + | ++ | + | + | ++++ | + |
| 223 | + | + | + | | | + |
| 224 | + | + | + | + | ++ | + |
| 225 | + | +++ | + | | ++++ | + |
| 226 | ++++ | | ++++ | | ++++ | |
| 227 | ++++ | ++++ | | | | |
| 229 | ++ | + | + | + | ++++ | |
| 230 | + | + | + | | +++ | + |
| 231 | + | | + | | ++++ | |
| 233 | +++ | | ++++ | | ++++ | |
| 235 | + | ++ | + | + | ++++ | ++ |
| 236 | ++++ | ++ | +++ | | ++++ | |
| 237 | ++++ | +++ | | | | |
| 238 | + | ++ | + | | ++++ | ++ |
| 239 | + | | | | | |
| 240 | ++ | ++ | | | | |
| 241 | + | + | + | | +++ | ++ |
| 242 | +++ | ++ | ++ | | | |
| 245 | + | + | + | + | ++++ | + |
| 246 | ++ | ++ | | | | |
| 247 | ++++ | ++ | | | | |
| 248 | ++ | | | | | |
| 249 | + | ++ | + | + | ++++ | + |
| 250 | ++ | ++ | ++ | | ++++ | |
| 251 | + | ++ | + | | ++++ | + |
| 252 | ++++ | | +++ | | ++++ | |
| 253 | ++ | ++ | + | | ++++ | |
| 254 | ++++ | ++++ | ++++ | | ++++ | |
| 255 | + | ++ | + | | | |
| 256 | +++ | ++ | +++ | | ++++ | |
| 257 | + | | + | | ++++ | + |
| 258 | ++++ | ++++ | | | | |
| 259 | +++ | ++ | | | | |
| 261 | + | | | | | |
| 262 | + | | | + | ++++ | |
| 263 | ++++ | | +++ | | ++++ | |
| 264 | + | ++ | + | + | ++++ | |
| 265 | + | + | + | | ++++ | ++ |
| 266 | ++ | ++ | | | | |
| 267 | ++ | +++ | ++ | | ++++ | |
| 268 | ++ | ++ | | | | |
| 269 | + | + | | | | |
| 270 | ++ | ++ | ++ | | ++++ | |
| 271 | +++ | ++ | + | | ++++ | |
| 272 | ++++ | ++ | ++ | | ++++ | |
| 273 | ++++ | ++++ | ++++ | | ++++ | |
| 274 | + | + | + | + | ++++ | + |
| 275 | ++++ | | | | | |
| 276 | + | + | | | | |
| 277 | +++ | ++ | ++ | | | |
| 278 | ++++ | ++++ | ++++ | | ++++ | |
| 279 | ++ | ++ | + | | ++++ | + |
| 280 | ++ | ++ | + | | ++++ | |
| 281 | ++++ | ++ | ++++ | | ++++ | |
| 282 | + | +++ | ++ | | ++++ | + |
| 283 | ++ | ++ | ++ | | ++++ | |
| 284 | + | +++ | + | | ++++ | |
| 285 | ++++ | ++++ | ++++ | | | |
| 286 | +++ | ++ | ++ | | ++++ | |
| 287 | ++++ | +++ | ++ | | ++++ | |
| 288 | ++++ | ++++ | ++++ | | ++++ | |
| 289 | ++++ | | | | | |
| 290 | ++++ | ++++ | +++ | | ++++ | |
| 291 | ++ | ++ | + | | ++++ | |
| 292 | ++ | ++ | ++ | | ++++ | |
| 293 | ++ | | | | | |
| 294 | ++++ | ++ | | | | |
| 295 | +++ | ++ | ++ | | ++++ | |
| 297 | + | + | + | | ++++ | + |
| 298 | ++ | ++ | ++ | | ++++ | |
| 299 | ++ | ++ | +++ | | ++++ | |
| 300 | + | + | + | | ++++ | |
| 301 | ++ | ++ | ++ | | ++++ | |
| 302 | + | ++ | + | + | | + |
| 303 | + | + | + | + | | + |
| 304 | ++ | ++ | + | + | ++++ | + |
| 305 | ++ | ++ | ++ | | ++++ | |
| 306 | ++++ | ++++ | | | ++++ | |
| 307 | +++ | + | ++ | | ++++ | |
| 308 | + | + | + | + | ++++ | + |
| 309 | ++++ | ++++ | | | ++++ | |
| 310 | ++ | ++ | | | ++++ | |
| 311 | + | ++ | | | | |
| 312 | ++ | ++ | ++++ | | ++++ | |
| 313 | ++++ | ++ | ++++ | | | |
| 314 | ++ | +++ | +++ | | | |

TABLE K-continued

Inhibition of cell proliferation in A375 (1), H2405 (1), WM3928 (1), WM3629 (1), MiaPaca-2 (1), and combination with cobimetinib in MiaPaca-2 (1) by exemplary compounds ("Ex. No.").

| Ex. No. | A375 (1) IC$_{50}$ | H2405 (1) IC$_{50}$ | WM3928 (1) IC$_{50}$ | WM3629 (1) IC$_{50}$ | MiaPaca2 (1) IC$_{50}$ | MiaPaca-2 Combo (1) IC$_{50}$ |
|---|---|---|---|---|---|---|
| 315 | + | + | + | + |  | + |
| 316 | ++++ | ++++ |  |  |  |  |
| 317 | ++++ | ++++ |  |  |  |  |
| 318 | ++++ | ++++ |  |  |  |  |
| 319 | + | + |  |  |  | + |
| 320 | ++++ | ++++ | ++++ |  |  |  |
| 321 | ++ | ++ | ++ | + |  |  |
| 322 | ++++ | ++++ |  |  |  |  |
| 323 | ++ | ++ | ++ |  |  |  |
| 324 | ++++ |  |  |  |  |  |
| 325 | ++ | ++ | +++ | + |  |  |
| 326 | ++++ | ++++ | ++++ |  |  |  |
| 327 | ++++ | ++++ | ++++ | ++++ |  |  |
| 328 | ++ | ++ | ++++ |  |  |  |
| 329 | +++ | +++ | ++++ |  |  |  |
| 330 | ++++ | ++++ |  |  |  |  |
| 331 | ++ | ++ | +++ |  |  |  |
| 332 | ++++ | ++++ | ++++ |  |  |  |
| 333 | ++++ | ++++ |  |  |  |  |
| 341 | ++++ |  | ++++ |  |  |  |
| 346 | ++++ | ++++ |  |  |  |  |
| 347 | ++++ | ++++ |  |  |  |  |
| 348 | ++++ | ++++ | ++++ |  | ++++ |  |
| 357 | ++++ | ++++ |  |  |  |  |
| 358 | ++++ | ++++ | ++++ |  | ++++ |  |
| 359 | ++++ | ++++ |  |  |  |  |
| 360 | ++++ | ++++ | ++++ |  |  |  |
| 361 | ++++ | +++ |  |  |  |  |
| 362 | ++++ | ++++ |  |  |  |  |
| 363 | ++++ | ++++ |  |  |  |  |
| 364 | ++++ | +++ | ++++ |  |  |  |
| 365 | ++++ | ++++ |  |  |  |  |
| 366 | ++++ | ++++ |  |  |  |  |
| 367 | ++ | ++ |  |  |  |  |
| 368 | ++++ | ++++ |  |  |  |  |
| 369 | ++++ | +++ |  |  |  |  |
| 370 | ++++ | +++ | ++++ |  |  |  |
| 371 | ++ | ++ | ++ |  |  |  |
| 372 | ++++ | ++++ |  |  |  |  |
| 373 | ++++ | ++++ |  |  |  |  |
| 374 | ++++ | ++++ |  |  |  |  |
| 375 | ++ | ++ | + |  |  |  |
| 376 | + | ++ | ++ |  |  |  |
| 377 | ++ | ++ | + |  |  |  |
| 378 | + | ++ | ++ |  |  |  |
| 379 | + | ++ | + |  | ++++ |  |
| 380 | ++ | ++ | + |  |  |  |
| 381 | ++++ | ++++ |  |  |  |  |
| 382 | ++++ | ++++ |  |  |  |  |
| 383 | ++++ | ++++ |  |  |  |  |
| 384 | + | ++ | + |  | ++++ |  |
| 385 | ++++ | ++++ | ++++ |  |  |  |
| 386 | ++ | +++ | ++ |  |  |  |
| 387 | ++++ | ++++ | ++ |  |  |  |
| 388 | ++++ | ++++ | +++ |  |  |  |
| 389 | ++++ | ++++ | +++ |  |  |  |
| 391 | + | +++ | + |  | ++++ |  |
| 392 | ++++ | ++++ | ++++ |  |  |  |
| 393 | ++ | ++ | + |  | ++++ |  |
| 394 | + | + | + | + | ++ | ++++ |
| 395 | + | + | + | + | ++ |  |
| 396 | + | + | + |  | ++++ |  |
| 397 | + | + | + | + | ++ |  |
| 398 | + | + | + |  | +++ |  |
| 399 | + | + | + |  |  |  |
| 400 | ++++ | ++++ | ++++ |  |  |  |
| 401 | + | ++ | + |  | ++++ |  |
| 402 | ++ | +++ | ++ |  |  |  |
| 403 | ++ | ++ | + |  |  |  |
| 404 | ++ | ++++ | ++ |  |  |  |
| 405 | + | + | + |  | +++ |  |
| 406 | + | + | + |  | +++ |  |
| 407 | ++++ | +++ | ++++ |  |  |  |
| 408 | ++ | ++ | ++ |  |  |  |
| 409 | ++++ | ++++ | ++++ |  |  |  |
| 410 | + | ++ | + |  | ++++ |  |
| 411 | +++ | ++ | + |  | ++++ |  |
| 412 | + | + | + |  | +++ |  |
| 413 | + | + | + |  | ++++ | ++ |
| 414 | + | + | + |  | ++ |  |
| 415 | ++++ |  | ++++ |  |  |  |
| 416 | ++ | ++ | + |  | +++ |  |
| 417 | + | + | + |  | +++ |  |
| 418 | + | + | + |  | ++ |  |
| 419 | + | + | + |  | ++ |  |
| 420 | + | + | + |  |  |  |
| 421 | + | + | + |  | ++++ |  |
| 422 | ++++ | ++ | ++ |  |  |  |
| 423 | + |  | + |  |  |  |
| 424 | + |  | + |  |  |  |
| 425 | + | + | + |  |  |  |
| 427 | ++ | ++ | + |  | ++++ |  |
| 428 | ++ | ++ | ++ |  |  |  |
| 429 | + | + | + |  |  |  |
| 430 | ++ | ++ | + |  | ++++ |  |
| 431 | + | + | + |  | ++++ |  |
| 432 | +++ |  | ++ |  |  |  |
| 433 | + |  | + |  | +++ |  |
| 434 | + | + | + |  | ++ |  |
| 435 | + | + | + |  | +++ |  |
| 436 | ++ | + | + |  | ++++ |  |
| 437 | ++++ | ++ | +++ |  | ++++ |  |
| 438 | + | ++ | + |  | ++++ | ++ |

For Table K, "+" refers to an IC$_{50}$ less than or equal to 100 nM; "++" refers to an IC$_{50}$ greater than 100 nM and less than or equal to 500 nM; "+++" refers to an IC$_{50}$ greater than 500 nM and less than or equal to 1000 nM; and "++++" refers to an IC$_{50}$ greater than 1000 nM and less than or equal to 10000 nM.

TABLE L

Inhibition of cell proliferation in A375 (2), H2405 (2), WM3928 (2), WM3629 (2), MiaPaca-2 (2), and combination with cobimetinib in MiaPaca-2 (2) by exemplary compounds ("Ex. No.").

| Ex. No. | A375 (2) IC$_{50}$ | H2405 (2) IC$_{50}$ | WM3928 (2) IC$_{50}$ | WM3629 (2) IC$_{50}$ | MiaPaca-2 (2) IC$_{50}$ | MiaPaca-2 Combo (2) IC$_{50}$ |
|---|---|---|---|---|---|---|
| 439 | ++ | ++ | ++ |  | ++++ |  |
| 440 | ++ | ++ | + |  | ++++ | +++ |
| 441 | + | + | + |  | ++++ | ++ |
| 442 | + | + | + |  | +++ |  |
| 443 | ++ | + | + | + | +++ | ++ |
| 444 | ++ |  | ++ |  |  |  |
| 445 | ++ | + | + | + | ++++ | ++ |
| 446 | ++ | ++ | + | + | ++++ |  |
| 447 | ++++ |  | +++ |  |  |  |
| 448 | ++ | ++ | + |  |  |  |
| 449 | + | + | + |  |  |  |
| 450 | ++ | ++ | ++ |  |  |  |
| 451 | + |  | + |  |  |  |
| 452 | ++ | ++ | ++ |  |  |  |
| 453 | ++ | ++ | ++ |  |  |  |
| 454 | + | + | + |  |  |  |
| 455 | + | + | + |  |  |  |
| 456 | + | + | + |  |  |  |
| 457 | + | + | + |  |  |  |
| 458 | ++ | + | + |  |  |  |

TABLE L-continued

Inhibition of cell proliferation in A375 (2), H2405 (2), WM3928 (2), WM3629 (2), MiaPaca-2 (2), and combination with cobimetinib in MiaPaca-2 (2) by exemplary compounds ("Ex. No.").

| Ex. No. | A375 (2) IC$_{50}$ | H2405 (2) IC$_{50}$ | WM3928 (2) IC$_{50}$ | WM3629 (2) IC$_{50}$ | MiaPaca-2 (2) IC$_{50}$ | MiaPaca-2 Combo (2) IC$_{50}$ |
|---|---|---|---|---|---|---|
| 459 | + | + | + | | | |
| 460 | ++ | ++ | + | | | |
| 461 | + | + | + | | | |
| 462 | ++++ | +++ | +++ | | | |
| 463 | +++ | | ++ | | | |
| 464 | ++ | | ++ | | | |
| 465 | +++ | ++ | ++ | | | |
| 466 | ++ | ++ | + | + | | |
| 467 | + | + | + | | +++ | |
| 468 | ++ | + | + | | +++ | |
| 469 | ++ | ++ | ++ | + | ++++ | |
| 470 | ++ | + | + | + | ++++ | |
| 471 | ++++ | ++++ | ++++ | | | |
| 472 | ++ | ++ | +++ | | | |
| 473 | + | ++ | + | + | | |
| 474 | + | + | + | + | | |
| 475 | ++++ | ++++ | ++++ | | | |
| 476 | + | + | + | + | ++++ | ++ |
| 477 | ++++ | ++++ | +++ | + | | |
| 478 | ++++ | + | ++ | | | |
| 479 | ++ | ++ | + | + | ++++ | ++++ |
| 480 | ++ | ++ | + | + | ++++ | |
| 481 | ++++ | ++++ | ++++ | ++++ | | |
| 482 | ++ | ++ | ++ | + | ++++ | ++++ |
| 483 | ++++ | ++++ | +++ | + | | |
| 484 | + | ++ | + | + | ++++ | +++ |
| 485 | + | ++ | + | + | ++++ | |
| 486 | ++ | +++ | ++ | + | ++++ | ++++ |
| 487 | + | + | + | + | ++++ | ++ |
| 488 | ++ | ++ | ++ | + | | |
| 489 | + | + | + | + | ++++ | ++ |
| 490 | ++ | ++ | ++ | + | | |
| 491 | ++++ | ++ | +++ | + | | |
| 492 | ++ | ++ | ++ | + | | |
| 493 | + | ++ | + | + | ++++ | ++ |
| 494 | ++++ | ++++ | +++ | + | ++++ | |
| 495 | + | ++ | + | + | ++++ | |
| 496 | + | ++ | + | + | ++++ | |
| 497 | ++ | ++ | ++ | + | ++++ | |
| 498 | ++ | ++ | + | + | ++++ | |
| 499 | + | ++ | ++ | + | ++++ | |
| 500 | ++++ | ++++ | +++ | + | ++++ | |
| 501 | ++ | ++ | ++ | + | ++++ | |
| 502 | + | + | + | + | +++ | |
| 503 | ++ | ++ | + | + | ++++ | |

For Table L, "+" refers to an IC$_{50}$ less than or equal to 100 nM; "++" refers to an IC$_{50}$ greater than 100 nM and less than or equal to 500 nM; "+++" refers to an IC$_{50}$ greater than 500 nM and less than or equal to 1000 nM; and "++++" refers to an IC$_{50}$ greater than 1000 nM and less than or equal to 10000 nM.

EQUIVALENTS

While specific embodiments have been discussed, the above specification is illustrative and not restrictive. Many variations of the embodiments will become apparent to those skilled in the art upon review of this specification. The full scope of what is disclosed should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A compound represented by Formula I:

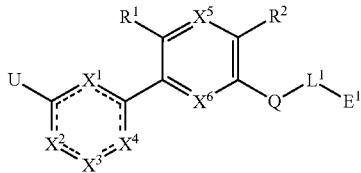

Formula I or a pharmaceutically acceptable salt, enantiomer, stereoisomer, or tautomer thereof,
wherein:
  each of $X^1$ and $X^4$ is independently selected from $CR^3$ and N;
  $X^2$ is selected from the group consisting of N, CH, C=O, C—O-$L^2$-$E^2$, C-$L^2$-$E^2$, C—N($R^4$)-$L^2$-$E^2$, and N-$L^2$-$E^2$;
  $X^3$ is selected from the group consisting of CH, C-$L^3$-$E^3$, C—O-$L^3$-$E^3$, C—N($R^4$)-$L^3$-$E^3$, C=O, N, and N-$L^3$-$E^3$;
    provided that not more than two of $X^1$, $X^2$, $X^3$, and $X^4$ are N;
    when $X^2$ is N, $X^3$ is selected from the group consisting of CH, C-$L^3$-$E^3$, C—O-$L^3$-$E^3$, C—N($R^4$)-$L^3$-$E^3$, and N;
    when $X^3$ is N, $X^2$ is selected from the group consisting of N, CH, C—O-$L^2$-$E^2$, C-$L^2$-$E^2$, and C—N($R^4$)-$L^2$-$E^2$;
    when $X^2$ is C=O, $X^3$ is N-$L^3$-$E^3$;
    when $X^3$ is C=O, $X^2$ is N-$L^2$-$E^2$;
  $X^5$ is independently selected from the group consisting of CH, CF, and N;
  $X^6$ is independently selected from the group consisting of CH and CF;
  $L^1$ is selected from the group consisting of a direct bond and optionally substituted $C_1$-$C_6$alkyl, wherein the optionally substituted substituent, at each occurrence, is $(E^{11})_m$;
  $L^2$ is selected from the group consisting of a direct bond and optionally substituted $C_1$-$C_6$alkyl, wherein the optionally substituted substituent, at each occurrence, is $(E^{21})_p$;
  $L^3$ is selected from the group consisting of a direct bond and optionally substituted $C_1$-$C_6$alkyl, wherein the optionally substituted substituent, at each occurrence, is $(E^{31})_p$;
  Q is selected from the group consisting of —NH—C(O)— and —C(O)—NH—;
  $E^1$ is selected from the group consisting of:
    i) H,
    ii) alkoxy,
    ii) cyano,
    iv) haloalkoxy,
    v) halogen, vi) optionally substituted alkyl wherein the optionally substituted substituent, at each occurrence, is independently selected from the group consisting of alkyl, alkoxy, amine, haloalkyl, haloalkoxy, halogen, hydroxy, and cyano, vii) optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, viii) optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl, and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, ix) optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
the alkyl substituent is independently optionally substituted, at each occurrence, with a substituent selected from the group consisting of cycloalkyl, cyano, alkoxy, and aminoalkyl,
the cycloalkyl substituent is independently optionally substituted, at each occurrence, with a substituent selected from the group consisting of cycloalkyl, cyano, alkoxy, and aminoalkyl, and
the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and x) optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^2$ is selected from the group consisting of hydroxy, alkoxy, alkoxyalkyl, cyano, sulfonyl, H, alkyl, amine, amide, acyl, haloalkoxy, haloalkyl, and optionally substituted heterocyclyl wherein the optionally substituted substituent, at each occurrence, is independently selected from the group consisting of alkyl, alkoxy, amide, amine, acyl, haloalkyl, haloalkoxy, halogen, hydroxy, hydroxyalkyl, oxo, cyano, and cyanoalkyl;

$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen;

or wherein two occurrences of $E^{21}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, optionally substituted heteroaryl, wherein the optionally substituted substituent, at each occurrence, is independently selected from the group consisting of alkyl, alkoxy, amide, amine, acyl, alkoxyalkyl, haloalkyl, haloalkoxy, halogen, hydroxy, hydroxyalkyl, cyano, cyanoalkyl, and heterocyclyl, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

U is

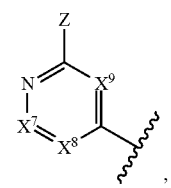

wherein $X^7$, $X^8$, and $X^9$ are independently selected from $CR^3$ and N, provided that not more than one of $X^7$, $X^8$ and $X^9$ is N;

Z is —NHC(O)$R^6$, —NHC(O)O$R^6$, or —C(O)NH$R^7$, wherein $R^6$, each occurrence, is independently selected from the group consisting of H, alkyl, cycloalkyl, and heterocyclyl, wherein each of alkyl and cycloalkyl is optionally substituted with one or more independent occurrences of $R^8$; and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$R^7$ is selected from the group consisting of H, alkyl, cycloalkyl, and heterocyclyl, wherein each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl amide, amine, aminoalkyl, acyl, haloalkyl, haloalkoxy, halogen, hydroxy, hydroxyalkyl, oxo, cyano, cyanoalkyl, and sulfone; and $R^8$ is selected from the group consisting of alkyl, cycloalkyl, and heterocyclyl, wherein each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone;

$R^1$ is selected from the group consisting of H, alkyl, alkoxy, haloalkyl, haloalkoxy, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

each occurrence of p is independently 0, 1, or 2; and each occurrence of m is independently 0, 1, 2, 3, or 4;

with the proviso that:

1) when $X^1$ and $X^2$ are N, each of $X^5$ and $X^6$ is independently selected from CH and CF, $X^4$ is $CR^3$, $R^3$ is selected from H and alkyl, $X^3$ is $C$-$L^3$-$E^3$, and $L^3$ is a direct bond, $E^3$ is not morpholinyl; or 2) when $X^1$ and $X^4$ are N, each of $X^5$ and $X^6$ is independently selected from CH, and CF, $X^2$ is $C$-$L^2$-$E^2$, $L^2$ is a direct bond, $E^2$ is selected from H and alkyl, $X^3$ is $C$-$L^3$-$E^3$, and $L^3$ is a direct bond, $E^3$ is not morpholinyl; or 3) when $X^2$ is selected from $C$—O-$L^2$-$E^2$ and $C$—N($R^4$)-$L^2$-$E^2$, $R^4$ is H, and each $L^2$ is a direct bond, each $E^2$ is not a 6-, 7-, 8-, 9-, 10- or 11-membered bicyclic ring containing 0, 1, 2, 3 or 4 atoms selected from N, O, and S; or 4) when $X^3$ is selected from $C$—O-$L^3$-$E^3$ and $C$—N($R^4$)-$L^3$-$E^3$, $R^4$ is H, and each $L^3$ is a direct bond, each $E^3$ is not a 6-, 7-, 8-, 9-, 10- or 11-membered bicyclic ring containing 0, 1, 2, 3 or 4 atoms selected from N, O, and S; or 5) when $L^1$ is direct bond, then $E^1$ is not N-bound heterocyclyl; or 6) when $X^6$ is CH, $X^5$ is CH or CF, $X^4$ is $CR^3$, $X^3$ is N, Q is —C(O)NH—, $L^1$ is direct bond, and $E^1$ is selected from the group consisting of $C_3$-$C_8$ cycloalkyl, $C_2$-$C_8$ heterocyclyl, $C_6$-$C_{14}$ aryl, and $C_1$-$C_9$ heteroaryl, $X^2$ is not $C$—N($R^4$)-$L^2$-$E^2$; or 7) when Q is —C(O)—NH— and $L^1$ is direct bond, $E^1$ is not H; or 8) when Q is —NH—C(O)—, $L^1$-$E^1$ is not unsubstituted methyl; or 9) when $X^3$ is N, $X^1$ is CH or N, $X^4$ is CH, $X^5$ and $X^6$ are CH, $X^2$ is CH or $C$—$NH_2$, and Q is —C(O)—NH—, then $L^1$-$E^1$ is not alkyl substituted with amine.

2. A compound represented by Formula I-AB:

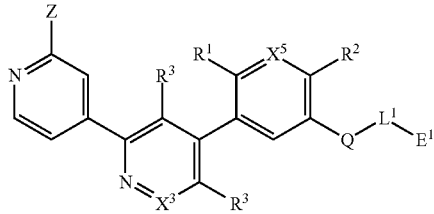

Formula I-AB or a pharmaceutically acceptable salt, enantiomer, stereoisomer, or tautomer thereof, wherein:

$X^3$ is selected from the group consisting of $C$-$L^3$-$E^3$, $C$—O-$L^3$-$E^3$, and $C$—N($R^4$)-$L^3$-$E^3$;

$X^5$ is selected from the group consisting of N, CH, and CF;

$L^3$ is selected from the group consisting of a direct bond and optionally substituted $C_1$-$C_6$alkyl, wherein the optionally substituted substituent, at each occurrence, is $(E^{31})_p$;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of:

i) optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, ii) optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, iii) optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein the alkyl substituent is independently optionally substituted, at each occurrence, with a substituent selected from the group consisting of cycloalkyl, cyano, alkoxy, and aminoalkyl, the cycloalkyl substituent is independently optionally substituted, at each occurrence, with a substituent selected from the group consisting of cycloalkyl, cyano, alkoxy, and aminoalkyl, and the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and iv) optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyanoalkyl, and sulfone, wherein when $L^1$ is a direct bond and $E^1$ is an optionally substituted heterocyclyl or optionally substituted heteroaryl, the heterocyclyl or heteroaryl is C-bound;

$E^{11}$, at each occurrence, is independently selected from the group consisting of H, alkyl, cycloalkyl, alkoxy, cyano, haloalkoxy, haloalkyl, hydroxy, hydroxyalkyl, and halogen;

or wherein two occurrences of $E^{11}$ taken together with the carbon atom to which they are attached form a cycloalkyl or a heterocyclyl ring having from 3 to 6 atoms in the ring structure;

$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone, optionally substituted monocyclic heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, and optionally substituted cycloalkyl, wherein the optionally substituted substituent, at each occurrence, is independently selected from the group consisting of alkyl, alkoxy, haloalkyl, haloalkoxy, halogen, hydroxy, and cyano;

$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;

or wherein two occurrences of $E^{31}$ taken together with the carbon atom to which they are attached form a cycloalkyl or a heterocyclyl ring having from 3 to 6 atoms in the ring structure;

Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl$(CH_2)_m$NH—, wherein the optionally substituted substituent on the heterocyclyl ring, at each occurrence, is independently $R^9$;

$R^1$ is selected from the group consisting of H, alkyl, alkoxy, haloalkyl, cyano, and halogen;

$R^2$ is selected from the group consisting of H and F;

$R^3$, at each occurrence, is independently selected from the group consisting of H, alkyl, and halogen;

$R^4$, at each occurrence, is independently selected from H and alkyl;

$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;

each p is independently 0, 1, or 2; and each m is independently 0, 1, 2, 3, or 4.

3. A compound represented by Formula I-DB:

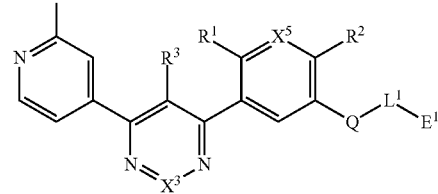

Formula I-DB or a pharmaceutically acceptable salt, enantiomer, stereoisomer, or tautomer thereof, wherein:

$X^3$ is selected from the group consisting of C-$L^3$-$E^3$, C—O-$L^3$-$E^3$, and C—N($R^4$)-$L^3$-$E^3$;

$X^5$ is selected from the group consisting of N, CH, and CF;

$L^3$ is selected from the group consisting of a direct bond and optionally substituted $C_1$-$C_6$alkyl, wherein the optionally substituted substituent, at each occurrence, is $(E^{31})_p$;

Q is selected from the group consisting of —NH—C(O)— and —C(O)—NH—;

$L^1$ is selected from the group consisting of a direct bond and optionally substituted $C_1$-$C_6$alkyl, wherein the optionally substituted substituent, at each occurrence, is $(E^{11})_m$;

$E^1$ is selected from the group consisting of:

i) optionally substituted cycloalkyl wherein the optionally substituted substituent, at each occurrence, is independently selected from the group consisting of alkyl, alkoxy, amine, haloalkyl, haloalkoxy, halogen, hydroxy, and cyano, ii) optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
  the alkyl substituent is independently optionally substituted, at each occurrence, with a substituent selected from the group consisting of cycloalkyl, cyano, alkoxy, and aminoalkyl,
  the cycloalkyl substituent is independently optionally substituted, at each occurrence, with a substituent selected from the group consisting of cycloalkyl, cyano, alkoxy, and aminoalkyl, and
  the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
iii) optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
  the alkyl substituent is independently optionally substituted, at each occurrence, with a substituent selected from the group consisting of cycloalkyl, cyano, alkoxy, and aminoalkyl,
  the cycloalkyl substituent is independently optionally substituted, at each occurrence, with a substituent selected from the group consisting of cycloalkyl, cyano, alkoxy, and aminoalkyl, and
  the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
iv) optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
  wherein when $L^1$ is a direct bond and $E^1$ is an optionally substituted heterocyclyl or optionally substituted heteroaryl, the heterocyclyl or heteroaryl is C-bound;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone,
optionally substituted monocyclic heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, and
optionally substituted cycloalkyl, wherein the optionally substituted substituent, at each occurrence, is independently selected from the group consisting of alkyl, alkoxy, haloalkyl, haloalkoxy, halogen, hydroxy, and cyano;
$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;
or wherein two occurrences of $E^{31}$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl($CH_2$)$_m$NH—, wherein the optionally substituted substituent on the heterocyclyl ring, at each occurrence, is independently $R^9$;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^4$, at each occurrence, is independently selected from H and alkyl;
$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;
each p is independently 0, 1 or 2; and
each m is independently 0, 1, 2, 3, or 4.

4. A compound represented by Formula I-EB:

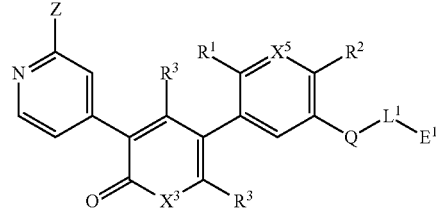

Formula I-EB or a pharmaceutically acceptable salt, enantiomer, stereoisomer, or tautomer thereof,
wherein:
$X^3$ is N-$L^3$-$E^3$;
$X^5$ is selected from the group consisting of N, CH, and CF;
$L^3$ is selected from the group consisting of a direct bond and optionally substituted $C_1$-$C_6$alkyl, wherein the optionally substituted substituent, at each occurrence, is ($E^{31}$)$_p$;
Q is selected from the group consisting of —NH—C(O)— and —C(O)—NH—;
$L^1$ is selected from the group consisting of a direct bond and optionally substituted $C_1$-$C_6$alkyl, wherein the optionally substituted substituent, at each occurrence, is ($E^{11}$)$_m$;

$E^1$ is selected from the group consisting of:
i) optionally substituted cycloalkyl wherein the optionally substituted substituent, at each occurrence, is independently selected from the group consisting of alkyl, alkoxy, amine, haloalkyl, haloalkoxy, halogen, hydroxy, and cyano,
ii) optionally substituted heteroaryl wherein the optionally substituted substituent, at each occurrence, is independently selected from the group consisting of alkyl, alkoxy, amine, amide, sulfone, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
    the alkyl substituent is independently optionally substituted, at each occurrence, with a substituent selected from the group consisting of cycloalkyl, cyano, alkoxy, and aminoalkyl,
    the cycloalkyl substituent is independently optionally substituted, at each occurrence, with a substituent selected from the group consisting of cycloalkyl, cyano, alkoxy, and aminoalkyl, and
    the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
iii) optionally substituted aryl wherein the optionally substituted substituent, at each occurrence, is independently selected from the group consisting of alkyl, alkoxy, amine, amide, acyl, alkoxyalkyl, haloalkyl, haloalkoxy, halogen, hydroxy, cyano, hydroxyalkyl, cyanoalkyl, aminoalkyl, cycloalkyl and heterocyclyl, wherein
    the alkyl substituent is independently optionally substituted, at each occurrence, with a substituent selected from the group consisting of cycloalkyl, cyano, alkoxy, and aminoalkyl,
    the cycloalkyl substituent is independently optionally substituted, at each occurrence, with a substituent selected from the group consisting of cycloalkyl, cyano, alkoxy, and aminoalkyl, and
    the heterocyclyl substituent is independently optionally substituted, at each occurrence, with a substituent selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone, and
iv) optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone,
    wherein when $L^1$ is a direct bond and $E^1$ is an optionally substituted heterocyclyl or optionally substituted heteroaryl, the heterocyclyl or heteroaryl is C-bound;
$E^{11}$, at each occurrence, is independently selected from the group consisting of H, alkyl, cycloalkyl, alkoxy, cyano, haloalkoxy, haloalkyl, hydroxy, hydroxyalkyl, and halogen;
or wherein two occurrences of $E^{11}$ taken together with the carbon atom to which they are attached form a cycloalkyl or a heterocyclyl ring having from 3 to 6 atoms in the ring structure;
$E^3$ is selected from the group consisting of hydroxy, alkoxy, alkoxylalkyl, cyano, sulfonyl, haloalkoxy, H, alkyl, acyl, amine, aminoalkyl, amide, haloalkyl, cyano, sulfone,
optionally substituted heterocyclyl, wherein the optionally substituted substituent, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, or sulfone, and
optionally substituted cycloalkyl, wherein the optionally substituted substituent, at each occurrence, is independently selected from the group consisting of alkyl, alkoxy, haloalkyl, haloalkoxy, halogen, hydroxy, and cyano;
$E^{31}$, at each occurrence, is independently selected from the group consisting of H, alkyl, cycloalkyl, alkoxy, alkoxyalkyl, cyano, cyanoalkyl, haloalkoxy, haloalkyl, hydroxy, hydroxyalkyl, and halogen;
or wherein two occurrences of $E^{31}$ taken together with the carbon atom to which they are attached form a cycloalkyl or a heterocyclyl ring having from 3 to 6 atoms in the ring structure;
Z is selected from the group consisting of acyl, carbamoyl, formyl, amide, alkoxy, alkoxyalkyl, urea, amine, amidine, alkyl, cycloalkyl, cyano, cyanoalkyl, sulfonamide, hydroxy, hydroxyalkyl, halogen, sulfone, optionally substituted heterocyclyl, optionally substituted heterocyclyl$(CH_2)_m$NH—, wherein the optionally substituted substituent on the heterocyclyl ring, at each occurrence, is independently $R^9$;
$R^1$ is selected from the group consisting of H, alkyl, alkoxy, haloalkyl, cyano, and halogen;
$R^2$ is selected from the group consisting of H and F;
$R^3$, at each occurrence, is independently selected from the group consisting of H, alkyl, and halogen;
$R^9$, at each occurrence, is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl;
each p is independently 0, 1, or 2; and
each m is independently 0, 1, 2, 3, or 4.

5. The compound of any one of claims 2, 3, and 4, wherein Z is —NHC(O)$R^6$, —NHC(O)O$R^6$, or —C(O)NH$R^7$, wherein
$R^6$, at each occurrence, is independently selected from the group consisting of H, alkyl, cycloalkyl, and heterocyclyl, wherein
each of alkyl and cycloalkyl is optionally substituted with one or more independent occurrences of $R^8$, and
the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and
$R^7$ is selected from the group consisting of H, alkyl, cycloalkyl, and heterocyclyl, wherein
each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone; and $R^8$ is selected from the group consisting of alkyl, cycloalkyl, and heterocyclyl, wherein each of alkyl and cycloalkyl is optionally substituted with one or more occurrences of a substituent independently selected from the group consisting of alkyl, cyano, amino, hydroxy, alkoxy, and heterocyclyl, and the heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfone.

6. The compound of claim 1, wherein Q is —NH—C(O)—.

7. The compound of claim 1, wherein $X^1$ is $CR^3$; $X^2$ and $X^4$ are each N; $X^3$ is selected from the group consisting of CH, C-$L^3$-$E^3$, C—O-$L^3$-$E^3$, and C—N($R^4$)-$L^3$-$E^3$; $X^5$ is CH or N; and $X^6$ is CH.

8. The compound of claim 1, wherein $X^1$ is $CR^3$; $X^4$ is $CR^3$ or N; $X^3$ is N-$L^3$-$E^3$; $X^2$ is C=O; and $X^5$ and $X^6$ are CH.

9. The compound of claim 1, wherein $X^1$ and $X^4$ are $CR^3$; $X^2$ is N; $X^3$ is selected from the group consisting of CH, C-$L^3$-$E^3$, C—O-$L^3$-$E^3$, C—N($R^4$)-$L^3$-$E^3$ and N; and $X^5$ and $X^6$ are CH.

10. The compound of claim 1, wherein $E^3$ is selected from the group consisting of H, alkyl, and cycloalkyl, wherein cycloalkyl is optionally substituted with one or more occurrences of a substituent independently selected from the group consisting of alkyl, alkoxy, haloalkyl, haloalkoxy, halogen, hydroxy, and cyano.

11. The compound of claim 1, wherein $E^3$ is heterocyclyl, wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

12. The compound of claim 1, wherein $E^2$ is selected from the group consisting of H, hydroxy, alkoxy, alkoxyalkyl, cyano, sulfonyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl, alkyl, amine, haloalkoxy, haloalkyl, and sulfonyl.

13. The compound of claim 1, wherein $R^1$ is selected from the group consisting of H, alkyl, haloalkyl, and halogen.

14. The compound of claim 1, wherein $R^2$ is F.

15. The compound of any one of claims 2, 3, and 4, wherein the Z-substituted ring is selected from the group consisting of

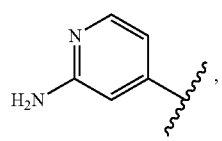

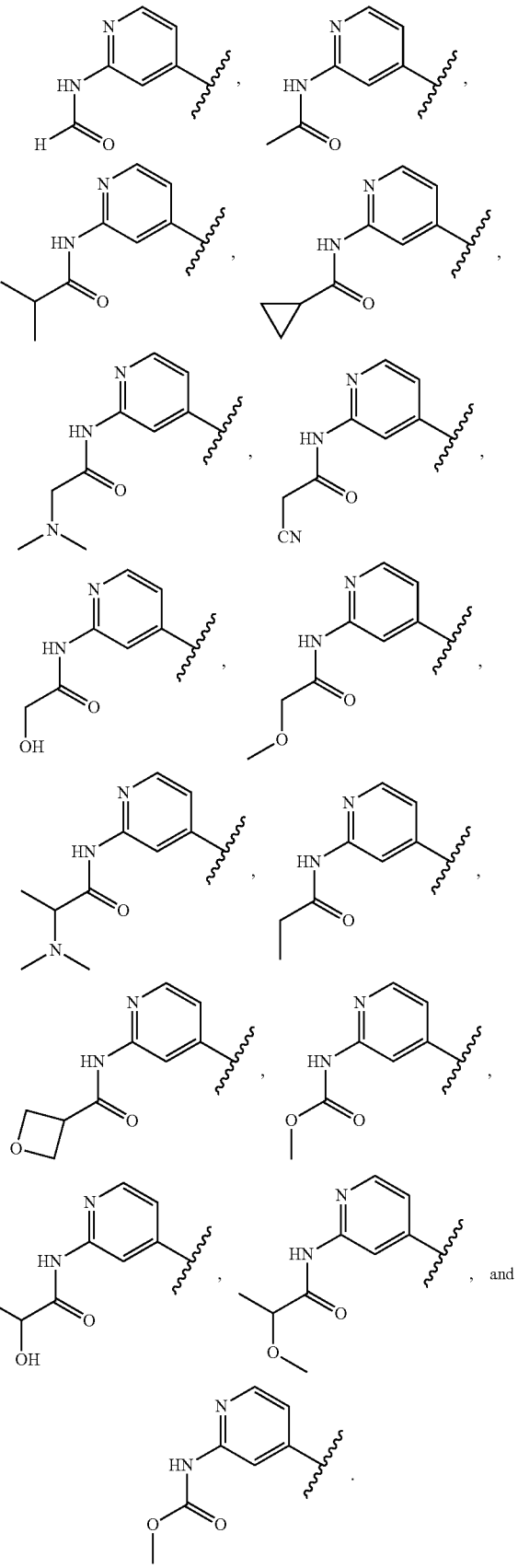

, and

16. The compound of any one of claims 2, 3, and 4, wherein the Z-substituted ring is selected from the group consisting of
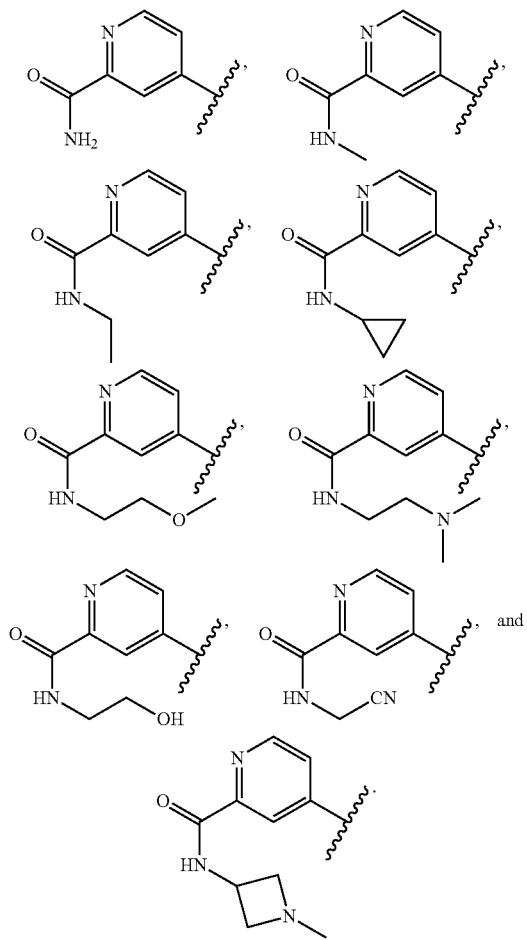
17. The compound of any one of claims 2, 3, and 4, wherein the Z-substituted ring is selected from the group consisting of
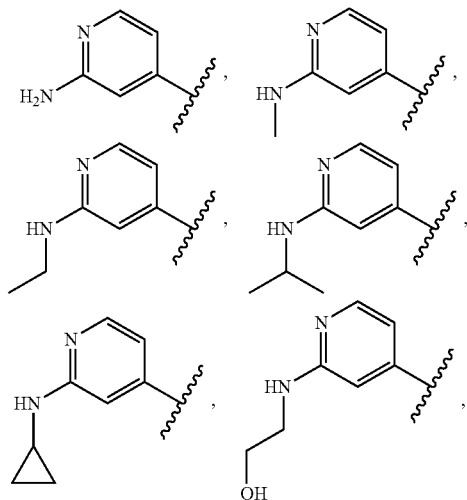
-continued
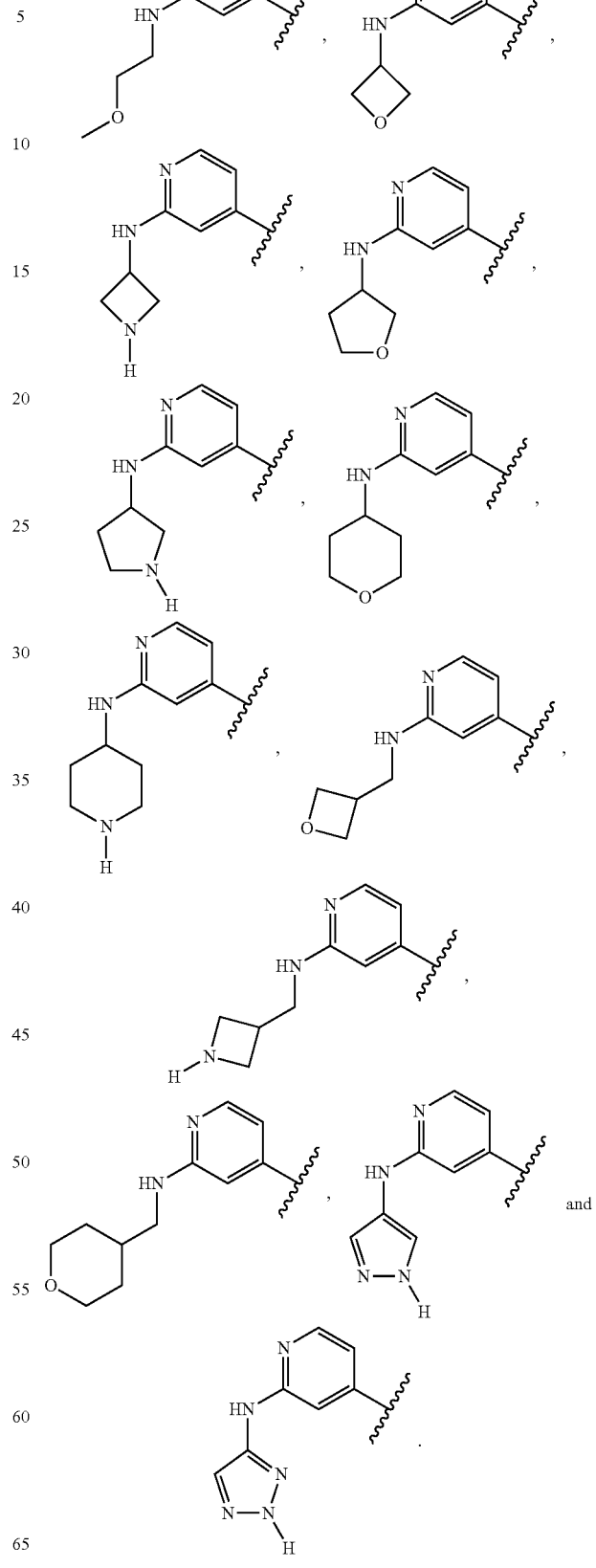

18. The compound of any one of claims 2, 3, and 4, wherein the Z-substituted ring is selected from the group consisting of

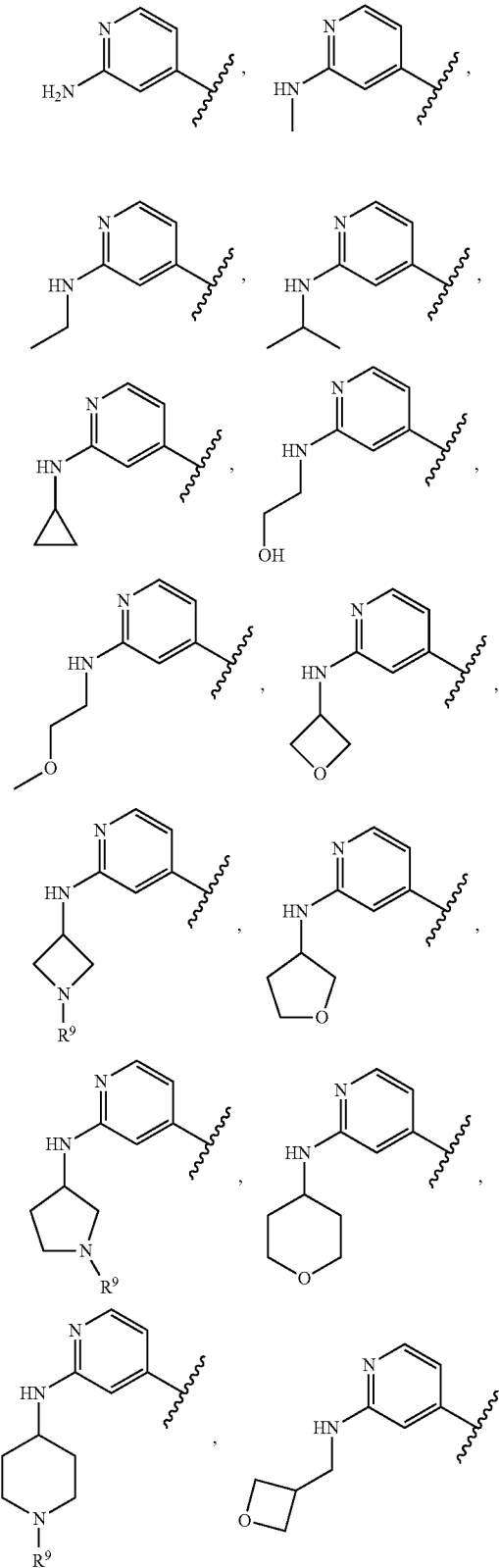

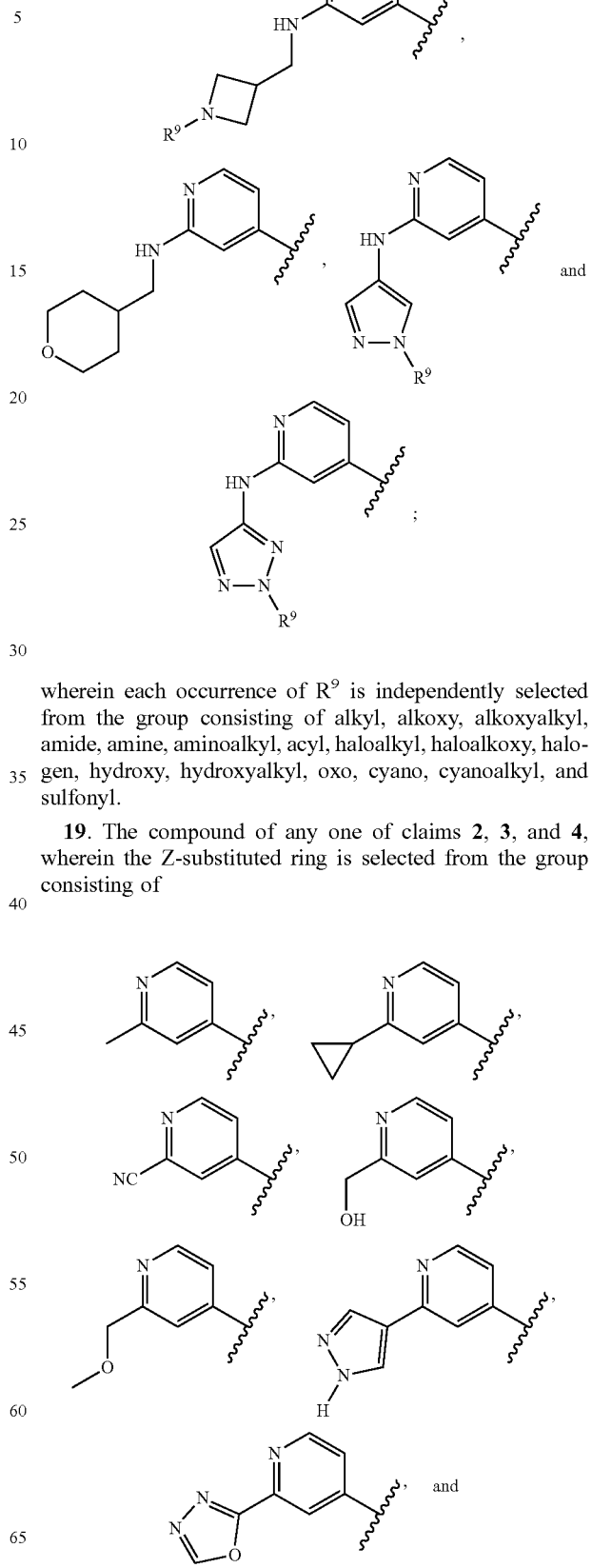

wherein each occurrence of $R^9$ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

19. The compound of any one of claims 2, 3, and 4, wherein the Z-substituted ring is selected from the group consisting of

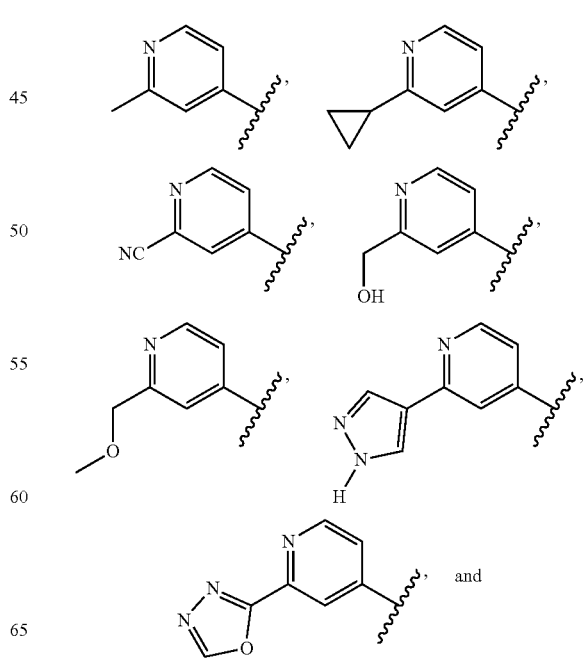

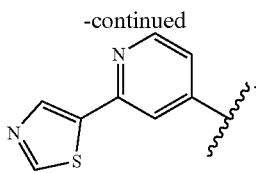

20. The compound of any one of claims 2, 3, and 4, wherein the Z-substituted ring is selected from the group consisting of

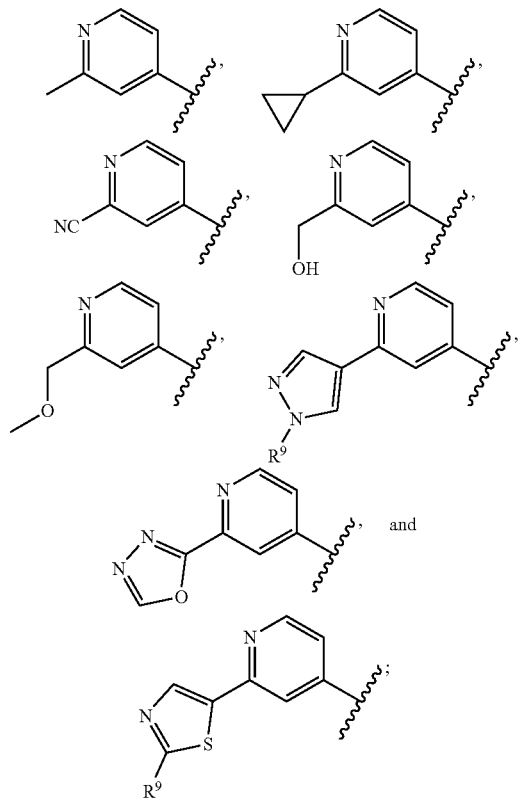

and wherein each occurrence of $R^9$ is independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

21. The compound of claim 1, wherein $E^1$ is selected from the group consisting of:

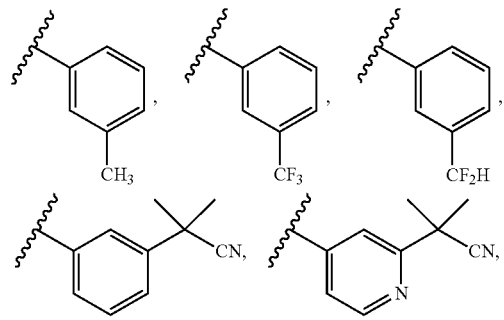

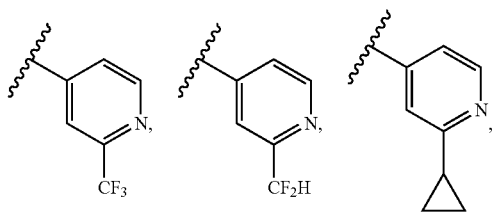
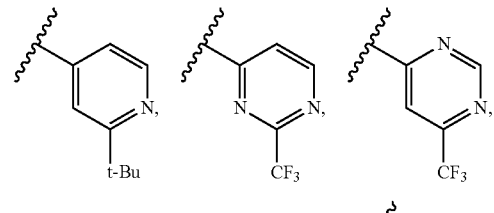
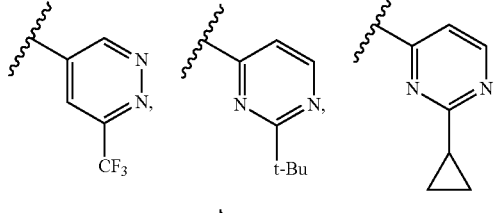
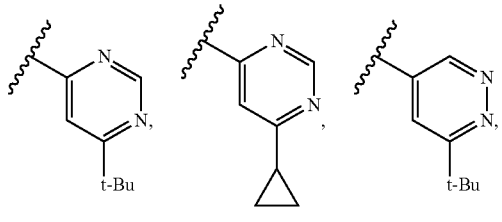
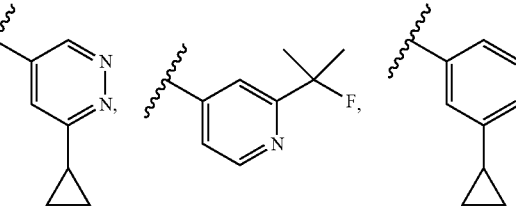
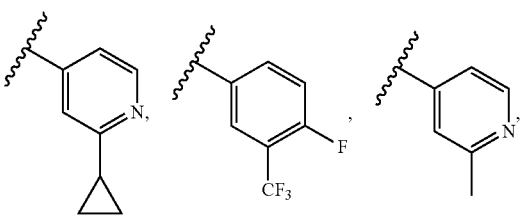
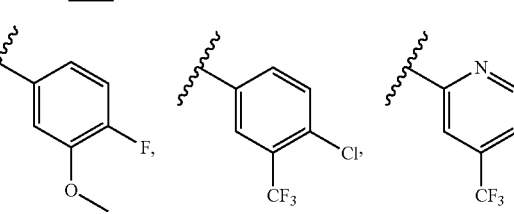
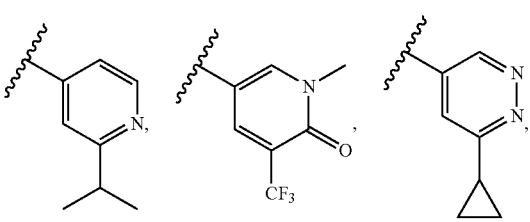

-continued
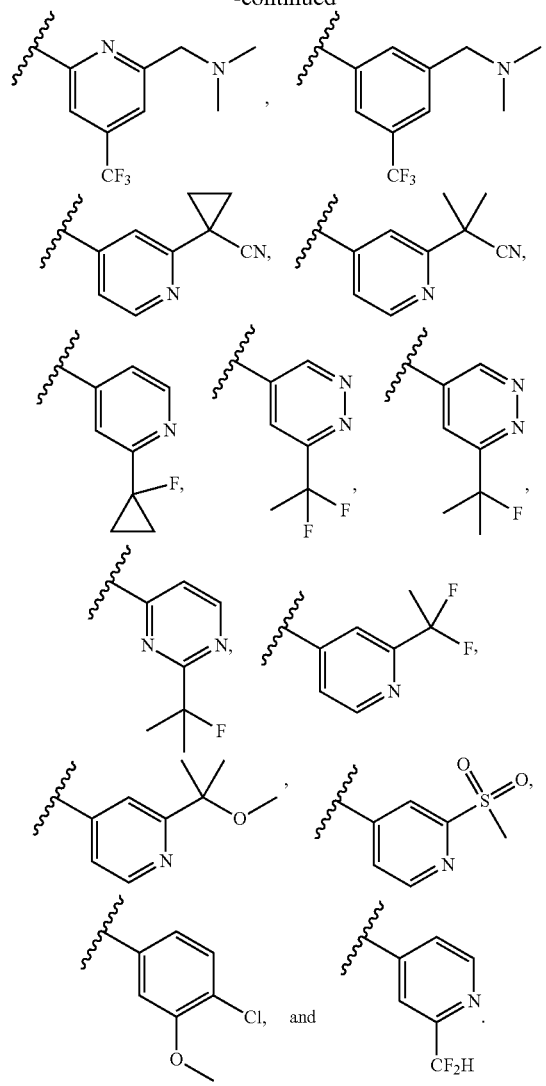
22. The compound of claim 1, wherein $E^1$ is selected from the group consisting of:
-continued
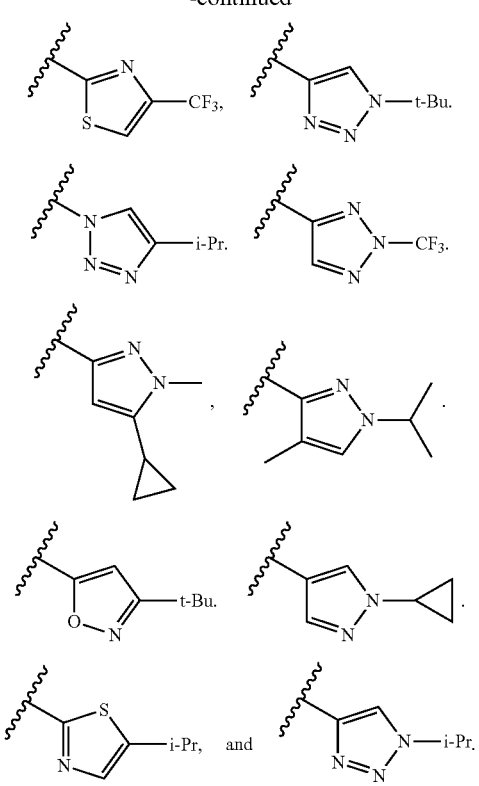
23. The compound of claim 1, wherein $E^1$ is selected from the group consisting of
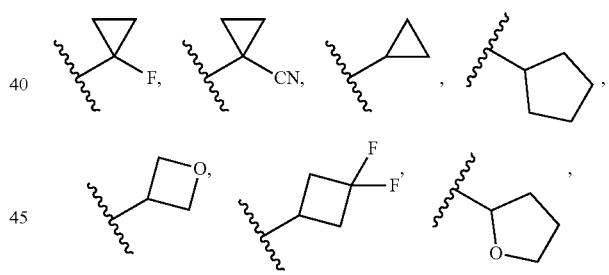
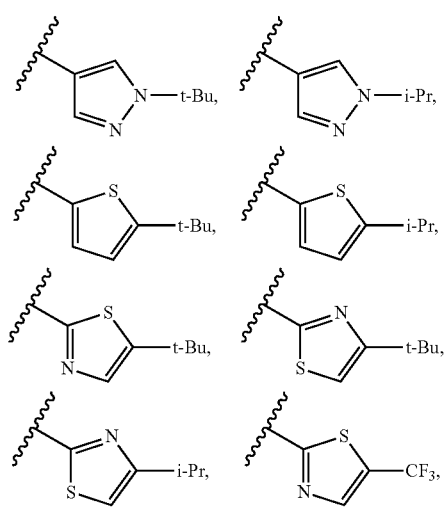

24. The compound of claim 1, wherein when $L^1$ is a direct bond and m is 0, $E^1$ is selected from the group consisting of
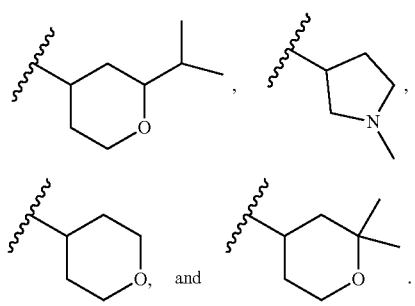
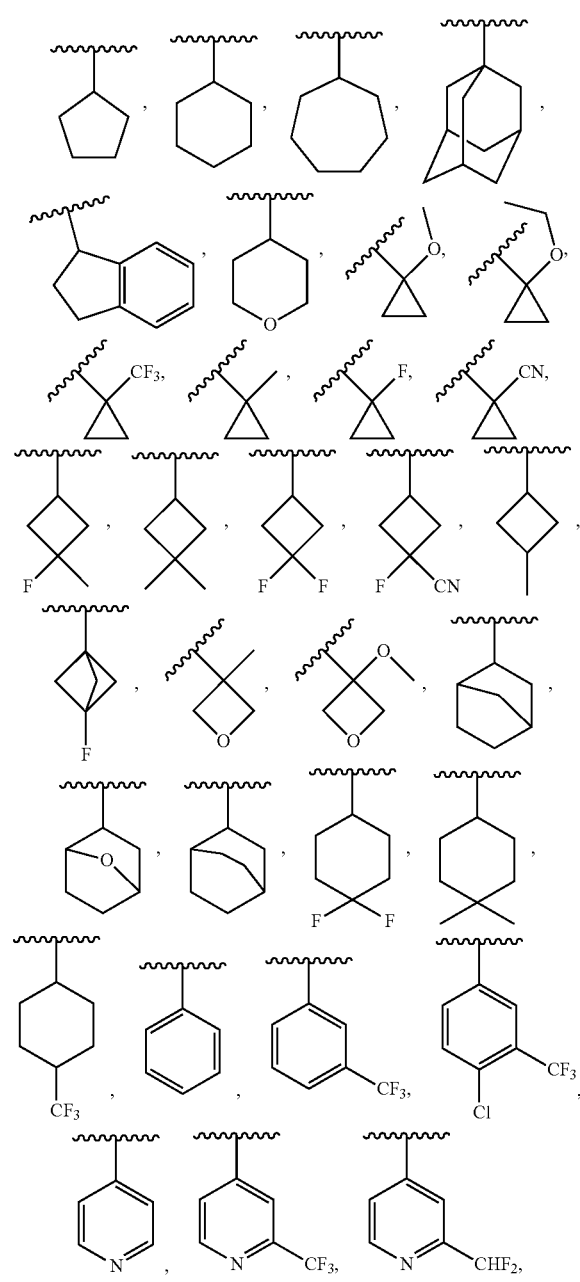
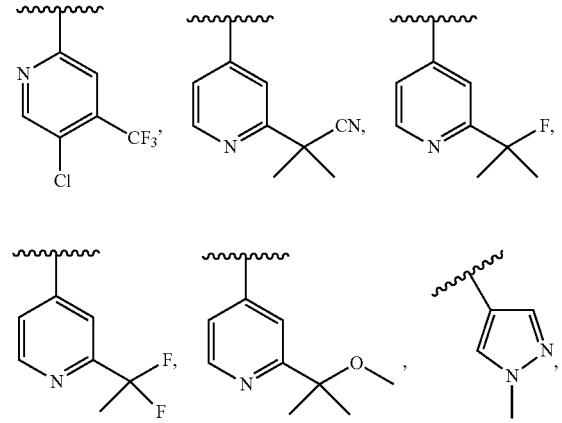
25. The compound of claim 1, wherein
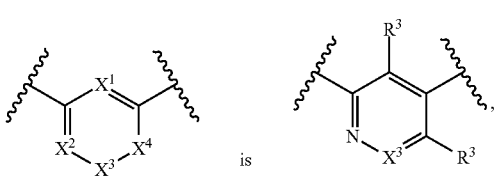
wherein $X^3$ is selected from the group consisting of CH, C-$L^3$-$E^3$, C—O-$L^3$-$E^3$, and C—N($R^4$)-$L^3$-$E^3$.

26. The compound of claim 1, wherein
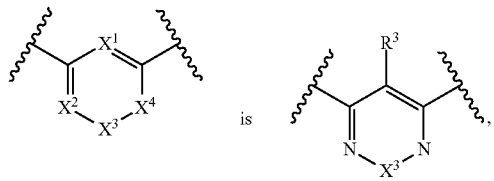 is 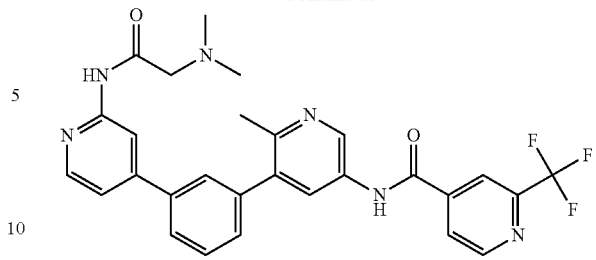,
wherein X³ is selected from the group consisting of CH, C-L³-E³, C—O-L³-E³, and C—N(R⁴)-L³-E³.
27. The compound of claim 1, wherein
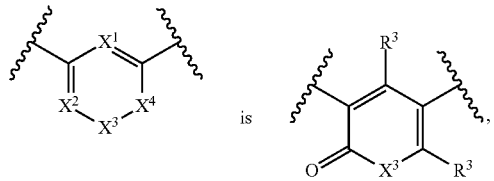 is 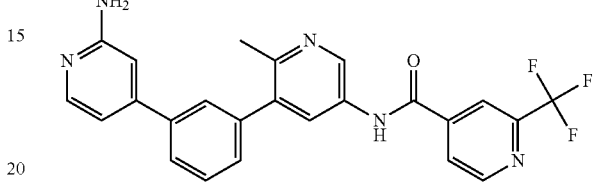,
wherein X³ is N-L³-E³.
28. A compound selected from the group consisting of:
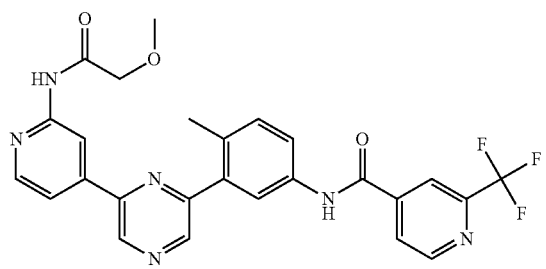
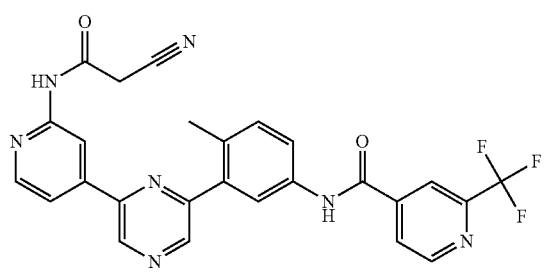
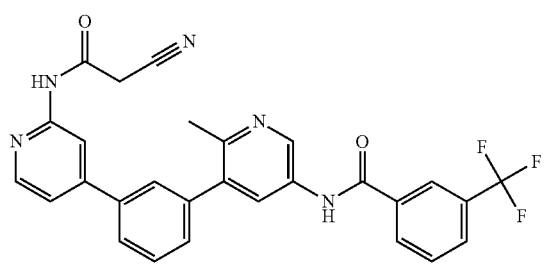
-continued
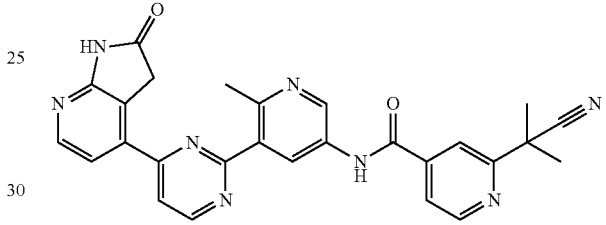
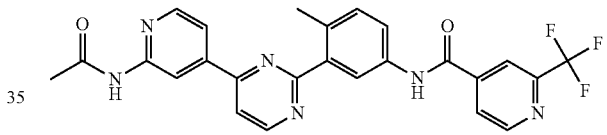
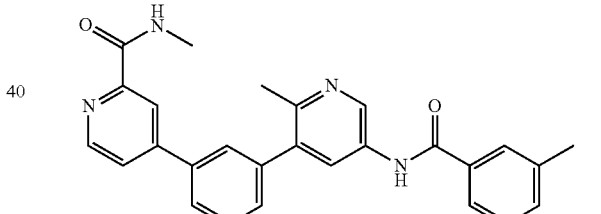
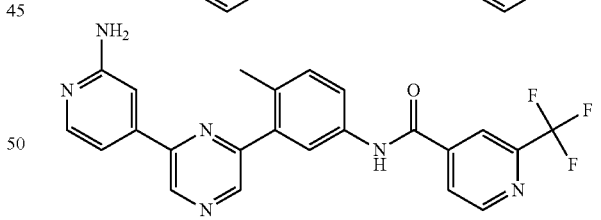
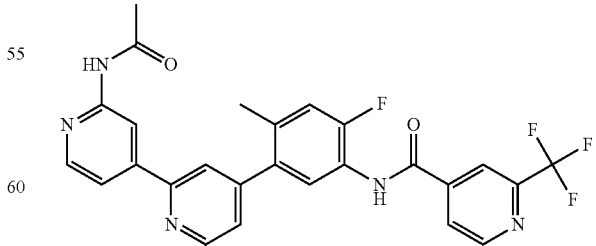
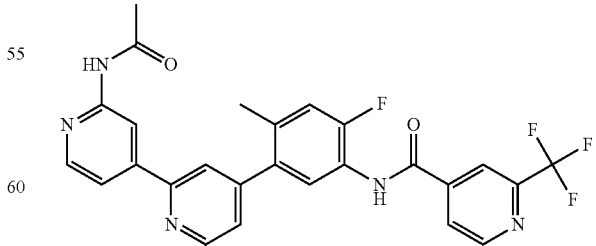
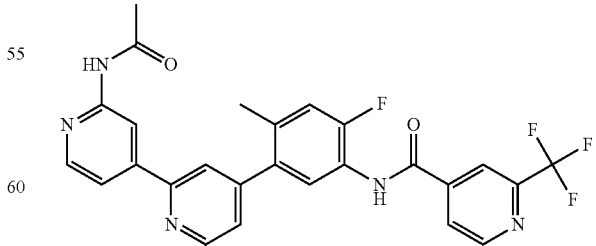

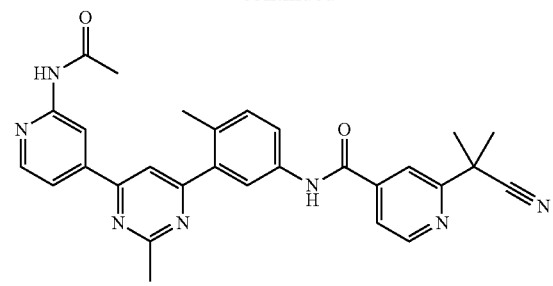
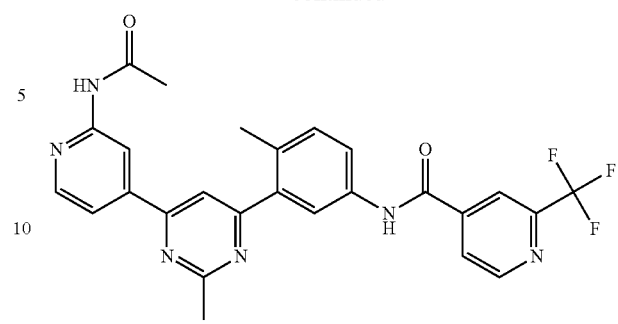
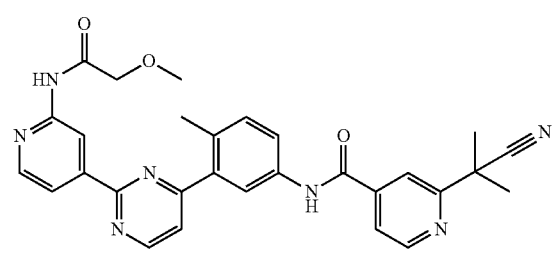
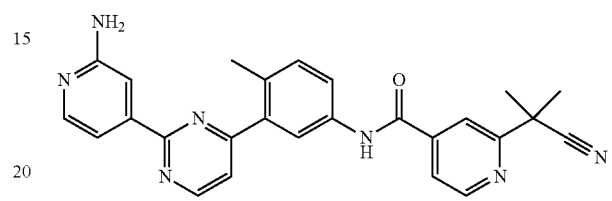
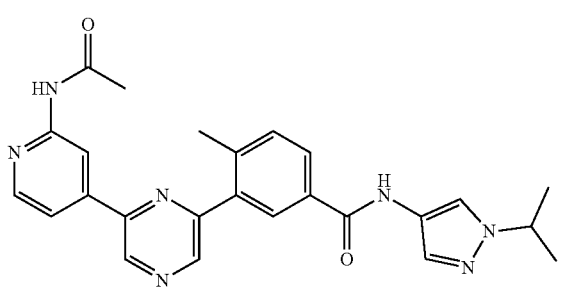
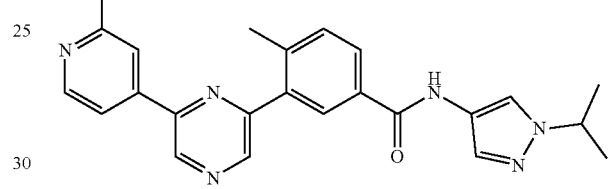
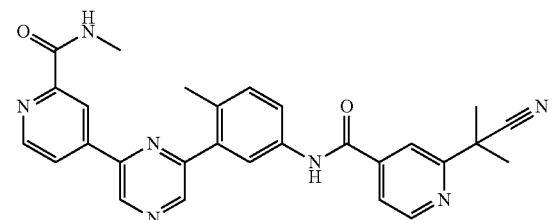
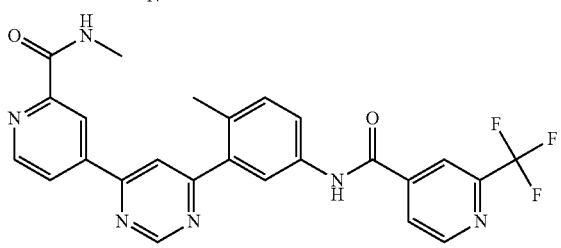
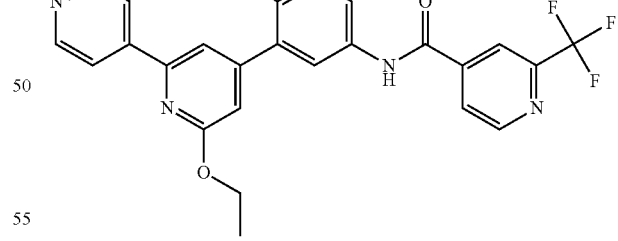
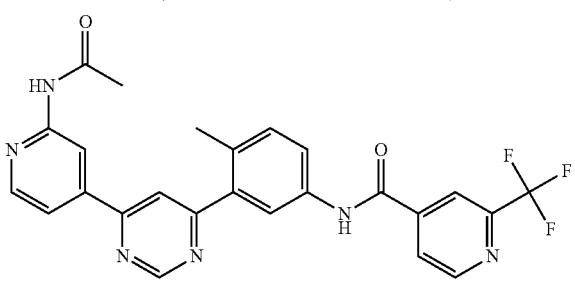
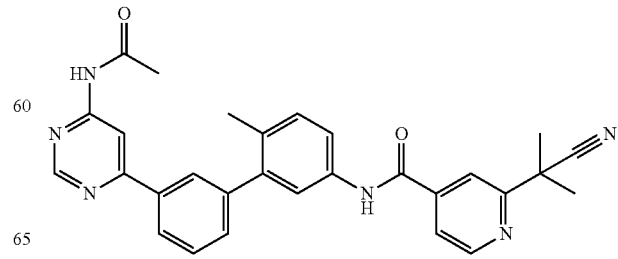

641
-continued
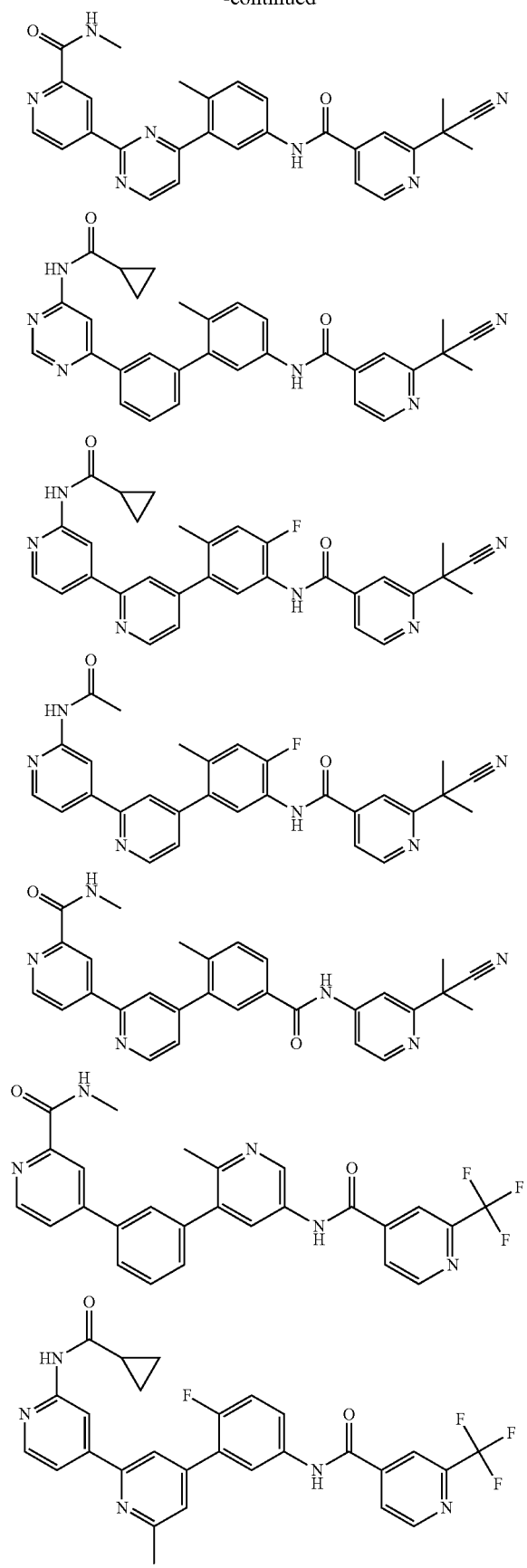
642
-continued
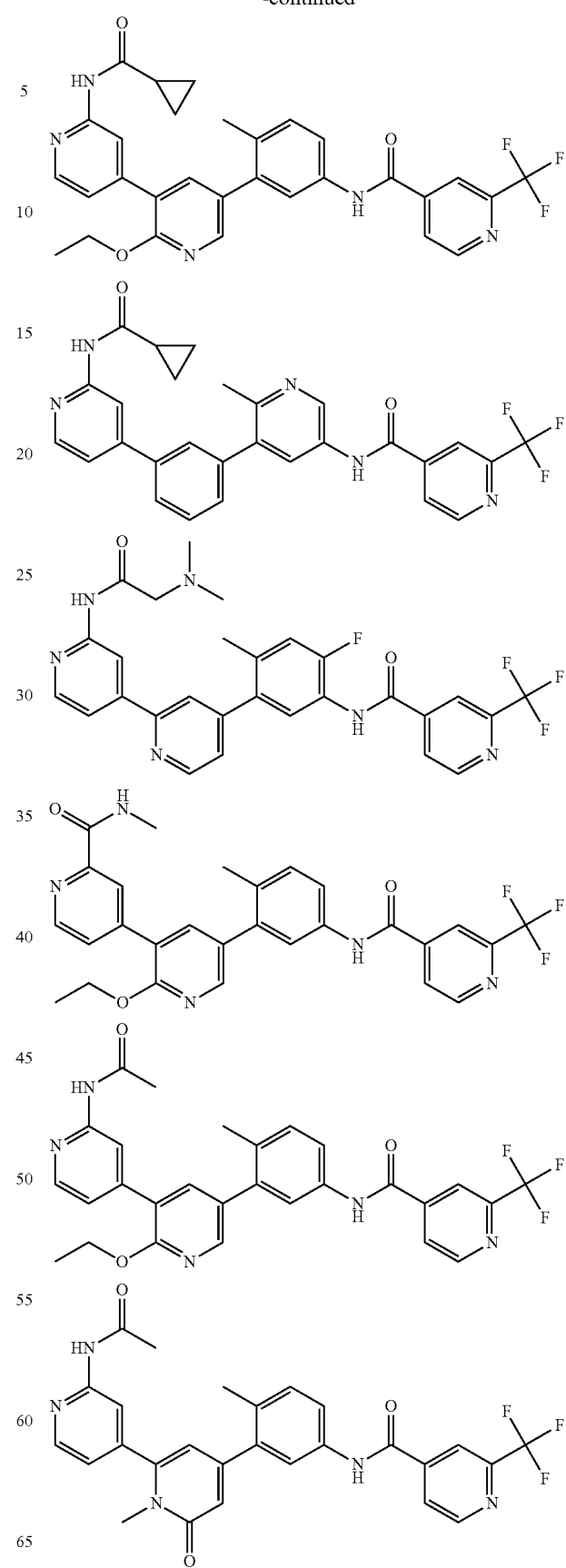

643
-continued
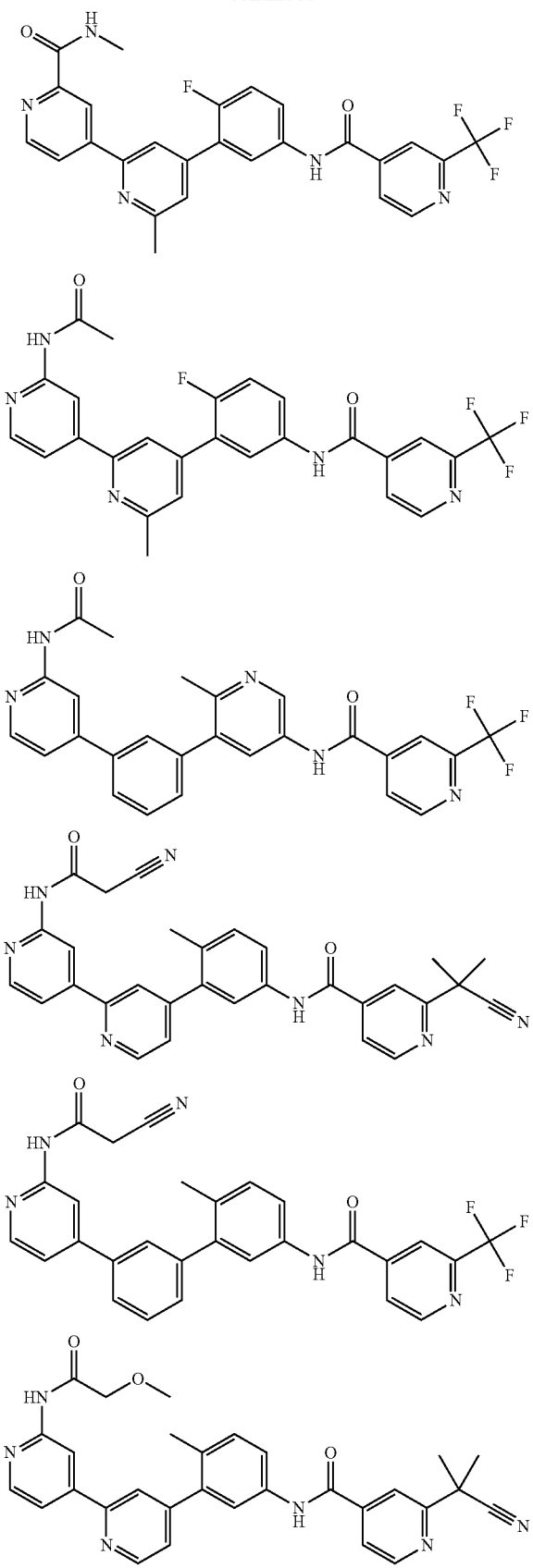
644
-continued
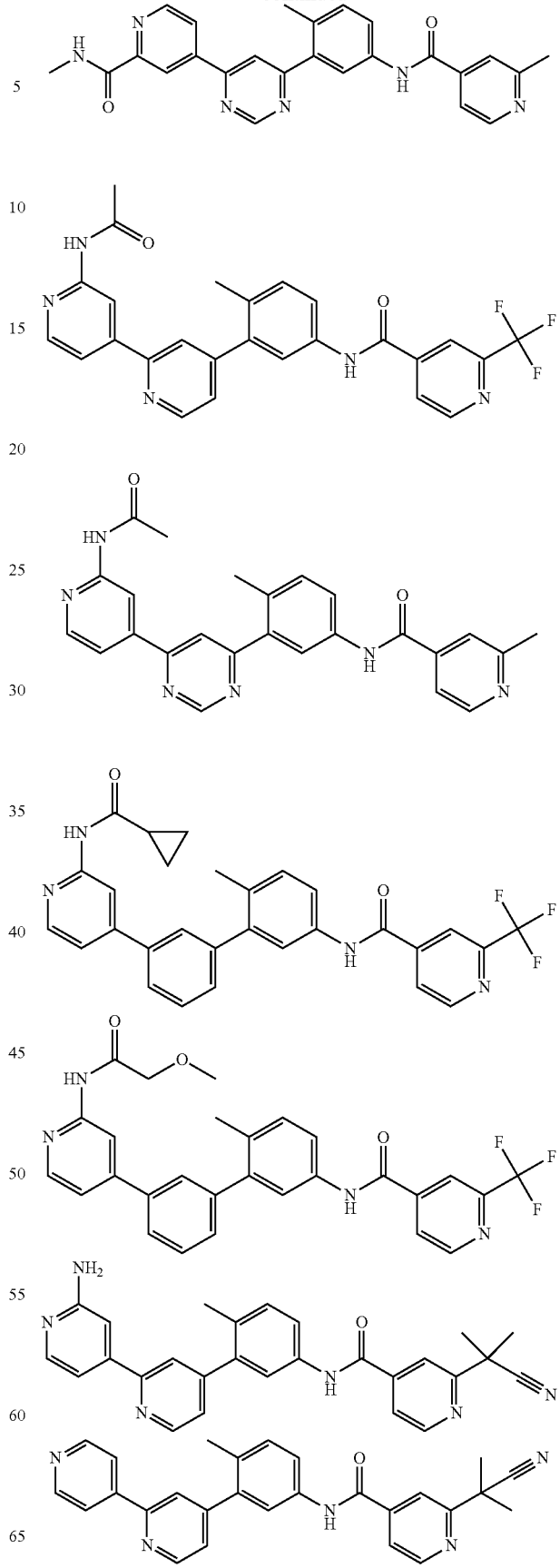

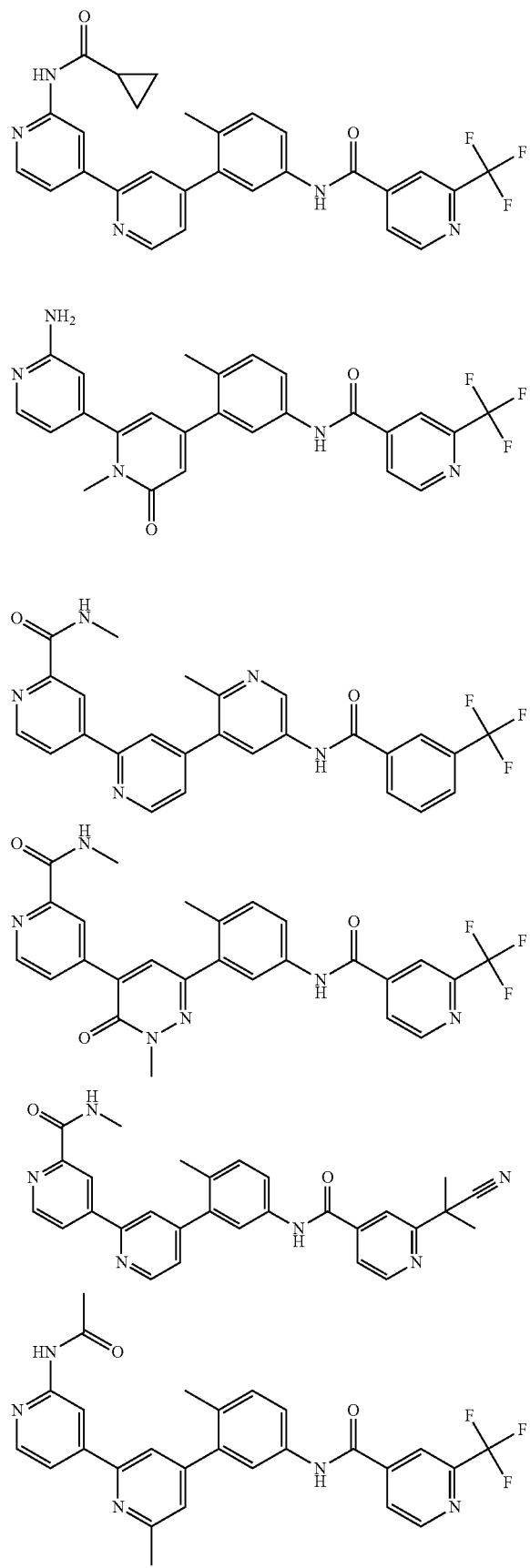
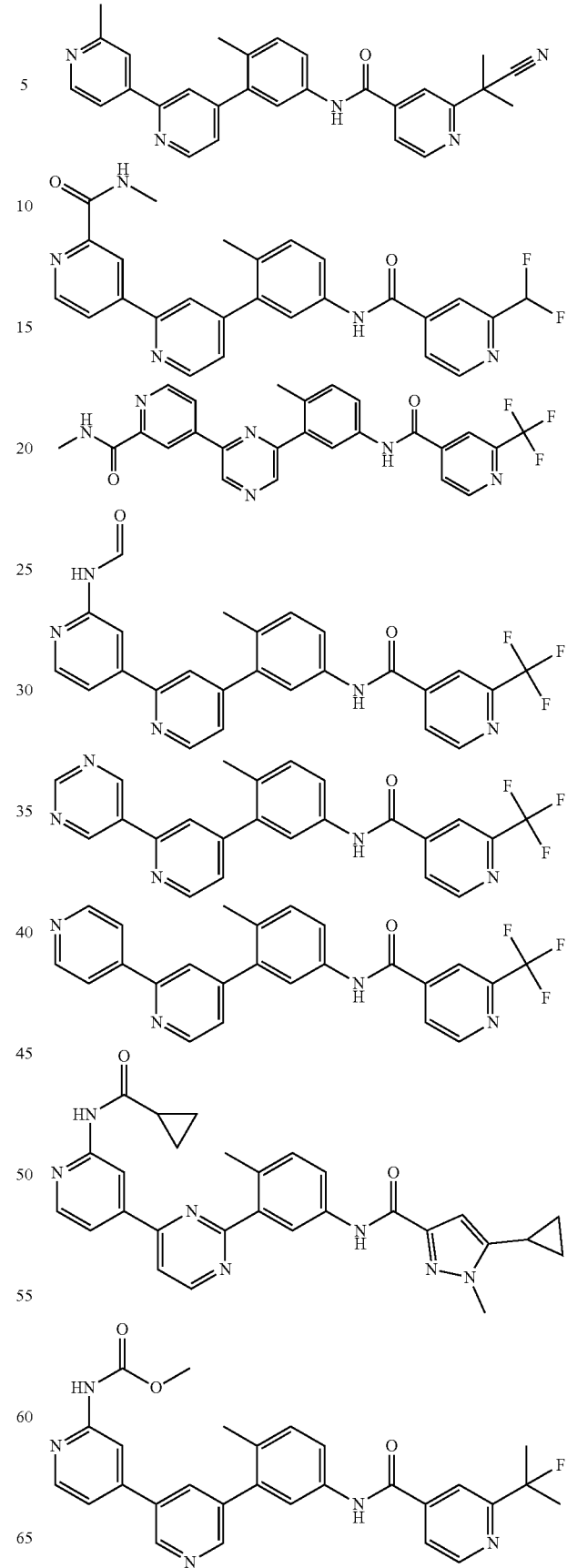

647
-continued
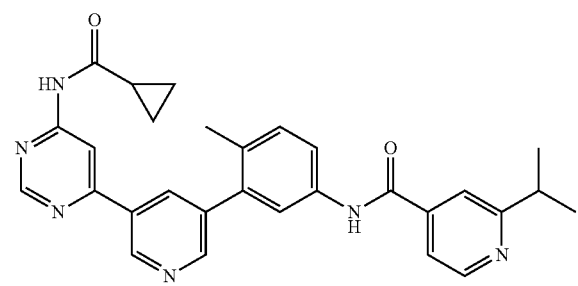
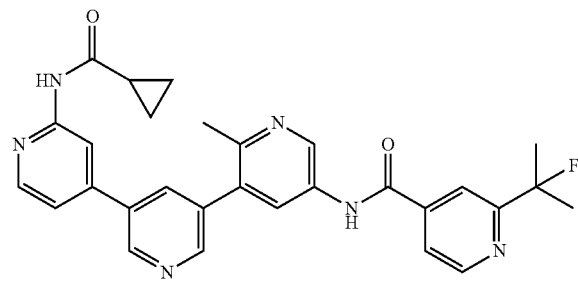
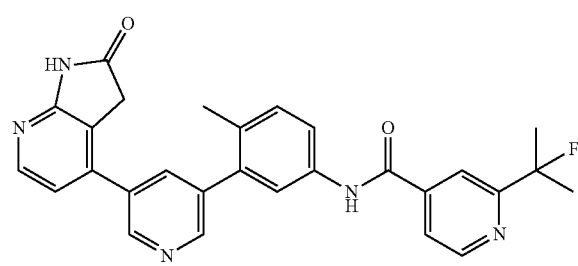
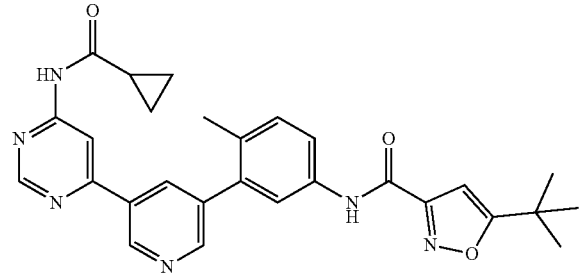
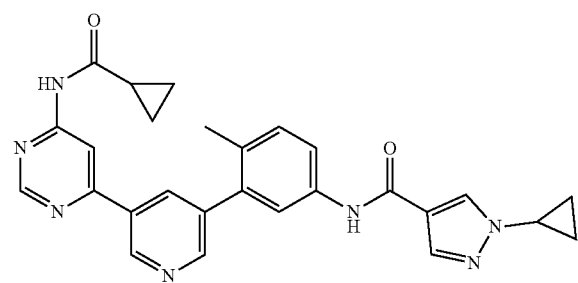
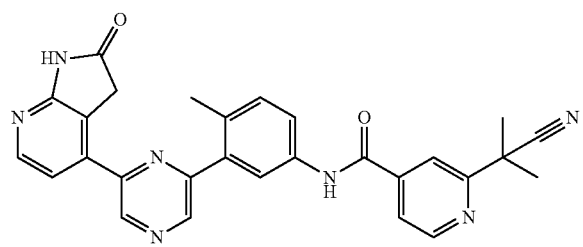
648
-continued
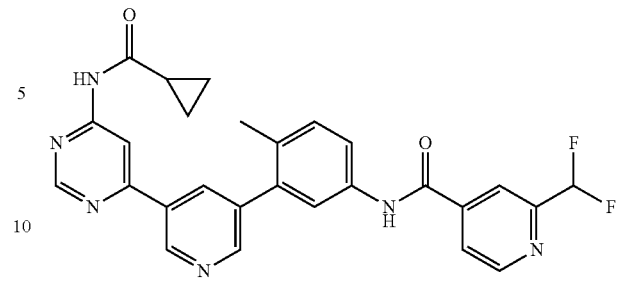
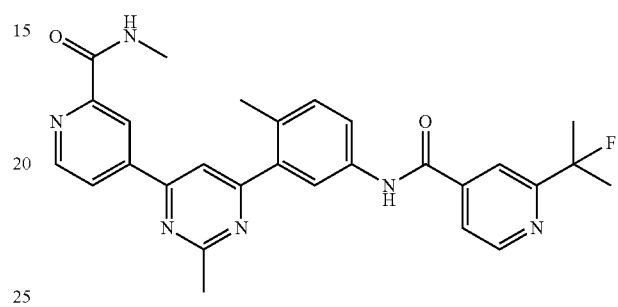
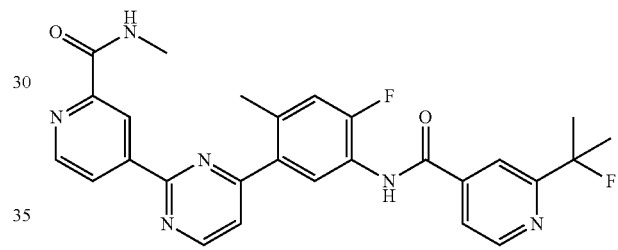
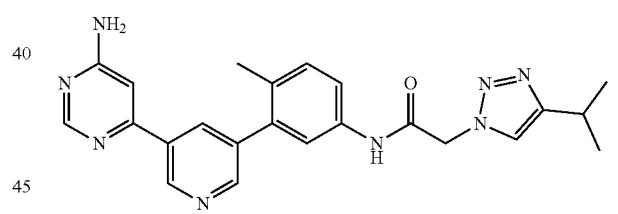
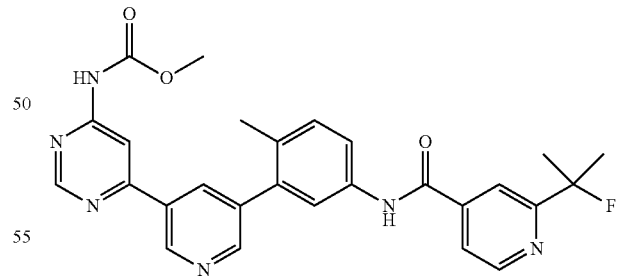
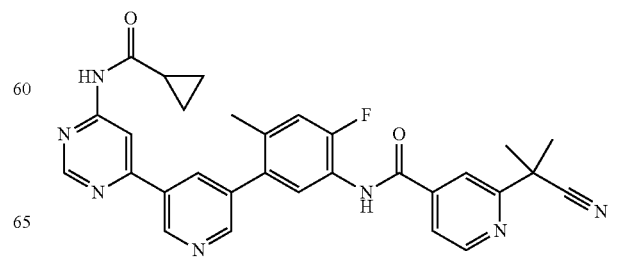

649
-continued
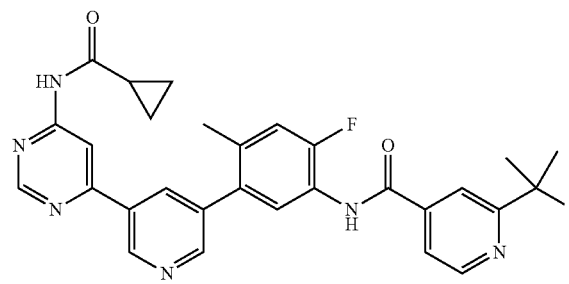
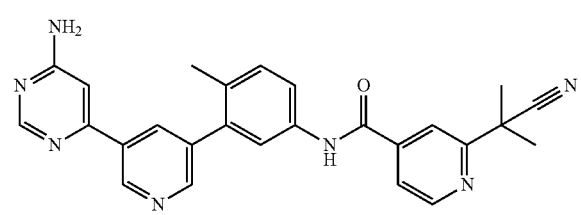
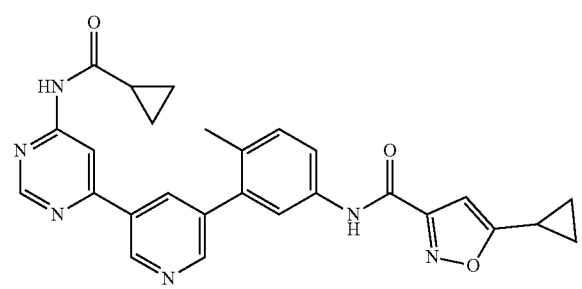
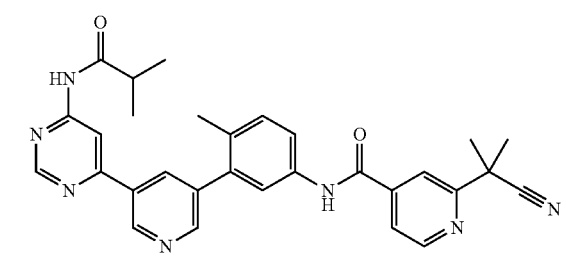
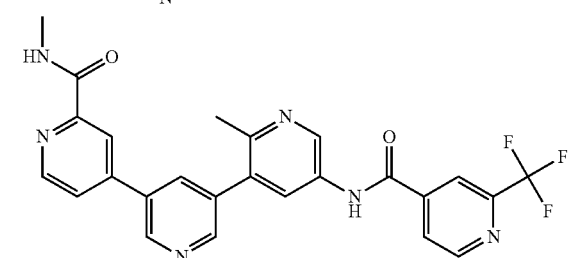
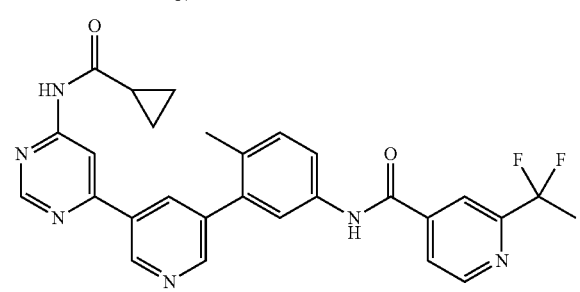
650
-continued
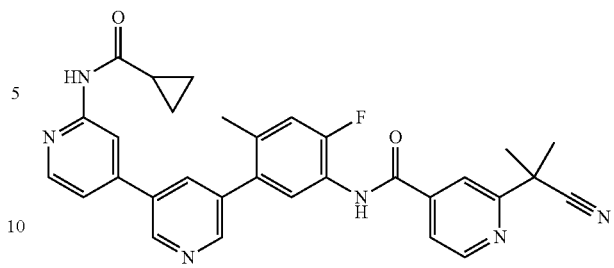
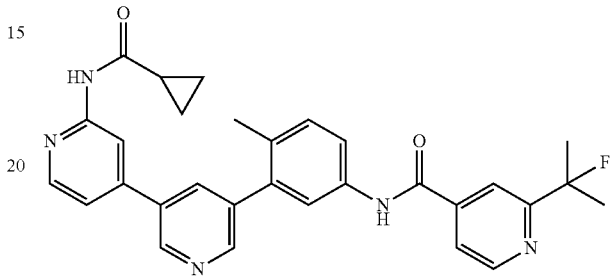
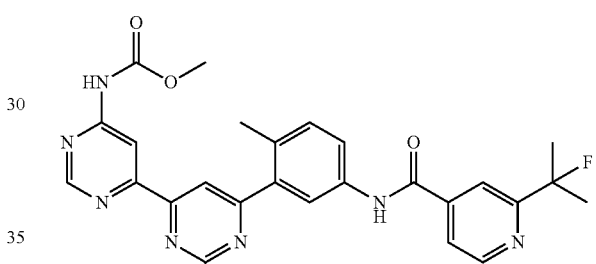
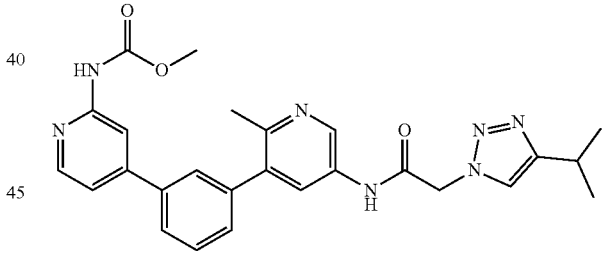
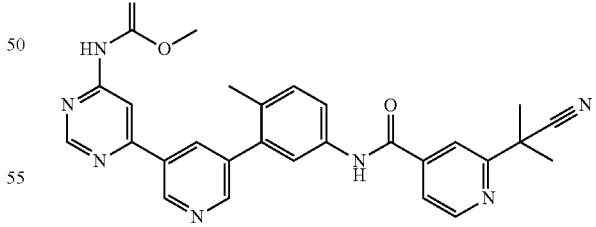
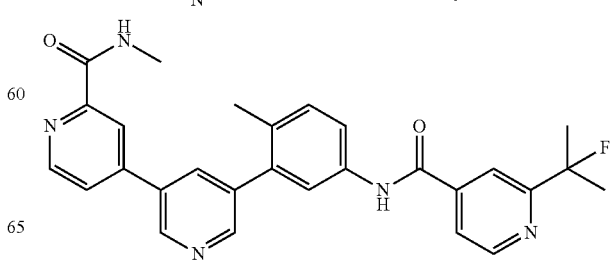

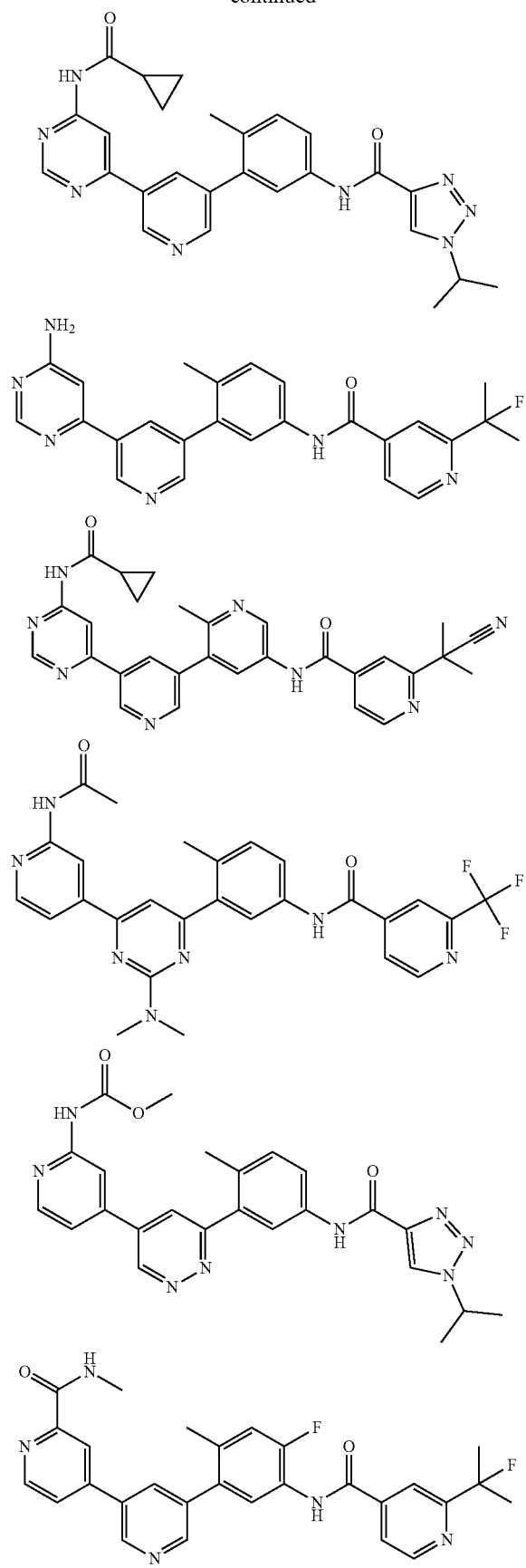
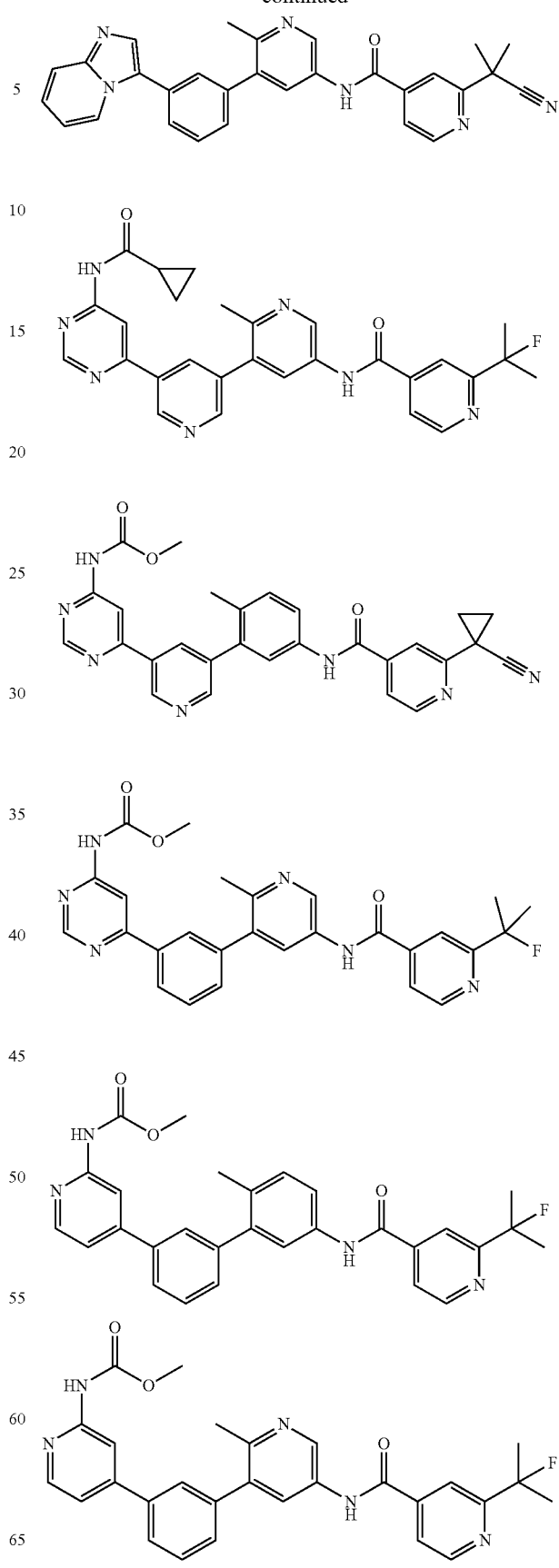

653
-continued
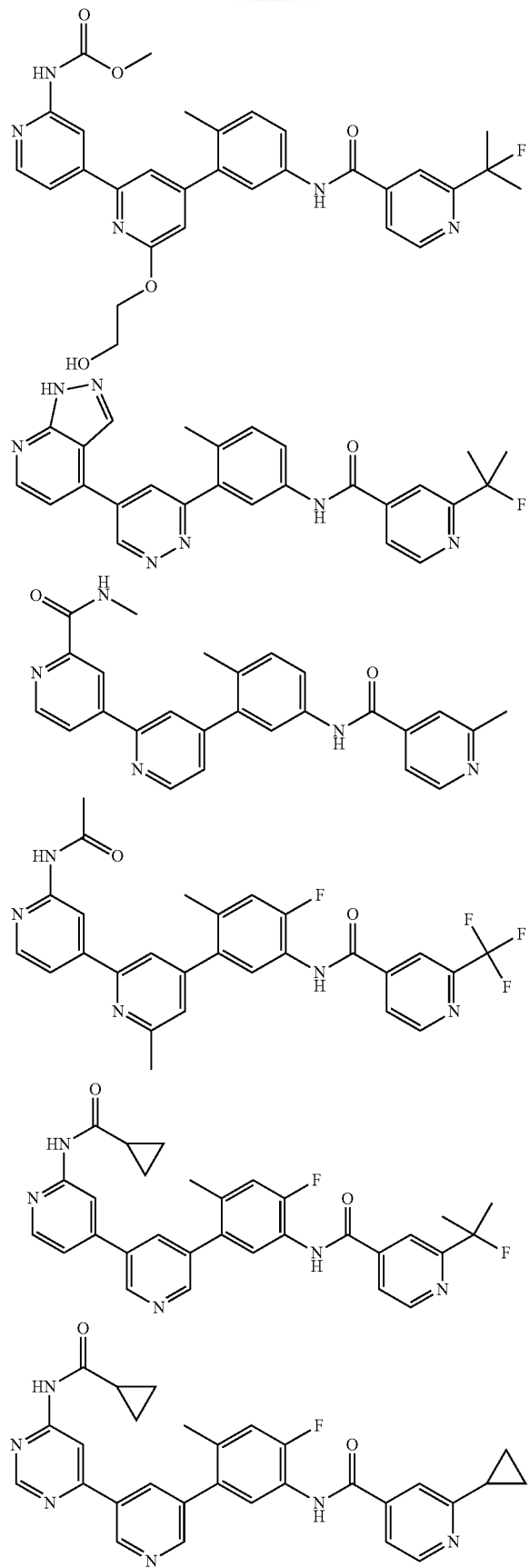
654
-continued
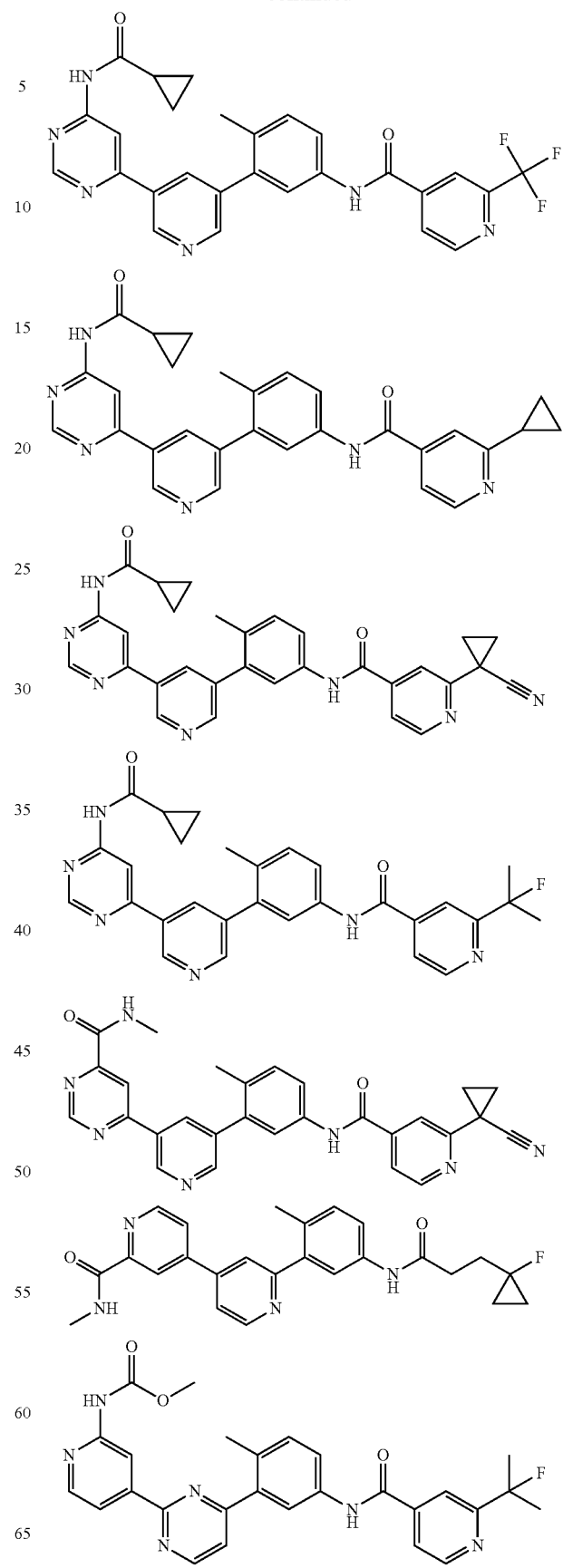

655
-continued
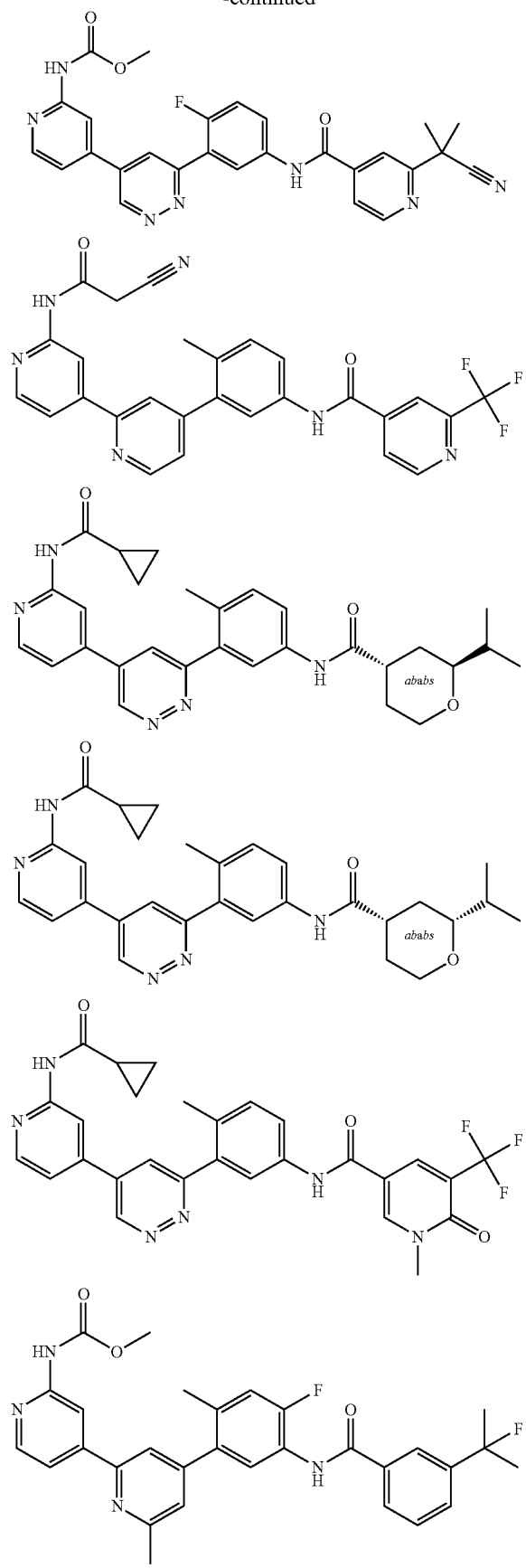
656
-continued
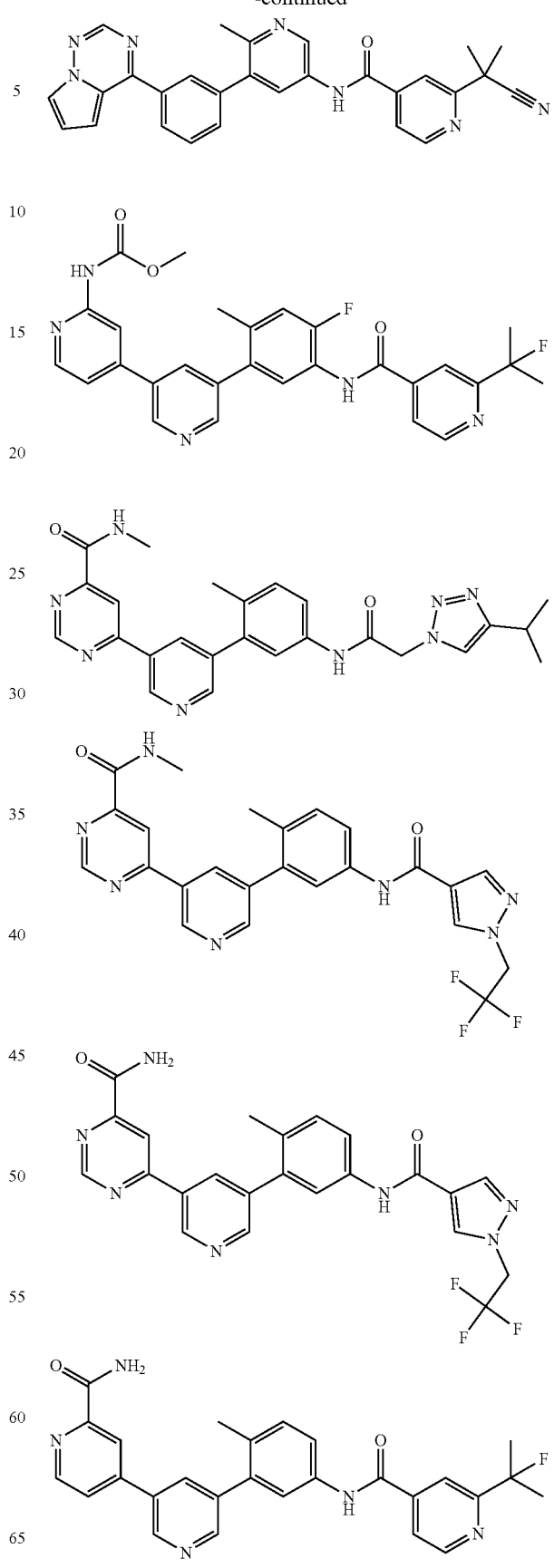

657
-continued
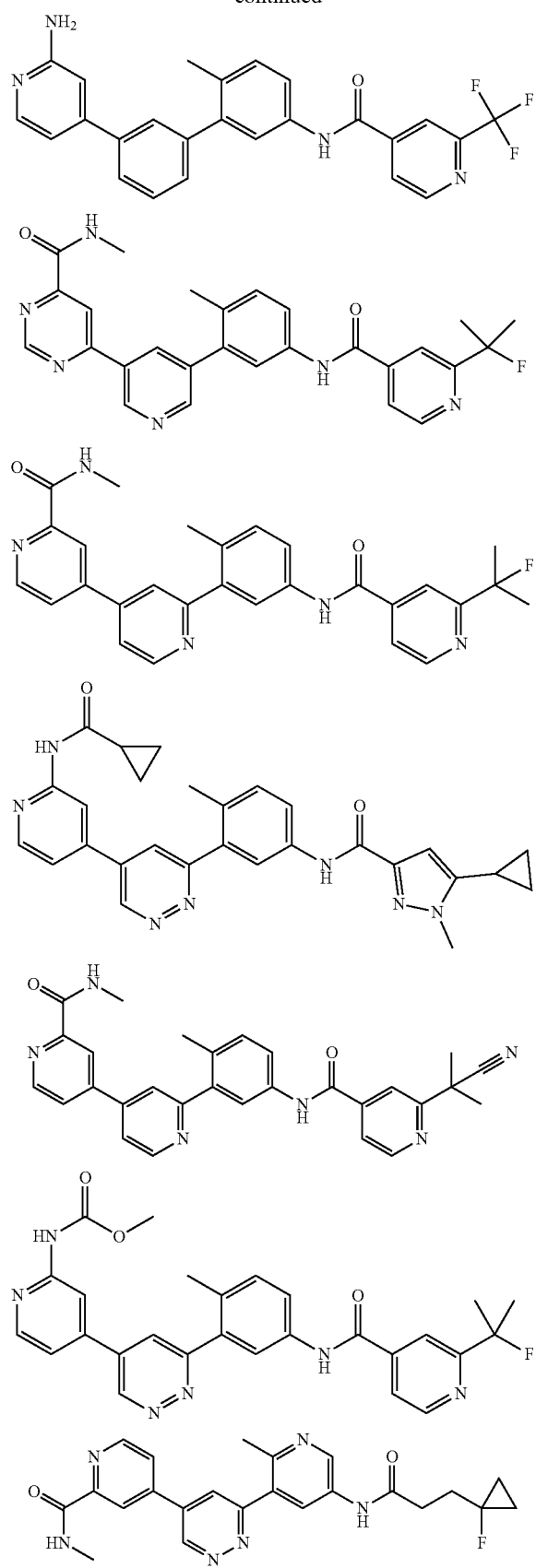
658
-continued
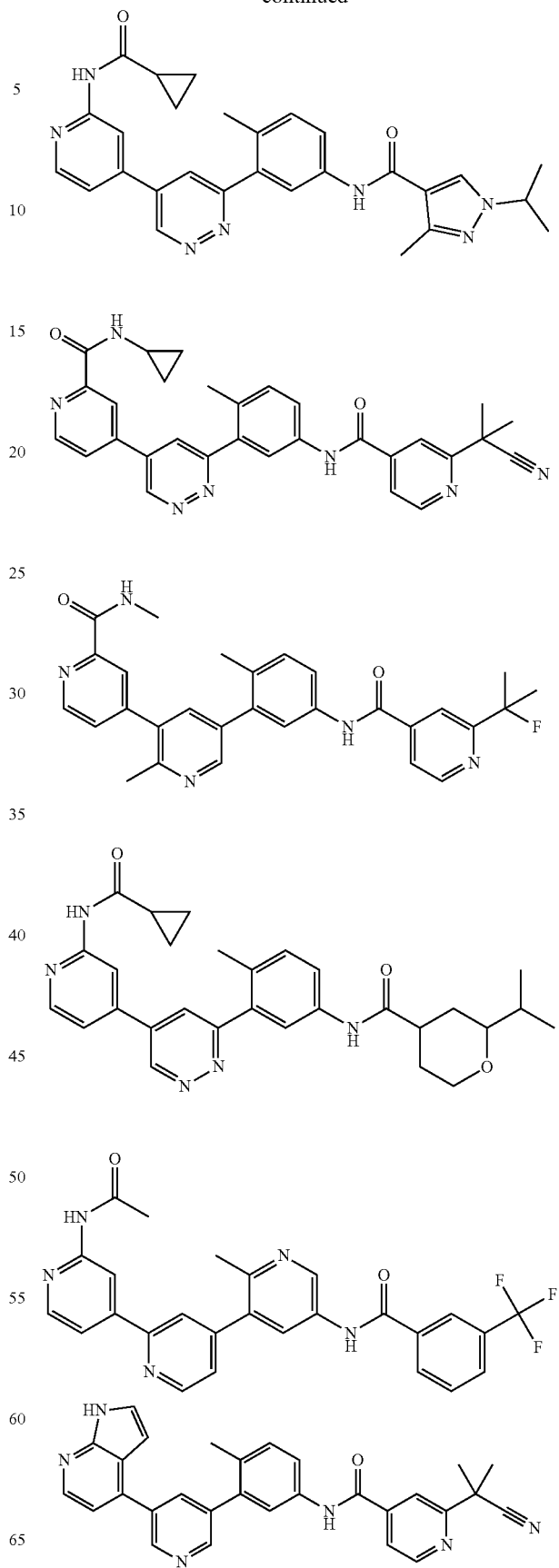

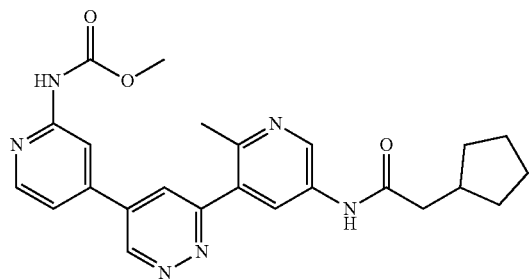
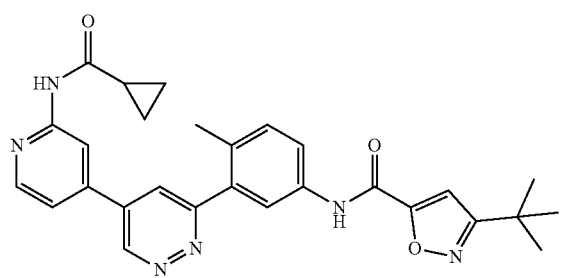
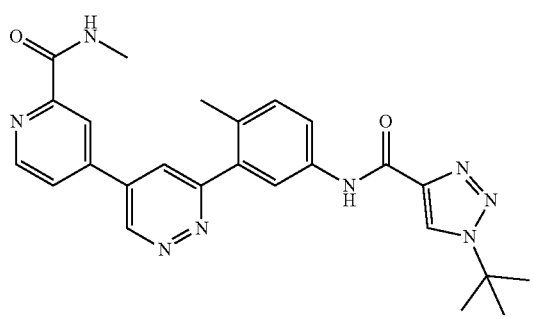
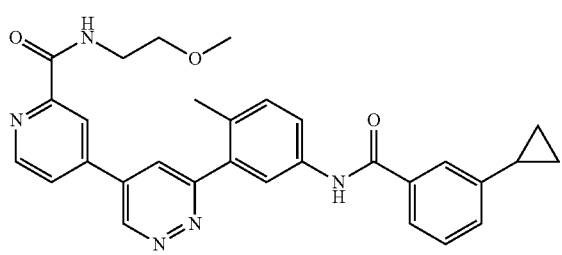
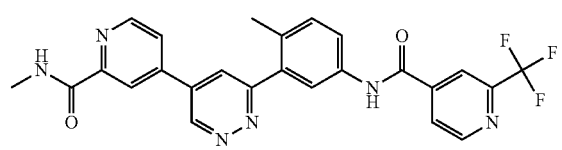
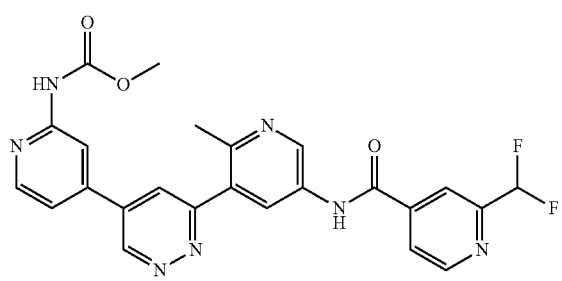
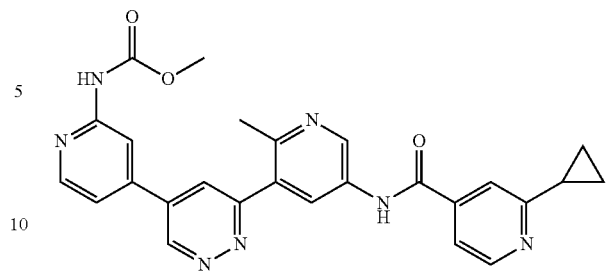
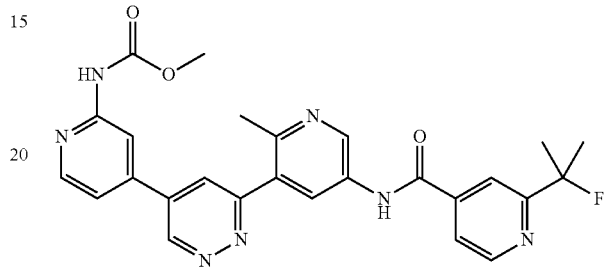
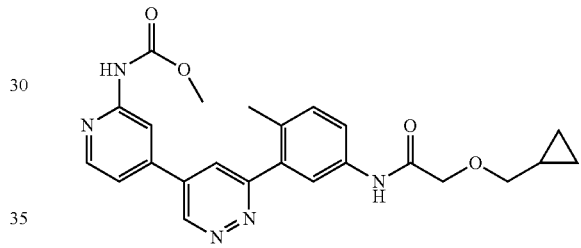
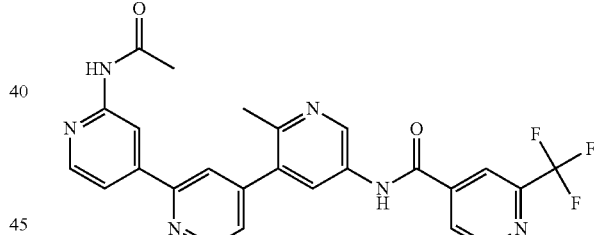
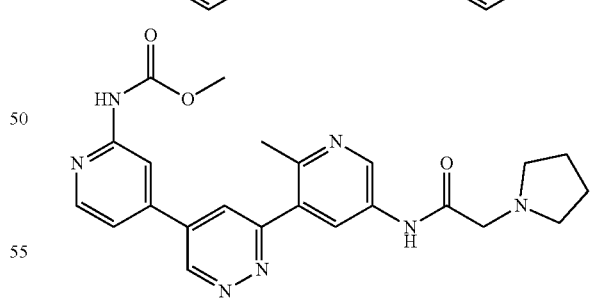
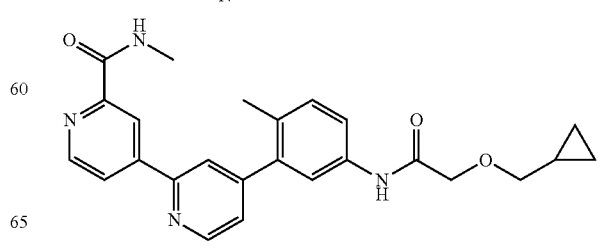

| 661 -continued | 662 -continued |
|---|---|
| 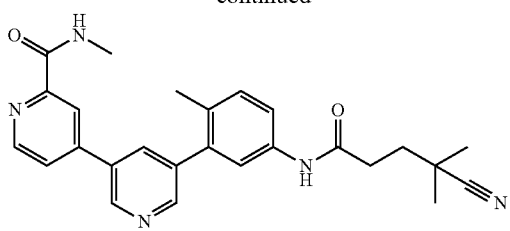 | 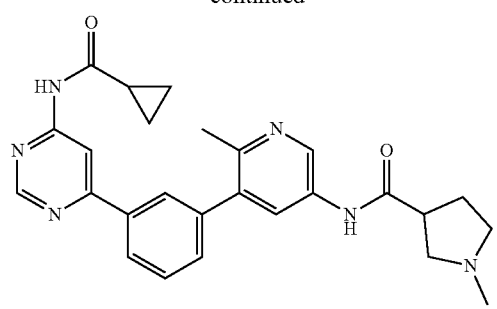 |
| 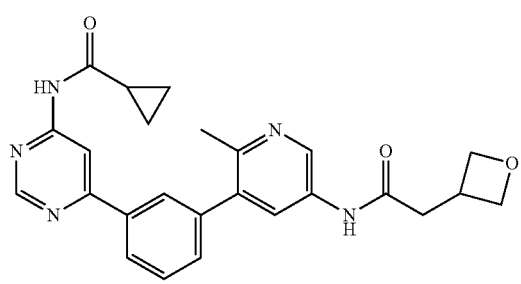 | 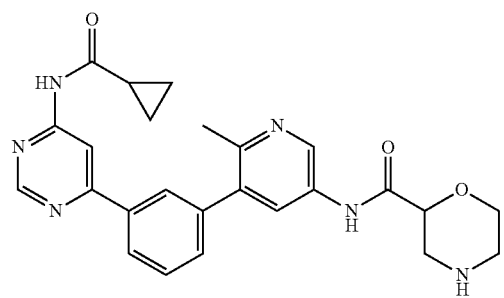 |
| 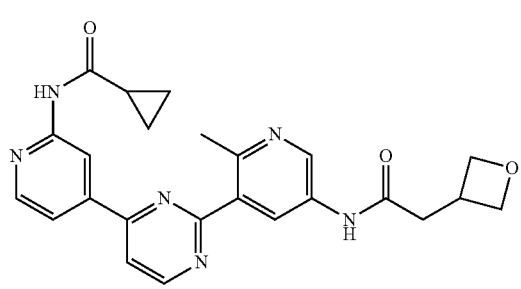 | 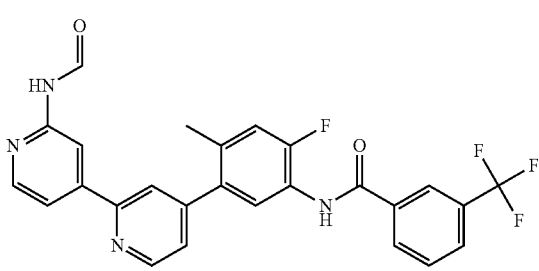 |
| 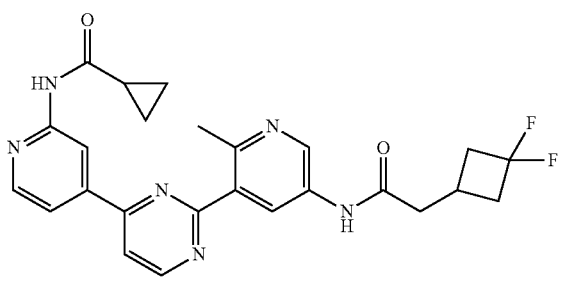 | 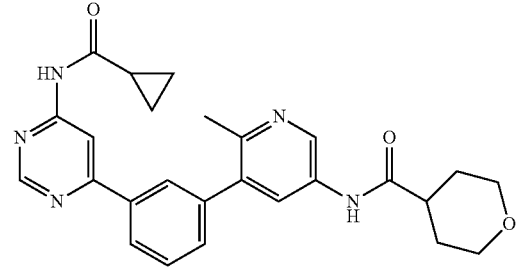 |
| 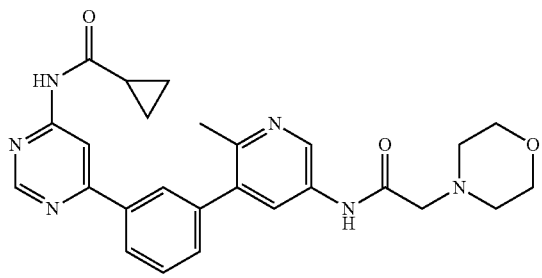 | 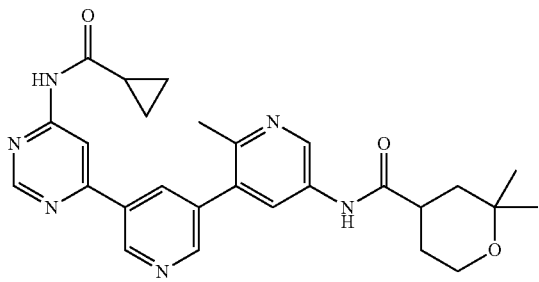 |
| 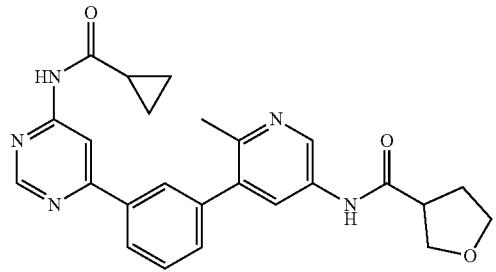 | 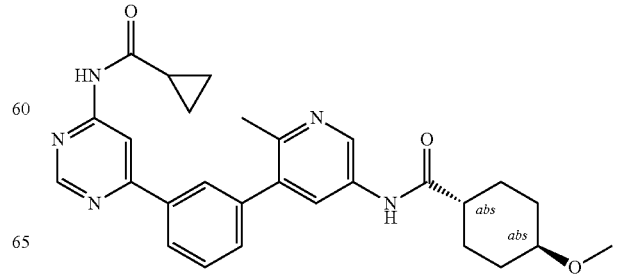 |

663
-continued
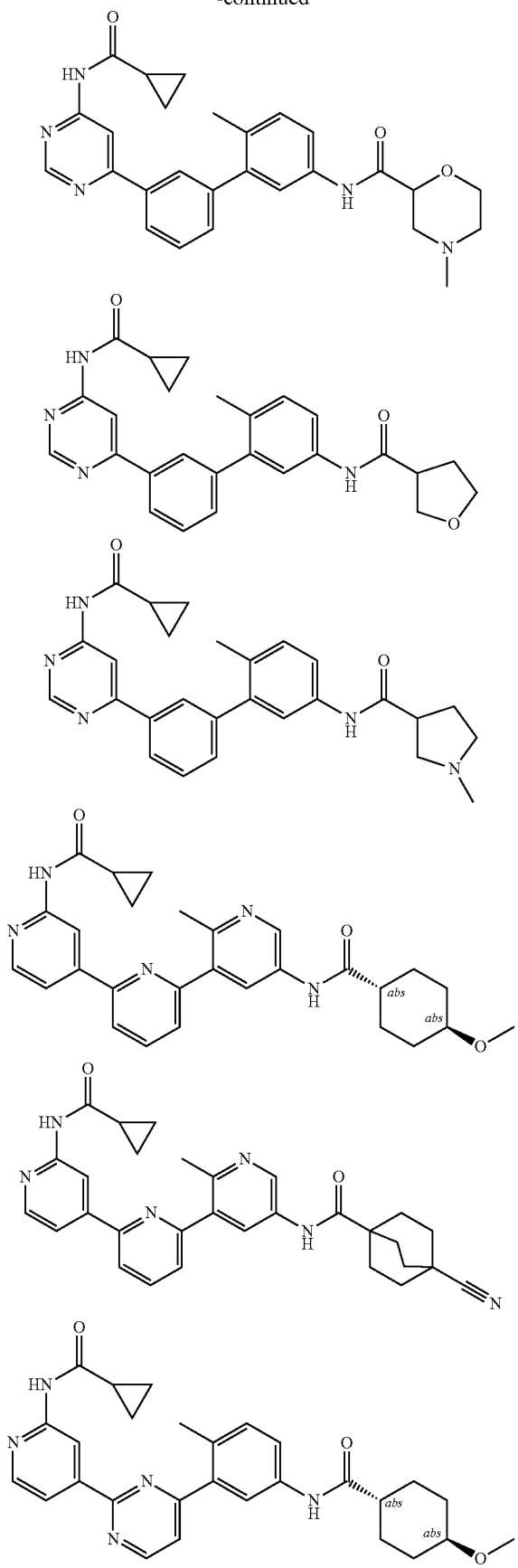
664
-continued
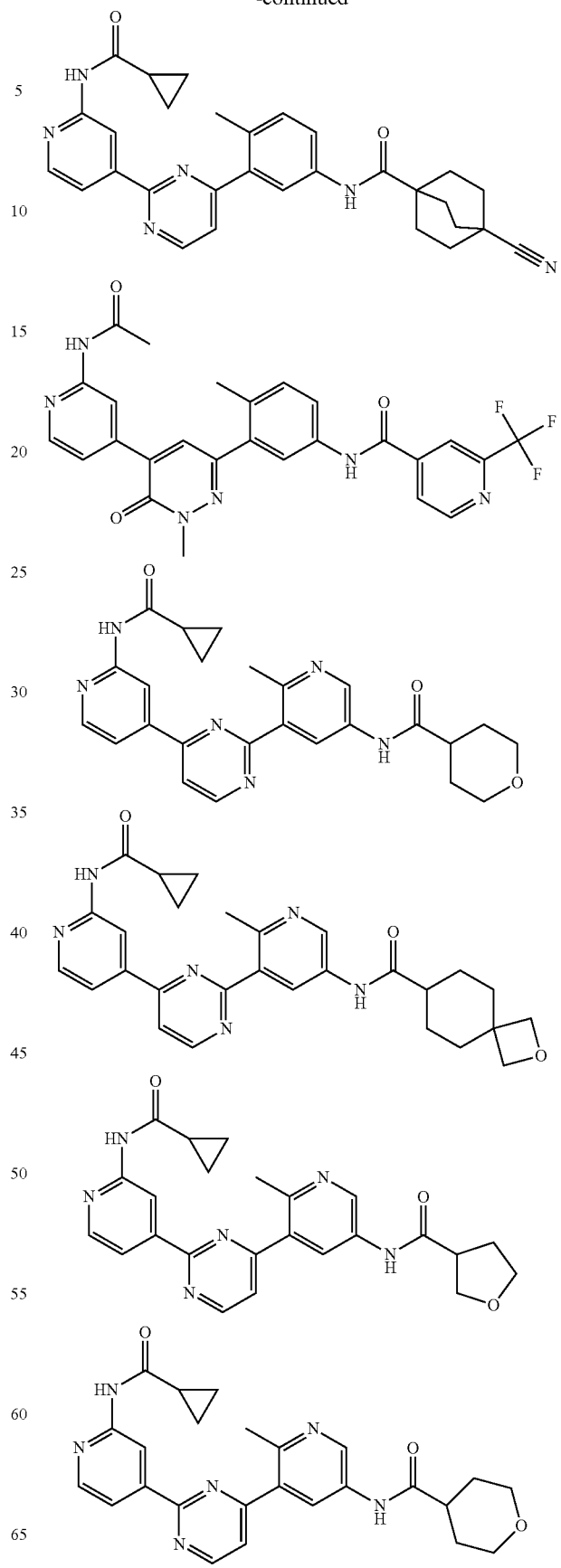

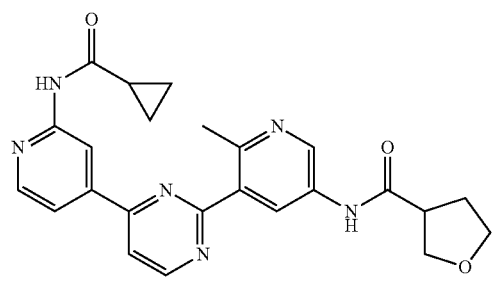
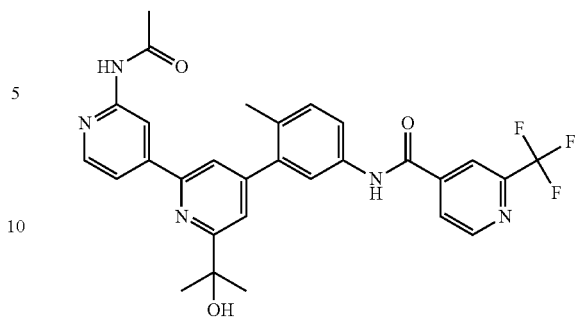
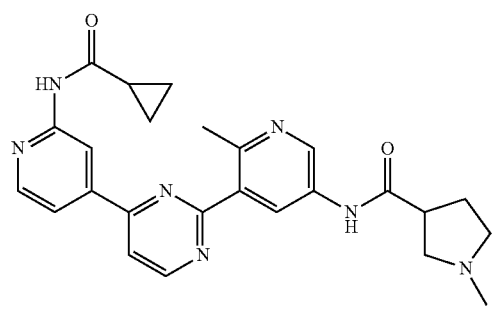
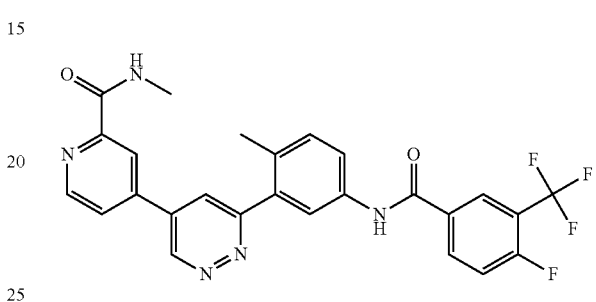
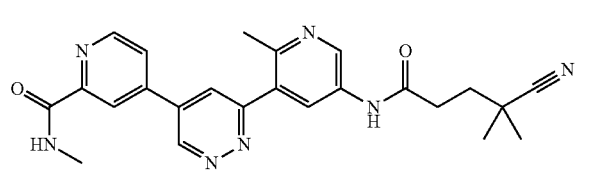
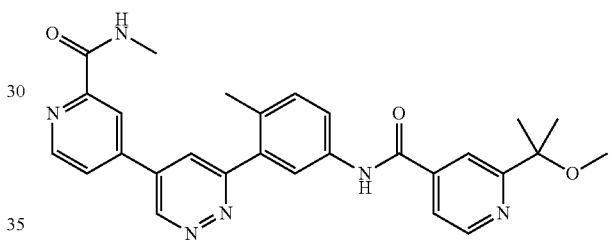
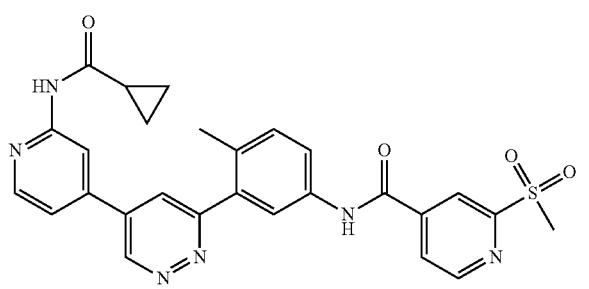
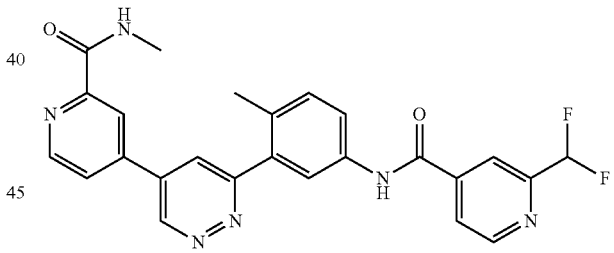
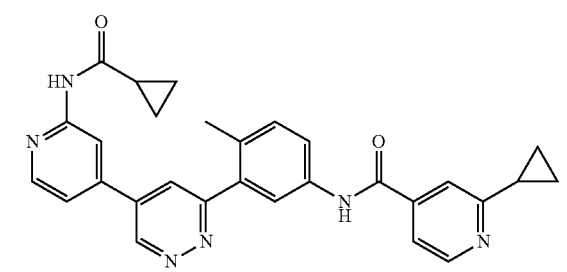
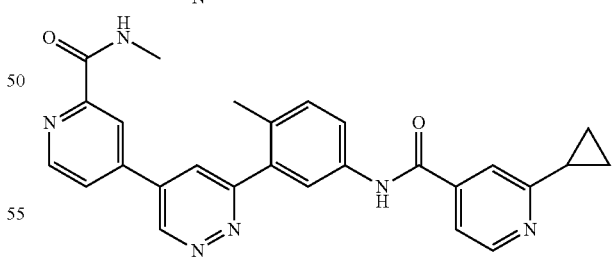
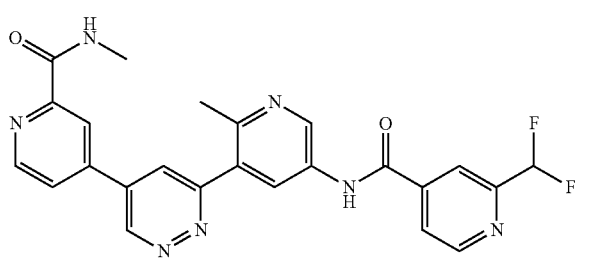
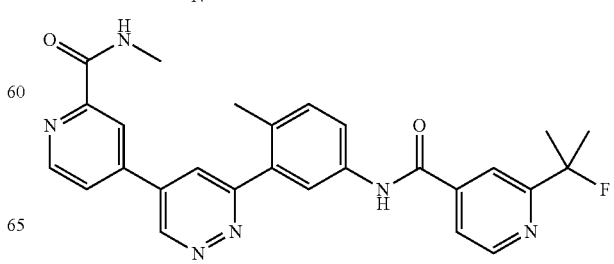

667
-continued
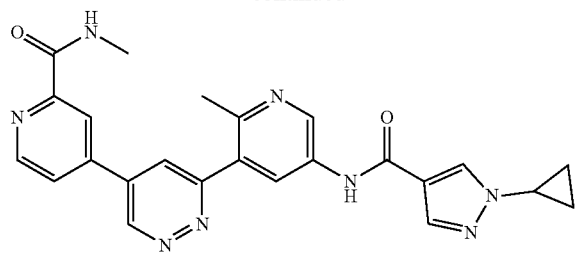
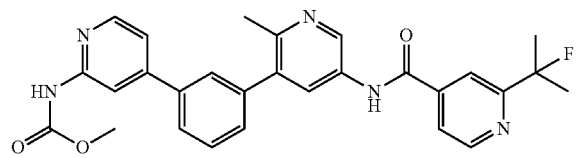
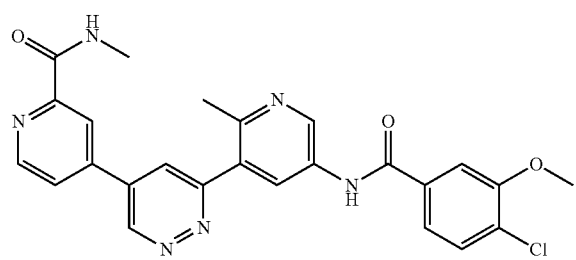
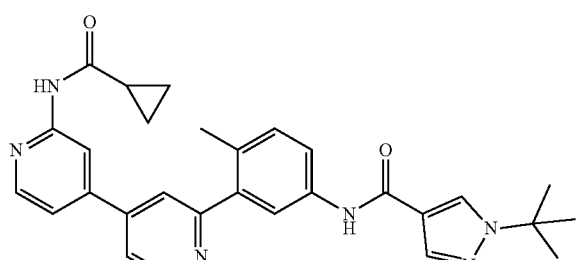
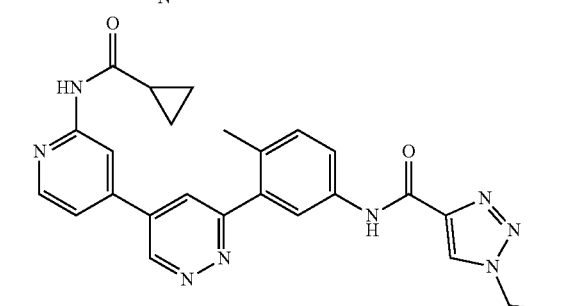
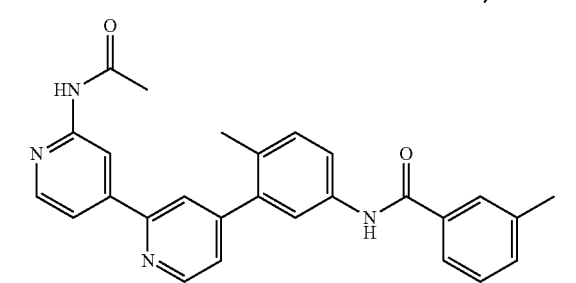
668
-continued
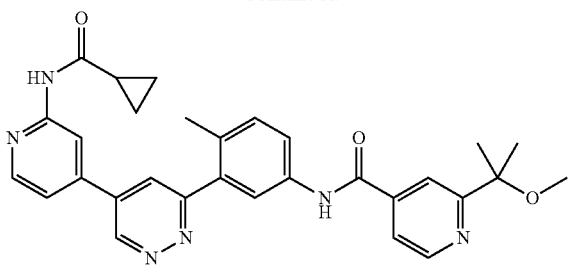
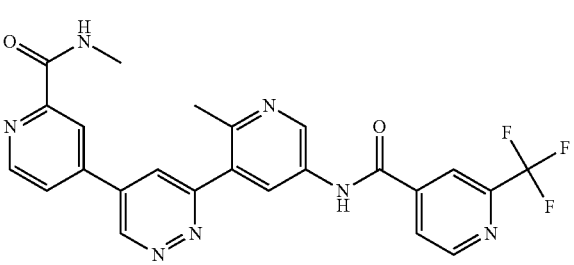
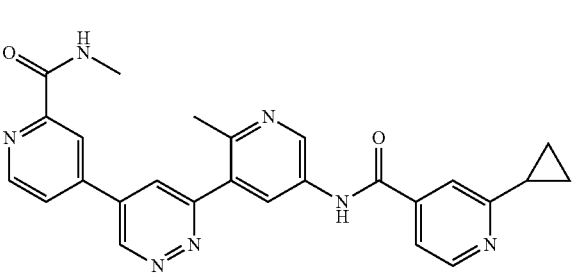
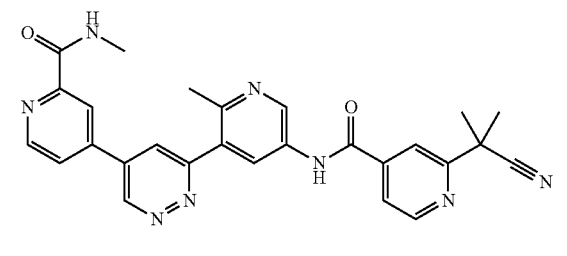
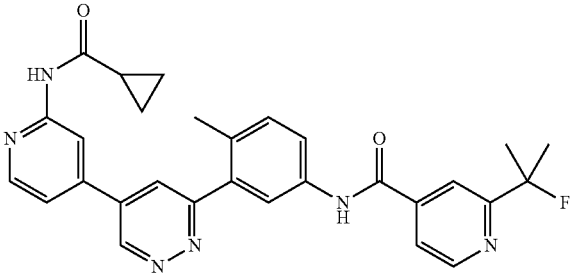
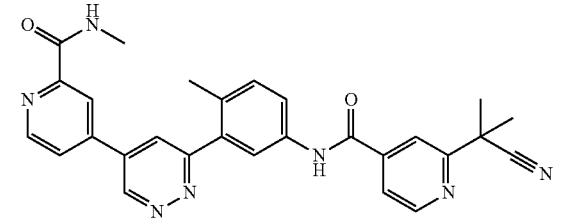

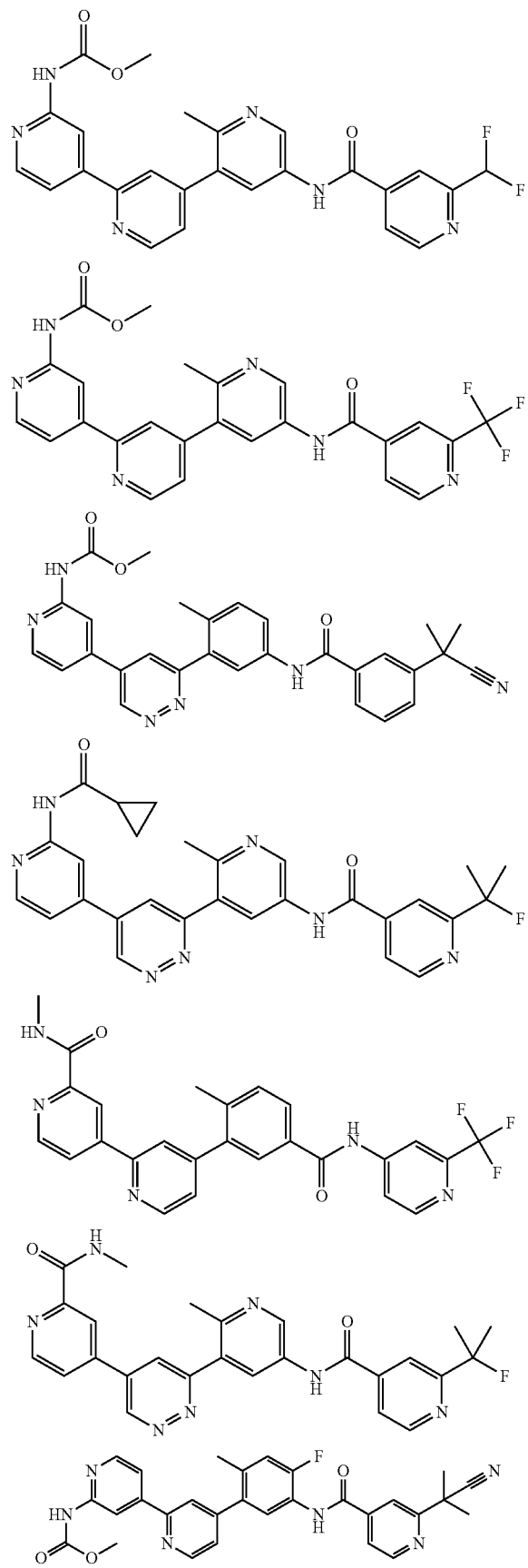
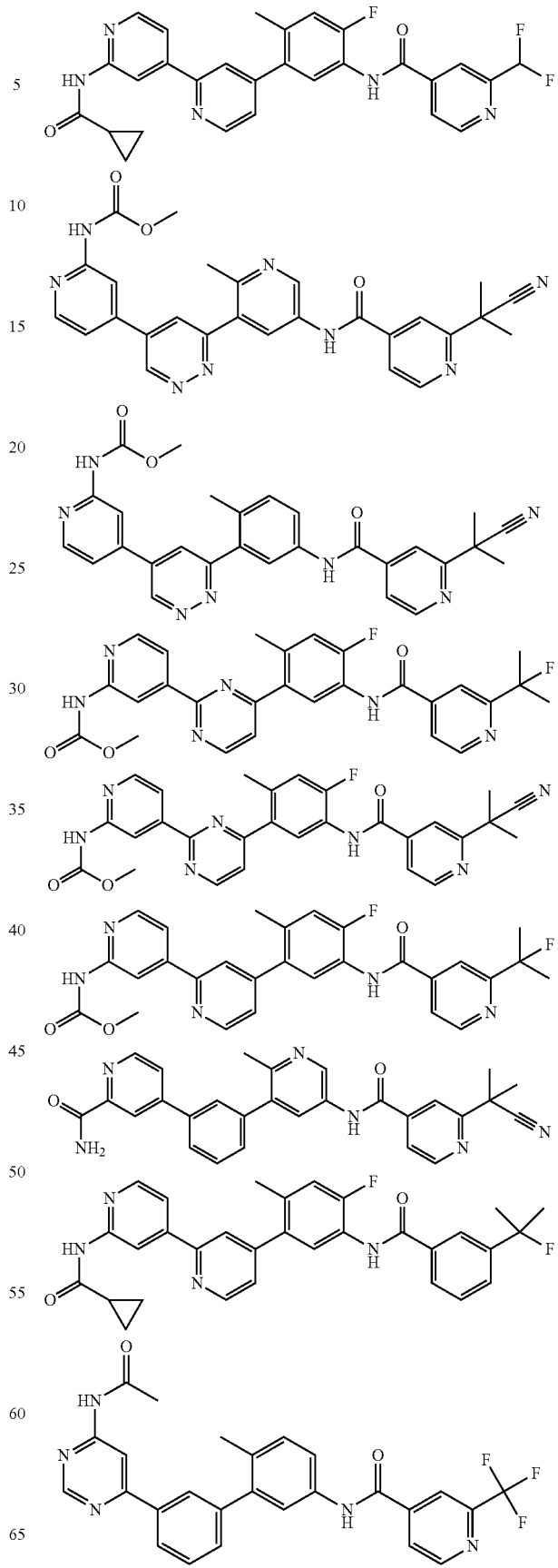

671
-continued
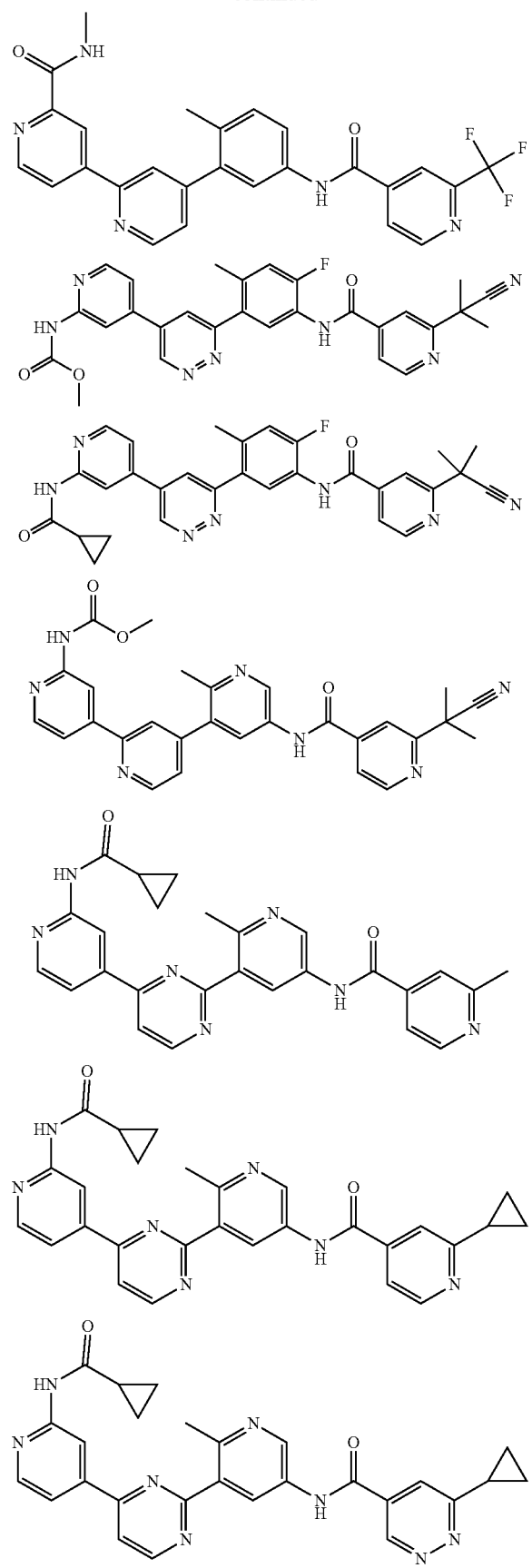
672
-continued
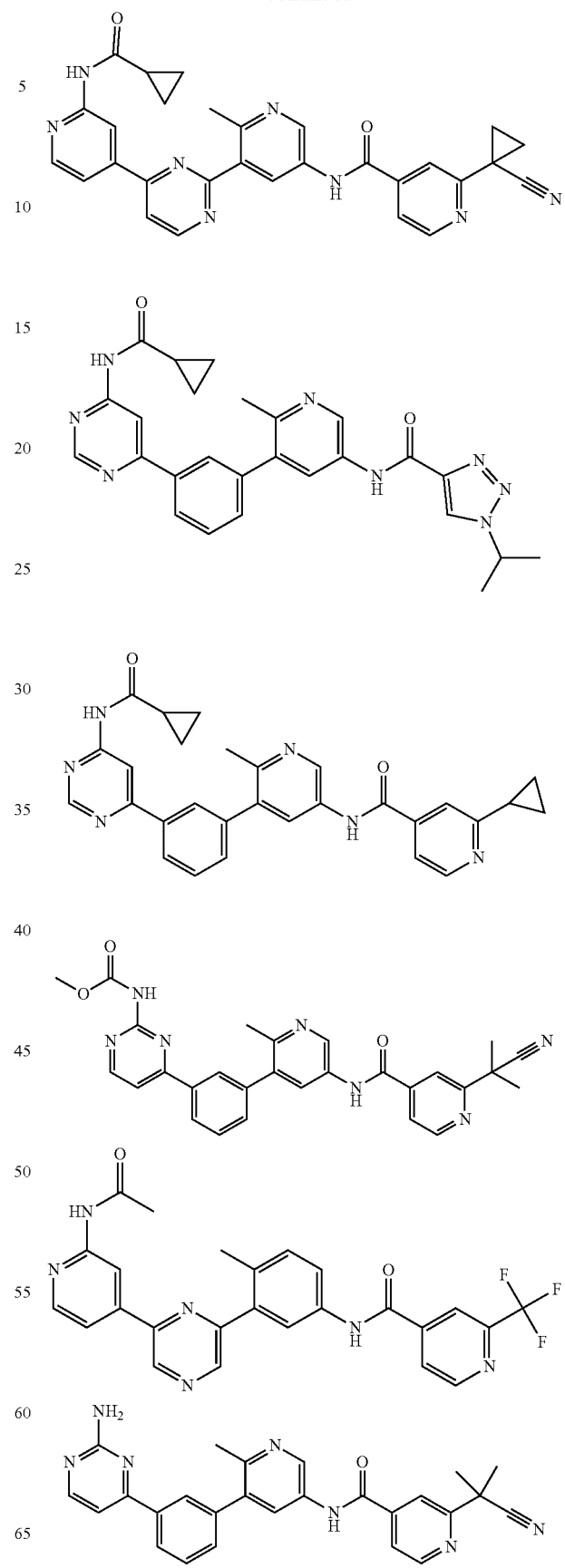

673
-continued
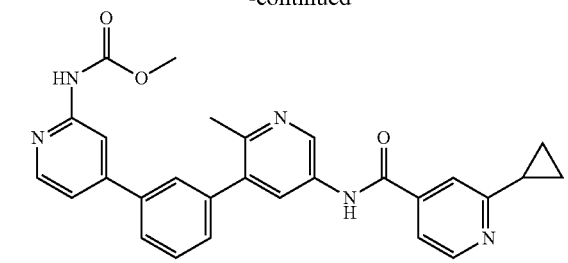
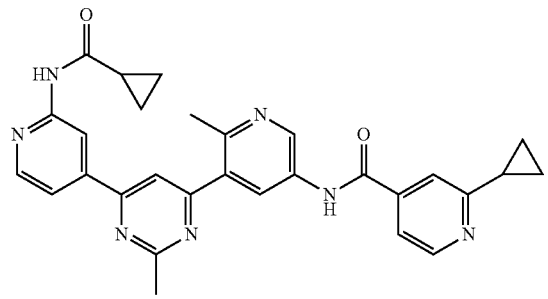
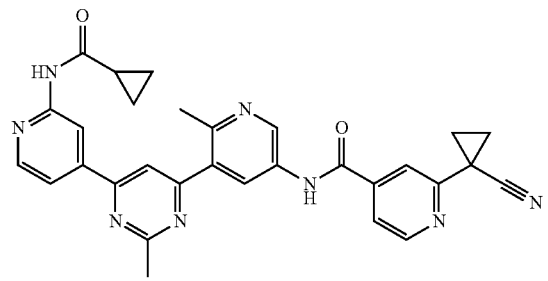
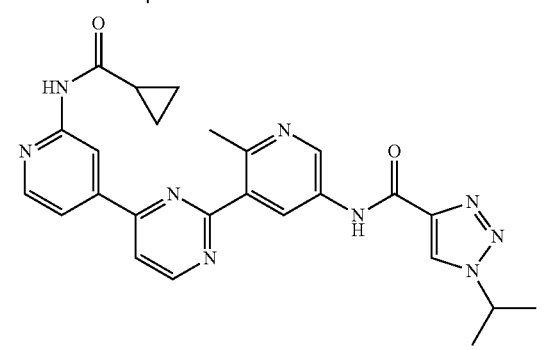
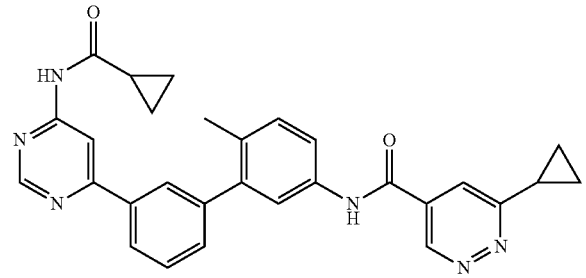
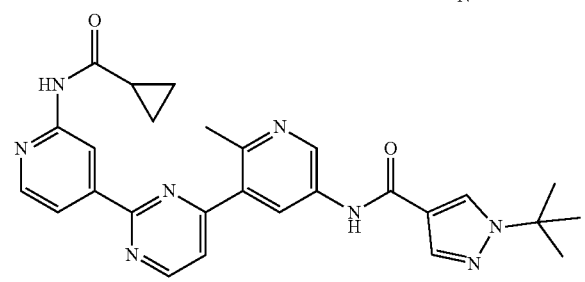
674
-continued
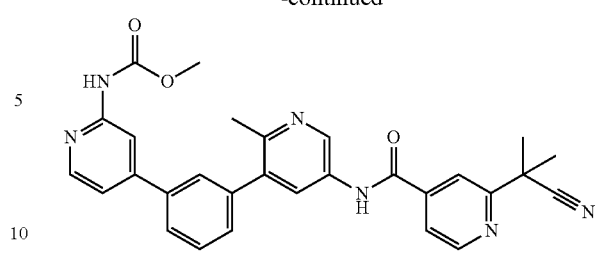
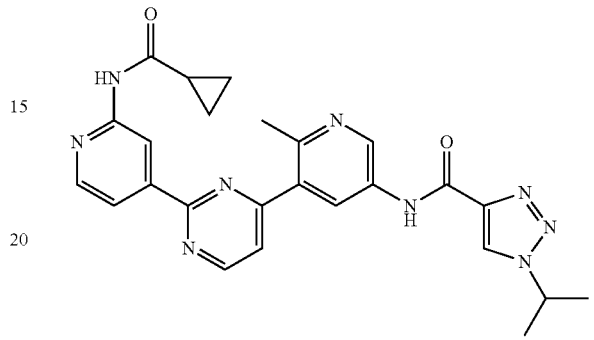
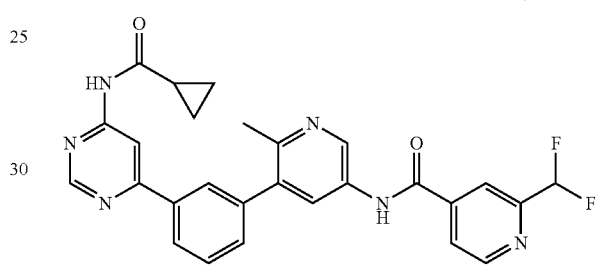
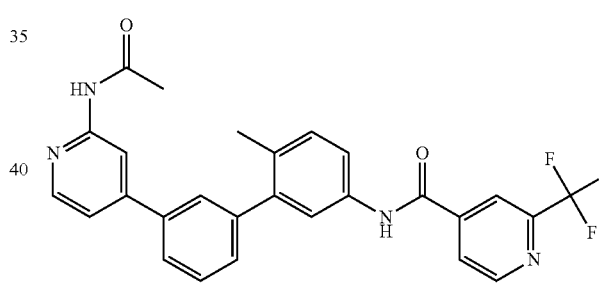
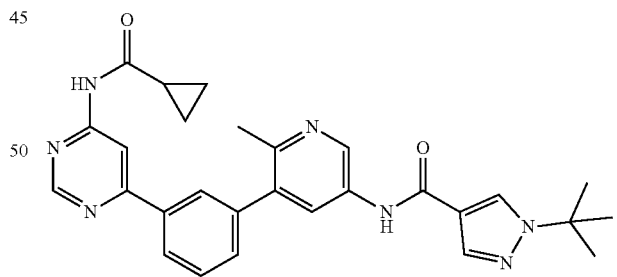
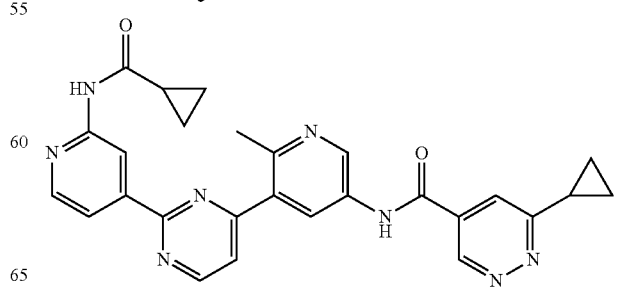

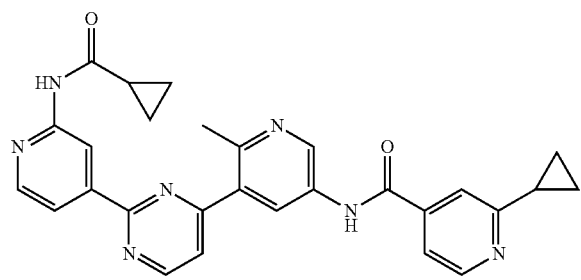
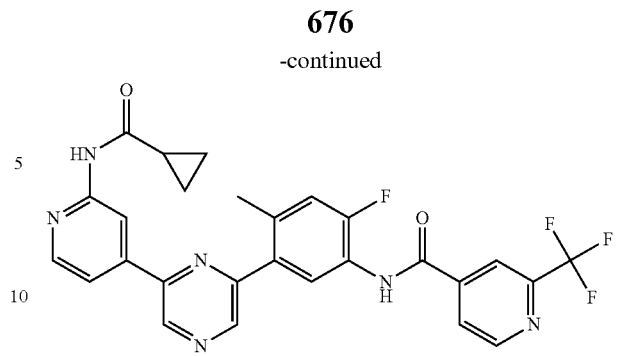
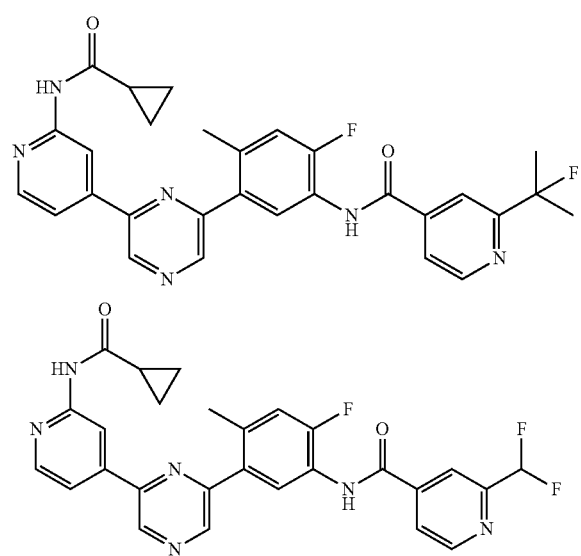
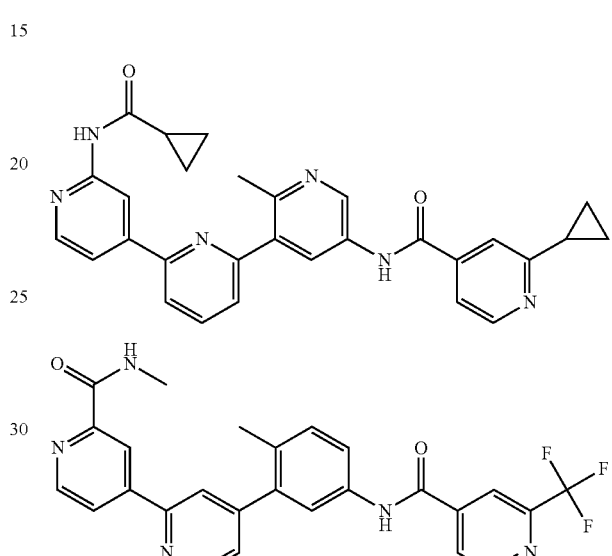
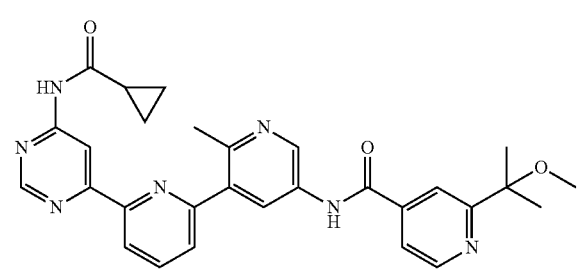
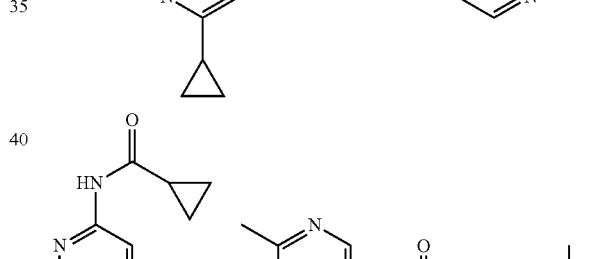
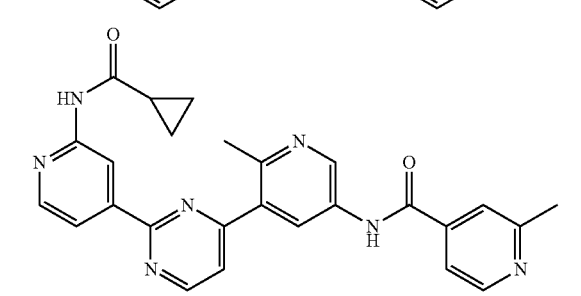
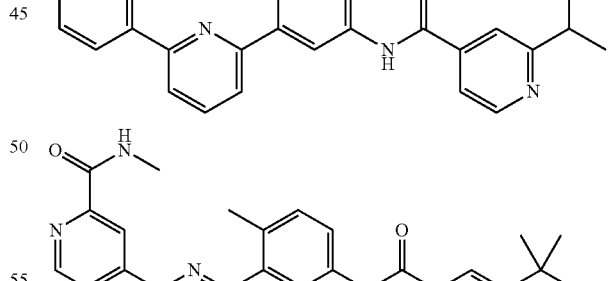
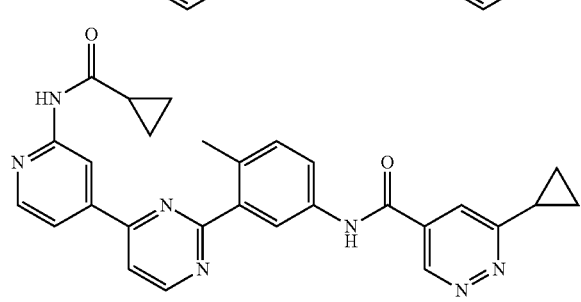
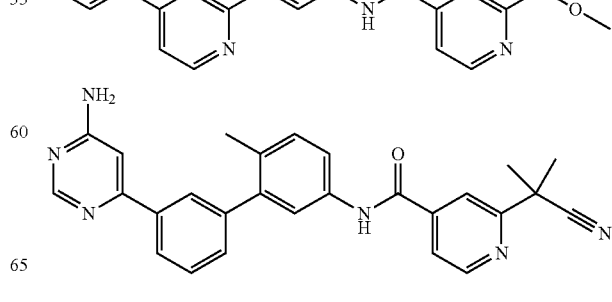

677
-continued
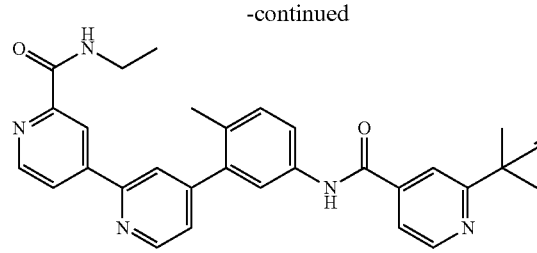
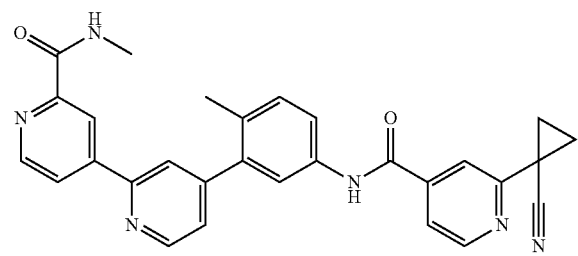
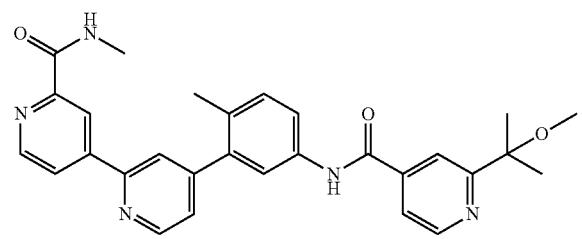
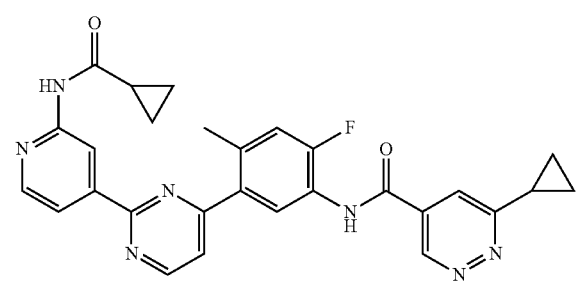
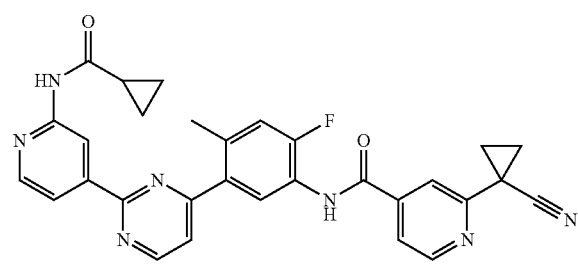
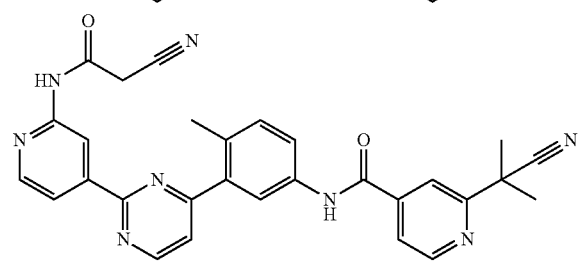
678
-continued
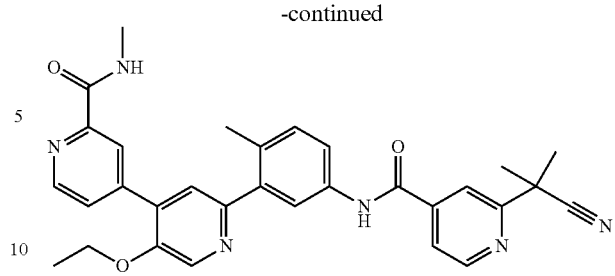
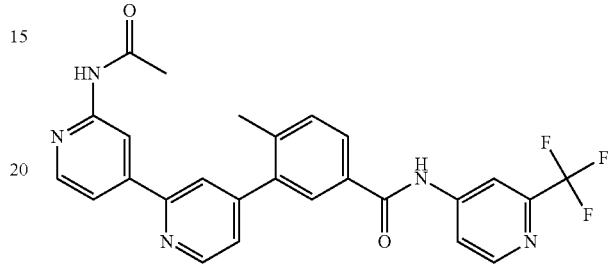
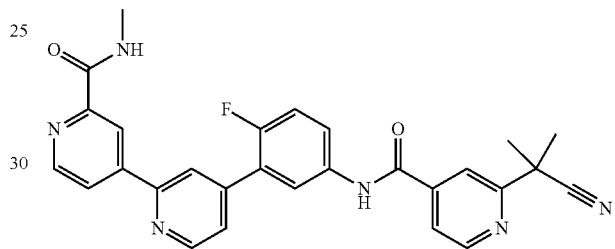
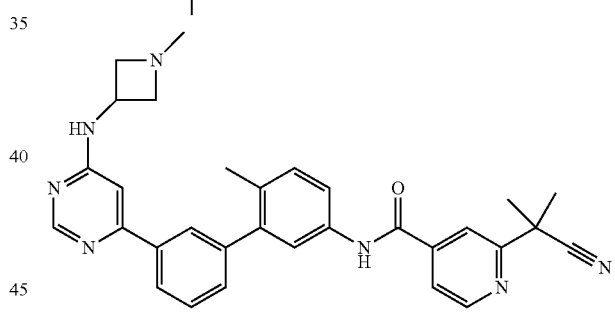
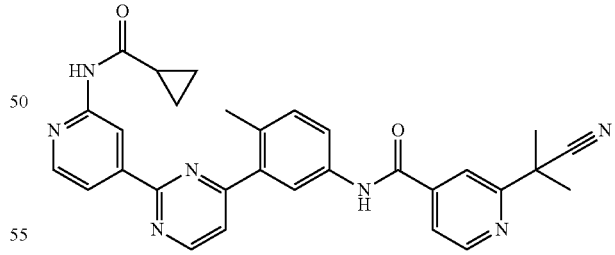
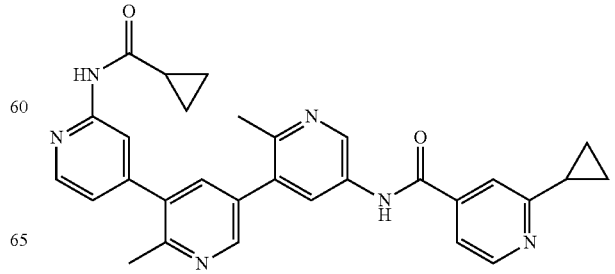

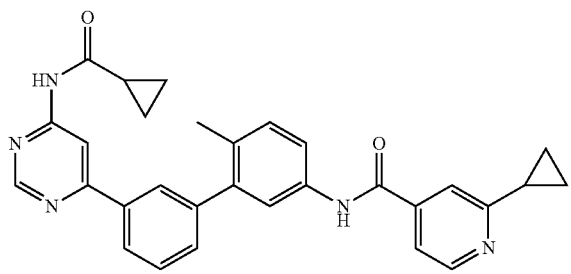
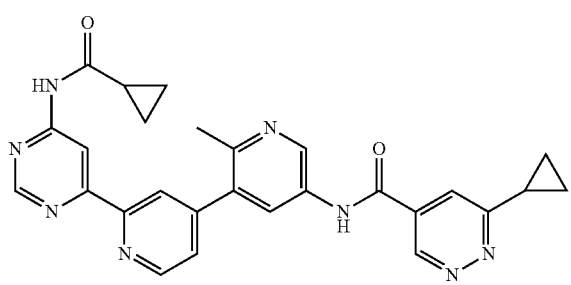
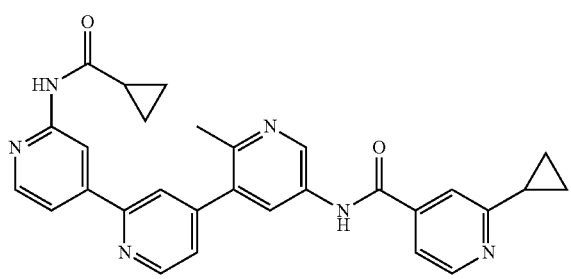
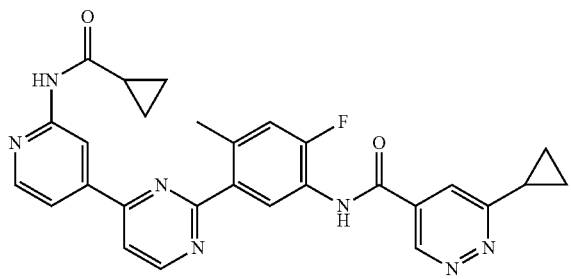
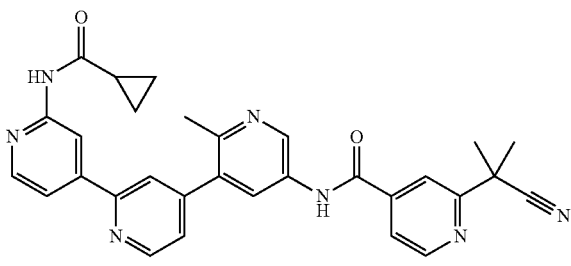
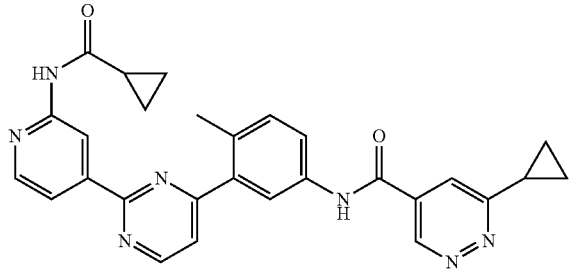
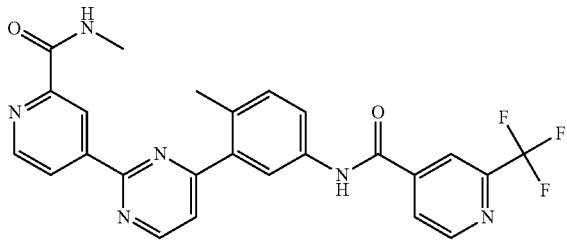
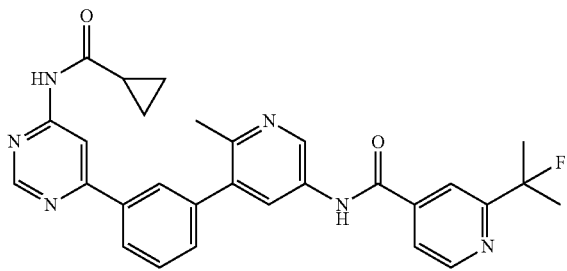
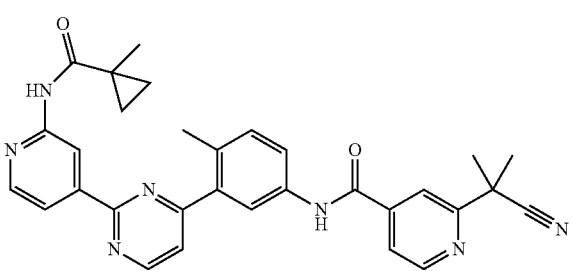
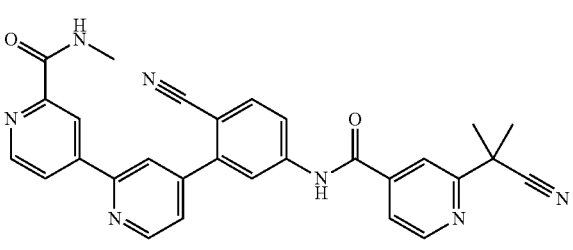
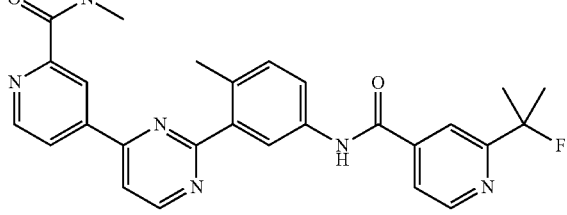
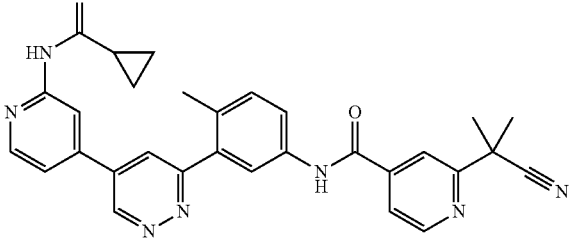

681
-continued
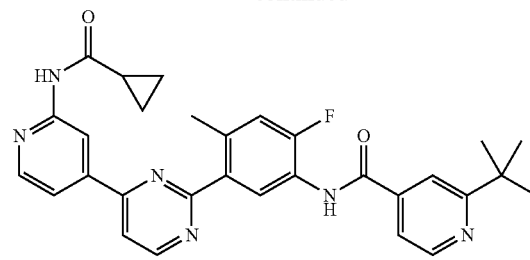
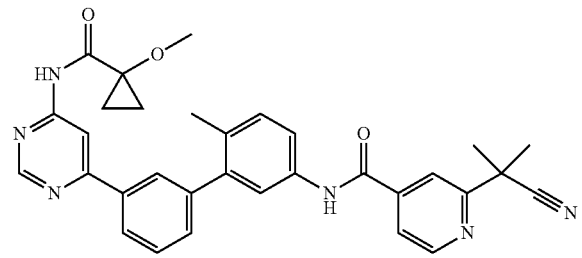
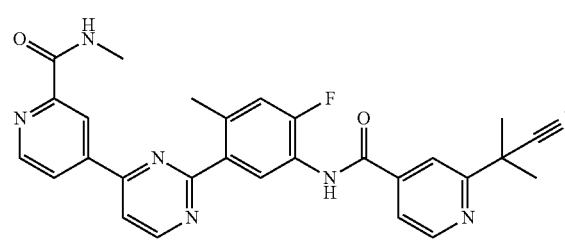
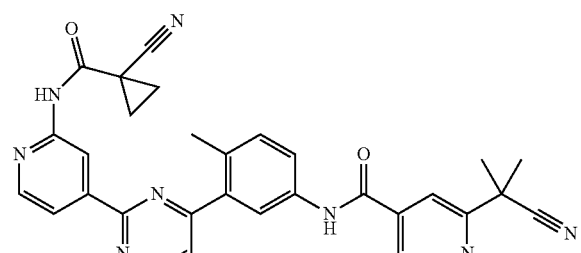
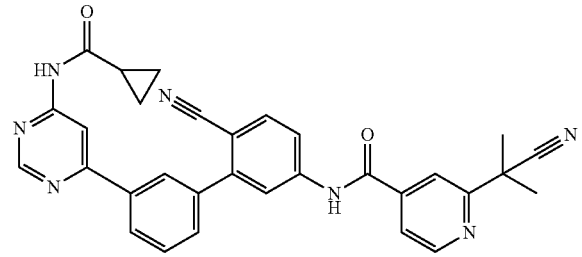
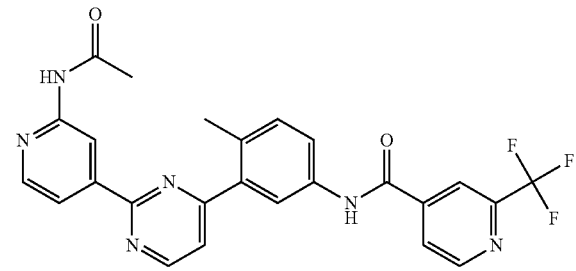
682
-continued
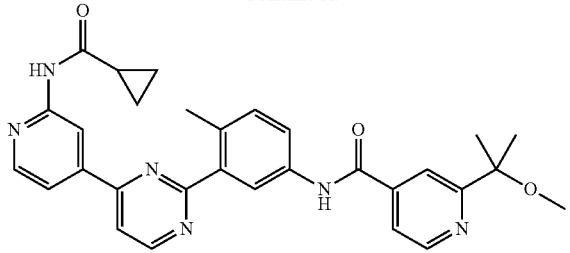
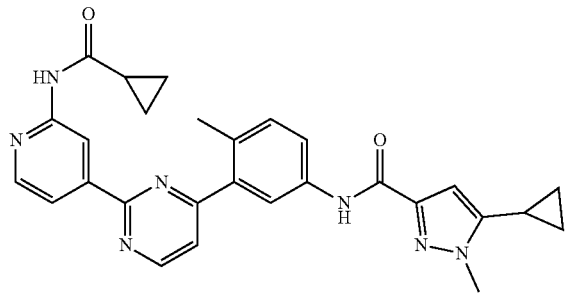
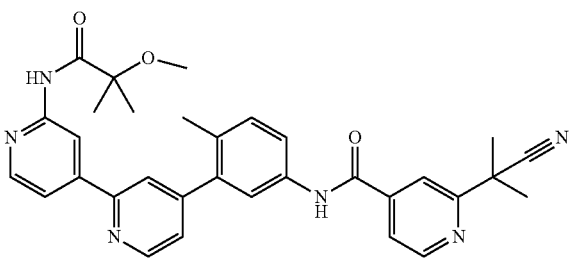
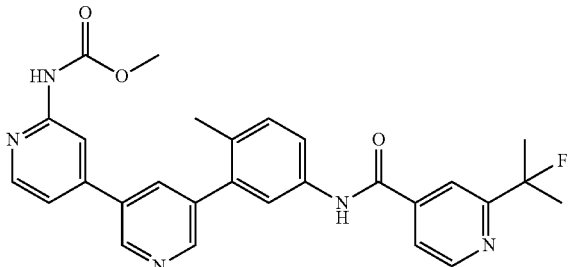
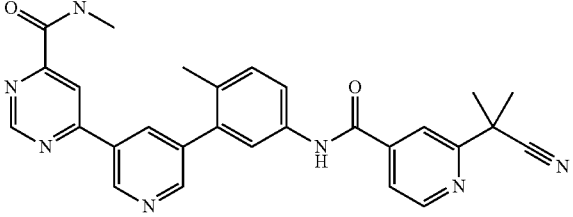
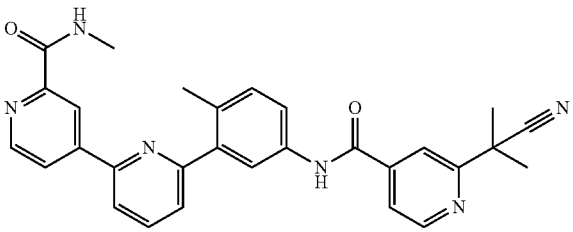

683
-continued
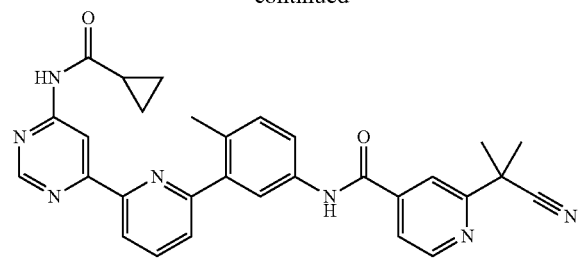
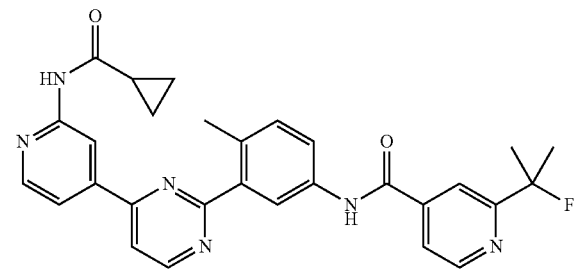
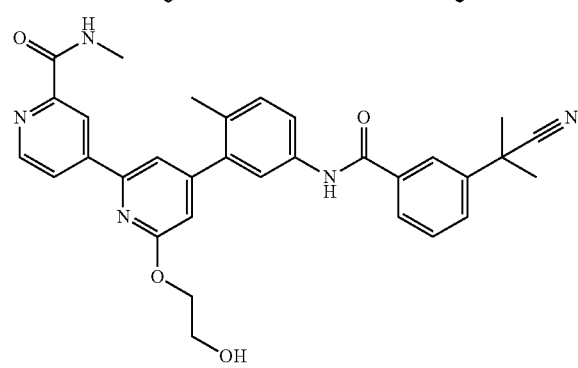
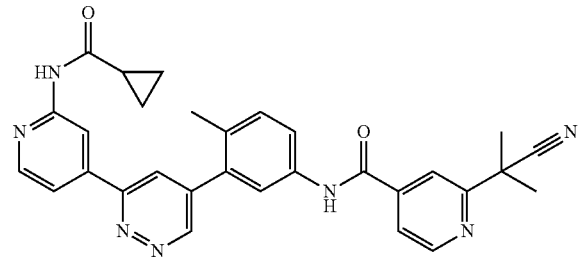
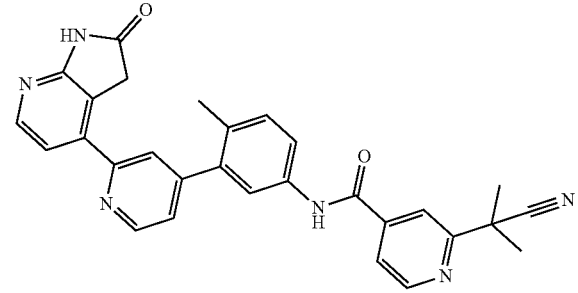
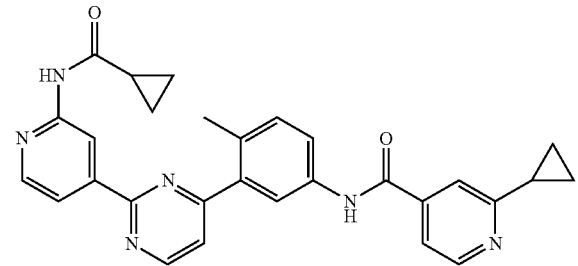
684
-continued
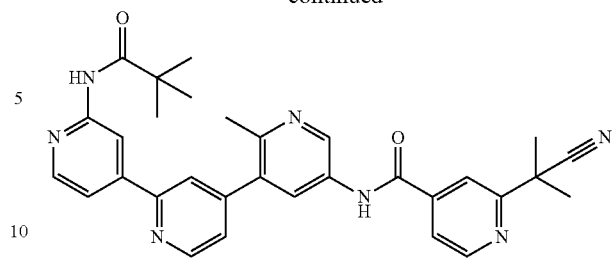
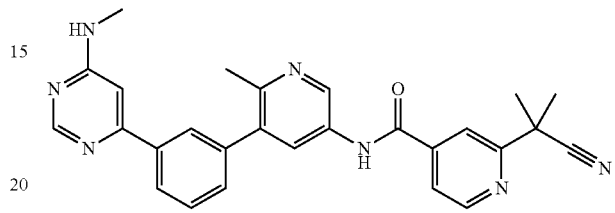
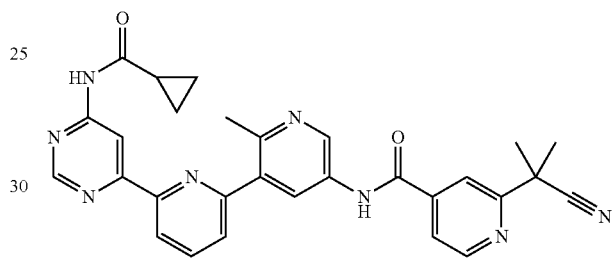
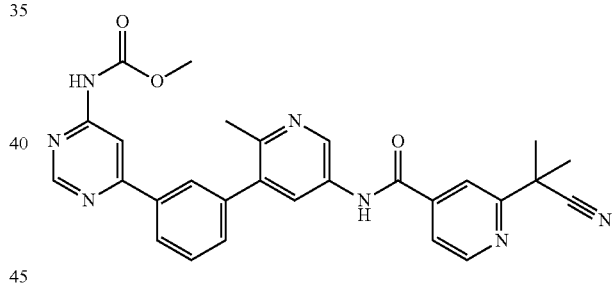
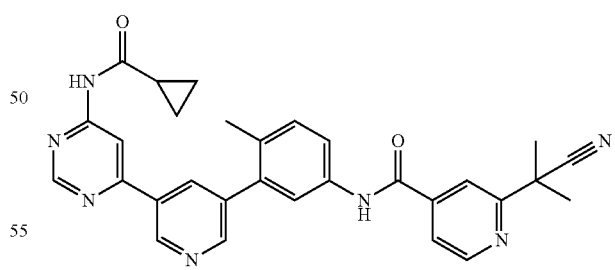
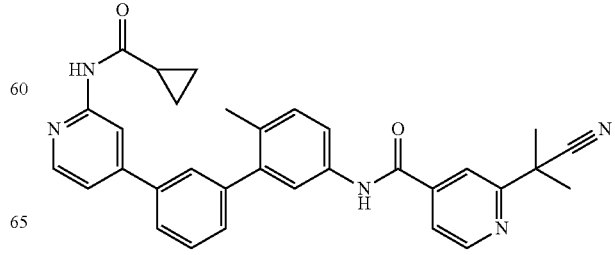

685
-continued
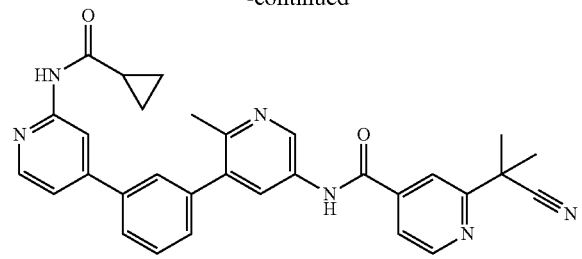
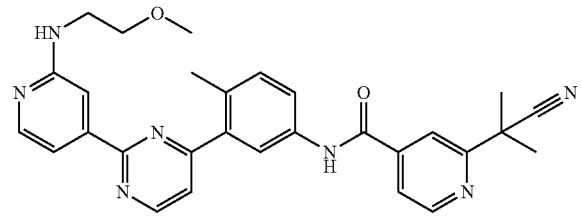
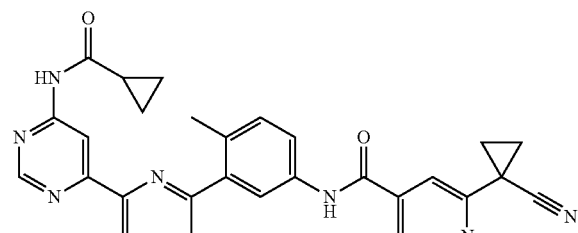
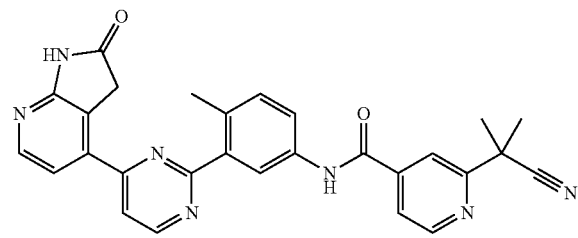
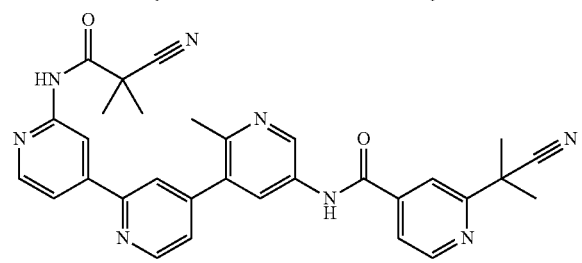
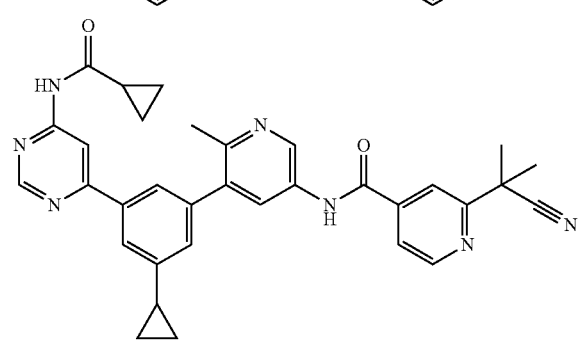
686
-continued
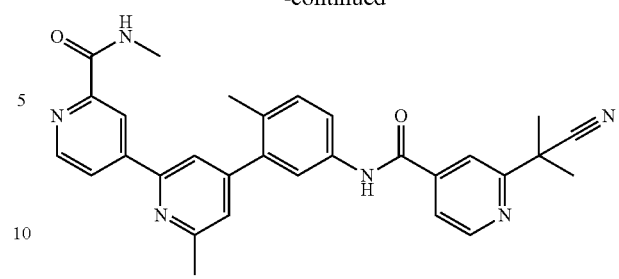
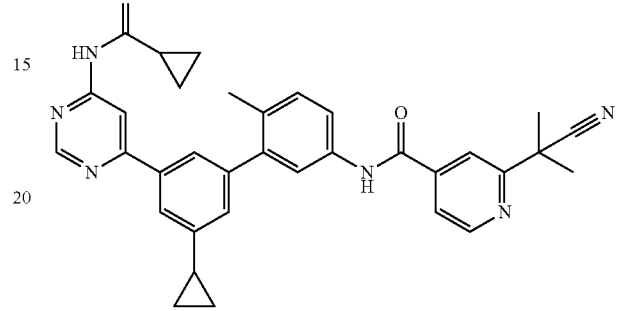
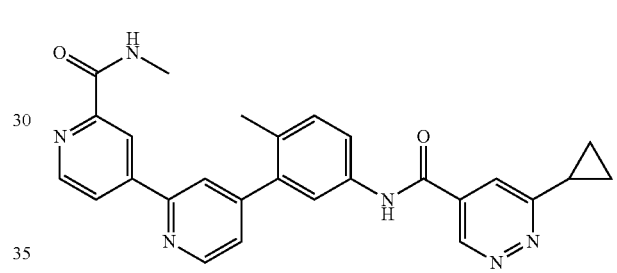
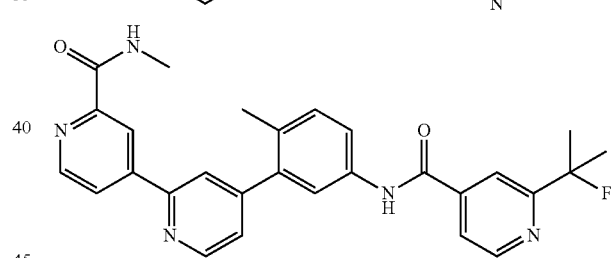
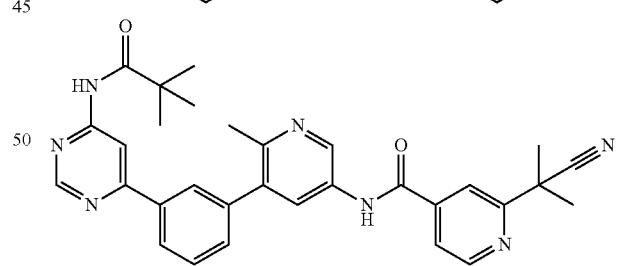
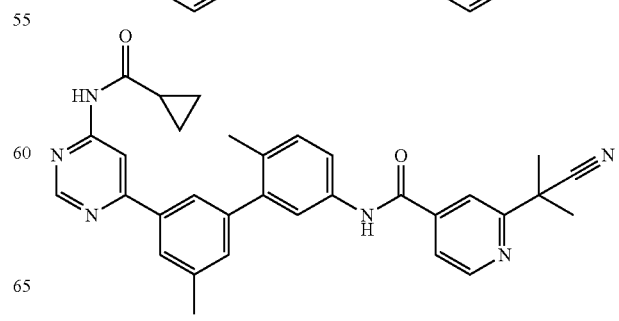

687
-continued
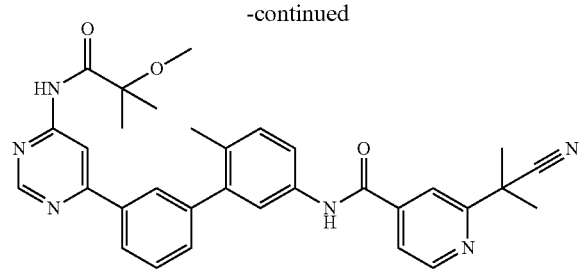
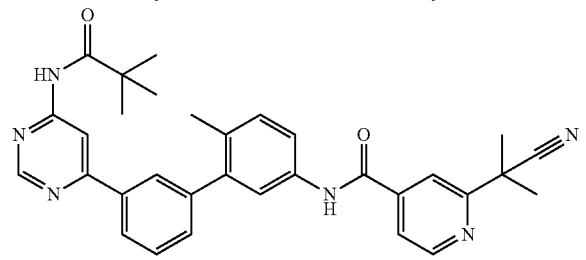
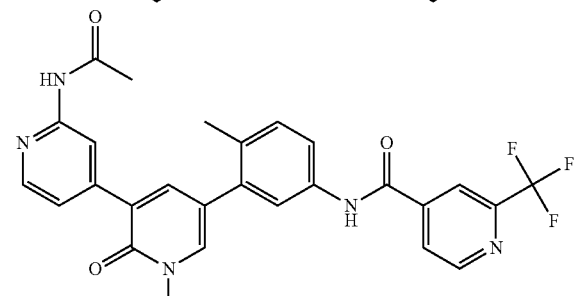
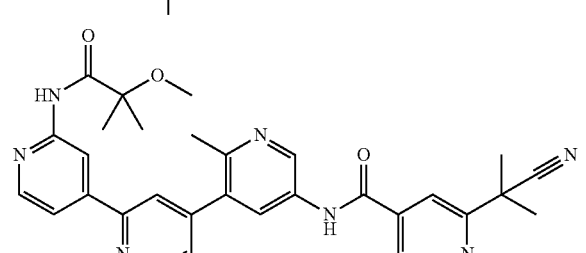
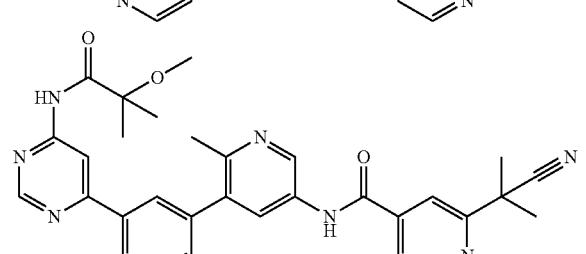
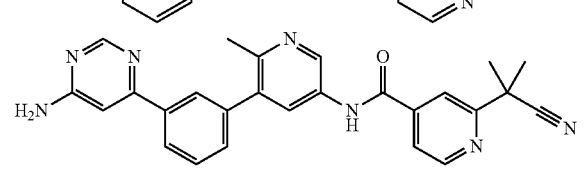
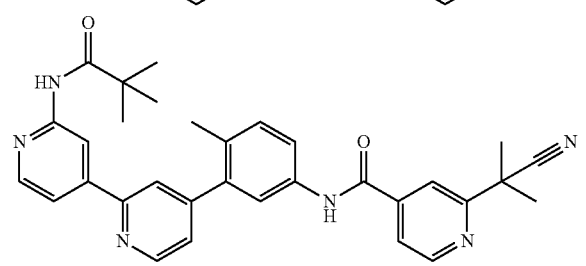
688
-continued
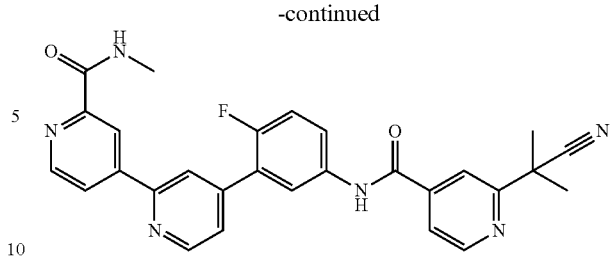
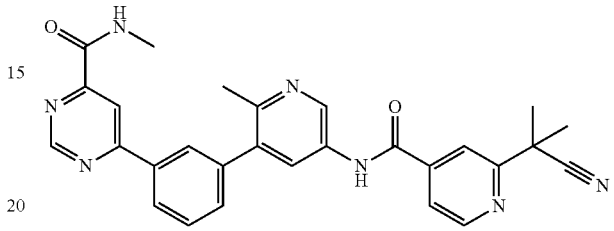
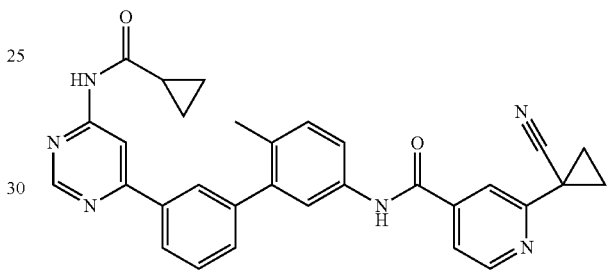
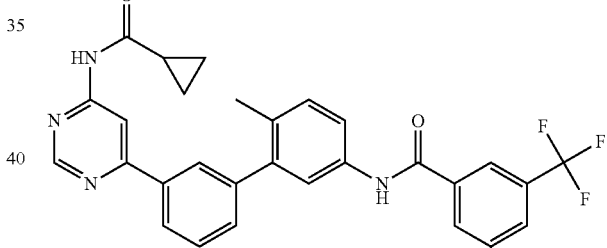
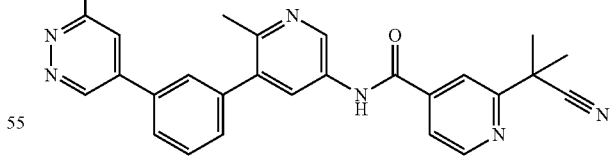
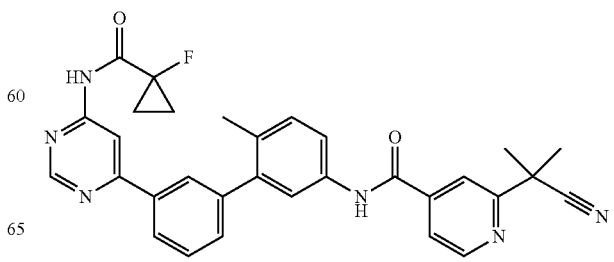

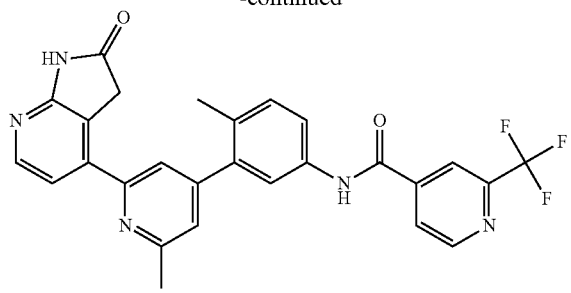
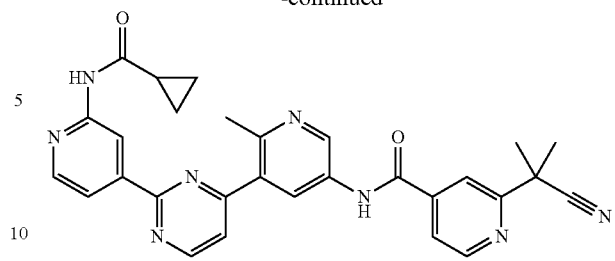
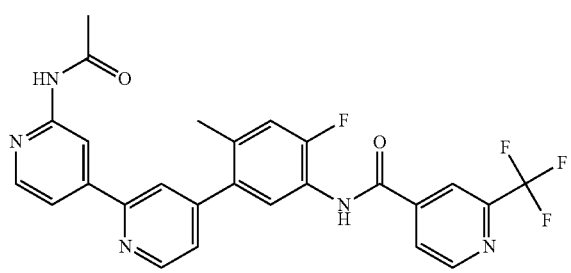
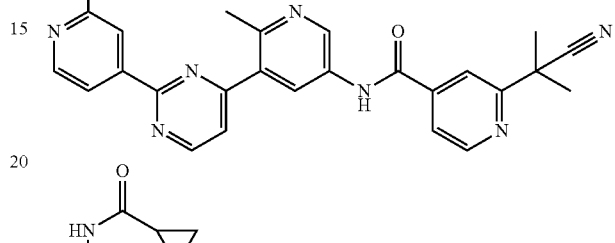
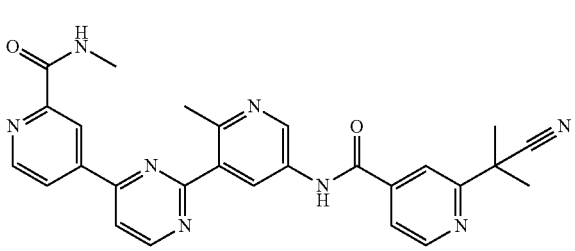
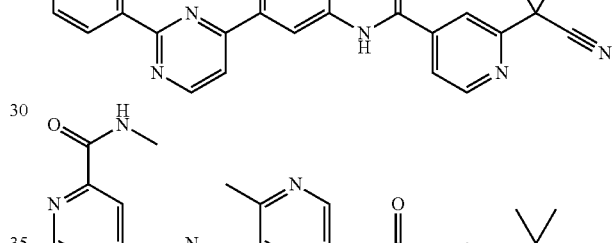
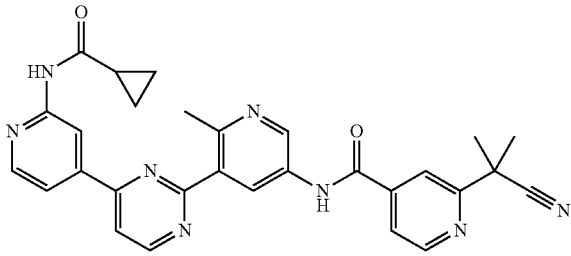
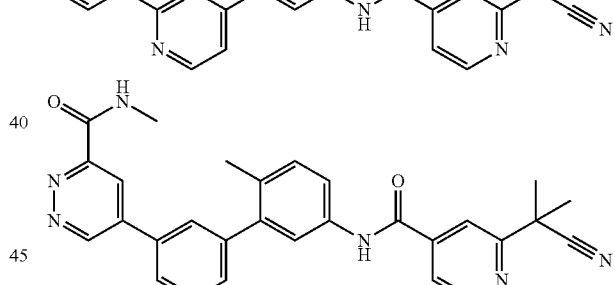
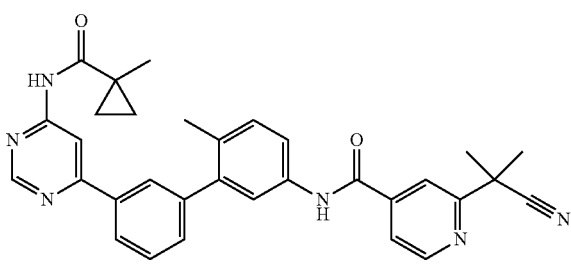
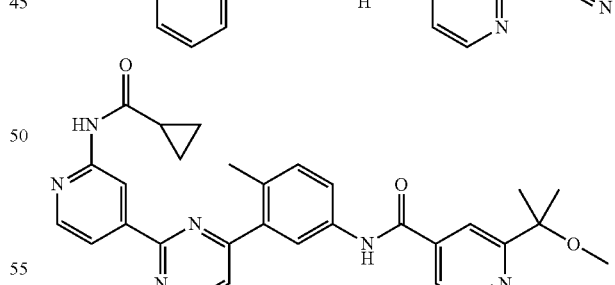
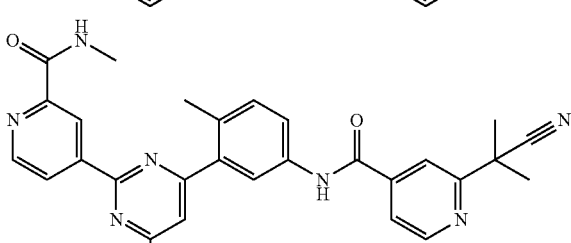
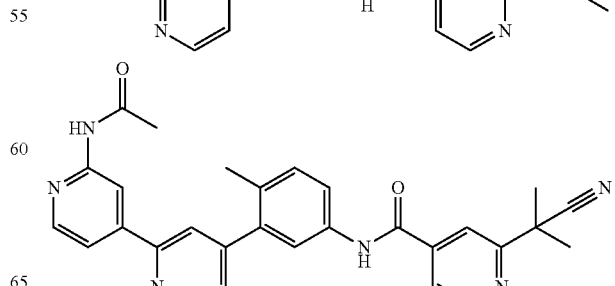

691
-continued
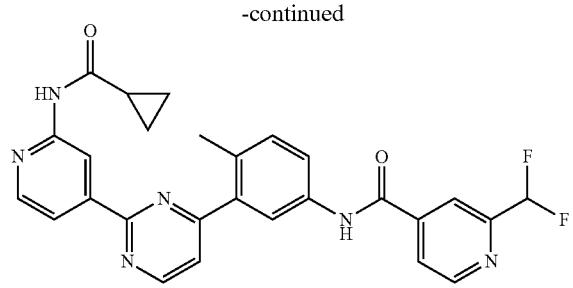
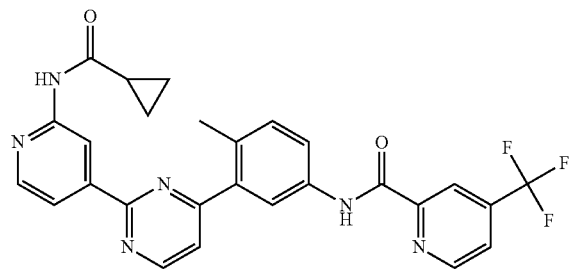
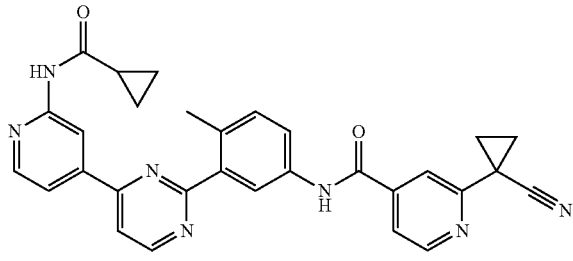
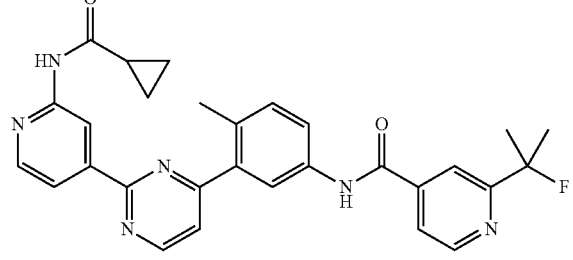
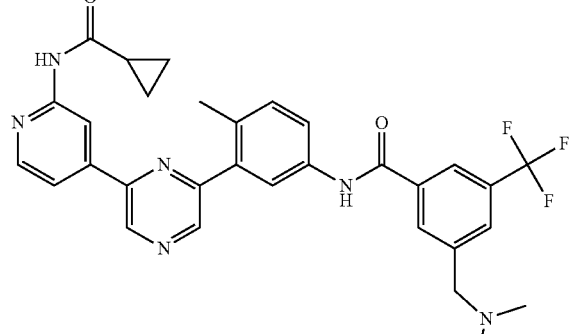
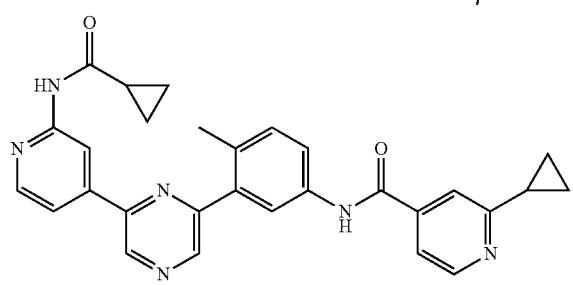
692
-continued
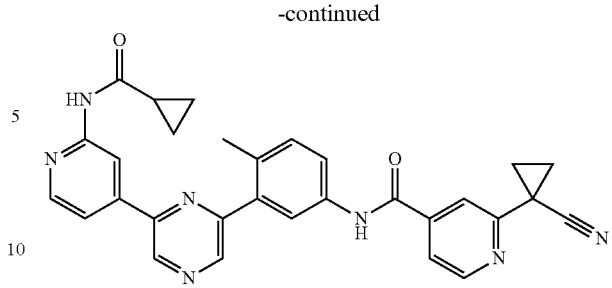
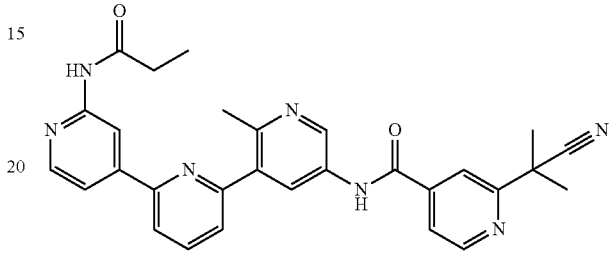
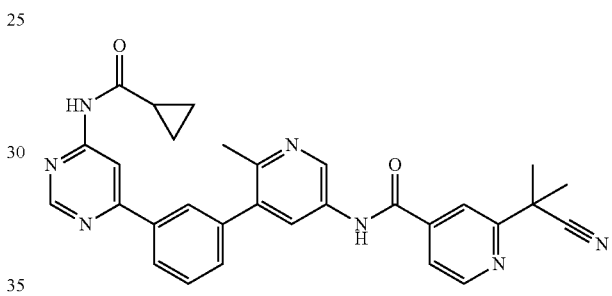
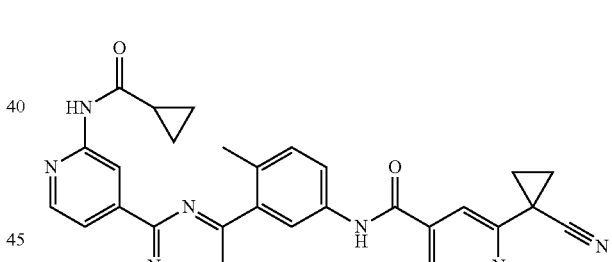
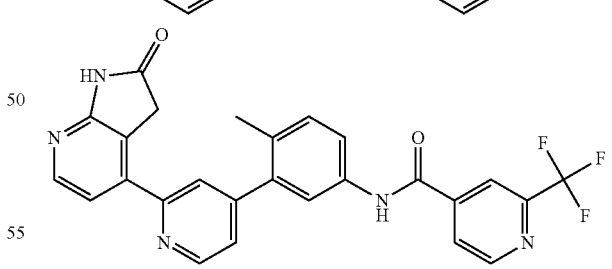
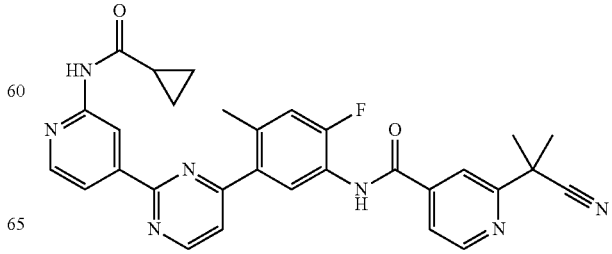

693
-continued
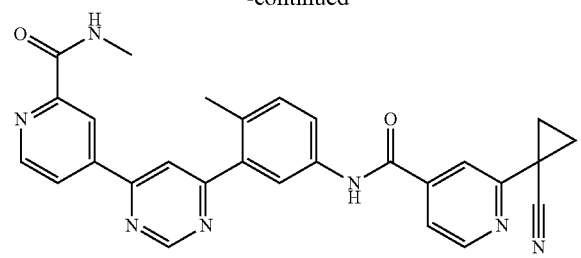
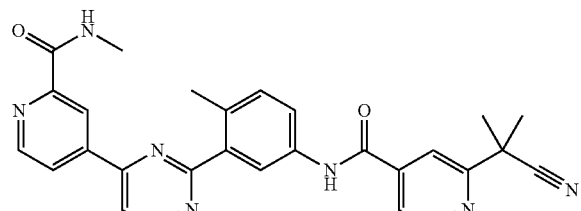
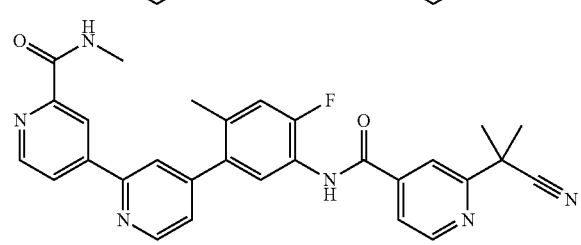
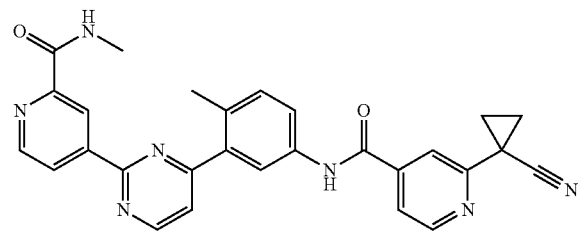
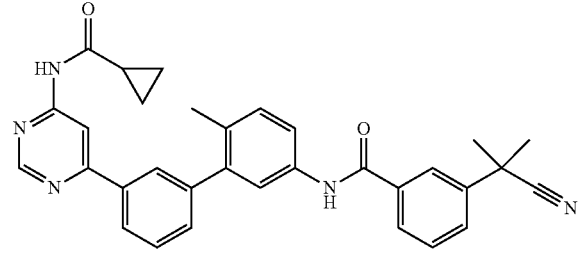
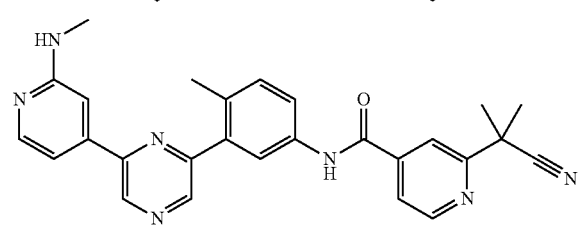
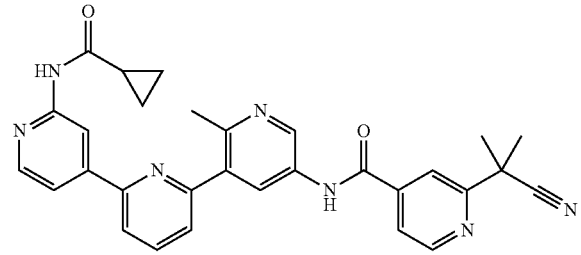
694
-continued
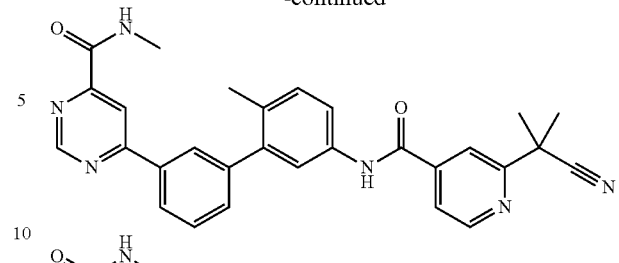
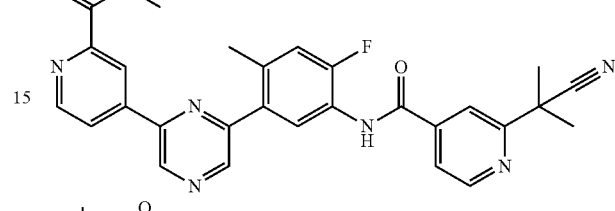
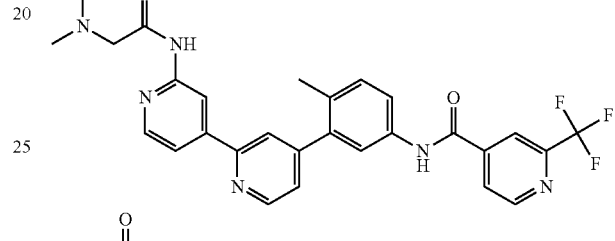
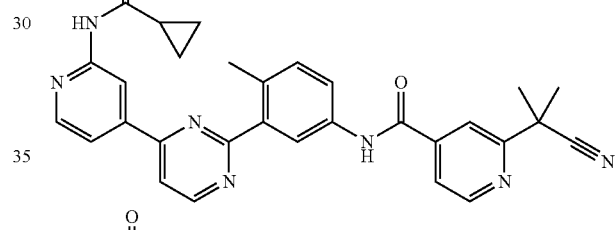
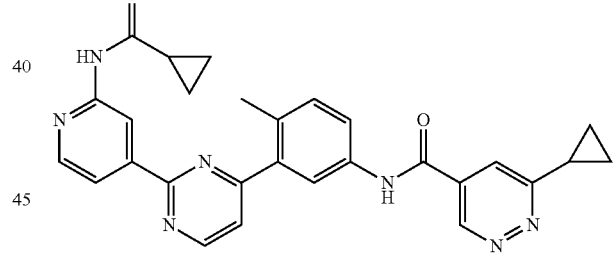
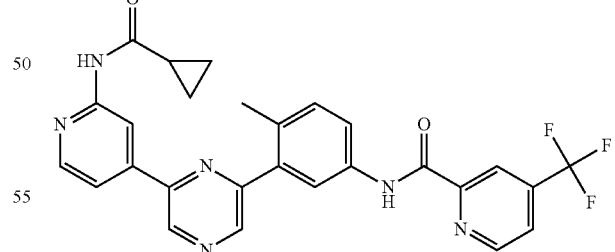
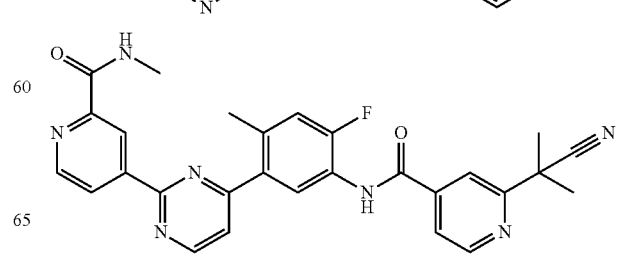

695
-continued
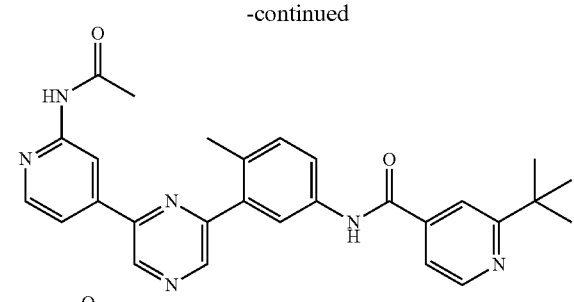
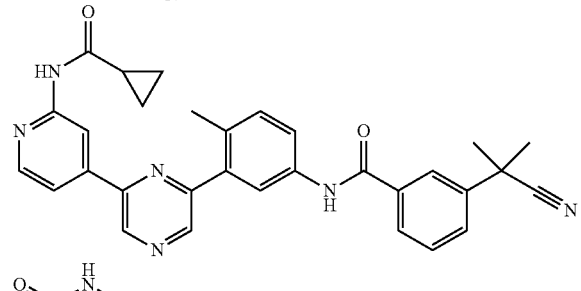
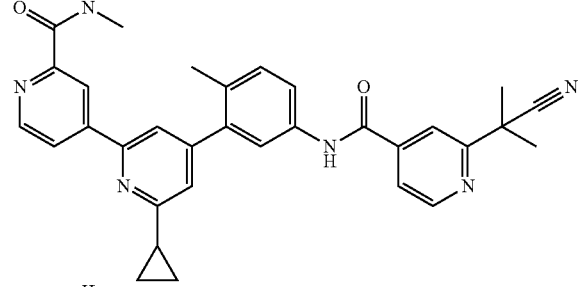
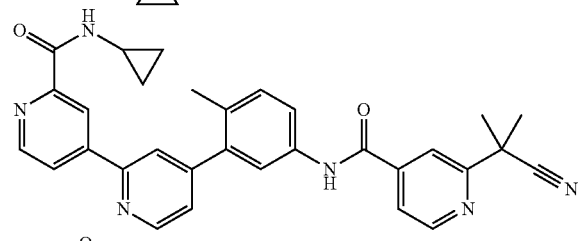
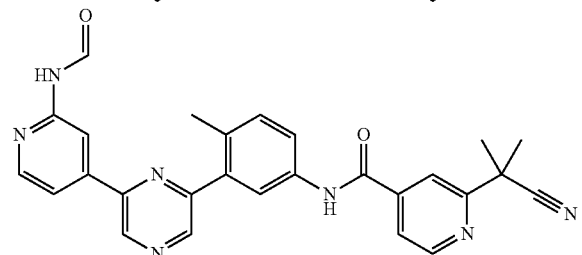
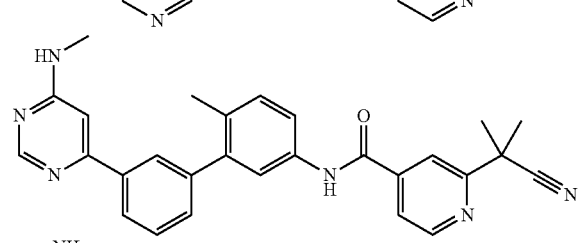
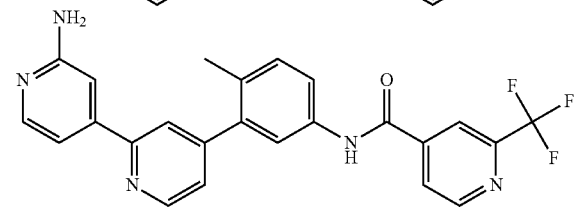
696
-continued
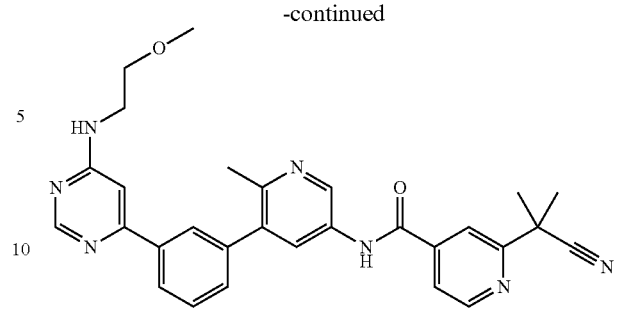
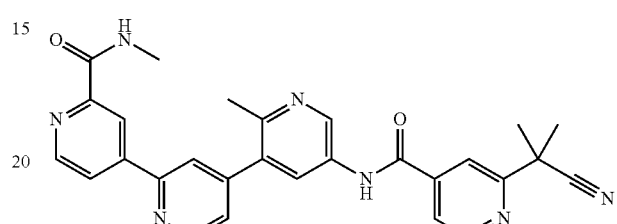
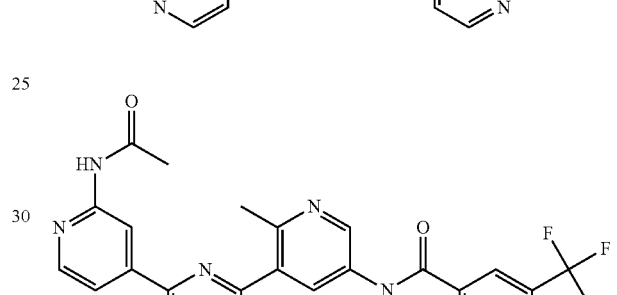
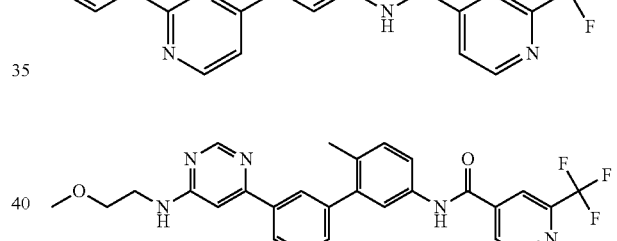
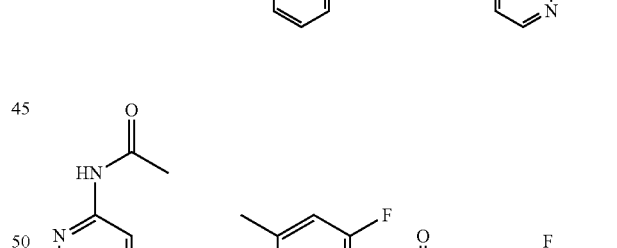
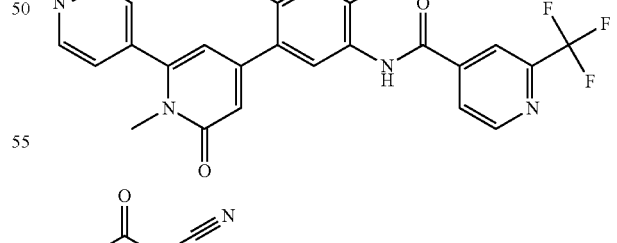
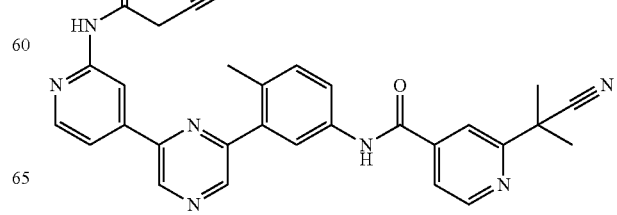

697
-continued
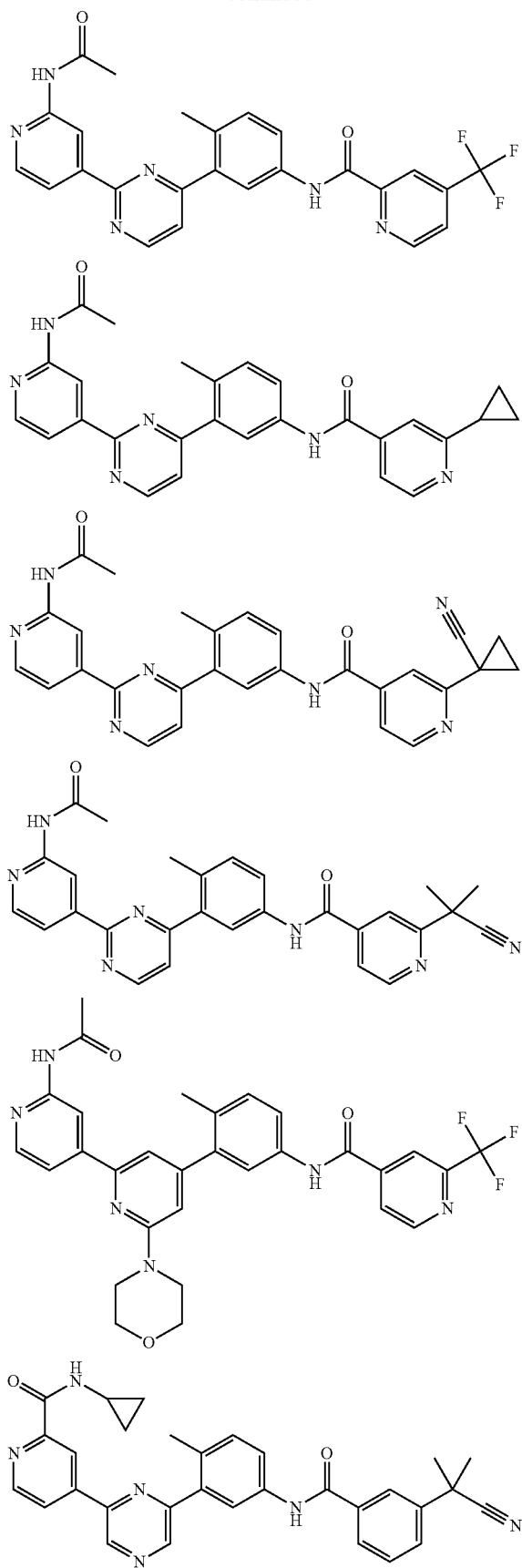
698
-continued
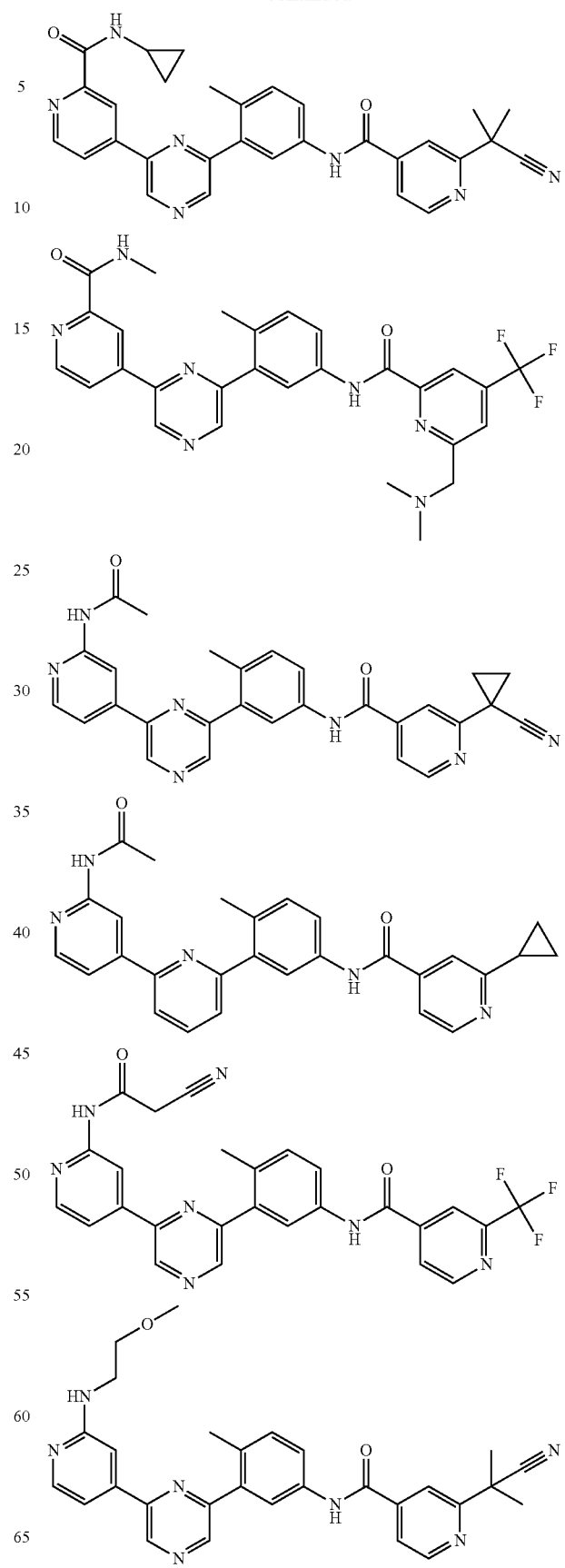

699
-continued
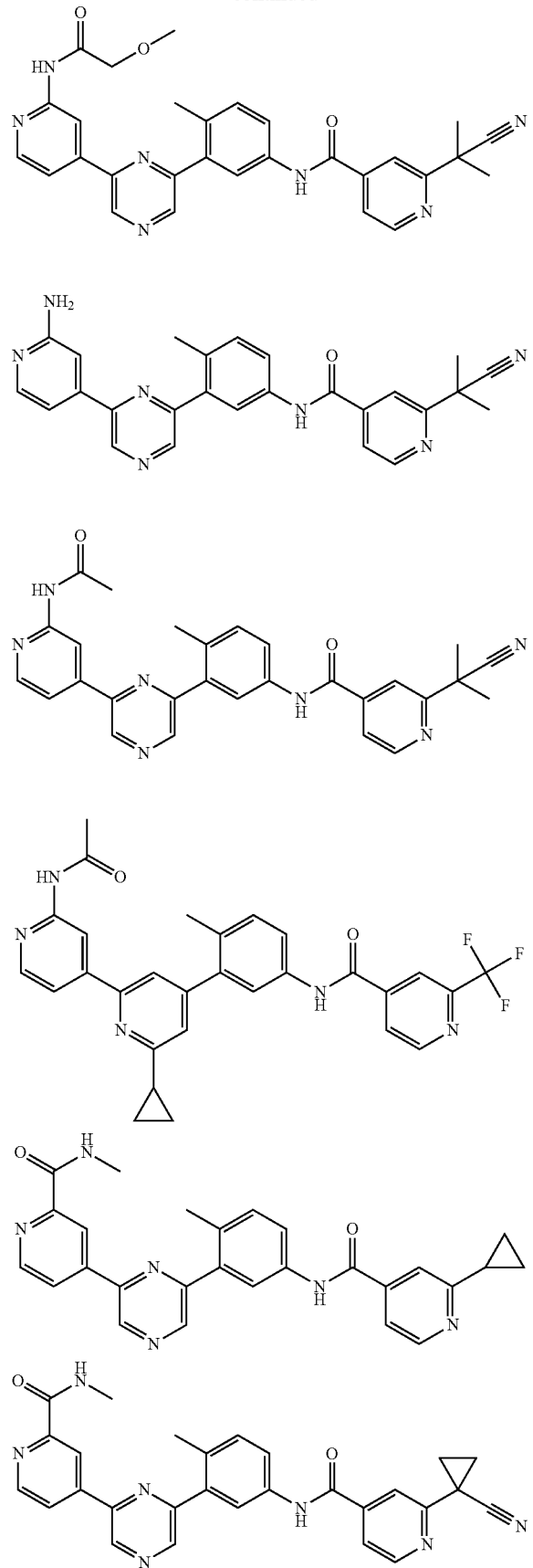
700
-continued
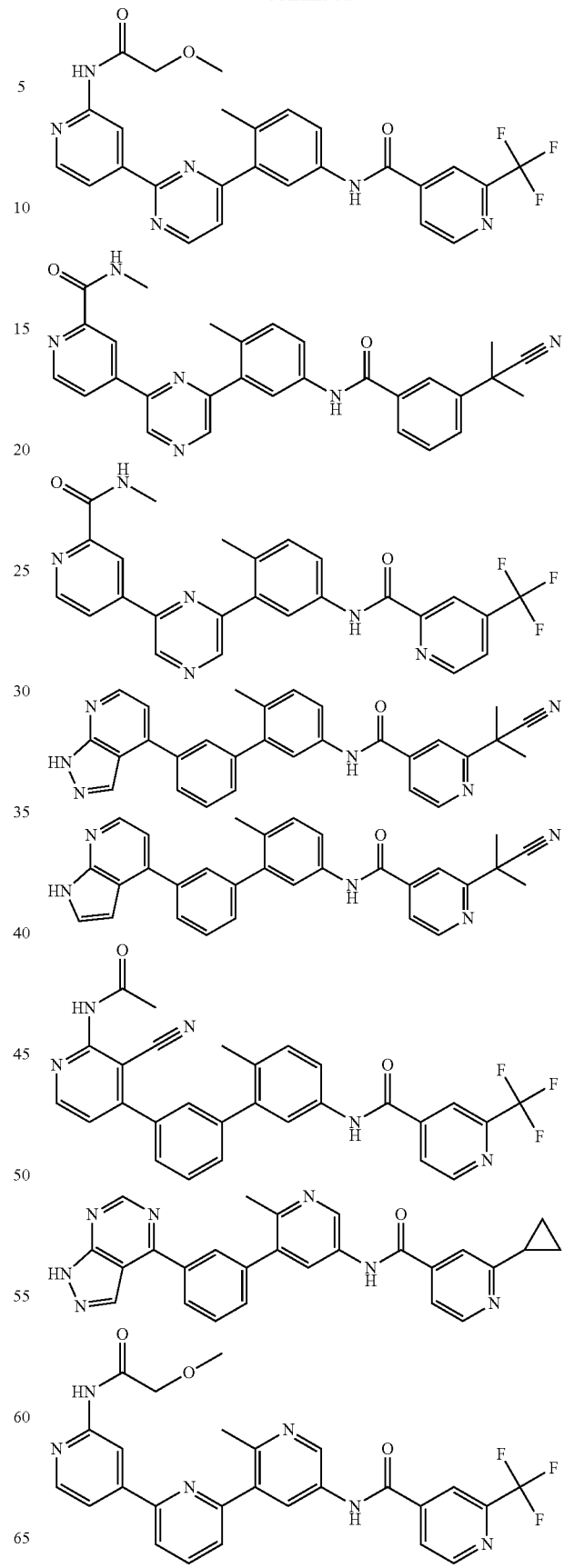

701
-continued
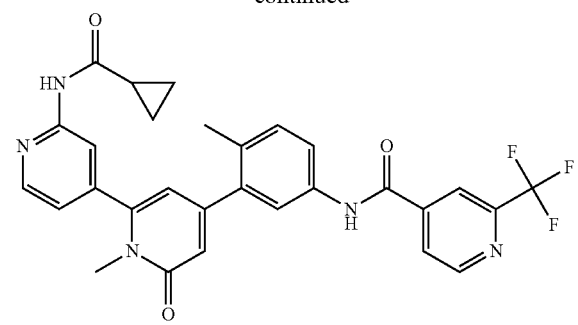
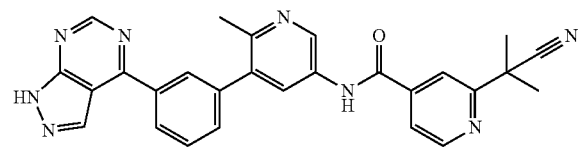
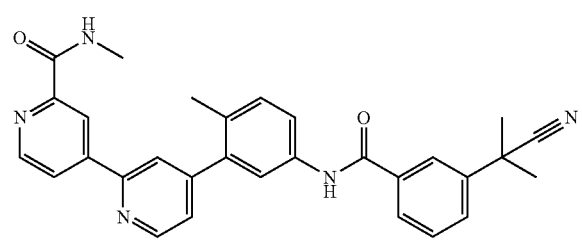
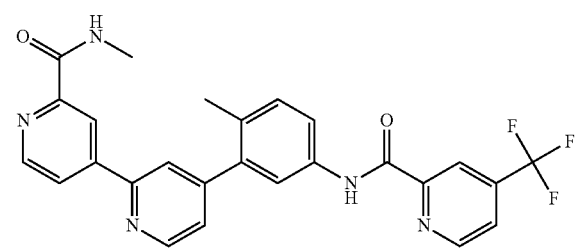
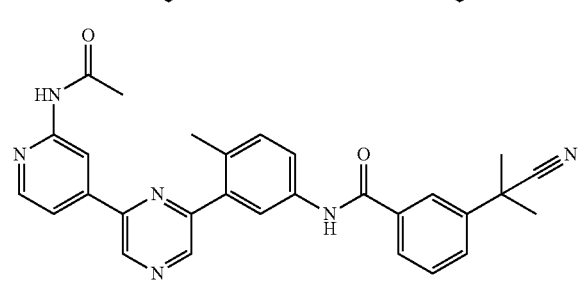
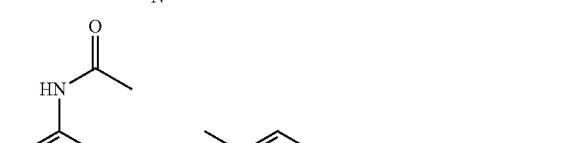
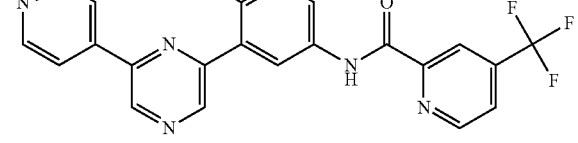
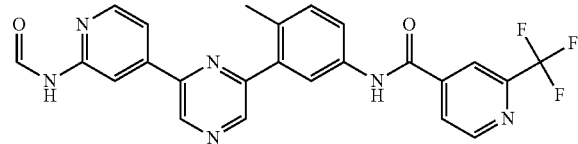
702
-continued
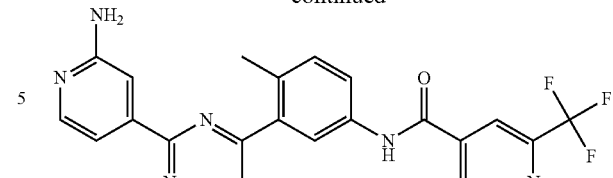
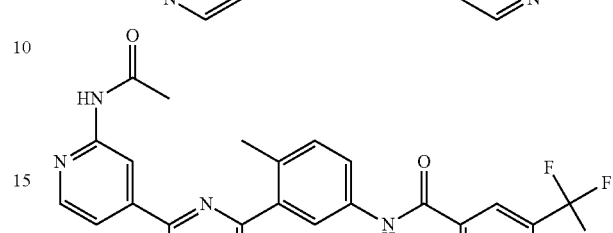
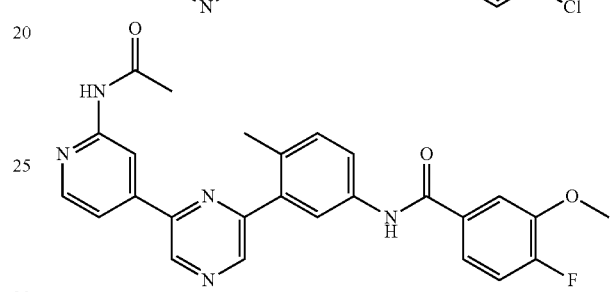
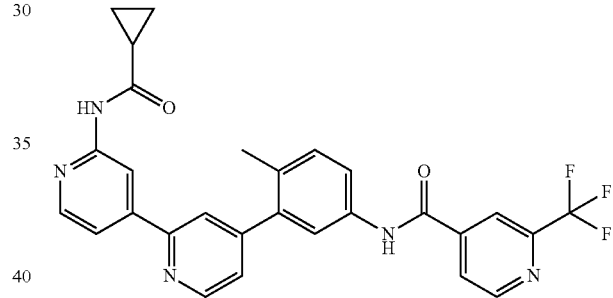
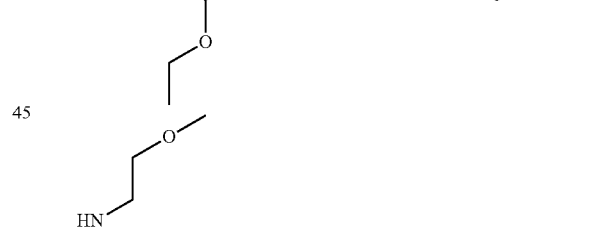
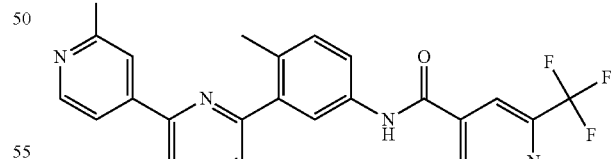
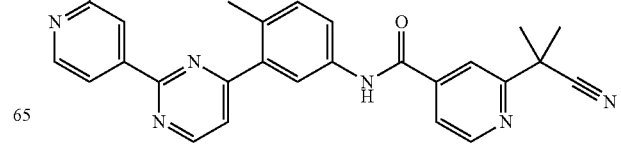

-continued
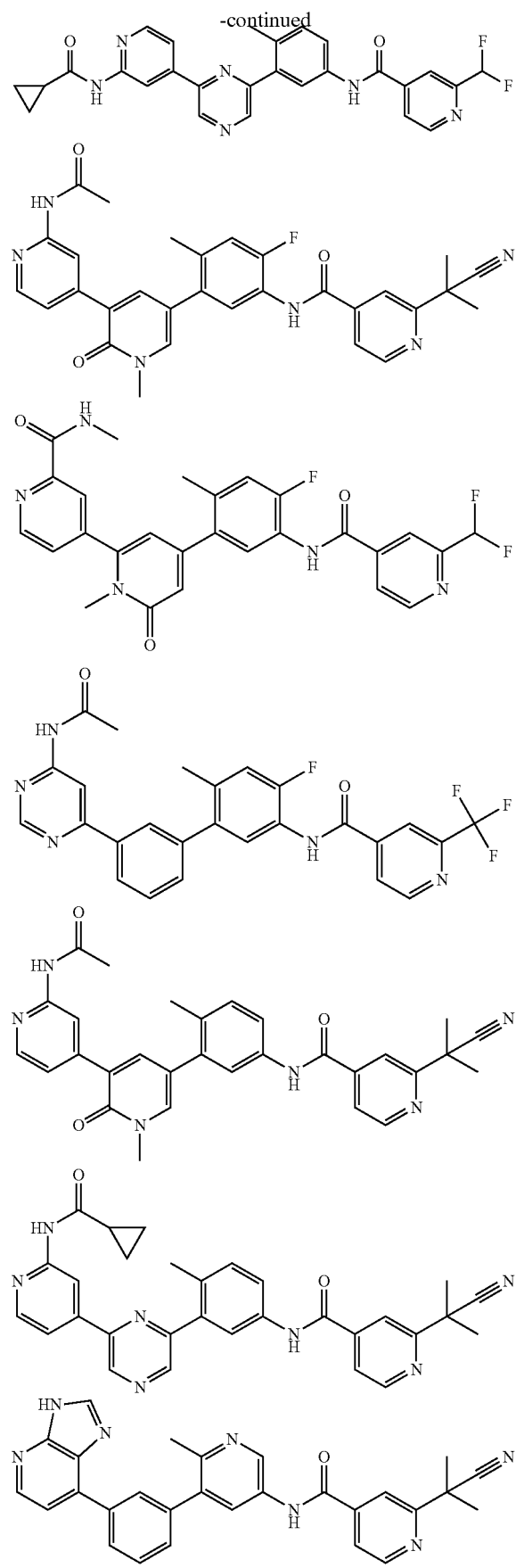
-continued
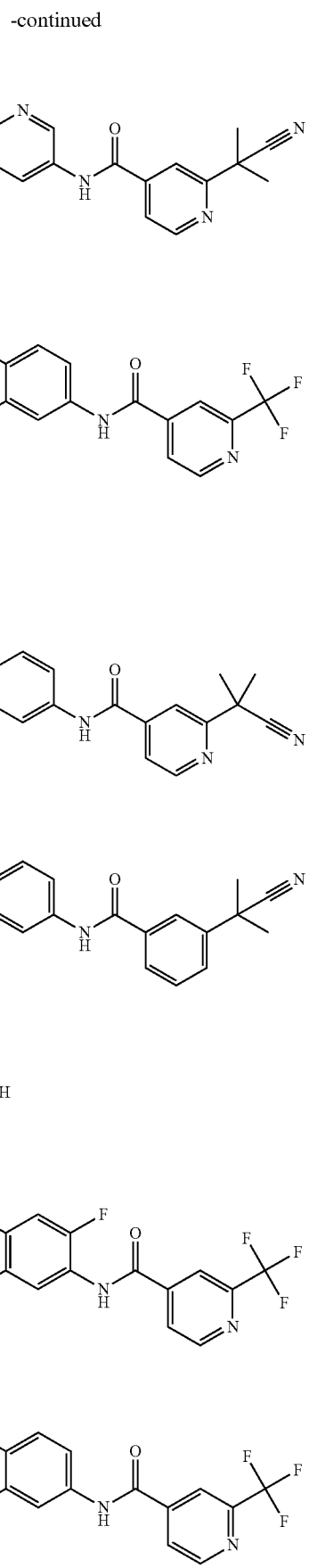

705
-continued
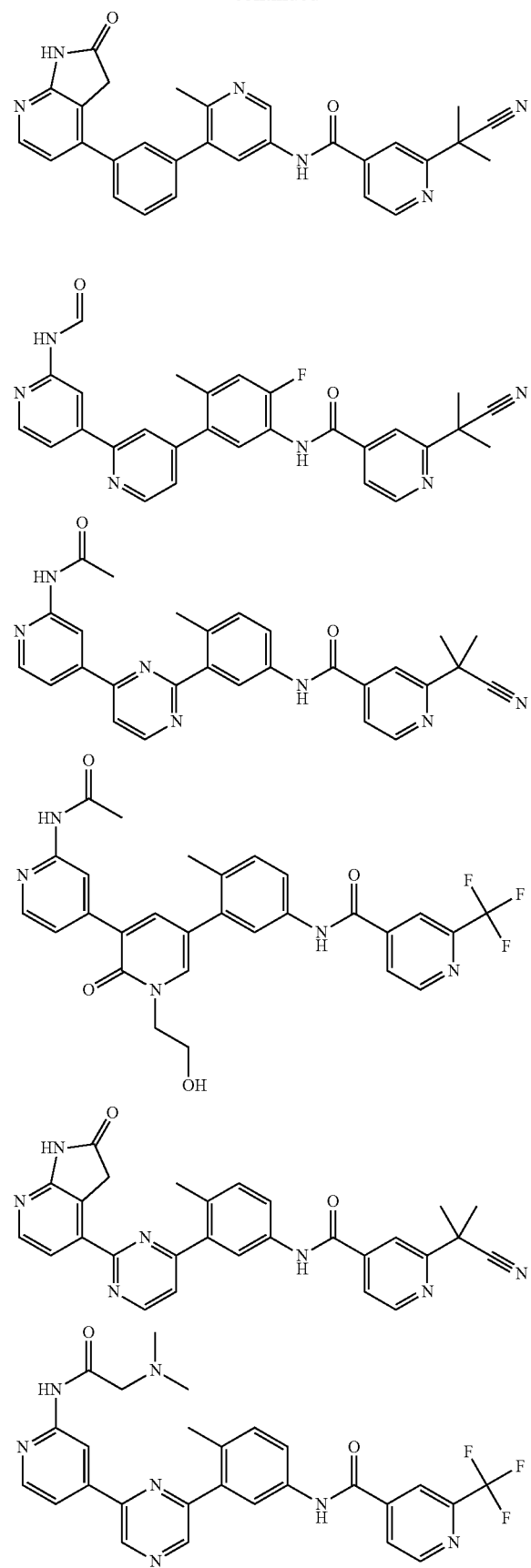
706
-continued
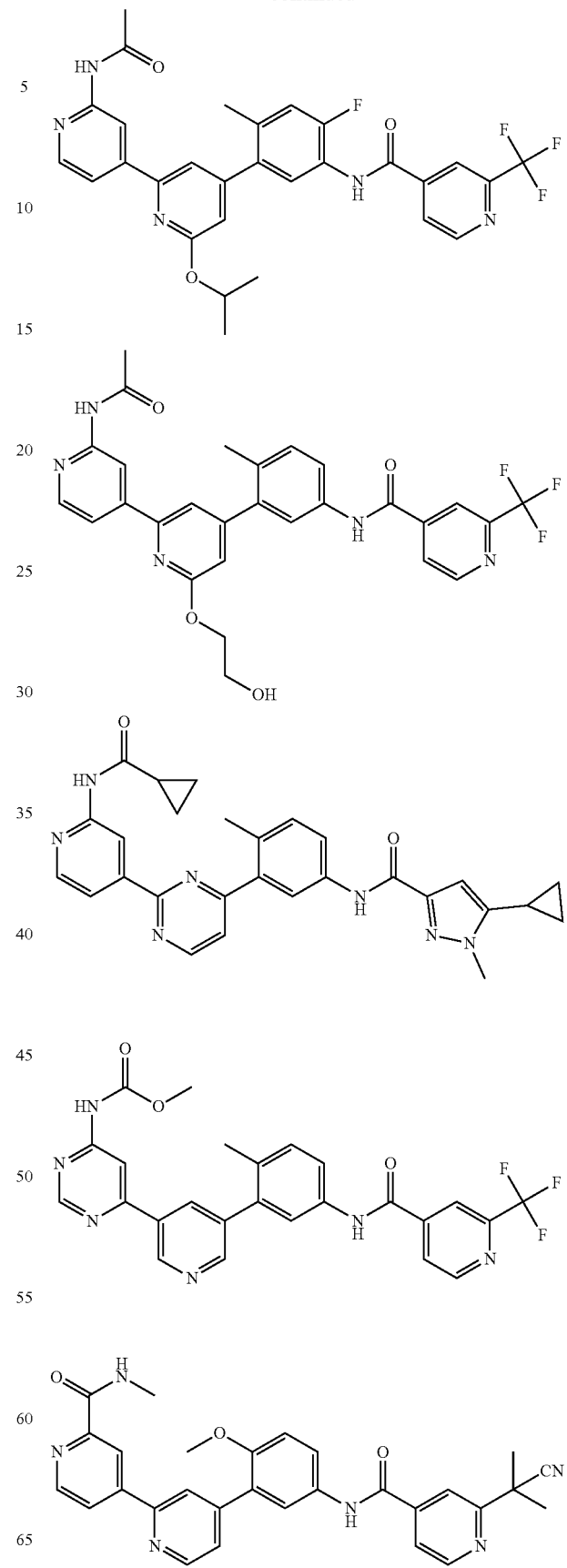

707
-continued
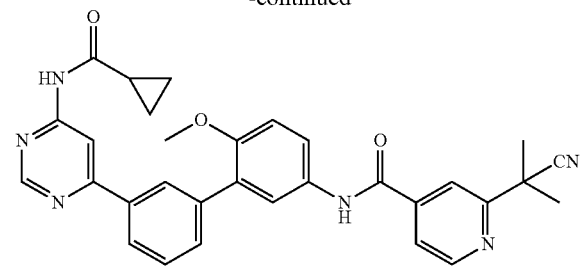
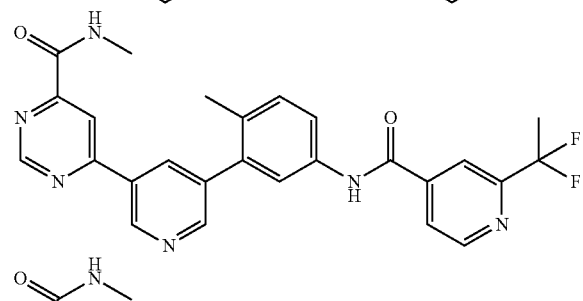
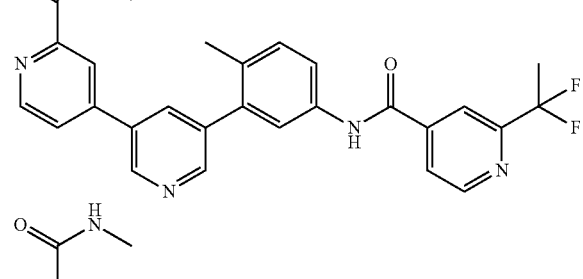
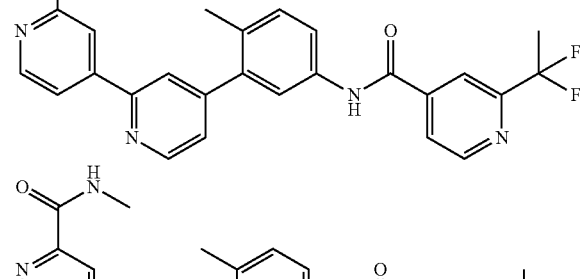
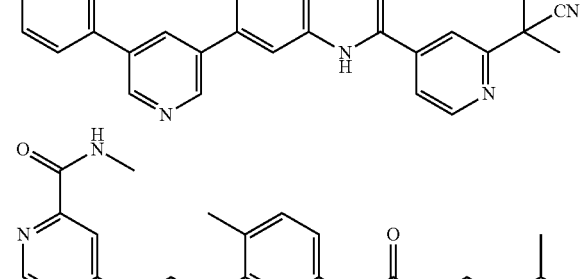
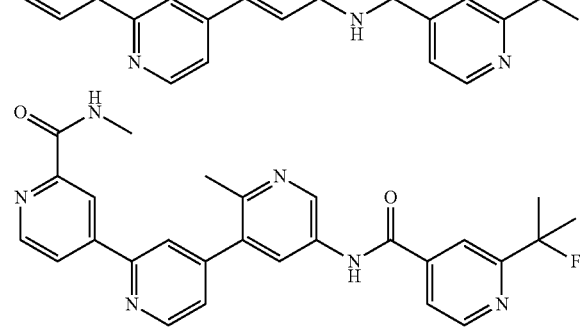
708
-continued
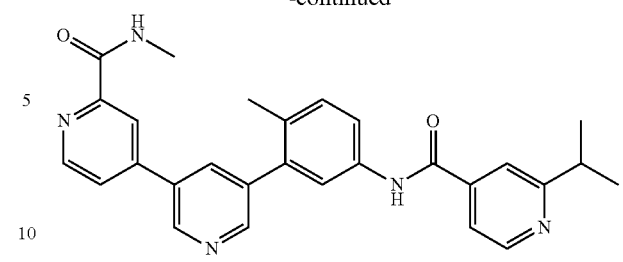
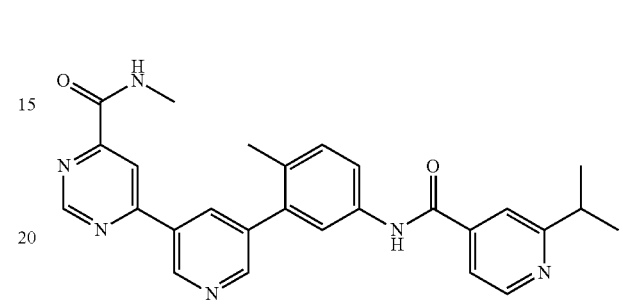
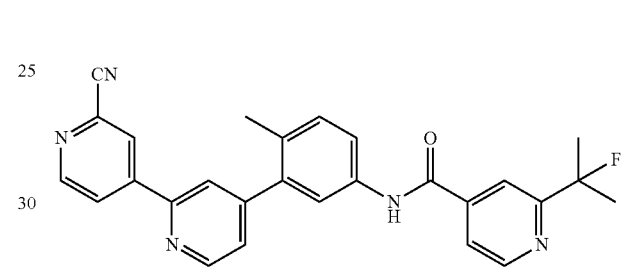
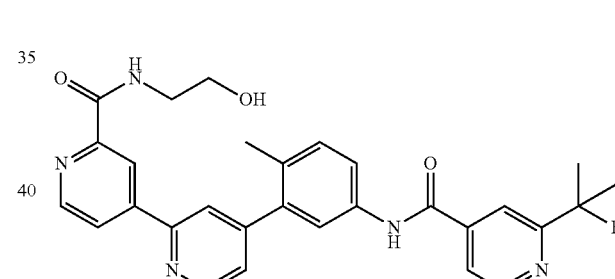
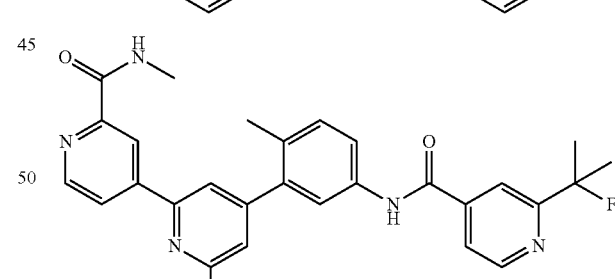
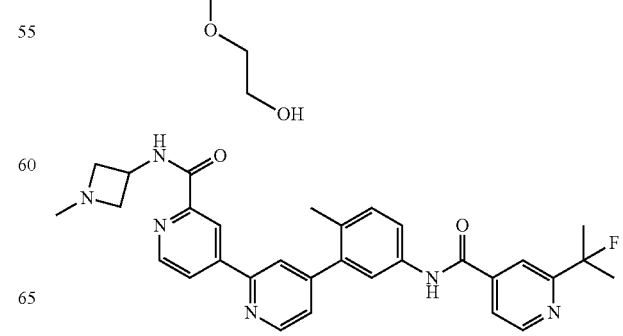

709
-continued
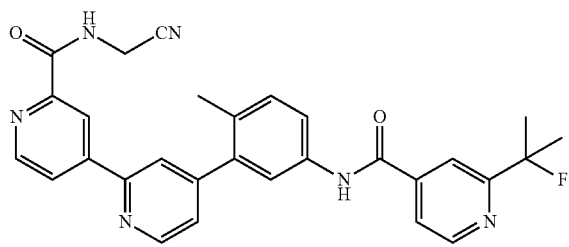
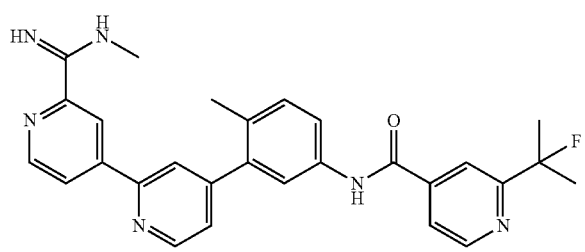
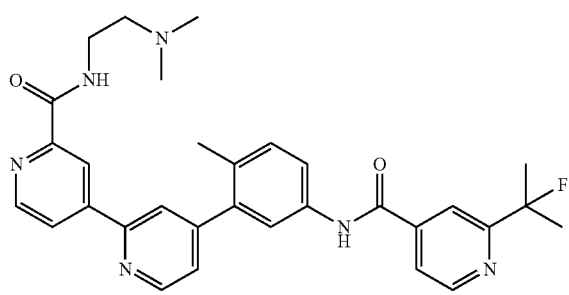
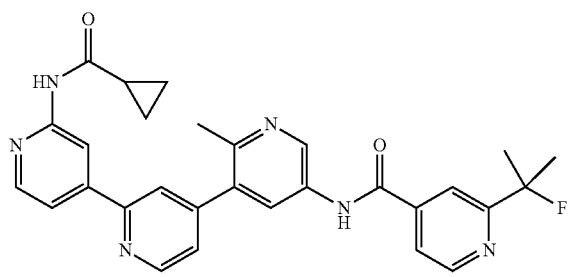
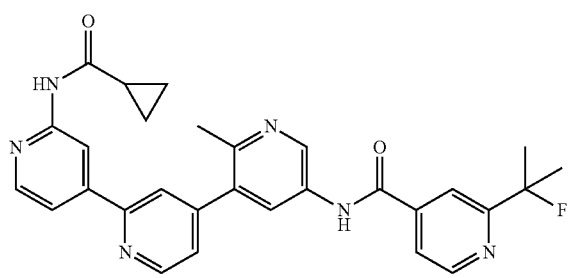
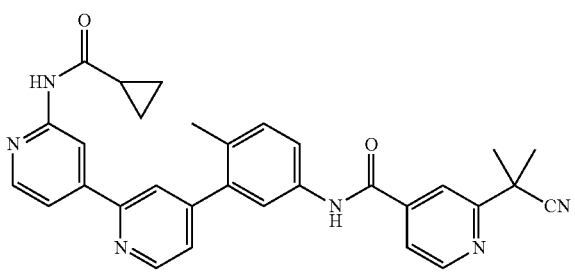
710
-continued
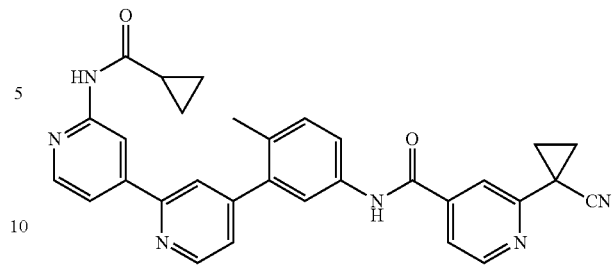
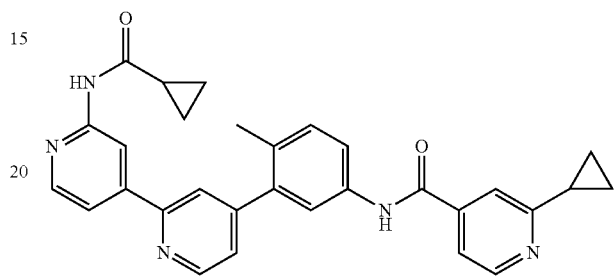
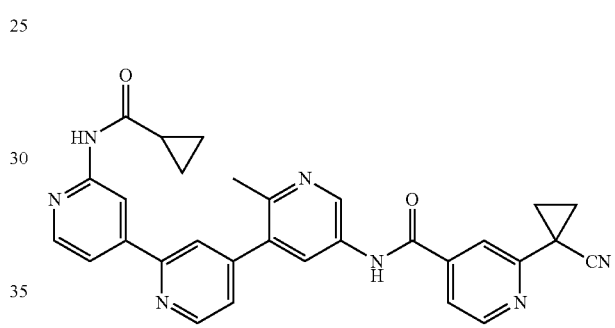
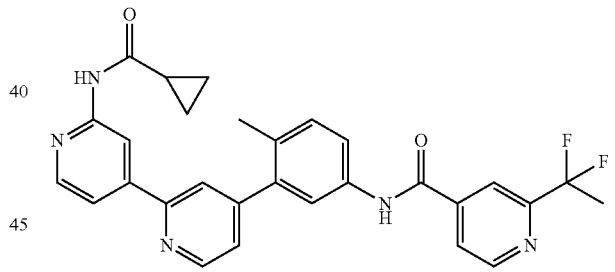
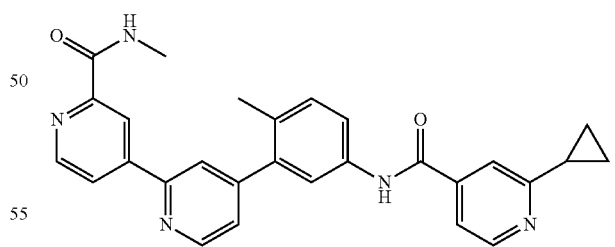
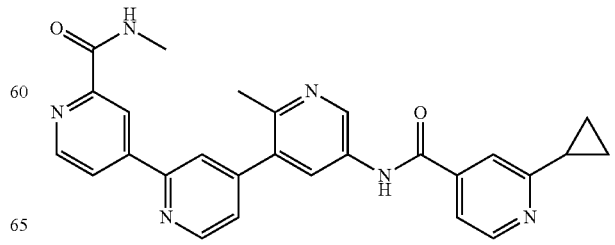

711
-continued
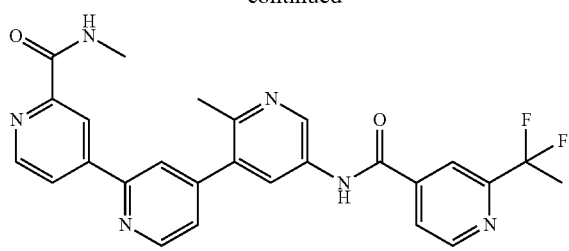
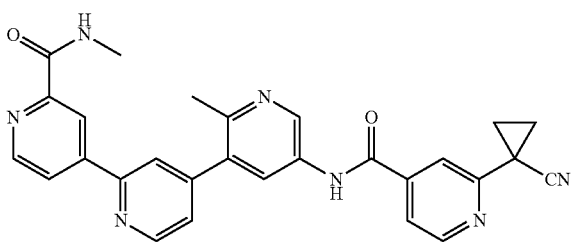
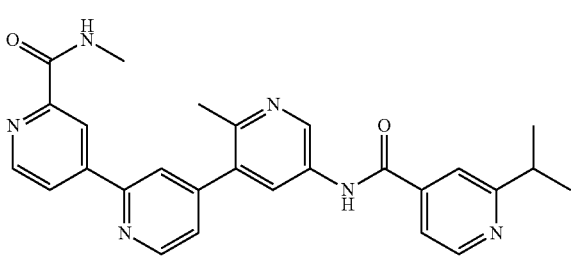
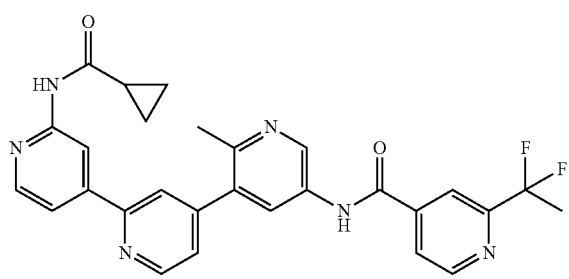
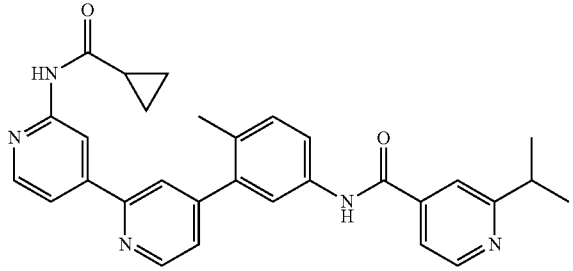
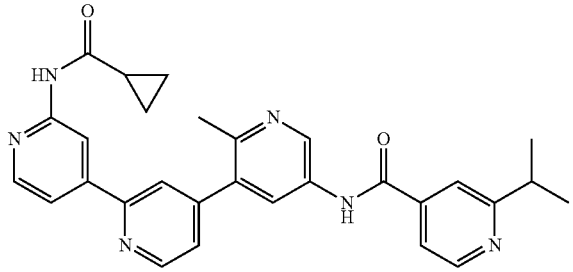
712
-continued
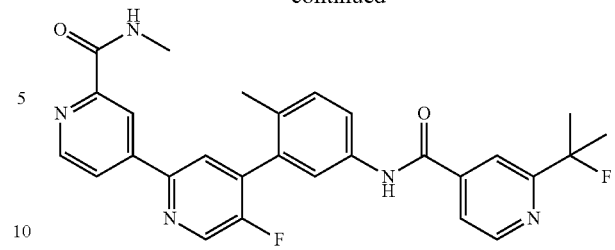
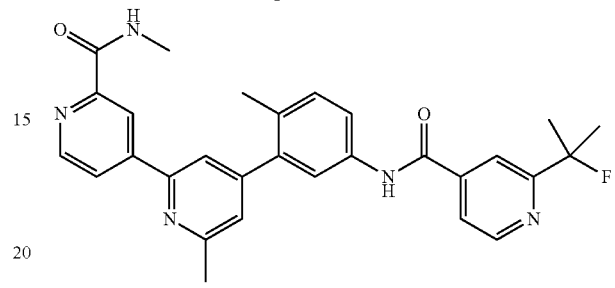
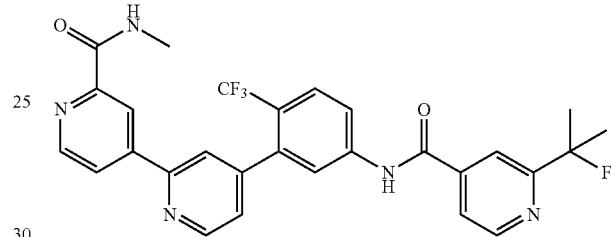
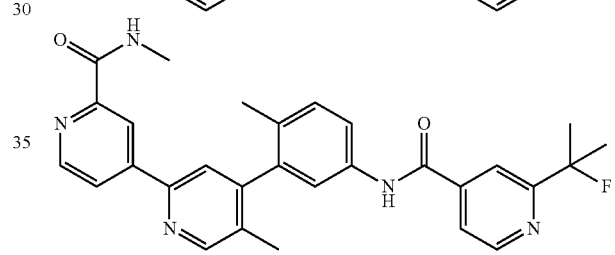
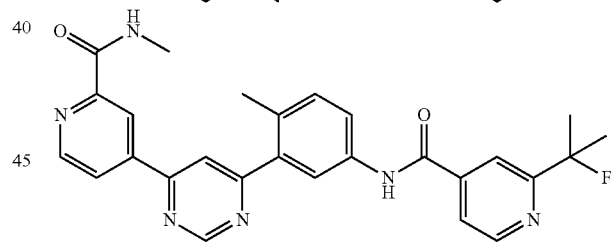
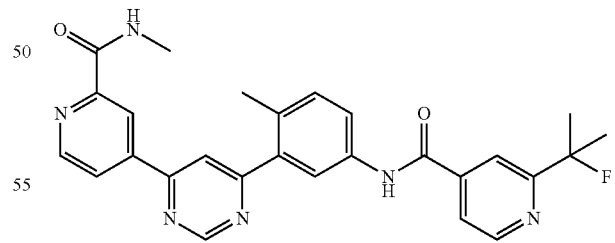
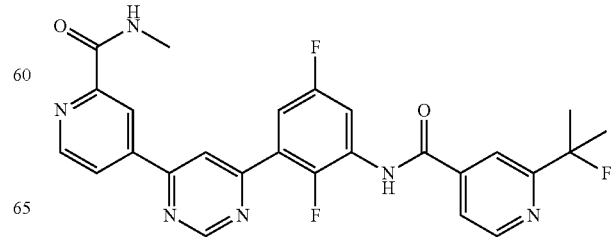

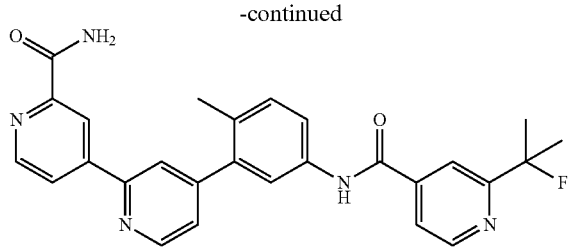
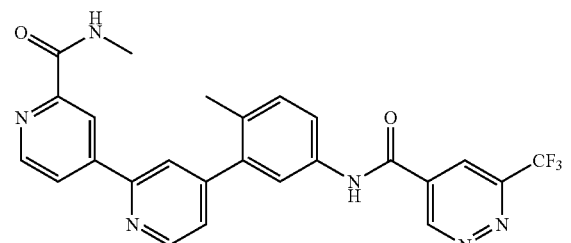
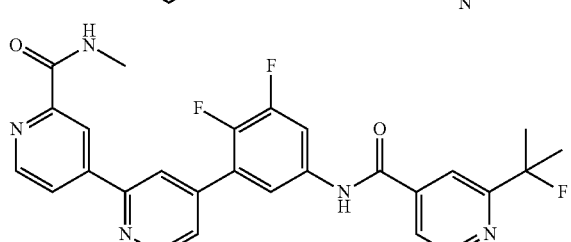
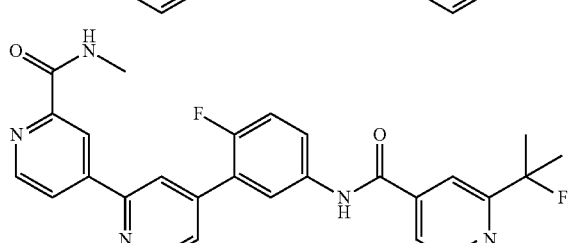
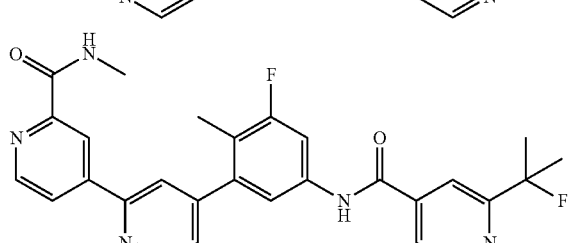
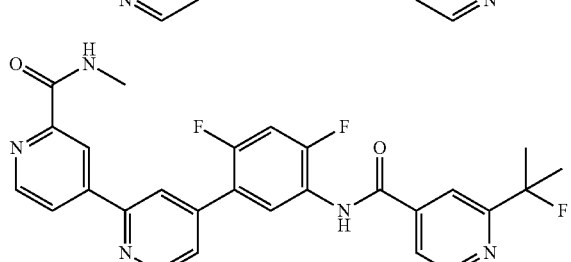
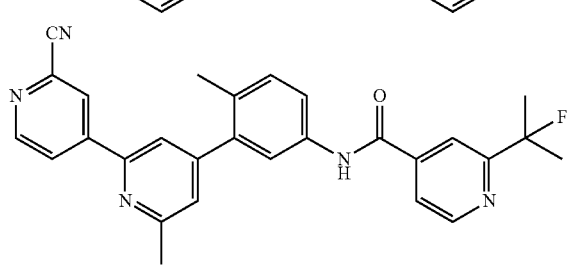
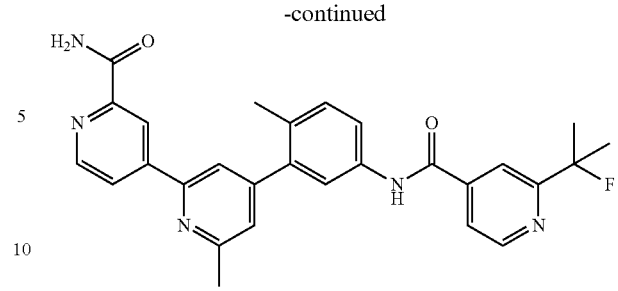
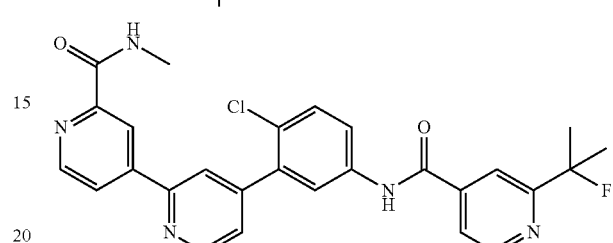
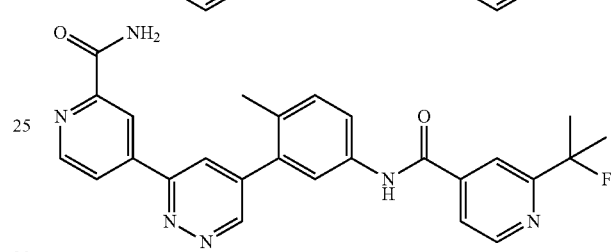
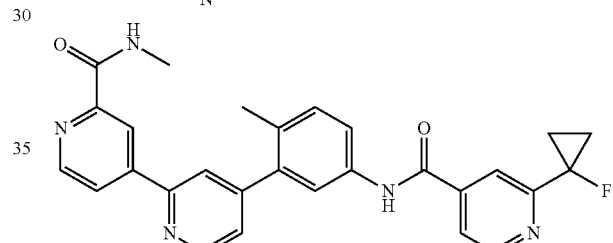
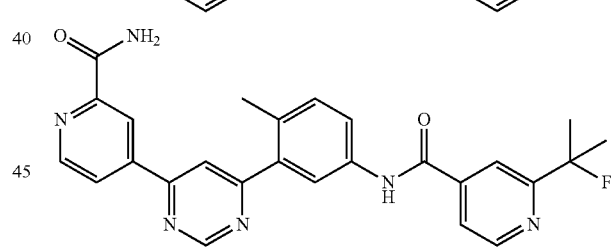
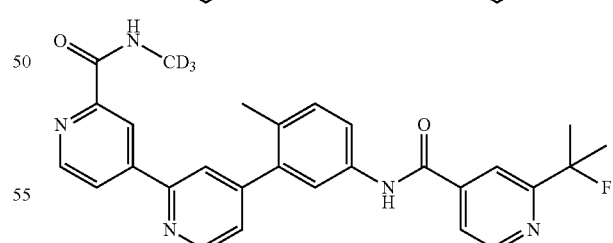
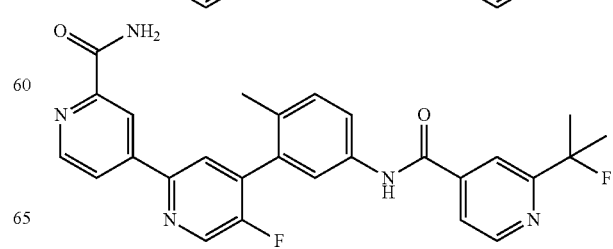

715
-continued
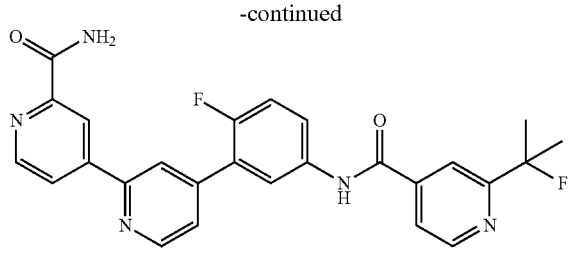
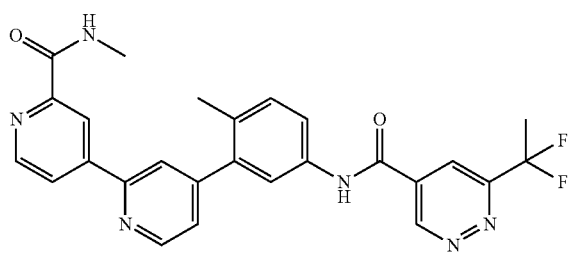
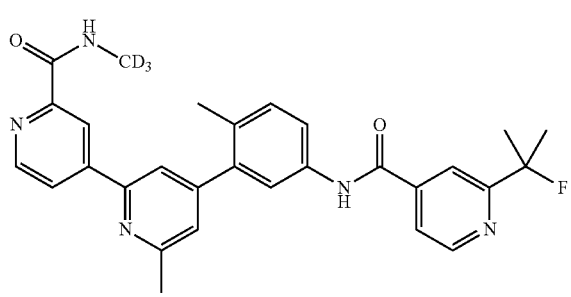
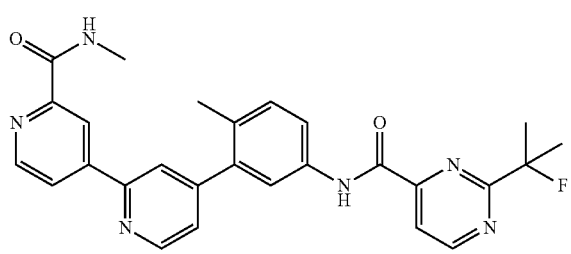
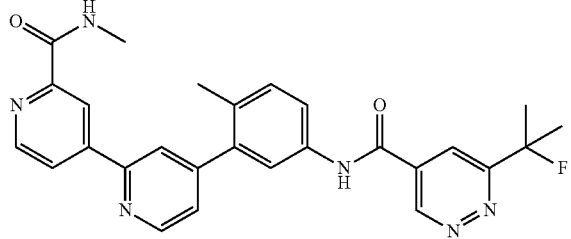
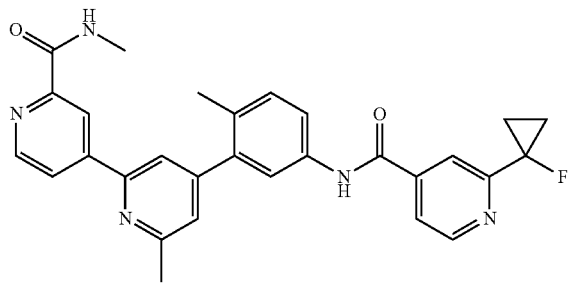
716
-continued
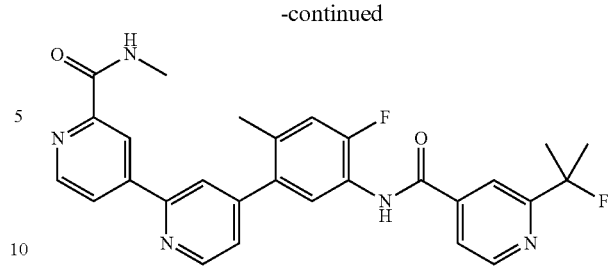
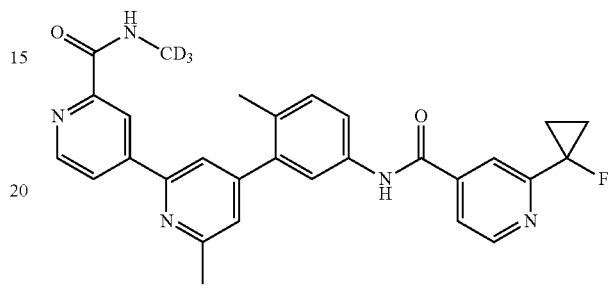
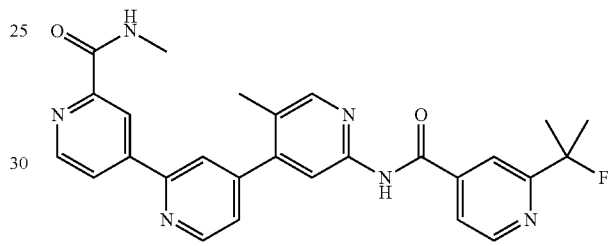
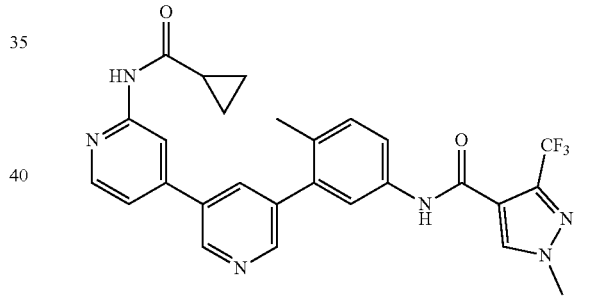
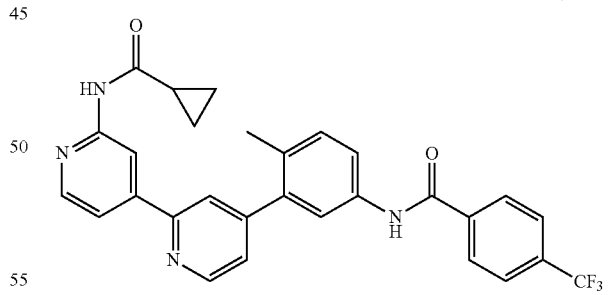
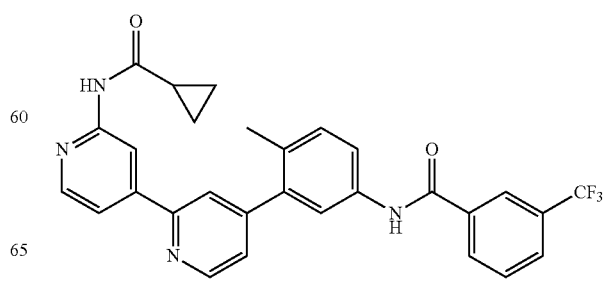

-continued

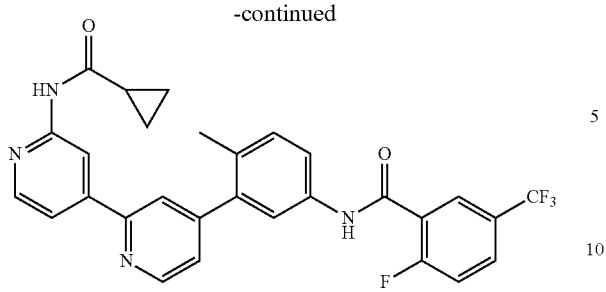

and pharmaceutically acceptable salts, enantiomers, stereoisomers, and tautomers thereof.

29. A pharmaceutical composition comprising the compound according to claim 1, or a pharmaceutically acceptable salt thereof, and a pharmaceutically acceptable carrier or excipient.

30. A method of treating a cancer in a patient in need thereof, comprising administering to the patient a therapeutically effective amount of a compound of claim 1, or a pharmaceutically acceptable salt thereof.

31. The method of claim 30, wherein the cancer is selected from the group consisting of melanoma, multiple myeloma, thyroid cancer, ovarian cancer, colorectal cancer, colon cancer, pancreatic cancer, lung cancer, bladder cancer, gastrointestinal stromal tumors, solid tumors, brain cancers, gliomas, glioblastomas, astrocytomas, blood-borne cancers, hairy cell leukemia, acute myelogenous leukemia (AML), or other cancers caused by activation of the RAS→RAF→MEK→ERK signaling pathway.

* * * * *

SEQUENCE LISTING

```
Sequence total quantity: 5
SEQ ID NO: 1            moltype = AA  length = 564
FEATURE                 Location/Qualifiers
source                  1..564
                        mol_type = protein
                        organism = synthetic construct
SEQUENCE: 1
MSPILGYWKI KGLVQPTRLL LEYLEEKYEE HLYERDEGDK WRNKKFELGL EFPNLPYYID   60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD LEVLFQGPEF KSPAEQRERK  240
SLADDKKKVK NLGYRDSGDD WEVPPSEVQL LKRIGTGSFG TVFRGRWHGD VAVKVLKVSQ  300
PTAEQAQAFK NEMQVLRKTR HVNILLFMGF MTRPGFAIIT QWCEGSSLYH HLHVADTRFD  360
MVQLIDVARQ TAQGMDYLHA KNIIHRDLKS NNIFLHEGLT VKIGDFGLAT VKTRWSGAQP  420
LEQPSGSVLW MAAEVIRMQD PNPYSFQSDV YAYGVVLYEL MTGSLPYSHI GCRDQIIFMV  480
GRGYLSPDLS KISSNCPKAM RRLLSDCLKF QREERPLFPQ ILATIELLQR SLPKIERSAS  540
EPSLHRTQAD ELPACLLSAA RLVP                                        564

SEQ ID NO: 2            moltype = AA  length = 351
FEATURE                 Location/Qualifiers
source                  1..351
                        mol_type = protein
                        organism = synthetic construct
SEQUENCE: 2
LQKSPGPQRE RKSSSSSEDR NRMKTLGRRD SSDDWEIPDG QITVGQRIGS GSFGTVYKGK   60
WHGDVAVKML NVTAPTPQQL QAFKNEVGVL RKTRHVNILL FMGYSTKPQL AIVTQWCEGS  120
SLYHHLHIIE TKFEMIKLID IARQTAQGMD YLHAKSIIHR DLKSNNIFLH EDLTVKIGDF  180
GLATVKSRWS GSHQFEQLSG SILWMAPEVI RMQDKNPYSF QSDVYAFGIV LYELMTGQLP  240
```

```
YSNINNRDQI IFMVGRGYLS PDLSKVRSNC PKAMKRLMAE CLKKKRDERP LFPQILASIE    300
LLARSLPKIH RSASEPSLNR AGFQTEDFSL YACASPKTPI QAGGYGAFPV H             351

SEQ ID NO: 3            moltype = AA  length = 342
FEATURE                 Location/Qualifiers
source                  1..342
                        mol_type = protein
                        organism = synthetic construct
SEQUENCE: 3
QPKTPVPAQR ERAPVSGTQE KNKIRPRGQR DSSDDWEIEA SEVMLSTRIG SGSFGTVYKG    60
KWHGDVAVKI LKVVDPTPEQ FQAFRNEVAV LRKTRHVNIL LFMGYMTKDN LAIVTQWCEG    120
SSLYKHLHVQ ETKFQMFQLI DIARQTAQGM DYLHAKNIIH RDMKSNNIFL HEGLTVKIGD    180
FGLATVKSRW SGSQQVEQPT GSVLWMAPEV IRMQDNNPFS FQSDVYSYGI VLYELMTGEL    240
PYSHINNRDQ IIFMVGRGYA SPDLSKLYKN CPKAMKRLVA DCVKKVKEER PLFPQILSSI    300
ELLQHSLPKI NRSASEPSLH RAAHTEDINA CTLTTSPRLP VF                      342

SEQ ID NO: 4            moltype = AA  length = 351
FEATURE                 Location/Qualifiers
source                  1..351
                        mol_type = protein
                        organism = synthetic construct
SEQUENCE: 4
LQKSPGPQRE RKSSSSSEDR NRMKTLGRRD SSDDWEIPDG QITVGQRIGS GSFGTVYKGK    60
WHGDVAVKML NVTAPTPQQL QAFKNEVGVL RKTRHVNILL FMGYSTKPQL AIVTQWCEGS    120
SLYHHLHIIE TKFEMIKLID IARQTAQGMD YLHAKSIIHR DLKSNNIFLH EDLTVKIGDF    180
GLATEKSRWS GSHQFEQLSG SILWMAPEVI RMQDKNPYSF QSDVYAFGIV LYELMTGQLP    240
YSNINNRDQI IFMVGRGYLS PDLSKVRSNC PKAMKRLMAE CLKKKRDERP LFPQILASIE    300
LLARSLPKIH RSASEPSLNR AGFQTEDFSL YACASPKTPI QAGGYGAFPV H             351

SEQ ID NO: 5            moltype = AA  length = 10
FEATURE                 Location/Qualifiers
source                  1..10
                        mol_type = protein
                        organism = synthetic construct
MOD_RES                 1
                        note = pyro-Glutamic acid
MOD_RES                 6
                        note = O-t-butyl-D-Serine
MOD_RES                 10
                        note = Amidated azaglycine
SEQUENCE: 5
EHWSYSLRPG                                                          10
```